US007262200B2

(12) United States Patent
Aronov et al.

(10) Patent No.: US 7,262,200 B2
(45) Date of Patent: Aug. 28, 2007

(54) INDAZOLINONE COMPOSITIONS USEFUL AS KINASE INHIBITORS

(75) Inventors: Alex Aronov, Watertown, MA (US); David J. Lauffer, Stow, MA (US); Huan Qui Li, Cambridge, MA (US); Ronald Charles Tomlinson, Marlborough, MA (US); Pan Li, Arlington, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 118 days.

(21) Appl. No.: 10/694,534

(22) Filed: Oct. 27, 2003

(65) Prior Publication Data

US 2004/0167121 A1    Aug. 26, 2004

Related U.S. Application Data

(60) Provisional application No. 60/421,398, filed on Oct. 25, 2002.

(51) Int. Cl.
*A61K 31/517* (2006.01)
*C07D 403/14* (2006.01)

(52) U.S. Cl. ............... 514/260; 544/284; 544/122; 544/182; 544/279; 544/291; 544/324; 546/275.7; 548/181; 548/361.5; 435/184; 514/242; 514/338; 514/370; 514/405

(58) Field of Classification Search ............... 514/260, 514/338, 370, 405, 242; 544/284, 122, 182, 544/279, 291, 324; 546/275.7; 548/361.5, 548/181; 435/184
See application file for complete search history.

(56) References Cited

U.S. PATENT DOCUMENTS 3,816,121 A    6/1974    Shiba et al. ............... 96/97

FOREIGN PATENT DOCUMENTS

| DE | 25 33 958 A1 | 2/1977 |
|---|---|---|
| EP | 0 075 808 A2 | 4/1983 |
| EP | 1 199 306 A1 | 4/2002 |
| EP | 1 256 574 A1 | 11/2002 |
| EP | 1 380 576 A1 | 1/2004 |
| FR | 1 516 610 | 3/1968 |
| JP | 3-150560 | 6/1991 |
| JP | 3-179345 | 8/1991 |
| JP | 2001-354511 | 12/2001 |
| WO | WO98/24771 A1 | 6/1998 |
| WO | WO 02/062795 | 8/2002 |
| WO | WO 03/024962 A1 | 3/2003 |
| WO | WO 03/040096 A2 | 5/2003 |
| WO | WO 03/063797 A2 | 8/2003 |
| WO | WO 03/068743 A1 | 8/2003 |
| WO | WO 03/078402 A1 | 9/2003 |

OTHER PUBLICATIONS

Patel, M. et al.: Unsymmetrical cyclic urea as HIV-1 protease inhibitors: Novel biaryl indazoles as P2/P2' substituents. Bioorg. & medicin. Chem. Lett. vol. 9, pp. 3217-3220, 1999.*
File Chemical Abstracts, STN Caesar accession No. 1189, AN 52:25500.
File Chemical Abstracts, STN Caesar accession No. 1146, AN 132:122591.
Cui et al. "Non-covalent Thrombin Inhibitors Featuring $P_3$-Heterocycles with $P_1$-Bicyclic Arginine Surrogates", Bioorganic & Medicinal Chemistry Letters: 12 2925-2930 (2002).
Duman, "Protein Kinase Inhibitors: Emerging Pharmacophores 1997-2001", Exp. Opin. Ther. Patents 11(3): 405-429 (2001).

* cited by examiner

*Primary Examiner*—Charanjit S. Aulakh
(74) *Attorney, Agent, or Firm*—Lisa A. Dixon; Jennifer G. Che

(57) ABSTRACT

The present invention provides compounds of formula I:

$$\text{I}$$

These compounds, and pharmaceutically acceptable compositions thereof, are useful generally as kinase inhibitors, particularly as inhibitors of PRAK, GSK3, ERK2, CDK2, MK2, SRC, SYK, and Aurora-2. Accordingly, compounds and compositions of the invention are useful for treating or lessening the severity of a variety of disorders, including, but not limited to, heart disease, diabetes, Alzheimer's disease, immunodeficiency disorders, inflammatory diseases, allergic diseases, autoimmune diseases, destructive bone disorders such as osteoporosis, proliferative disorders, infectious diseases and viral diseases.

63 Claims, No Drawings

INDAZOLINONE COMPOSITIONS USEFUL AS KINASE INHIBITORS

CROSS-REFERENCE TO RELATED APPLICATIONS

The present application claims priority under 35 U.S.C. § 119(e) to U.S. Provisional Application No. 60/421,398, filed Oct. 25, 2002, entitled "Indazolinone Compositions Useful as Kinase Inhibitors", the entire contents of which are hereby incorporated by reference.

TECHNICAL FIELD OF INVENTION

The present invention relates to indazolinones useful as kinase inhibitors. These compounds are useful for treating or modulating disease in which kinases may be involved, symptoms of such disease or the effect of other physiological events mediated by kinases. Accordingly, the invention also provides pharmaceutically acceptable compositions comprising the compounds of the invention and methods of using the compositions for treating diseases in which kinase activity is involved.

BACKGROUND OF THE INVENTION

The search for new therapeutic agents has been greatly aided in recent years by a better understanding of the structure of enzymes and other biomolecules associated with target diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. (1995) *The Protein Kinase Facts Book, I and II*, Academic Press, San Diego, Calif.). Protein kinases are thought to have evolved from a common ancestral gene due to the conservation of their structure and catalytic function. Almost all kinases contain a similar 250–300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.*, 9:576–596 (1995); Knighton et al., *Science*, 253:407–414 (1991); Hiles et al., *Cell*, 70:419–429 (1992); Kunz et al., *Cell*, 73:585–596 (1993); Garcia-Bustos et al., *EMBO J.*, 13:2352–2361 (1994)).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents. However, considering the lack of currently available treatment options for the majority of the conditions associated with protein kinases, there is still a great need for new therapeutic agents that inhibit these protein targets.

SUMMARY OF THE INVENTION

It has now been found that compounds of this invention, and pharmaceutically acceptable compositions thereof, are effective as kinase inhibitors. In certain embodiments, compounds of the invention are inhibitors of PRAK, GSK3, ERK2, CDK2, MK2, SRC, SYK, and Aurora-2. These compounds have the general formula I:


These compounds, and pharmaceutically acceptable compositions thereof, are useful for treating or lessening the severity of a variety of disorders, including, but not limited to, heart disease, diabetes, Alzheimer's disease, immunodeficiency disorders, inflammatory diseases, allergic diseases, autoimmune diseases, destructive bone disorders such as osteoporosis, proliferative disorders, infectious diseases and viral diseases.

DETAILED DESCRIPTION OF THE INVENTION

I. Description of Compounds of the Invention:

The present invention relates to a compound of formula I:


or a pharmaceutically acceptable derivative thereof, wherein:

$R^1$ and $R^2$ are each independently hydrogen or a nitrogen protecting group;

one of $R^3$ or $R^4$ is —R and the other one of $R^3$ or $R^4$ is —$Q^1$—A—$Q^2$—Y, wherein $Q^1$ is a valence bond, —$NR^4$—, —$C(R^4)_2$—, —S—, —O—, —$SO_2$—, —$NR^4SO_2$—, —$SO_2NR^4$—, —CO—, —$NR^4CO$—, —CONR$^A$—, —OC(O)—, —C(O)O—, —OC(O)NR$^A$, 1,2-cyclopropyl, 1,2-cyclobutanediyl, or 1,3-cyclobutanediyl, or is an optionally substituted C$_{2-4}$alkylidene chain, wherein one or more methylene units of the optionally substituted C$_{2-4}$alkylidene chain is optionally replaced by —O—, —S—, —NR$^A$—, —NR$^A$CO—, —NR$^A$CONR$^A$—, —NR$^A$CO$_2$—, —CO—, —CO$_2$—, —CONR$^A$—, —OC(O)NR$^A$—, —SO$_2$—, —SO$_2$NR$^A$—, —NR$^A$SO$_2$—, —NR$^A$SO$_2$NR$^A$—, —C(O)C(O)—, or —C(O)C(R$^A$)$_2$C(O)—, wherein each occurrence of R$^A$ is independently hydrogen or optionally substituted C$_{1-4}$aliphatic, or two occurrences of R$^A$ on the same carbon atom are taken together to form an optionally substituted 3–6-membered carbocyclic ring;

A is an optionally substituted group selected from a 5–7-membered monocyclic or 8–10-membered bicyclic aryl, heteroaryl, heterocyclic or carbocyclic ring, or is an optionally substituted C$_{2-6}$ alkylidene chain wherein one or more methylene units of said C$_{2-6}$ alkylidene chain is optionally replaced by —O—, —S—, —NR$^B$—, NR$^B$CO—, NR$^B$CONR$^B$, —NR$^B$CO$_2$—, —CO—, —C(O)O—, —OC(O)—, —CONR$^B$—, —OC(O)NR$^B$—, —SO$_2$—, —SO$_2$NR$^B$—, —NR$^B$SO$_2$—, NR$^B$SO$_2$NR$^B$—, —C(O)C(O)—, or —C(O)C(R$^B$)$_2$C(O)—, and each occurrence of R$^B$ is independently hydrogen or optionally substituted group selected from C$_{1-6}$ aliphatic, C$_{1-6}$heteroaliphatic, aryl or heteroaryl;

Q$^2$ is NR$^C$, S, O, or C(R$^C$)$_2$, wherein each occurrence of R$^C$ is independently hydrogen or optionally substituted C$_{1-4}$aliphatic;

Y is an optionally substituted group selected from a 5–7-membered monocyclic or 8–10 membered bicyclic aryl, heteroaryl, heterocyclic or carbocyclic ring;

R$^5$ is —R;

Z is N or CR$^6$, wherein R$^6$ is —R; and each occurrence of —R is independently hydrogen, Q$_{(n)}$halogen, Q$_{(n)}$CN, Q$_{(n)}$NO$_2$, or Q$_{(n)}$R$^7$ wherein n is zero or one, Q is an optionally substituted C$_{1-4}$ alkylidene chain wherein one or more methylene units of Q is optionally replaced by —O—, —S—, —NR$^7$—, —NR$^7$CO—, —NR$^7$CONR$^7$—, —NR$^7$CO$_2$—, —CO—, —CO$_2$—, —CONR$^7$—, —OC(O)NR$^7$—, —SO$_2$—, —SO$_2$NR$^7$—, —NR$^7$SO$_2$—, —NR$^7$SO$_2$NR$^7$—, —C(O)C(O)—, or —C(O)C(R$^7$)$_2$C(O)—, and each occurrence of R$^7$ is independently hydrogen, an optionally substituted group selected from aliphatic, heteroaliphatic, aryl or heteroaryl, or two occurrences of R$^7$ on the same nitrogen atom are taken together with the nitrogen atom to form an optionally substituted group selected from a 5–8-membered heterocyclic or 5–8-membered heteroaryl ring.

In certain embodiments for the compounds described generally above and herein, when Z is CH, R$^1$, R$^2$, R$^4$ and R$^5$ are each hydrogen, then —Q$^1$—A—Q$^2$—Y is not:

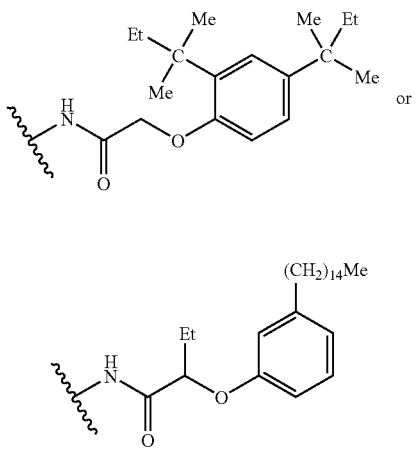

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1–20 aliphatic carbon atoms. In some embodiments, aliphatic groups contain 1–10 aliphatic carbon atoms. In other embodiments, aliphatic groups contain 1–8 aliphatic carbon atoms. In still other embodiments, aliphatic groups contain 1–6 aliphatic carbon atoms, and in yet other embodiments aliphatic groups contain 1–4 aliphatic carbon atoms. In some embodiments, "cycloaliphatic" (or "carbocycle" or "cycloalkyl") refers to a monocyclic $C_3$–$C_8$ hydrocarbon or bicyclic $C_8$–$C_{12}$ hydrocarbon that is completely saturated or that contains one or more units of unsaturation, but which is not aromatic, that has a single point of attachment to the rest of the molecule wherein any individual ring in said bicyclic ring system has 3–7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —$R^\circ$; —$OR^\circ$; —$SR^\circ$; 1,2-methylenedioxy; 1,2-ethylenedioxy; phenyl (Ph) optionally substituted with $R^\circ$; —O(Ph) optionally substituted with $R^\circ$; —$(CH_2)_{1-2}$(Ph), optionally substituted with $R^\circ$; —CH=CH(Ph), optionally substituted with $R^\circ$; —$NO_2$; —CN; —$N(R^\circ)_2$; —$NR^\circ C(O)R^\circ$; —$NR^\circ C(S)R^\circ$; —$NR^\circ C(O)N(R^\circ)_2$; —$NR^\circ C(S)N(R^\circ)_2$; —$NR^\circ CO_2R^\circ$; —$NR^\circ NR^\circ C(O)R^\circ$; —$NR^\circ NR^\circ C(O)N(R^\circ)_2$; —$NR^\circ NR^\circ CO_2R^\circ$; —$C(O)C(O)R^\circ$; —$C(O)CH_2C(O)R^\circ$; —$CO_2R^\circ$; —$C(O)R^\circ$; —$C(S)R^\circ$; —$C(O)N(R^\circ)_2$; —$C(S)N(R^\circ)_2$; —$OC(O)N(R^\circ)_2$; —$OC(O)R^\circ$; —$C(O)N(OR^\circ)$ $R^\circ$; —$C(NOR^\circ)$ $R^\circ$; —$S(O)_2R^\circ$; —$S(O)_3R^\circ$; —$SO_2N(R^\circ)_2$; —$S(O)R^\circ$; —$NR^\circ SO_2N(R^\circ)_2$; —$NR^\circ SO_2R^\circ$; —$N(OR^\circ)R^\circ$; —C(=NH)—$N(R^\circ)_2$; or —$(CH_2)_{0-2}NHC(O)R^\circ$ wherein each independent occurrence of $R^\circ$ is selected from hydrogen, optionally substituted $C_{1-6}$ aliphatic, an unsubstituted 5–6 membered heteroaryl or heterocyclic ring, phenyl, —O(Ph), or —$CH_2$(Ph), or, notwithstanding the definition above, two independent occurrences of $R^\circ$, on the same substituent or different substituents, taken together with the atom(s) to which each $R^\circ$ group is bound, form a 5–8-membered heterocyclyl, aryl, or heteroaryl ring or a 3–8-membered cycloalkyl ring having 0–3 heteroatoms independently selected from nitrogen, oxygen, or sulfur. Optional substituents on the aliphatic group of $R^\circ$ are selected from $NH_2$, $NH(C_{1-4}aliphatic)$, $N(C_{1-4}aliphatic)_2$, halogen, $C_{1-4}$aliphatic, OH, O($C_{1-4}$ aliphatic), $NO_2$, CN, $CO_2H$, $CO_2$($C_{1-4}$aliphatic), O(halo$C_{1-4}$ aliphatic), or halo$C_{1-4}$aliphatic, wherein each of the foregoing $C_{1-4}$aliphatic groups of $R^\circ$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R are selected from NH2, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

Optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^{+1}$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5–6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 5–8-membered heterocyclyl, aryl, or heteroaryl ring or a 3–8-membered cycloalkyl ring having 0–3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R$^o$ (or R$^+$, or any other variable similarly defined herein), are taken together together with the atom(s) to which each variable is bound to form a 5–8-membered heterocyclyl, aryl, or heteroaryl ring or a 3–8-membered cycloalkyl ring having 0–3 heteroatoms independently selected from nitrogen, oxygen, or sulfur. Exemplary rings that are formed when two independent occurrences of R$^o$ (or R$^+$, or any other variable similarly defined herein) are taken together with the atom(s) to which each variable is bound include, but are not limited to the following: a) two independent occurrences of R$^o$ (or R$^+$, or any other variable similarly defined herein) that are bound to the same atom and are taken together with that atom to form a ring, for example, N(R$^o$)$_2$, where both occurrences of R$^o$ are taken together with the nitrogen atom to form a piperidin-1-yl, piperazin-1-yl, or morpholin-4-yl group; and b) two independent occurrences of R$^o$ (or R$^+$, or any other variable similarly defined herein) that are bound to different atoms and are taken together with both of those atoms to form a ring, for example where a phenyl group is substituted with two occurrences of

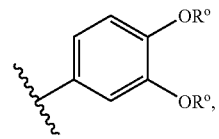

these two occurrences of R$^o$ are taken together with the oxygen atoms to which they are bound to form a fused 6-membered oxygen containing ring:

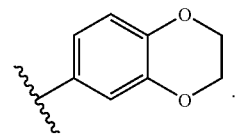

It will be appreciated that a variety of other rings can be formed when two independent occurrences of R$^o$ (or R$^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis", Third Edition, John Wiley & Sons, New York: 1999, the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

II. Description of Certain Exemplary Compounds:

In certain exemplary embodiments, for compounds as described generally above, Z is $CR^6$ and the compound has the structure (Ia):

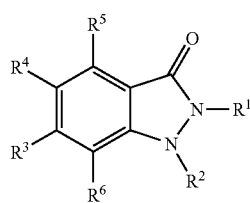

Ia

In certain other exemplary embodiments, for compounds as described generally above, Z is N and the compound has the structure (Ib):

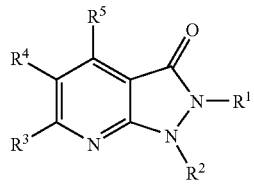

Ib

In one exemplary class, for compounds of general formulas I, Ia and Ib, either of $R^3$ or $R^4$ is —$Q^1$—A—$Q^2$—Y, wherein A is a substituted or unsubstituted aryl or heteroaryl moiety and compounds have the general formula Ia or IIb:

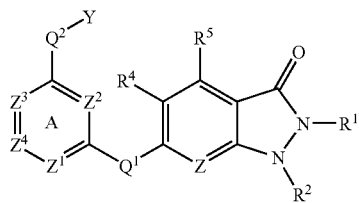

IIa

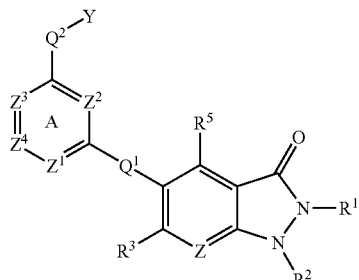

IIb wherein $R^1$, $R^2$, $R^3$, $R^4$, $R^5$, $Q^1$, $Q^2$ and Y are as defined generally above and in classes and subclasses herein;

$Z^1$ is N or $CR^V$, $Z^2$ is N or $CR^W$, $Z^3$ is N or $CR^X$ and $Z^4$ is N or $CR^Y$, wherein $R^V$, $R^W$, $R^X$ and $R^Y$ are each independently $R^8$, or $R^X$ and $R^Y$, or $R^V$ and $R^Y$ are taken together with their intervening atoms to form a fused, unsaturated or partially unsaturated, 5–8 membered ring having 0–3 ring heteroatoms selected from oxygen, sulfur, or nitrogen, wherein any substitutable carbon on said fused ring formed by $R^X$ and $R^Y$ or by $R^V$ and $R^Y$ is substituted by oxo or $R^8$, and any substitutable nitrogen on said ring formed by $R^X$ and $R^Y$ or by $R^V$ and $R^Y$ is substituted by $R^9$;

wherein each occurrence of $R^8$ is independently —R; and each occurrence of $R^9$ is independently hydrogen, —R', —COR', —$CO_2$(R'), —CON(R')$_2$, or —$SO_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

As described generally above, A can be an aryl or heteroaryl ring optionally substituted and optionally fused. In certain exemplary embodiments, for compounds of formulas I, Ia, Ib, Ia, or IIb (and subsets thereof as detailed herein), A represents one of the following moieties:

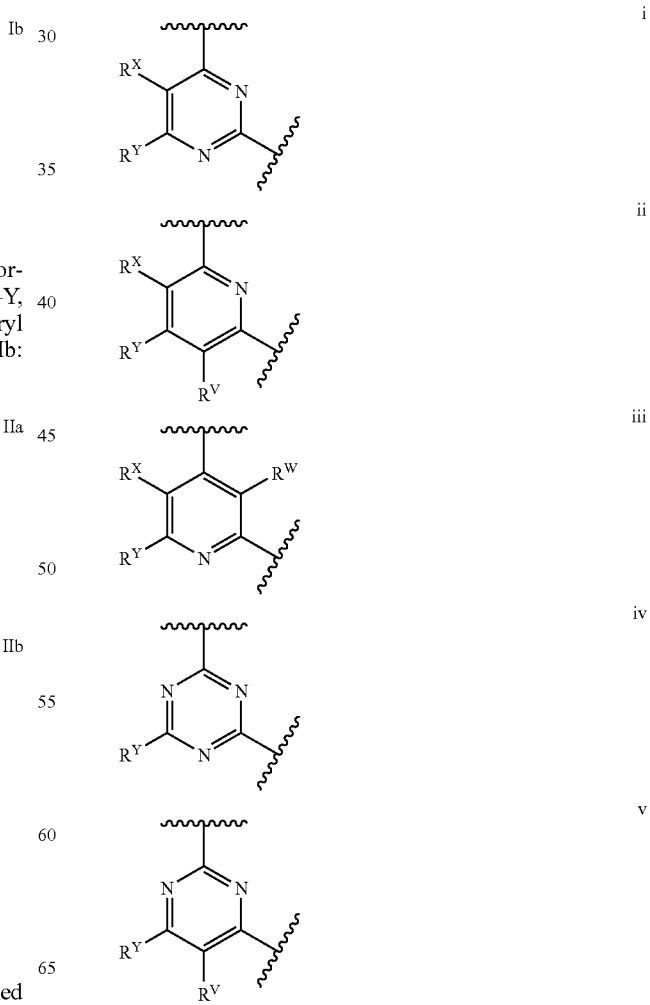

-continued

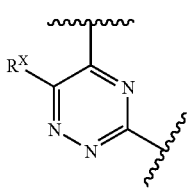
vi

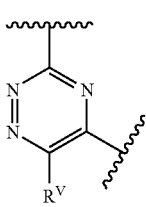
vii

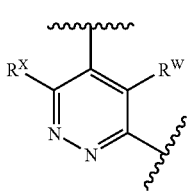
viii

ix
and

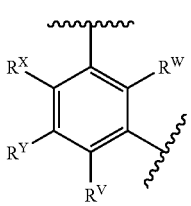
x wherein $R^V$, $R^W$, $R^X$, and $R^Y$ are as defined generally above and in classes and subclasses herein.

Examples of certain preferred ring A systems include those represented by formula i, ii, iii or x.

In certain embodiments, ring A systems described generally above, and preferred ring systems i, ii, iii or x are monocyclic ring systems.

In certain other embodiments, ring A systems described generally above, and preferred ring systems i, ii, iii, or x are bicyclic ring systems. Thus, in certain embodiments, adjacent groups $R^X$ and $R^Y$ are taken together to form a ring. Preferred $R^X/R^Y$ rings include a 5-, 6-, 7-, or 8-membered unsaturated or partially unsaturated ring having 0–2 heteroatoms, wherein said $R^X/R^Y$ ring is optionally substituted at any substitutable carbon atom by one or more occurrences of oxo or $R^8$, and at any substitutable nitrogen atom by $R^9$.

Examples of certain preferred Ring A systems for compounds of formulas I, Ia, Ib, IIa, or IIb (and subsets thereof as described in detail herein) are depicted below by compounds II-A through II-DD, wherein $Z^1$ is nitrogen or $CR^V$, $Z^2$ is nitrogen or $CR^W$, p is 0–4, and $Q^1$, $Q^2$, $R^8$, $R^9$ and Y are as defined generally above and in classes and subclasses herein.

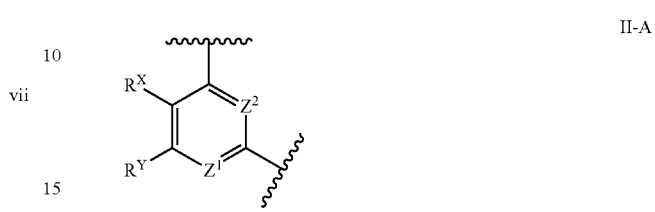
II-A

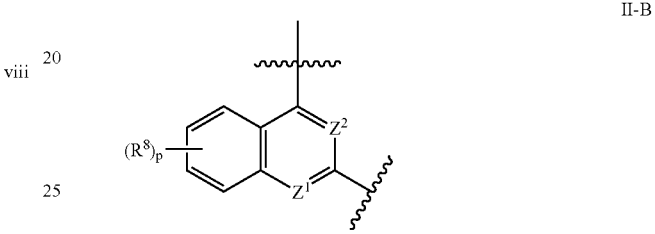
II-B

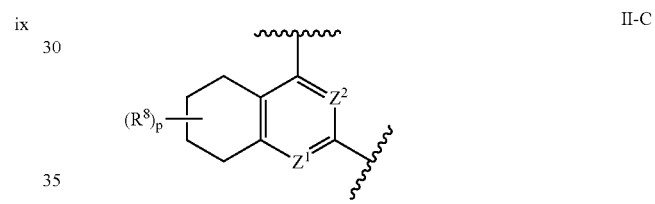
II-C

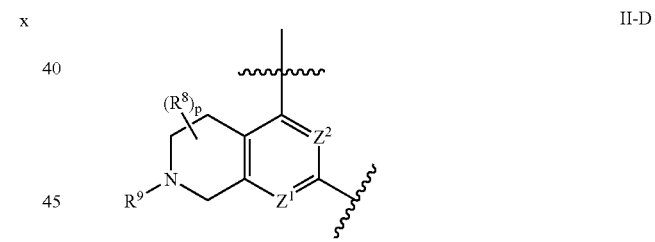
II-D

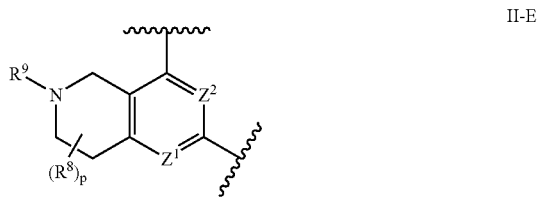
II-E

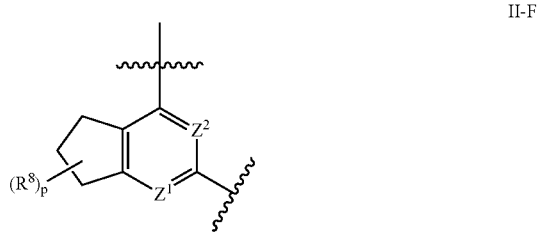
II-F

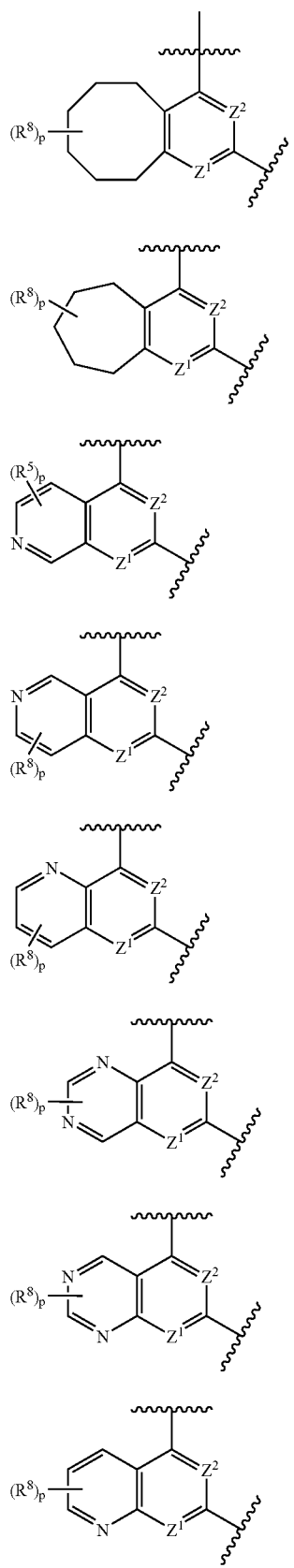
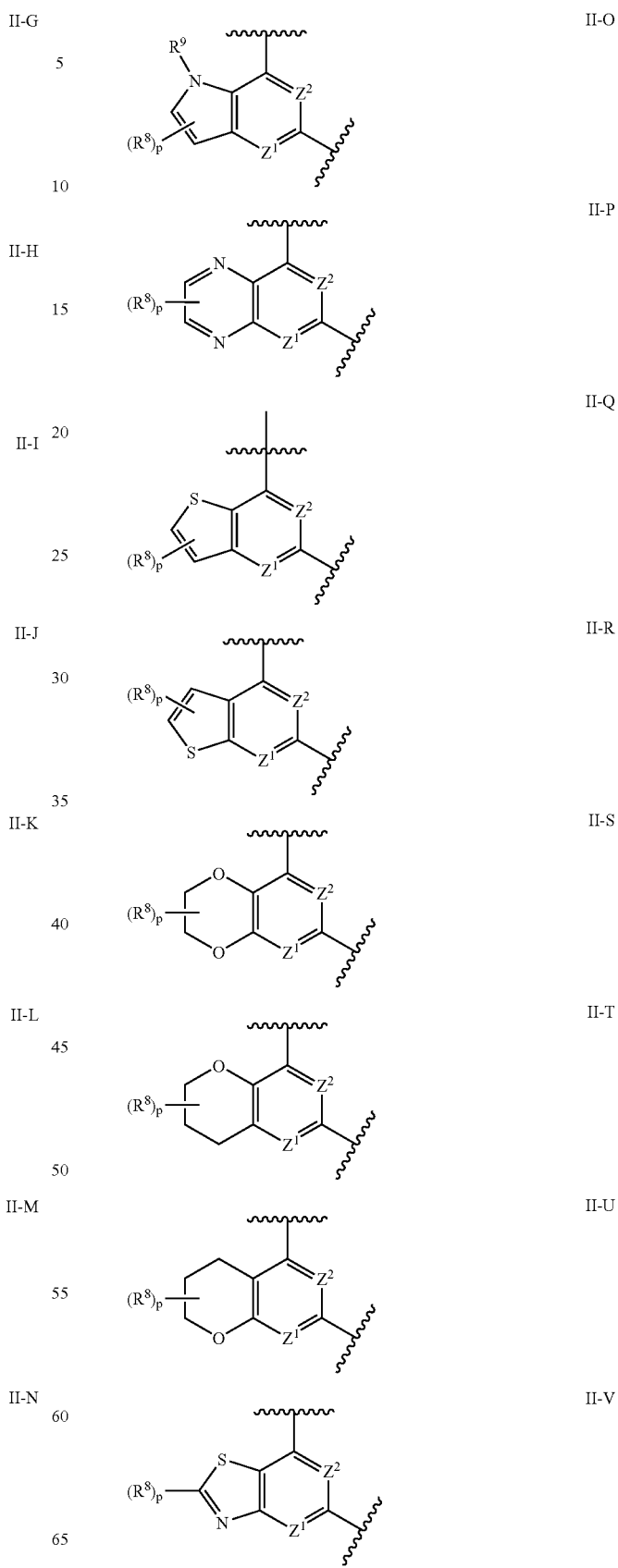

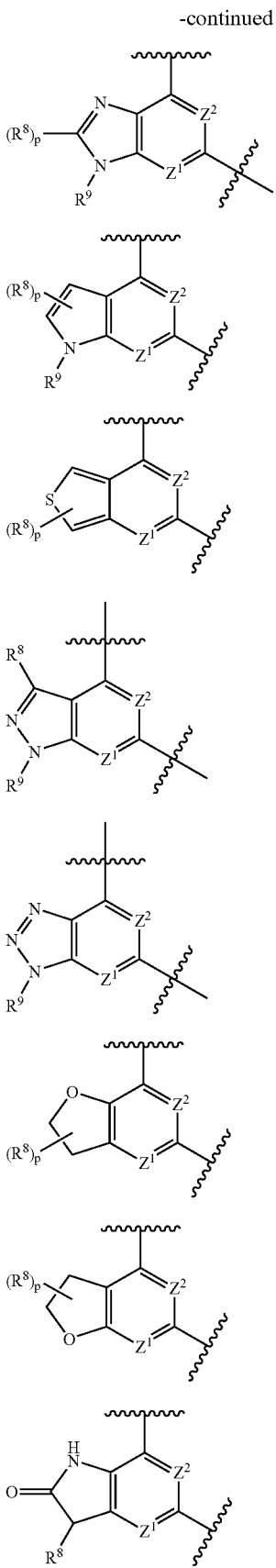

Preferred Ring A systems include II-A, II-B, II-C, II-D, II-E, II-F, II-H, II-I, II-J, II-K, II-L, II-N, II-O, and II-DD, more preferably II-A, II-B, II-C, II-D, II-E, II-H, and II-K, and most preferably II-A and II-B.

In certain embodiments, for each of the ring systems described generally above and in preferred subsets, $Z^1$ is $CR^V$ and $Z^2$ is $CR^W$.

In other embodiments, for each of the ring systems described generally above and in preferred subsets, $Z^1$ is N and $Z^2$ is N.

In still other embodiments, for each of the ring systems described generally above and in preferred subsets, $Z^1$ is N and $Z^2$ is $CR^W$.

In yet other embodiments, for each of the ring systems described generally above and in preferred subsets, $Z^1$ is $CR^V$ and $Z^2$ is N.

As described generally above, in certain embodiments, A is a monocyclic ring system and $R^V$, $R^W$, $R^X$ and $R^Y$ are each independently —R. For monocyclic ring systems, preferred $R^X$ groups, when present, include hydrogen, alkyl- or dialkylamino, acetamido, or a $C_{1-4}$ aliphatic group such as methyl, ethyl, cyclopropyl, or isopropyl. For monocyclic ring systems, preferred $R^Y$ groups, when present, include hydrogen, an optionally substituted group selected from $C_{1-6}$ aliphatic, $C_{1-6}$ heteroaliphatic, aryl, or heteroaryl, —$Q_{(n)}N(R^7)_2$, —$Q_{(n)}OR^7$, —$Q_{(n)}SR^7$, —$Q_{(n)}(C=O)O(R^7)$, —$Q_{(n)}C(O)N(R^7)_2$, —$Q_{(n)}NHC(O)R^7$, —$Q_{(n)}NHSO_2R^7$, or —$Q_{(n)}SO_2N(R^7)_2$, wherein n is 0 or 1, and wherein Q is preferably —$(C(R'')_2)$—, wherein R'' is hydrogen or $C_{1-3}$alkyl, and wherein each occurrence of $R^7$ is independently hydrogen, optionally substituted aliphatic, heteroaliphatic, aryl or heteroaryl, or two occurrences of $R^7$ on the same nitrogen atom are taken together with the nitrogen atom to form an optionally group selected from a 5–8 membered heterocyclic or 5–8 membered heteroaryl ring.

Exemplary $R^Y$ groups include, but are not limited to, groups selected from optionally substituted 5–6 membered heteroaryl or heterocyclyl rings, such as 2-pyridyl, 4-pyridyl, pyrrolidinyl, piperidinyl, morpholinyl, or piperazinyl; optionally substituted aryl or cycloalkyl rings such as phenyl, halogen substituted phenyl, alkoxy substituted phenyl, trifluoromethyl substituted phenyl, nitro substituted phenyl, methyl substituted phenyl; optionally substituted $C_{1-6}$ aliphatic, such as methyl, ethyl, cyclopropyl, cyclopentyl, cyclohexyl, amino substituted cycloalkyl, acetamido substituted cycloalkyl, isopropyl, or t-butyl; alkoxyalkylamino such as methoxyethylamino; alkoxyalkyl such as methoxymethyl or methoxyethyl; aminoalkyl such as aminoethyl, dimethylaminoethyl; alkyl- or dialkylamino such as ethylamino or dimethylamino; alkyl- or dialkylaminoalkoxy such as dimethylaminopropyloxy; alkyl- or dialkylaminoalkoxyalkyl such as dimethylaminoethoxymethyl; and acetamido.

For a bicyclic Ring A system, the ring formed when $R^x$ and $R^y$ are taken together may be substituted or unsubstituted. As described generally above, the bicyclic ring system A may be substituted by one or more occurrences of oxo, $R^8$ or $R^9$, as defined generally above. In certain preferred embodiments, suitable $R^8$ substituents include —$R^7$, halo, —$O(CH_2)_{2-4}$—$N(R^7)_2$, —$O(CH_2)_{2-4}$—$R^7$, —$OR^7$, —$N(R^7)$—$(CH_2)_{2-4}$—$N(R^7)_2$, —$N(R^7)$—$(CH_2)_{2-4}$—$R^7$, —$C(=O)R^7$, —$CO_2R^7$, —$COCOR^7$, —$NO_2$, —CN, —$S(O)R^7$, —$SO_2R^7$, —$SR^7$, —$N(R^7)_2$, —$CON(R^7)_2$, —$SO_2N(R^7)_2$, —$OC(=O)R^7$, —$N(R^7)COR^7$, —$N(R^7)CO_2$ (optionally substituted $C_{1-6}$ aliphatic), —$N(R^7)N(R^7)_2$, —C=$NN(R^7)_2$, —C=N—OR, —$NHOR^7$, —$N(R^7)CON(R^7)_2$, —$N(R^7)SO_2N(R^7)_2$, —$N(R^7)SO_2R^7$, or —$OC(=O)$ $N(R^7)_2$. Most preferred $R^x/R^y$ ring substituents include -halo, —$R^7$, —$OR^7$, —$COR^7$, —$CO_2R^7$, —$CON(R^7)_2$, —$O(C=O)N(R^7)_2$, —CN, —$O(CH_2)_{2-4}$—$N(R^7)_2$, —$O(CH_2)_{2-4}$—$R^7$, —$NO_2$—$N(R^7)_2$, —$NR^7COR^7$, —$NR^7SO_2R^7$, —$SO_2N(R^7)_2$ wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring.

In certain preferred embodiments, A is a ring of general formula II-A wherein the ring is a monocyclic system and is substituted by preferred substituents described above.

In certain other preferred embodiments, A is a ring of general formula II-A, wherein the ring is a bicyclic system and the bicyclic ring is substituted by preferred substituents described above.

As described generally above, Y is an optionally substituted aryl, heteoaryl, aliphatic or heteoraliphatic moiety. In certain exemplary embodiments, for compounds of general formulas I, Ia, Ib, IIa or IIb (and subsets thereof as described in detail herein) Y is an optionally substituted heteroaryl moiety. In certain preferred embodiments, Y is selected from one of the following heteroaryl moieties a–y:

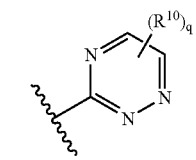 a

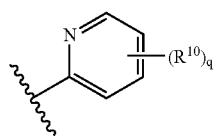 b

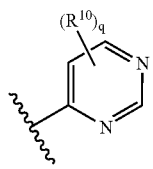 c

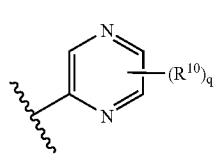 d

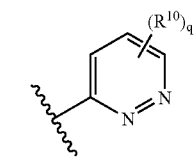 e

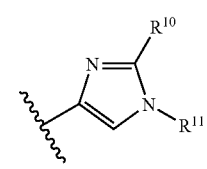 f

-continued

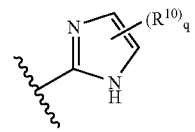 g

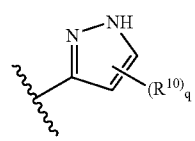 h

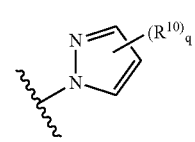 i

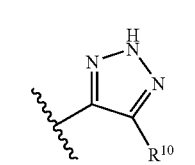 j

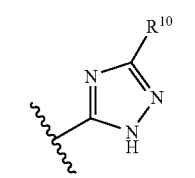 k

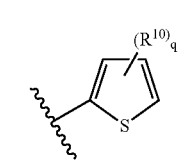 l

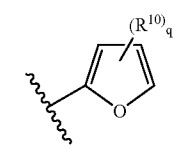 m

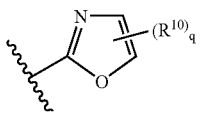 n

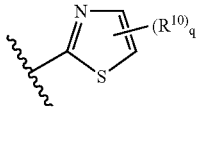 o

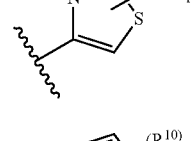 p

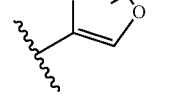 q

-continued

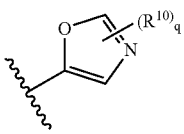   r

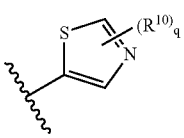   s

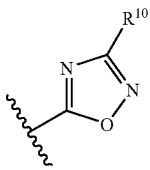   t

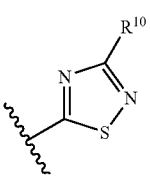   u

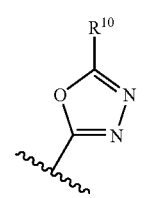   v

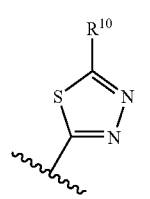   w

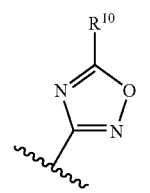   x

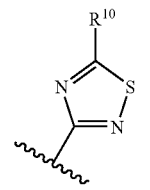   y wherein q is 0–4, $R^{10}$ is —R, wherein —R is defined generally above and in classes and subclasses herein, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

In certain other exemplary embodiments, Y is one of the following heteroaryl moieties:

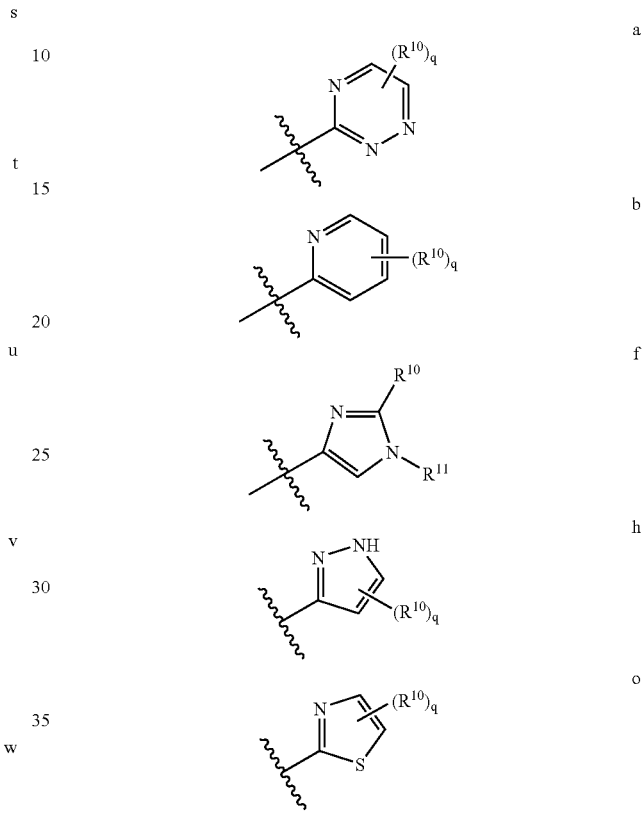

wherein q is 0–4, $R^{10}$ is —R, wherein —R is defined generally above and in classes and subclasses herein, and wherein each occurrence of $R^{11}$ is independently hydrogen, —R', —COR', —CO$_2$(R'), —CON(R')$_2$, or —SO$_2$R', wherein each occurrence of R' is independently hydrogen, optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

In certain preferred embodiments, Y is a pyrazole moiety, h.

Preferred $R^{10}$ groups include hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle) carbonyl. Examples of such preferred $R^{10}$ substituents include methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl).

In certain preferred embodiments, Y is a pyrazole moiety, h', wherein the pyrazole is substituted with two occurrences of R$^{10}$ (R$^{10a}$ and R$^{10b}$ as depicted), wherein R$^{10a}$ and R$^{10b}$ are each independently —R.

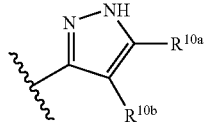

h'

Preferred groups for R$^{10a}$ and R$^{10b}$ include those preferred groups exemplified for R$^{10}$ above. In certain embodiments, preferred groups for R$^{10a}$ include hydrogen, C$_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle) carbonyl. Examples of such preferred R$^{10a}$ substituents include methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl). A preferred group for R$^{10b}$ is hydrogen.

As described generally above, two occurrences of R$^{10}$ (e.g., R$^{10a}$ and R$^{10b}$ as depicted above in formula h') taken together may represent a substituted or unsubstituted cycloaliphatic, cycloheteroaliphatic, aryl or heteroaryl moiety. In certain preferred embodiments, Y is one of the following groups:

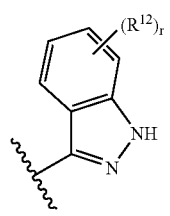

h-i

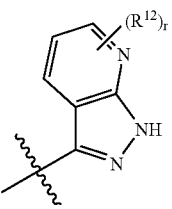

h-ii

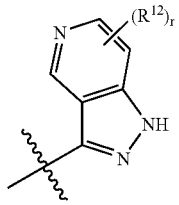

h-iii

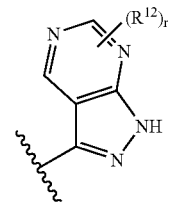

h-iv

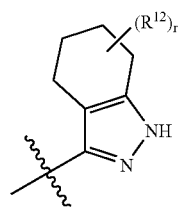

h-v wherein r is 0–4 and R$^{12}$ is —R, wherein —R is defined generally above and in classes and subclasses herein. Preferred substituents R$^{12}$ on the fused ring include one or more of the following: -halo, —N(R$^7$)$_2$, —C$_{1-3}$ alkyl, —C$_{1-3}$ haloalkyl, —NO$_2$, —O(C$_{1-3}$ alkyl), —CO$_2$(C$_{1-3}$ alkyl), —CN, —SO$_2$(C$_{1-3}$ alkyl), —SO$_2$NH$_2$, —OC(O)NH$_2$, —NH$_2$SO$_2$(C$_{1-3}$ alkyl), —NHC(O)(C$_{1-3}$ alkyl), —C(O)NH$_2$, and —CO(C$_{1-3}$ alkyl), wherein the (C$_{1-3}$ alkyl) is most preferably methyl, wherein each occurrence of R$^7$ is independently hydrogen, an optionally substituted group selected from aliphatic, heteroaliphatic, aryl or heteroaryl, or two occurrences of R$^7$ on the same nitrogen atom are taken together with the nitrogen atom to form an optionally substituted group selected from a 5–8 membered heterocyclic or 5–8 membered heteroaryl ring.

In still other embodiments, for compounds of formulas I, Ia, Ib, IIa or IIb (or subsets thereof as detailed herein) when R$^3$ is —Q$^1$—A—Q$^2$—Y, R$^4$ is preferably hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl. In most preferred embodiments R$^4$ is hydrogen, methyl, ethyl, cyclopropyl, hydroxy, phenyl or —CH$_2$NH$_2$.

In yet other embodiments, for compounds of formulas I, Ia, Ib, IIa or IIb (or subsets thereof as detailed herein), when R$^4$ is —Q$^1$—A—Q$^2$—Y, R$^3$ is preferably hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl. In most preferred embodiments R$^3$ is hydrogen, methyl, ethyl, cyclopropyl, hydroxy, phenyl or —CH$_2$NH$_2$.

In certain other preferred embodiments, for compounds of formulas I, Ia, Ib, IIa or IIb (or subsets thereof as detailed herein), R$^5$ is hydrogen, halogen, —NO$_2$, —CN, hydroxy, optionally substituted C$_{1-3}$alkyl, optionally substituted alkoxy, —SO$_2$NH$_2$, or —C(O)alkyl. In more preferred embodiments, R$^5$ is Cl, CF$_3$, OCF$_3$, CH$_3$, —CN, —SO$_2$NH$_2$ or —C(O)Me.

It will be appreciated that for the compounds as generally described above, certain subclasses of these compounds are of special interest, as described in more detail below.

In certain embodiments, a preferred subclass of compounds of general formula Ia or IIb includes those compounds where $Q^1$ is NH and $Q^2$ is NH. These compounds are defined by the general formula IIa(i) or IIb(i) and are depicted generally below:

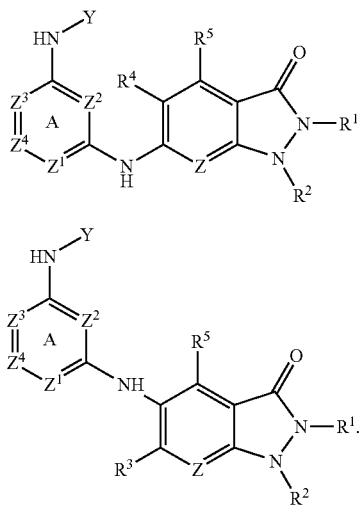

It will be appreciated that, for compounds of general formulas IIa(i) and IIb(i) certain additional subclasses are of special interest. Certain preferred embodiments of compounds of formula IIa(i) or IIb(i) include those compounds having any combination of the following features for each variable for formula IIa(i) or IIb(i):

i) Z is $CR^6$ or N;

ii) $R^1$, $R^2$, $R^4$ and $R^5$ are each hydrogen and wherein Z is $CHR^6$ and $R^6$ is hydrogen; or $R^1$, $R^2$, $R^3$ and $R^5$ are each hydrogen and wherein Z is CHHR and $R^6$ is hydrogen;

iii) ring A is defined according to one of the following groups:

a. ring A is one of formulas i, ii, iii, iv, v, vi, vii, viii, ix, or x;

b. ring A is one of formulas II-A, II-B, II-C, II-D, II-E, II-F, II-G, II-H, II-I, II-J, II-K, II-L, II-M, II-N, II-O, II-P, II-Q, II-R, II-S, II-T, II-U, II-V, II-W, II-X, II-Y, II-Z, II-AA, II-BB, II-CC, or II-DD;

c. ring A is one of formulas II-A, II-B, II-C, II-D, II-E, I-F, II-H, II-I, II-J, II-K, II-L, II-N, II-O, or II-DD;

d. ring A is one of formulas II-A, II-B, II-C, II-D, II-E, II-H, or II-K;

e. ring A is one of formulas II-A or II-B;

f. ring A is II-A and $Z^1$ is $CR^V$ and $Z^2$ is $CR^W$;

g. ring A is II-A and $Z^1$ is N and $Z^2$ is N;

h. ring A is II-A and $Z^1$ is N and $Z^2$ is $CR^W$;

i. ring A is II-A and $Z^1$ is $CR^V$ and $Z^2$ is N;

j. ring A is an optionally substituted aryl or heteroaryl moiety of formula i, ii, iii or x;

k. ring A is a monocyclic ring system and $R^V$ and $R^W$, when present, are hydrogen or amino; $R^X$ groups, when present, is hydrogen, alkyl- or dialkylamino, acetamido, or a $C_{1-4}$ aliphatic group such as methyl, ethyl, cyclopropyl, or isopropyl; $R^Y$ groups, when present, is hydrogen, an optionally substituted group selected from hydrogen, $C_{1-6}$ aliphatic, $C_{1-6}$ heteroaliphatic, aryl, or heteroaryl, $-Q_{(n)}N(R^7)_2$, $-Q_{(n)}OR^7$, $-Q_{(n)}SR^7$, $-Q_{(n)}(C=O)O(R^7)$, $-Q_{(n)}C(O)N(R^7)_2$, $-Q_{(n)}NHC(O)R^7$, $-Q_{(n)}NHSO_2R^7$, or $-Q_{(n)}SO_2N(R^7)_2$, wherein n is 0 or 1, and wherein Q is preferably $-(C(R'')_2)-$, wherein R'' is hydrogen or $C_{1-3}$alkyl, and wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring;

l. ring A is a monocyclic ring system and $R^V$, $R^W$ and $R^X$ groups, when present, are hydrogen or amino; $R^Y$ groups include groups selected from optionally substituted 5–6 membered heteroaryl or heterocyclyl rings, such as 2-pyridyl, 4-pyridyl, pyrrolidinyl, piperidinyl, morpholinyl, or piperazinyl; optionally substituted aryl or cycloalkyl rings such as phenyl, halogen substituted phenyl, alkoxy substituted phenyl, trifluoromethyl substituted phenyl, nitro substituted phenyl, methyl substituted phenyl; optionally substituted $C_{1-6}$ aliphatic, such as methyl, ethyl, cyclopropyl, cyclopentyl, cyclohexyl, amino substituted cycloalkyl, acetamido substituted cycloalkyl, isopropyl, or t-butyl; alkoxyalkylamino such as methoxyethylamino; alkoxyalkyl such as methoxymethyl or methoxyethyl; aminoalkyl such as aminoethyl, dimethylaminoethyl; alkyl- or dialkylamino such as ethylamino or dimethylamino; alkyl- or dialkylaminoalkoxy such as dimethylaminopropyloxy; alkyl- or dialkylaminoalkoxyalkyl such as dimethylaminoethoxymethyl; and acetamido;

m. ring A system is a bicyclic ring system and the ring formed when $R^x$ and $R^y$ are taken together may be substituted or unsubstituted;

n. ring A system is a bicyclic ring system formed by $R^X$ and $R^Y$ taken together and substituted by one or more occurrences of $R^8$ or $R^9$, wherein each occurrence of $R^8$ is independently $-R^7$, halo, $-O(CH_2)_{2-4}-N(R^7)_2$, $-O(CH_2)_{2-4}-R^7$, $-OR^7$, $-N(R^7)-(CH_2)_{2-4}-N(R^7)_2$, $-N(R^7)-(CH_2)_{2-4}-R^7$, $-C(=O)R^7$, $-CO_2R^7$, $-COCOR^7$, $-NO_2$, $-CN$, $-S(O)R^7$, $-SO_2R^7$, $-SR^7$, $-N(R^7)_2$, $-CON(R^7)_2$, $-SO_2N(R^7)_2$, $-OC(=O)R^7$, $-N(R^7)COR^7$, $-N(R^7)CO_2$ (optionally substituted $C_{1-6}$ aliphatic), $-N(R^7)N(R^7)_2$, $-C=NN(R^7)_2$, $-C=N-OR$, $-NHOR^7$, $-N(R^7)CON(R^7)_2$, $-N(R^7)SO_2N(R^7)_2$, $-N(R^7)SO_2R^7$, or $-OC(=O)N(R^7)_2$, wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring; and each occurrence of $R^9$ is independently hydrogen, $-R'$, $-COR'$, $-CO_2(R')$, $-CON(R')_2$, or $-SO_2R'$, wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring, iv) Y is defined according to one of the following groups:

a. Y is an optionally substituted heteroaryl moiety;

b. Y is selected from one of the heteroaryl moieties a–y;
c. Y is selected from one of the following heteroaryl moieties:

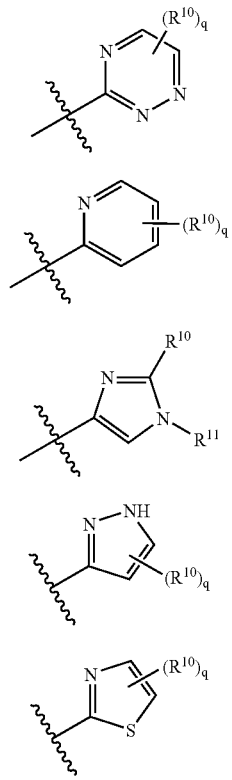

wherein q is 0–4, $R^{10}$ is —R, wherein —R is defined generally above and in classes and subclasses herein, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

d. Y is a pyrazole moiety, h;
e. Y is one of a, b, f, h or o, optionally substituted with one or more $R^{10}$ groups, wherein each occurrence of $R^{10}$ is independently hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl;
f. Y is one of a, b, f, h or o, optionally substituted with one or more $R^{10}$ groups, wherein each occurrence of $R^{10}$ is independently hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl).
g. Y is a pyrazole moiety, h', wherein the pyrazole is substituted with two occurrences of $R^{10}$ ($R^{10a}$ and $R^{10b}$ as depicted),

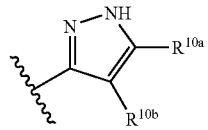

wherein each occurrence of $R^{10a}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl, and $R^{10b}$ is hydrogen;
h. Y is a pyrazole moiety, h', wherein the pyrazole is substituted with two occurrences of $R^{10}$ ($R^{10a}$ and $R^{10b}$ as depicted),

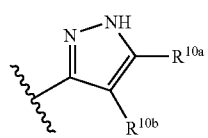

wherein each occurrence of $R^{10a}$ is hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl, and $R^{10b}$ is hydrogen;
i. Y is heteroaryl moiety substituted by at least two occurrences of $R^{10}$ and where two occurrences of $R^{10}$ taken together may represent an optionally substituted group selected from cycloaliphatic, cycloheteroaliphatic, aryl or heteroaryl;
j. Y represents one of the following heteroaryl moieties:

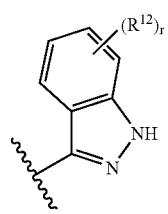

-continued

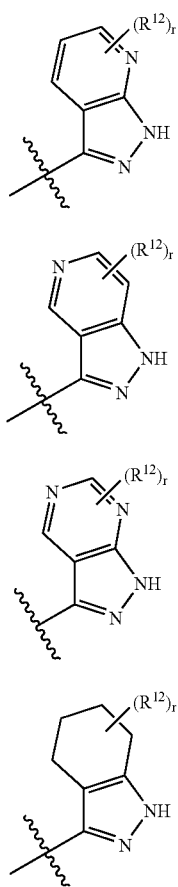

wherein r is 0–4 and $R^{12}$ is hydrogen, -halo, —N($R^7$)$_2$, —C$_{1-3}$ alkyl, —C$_{1-3}$ haloalkyl, —NO$_2$, —O(C$_{1-3}$ alkyl), —CO$_2$(C$_{1-3}$ alkyl), —CN, —SO$_2$(C$_{1-3}$ alkyl), —SO$_2$NH$_2$— OC(O)NH$_2$, —NH$_2$SO$_2$(C$_{1-3}$ alkyl), —NHC(O)(C$_{1-3}$ alkyl), —C(O)NH$_2$, and —CO(C$_{1-3}$ alkyl), wherein the (C$_{1-3}$ alkyl) is most preferably methyl;

v) for compounds of formula IIa(i), $R^4$ is defined according to one of the following groups:
  a. $R^4$ is hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl, or
  b. $R^4$ is hydrogen, methyl, ethyl, cyclopropyl, hydroxy, phenyl or —CH$_2$NH$_2$;

vi) for compounds of formula IIb(i), $R^3$ is defined according to one of the following groups:
  a. $R^3$ is hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl, or
  b. $R^3$ is hydrogen, methyl, ethyl, cyclopropyl, hydroxy, phenyl or —CH$_2$NH$_2$; and vii) $R^5$ is defined according to one of the following groups:
  a. hydrogen, halogen, —NO$_2$, —CN, hydroxy, optionally substituted C$_{1-3}$alkyl, optionally substituted alkoxy, —SO$_2$NH$_2$, or —C(O)alkyl, or
  b. $R^5$ is hydrogen, Cl, CF$_3$, OCF$_3$, CH$_3$, —CN, —SO$_x$NH$_2$ or —C(O)Me.

In certain preferred embodiments, compounds of the invention include those compounds having general formula IIa(i) wherein the compounds have one or more of the following features:
  a. Z is NR$^6$, wherein R$^1$ and R$^2$ are each independently hydrogen or a protecting group and R$^4$, R$^5$ and R$^6$ are each hydrogen,
  b. ring A comprises the general formula II-A; and
  c. Y is an optionally substituted heteroaryl moiety selected from one of formulas a–y.

In most preferred embodiments, for compounds described directly above, ring A is selected from one of the following:
  a. an optionally substituted monocyclic aryl or heteroaryl moiety of formula i, ii, iii or x; wherein $R^V$, $R^W$, $R^X$ and $R^Y$ are each independently —R; wherein preferred $R^V$ and $R^W$ groups, when present, are hydrogen or amino; preferred $R^X$ groups, when present, include hydrogen, alkyl- or dialkylamino, acetamido, or a C$_{1-4}$ aliphatic group such as methyl, ethyl, cyclopropyl, or isopropyl; preferred $R^Y$ groups, when present, include hydrogen, an optionally substituted group selected from C$_{1-6}$ aliphatic, C$_{1-6}$ heteroaliphatic, aryl, or heteroaryl, —Q$_{(n)}$N(R$^7$)$_2$, —Q$_{(n)}$OR$^7$, —Q$_{(n)}$SR$^7$, —Q$_{(n)}$(C=O)O(R$^7$), —Q$_{(n)}$C(O)N(R$^7$)$_2$, —Q$_{(n)}$NHC(O)R$^7$, —Q$_{(n)}$NHSO$_2$R$^7$, or —Q$_{(n)}$SO$_2$N(R$^7$)$_2$, wherein n is 0 or 1, and wherein Q is preferably —C(R")$_2$)—, wherein R" is hydrogen or C$_{1-3}$alkyl, and wherein each occurrence of R$^7$ is independently hydrogen, an optionally substituted group selected from aliphatic, heteroaliphatic, aryl or heteroaryl, or two occurrences of R$^7$ on the same nitrogen atom are taken together with the nitrogen atom to form an optionally substituted group selected from a 5–8 membered heterocyclic or 5–8 membered heteroaryl ring; or
  b. a bicyclic aryl or heteroaryl moiety of formula i, ii, iii or x optionally substituted by one or more occurrences of R$^8$ or R$^9$, wherein R$^8$ substituents include —R$^7$, halo, —O(CH$_2$)$_{2-4}$—N(R$^7$)$_2$, —O(CH$_2$)$_{2-4}$—R$^7$, —OR$^7$, —N(R$^7$)—(CH$_2$)$_{2-4}$—N(R$^7$)$_2$, —N(R$^7$)—(CH$_2$)$_{2-4}$—R$^7$, —C(=O)R$^7$, —CO$_2$R$^7$, —COCOR$^7$, —NO$_2$, —CN, —S(O)R$^7$, —SO$_2$R$^7$, —SR$^7$, —N(R$^7$)$_2$, —CON(R$^7$)$_2$, —SO$_2$N(R$^7$)$_2$, —OC(=O)R$^7$, —N(R$^7$)COR$^7$, —N(R$^7$)CO$_2$(optionally substituted C$_{1-6}$ aliphatic), —N(R$^7$)N(R$^7$)$_2$, —C=NN(R$^7$)$_2$, —C=N—OR, —NHOR$^7$, —N(R$^7$)CON(R$^7$)$_2$, —N(R$^7$)SO$_2$N(R$^7$)$_2$, —N(R$^7$)SO$_2$R$^7$, or —OC(=O)N(R$^7$)$_2$, wherein each occurrence of R$^7$ is independently hydrogen, an optionally substituted aliphatic, heteroaliphatic, aryl or heteroaryl, or two occurrences of R$^7$ on the same nitrogen atom are taken together with the nitrogen atom to form an optionally substituted group selected from a 5–8 membered heterocyclic or heteroaryl ring; and Y is selected from one of the following heteroaryl moieties:

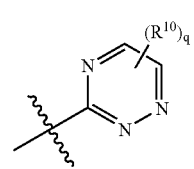

a

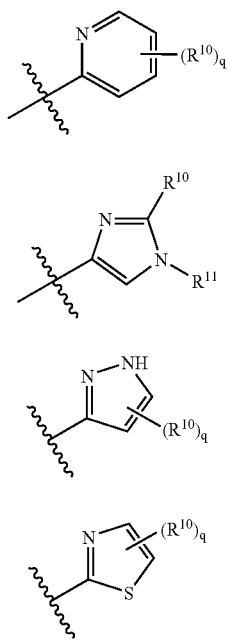

wherein q is 0–4, $R^{10}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, or (N-heterocycle)carbonyl, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

Additional preferred embodiments for the compounds described directly above include those preferred subsets for ring A and Y as exemplified in subclasses and species herein.

Representative examples of compounds of formula IIa(i) or IIb(i) (described generally as II(i) below but encompassing compounds of both formulas IIa(i) and IIb(i)), are depicted below in Table 1.

TABLE I

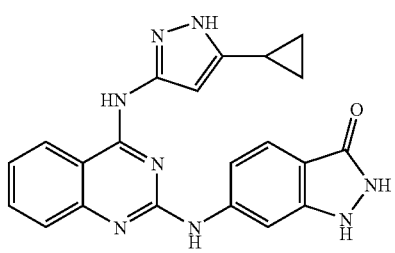

II-(i)-1

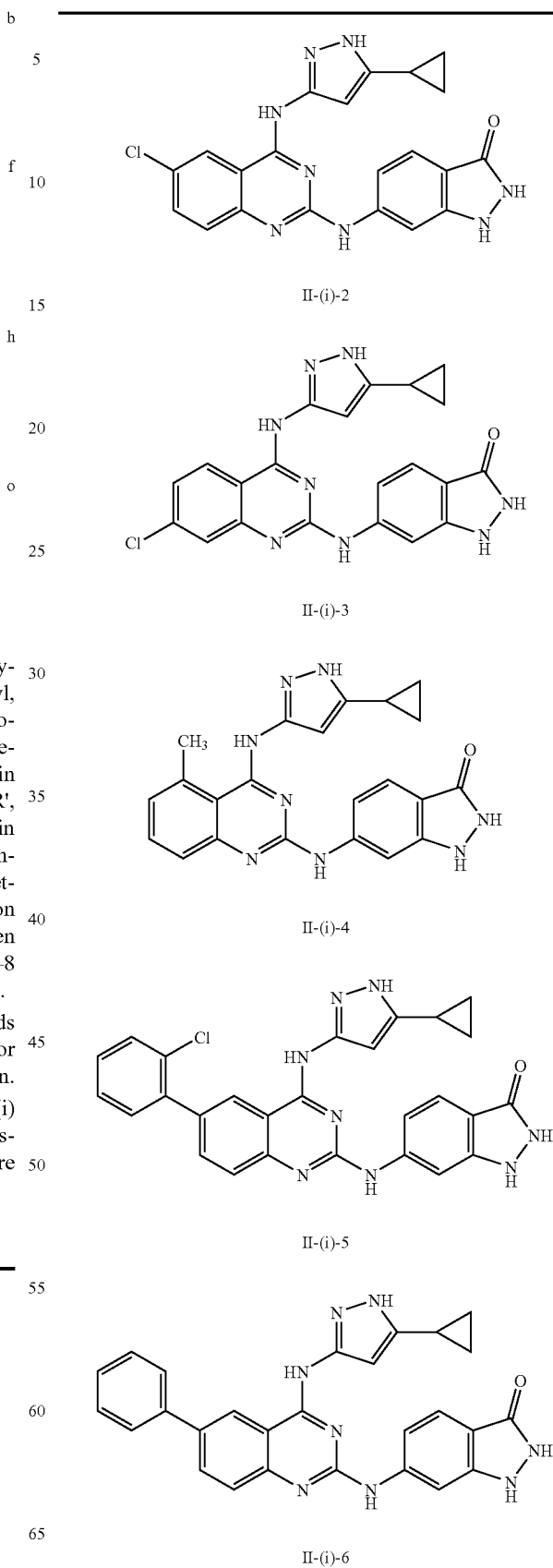

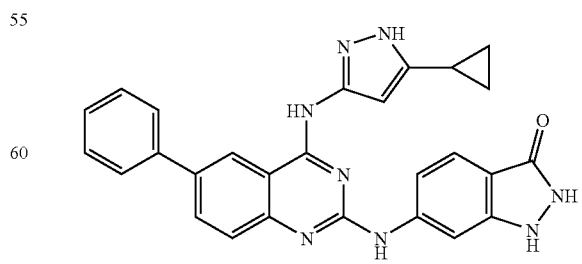

II-(i)-6

TABLE I-continued
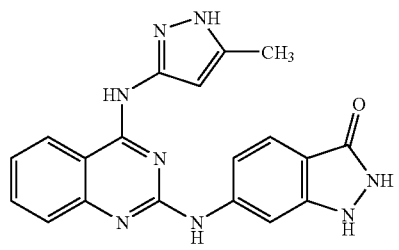
II-(i)-7
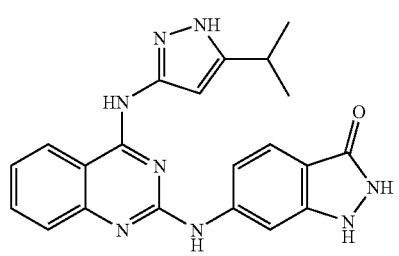
II-(i)-8
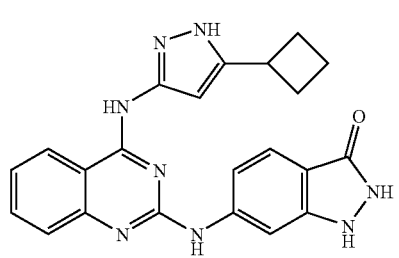
II-(i)-9
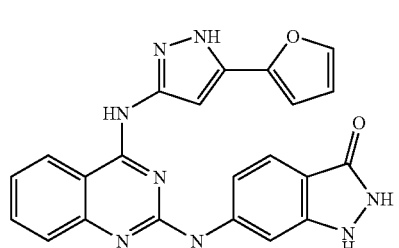
II-(i)-10
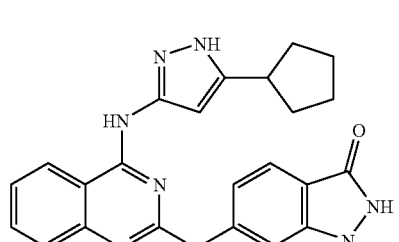
II-(i)-11
TABLE I-continued
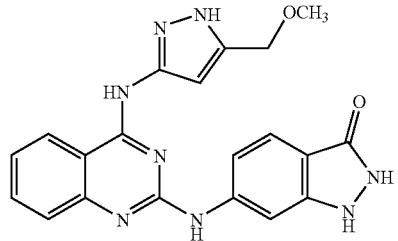
II-(i)-12
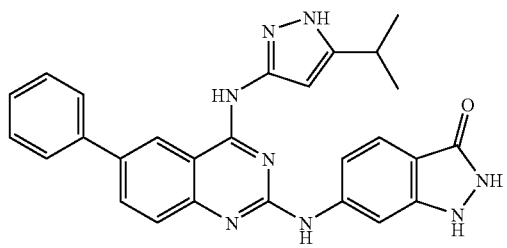
II-(i)-13
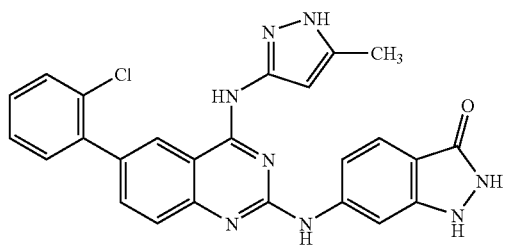
II-(i)-14
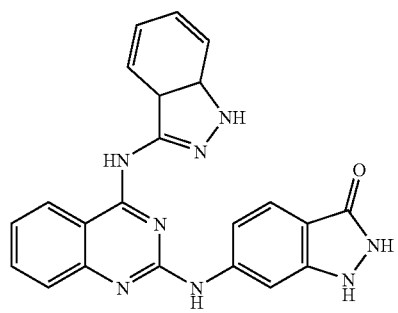
II-(i)-15
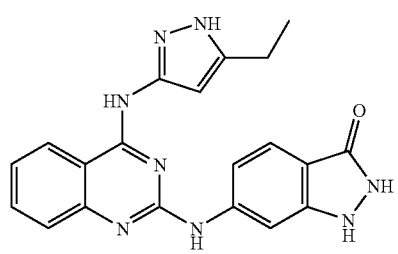
II-(i)-16

TABLE I-continued
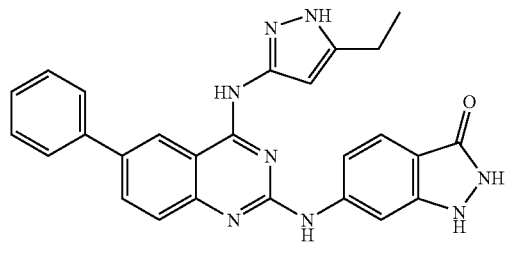
II-(i)-17
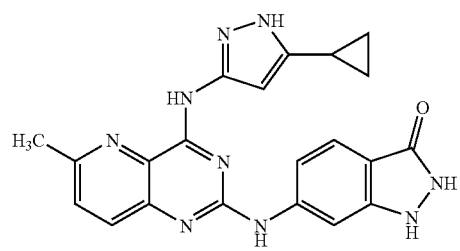
II-(i)-18
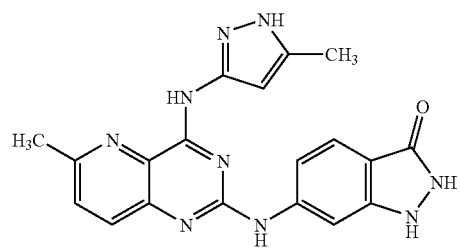
II-(i)-20
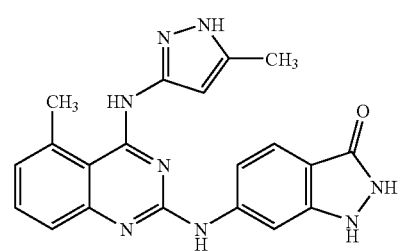
II-(i)-21
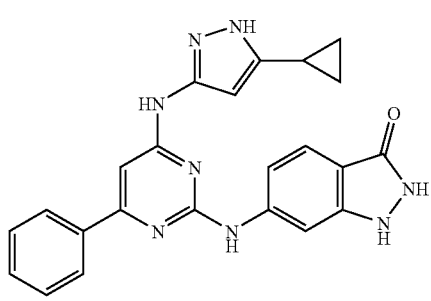
II-(i)-22
TABLE I-continued
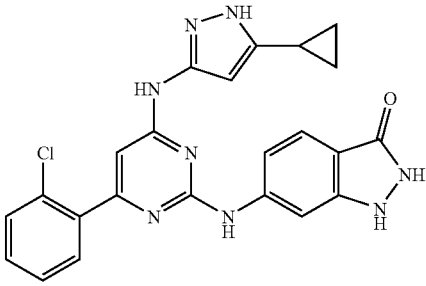
II-(i)-23
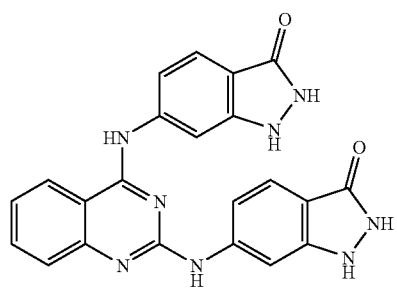
II-(i)-24
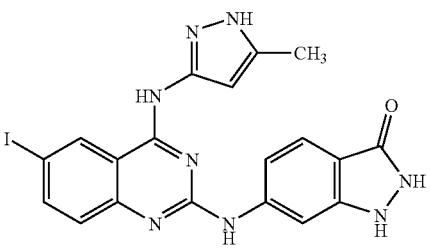
II-(i)-25
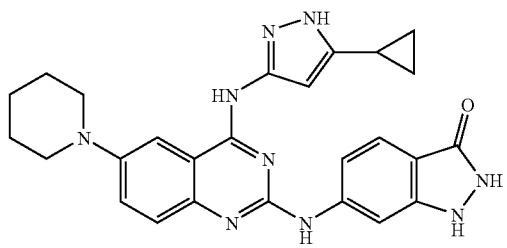
II-(i)-26
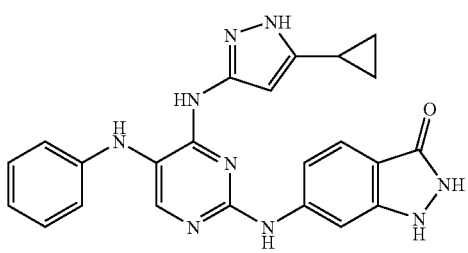
II-(i)-27

TABLE I-continued
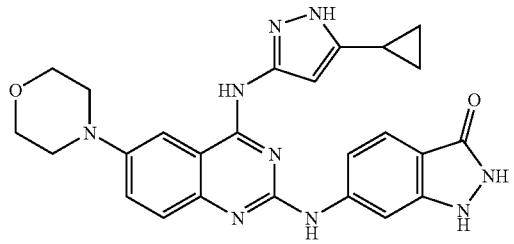
II-(i)-28
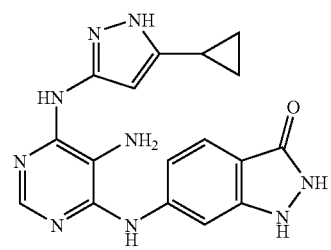
II-(i)-29
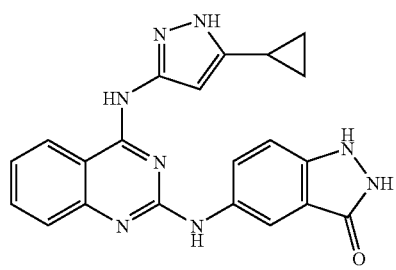
II-(i)-30
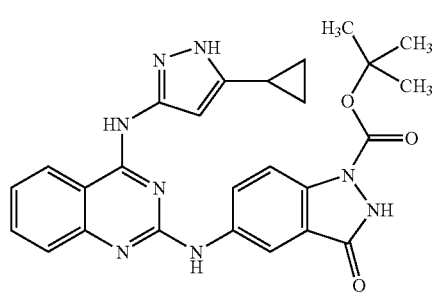
II-(i)-31
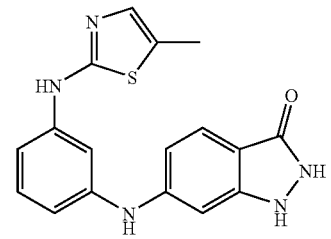
II-(i)-32
TABLE I-continued
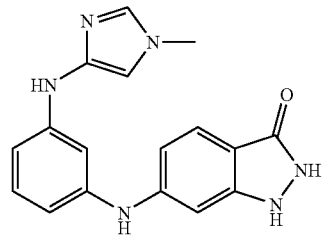
II-(i)-33
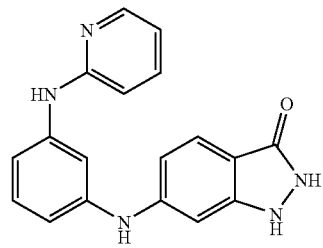
II-(i)-34
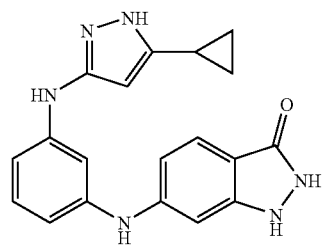
II-(i)-35
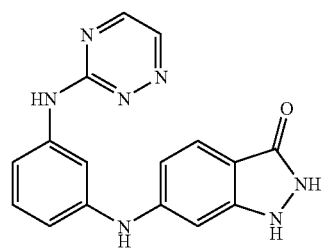
II-(i)-36
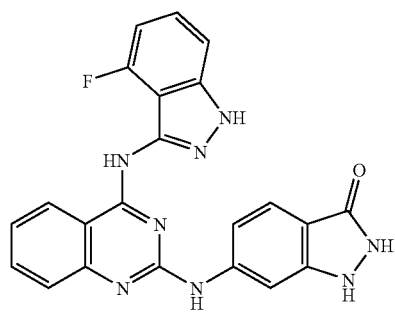
II-(i)-37

TABLE I-continued
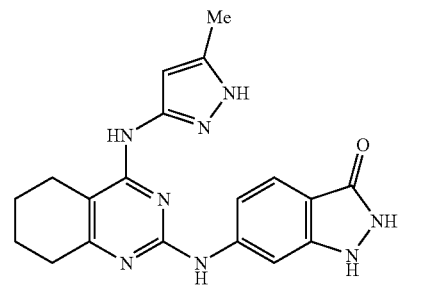
II-(i)-38
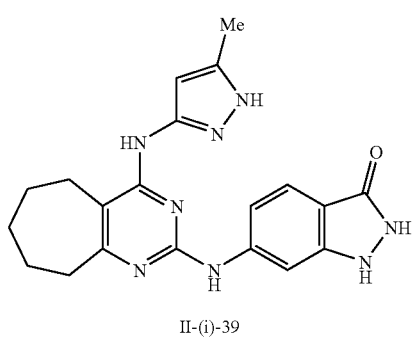
II-(i)-39
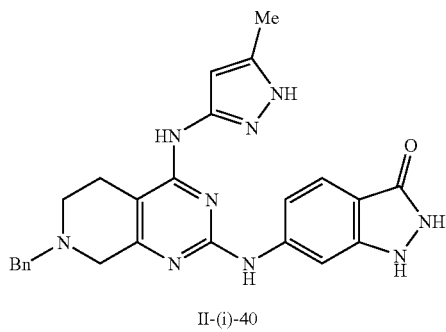
II-(i)-40
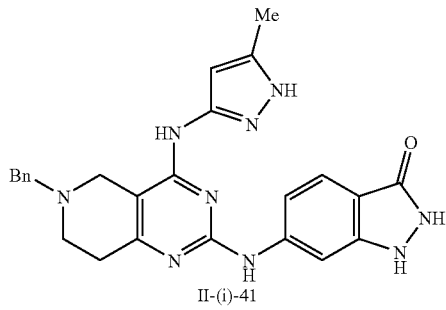
II-(i)-41
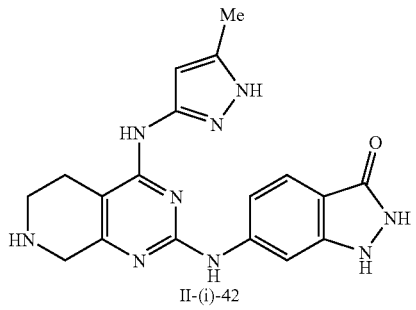
II-(i)-42
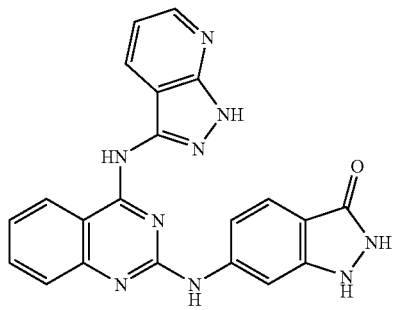
II-(i)-43
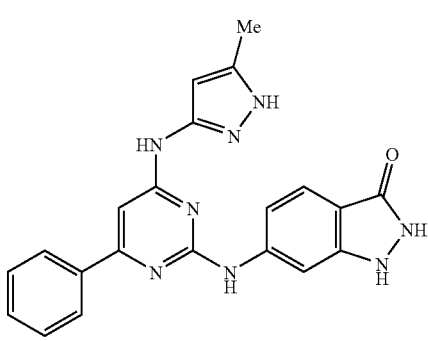
II-(i)-44
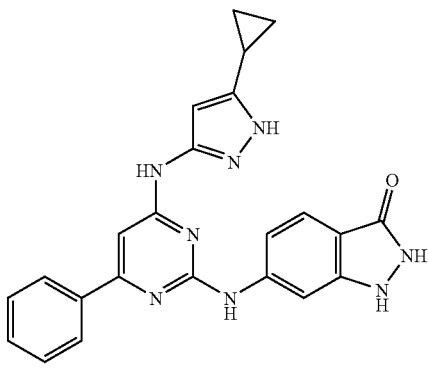
II-(i)-45
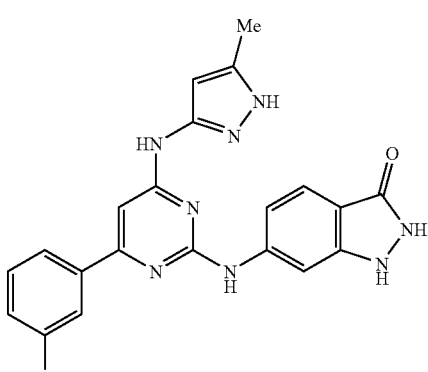
II-(i)-46

TABLE I-continued
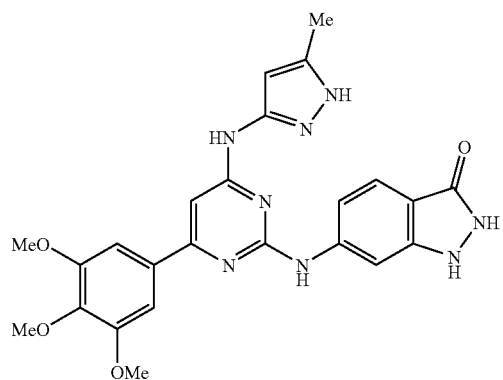
II-(i)-47
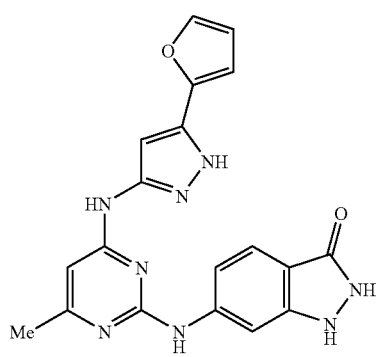
II-(i)-48
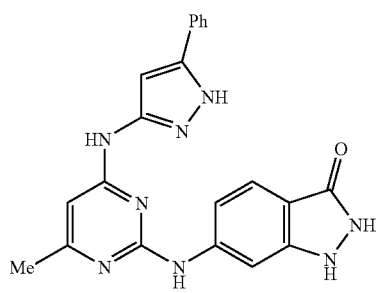
II-(i)-49
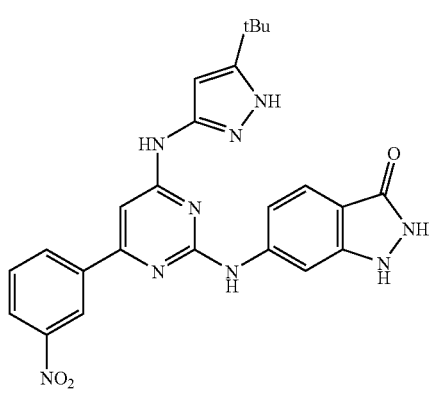
II-(i)-50
TABLE I-continued
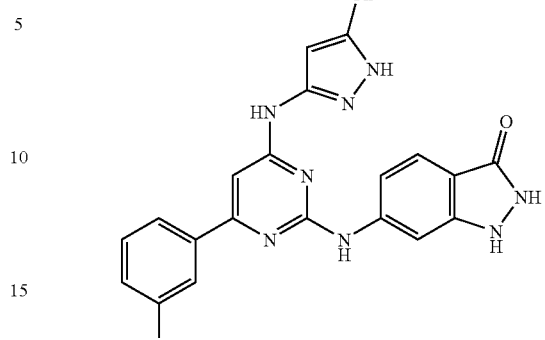
II-(i)-51
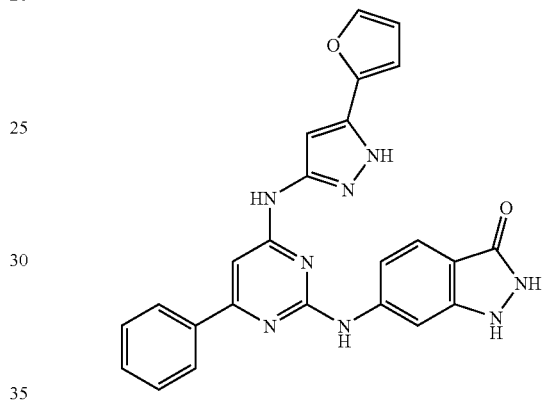
II-(i)-52
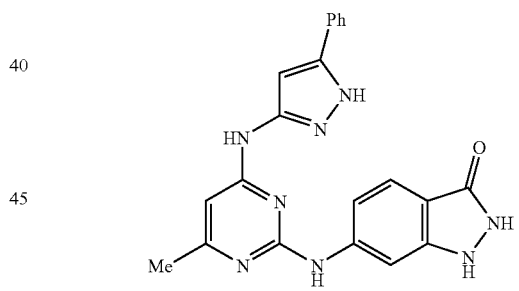
II-(i)-53
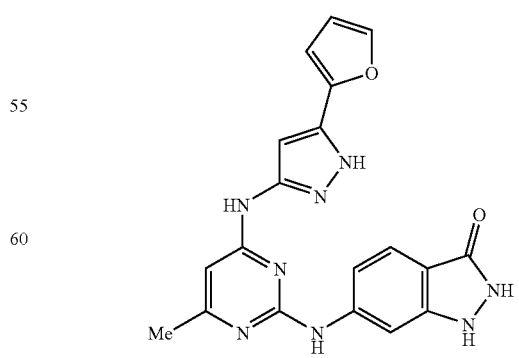
II-(i)-54

TABLE I-continued
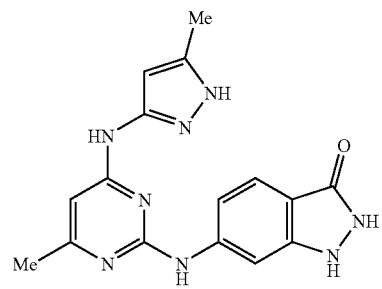
II-(i)-55
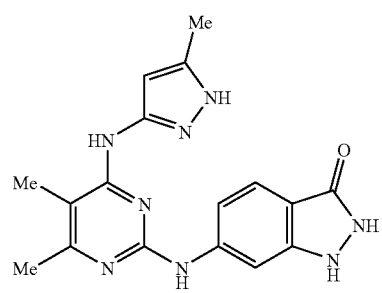
II-(i)-56
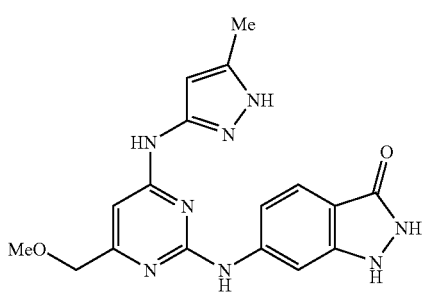
II-(i)-57
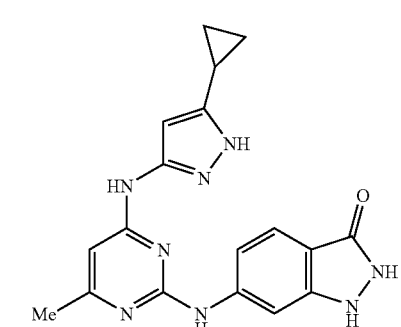
II-(i)-58
TABLE I-continued
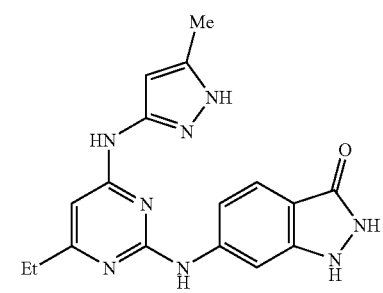
II-(i)-59
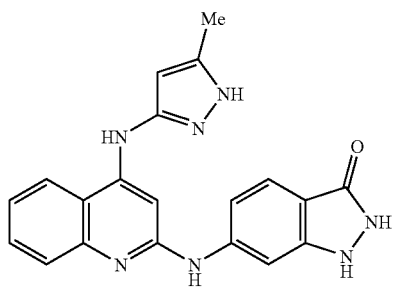
II-(i)-60
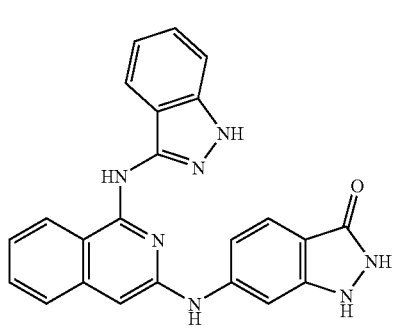
II-(i)-61
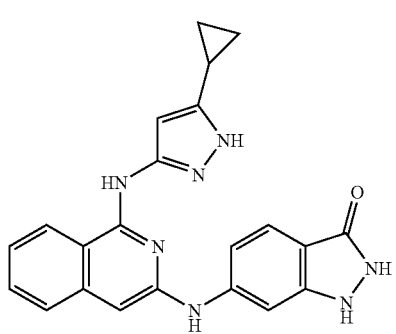
II-(i)-62

TABLE I-continued
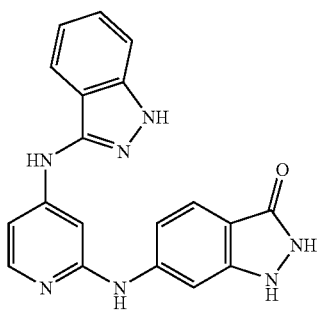
II-(i)-63
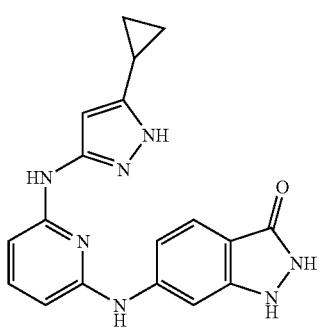
II-(i)-64
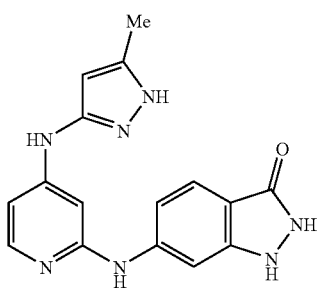
II-(i)-65
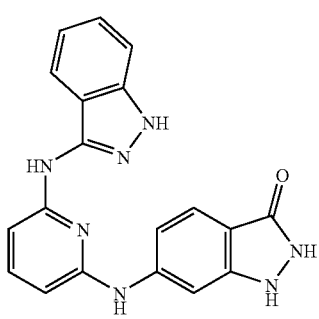
II-(i)-66
TABLE I-continued
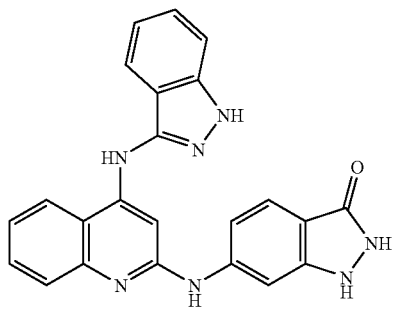
II-(i)-67
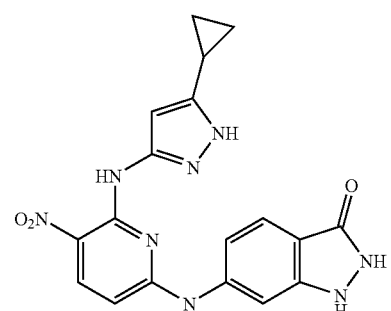
II-(i)-68
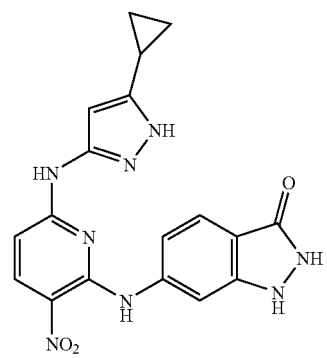
II-(i)-69
In certain embodiments, a preferred subclass of compounds of general formula IIa or IIb include those compounds where $Q^1$ is S, $Q^2$ is NH and Y is an optionally substituted heteroaryl moiety. These compounds are defined by the general formula IIa(ii) or IIb(ii) and are depicted generally below:
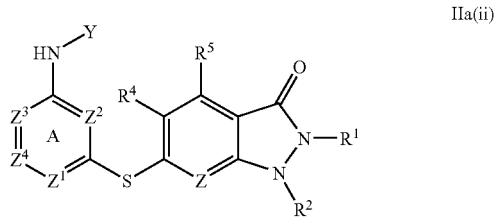
IIa(ii)

-continued

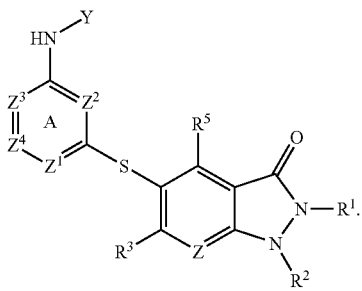

IIb(ii)

It will be appreciated that, for compounds of general formulas IIa(ii) and IIb(ii) certain additional subclasses are of special interest. Certain preferred embodiments of compounds of formula IIa(ii) or IIb(ii) include those compounds having any combination of the following features for each variable for formula IIa(ii) or IIb(ii):

i) Z is $CR^6$ or N;

ii) $R^1$, $R^2$, $R^4$ and $R^5$ are each hydrogen and wherein Z is $CHR^6$ and $R^6$ is hydrogen; or $R^1$, $R^2$, $R^3$ and $R^5$ are each hydrogen and wherein Z is $CHR^6$ and $R^6$ is hydrogen;

iii) ring A is defined according to one of the following groups:
  a. ring A is one of formulas i, ii, iii, iv, v, vi, vii, viii, ix, or x;
  b. ring A is one of formulas II-A, II-B, II-C, II-D, II-E, I-F, II-G, II-H, II-I, II-J, II-K, II-L, II-M, II-N, II-O, II-P, II-Q, II-R, II-S, II-T, II-U, II-V, II-W, II-X, II-Y, II-Z, II-AA, II-BB, II-CC, or II-DD;
  c. ring A is one of formulas II-A, II-B, II-C, II-D, II-E, II-F, II-H, II-I, II-J, II-K, II-L, II-N, II-O, or II-DD;
  d. ring A is one of formulas II-A, II-B, II-C, II-D, II-E, II-H, or II-K;
  e. ring A is one of formulas II-A or II-B;
  f. ring A is II-A and $Z^1$ is $CR^V$ and $Z^2$ is $CR^W$;
  g. ring A is II-A and $Z^1$ is N and $Z^2$ is N;
  h. ring A is II-A and $Z^1$ is N and $Z^2$ is $CR^W$;
  i. ring A is II-A and $Z^1$ is $CR^V$ and $Z^2$ is N;
  j. ring A is an optionally substituted aryl or heteroaryl moiety of formula i, ii, iii or x;
  k. ring A is a monocyclic ring system and $R^V$ and $R^W$, when present, are hydrogen or amino; $R^X$ groups, when present, is hydrogen, alkyl- or dialkylamino, acetamido, or a $C_{1-4}$ aliphatic group such as methyl, ethyl, cyclopropyl, or isopropyl; $R^Y$ groups, when present, is hydrogen, an optionally substituted group selected from hydrogen, $C_{1-6}$ aliphatic, $C_{1-6}$ heteroaliphatic, aryl, or heteroaryl, $—Q_{(n)}N(R^7)_2$, $—Q_{(n)}OR^7$, $—Q_{(n)}SR^7$, $—Q_{(n)}(C=O)O(R^7)$, $—Q_{(n)}C(O)N(R^7)_2$, $—Q_{(n)}NHC(O)R^7$, $—Q_{(n)}NHSO_2R^7$, or $—Q_{(n)}SO_2N(R^7)_2$, wherein n is 0 or 1, and wherein Q is preferably $—(C(R")_2)—$, wherein R" is hydrogen or $C_{1-3}$alkyl, and wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring;
  l. ring A is a monocyclic ring system and $R^V$, $R^W$ and $R^X$ groups, when present, are hydrogen or amino; $R^Y$ groups include groups selected from optionally substituted 5–6 membered heteroaryl or heterocyclyl rings, such as 2-pyridyl, 4-pyridyl, pyrrolidinyl, piperidinyl, morpholinyl, or piperazinyl; optionally substituted aryl or cycloalkyl rings such as phenyl, halogen substituted phenyl, alkoxy substituted phenyl, trifluoromethyl substituted phenyl, nitro substituted phenyl, methyl substituted phenyl; optionally substituted $C_{1-6}$ aliphatic, such as methyl, ethyl, cyclopropyl, cyclopentyl, cyclohexyl, amino substituted cycloalkyl, acetamido substituted cycloalkyl, isopropyl, or t-butyl; alkoxyalkylamino such as methoxyethylamino; alkoxyalkyl such as methoxymethyl or methoxyethyl; aminoalkyl such as aminoethyl, dimethylaminoethyl; alkyl- or dialkylamino such as ethylamino or dimethylamino; alkyl- or dialkylaminoalkoxy such as dimethylaminopropyloxy; alkyl- or dialkylaminoalkoxyalkyl such as dimethylaminoethoxymethyl; and acetamido;
  m. ring A system is a bicyclic ring system and the ring formed when $R^X$ and $R^Y$ are taken together may be substituted or unsubstituted;
  n. ring A system is a bicyclic ring system formed by $R^X$ and $R^Y$ taken together and substituted by one or more occurrences of $R^8$ or $R^9$, wherein each occurrence of $R^8$ is independently $—R^7$, halo, $—O(CH_2)_{2-4}—N(R^7)_2$, $—O(CH_2)_{2-4}—R^7$, $—OR^7$, $—N(R^7)—(CH_2)_{2-4}—N(R^7)_2$, $—N(R^7)—(CH_2)_{2-4}—R^7$, $—C(=O)R^7$, $—CO_2R^7$, $—COCOR^7$, $—NO_2$, $—CN$, $—S(O)R^7$, $—SO_2R^7$, $—SR^7$, $—N(R^7)_2$, $—CON(R^7)_2$, $—SO_2N(R^7)_2$, $—OC(=O)R^7$, $—N(R^7)COR^7$, $—N(R^7)CO_2$ (optionally substituted $C_{1-6}$ aliphatic), $—N(R^7)N(R^7)_2$, $—C=NN(R^7)_2$, $—C=N—OR$, $—NHOR^7$, $—N(R^7)CON(R^7)_2$, $—N(R^7)SO_2N(R^7)_2$, $—N(R^7)SO_2R^7$, or $—OC(=O)N(R^7)_2$, wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring; and each occurrence of $R^9$ is independently hydrogen, $—R'$, $—COR'$, $—CO_2(R')$, $—CON(R')_2$, or $—SO_2R'$, wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring, iv) Y is defined according to one of the following groups:
  a. Y is an optionally substituted heteroaryl moiety;
  b. Y is selected from one of the heteroaryl moieties a–y;
  c. Y is selected from one of the following heteroaryl moieties:

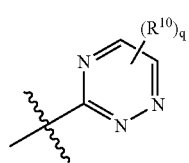

a

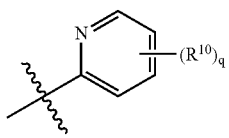
b

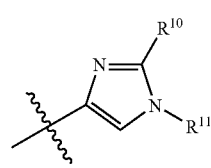
f

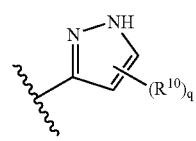
h

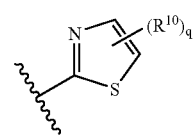
o wherein q is 0–4, $R^{10}$ is —R, wherein —R is defined generally above and in classes and subclasses herein, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

d. Y is a pyrazole moiety, h;

e. Y is one of a, b, f, h or o, optionally substituted with one or more $R^{10}$ groups, wherein each occurrence of $R^{10}$ is independently hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl;

f. Y is one of a, b, f, h or o, optionally substituted with one or more $R^{10}$ groups, wherein each occurrence of $R^{10}$ is independently hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH═CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl).

g. Y is a pyrazole moiety, h', wherein the pyrazole is substituted with two occurrences of $R^{10}$ ($R^{10a}$ and $R^{10b}$ as depicted),

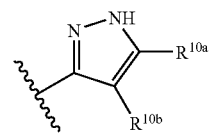
h' wherein each occurrence of $R^{10a}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl, and $R^{10b}$ is hydrogen;

h. Y is a pyrazole moiety, h', wherein the pyrazole is substituted with two occurrences of $R^{10}$ ($R^{10a}$ and $R^{10b}$ as depicted),

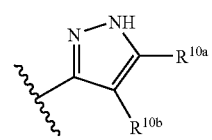
h' wherein each occurrence of $R^{10a}$ is hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH═CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl, and $R^{10b}$ is hydrogen;

i. Y is heteroaryl moiety substituted by at least two occurrences of $R^{10}$ and where two occurrences of $R^{10}$ taken together may represent an optionally substituted group selected from cycloaliphatic, cycloheteroaliphatic, aryl or heteroaryl;

j. Y represents one of the following heteroaryl moieties:

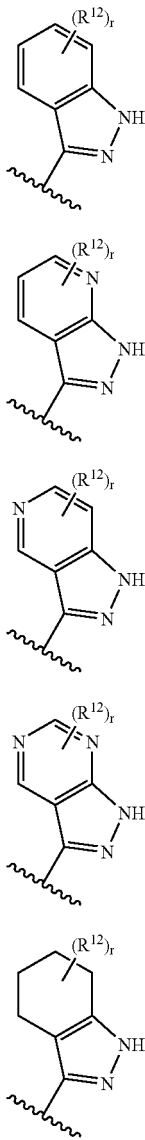

wherein r is 0–4 and $R^{12}$ is hydrogen, -halo, $-N(R^7)_2$, $-C_{1-3}$ alkyl, $-C_{1-3}$ haloalkyl, $-NO_2$, $-O(C_{1-3}$ alkyl), $-CO_2(C_{1-3}$ alkyl), $-CN$, $-SO_2(C_{1-3}$ alkyl), $-SO_2NH_2$, $-OC(O)NH_2$, $-NH_2SO_2(C_{1-3}$ alkyl), $-NHC(O)(C_{1-3}$ alkyl), $-C(O)NH_2$, and $-CO(C_{1-3}$ alkyl), wherein the $(C_{1-3}$ alkyl) is most preferably methyl;

v) for compounds of formula IIa(ii), $R^4$ is defined according to one of the following groups:
  a. $R^4$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
  b. $R^4$ is hydrogen, methyl, ethyl, cyclopropyl, hydroxy, phenyl or $-CH_2NH_2$;

vi) for compounds of formula IIb(ii), $R^3$ is defined according to one of the following groups:
  a. $R^3$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
  b. $R^3$ is hydrogen, methyl, ethyl, cyclopropyl, hydroxy, phenyl or $-CH_2NH_2$; and vii) $R^5$ is defined according to one of the following groups:
  a. hydrogen, halogen, $-NO_2$, $-CN$, hydroxy, optionally substituted $C_{1-3}$alkyl, optionally substituted alkoxy, $-SO_2NH_2$, or $-C(O)$alkyl, or
  b. $R^5$ is hydrogen, Cl, $CF_3$, $OCF_3$, $CH_3$, $-CN$, $-SO_2NH_2$ or $-C(O)Me$.

In certain preferred embodiments, compounds of the invention include those compounds having general formula IIa(ii) wherein the compounds have one or more of the following features:
  a. Z is $NR^6$, wherein $R^1$ and $R^2$ are each independently hydrogen or a protecting group and $R^4$, $R^5$ and $R^6$ are each hydrogen,
  b. ring A comprises the general formula II-A; and
  c. Y is an optionally substituted heteroaryl moiety selected from one of formulas a–y.

In most preferred embodiments, for compounds described directly above, ring A is selected from one of the following:
  a. an optionally substituted monocyclic aryl or heteroaryl moiety of formula i, ii, iii or x; wherein $R^V$, $R^W$, $R^X$ and $R^Y$ are each independently $-R$; wherein preferred $R^V$ and $R^W$ groups, when present, are hydrogen or amino; preferred $R^X$ groups, when present, include hydrogen, alkyl- or dialkylamino, acetamido, or a $C_{1-4}$ aliphatic group such as methyl, ethyl, cyclopropyl, or isopropyl; preferred $R^Y$ groups, when present, include hydrogen, an optionally substituted group selected from $C_{1-6}$ aliphatic, $C_{1-6}$ heteroaliphatic, aryl, or heteroaryl, $-Q_{(n)}N(R^7)_2$, $-Q_{(n)}OR^7$, $-Q_{(n)}SR^7$, $-Q_{(n)}(C=O)O(R^7)$, $-Q_{(n)}C(O)N(R^7)_2$, $-Q_{(n)}NHC(O)R^7$, $-Q_{(n)}NHSO_2R^7$, or $-Q_{(n)}SO_2N(R^7)_2$, wherein n is 0 or 1, and wherein Q is preferably $-(C(R")_2)-$, wherein R" is hydrogen or $C_{1-3}$alkyl, and wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring; or
  b. a bicyclic aryl or heteroaryl moiety of formula i, ii, iii or x optionally substituted by one or more occurrences of $R^8$ or $R^9$, wherein $R^8$ substituents include $-R^7$, halo, $-O(CH_2)_{2-4}-N(R^7)_2$, $-O(CH_2)_{2-4}-R^7$, $-OR^7$, $-N(R^7)-(CH_2)_{2-4}-N(R^7)_2$, $-N(R^7)-(CH_2)_{2-4}-R^7$, $-C(=O)R^7$, $-CO_2R^7$, $-COCOR^7$, $-NO_2$, $-CN$, $-S(O)R^7$, $-SO_2R^7$, $-SR^7$, $-N(R^7)_2$, $-CON(R^7)_2$, $-SO_2N(R^7)_2$, $-OC(=O)R^7$, $-N(R^7)COR^7$, $-N(R^7)CO_2$(optionally substituted $C_{1-6}$ aliphatic), $-N(R^7)N(R^7)_2$, $-C=NN(R^7)_2$, $-C=N-OR$, $-NHOR^7$, $-N(R^7)CON(R^7)_2$, $-N(R^7)SO_2N(R^7)_2$, $-N(R^7)SO_2R^7$, or $-OC(=O)N(R^7)_2$, wherein each occurrence of $R^7$ is independently hydrogen, an optionally substituted aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or heteroaryl ring; and Y is selected from one of the following heteroaryl moieties:

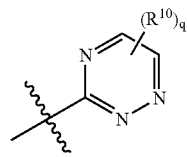
a

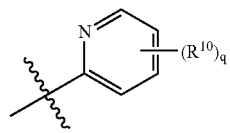
b

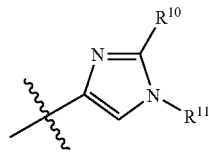
f

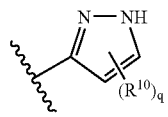
h

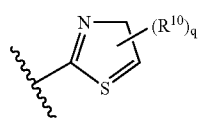
o wherein q is 0–4, $R^{10}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, or (N-heterocycle)carbonyl, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

Additional preferred embodiments for the compounds described directly above include those preferred subsets for ring A and Y as exemplified in subclasses and species herein.

Representative examples of compounds of formula IIa(ii) or IIb(ii) (described generally as II(ii) below but encompassing compounds of both formulas IIa(ii) and IIb(ii)), are depicted below in Table 2.

TABLE 2

II-(ii)-1

II-(ii)-2

II-(ii)-3

II-(ii)-4

TABLE 2-continued
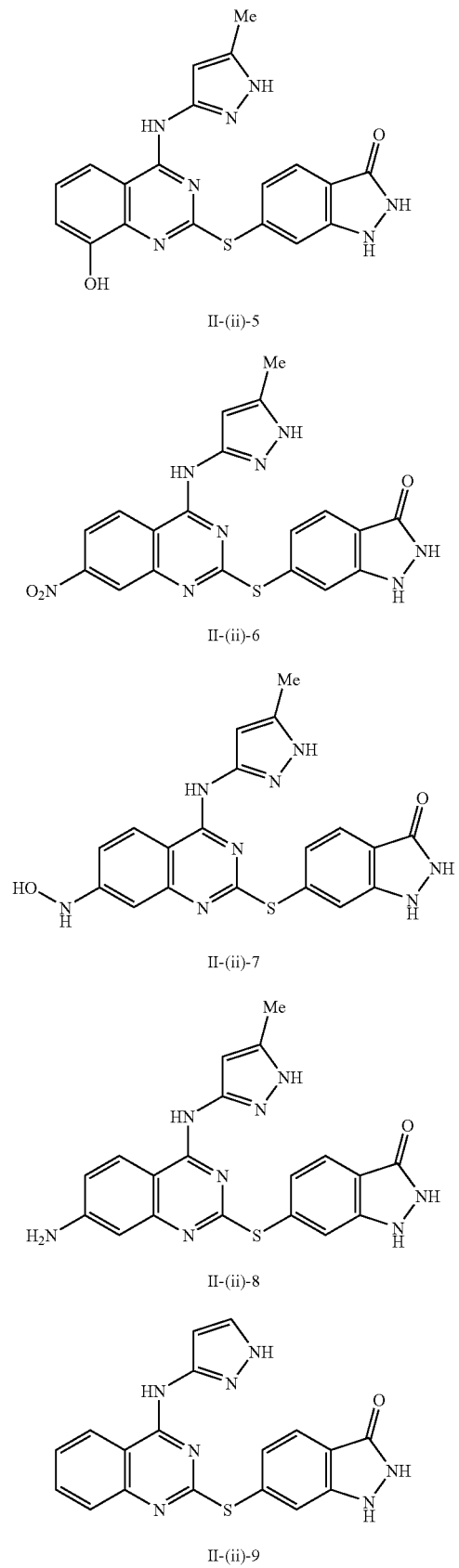
II-(ii)-5
II-(ii)-6
II-(ii)-7
II-(ii)-8
II-(ii)-9
TABLE 2-continued
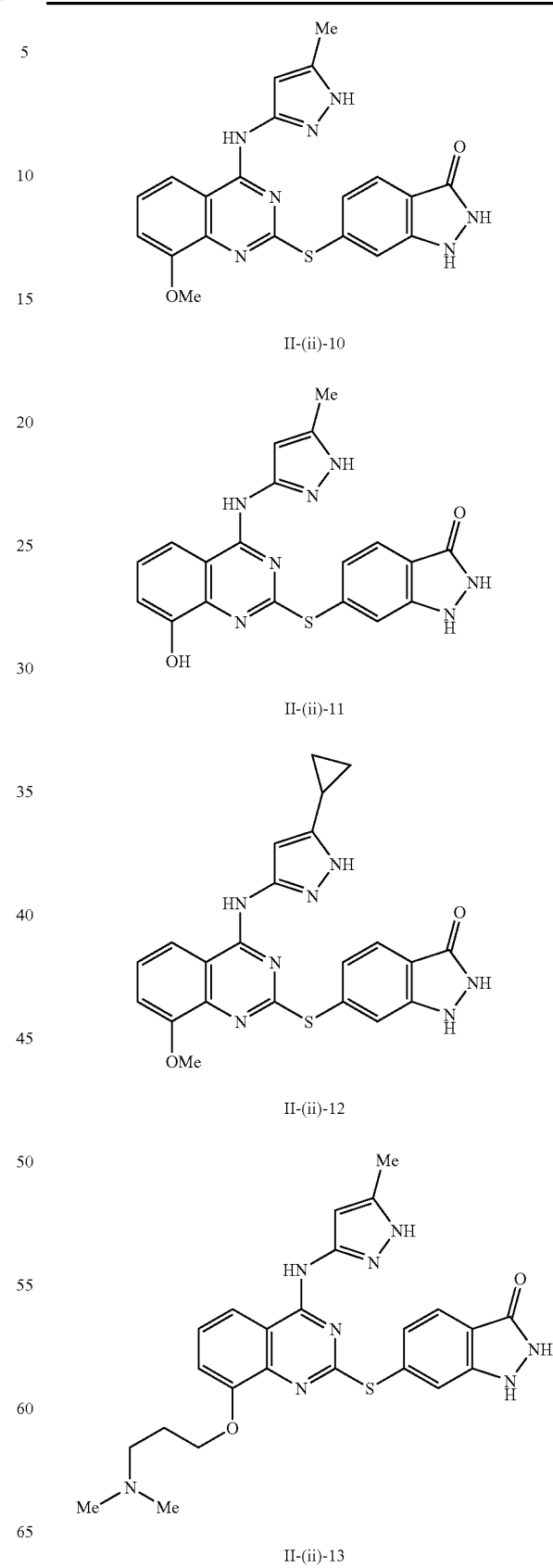
II-(ii)-10
II-(ii)-11
II-(ii)-12
II-(ii)-13

TABLE 2-continued
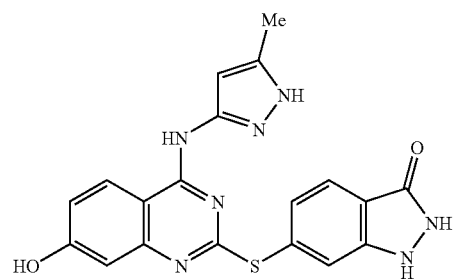
II-(ii)-14
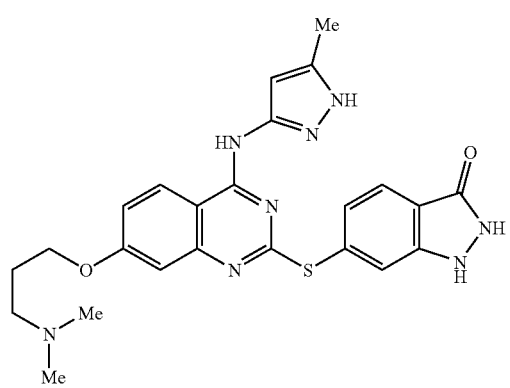
II-(ii)-15
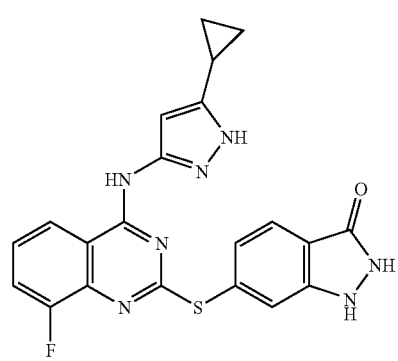
II-(ii)-16
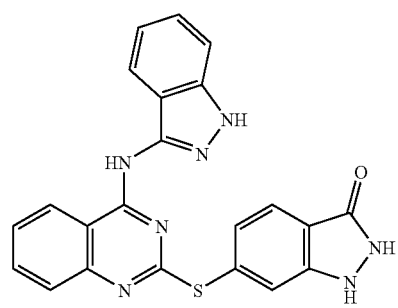
II-(ii)-17
TABLE 2-continued
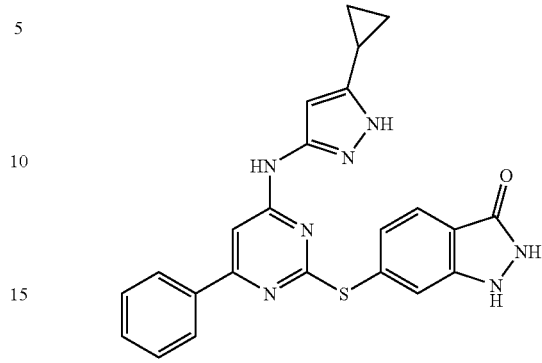
II-(ii)-18
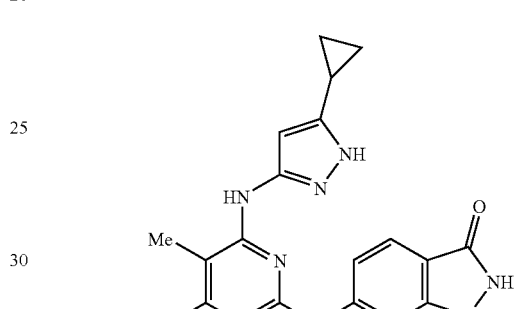
II-(ii)-19
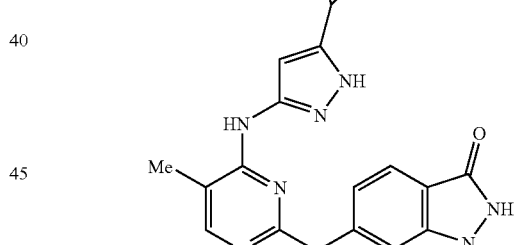
II-(ii)-20
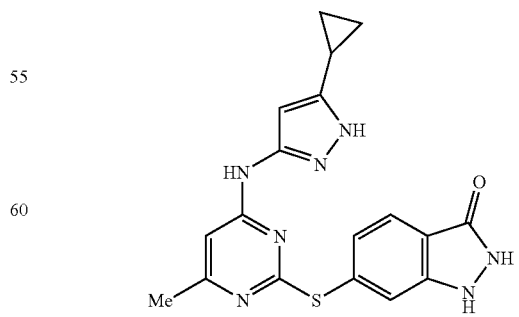
II-(ii)-21

TABLE 2-continued
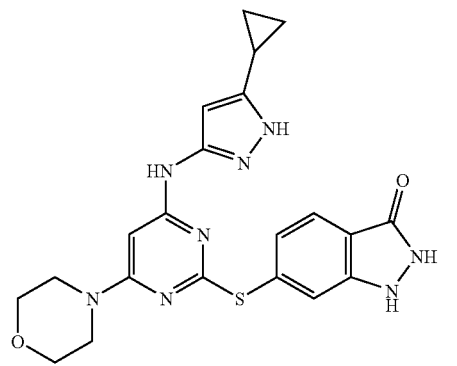
II-(ii)-22
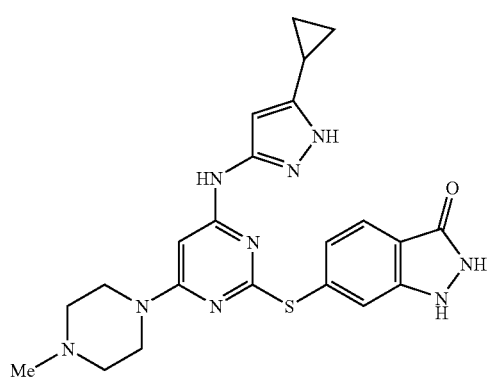
II-(ii)-23
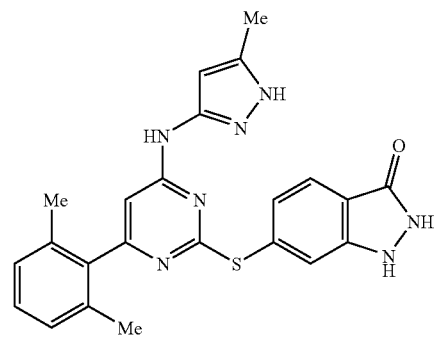
II-(ii)-24
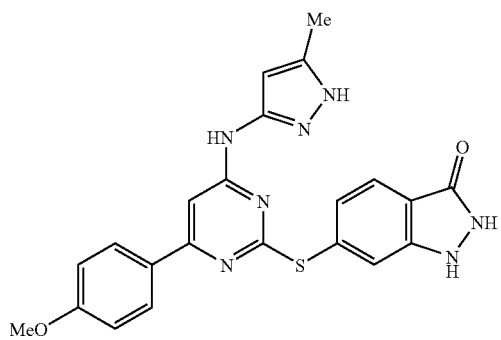
II-(ii)-25
TABLE 2-continued
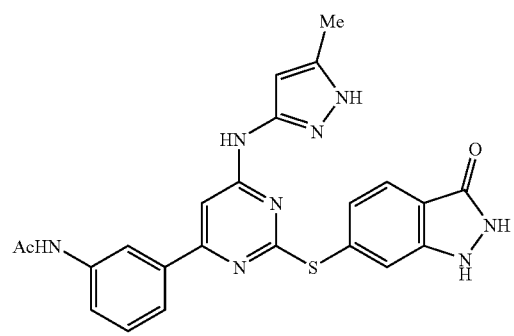
II-(ii)-26
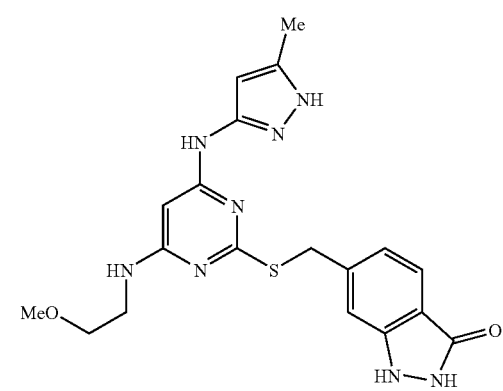
II-(ii)-27
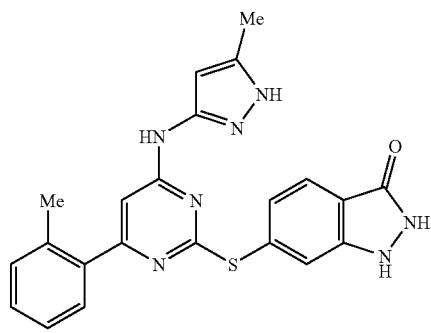
II-(ii)-28
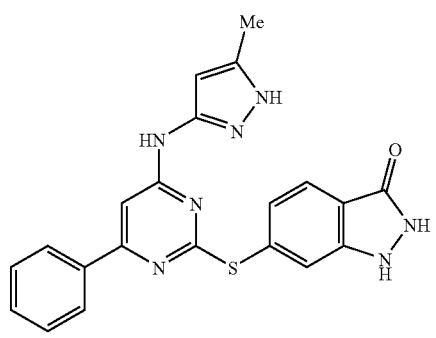
II-(ii)-29

TABLE 2-continued
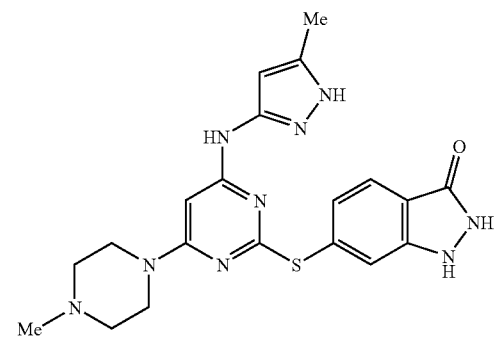
II-(ii)-30
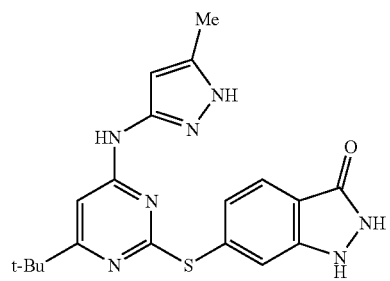
II-(ii)-31
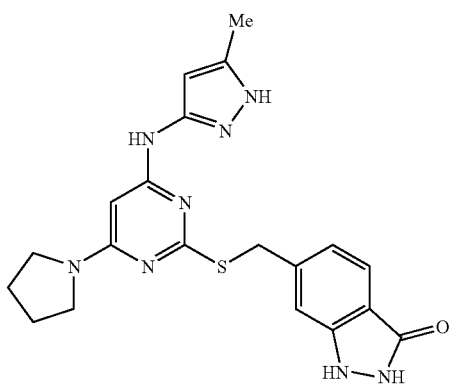
II-(ii)-32
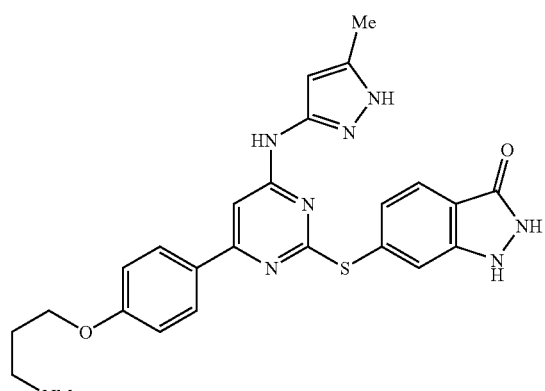
II-(ii)-33
TABLE 2-continued
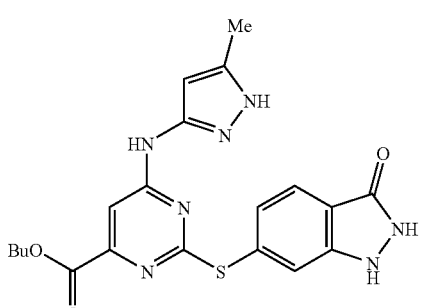
II-(ii)-34
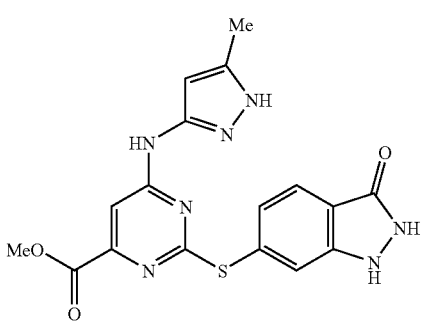
II-(ii)-35
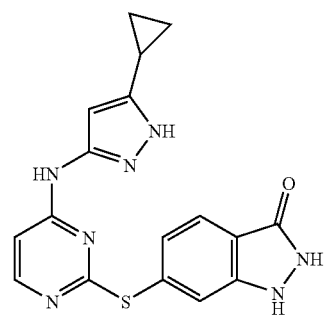
II-(ii)-36
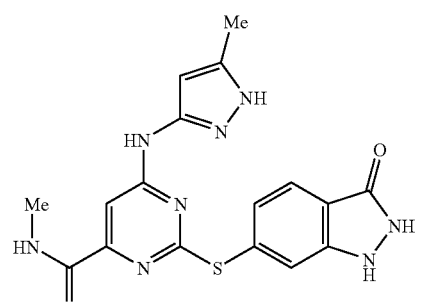
II-(ii)-37

TABLE 2-continued
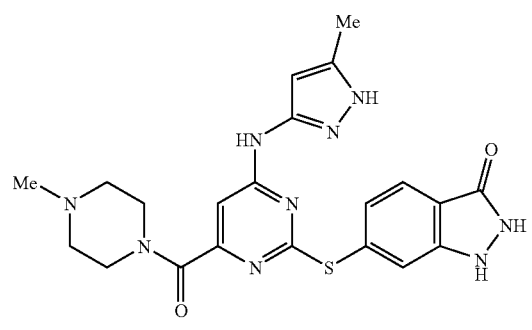
II-(ii)-38
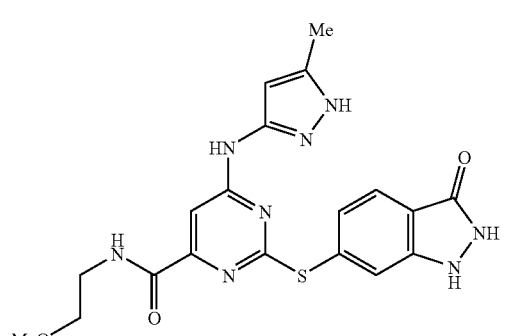
II-(ii)-39
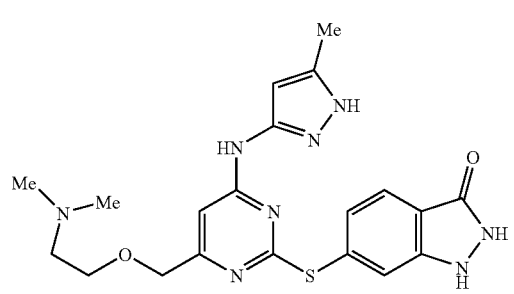
II-(ii)-40
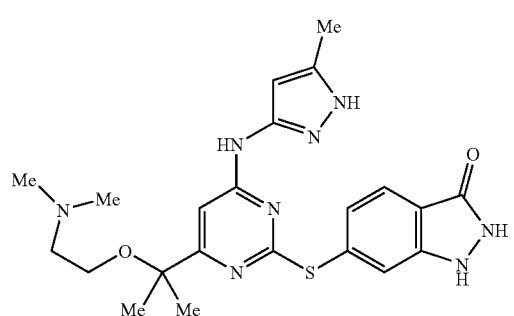
II-(ii)-41
TABLE 2-continued
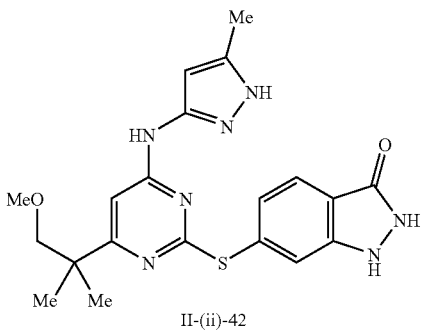
II-(ii)-42
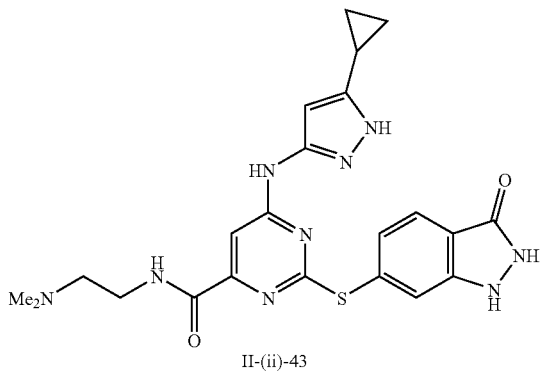
II-(ii)-43
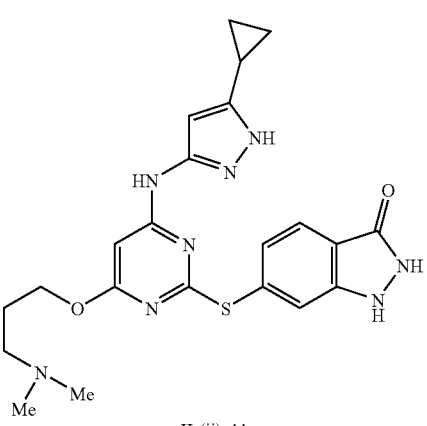
II-(ii)-44
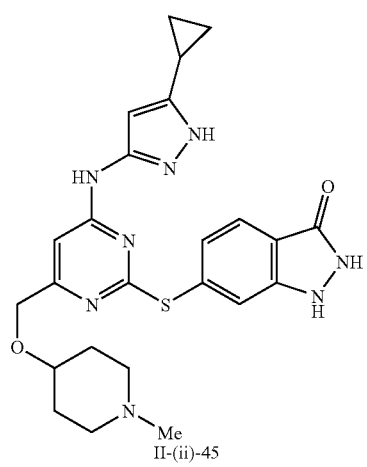
II-(ii)-45

TABLE 2-continued
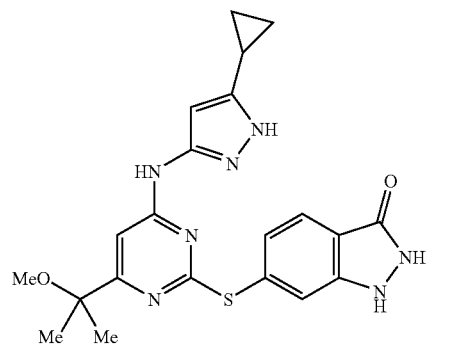
II-(ii)-46
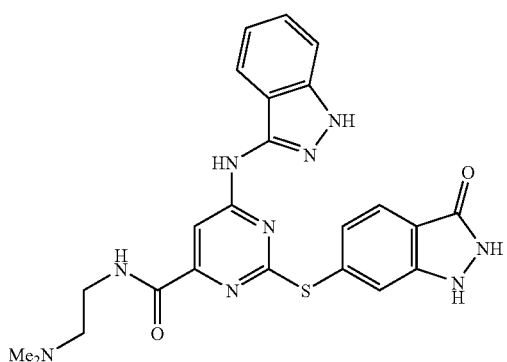
II-(ii)-47
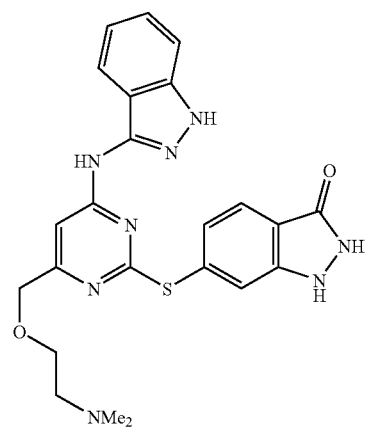
II-(ii)-48
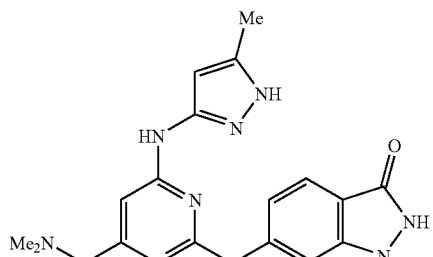
II-(ii)-49
TABLE 2-continued
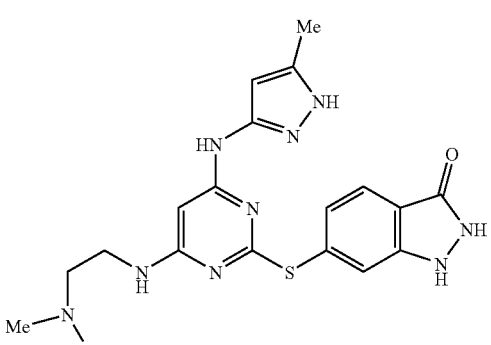
II-(ii)-50
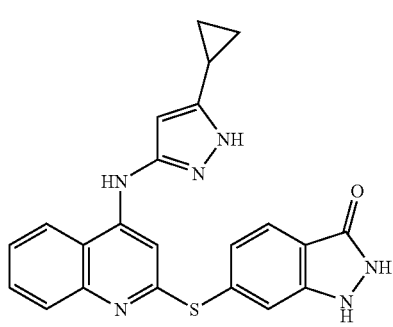
II-(ii)-51
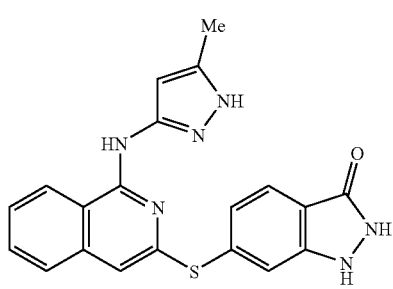
II-(ii)-52
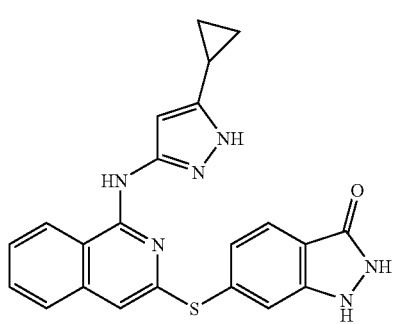
II-(ii)-53

TABLE 2-continued

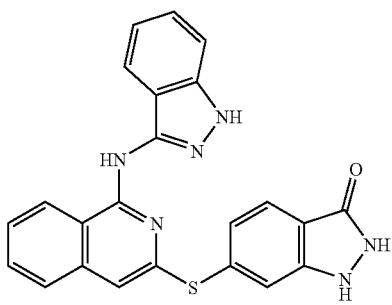

II-(ii)-54

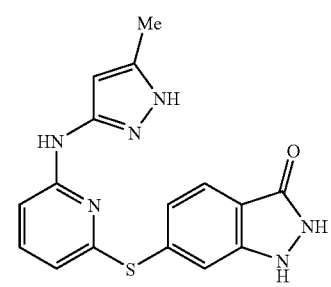

II-(ii)-55

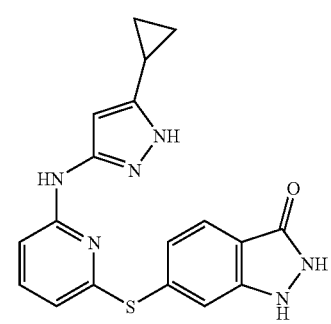

II-(ii)-56

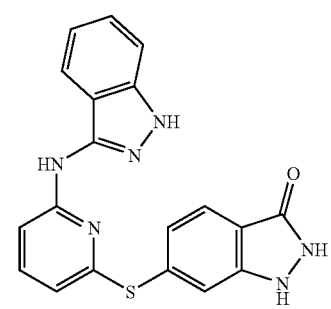

II-(ii)-57

TABLE 2-continued

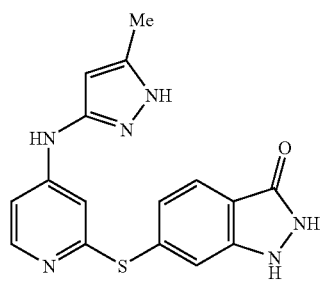

II-(ii)-58

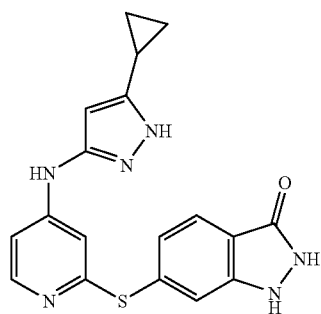

II-(ii)-59

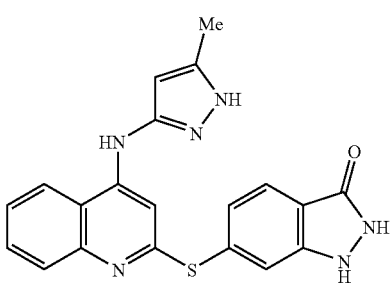

II-(ii)-60

In certain embodiments, a preferred subclass of compounds of general formula IIa or IIb include those compounds where $Q^1$ is O, $Q^2$ is NH and Y is an optionally substituted heteroaryl moiety. These compounds are defined by the general formula IIa(iii) or IIb(iii) and are depicted generally below:

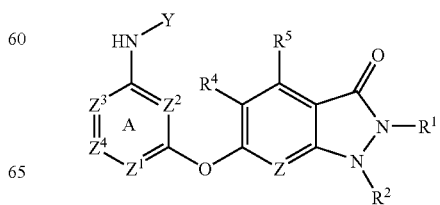

IIa(iii)

-continued

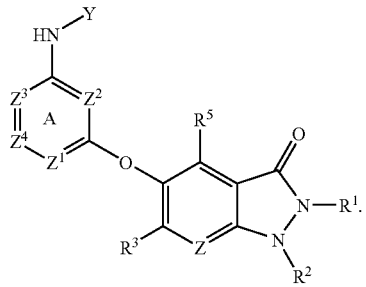

IIb(iii)

It will be appreciated that, for compounds of general formulas IIa(iii) and IIb(iii) certain additional subclasses are of special interest. Certain preferred embodiments of compounds of formula IIa(iii) or IIb(iii) include those compounds having any combination of the following features for each variable for formula IIa(iii) or IIb(iii):

i) Z is $CR^6$ or N;
ii) $R^1$, $R^2$, $R^4$ and $R^5$ are each hydrogen and wherein Z is $CHR^6$ and $R^6$ is hydrogen; or $R^1$, $R^2$, $R^3$ and $R^5$ are each hydrogen and wherein Z is $CHR^6$ and $R^6$ is hydrogen;
iii) ring A is defined according to one of the following groups:
  a. ring A is one of formulas i, ii, iii, iv, v, vi, vii, viii, ix, or x;
  b. ring A is one of formulas II-A, II-B, II-C, II-D, II-E, II-F, II-G, II-H, II-I, II-J, II-K, II-L, II-M, II-N, II-O, II-P, II-Q, II-R, II-S, II-T, II-U, II-V, II-W, II-X, II-Y, II-Z, II-AA, II-BB, II-CC, or II-DD;
  c. ring A is one of formulas II-A, II-B, II-C, II-D, II-E, II-F, II-H, II-I, II-J, II-K, II-L, II-N, II-O, or II-DD;
  d. ring A is one of formulas II-A, II-B, II-C, II-D, II-E, II-H, or II-K;
  e. ring A is one of formulas II-A or II-B;
  f. ring A is II-A and $Z^1$ is $CR^V$ and $Z^2$ is $CR^W$;
  g. ring A is II-A and $Z^1$ is N and $Z^2$ is N;
  h. ring A is II-A and $Z^1$ is N and $Z^2$ is $CR^W$;
  i. ring A is II-A and $Z^1$ is $CR^V$ and $Z^2$ is N;
  j. ring A is an optionally substituted aryl or heteroaryl moiety of formula i, ii, iii or x;
  k. ring A is a monocyclic ring system and $R^V$ and $R^W$, when present, are hydrogen or amino; $R^X$ groups, when present, is hydrogen, alkyl- or dialkylamino, acetamido, or a $C_{1-4}$ aliphatic group such as methyl, ethyl, cyclopropyl, or isopropyl; $R^Y$ groups, when present, is hydrogen, an optionally substituted group selected from hydrogen, $C_{1-6}$ aliphatic, $C_{1-6}$ heteroaliphatic, aryl, or heteroaryl, $-Q_{(n)}N(R^7)_2$, $-Q_{(n)}OR^7$, $-Q_{(n)}SR^7$, $-Q_{(n)}(C=O)O(R^7)$, $-Q_{(n)}C(O)N(R^7)_2$, $-Q_{(n)}NHC(O)R^7$, $-Q_{(n)}NHSO_2R^7$, or $-Q_{(n)}SO_2N(R^7)_2$, wherein n is 0 or 1, and wherein Q is preferably $-(C(R'')_2)-$, wherein R'' is hydrogen or $C_{1-3}$alkyl, and wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring;
  l. ring A is a monocyclic ring system and $R^V$, $R^W$ and $R^X$ groups, when present, are hydrogen or amino; $R^Y$ groups include groups selected from optionally substituted 5–6 membered heteroaryl or heterocyclyl rings, such as 2-pyridyl, 4-pyridyl, pyrrolidinyl, piperidinyl, morpholinyl, or piperazinyl; optionally substituted aryl or cycloalkyl rings such as phenyl, halogen substituted phenyl, alkoxy substituted phenyl, trifluoromethyl substituted phenyl, nitro substituted phenyl, methyl substituted phenyl; optionally substituted $C_{1-6}$ aliphatic, such as methyl, ethyl, cyclopropyl, cyclopentyl, cyclohexyl, amino substituted cycloalkyl, acetamido substituted cycloalkyl, isopropyl, or t-butyl; alkoxyalkylamino such as methoxyethylamino; alkoxyalkyl such as methoxymethyl or methoxyethyl; aminoalkyl such as aminoethyl, dimethylaminoethyl; alkyl- or dialkylamino such as ethylamino or dimethylamino; alkyl- or dialkylaminoalkoxy such as dimethylaminopropyloxy; alkyl- or dialkylaminoalkoxyalkyl such as dimethylaminoethoxymethyl; and acetamido;
  m. ring A system is a bicyclic ring system and the ring formed when $R^X$ and $R^Y$ are taken together may be substituted or unsubstituted;
  n. ring A system is a bicyclic ring system formed by $R^X$ and $R^Y$ taken together and substituted by one or more occurrences of $R^8$ or $R^9$, wherein each occurrence of $R^8$ is independently $-R^7$, halo, $-O(CH_2)_{2-4}-N(R^7)_2$, $-O(CH_2)_{2-4}-R^7$, $-OR^7$, $-N(R^7)-(CH_2)_{2-4}-N(R^7)_2$, $-N(R^7)-(CH_2)_{2-4}-R^7$, $-C(=O)R^7$, $-CO_2R^7$, $-COCOR^7$, $-NO_2$, $-CN$, $-S(O)R^7$, $-SO_2R^7$, $-SR^7$, $-N(R^7)_2$, $-CON(R^7)_2$, $-SO_2N(R^7)_2$, $-OC(=O)R^7$, $-N(R^7)COR^7$, $-N(R^7)CO_2$(optionally substituted $C_{1-6}$ aliphatic), $-N(R^7)N(R^7)_2$, $-C=NN(R^7)_2$, $-C=N-OR$, $-NHOR^7$, $-N(R^7)CON(R^7)_2$, $-N(R^7)SO_2N(R^7)_2$, $-N(R^7)SO_2R^7$, or $-OC(=O)N(R^7)_2$, wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring; and each occurrence of $R^9$ is independently hydrogen, $-R'$, $-COR'$, $-CO_2(R')$, $-CON(R')_2$, or $-SO_2R'$, wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring, iv) Y is defined according to one of the following groups:
  a. Y is an optionally substituted heteroaryl moiety;
  b. Y is selected from one of the heteroaryl moieties a–y;
  c. Y is selected from one of the following heteroaryl moieties:

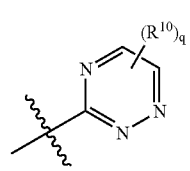

a

-continued

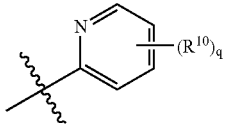
b

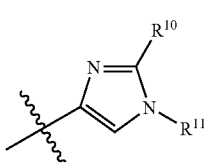
f

h

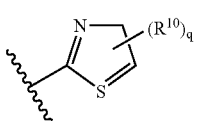
o wherein q is 0–4, $R^{10}$ is —R, wherein —R is defined generally above and in classes and subclasses herein, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

d. Y is a pyrazole moiety, h;

e. Y is one of a, b, f, h or o, optionally substituted with one or more $R^{10}$ groups, wherein each occurrence of $R^{10}$ is independently hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl;

f. Y is one of a, b, f, h or o, optionally substituted with one or more $R^{10}$ groups, wherein each occurrence of $R^{10}$ is independently hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl).

g. Y is a pyrazole moiety, h', wherein the pyrazole is substituted with two occurrences of $R^{10}$ ($R^{10a}$ and $R^{10b}$ as depicted),

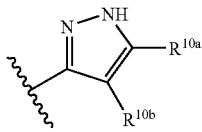
h' wherein each occurrence of $R^{10a}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl, and $R^{10b}$ is hydrogen;

h. Y is a pyrazole moiety, h', wherein the pyrazole is substituted with two occurrences of $R^{10}$ ($R^{10a}$ and $R^{10b}$ as depicted),

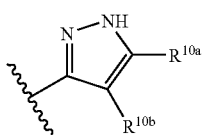
h' wherein each occurrence of $R^{10a}$ is hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl, and $R^{10b}$ is hydrogen;

i. Y is heteroaryl moiety substituted by at least two occurrences of $R^{10}$ and where two occurrences of $R^{10}$ taken together may represent an optionally substituted group selected from cycloaliphatic, cycloheteroaliphatic, aryl or heteroaryl;

j. Y represents one of the following heteroaryl moieties:

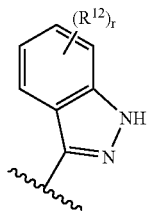
h-i

-continued

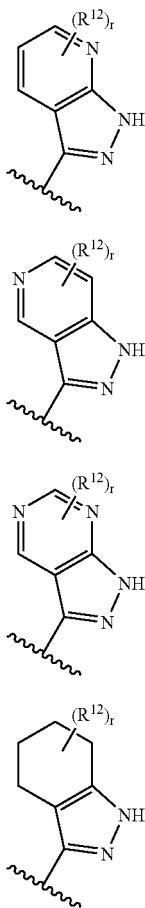

h-ii h-iii h-iv h-v wherein r is 0–4 and $R^{12}$ is hydrogen, -halo, —N(R$^7$)$_2$, —C$_{1-3}$ alkyl, —C$_{1-3}$ haloalkyl, —NO$_2$, —O(C$_{1-3}$ alkyl), —CO$_2$(C$_{1-3}$ alkyl), —CN, —SO$_2$(C$_{1-3}$ alkyl), —SO$_2$NH$_2$, —OC(O)NH$_2$, —NH$_2$SO$_2$(C$_{1-3}$ alkyl), —NHC(O)(C$_{1-3}$ alkyl), —C(O)NH$_2$, and —CO(C$_{1-3}$ alkyl), wherein the (C$_{1-3}$ alkyl) is most preferably methyl;

v) for compounds of formula IIa(iii), $R^4$ is defined according to one of the following groups:

a. $R^4$ is hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl, or b. $R^4$ is hydrogen, methyl, ethyl, cyclopropyl, hydroxy, phenyl or —CH$_2$NH$_2$;

vi) for compounds of formula IIb(iii), $R^3$ is defined according to one of the following groups:

a. $R^3$ is hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl, or b. $R^3$ is hydrogen, methyl, ethyl, cyclopropyl, hydroxy, phenyl or —CH$_2$NH$_2$; and vii) $R^5$ is defined according to one of the following groups:

a. hydrogen, halogen, —NO$_2$, —CN, hydroxy, optionally substituted C$_{1-3}$alkyl, optionally substituted alkoxy, —SO$_2$NH$_2$, or —C(O)alkyl, or b. $R^5$ is hydrogen, Cl, CF$_3$, OCF$_3$, CH$_3$, —CN, —SO$_2$NH$_2$ or —C(O)Me.

In certain preferred embodiments, compounds of the invention include those compounds having general formula IIa(iii) wherein the compounds have one or more of the following features:

a. Z is NR$^6$, wherein $R^1$ and $R^2$ are each independently hydrogen or a protecting group and $R^4$, $R^5$ and $R^6$ are each hydrogen, b. ring A comprises the general formula II-A; and c. Y is an optionally substituted heteroaryl moiety selected from one of formulas a–y.

In most preferred embodiments, for compounds described directly above, ring A is selected from one of the following:

a. an optionally substituted monocyclic aryl or heteroaryl moiety of formula i, ii, iii or x; wherein $R^V$, $R^W$, $R^X$ and $R^Y$ are each independently —R; wherein preferred $R^V$ and $R^W$ groups, when present, are hydrogen or amino; preferred $R^X$ groups, when present, include hydrogen, alkyl- or dialkylamino, acetamido, or a C$_{1-4}$ aliphatic group such as methyl, ethyl, cyclopropyl, or isopropyl; preferred $R^Y$ groups, when present, include hydrogen, an optionally substituted group selected from C$_{1-6}$ aliphatic, C$_{1-6}$ heteroaliphatic, aryl, or heteroaryl, —Q$_{(n)}$N(R$^7$)$_2$, —Q$_{(n)}$OR$^7$, —Q$_{(n)}$SR$^7$, —Q$_{(n)}$(C=O)O(R$^7$), —Q$_{(n)}$C(O)N(R$^7$)$_2$, —Q$_{(n)}$NHC(O)R$^7$, —Q$_{(n)}$NHSO$_2$R$^7$, or —Q$_{(n)}$SO$_2$N(R$^7$)$_2$, wherein n is 0 or 1, and wherein Q is preferably —(C(R")$_2$)—, wherein R" is hydrogen or C$_{1-3}$alkyl, and wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring; or b. a bicyclic aryl or heteroaryl moiety of formula i, ii, iii or x optionally substituted by one or more occurrences of $R^8$ or $R^9$, wherein $R^8$ substituents include —R$^7$, halo, —O(CH$_2$)$_{2-4}$—N(R$^7$)$_2$, —O(CH$_2$)$_{2-4}$—R$^7$, —OR$^7$, —N(R$^7$)—(CH$_2$)$_{2-4}$—N(R$^7$)$_2$, —N(R$^7$)—(CH$_2$)$_{2-4}$—R$^7$, —C(=O)R$^7$, —CO$_2$R$^7$, —COCOR$^7$, —NO$_2$, —CN, —S(O)R$^7$, —SO$_2$R$^7$, —SR$^7$, —N(R$^7$)$_2$, —CONR$^7$)$_2$, —SO$_2$N(R$^7$)$_2$, —OC(=O)R$^7$, —N(R$^7$)COR$^7$, —N(R$^7$)CO$_2$(optionally substituted C$_{1-6}$ aliphatic), —N(R$^7$)N(R$^7$)$_2$, —C=NN(R$^7$)$_2$, —C=N—OR, —NHOR$^7$, —N(R$^7$)CON(R$^7$)$_2$, —N(R$^7$)SO$_2$N(R$^7$)$_2$, —N(R$^7$)SO$_2$R$^7$, or —OC(=O)N(R$^7$)$_2$, wherein each occurrence of $R^7$ is independently hydrogen, an optionally substituted aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or heteroaryl ring; and Y is selected from one of the following heteroaryl moieties:

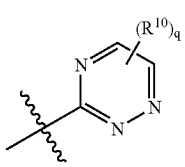

a

-continued

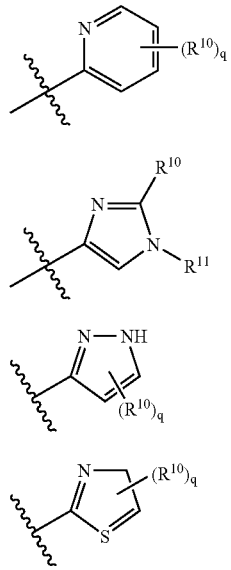

wherein q is 0–4, $R^{10}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, or (N-heterocycle)carbonyl, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

Additional preferred embodiments for the compounds described directly above include those preferred subsets for ring A and Y as exemplified in subclasses and species herein.

Representative examples of compounds of formula IIa(iii) or IIb(iii) (described generally as II(iii) below but encompassing compounds of both formulas IIa(iii) and IIb(iii)), are depicted below in Table 3.

TABLE 3

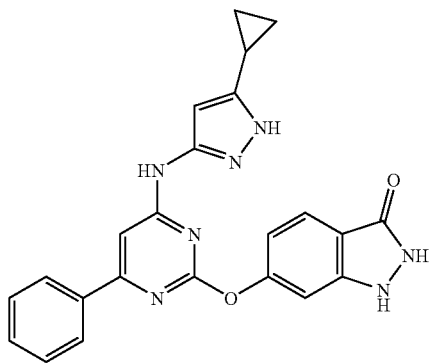

II-(iii)-1

TABLE 3-continued

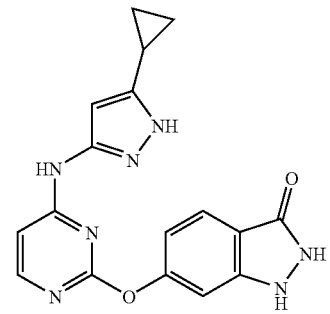

II-(iii)-2

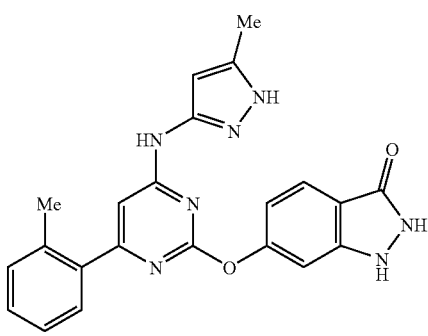

II-(iii)-3

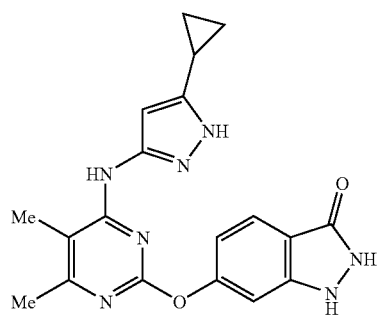

II-(iii)-4

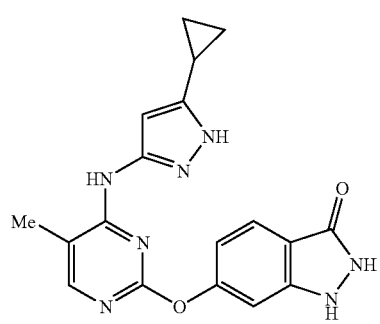

II-(iii)-5

TABLE 3-continued
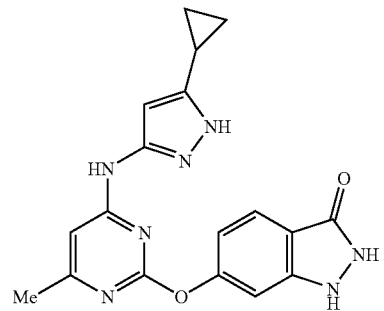
II-(iii)-6
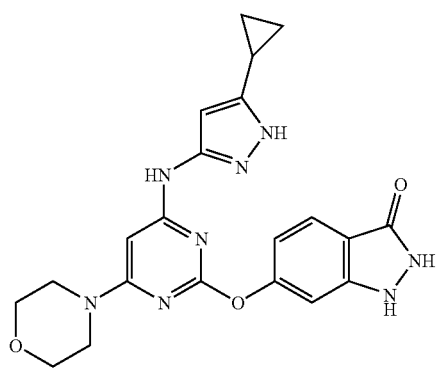
II-(iii)-7
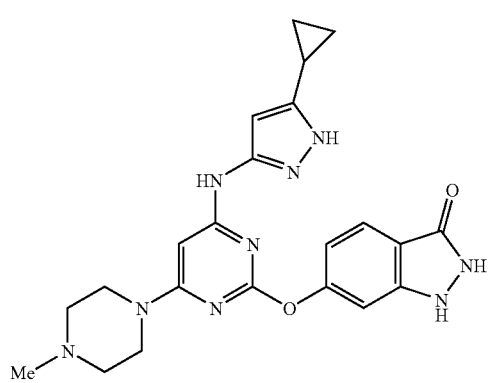
II-(iii)-8
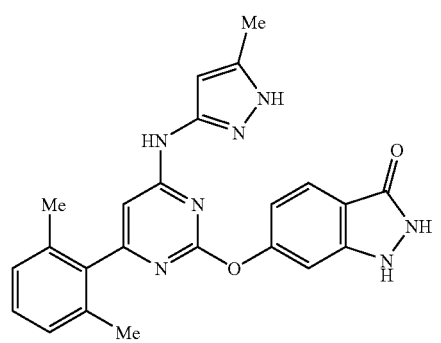
II-(iii)-9
TABLE 3-continued
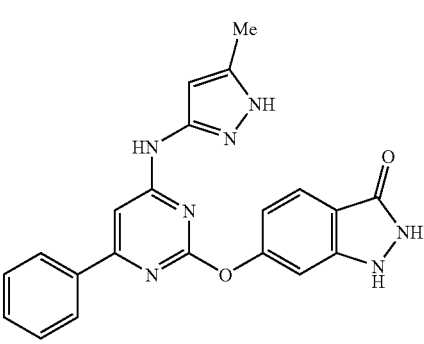
II-(iii)-10
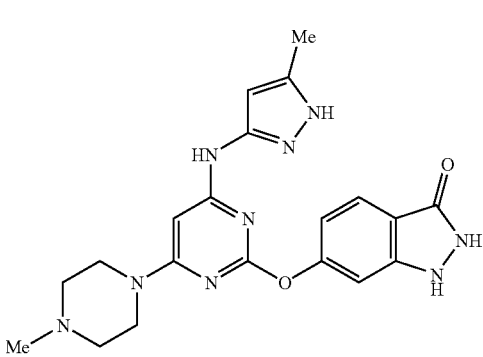
II-(iii)-11
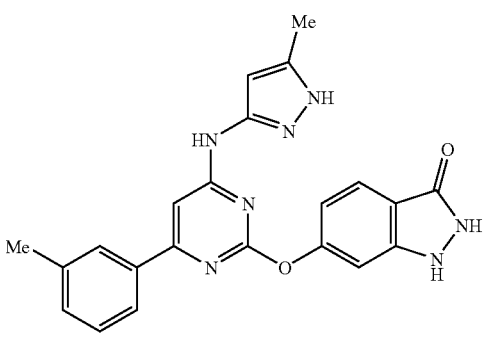
II-(iii)-12
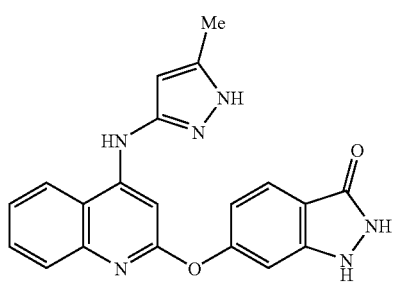
II-(iii)-13

TABLE 3-continued
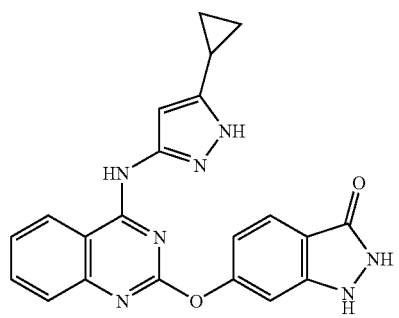
II-(iii)-14
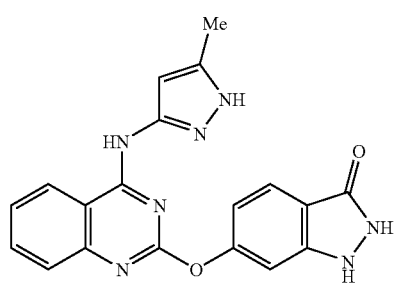
II-(iii)-15
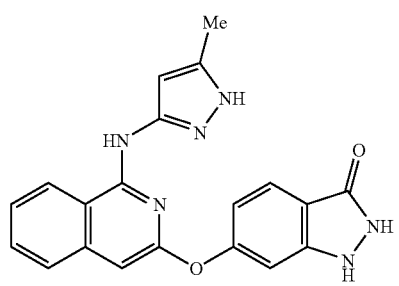
II-(iii)-16
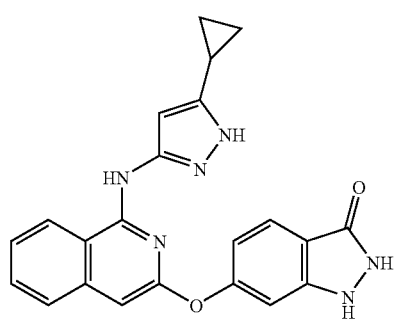
II-(iii)-17
TABLE 3-continued
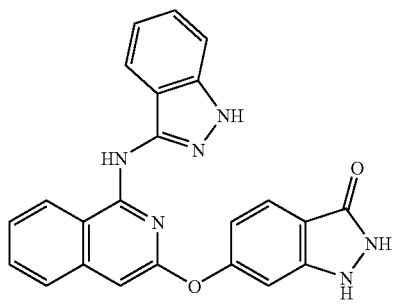
II-(iii)-18
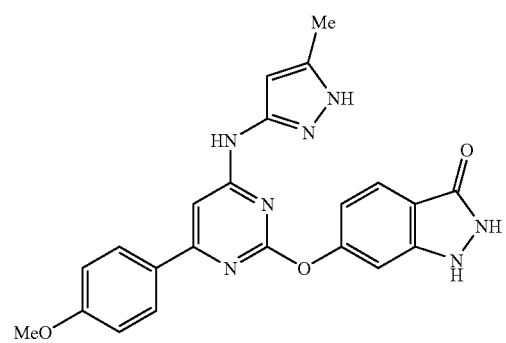
II-(iii)-19
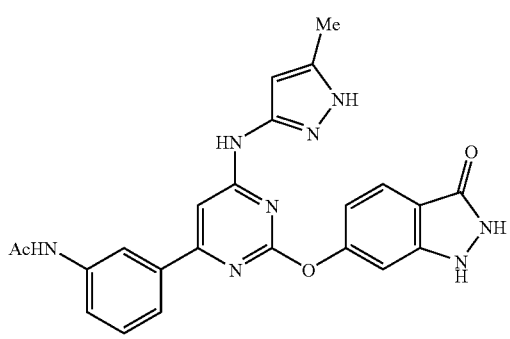
II-(iii)-20
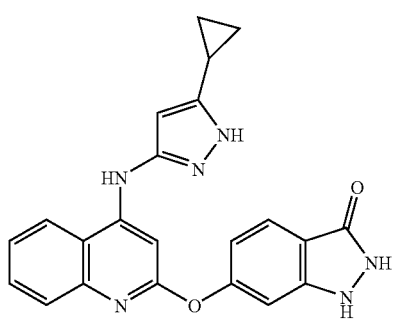
II-(iii)-20

TABLE 3-continued
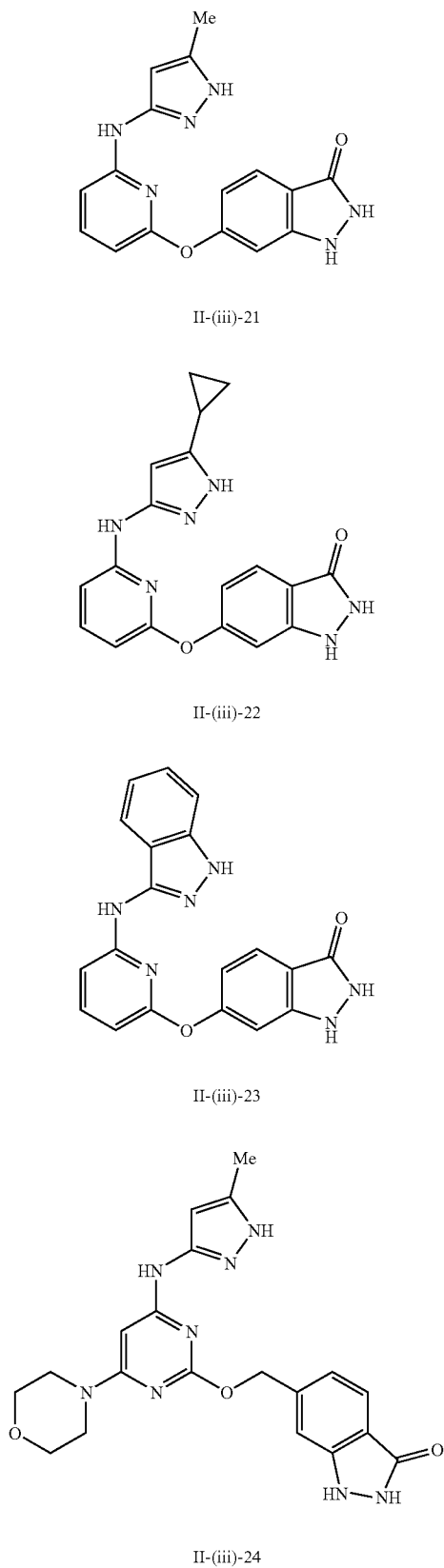
II-(iii)-21
II-(iii)-22
II-(iii)-23
II-(iii)-24
TABLE 3-continued
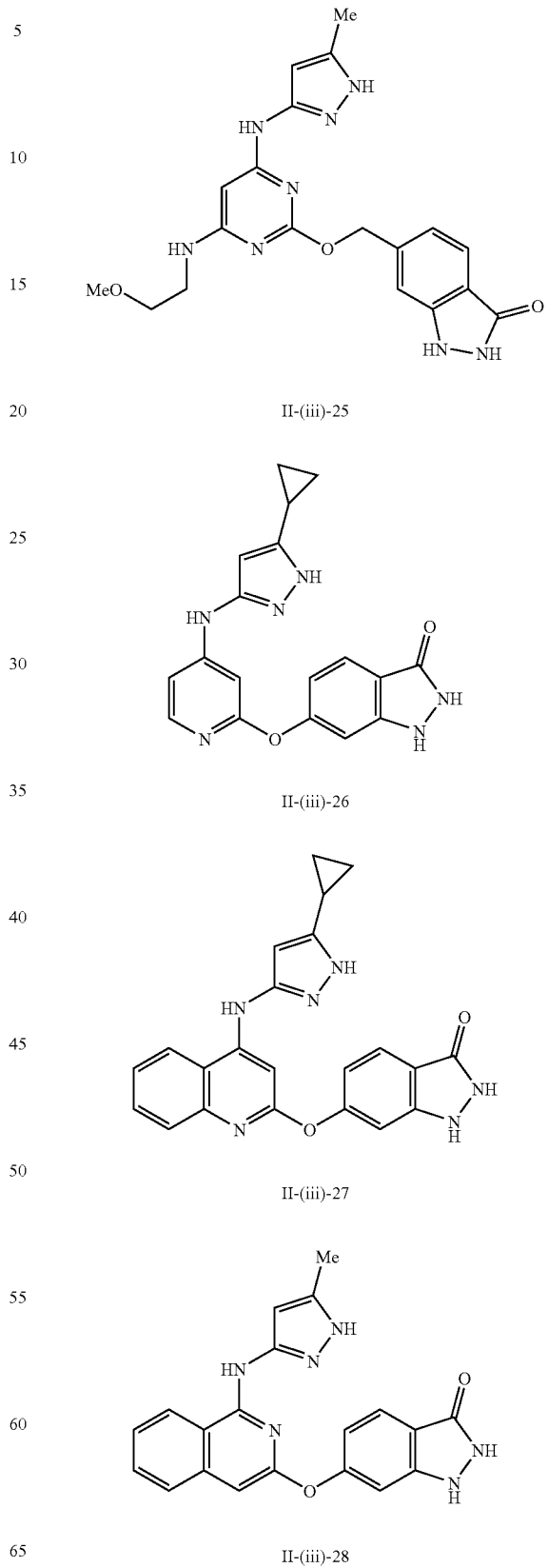
II-(iii)-25
II-(iii)-26
II-(iii)-27
II-(iii)-28

TABLE 3-continued

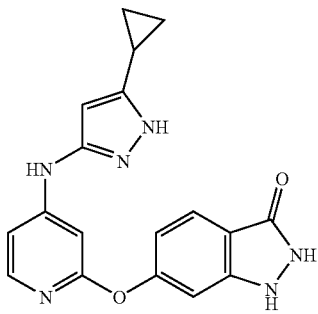

II-(iii)-29

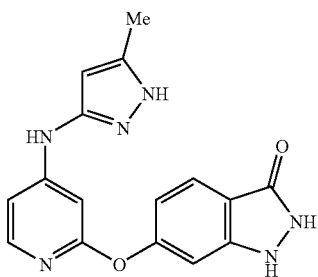

II-(iii)-30

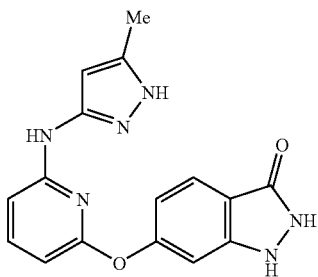

II-(iii)-31

In certain embodiments, a preferred subclass of compounds of general formula Ia or IIb include those compounds where $Q^2$ is NH and Y is an optionally substituted heteroaryl moiety. These compounds are defined by the general formula IIa(iv) or IIb(iv) and are depicted generally below:

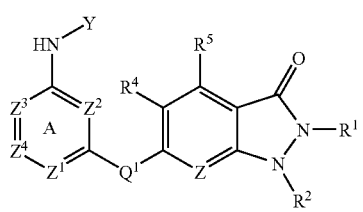

IIa(iv)

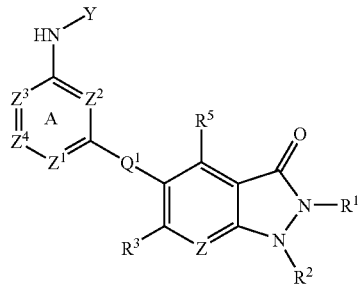

IIb(iv)

wherein $Q^1$ is —$C(R^A)_2$—, 1,2-cyclopropyl, 1,2-cyclobutanediyl, or 1,3-cyclobutanediyl, an optionally substituted $C_{2-4}$alkylidene group, wherein one methylene unit of the optionally substituted $C_{2-4}$alkylidene chain is optionally replaced by —O—, —S—, or —$NR^A$—, wherein each occurrence of $R^A$ is independently hydrogen or optionally substituted $C_{1-4}$aliphatic.

It will be appreciated that, for compounds of general formulas IIa(iv) and IIb(iv) certain additional subclasses are of special interest. Certain preferred embodiments of compounds of formula IIa(iv) or IIb(iv) include those compounds having any combination of the following features for each variable for formula IIa(iv) or IIb(iv):

i) Z is $CR^6$ or N;

ii) $R^1$, $R^2$, $R^4$ and $R^5$ are each hydrogen and wherein Z is $CHR^6$ and $R^6$ is hydrogen; or $R^1$, $R^2$, $R^3$ and $R^5$ are each hydrogen and wherein Z is $CHR^6$ and $R^6$ is hydrogen;

iii) ring A is defined according to one of the following groups:
  a. ring A is one of formulas i, ii, iii, iv, v, vi, vii, viii, ix, or x;
  b. ring A is one of formulas II-A, II-B, II-C, II-D, II-E, II-F, II-G, II-H, II-I, II-J, II-K, II-L, II-M, II-N, II-O, II-P, II-Q, II-R, II-S, II-T, II-U, II-V, II-W, II-X, II-Y, II-Z, II-AA, II-BB, II-CC, or II-DD;
  c. ring A is one of formulas II-A, II-B, II-C, II-D, II-E, II-F, II-H, II-I, II-J, II-K, II-L, II-N, II-O, or II-DD;
  d. ring A is one of formulas II-A, II-B, II-C, II-D, II-E, II-H, or II-K;
  e. ring A is one of formulas II-A or II-B;
  f. ring A is II-A and $Z^1$ is $CR^V$ and $Z^2$ is $CR^W$;
  g. ring A is II-A and $Z^1$ is N and $Z^2$ is N;
  h. ring A is II-A and $Z^1$ is N and $Z^2$ is $CR^W$;
  i. ring A is II-A and $Z^1$ is $CR^V$ and $Z^2$ is N;
  j. ring A is an optionally substituted aryl or heteroaryl moiety of formula i, ii, iii or x;
  k. ring A is a monocyclic ring system and $R^V$ and $R^W$, when present, are hydrogen or amino; $R^X$ groups, when present, is hydrogen, alkyl- or dialkylamino, acetamido, or a $C_{1-4}$ aliphatic group such as methyl, ethyl, cyclopropyl, or isopropyl; $R^Y$ groups, when present, is hydrogen, an optionally substituted group selected from hydrogen, $C_{1-6}$ aliphatic, $C_{1-6}$ heteroaliphatic, aryl, or heteroaryl, —$Q_{(n)}N(R^7)_2$, —$Q_{(n)}OR^7$, —$Q_{(n)}SR^7$, —$Q_{(n)}(C=O)O(R^7)$, —$Q_{(n)}C(O)N(R^7)_2$, —$Q_{(n)}NHC(O)R^7$—$Q_{(n)}NHSO_2R^7$, or —$Q_{(n)}SO_2N(R^7)_2$, wherein n is 0 or 1, and wherein Q is preferably —$(C(R'')_2)$—, wherein R'' is hydrogen or $C_{1-3}$alkyl, and wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring;

l. ring A is a monocyclic ring system and $R^V$, $R^W$ and $R^X$ groups, when present, are hydrogen or amino; R y groups include groups selected from optionally substituted 5–6 membered heteroaryl or heterocyclyl rings, such as 2-pyridyl, 4-pyridyl, pyrrolidinyl, piperidinyl, morpholinyl, or piperazinyl; optionally substituted aryl or cycloalkyl rings such as phenyl, halogen substituted phenyl, alkoxy substituted phenyl, trifluoromethyl substituted phenyl, nitro substituted phenyl, methyl substituted phenyl; optionally substituted $C_{1-6}$ aliphatic, such as methyl, ethyl, cyclopropyl, cyclopentyl, cyclohexyl, amino substituted cycloalkyl, acetamido substituted cycloalkyl, isopropyl, or t-butyl; alkoxyalkylamino such as methoxyethylamino; alkoxyalkyl such as methoxymethyl or methoxyethyl; aminoalkyl such as aminoethyl, dimethylaminoethyl; alkyl- or dialkylamino such as ethylamino or dimethylamino; alkyl- or dialkylaminoalkoxy such as dimethylaminopropyloxy; alkyl- or dialkylaminoalkoxyalkyl such as dimethylaminoethoxymethyl; and acetamido;

m. ring A system is a bicyclic ring system and the ring formed when $R^X$ and $R^Y$ are taken together may be substituted or unsubstituted;

n. ring A system is a bicyclic ring system formed by $R^x$ and $R^y$ taken together and substituted by one or more occurrences of $R^8$ or $R^9$, wherein each occurrence of $R^8$ is independently —$R^7$, halo, —O(CH$_2$)$_{2-4}$—N(R$^7$)$_2$, —O(CH$_2$)$_{2-4}$—R$^7$, —OR$^7$, —N(R$^7$)—(CH$_2$)$_{2-4}$—N(R$^7$)$_2$, —N(R$^7$)—(CH$_2$)$_{2-4}$—R$^7$, —C(=O)R$^7$, —CO$_2$R$^7$, —COCOR$^7$, —NO$_2$, —CN, —S(O)R$^7$, —SO$_2$R$^7$, —SR$^7$, —N(R$^7$)$_2$, —CON(R$^7$)$_2$, —SO$_2$N(R$^7$)$_2$, —OC(=O)R$^7$, —N(R$^7$)COR$^7$, —N(R$^7$)CO$_2$ (optionally substituted $C_{1-6}$ aliphatic), —N(R$^7$)N(R$^7$)$_2$, —C=NN(R$^7$)$_2$, —C=N—OR, —NHOR$^7$, —N(R$^7$)CON(R$^7$)$_2$, —N(R$^7$)SO$_2$N(R$^7$)$_2$, —N(R$^7$)SO$_2$R$^7$, or —OC(=O)N(R$^7$)$_2$, wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring; and each occurrence of $R^9$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring, iv) Y is defined according to one of the following groups:

a. Y is an optionally substituted heteroaryl moiety;

b. Y is selected from one of the heteroaryl moieties a–y;

c. Y is selected from one of the following heteroaryl moieties:

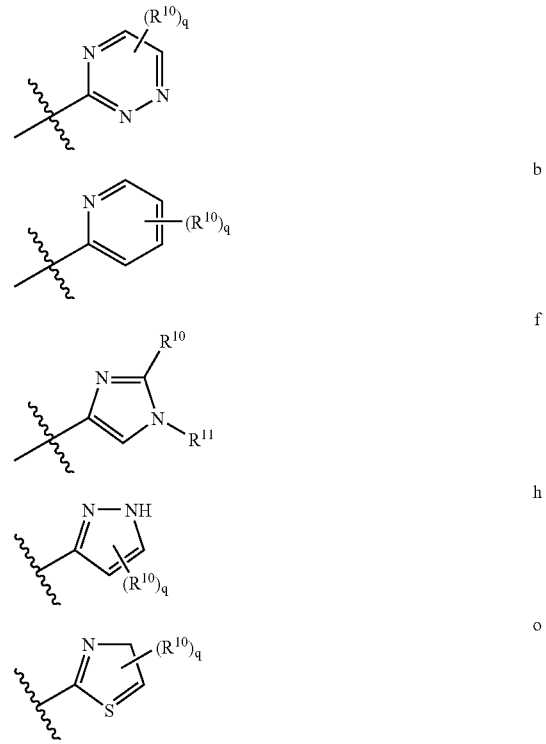

wherein q is 0–4, $R^{10}$ is —R, wherein —R is defined generally above and in classes and subclasses herein, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

d. Y is a pyrazole moiety, h;

e. Y is one of a, b, f, h or o, optionally substituted with one or more $R^{10}$ groups, wherein each occurrence of $R^{10}$ is independently hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle) carbonyl;

f. Y is one of a, b, f, h or o, optionally substituted with one or more $R^{10}$ groups, wherein each occurrence of $R^{10}$ is independently hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl).

g. Y is a pyrazole moiety, h', wherein the pyrazole is substituted with two occurrences of R$^{10}$ (R$^{10a}$ and R$^{10b}$ as depicted), h' wherein each occurrence of R$^{10a}$ is hydrogen, C$_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl, and R$^{10b}$ is hydrogen;

h. Y is a pyrazole moiety, h', wherein the pyrazole is substituted with two occurrences of R$^{10}$ (R$^{10a}$ and R$^{10b}$ as depicted), h' wherein each occurrence of R$^{10a}$ is hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$CH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl, and R$^{10b}$ is hydrogen;

i. Y is heteroaryl moiety substituted by at least two occurrences of R$^{10}$ and where two occurrences of R$^{10}$ taken together may represent an optionally substituted group selected from cycloaliphatic, cycloheteroaliphatic, aryl or heteroaryl;

j. Y represents one of the following heteroaryl moieties:

h-i

-continued h-ii h-iii h-iv h-v wherein r is 0-4 and R$^{12}$ is hydrogen, -halo, —N(R$^7$)$_2$, —C$_{1-3}$ alkyl, —C$_{1-3}$ haloalkyl, —NO$_2$, —O(C$_{1-3}$ alkyl), —CO$_2$(C$_{1-3}$ alkyl), —CN, —SO$_2$(C$_{1-3}$ alkyl), —SO$_2$NH$_2$, —OC(O)NH$_2$, —NH$_2$SO$_2$(C$_{1-3}$ alkyl), —NHC(O)(C$_{1-3}$ alkyl), —C(O)NH$_2$, and —CO(C$_{1-3}$ alkyl), wherein the (C$_{1-3}$ alkyl) is most preferably methyl;

v) for compounds of formula IIa(iv), R$^4$ is defined according to one of the following groups:
a. R$^4$ is hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl, or
b. R$^4$ is hydrogen, methyl, ethyl, cyclopropyl, hydroxy, phenyl or —CH$_2$NH$_2$;

vi) for compounds of formula IIb(iv), R$^3$ is defined according to one of the following groups:
a. R$^3$ is hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl, or
b. R$^3$ is hydrogen, methyl, ethyl, cyclopropyl, hydroxy, phenyl or —CH$_2$NH$_2$; and vii) R$^5$ is defined according to one of the following groups:
a. hydrogen, halogen, —NO$_2$, —CN, hydroxy, optionally substituted C$_{1-3}$alkyl, optionally substituted alkoxy, —SO$_2$NH$_2$, or —C(O)alkyl, or b. R⁵ is hydrogen, C₁, CF₃, OCF₃, CH₃, —CN, —SO₂NH₂ or —C(O)Me.

In certain preferred embodiments, compounds of the invention include those compounds having general formula IIa(iv) wherein the compounds have one or more of the following features:
  a. Z is NR⁶, wherein R¹ and R² are each independently hydrogen or a protecting group and R⁴, R⁵ and R⁶ are each hydrogen,
  b. ring A comprises the general formula II-A; and
  c. Y is an optionally substituted heteroaryl moiety selected from one of formulas a–y.

In most preferred embodiments, for compounds described directly above, ring A is selected from one of the following:
  a. an optionally substituted monocyclic aryl or heteroaryl moiety of formula i, ii, iii or x; wherein $R^V$, $R^W$, $R^X$ and $R^Y$ are each independently —R; wherein preferred $R^V$ and $R^W$ groups, when present, are hydrogen or amino; preferred $R^X$ groups, when present, include hydrogen, alkyl- or dialkylamino, acetamido, or a $C_{1-4}$ aliphatic group such as methyl, ethyl, cyclopropyl, or isopropyl; preferred $R^Y$ groups, when present, include hydrogen, an optionally substituted group selected from $C_{1-6}$ aliphatic, $C_{1-6}$ heteroaliphatic, aryl, or heteroaryl, —Q₍ₙ₎N(R⁷)₂, —Q₍ₙ₎OR⁷, —Q₍ₙ₎SR⁷, —Q₍ₙ₎(C=O)O(R⁷), —Q₍ₙ₎C(O)N(R⁷)₂, —Q₍ₙ₎NHC(O)R⁷, —Q₍ₙ₎NHSO₂R⁷, or —Q₍ₙ₎SO₂N(R⁷)₂, wherein n is 0 or 1, and wherein Q is preferably —(C(R")₂)—, wherein R" is hydrogen or $C_{1-3}$alkyl, and wherein each occurrence of R⁷ is independently hydrogen, an optionally substituted group selected from aliphatic, heteroaliphatic, aryl or heteroaryl, or two occurrences of R⁷ on the same nitrogen atom are taken together with the nitrogen atom to form an optionally substituted group selected from a 5–8 membered heterocyclic or 5–8 membered heteroaryl ring; or
  b. a bicyclic aryl or heteroaryl moiety of formula i, ii, iii or x optionally substituted by one or more occurrences of R⁸ or R⁹, wherein R⁸ substituents include —R⁷, halo, —O(CH₂)₂₋₄—N(R⁷)₂, —O(CH₂)₂₋₄—R⁷, —OR⁷, —N(R⁷)—(CH₂)₂₋₄—N(R⁷)₂, —N(R⁷)—(CH₂)₂₋₄—R⁷, —C(=O)R⁷, —CO₂R⁷, —COCOR⁷, —NO₂, —CN, —S(O)R⁷, —SO₂R⁷, —SR⁷, —N(R⁷)₂, —CON(R⁷)₂, —SO₂N(R⁷)₂, —OC(=O)R⁷, —N(R⁷)COR⁷, —N(R⁷)CO₂(optionally substituted $C_{1-6}$ aliphatic), —N(R⁷)N(R⁷)₂, —C=NN(R⁷)₂, —C=N—OR, —NHOR⁷, —N(R⁷)CON(R⁷)₂, —N(R⁷)SO₂N(R⁷)₂, —N(R⁷)SO₂R⁷, or —OC(=O)N(R⁷)₂, wherein each occurrence of R⁷ is independently hydrogen, an optionally substituted aliphatic, heteroaliphatic, aryl or heteroaryl, or two occurrences of R⁷ on the same nitrogen atom are taken together with the nitrogen atom to form an optionally substituted group selected from a 5–8 membered heterocyclic or heteroaryl ring; and Y is selected from one of the following heteroaryl moieties:

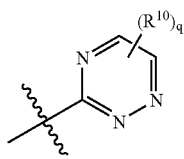
a

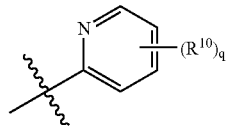
b

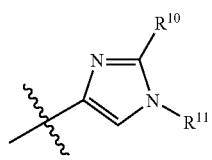
f

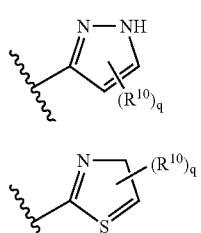
h

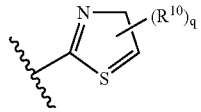
o wherein q is 0–4, $R^{10}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, or (N-heterocycle)carbonyl, and wherein each occurrence of $R^{11}$ is independently hydrogen, —R', —COR', —CO₂(R'), —CON(R')₂, or —SO₂R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

Additional preferred embodiments for the compounds described directly above include those preferred subsets for ring A and Y as exemplified in subclasses and species herein.

Representative examples of compounds of formula IIa(iv) or IIb(iv) (described generally as II(iv) below but encompassing compounds of both formulas IIa(iv) and IIb(iv)), are depicted below in Table 4.

TABLE 4

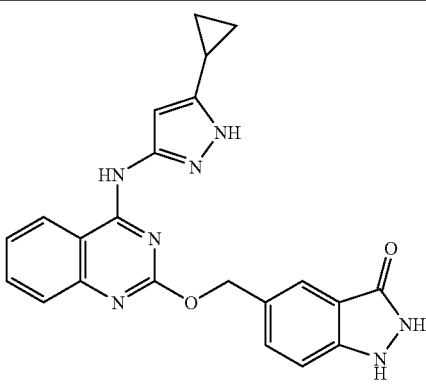

II-(iv)-1

TABLE 4-continued
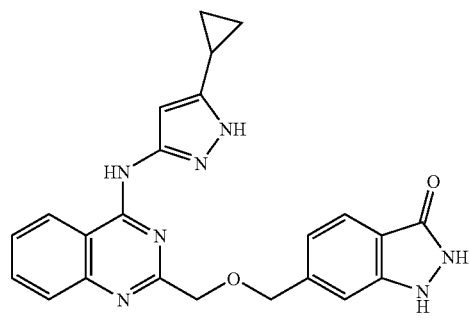
II-(iv)-2
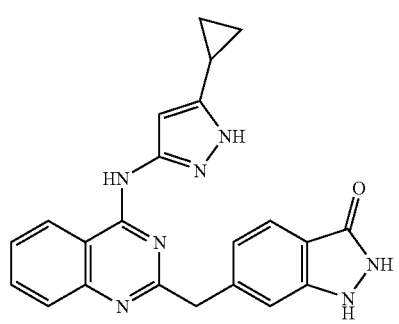
II-(iv)-3
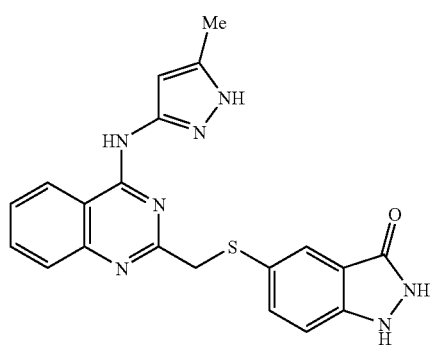
II-(iv)-4
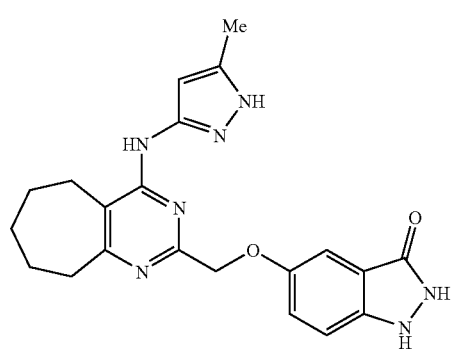
II-(iv)-5
TABLE 4-continued
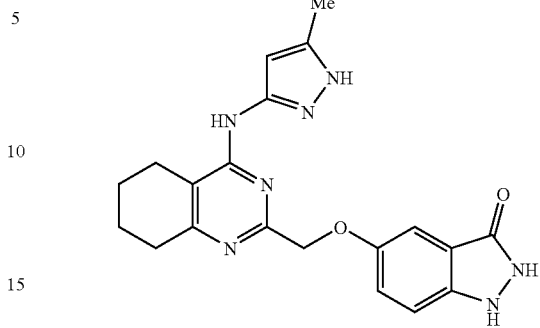
II-(iv)-6
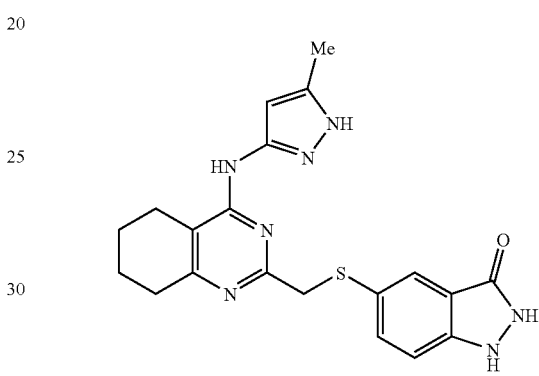
II-(iv)-7
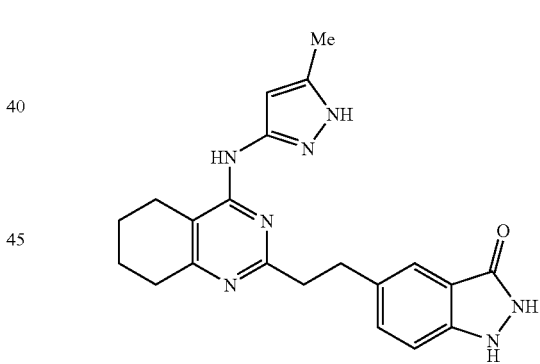
II-(iv)-8
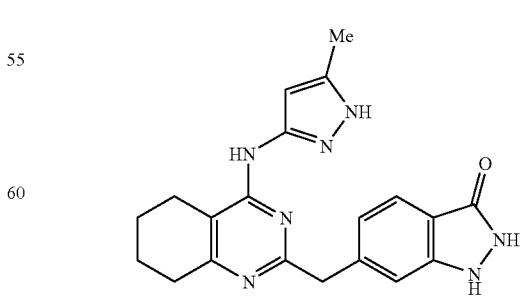
II-(iv)-9

TABLE 4-continued
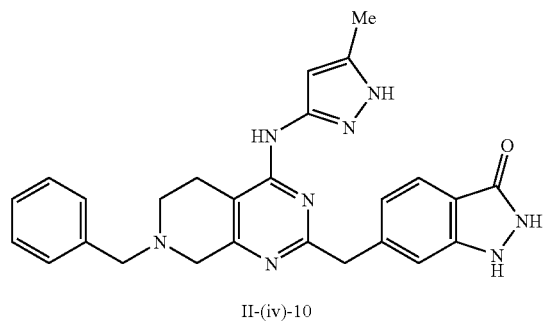
II-(iv)-10
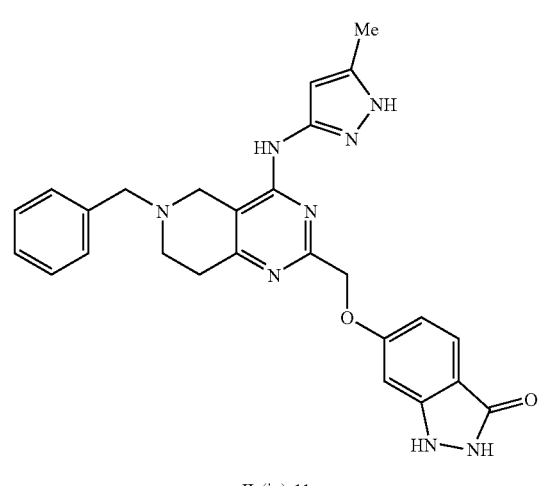
II-(iv)-11
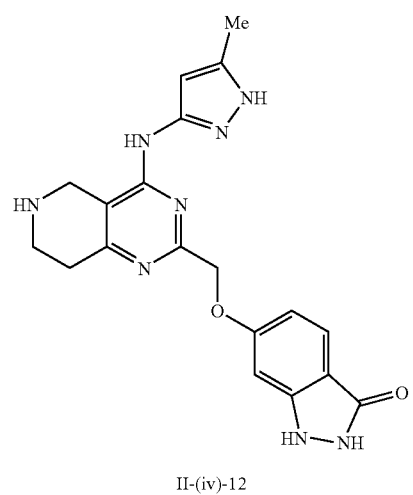
II-(iv)-12
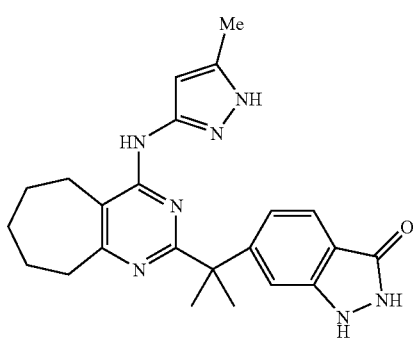
TABLE 4-continued
II-(iv)-13
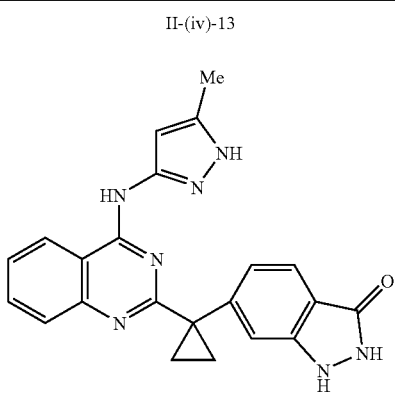
II-(iv)-14
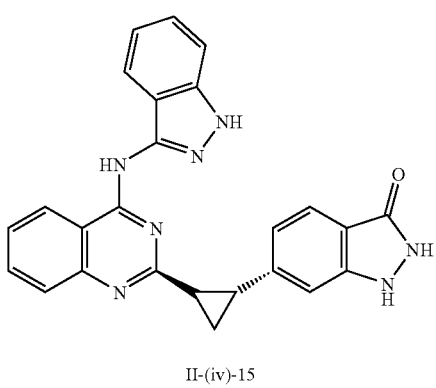
II-(iv)-15
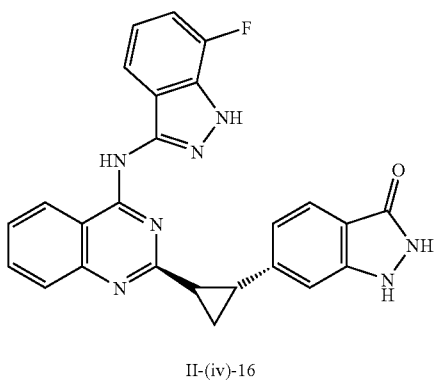
II-(iv)-16
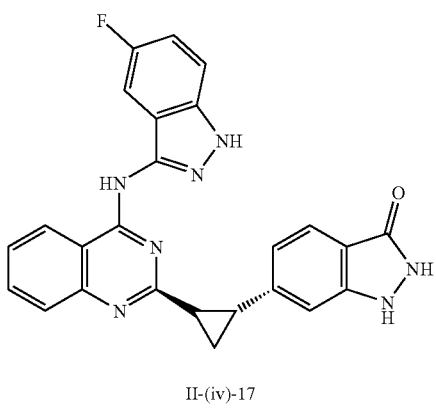
II-(iv)-17

TABLE 4-continued
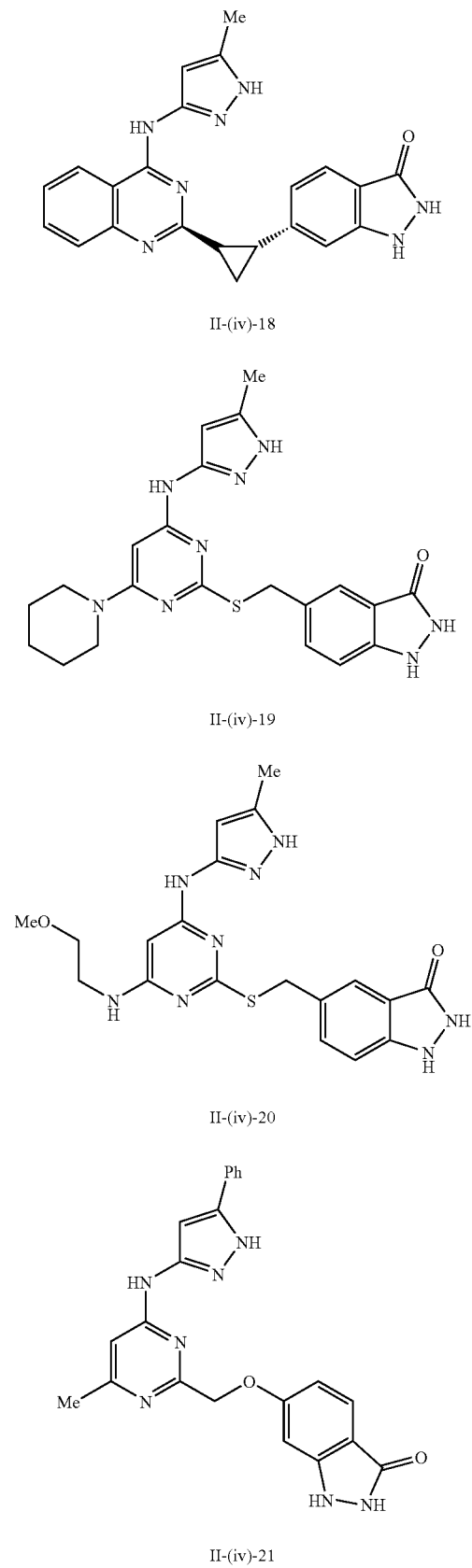
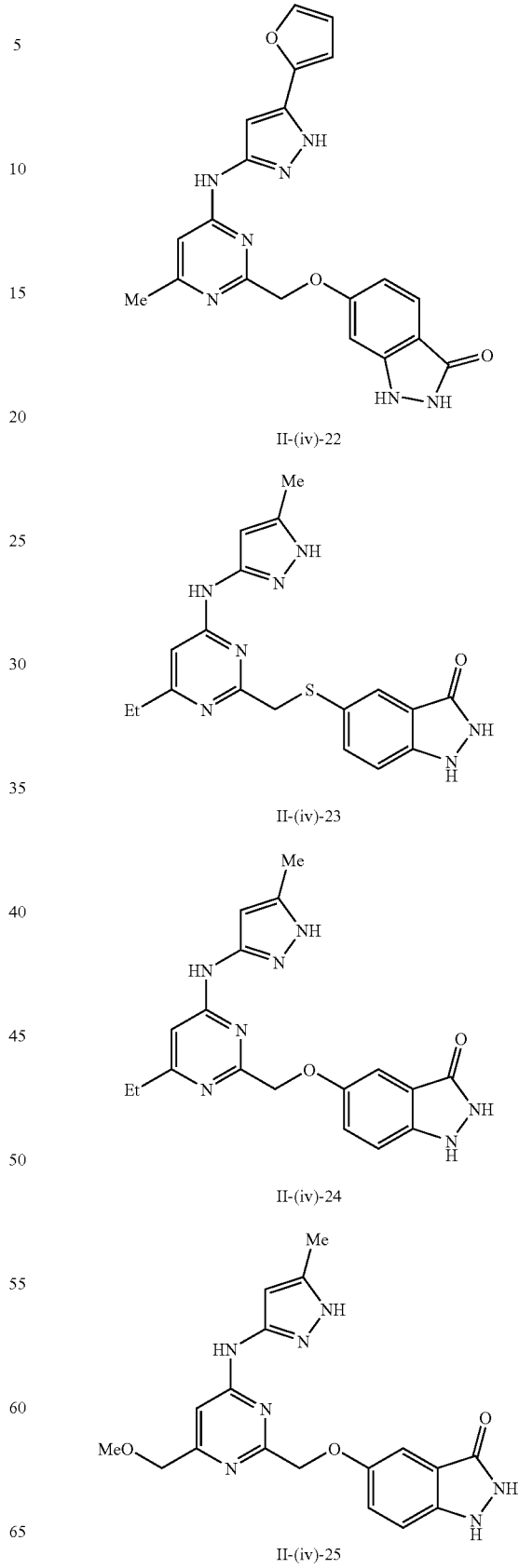

TABLE 4-continued
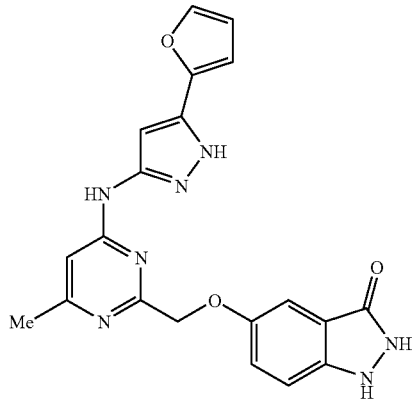
II-(iv)-26
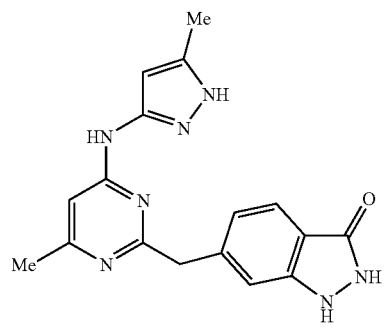
II-(iv)-27
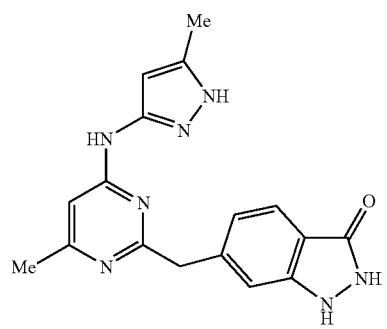
II-(iv)-28
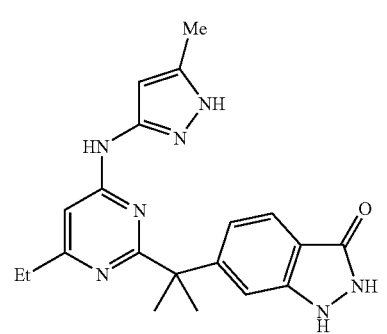
II-(iv)-29
TABLE 4-continued
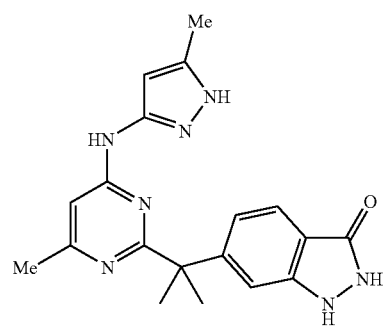
II-(iv)-30
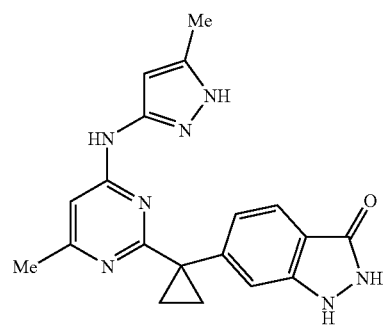
II-(iv)-31
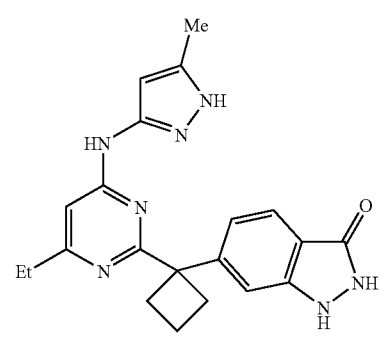
II-(iv)-32
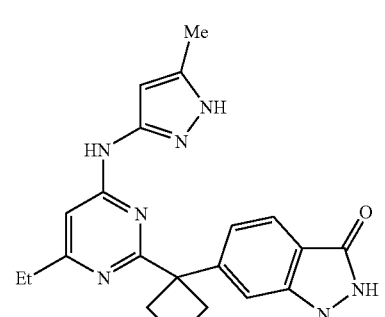
II-(iv)-33

TABLE 4-continued
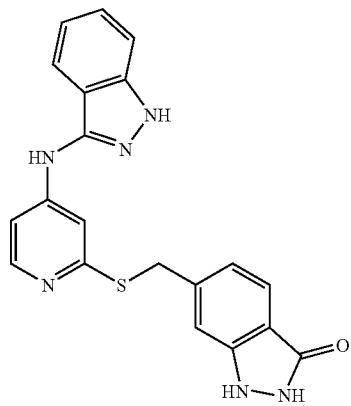
II-(iv)-34
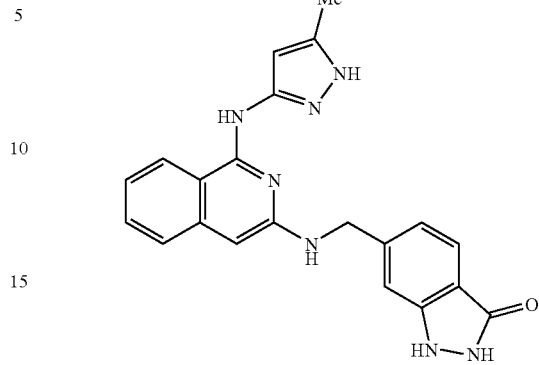
II-(iv)-37
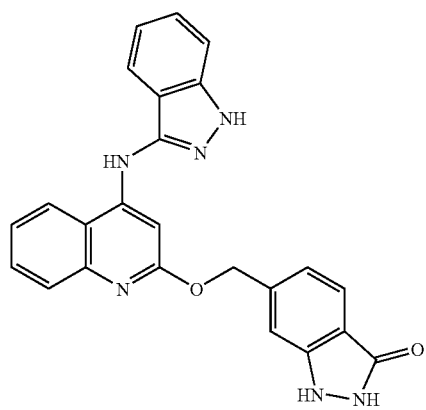
II-(iv)-35
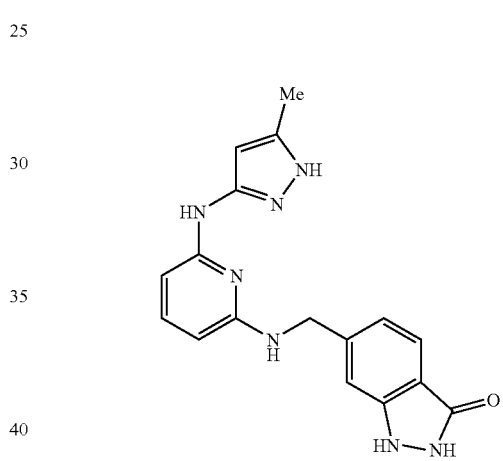
II-(iv)-38
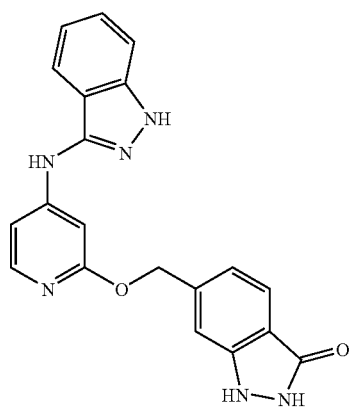
II-(iv)-36
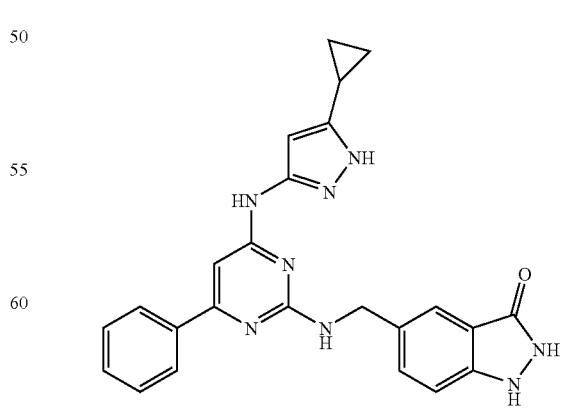
II-(iv)-39

TABLE 4-continued
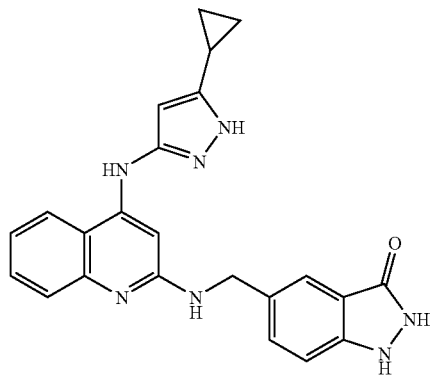
II-(iv)-40
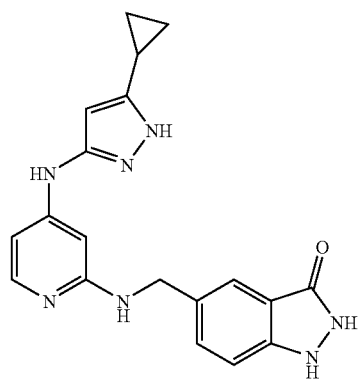
II-(iv)-41
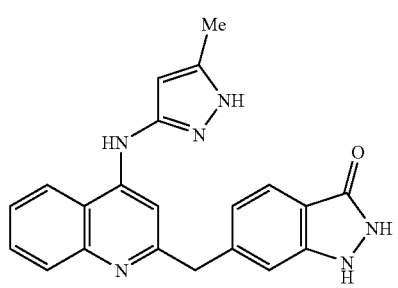
II-(iv)-42
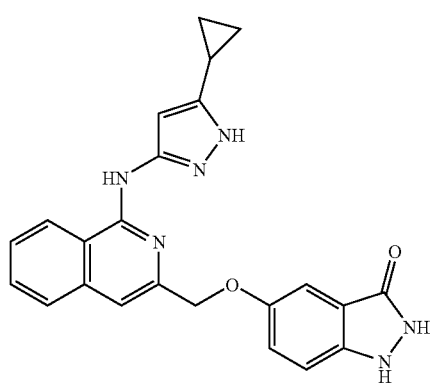
II-(iv)-43
TABLE 4-continued
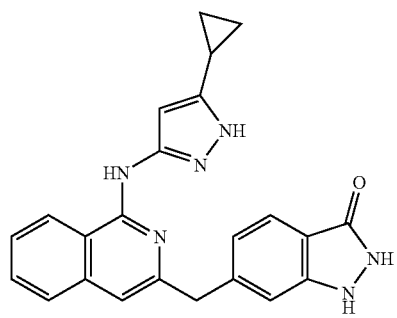
II-(iv)-44
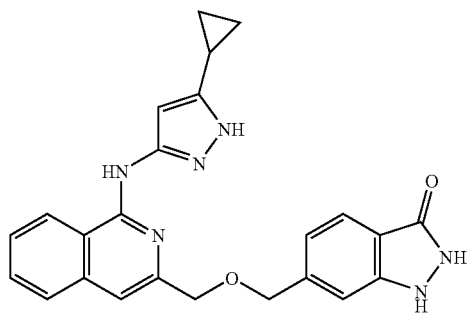
II-(iv)-45
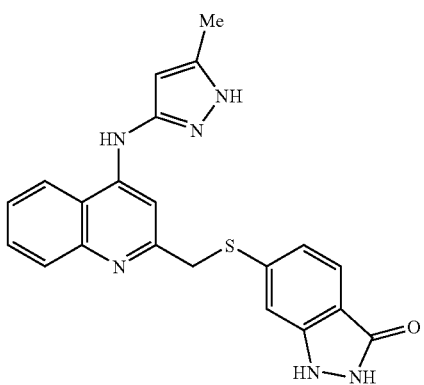
II-(iv)-46
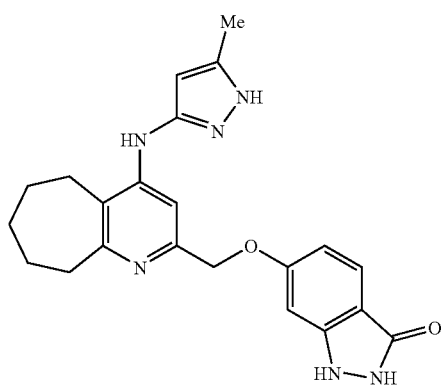
II-(iv)-47

TABLE 4-continued

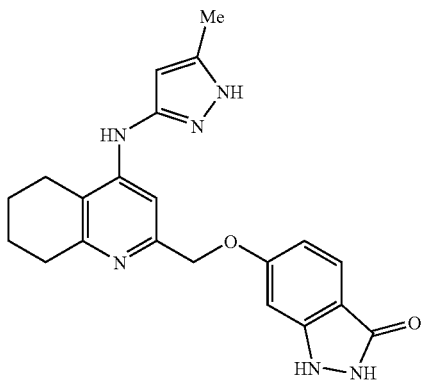

II-(iv)-48

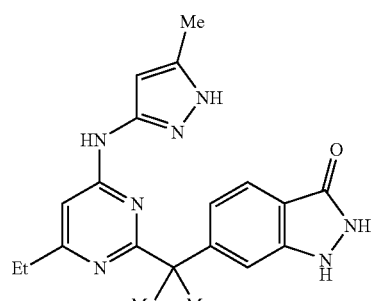

II-(iv)-49

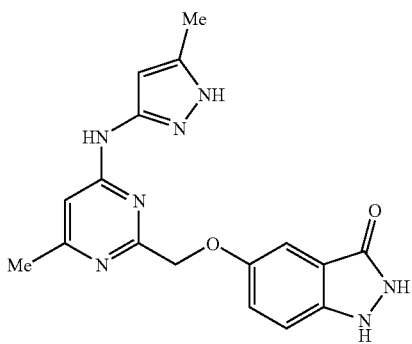

II-(iv)-50

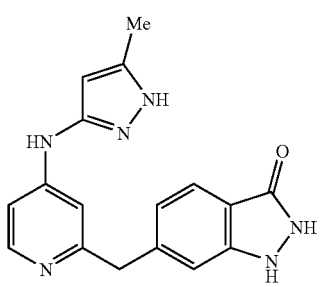

II-(iv)-51

TABLE 4-continued

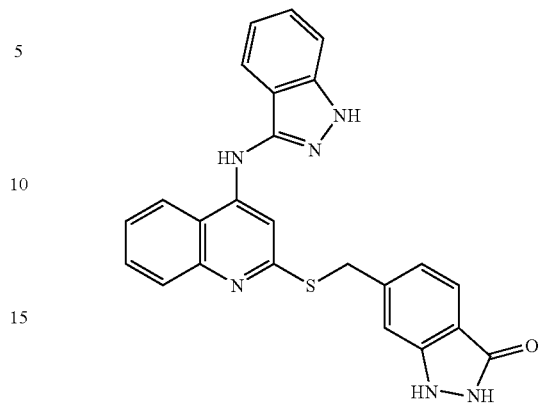

II-(iv)-52

In certain embodiments, a preferred subclass of compounds of general formula IIa or IIb include those compounds where $Q^2$ is NH and Y is an optionally substituted heteroaryl moiety. These compounds are defined by the general formula IIa(v) or IIb(v) and are depicted generally below:

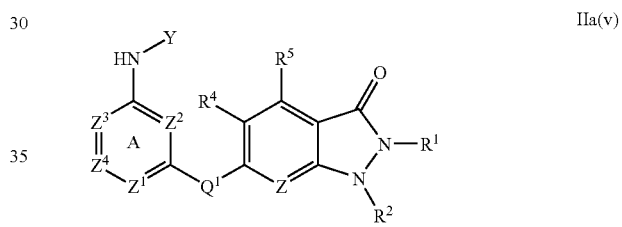

IIa(v)

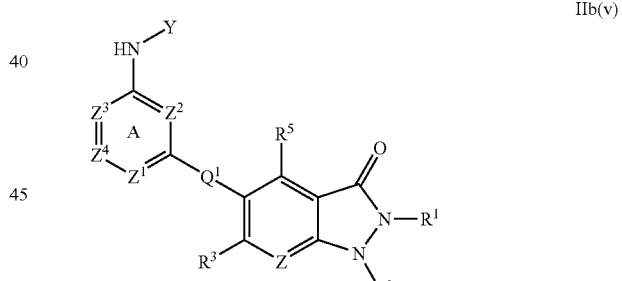

IIb(v)

wherein $Q^1$ is a direct bond.

It will be appreciated that, for compounds of general formulas IIa(v) and IIb(v) certain additional subclasses are of special interest. Certain preferred embodiments of compounds of formula IIa(v) or IIb(v) include those compounds having any combination of the following features for each variable for formula IIa(v) or IIb(v):

i) Z is $CR^6$ or N;

ii) $R^1$, $R^2$, $R^4$ and $R^5$ are each hydrogen and wherein Z is $CHR^6$ and $R^6$ is hydrogen; or $R^1$, $R^2$, $R^3$ and $R^5$ are each hydrogen and wherein Z is $CHR^6$ and $R^6$ is hydrogen;

iii) ring A is defined according to one of the following groups:

a. ring A is one of formulas i, ii, iii, iv, v, vi, vii, viii, ix, or x;

b. ring A is one of formulas II-A, II-B, II-C, II-D, II-E, II-F, II-G, II-H, II-I, II-J, II-K, II-L, II-M, II-N, II-O, II-P, II-Q, II-R, II-S, II-T, II-U, II-V, II-W, II-X, II-Y, II-Z, II-AA, II-BB, II-CC, or II-DD;
c. ring A is one of formulas II-A, II-B, II-C, II-D, II-E, II-F, II-H, II-I, II-J, II-K, II-L, II-N, II-O, or II-DD;
d. ring A is one of formulas II-A, II-B, II-C, II-D, II-E, II-H, or II-K;
e. ring A is one of formulas II-A or II-B;
f. ring A is II-A and $Z^1$ is $CR^V$ and $Z^2$ is $CR^W$;
g. ring A is II-A and $Z^1$ is N and $Z^2$ is N;
h. ring A is II-A and $Z^1$ is N and $Z^2$ is $CR^W$;
i. ring A is II-A and $Z^1$ is $CR^V$ and $Z^2$ is N;
j. ring A is an optionally substituted aryl or heteroaryl moiety of formula i, ii, iii or x;
k. ring A is a monocyclic ring system and $R^V$ and $R^W$, when present, are hydrogen or amino; $R^X$ groups, when present, is hydrogen, alkyl- or dialkylamino, acetamido, or a $C_{1-4}$ aliphatic group such as methyl, ethyl, cyclopropyl, or isopropyl; $R^Y$ groups, when present, is hydrogen, an optionally substituted group selected from hydrogen, $C_{1-6}$ aliphatic, $C_{1-6}$ heteroaliphatic, aryl, or heteroaryl, $—Q_{(n)}N(R^7)_2$, $—Q_{(n)}OR^7$, $—Q_{(n)}SR^7$, $—Q_{(n)}(C=O)O(R^7)$, $—Q_{(n)}C(O)N(R^7)_2$, $—Q_{(n)}NHC(O)R^7$, $—Q_{(n)}NHSO_2R^7$, or $—Q(n)SO_2N(R^7)_2$, wherein n is 0 or 1, and wherein Q is preferably $—(C(R'')_2)—$, wherein R" is hydrogen or $C_{1-3}$alkyl, and wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring;
l. ring A is a monocyclic ring system and $R^V$, $R^W$ and $R^X$ groups, when present, are hydrogen or amino; $R^Y$ groups include groups selected from optionally substituted 5–6 membered heteroaryl or heterocyclyl rings, such as 2-pyridyl, 4-pyridyl, pyrrolidinyl, piperidinyl, morpholinyl, or piperazinyl; optionally substituted aryl or cycloalkyl rings such as phenyl, halogen substituted phenyl, alkoxy substituted phenyl, trifluoromethyl substituted phenyl, nitro substituted phenyl, methyl substituted phenyl; optionally substituted $C_{1-6}$ aliphatic, such as methyl, ethyl, cyclopropyl, cyclopentyl, cyclohexyl, amino substituted cycloalkyl, acetamido substituted cycloalkyl, isopropyl, or t-butyl; alkoxyalkylamino such as methoxyethylamino; alkoxyalkyl such as methoxymethyl or methoxyethyl; aminoalkyl such as aminoethyl, dimethylaminoethyl; alkyl- or dialkylamino such as ethylamino or dimethylamino; alkyl- or dialkylaminoalkoxy such as dimethylaminopropyloxy; alkyl- or dialkylaminoalkoxyalkyl such as dimethylaminoethoxymethyl; and acetamido;
m. ring A system is a bicyclic ring system and the ring formed when $R^x$ and $R^y$ are taken together may be substituted or unsubstituted;
n. ring A system is a bicyclic ring system formed by $R^X$ and $R^Y$ taken together and substituted by one or more occurrences of $R^8$ or $R^9$, wherein each occurrence of $R^8$ is independently $—R^7$, halo, $—O(CH_2)_{2-4}—N(R^7)_2$, $—O(CH_2)_{2-4}—R^7$, $—OR^7$, $—N(R^7)—(CH_2)_{2-4}—N(R^7)_2$, $—N(R^7)—(CH_2)_{2-4}—R^7$, $—C(=O)R^7$, $—CO_2R^7$, $—COCOR^7$, $—NO_2$, $—CN$, $—S(O)R^7$, $—SO_2R^7$, $—SR^7$, $—N(R^7)_2$, $—CON(R^7)_2$, $—SO_2N(R^7)_2$, $—OC(=O)R^7$, $—N(R^7)COR^7$, $—N(R^7)CO_2$ (optionally substituted $C_{1-6}$ aliphatic), $—N(R^7)N(R^7)_2$, $—C=NN(R^7)_2$, $—C=N—OR$, $—NHOR^7$, $—N(R^7)CON(R^7)_2$, $—N(R^7)SO_2N(R^7)_2$, $—N(R^7)SO_2R^7$, or $—OC(=O)N(R^7)_2$, wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring; and each occurrence of $R^9$ is independently hydrogen, $—R'$, $—COR'$, $—CO_2(R')$, $—CON(R')_2$, or $—SO_2R'$, wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring,
iv) Y is defined according to one of the following groups:
a. Y is an optionally substituted heteroaryl moiety;
b. Y is selected from one of the heteroaryl moieties a–y;
c. Y is selected from one of the following heteroaryl moieties:

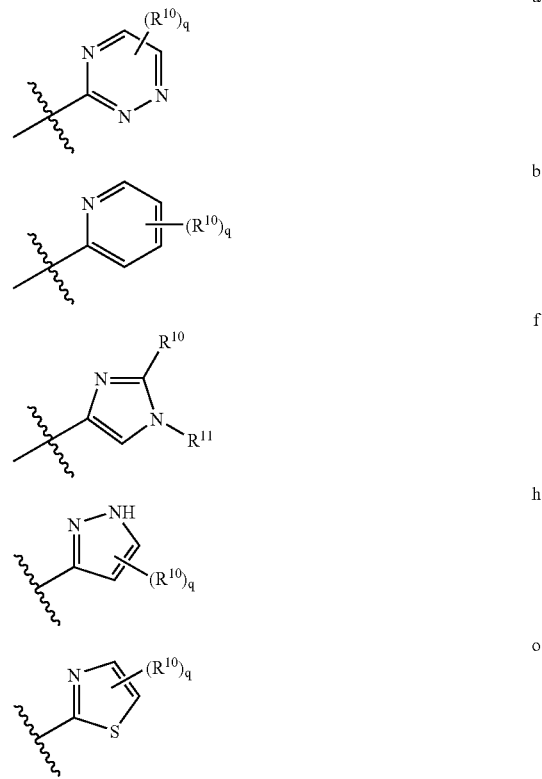

wherein q is 0–4, $R^{10}$ is $—R$, wherein $—R$ is defined generally above and in classes and subclasses herein, and wherein each occurrence of $R^{11}$ is independently hydrogen, $—R'$, $—COR'$, $—CO_2(R')$, $—CON(R')_2$, or $—SO_2R'$, wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

d. Y is a pyrazole moiety, h;
e. Y is one of a, b, f, h or o, optionally substituted with one or more $R^{10}$ groups, wherein each occurrence of $R^{10}$ is independently hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl;
f. Y is one of a, b, f, h or o, optionally substituted with one or more $R^{10}$ groups, wherein each occurrence of $R^{10}$ is independently hydrogen, methyl, cyclopropyl, ethyl, isopropyl, propyl, t-butyl, cyclopentyl, phenyl, $CO_2H$, $CO_2CH_3$, $CH_2OH$, $CH_2OCH_3$, $CH_2CH_2CH_2OH$, $CH_2CH_2CH_2OCH_3$, $CH_2CH_2CH_2OCH_2Ph$, $CH_2CH_2CH_2NH_2$, $CH_2CH_2CH_2NHCOOC(CH_3)_3$, $CONHCH(CH_3)_2$, $CONHCH_2CH=CH_2$, $CONHCH_2CH_2OCH_3$, $CONHCH_2Ph$, $CONH(cyclohexyl)$, $CON(Et)_2$, $CON(CH_3)CH_2Ph$, $CONH(n-C_3H_7)$, $CON(Et)CH_2CH_2CH_3$, $CONHCH_2CH(CH_3)_2$, $CON(n-C_3H_7)_2$, $CO(3-methoxymethylpyrrolidin-1-yl)$, $CONH(3-tolyl)$, $CONH(4-tolyl)$, $CONHCH_3$, $CO(morpholin-1-yl)$, $CO(4-methylpiperazin-1-yl)$, $CONHCH_2CH_2OH$, $CONH_2$, and $CO(piperidin-1-yl)$.
g. Y is a pyrazole moiety, h', wherein the pyrazole is substituted with two occurrences of $R^{10}$ ($R^{10a}$ and $R^{10b}$ as depicted),

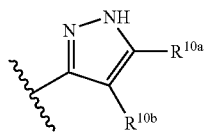

h' wherein each occurrence of $R^{10a}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl, and $R^{10b}$ is hydrogen;
h. Y is a pyrazole moiety, h', wherein the pyrazole is substituted with two occurrences of $R^{10}$ ($R^{10a}$ and $R^{10b}$ as depicted),

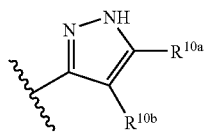

h' wherein each occurrence of $R^{10a}$ is hydrogen, methyl, cyclopropyl, ethyl, isopropyl, propyl, t-butyl, cyclopentyl, phenyl, $CO_2H$, $CO_2CH_3$, $CH_2OH$, $CH_2OCH_3$, $CH_2CH_2CH_2OH$, $CH_2CH_2CH_2OCH_3$, $CH_2CH_2CH_2OCH_2Ph$, $CH_2CH_2CH_2NH_2$, $CH_2CH_2CH_2NHCOOC(CH_3)_3$, $CONHCH(CH_3)_2$, $CONHCH_2CH=CH_2$, $CONHCH_2CH_2OCH_3$, $CONHCH_2Ph$, $CONH(cyclohexyl)$, $CON(Et)_2$, $CON(CH_3)CH_2Ph$, $CONH(n-C_3H_7)$, $CON(Et)CH_2CH_2CH_3$, $CONHCH_2CH(CH_3)_2$, $CON(n-C_3H_7)_2$, $CO(3-methoxymethylpyrrolidin-1-yl)$, $CONH(3-tolyl)$, $CONH(4-tolyl)$, $CONHCH_3$, $CO(morpholin-1-yl)$, $CO(4-methylpiperazin-1-yl)$, $CONHCH_2CH_2OH$, $CONH_2$, and $CO(piperidin-1-yl$, and $R^{10b}$ is hydrogen;
i. Y is heteroaryl moiety substituted by at least two occurrences of $R^{10}$ and where two occurrences of $R^{10}$ taken together may represent an optionally substituted group selected from cycloaliphatic, cycloheteroaliphatic, aryl or heteroaryl;
j. Y represents one of the following heteroaryl moieties:

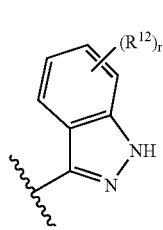

h-i

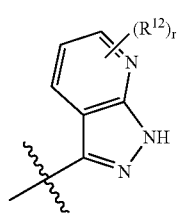

h-ii

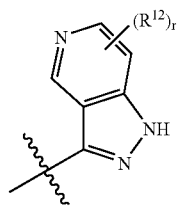

h-iii

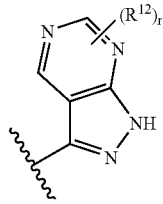

h-iv

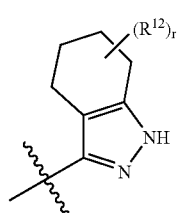

h-v wherein r is 0–4 and $R^{12}$ is hydrogen, -halo, $-N(R^7)_2$, $-C_{1-3}$ alkyl, $-C_{1-3}$ haloalkyl, $-NO_2$, $-O(C_{1-3}$ alkyl), $-CO_2(C_{1-3}$ alkyl), $-CN$, $-SO_2(C_{1-3}$ alkyl), $-SO_2NH_2$, $-OC(O)NH_2$, $-NH_2SO_2(C_{1-3}$ alkyl), $-NHC(O)(C_{1-3}$ alkyl), $-C(O)NH_2$, and $-CO(C_{1-3}$ alkyl), wherein the ($C_{1-3}$ alkyl) is most preferably methyl;
iv) for compounds of formula IIa(v), $R^4$ is defined according to one of the following groups:
a. $R^4$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or b. $R^4$ is hydrogen, methyl, ethyl, cyclopropyl, hydroxy, phenyl or —CH$_2$NH$_2$;
vi) for compounds of formula IIb(v), $R^3$ is defined according to one of the following groups:
  a. $R^3$ is hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl, or
  b. $R^3$ is hydrogen, methyl, ethyl, cyclopropyl, hydroxy, phenyl or —CH$_2$NH$_2$; and
vii) $R^5$ is defined according to one of the following groups:
  a. hydrogen, halogen, —NO$_2$, —CN, hydroxy, optionally substituted C$_{1-3}$alkyl, optionally substituted alkoxy, —SO$_2$NH$_2$, or —C(O)alkyl, or
  b. $R^5$ is hydrogen, C$_1$, CF$_3$, OCF$_3$, CH$_3$, —CN, —SO$_2$NH$_2$ or —C(O)Me.

In certain preferred embodiments, compounds of the invention include those compounds having general formula IIa(v) or IIb(v) wherein the compounds have one or more of the following features:
  a. Z is NR$^6$, wherein R$^1$ and R$^2$ are each independently hydrogen or a protecting group and R$^4$, R$^5$ and R$^6$ are each hydrogen,
  b. ring A comprises the general formula II-A; and
  c. Y is an optionally substituted heteroaryl moiety selected from one of formulas a–y.

In most preferred embodiments, for compounds described directly above, ring A is selected from one of the following:
  a. an optionally substituted monocyclic aryl or heteroaryl moiety of formula i, ii, iii or x; wherein R$^V$, R$^W$, R$^X$ and R$^Y$ are each independently —R; wherein preferred R$^V$ and R$^W$ groups, when present, are hydrogen or amino; preferred R$^X$ groups, when present, include hydrogen, alkyl- or dialkylamino, acetamido, or a C$_{1-4}$ aliphatic group such as methyl, ethyl, cyclopropyl, or isopropyl; preferred R$^Y$ groups, when present, include hydrogen, an optionally substituted group selected from C$_{1-6}$ aliphatic, C$_{1-6}$ heteroaliphatic, aryl, or heteroaryl, —Q$_{(n)}$N(R$^7$)$_2$, —Q$_{(n)}$OR$^7$, —Q$_{(n)}$SR$^7$, —Q$_{(n)}$(C═O)O(R$^7$), —Q$_{(n)}$C(O)N(R$^7$)$_2$, —Q$_{(n)}$NHC(O)R$^7$, —Q$_{(n)}$NHSO$_2$R$^7$, or —Q$_{(n)}$SO$_2$N(R$^7$)$_2$, wherein n is 0 or 1, and wherein Q is preferably —(C(R'')$_2$)—, wherein R'' is hydrogen or C$_{1-3}$alkyl, and wherein each occurrence of R$^7$ is independently hydrogen, an optionally substituted group selected from aliphatic, heteroaliphatic, aryl or heteroaryl, or two occurrences of R$^7$ on the same nitrogen atom are taken together with the nitrogen atom to form an optionally substituted group selected from a 5–8 membered heterocyclic or 5–8 membered heteroaryl ring; or
  b. a bicyclic aryl or heteroaryl moiety of formula i, ii, iii or x optionally substituted by one or more occurrences of R$^8$ or R$^9$, wherein R$^8$ substituents include —R$^7$, halo, —O(CH$_2$)$_{2-4}$—N(R$^7$)$_2$, —O(CH$_2$)$_{2-4}$—R$^7$, —OR$^7$, —N(R$^7$)—(CH$_2$)$_{2-4}$—N(R$^7$)$_2$, —N(R$^7$)—(CH$_2$)$_{2-4}$—R$^7$, —C(═O)R$^7$, —CO$_2$R$^7$, —COCOR$^7$, —NO$_2$, —CN, —S(O)R$^7$, —SO$_2$R$^7$, —SR$^7$, —N(R$^7$)$_2$, —CON(R$^7$)$_2$, —SO$_2$N(R$^7$)$_2$, —OC(═O)R$^7$, —N(R$^7$)COR$^7$, —N(R$^7$)CO$_2$(optionally substituted C$_{1-6}$ aliphatic), —N(R$^7$)N(R$^7$)$_2$, —C═NN(R$^7$)$_2$, —C═N—OR, —NHOR$^7$, —N(R$^7$)CON(R$^7$)$_2$, —N(R$^7$)SO$_2$N(R$^7$)$_2$, —N(R$^7$)SO$_2$R$^7$, or —OC(═O)N(R$^7$)$_2$, wherein each occurrence of R$^7$ is independently hydrogen, an optionally substituted aliphatic, heteroaliphatic, aryl or heteroaryl, or two occurrences of R$^7$ on the same nitrogen atom are taken together with the nitrogen atom to form an optionally substituted group selected from a 5–8 membered heterocyclic or heteroaryl ring; and Y is selected from one of the following heteroaryl moieties:

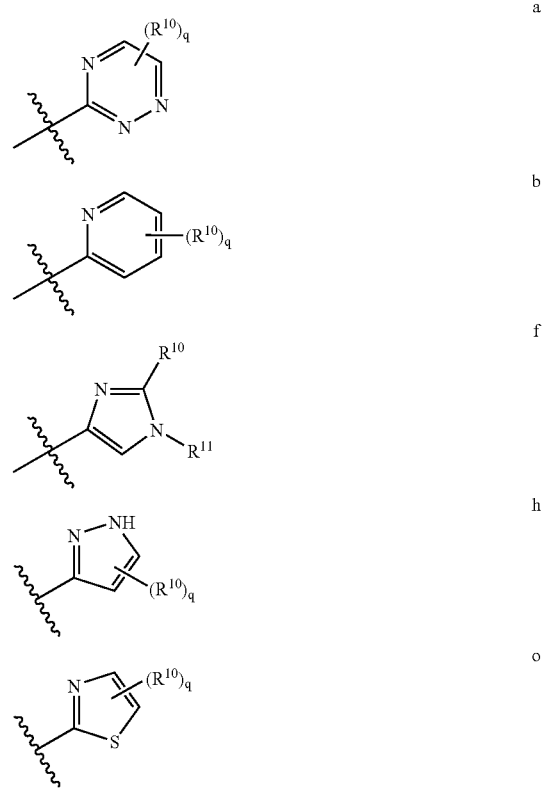

wherein q is 0–4, R$^{10}$ is hydrogen, C$_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, or (N-heterocycle)carbonyl, and wherein each occurrence of R$^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

Additional preferred embodiments for the compounds described directly above include those preferred subsets for ring A and Y as exemplified in subclasses and species herein.

Representative examples of compounds of formula IIa(v) or IIb(v) (described generally as II(v) below but encompassing compounds of both formulas IIa(v) and IIb(v)), are depicted below in Table 5.

TABLE 5
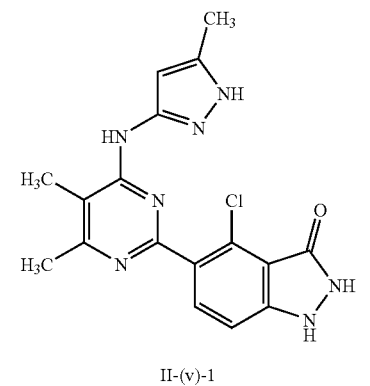
II-(v)-1
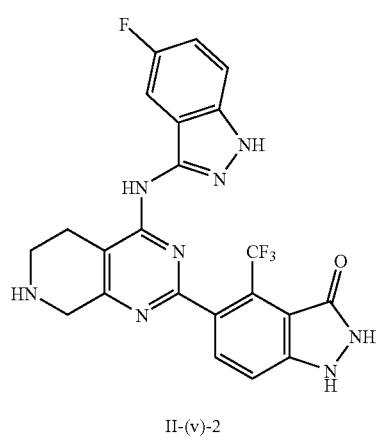
II-(v)-2
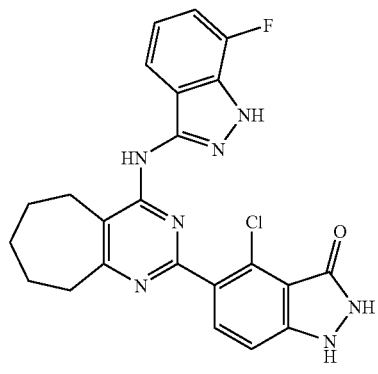
II-(v)-3
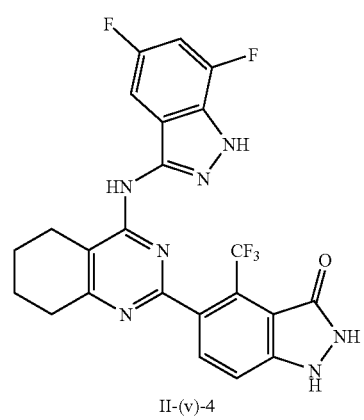
II-(v)-4
TABLE 5-continued
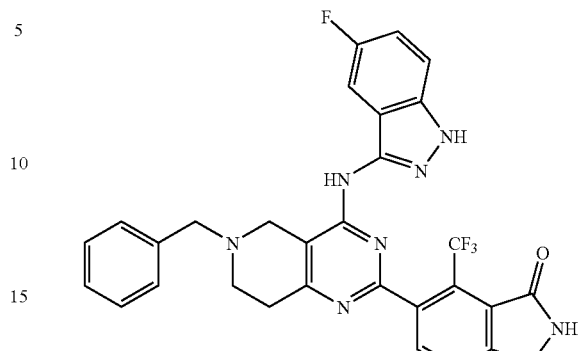
II-(v)-5
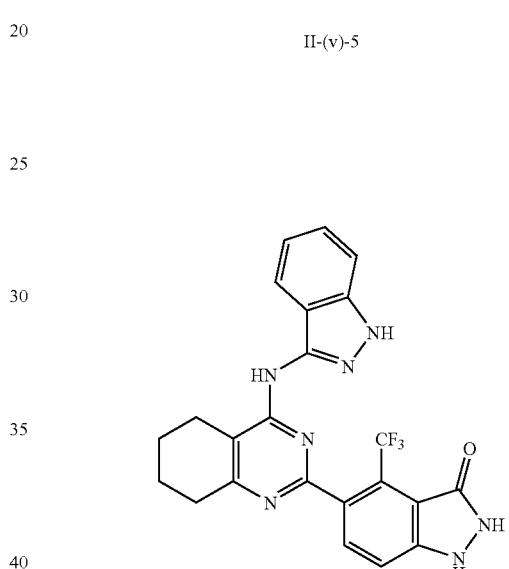
II-(v)-6
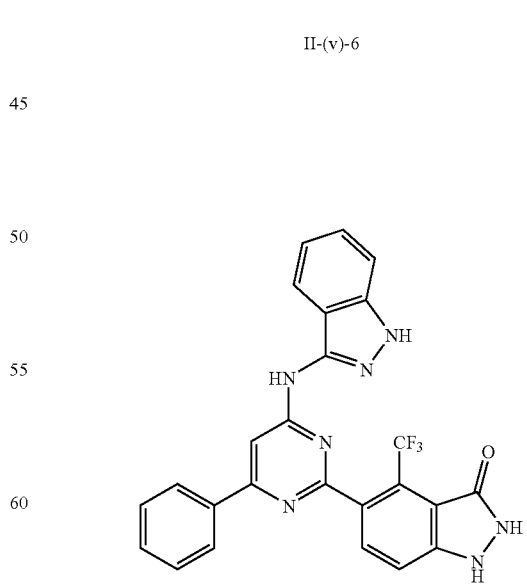
II-(v)-7

TABLE 5-continued
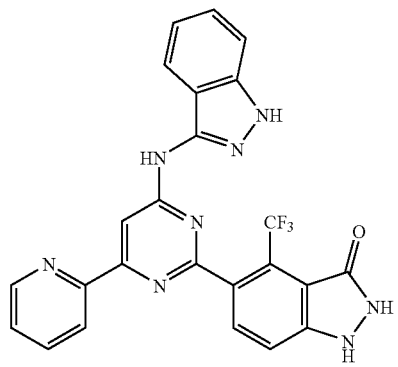
II-(v)-8
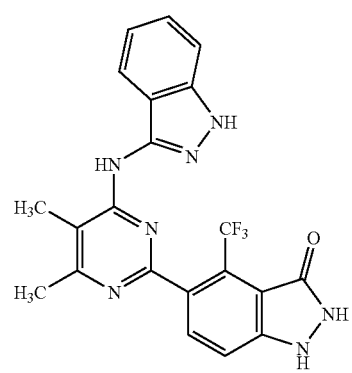
II-(v)-9
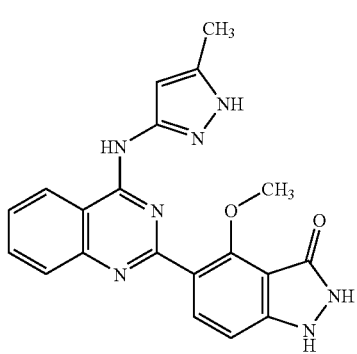
II-(v)-10
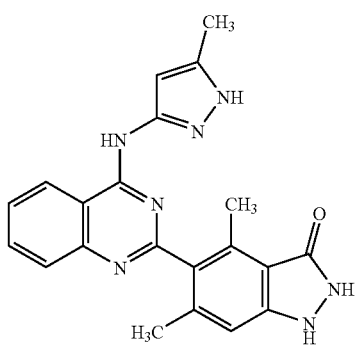
II-(v)-11
TABLE 5-continued
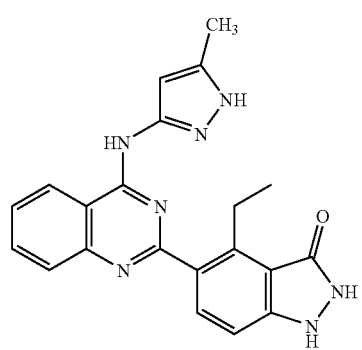
II-(v)-12
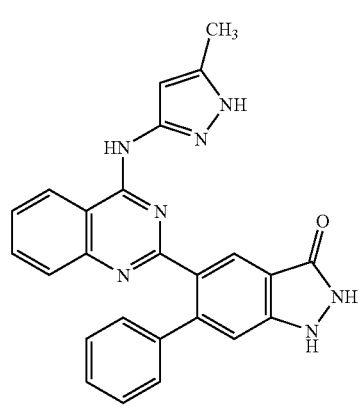
II-(v)-13
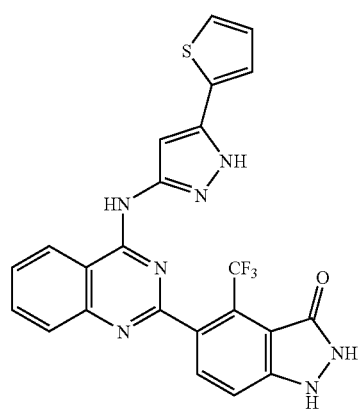
II-(v)-14

TABLE 5-continued
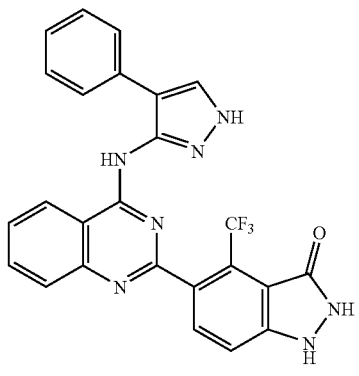
II-(v)-15
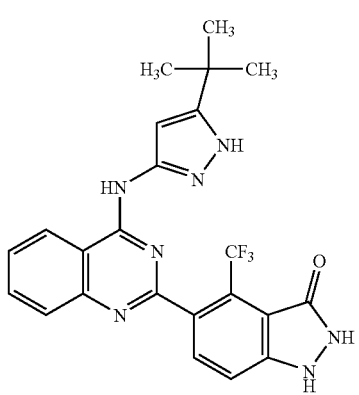
II-(v)-16
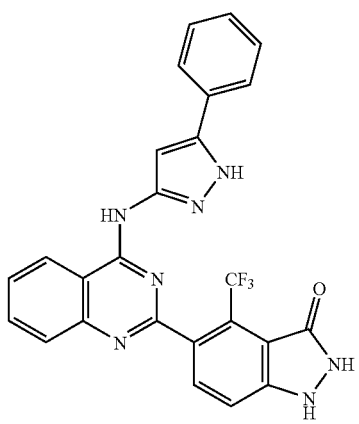
II-(v)-17
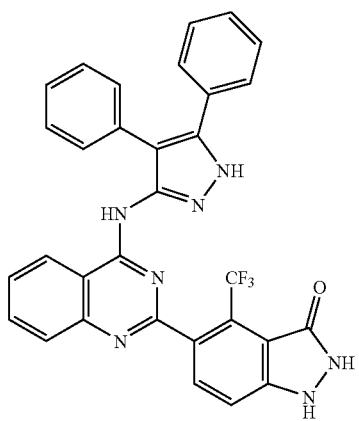
II-(v)-18
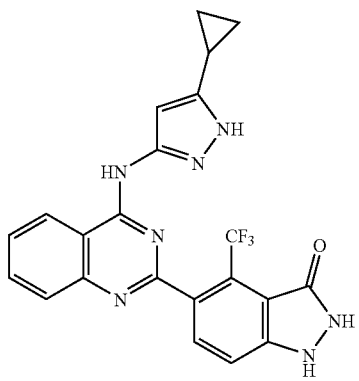
II-(v)-19
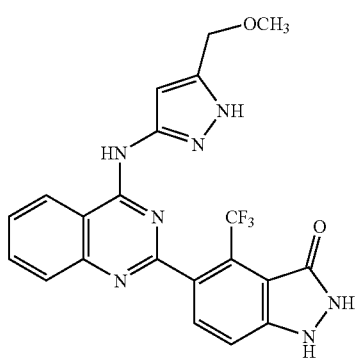
II-(v)-20

TABLE 5-continued
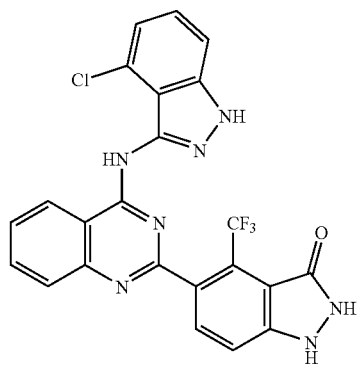
II-(v)-21
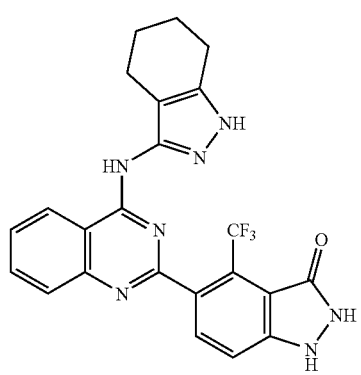
II-(v)-22
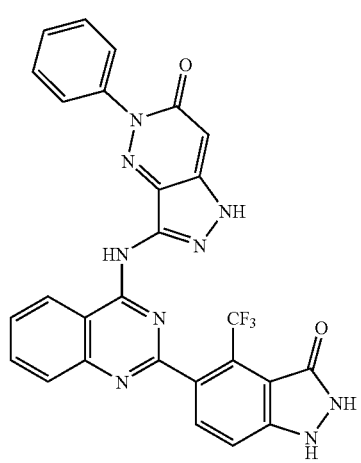
II-(v)-23
TABLE 5-continued
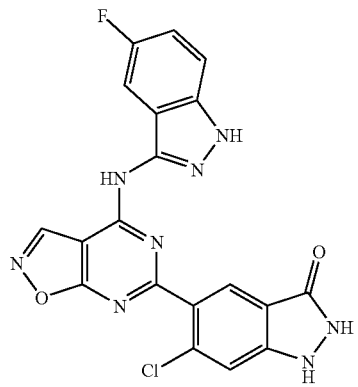
II-(v)-24
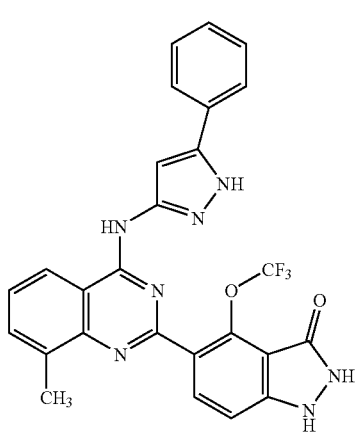
II-(v)-25
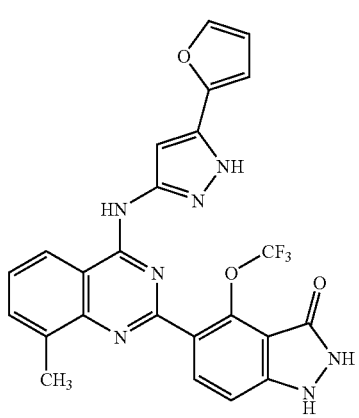
II-(v)-26

TABLE 5-continued
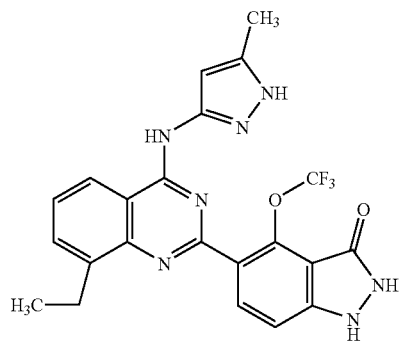
II-(v)-27
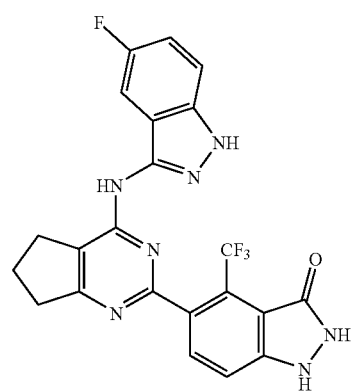
II-(v)-28
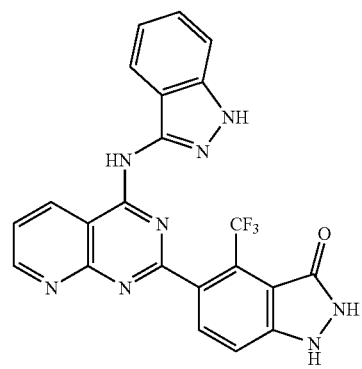
II-(v)-29
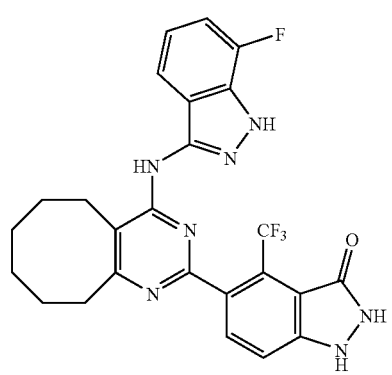
II-(v)-30
TABLE 5-continued
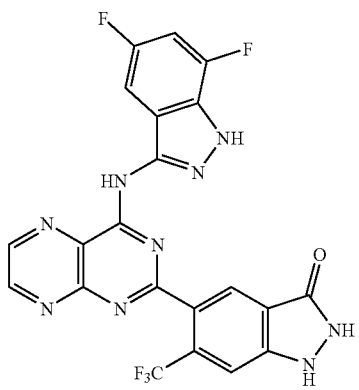
II-(v)-31
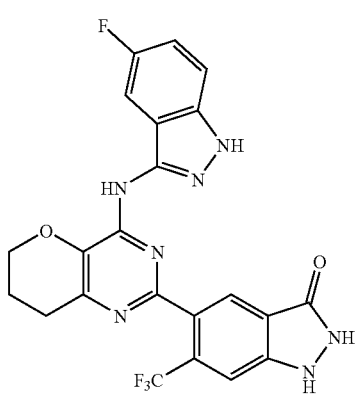
II-(v)-32
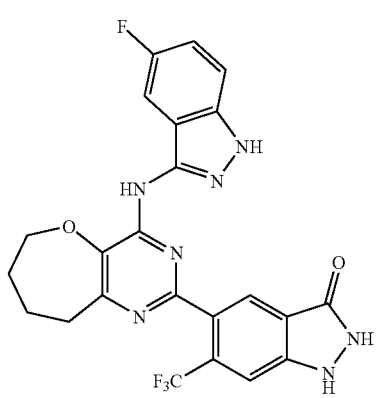
II-(v)-33

TABLE 5-continued
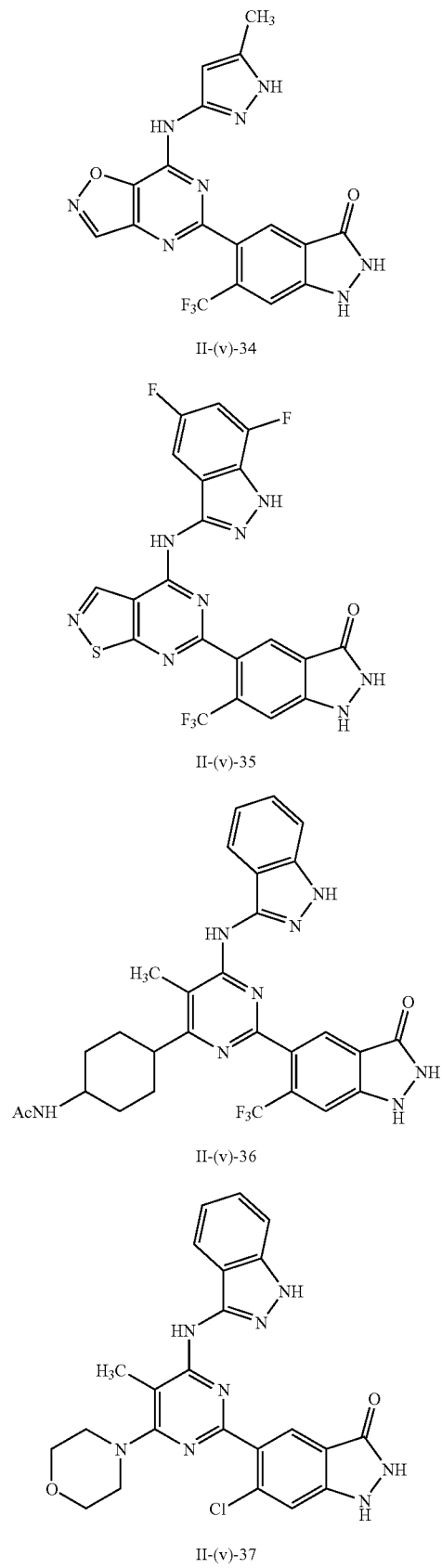
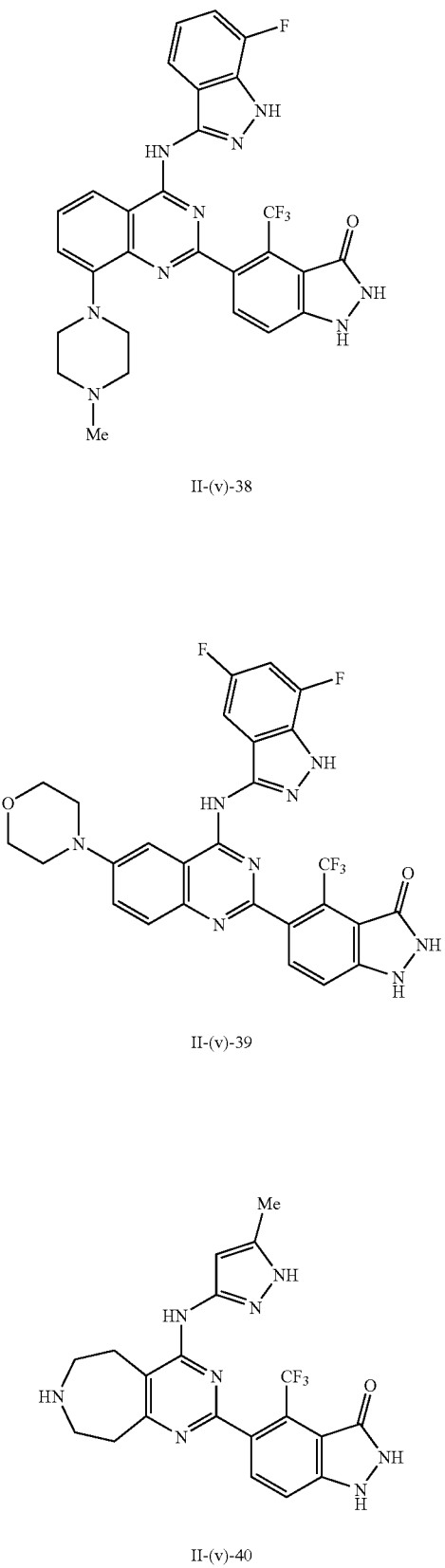

TABLE 5-continued
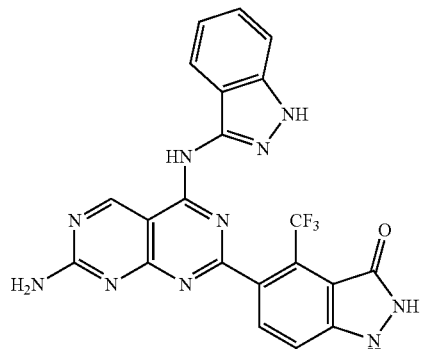
II-(v)-41
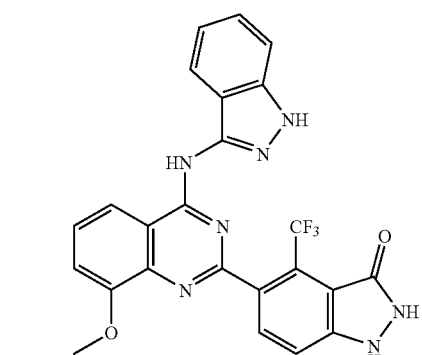
II-(v)-42
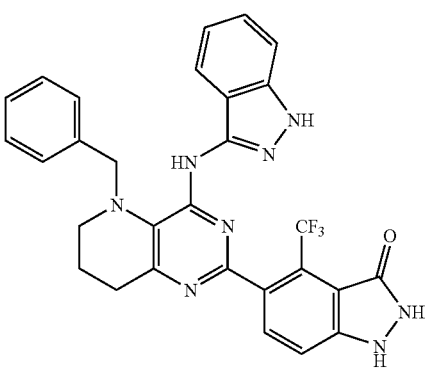
II-(v)-43
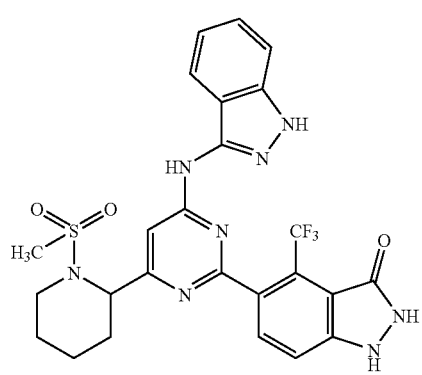
II-(v)-44
TABLE 5-continued
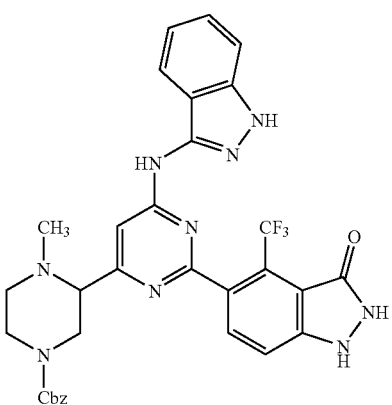
II-(v)-45
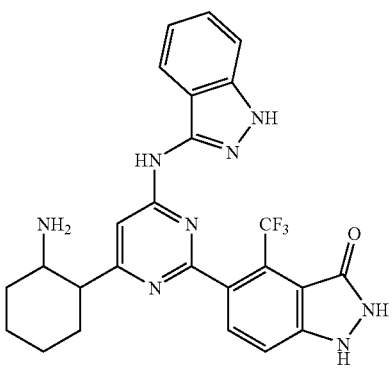
II-(v)-46
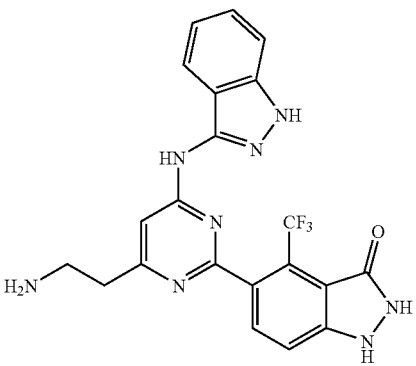
II-(v)-47

TABLE 5-continued
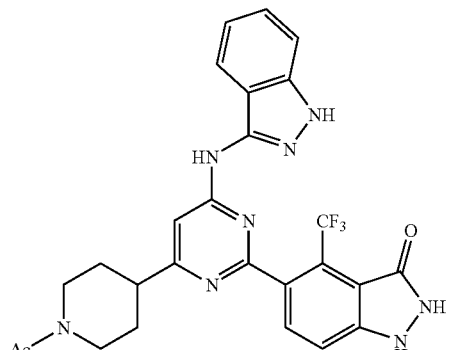
II-(v)-48
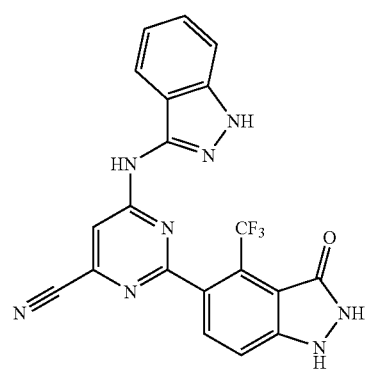
II-(v)-49
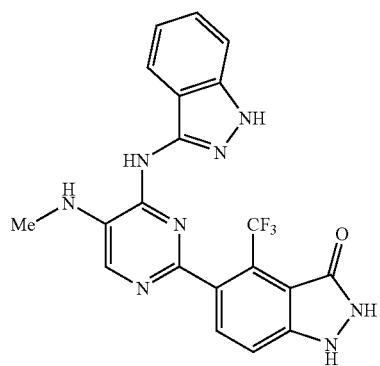
II-(v)-50
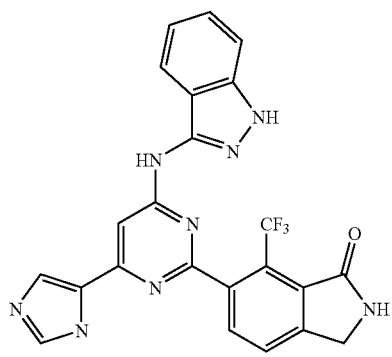
II-(v)-51
TABLE 5-continued
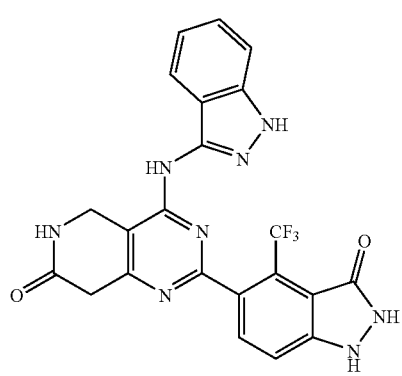
II-(v)-52
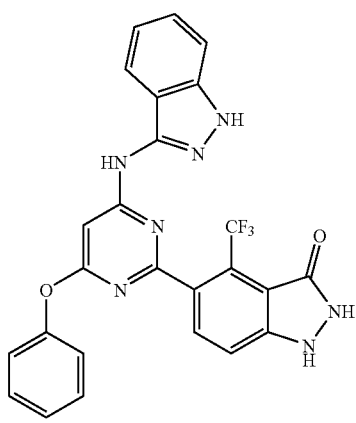
II-(v)-53
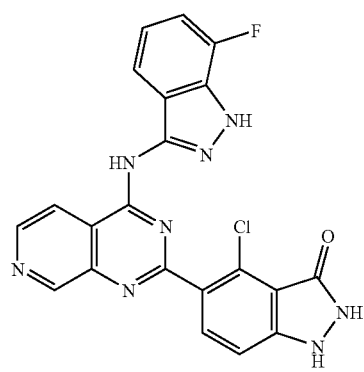
II-(v)-54

TABLE 5-continued
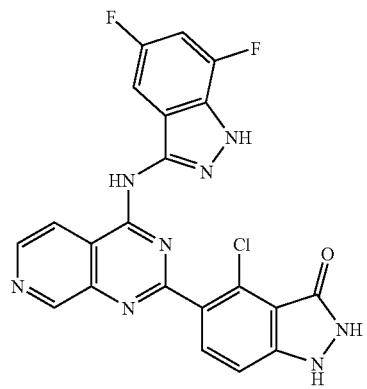
II-(v)-55
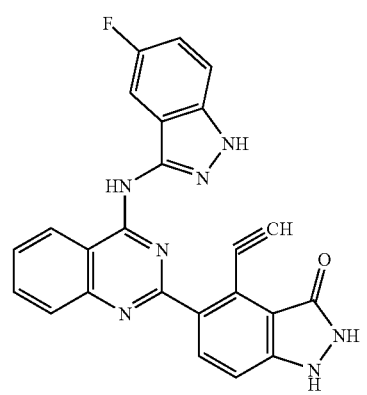
II-(v)-56
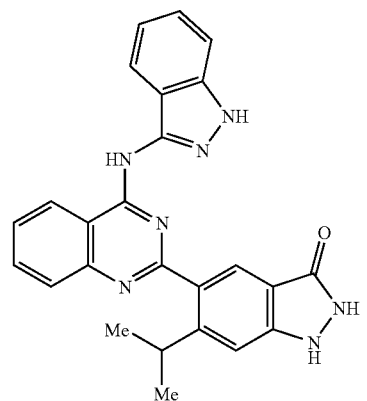
II-(v)-57
TABLE 5-continued
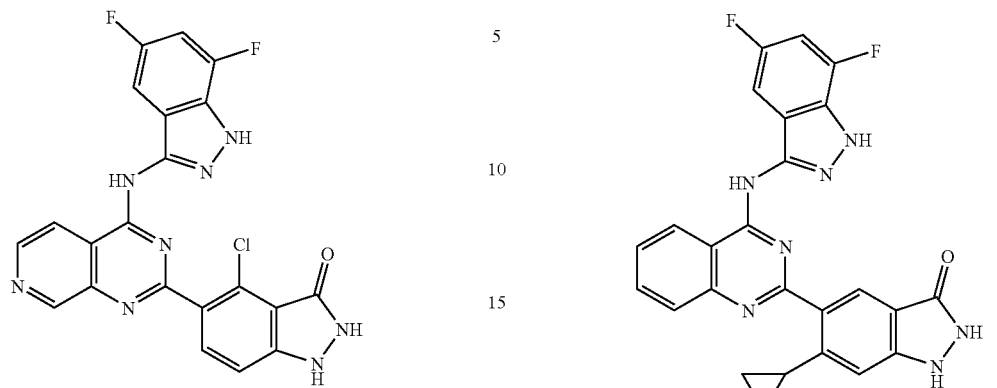
II-(v)-58
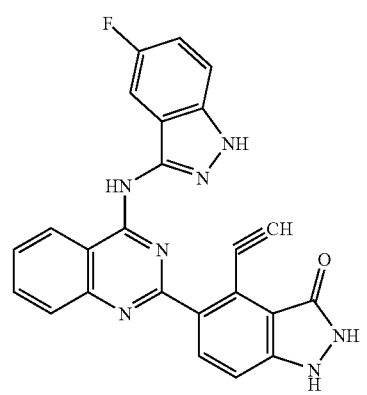
II-(v)-59
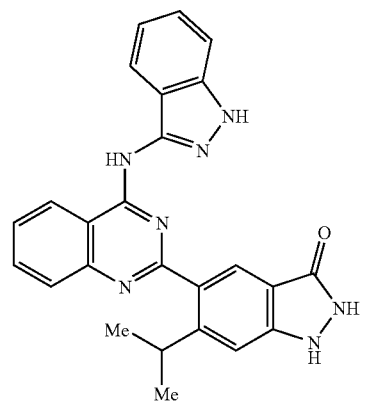
II-(v)-60

TABLE 5-continued
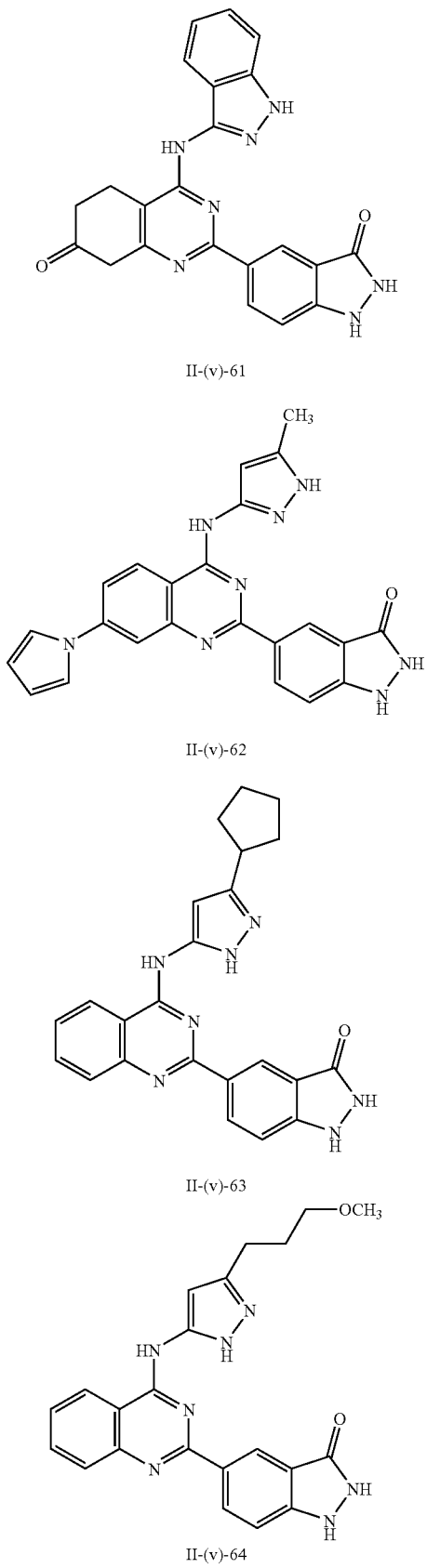
II-(v)-61
II-(v)-62
II-(v)-63
II-(v)-64
TABLE 5-continued
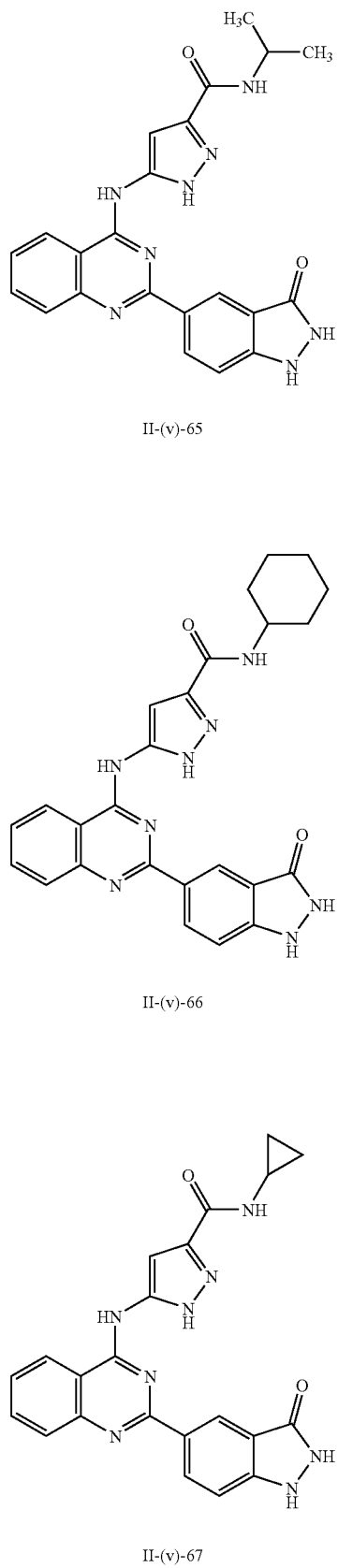
II-(v)-65
II-(v)-66
II-(v)-67

TABLE 5-continued
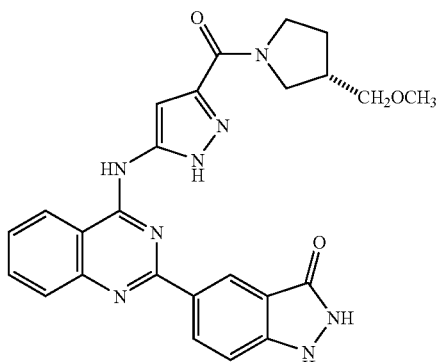
II-(v)-68
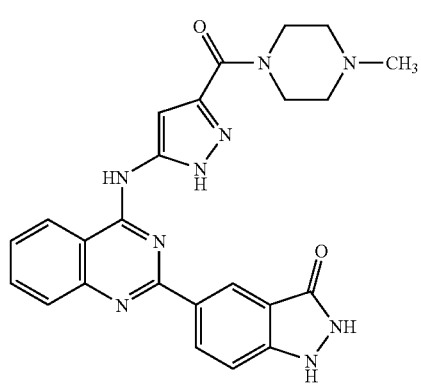
II-(v)-69
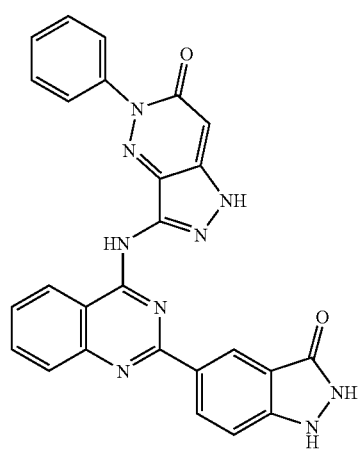
II-(v)-70
TABLE 5-continued
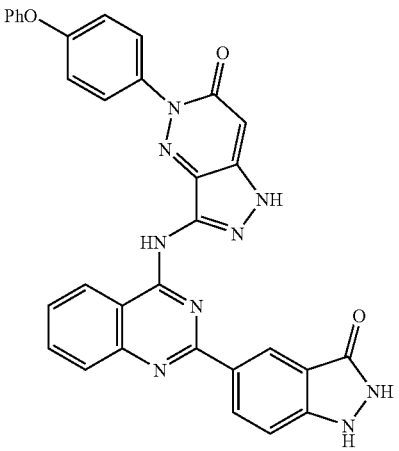
II-(v)-71
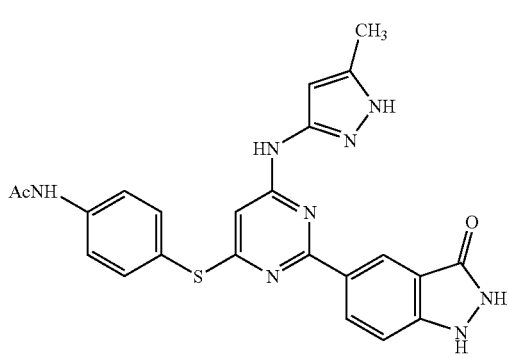
II-(v)-72
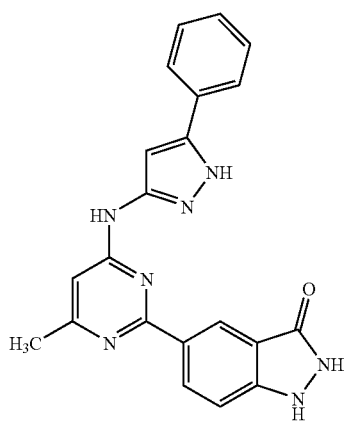
II-(v)-73

TABLE 5-continued
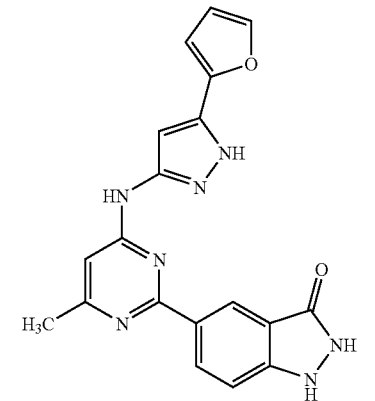
II-(v)-74
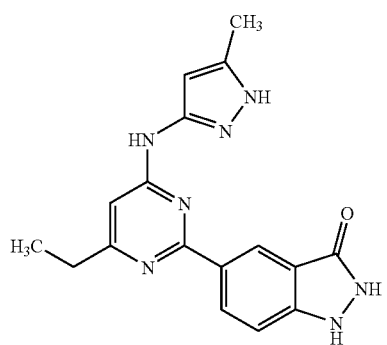
II-(v)-75
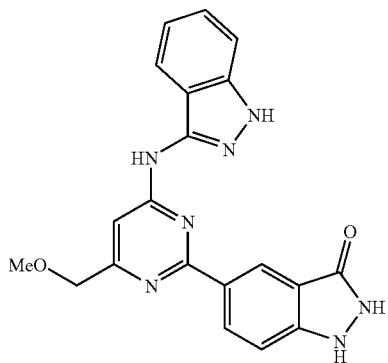
II-(v)-76
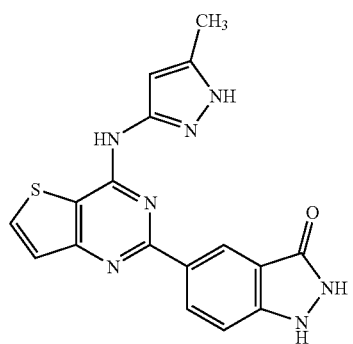
II-(v)-77
TABLE 5-continued
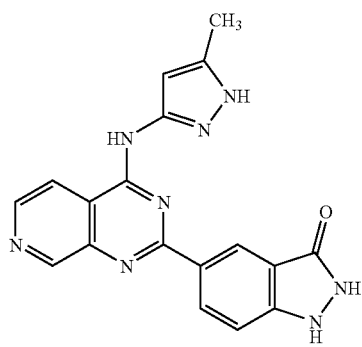
II-(v)-78
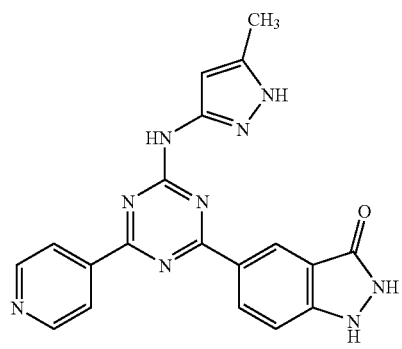
II-(v)-79
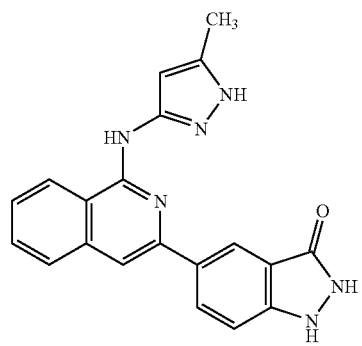
II-(v)-80
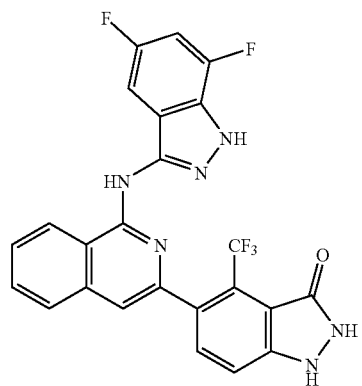
II-(v)-81

TABLE 5-continued
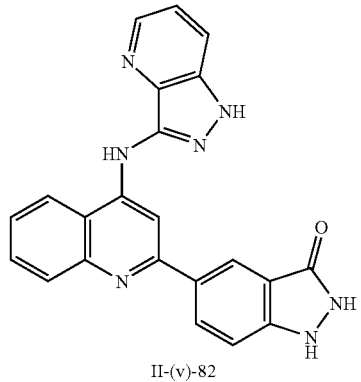
II-(v)-82
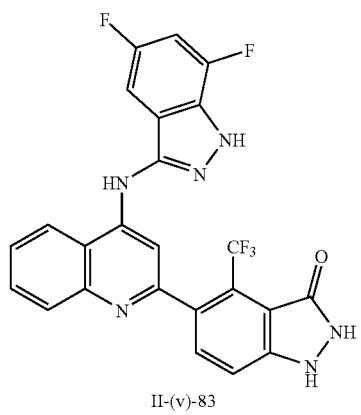
II-(v)-83
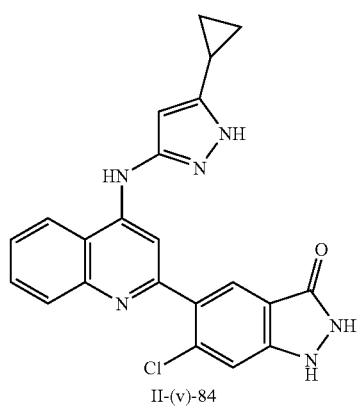
II-(v)-84
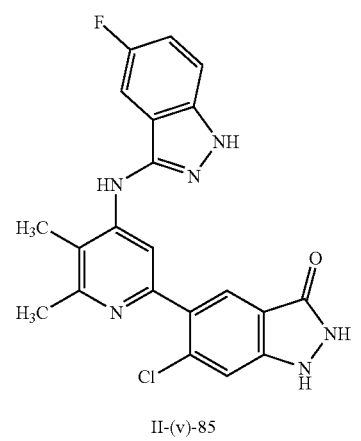
II-(v)-85
TABLE 5-continued
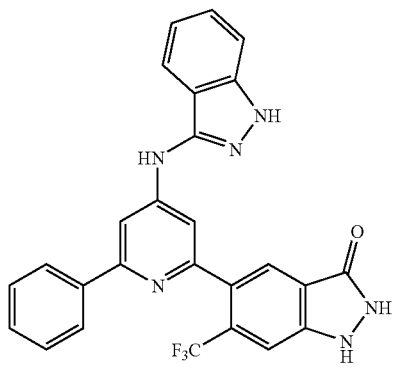
II-(v)-86
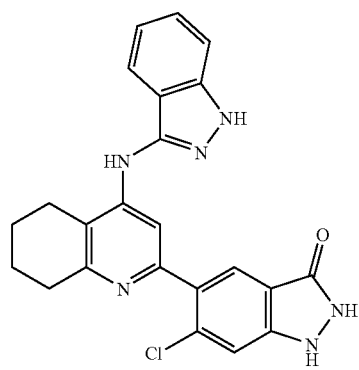
II-(v)-87
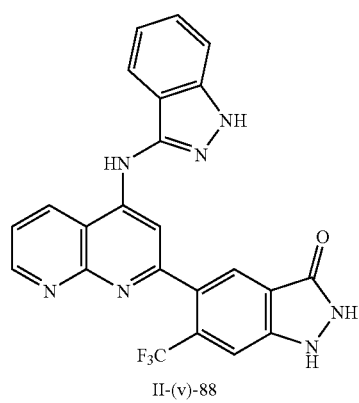
II-(v)-88

TABLE 5-continued
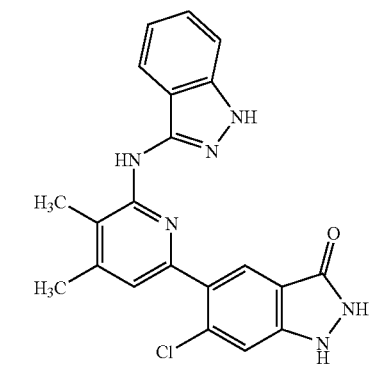
II-(v)-89
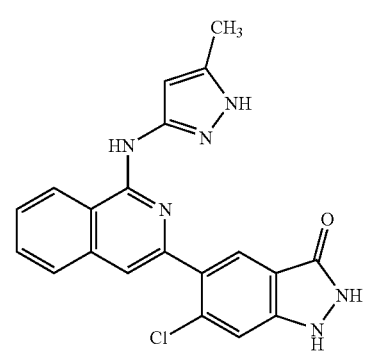
II-(v)-90
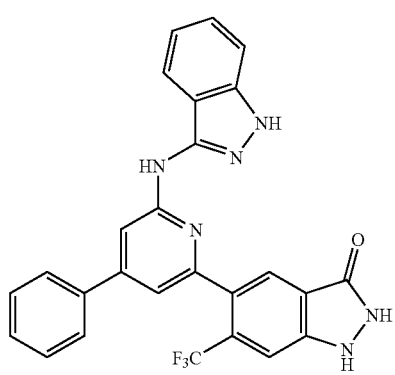
II-(v)-91
TABLE 5-continued
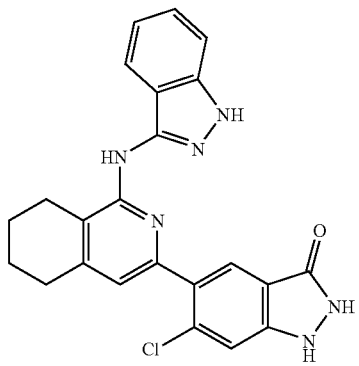
II-(v)-92
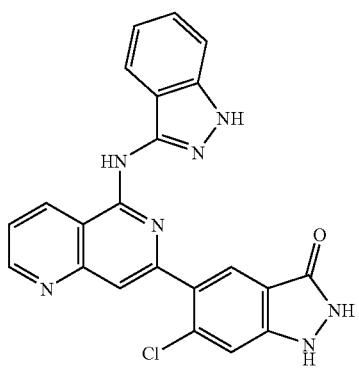
II-(v)-93
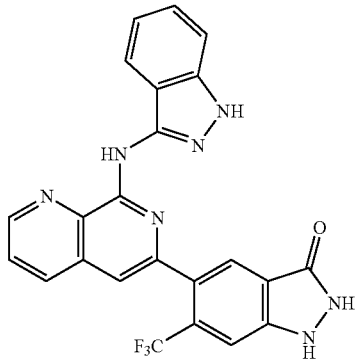
II-(v)-94
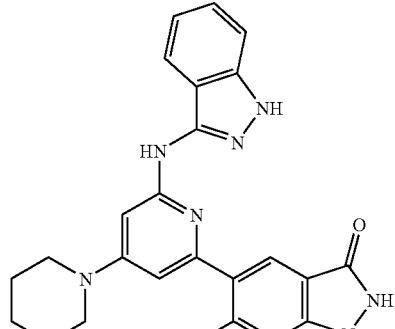
II-(v)-95

TABLE 5-continued
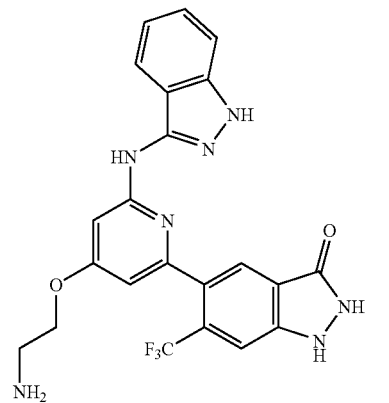
II-(v)-96
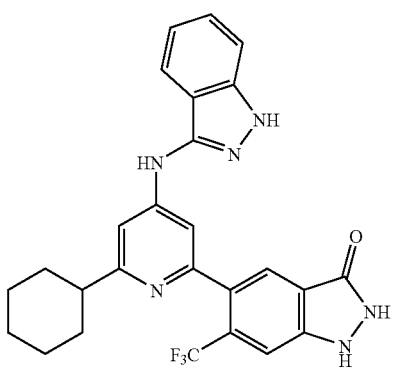
II-(v)-97
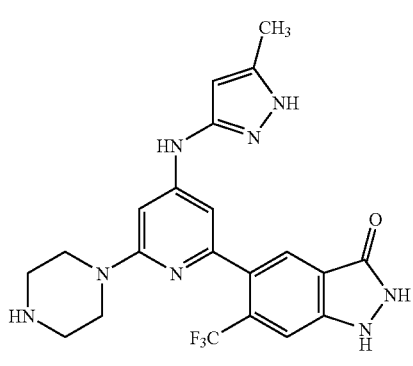
II-(v)-98
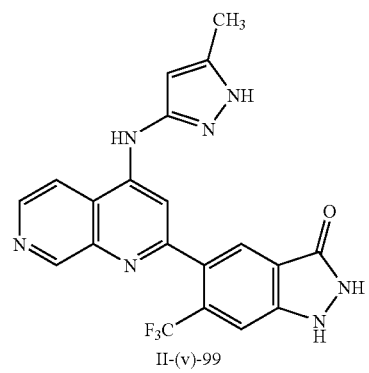
II-(v)-99
TABLE 5-continued
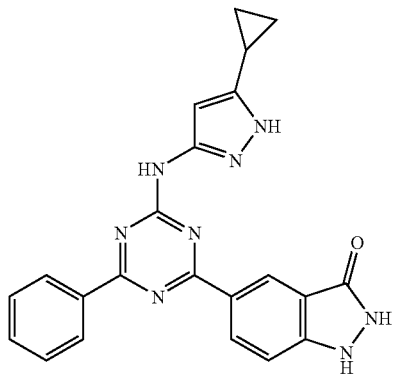
II-(v)-100
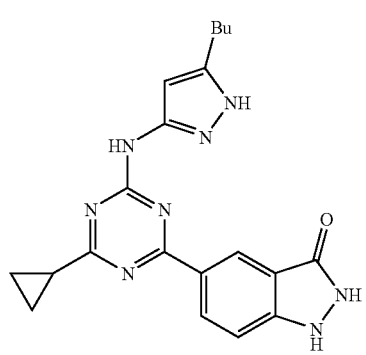
II-(v)-101
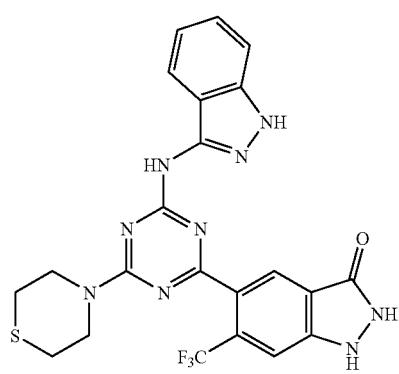
II-(v)-102
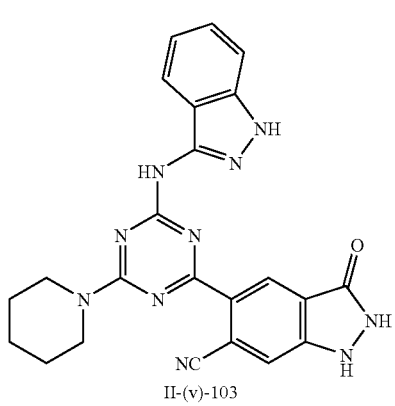
II-(v)-103

TABLE 5-continued
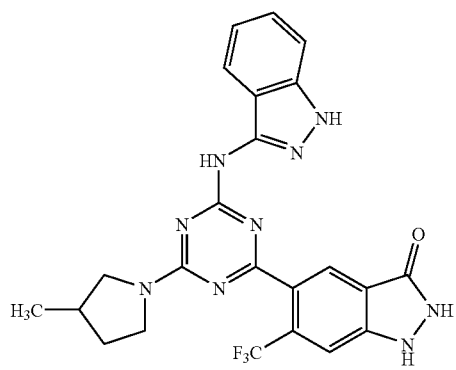
II-(v)-104
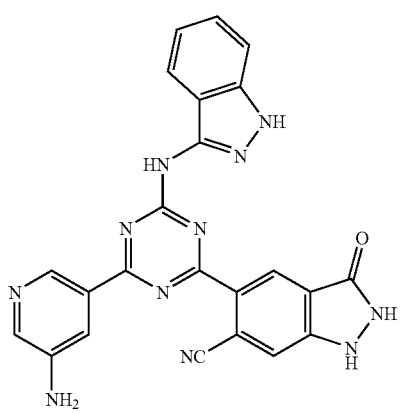
II-(v)-105
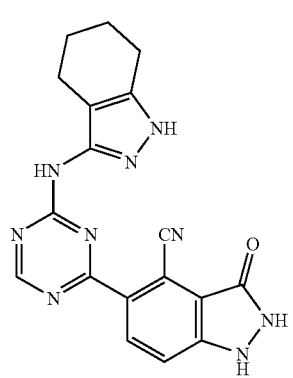
II-(v)-106
TABLE 5-continued
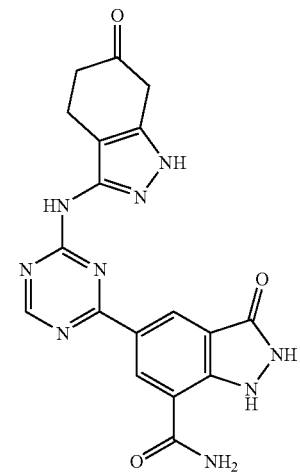
II-(v)-107
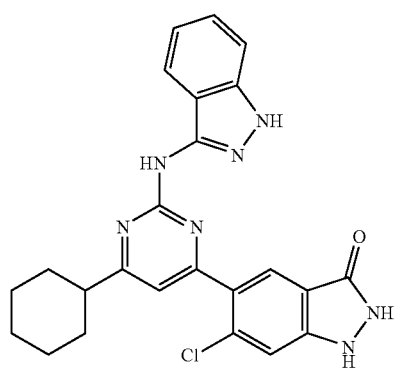
II-(v)-108
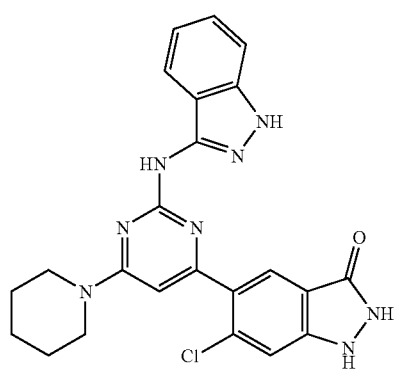
II-(v)-100

TABLE 5-continued
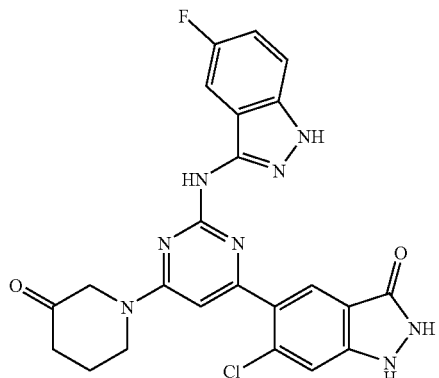
II-(v)-110
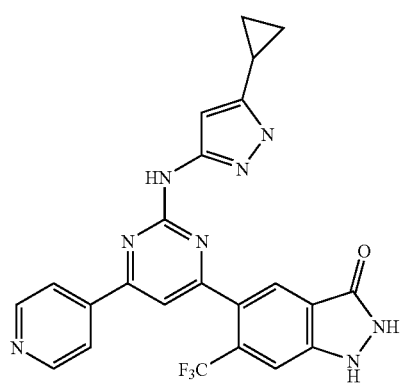
II-(v)-111
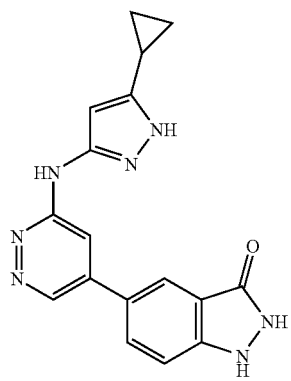
II-(v)-112
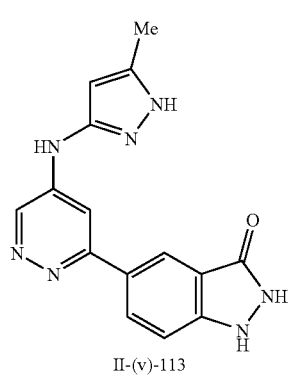
II-(v)-113
TABLE 5-continued
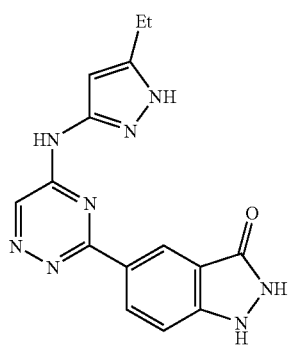
II-(v)-114
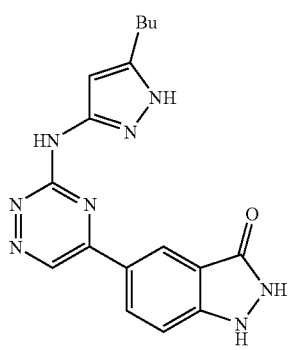
II-(v)-115
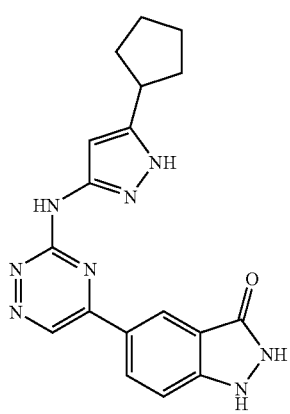
II-(v)-116

TABLE 5-continued
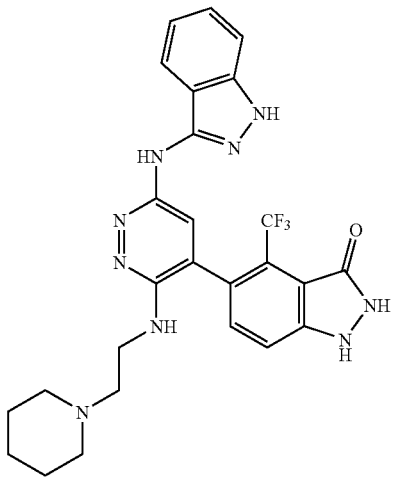
II-(v)-117
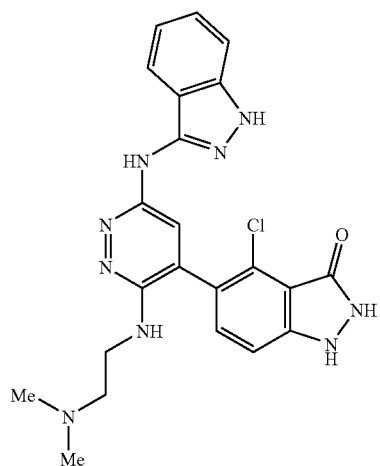
II-(v)-118
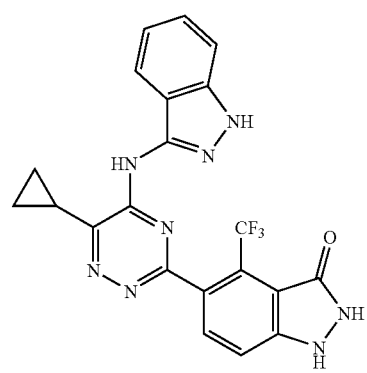
II-(v)-119
TABLE 5-continued
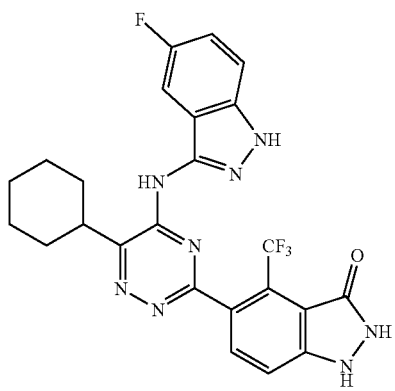
II-(v)-120
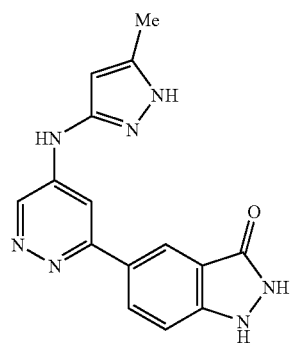
II-(v)-121
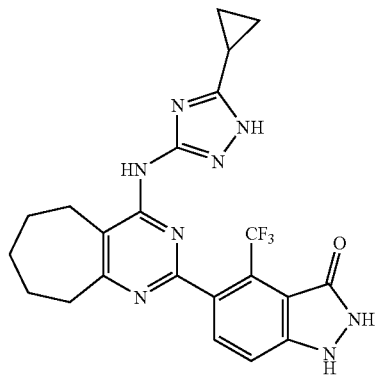
II-(v)-122

TABLE 5-continued
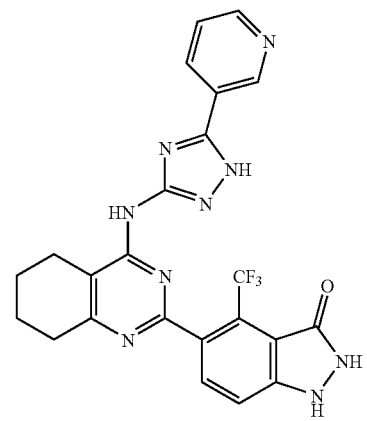
II-(v)-123
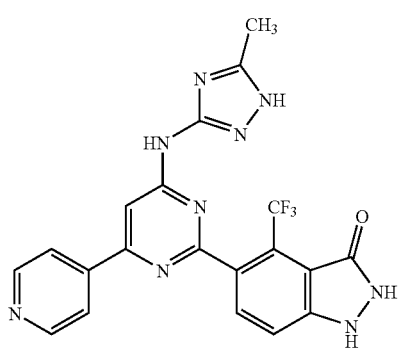
II-(v)-124
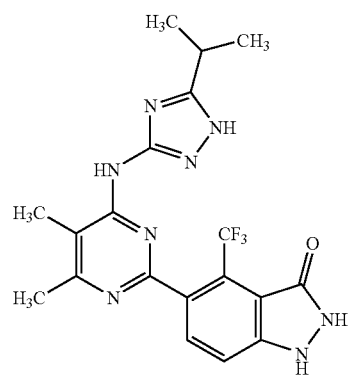
II-(v)-125
TABLE 5-continued
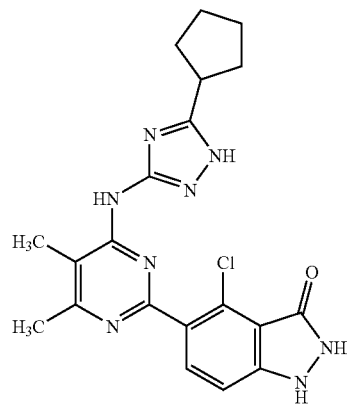
II-(v)-126
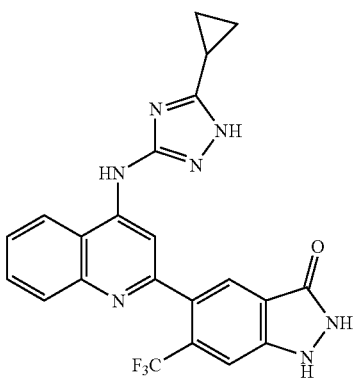
II-(v)-127
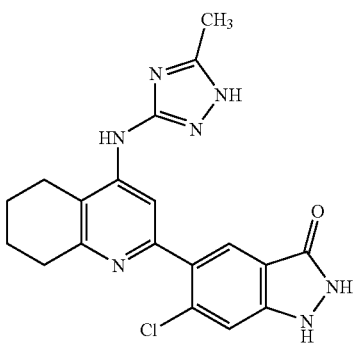
II-(v)-128
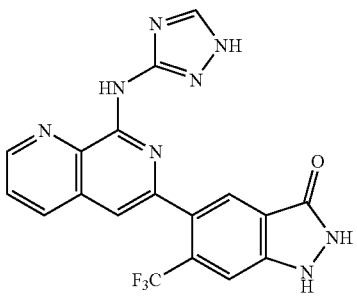
II-(v)-129

TABLE 5-continued

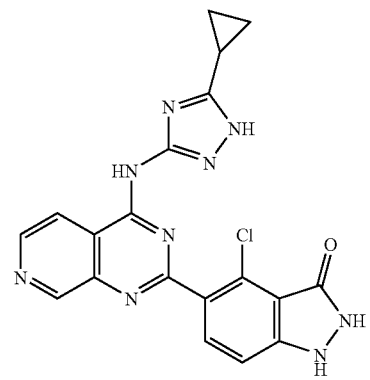

II-(v)-130

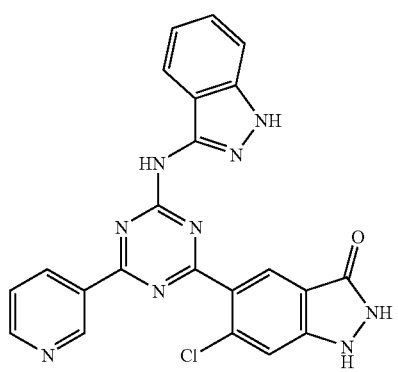

II-(v)-131

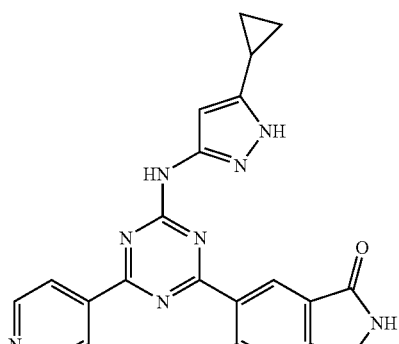

II-(v)-132

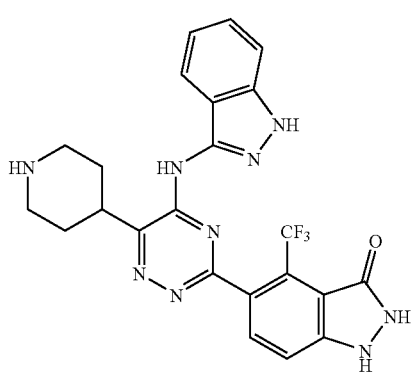

TABLE 5-continued

II-(v)-133

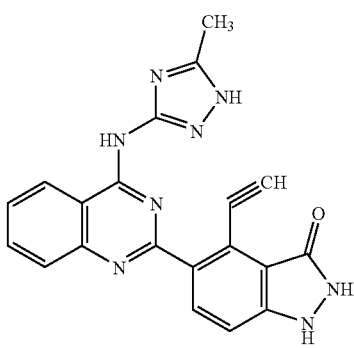

II-(v)-134

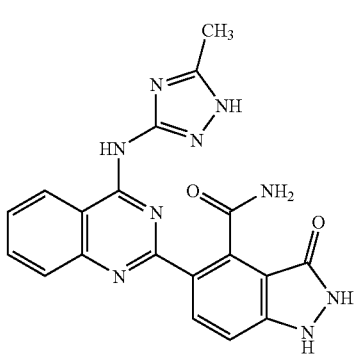

II-(v)-135

In certain other exemplary subsets, for compounds of formulas I, Ia and Ib, either of $R^3$ or $R^4$ is —$Q^1$—A—$Q^2$—Y, wherein A is an optionally substituted cycloaliphatic or heterocycloaliphatic moiety and compounds have the general formula IIIa or IIIb:

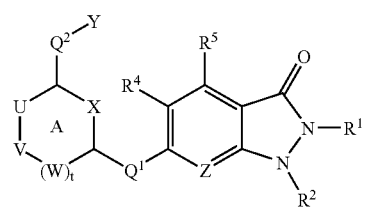

IIIa

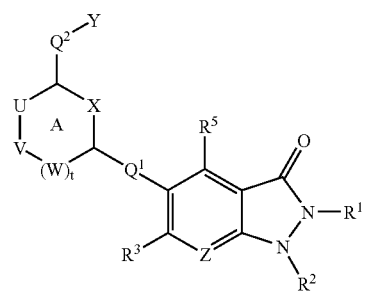

IIIb wherein $R^1$, $R^2$, $R^3$, $R^5$, $R^5$, Z, $Q^1$, $Q^2$, and Y are as defined generally above, U is $NR^{13}$, $C(R^{14})_2$, or O; V is $NR^{13}$, $C(R^{14})_2$, or O; W is $NR^{13}$, $C(R^{14})_2$, or O, and X is $NR^{13}$, $C(R^{14})_2$, or O, and t is 0, 1 or 2, wherein each occurrence of $R^{13}$ is independently hydrogen, —R', —COR', —CO$_2$(R'), —CON(R')$_2$, or —SO$_2$R', wherein each occurrence of R' is independently hydrogen, optionally substituted group selected from $C_{1-6}$ aliphatic, $C_{1-6}$heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring; and wherein each occurrence of $R^{14}$ is independently —R, with the proviso that when any one of U, V, W, or X is O or $NR^{13}$, an adjacent group U, V, W or X is $C(R^{14})_2$.

In certain embodiments, the ring A is selected from the following group:

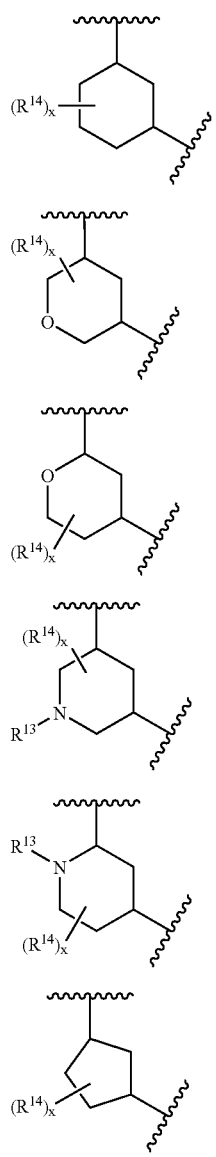

wherein $R^{13}$ is hydrogen, —R', —COR', —CO$_2$(R'), —CON(R')$_2$, or —SO$_2$R', wherein each occurrence of R' is independently hydrogen, optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or heteroaryl ring; $R^{14}$ is oxo or —R; and x is 0–4.

In certain preferred embodiments, x is 0 or 1 and $R^{14}$ is -halo, —N($R^7$)$_2$, —$C_{1-3}$ alkyl, —$C_{1-3}$ haloalkyl, —NO$_2$, —O($C_{1-3}$ alkyl), —CO$_2$($C_{1-3}$ alkyl), —CN, —SO$_2$($C_{1-3}$ alkyl), —SO$_2$NH$_2$, —OC(O)NH$_2$, —NH$_2$SO$_2$($C_{1-3}$ alkyl), —NHC(O)($C_{1-3}$ alkyl), —C(O)NH$_2$, and —CO($C_{1-3}$ alkyl), wherein the ($C_{1-3}$ alkyl) is most preferably methyl.

In certain preferred embodiments $R^{13}$ is hydrogen or $C_{1-4}$alkyl.

In still other preferred embodiments, ring A is selected from one of xi, xii or xvi and x is 0.

As described generally above, Y is an optionally substituted aryl, heteoaryl, aliphatic or heteroaliphatic moiety. In certain exemplary embodiments, for compounds of general formulas I, Ia, Ib, IIa or IIIb (and subsets thereof as described in detail herein) Y is an optionally substituted heteroaryl moiety. In certain preferred embodiments, Y is selected from one of the following heteroaryl moieties a–y:

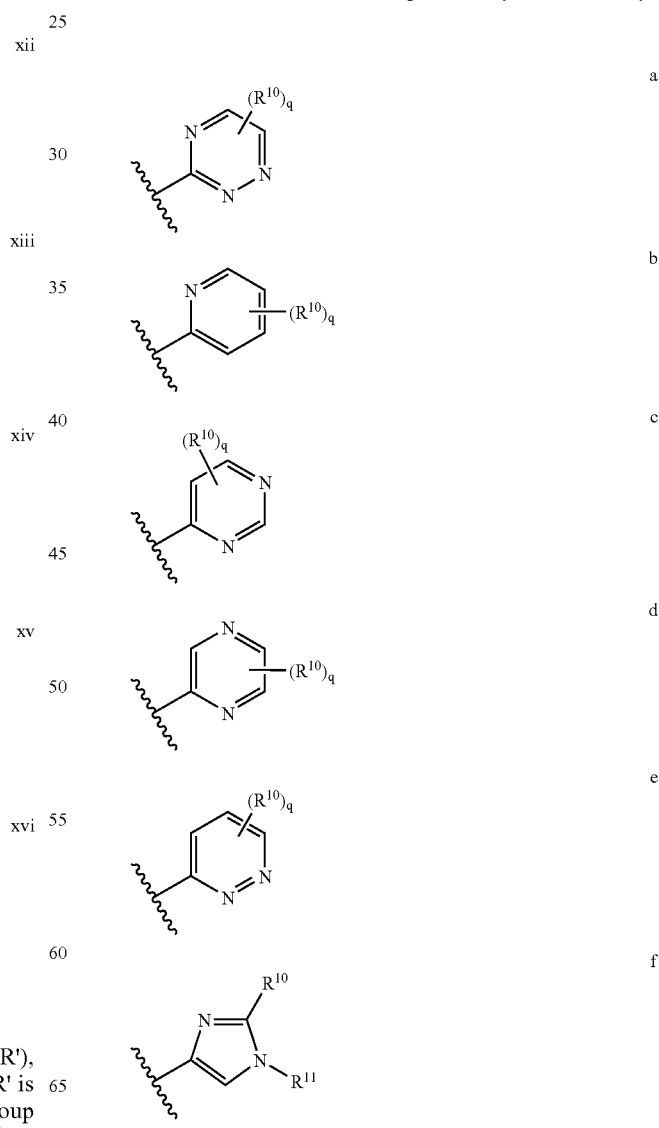

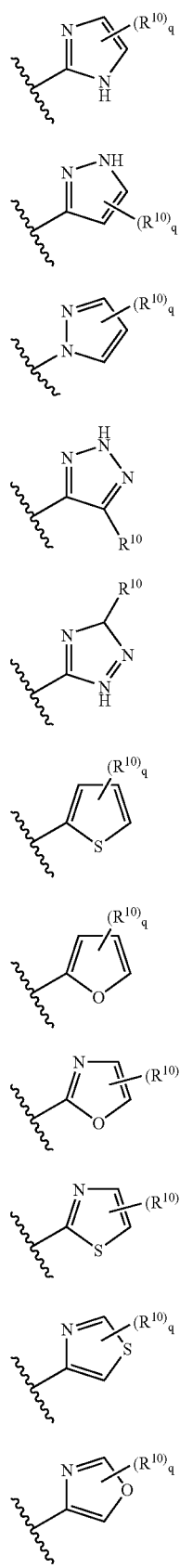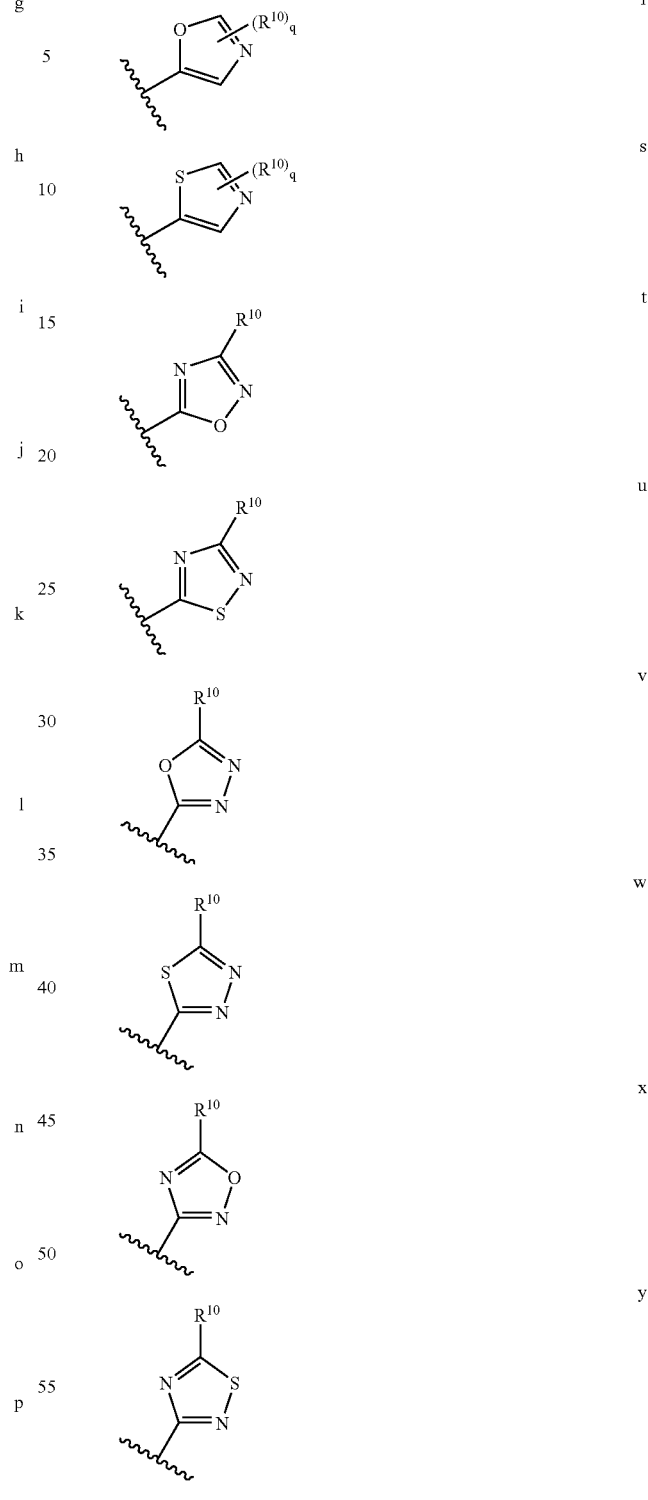

wherein q is 0–4, $R^{10}$ is —R, wherein —R is defined generally above and in classes and subclasses herein, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

In certain other exemplary embodiments, Y is one of the following heteroaryl moieties:

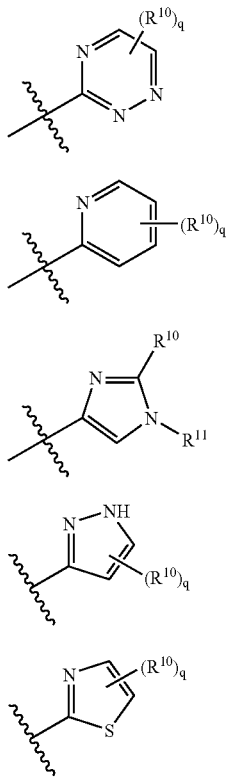

wherein q is 0–4, $R^{10}$ is —R, wherein —R is defined generally above and in classes and subclasses herein, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

In certain preferred embodiments, Y is a pyrazole moiety, h.

Preferred $R^{10}$ groups include hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle) carbonyl. Examples of such preferred $R^{10}$ substituents include methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl).

In certain preferred embodiments, Y is a pyrazole moiety, h', wherein the pyrazole is substituted with two occurrences of $R^{10}$ ($R^{10a}$ and $R^{10b}$ as depicted), wherein $R^{10a}$ and $R^{10b}$ are each independently —R.

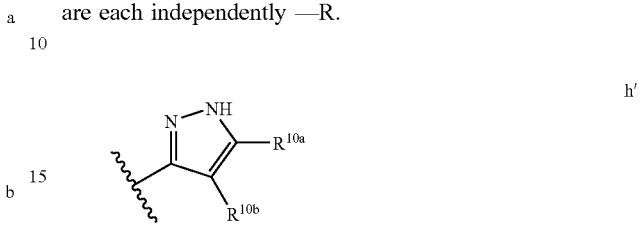

Preferred groups for $R^{10a}$ and $R^{10b}$ include those preferred groups exemplified for $R^{10}$ above. In certain embodiments, preferred groups for $R^{10a}$ include hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle) carbonyl. Examples of such preferred $R^{10a}$ substituents include methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl). A preferred group for $R^{10b}$ is hydrogen.

As described generally above, two occurrences of $R^{10}$ (e.g., $R^{10a}$ and $R^{10b}$ as depicted above in formula h') taken together may represent an optionally substituted group selected from a cycloaliphatic, cycloheteroaliphatic, aryl or heteroaryl moiety. In certain preferred embodiments, Y is one of the following groups:

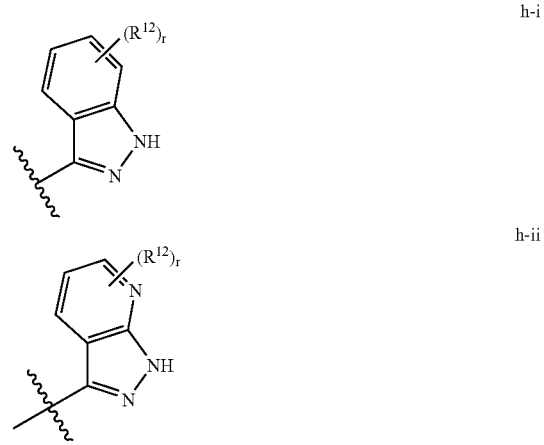

-continued

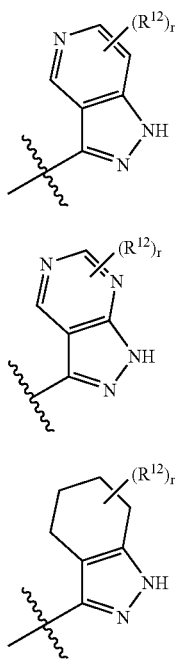

h-iii h-iv h-v wherein r is 0–4 and R$^{12}$ is —R, wherein —R is defined generally above and in classes and subclasses herein. Preferred substituents R$^{12}$ on the fused ring include one or more of the following: -halo, —N(R$^7$)$_2$, —C$_{1-3}$ alkyl, —C$_{1-3}$ haloalkyl, —NO$_2$, —O(C$_{1-3}$ alkyl), —CO$_2$(C$_{1-3}$ alkyl), —CN, —SO$_2$(C$_{1-3}$ alkyl), —SO$_2$NH$_2$, —OC(O)NH$_2$, —NH$_2$SO$_2$(C$_{1-3}$ alkyl), —NHC(O)(C$_{1-3}$ alkyl), —C(O)NH$_2$, and —CO(C$_{1-3}$ alkyl), wherein the (C$_{1-3}$ alkyl) is most preferably methyl, wherein each occurrence of R$^7$ is independently hydrogen, an optionally substituted group selected from aliphatic, heteroaliphatic, aryl or heteroaryl, or two occurrences of R$^7$ on the same nitrogen atom are taken together with the nitrogen atom to form an optionally substituted group selected from a 5–8 membered heterocyclic or 5–8 membered heteroaryl ring.

In still other embodiments, for compounds of formulas I, Ia, Ib, IIa or IIIb (or subsets thereof as detailed herein) when R$^3$ is —Q$^1$—A—Q$^2$—Y, R$^4$ is preferably hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl. In most preferred embodiments R$^4$ is hydrogen, methyl, ethyl, cyclopropyl, hydroxy, phenyl or —CH$_2$NH$_2$.

In yet other embodiments, for compounds of formulas I, Ia, Ib, IIa or IIIb (or subsets thereof as detailed herein), when R$^4$ is 4'—A—Q$^2$—Y, R$^3$ is preferably hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl. In most preferred embodiments R$^3$ is hydrogen, methyl, ethyl, cyclopropyl, hydroxy, phenyl or —CH$_2$NH$_2$.

In certain other preferred embodiments, for compounds of formulas I, Ia, Ib, IIIa or IIIb (or subsets thereof as detailed herein), R$^5$ is hydrogen, halogen, —NO$_2$, —CN, hydroxy, optionally substituted C$_{1-3}$alkyl, optionally substituted alkoxy, —SO$_2$NH$_2$, or —C(O)alkyl. In more preferred embodiments, R$^5$ is Cl, CF$_3$, OCF$_3$, CH$_3$, —CN, —SO$_2$NH$_2$ or —C(O)Me.

In certain embodiments, a preferred subclass of compounds of general formula IIIa or IIIb include those compounds where Q$^1$ is NH and Q$^2$ is NH. These compounds are defined by the general formula IIIa(i) or IIIb(i) and are depicted generally below:

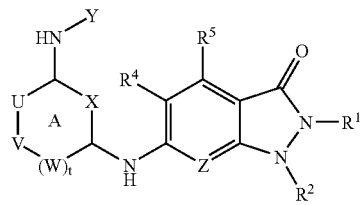

IIIa(i)

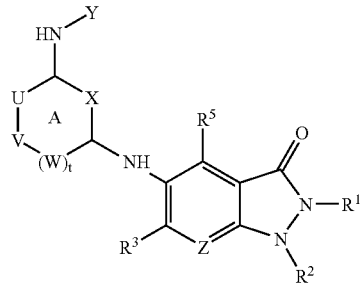

IIIb(i)

It will be appreciated that, for compounds of general formulas IIIa(i) and IIIb(i) certain additional subclasses are of special interest. Certain preferred embodiments of compounds of formula IIIa(i) or IIIb(i) include those compounds having any combination of the following features for each variable for formula IIIa(i) or IIIb(i):

i) Z is CR$^6$ or N;

ii) R$^1$, R$^2$, R$^4$ and R$^5$ are each hydrogen and wherein Z is CHR$^6$ and R$^6$ is hydrogen; or R$^1$, R$^2$, R$^3$ and R$^5$ are each hydrogen and wherein Z is CHR$^6$ and R$^6$ is hydrogen;

iii) ring A is defined according to one of the following groups:

a. ring A is selected from one of the groups:

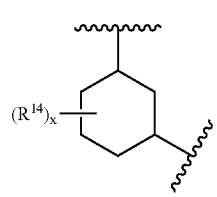

xi

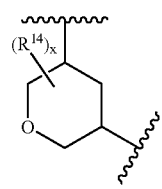

xii

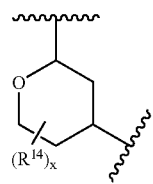

xiii

-continued

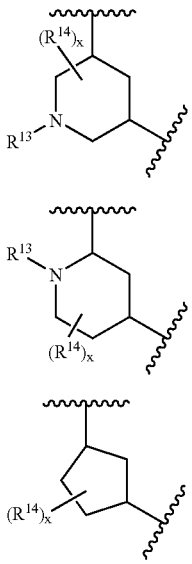

xiv

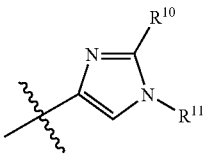

xv

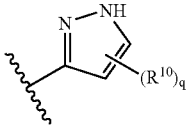

xvi

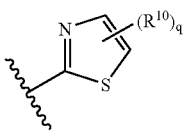

wherein $R^{13}$ is hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring; $R^{14}$ is oxo or —R; and x is 0–4; or b. ring A is selected from one of xi, xii or xvi and x is 0 or 1; $R^{14}$ is -halo, —N(R$^7$)$_2$, —C$_{1-3}$ alkyl, —C$_{1-3}$ haloalkyl, —NO$_2$, —O(C$_{1-3}$ alkyl), —CO$_2$(C$_{1-3}$ alkyl), —CN, —SO$_2$(C$_{1-3}$alkyl), —SO$_2$NH$_2$, —OC(O)NH$_2$, —NH$_2$SO$_2$(C$_{1-3}$ alkyl), —NHC(O)(C$_{1-3}$ alkyl), —C(O)NH$_2$, and —CO(C$_{1-3}$ alkyl), wherein the (C$_{1-3}$ alkyl) is most preferably methyl; and $R^{13}$ is hydrogen or C$_{1-4}$alkyl;

iv) Y is defined according to one of the following groups:

a. Y is an optionally substituted heteroaryl moiety;

b. Y is selected from one of the heteroaryl moieties a–y;

c. Y is selected from one of the following heteroaryl moieties:

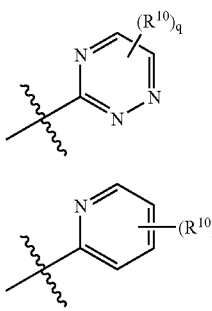

a b wherein q is 0–4, $R^{10}$ is —R, wherein —R is defined generally above and in classes and subclasses herein, and wherein each occurrence of $R^{11}$ is independently hydrogen, —R', —COR', —CO$_2$(R'), —CON(R')$_2$, or —SO$_2$R, wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

d. Y is a pyrazole moiety, h;

e. Y is one of a, b, f, h or o, optionally substituted with one or more $R^{10}$ groups, wherein each occurrence of $R^{10}$ is independently hydrogen, C$_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle) carbonyl;

f. Y is one of a, b, f, h or o, optionally substituted with one or more $R^{10}$ groups, wherein each occurrence of $R^{10}$ is independently hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl).

g. Y is a pyrazole moiety, h', wherein the pyrazole is substituted with two occurrences of $R^{10}$ ($R^{10a}$ and $R^{10b}$ as depicted),

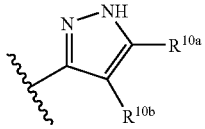
h' wherein each occurrence of $R^{10a}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl, and $R^{10b}$ is hydrogen;

h. Y is a pyrazole moiety, h', wherein the pyrazole is substituted with two occurrences of $R^{10}$ ($R^{10a}$ and $R^{10b}$ as depicted),

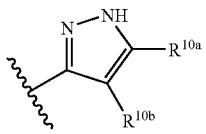
h' wherein each occurrence of $R^{10a}$ is hydrogen, methyl, cyclopropyl, ethyl, isopropyl, propyl, t-butyl, cyclopentyl, phenyl, $CO_2H$, $CO_2CH_3$, $CH_2OH$, $CH_2OCH_3$, $CH_2CH_2CH_2OH$, $CH_2CH_2CH_2OCH_3$, $CH_2CH_2CH_2OCH_2Ph$, $CH_2CH_2CH_2NH_2$, $CH_2CH_2CH_2NHCOOC(CH_3)_3$, $CONHCH(CH_3)_2$, $CONHCH_2CH=CH_2$, $CONHCH_2CH_2OCH_3$, $CONHCH_2Ph$, $CONH(cyclohexyl)$, $CON(Et)_2$, $CON(CH_3)CH_2Ph$, $CONH(n-C_3H_7)$, $CON(Et)CH_2CH_2CH_3$, $CONHCH_2CH(CH_3)_2$, $CON(n-C_3H_7)_2$, CO(3-methoxymethylpyrrolidin-1-yl), CONH(3-tolyl), CONH(4-tolyl), $CONHCH_3$, CO(morpholin-1-yl), CO(4-methylpiperazin-1-yl), $CONHCH_2CH_2OH$, $CONH_2$, and CO(piperidin-1-yl, and $R^{10b}$ is hydrogen;

i. Y is heteroaryl moiety substituted by at least two occurrences of $R^{10}$ and where two occurrences of $R^{10}$ taken together may represent an optionally substituted group selected from cycloaliphatic, cycloheteroaliphatic, aryl or heteroaryl;

j. Y represents one of the following heteroaryl moieties:

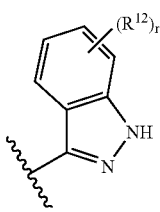
h-i

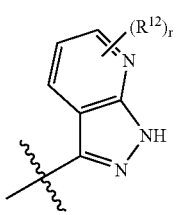
h-ii

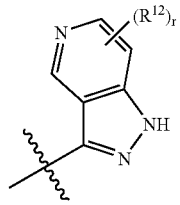
h-iii

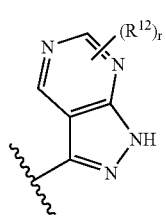
h-iv

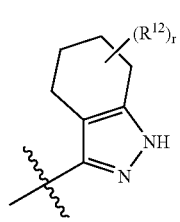
h-v wherein r is 0–4 and $R^{12}$ is hydrogen, -halo, $-N(R^7)_2$, $-C_{1-3}$ alkyl, $-C_{1-3}$ haloalkyl, $-NO_2$, $-O(C_{1-3}$ alkyl), $-CO_2(C_{1-3}$ alkyl), $-CN$, $-SO_2(C_{1-3}$ alkyl), $-SO_2NH_2$, $-OC(O)NH_2$, $-NH_2SO_2(C_{1-3}$ alkyl), $-NHC(O)(C_{1-3}$ alkyl), $-C(O)NH_2$, and $-CO(C_{1-3}$ alkyl), wherein the $(C_{1-3}$ alkyl) is most preferably methyl;

v) for compounds of formula IIa(v), $R^4$ is defined according to one of the following groups:
  a. $R^4$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
  b. $R^4$ is hydrogen, methyl, ethyl, cyclopropyl, hydroxy, phenyl or $-CH_2NH_2$;

vi) for compounds of formula IIb(v), $R^3$ is defined according to one of the following groups:
  a. $R^3$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
  b. $R^3$ is hydrogen, methyl, ethyl, cyclopropyl, hydroxy, phenyl or $-CH_2NH_2$; and vii) $R^5$ is defined according to one of the following groups:
  a. hydrogen, halogen, $-NO_2$, $-CN$, hydroxy, optionally substituted $C_{1-3}$alkyl, optionally substituted alkoxy, $-SO_2NH_2$, or $-C(O)alkyl$, or
  b. $R^5$ is hydrogen, $C_1$, $CF_3$, $OCF_3$, $CH_3$, $-CN$, $-SO_2NH_2$ or $-C(O)Me$.

In certain preferred embodiments, compounds of the invention include those compounds having general formula IIIa(i) and wherein the compounds have one or more of the following features:
  a. Z is $NR^6$, wherein $R^1$ and $R^2$ are each independently hydrogen or a protecting group; $R^4$, $R^5$ and $R^6$ are each hydrogen,
  b. ring A comprises one of the general formulas xi, xii or xvi, and c. Y is an optionally substituted heteroaryl moiety selected from one of formulas a–y.

It will be appreciated that for compounds described directly above, preferred groups for ring A of formulas xi, xii or xvi (and substituents thereon), and Y (and substituents thereon), include those preferred groups as exemplified in subclasses and species above and herein.

Representative examples of compounds of formula IIIa(i) or IIIb(i) (described generally as III(i) below but encompassing compounds of both formulas IIIa(i) and IIIb(i)), are depicted below in Table 6.

TABLE 6

Examples of Compounds of Formula III-(i):

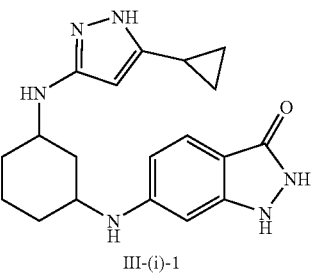

III-(i)-1

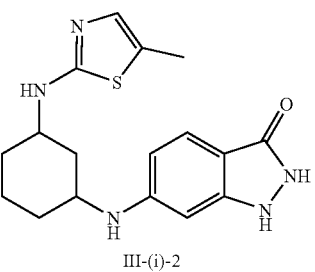

III-(i)-2


III-(i)-3

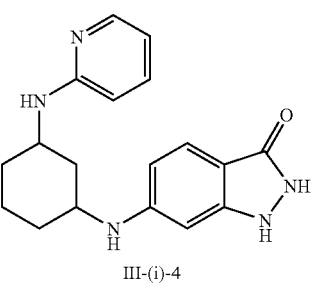

III-(i)-4

TABLE 6-continued

Examples of Compounds of Formula III-(i):

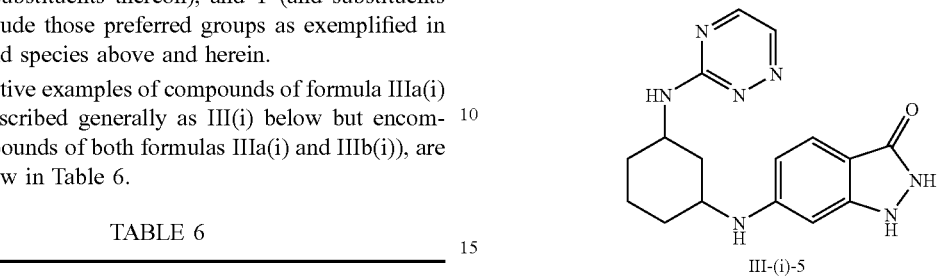

III-(i)-5

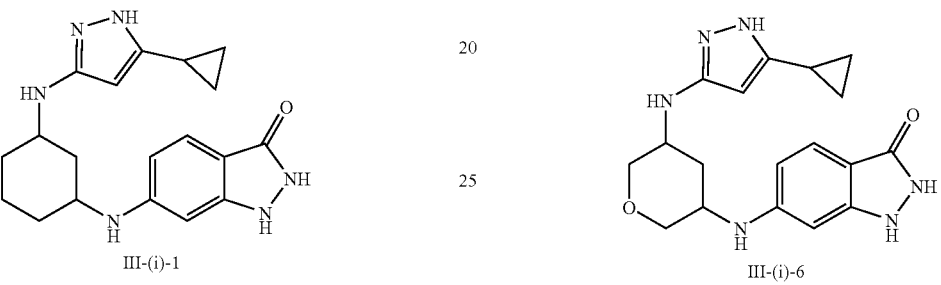

III-(i)-6

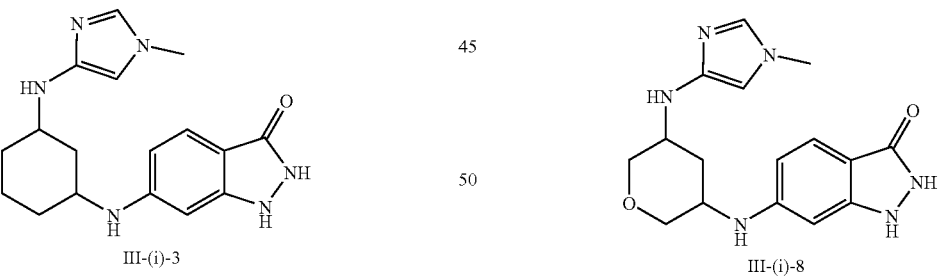

III-(i)-7

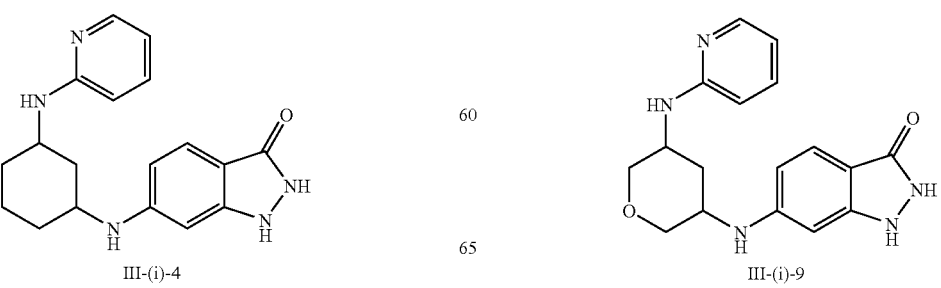

III-(i)-8

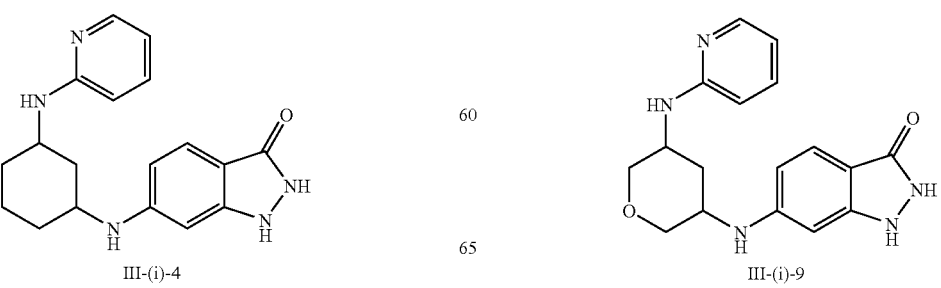

III-(i)-9

TABLE 6-continued

Examples of Compounds of Formula III-(i):

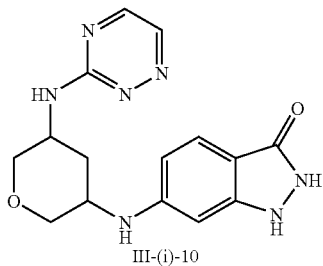
III-(i)-10

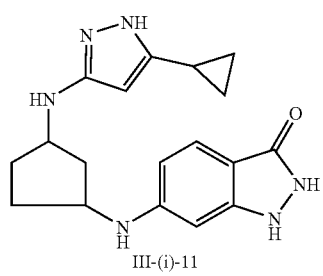
III-(i)-11

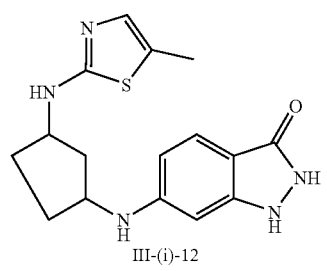
III-(i)-12

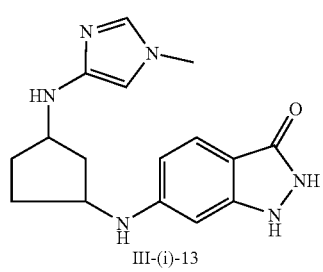
III-(i)-13

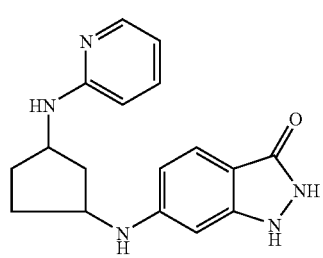

TABLE 6-continued

Examples of Compounds of Formula III-(i):

III-(i)-14

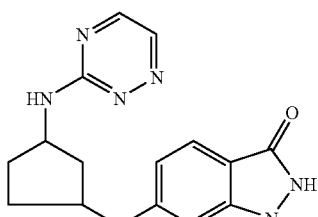

III-(i)-15

In certain embodiments, a preferred subclass of compounds of general formula IIIa or IIIb include those compounds where $Q^1$ is S, and $Q^2$ is NH. These compounds are defined by the general formula IIIa(ii) or IIIb(ii) and are depicted generally below:

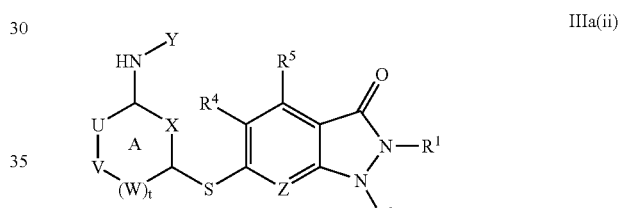
IIIa(ii)

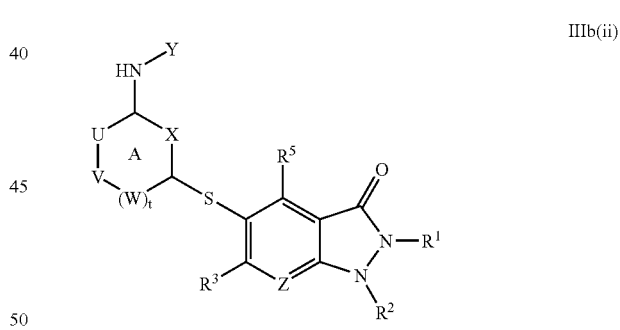
IIIb(ii)

It will be appreciated that, for compounds of general formulas IIIa(ii) and IIIb(ii) certain additional subclasses are of special interest. Certain preferred embodiments of compounds of formula IIIa(ii) or IIIb(ii) include those compounds having any combination of the following features for each variable for formula IIIa(ii) or IIIb(ii):

i) Z is $CR^6$ or N;

ii) $R^1$, $R^2$, $R^4$ and $R^5$ are each hydrogen and wherein Z is $CHR^6$ and $R^6$ is hydrogen; or $R^1$, $R^2$, $R^3$ and $R^5$ are each hydrogen and wherein Z is $CHR^6$ and $R^6$ is hydrogen;

iii) ring A is defined according to one of the following groups:

a. ring A is selected from one of the groups:

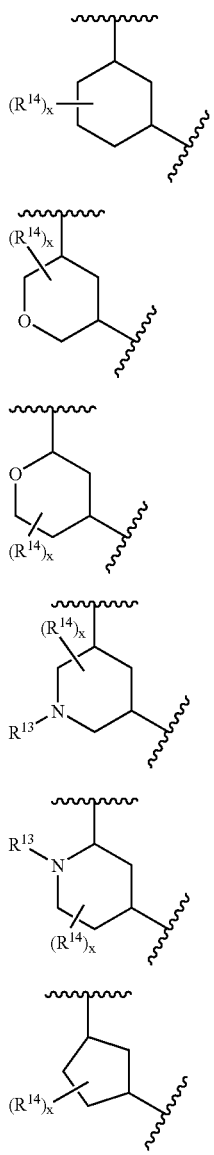

xi xii xiii xiv xv xvi wherein R¹³ is hydrogen, —R', —COR', —CO₂(R'), —CON(R')₂, or —SO₂R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring; R¹⁴ is oxo or —R; and x is 0–4; or b. ring A is selected from one of xi, xii or xvi and x is 0 or 1; R¹⁴ is -halo, —N(R⁷)₂, —C₁₋₃ alkyl, —C₁₋₃ haloalkyl, —NO₂, —O(C₁₋₃ alkyl), —CO₂(C₁₋₃ alkyl), —CN, —SO₂(C₁₋₃ alkyl), —SO₂NH₂, —OC(O)NH₂, —NH₂SO₂(C₁₋₃ alkyl), —NHC(O)(C₁₋₃ alkyl), —C(O)NH₂, and —CO(C₁₋₃ alkyl), wherein the (C₁₋₃ alkyl) is most preferably methyl; and R¹³ is hydrogen or C₁₋₄alkyl;

iv) Y is defined according to one of the following groups:
a. Y is an optionally substituted heteroaryl moiety;
b. Y is selected from one of the heteroaryl moieties a–y;
c. Y is selected from one of the following heteroaryl moieties:

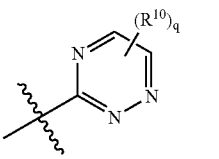
a

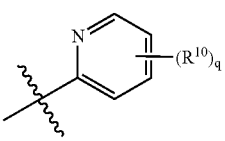
b

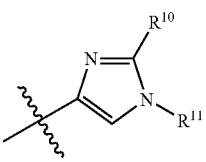
f

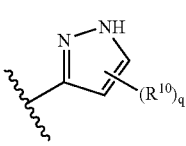
h

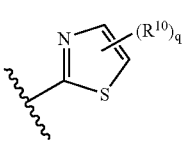
o wherein q is 0–4, R¹⁰ is —R, wherein —R is defined generally above and in classes and subclasses herein, and wherein each occurrence of R¹¹ is independently hydrogen, —R', —COR', —CO₂(R'), —CON(R')₂, or —SO₂R, wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

d. Y is a pyrazole moiety, h;
e. Y is one of a, b, f, h or o, optionally substituted with one or more R¹⁰ groups, wherein each occurrence of R¹⁰ is independently hydrogen, C₁₋₄aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle) carbonyl;
f. Y is one of a, b, f, h or o, optionally substituted with one or more R¹⁰ groups, wherein each occurrence of R¹⁰ is independently hydrogen, methyl, cyclopropyl, ethyl, isopropyl, propyl, t-butyl, cyclopentyl, phenyl, CO₂H, CO₂CH₃, CH₂OH, CH₂OCH₃, CH₂CH₂CH₂OH, CH₂CH₂CH₂OCH₃, CH₂CH₂CH₂OCH₂Ph, CH₂CH₂CH₂NH₂, CH₂CH₂CH₂NHCOOC(CH₃)₃, CONHCH(CH₃)₂, CONHCH₂CH=CH₂, CONHCH₂CH₂OCH₃, CONHCH₂Ph, CONH(cyclohexyl), CON(Et)₂, CON(CH₃)CH₂Ph, CONH(n-

C₃H₇), CON(Et)CH₂CH₂CH₃, CONHCH₂CH(CH₃)₂, CON(n-C₃H₇)₂, CO(3-methoxymethylpyrrolidin-1-yl), CONH(3-tolyl), CONH(4-tolyl), CONHCH₃, CO(morpholin-1-yl), CO(4-methylpiperazin-1-yl), CONHCH₂CH₂OH, CONH₂, and CO(piperidin-1-yl).

g. Y is a pyrazole moiety, h', wherein the pyrazole is substituted with two occurrences of $R^{10}$ ($R^{10a}$ and $R^{10b}$ as depicted),

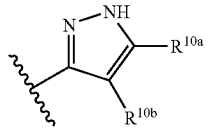

h' wherein each occurrence of $R^{10a}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl, and $R^{10b}$ is hydrogen;

h. Y is a pyrazole moiety, h', wherein the pyrazole is substituted with two occurrences of $R^{10}$ ($R^{10a}$ and $R^{10b}$ as depicted),

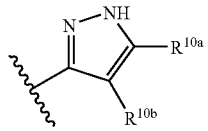

h' wherein each occurrence of $R^{10a}$ is hydrogen, methyl, cyclopropyl, ethyl, isopropyl, propyl, t-butyl, cyclopentyl, phenyl, CO₂H, CO₂CH₃, CH₂OH, CH₂OCH₃, CH₂CH₂CH₂OH, CH₂CH₂CH₂OCH₃, CH₂CH₂CH₂OCH₂Ph, CH₂CH₂CH₂NH₂, CH₂CH₂CH₂NHCOOC(CH₃)₃, CONHCH(CH₃)₂, CONHCH₂CH=CH₂, CONHCH₂CH₂OCH₃, CONHCH₂Ph, CONH(cyclohexyl), CON(Et)₂, CON(CH₃) CH₂Ph, CONH(n-C₃H₇), CON(Et)CH₂CH₂CH₃, CONHCH₂CH(CH₃)₂, CON(n-C₃H₇)₂, CO(3-methoxymethylpyrrolidin-1-yl), CONH(3-tolyl), CONH(4-tolyl), CONHCH₃, CO(morpholin-1-yl), CO(4-methylpiperazin-1-yl), CONHCH₂CH₂OH, CONH₂, and CO(piperidin-1-yl, and $R^{10b}$ is hydrogen;

i. Y is heteroaryl moiety substituted by at least two occurrences of $R^{10}$ and where two occurrences of $R^{10}$ taken together may represent an optionally substituted group selected from cycloaliphatic, cycloheteroaliphatic, aryl or heteroaryl;

j. Y represents one of the following heteroaryl moieties:

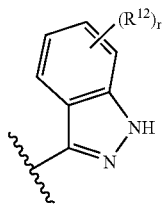

h-i

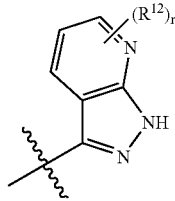

h-ii

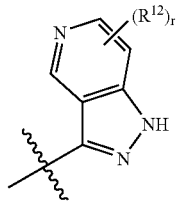

h-iii

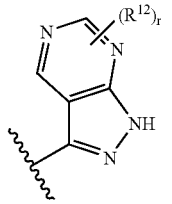

h-iv

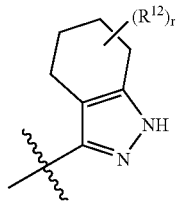

h-v wherein r is 0–4 and $R^{12}$ is hydrogen, -halo, —N(R⁷)₂, —C₁₋₃ alkyl, —C₁₋₃ haloalkyl, —NO₂, —O(C₁₋₃ alkyl), —CO₂(C₁₋₃ alkyl), —CN, —SO₂(C₁₋₃ alkyl), —SO₂NH₂, —OC(O)NH₂, —NH₂SO₂(C₁₋₃ alkyl), —NHC(O)(C₁₋₃ alkyl), —C(O)NH₂, and —CO(C₁₋₃ alkyl), wherein the (C₁₋₃ alkyl) is most preferably methyl;

v) for compounds of formula IIIa(ii), $R^4$ is defined according to one of the following groups:
  a. $R^4$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
  b. $R^4$ is hydrogen, methyl, ethyl, cyclopropyl, hydroxy, phenyl or —CH₂NH₂;

vi) for compounds of formula IIIb(ii), $R^3$ is defined according to one of the following groups:
  a. $R^3$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
  b. $R^3$ is hydrogen, methyl, ethyl, cyclopropyl, hydroxy, phenyl or —CH₂NH₂; and vii) $R^5$ is defined according to one of the following groups:
  a. hydrogen, halogen, —NO₂, —CN, hydroxy, optionally substituted $C_{1-3}$alkyl, optionally substituted alkoxy, —SO₂NH₂, or —C(O)alkyl, or
  b. $R^5$ is hydrogen, C₁, CF₃, OCF₃, CH₃, —CN, —SO₂NH₂ or —C(O)Me.

In certain preferred embodiments, compounds of the invention include those compounds having general formula IIIa(ii) and wherein the compounds have one or more of the following features:

a. Z is $NR^6$, wherein $R^1$ and $R^2$ are each independently hydrogen or a protecting group; $R^4$, $R^5$ and $R^6$ are each hydrogen,
b. ring A comprises one of the general formulas xi, xii or xvi, and
c. Y is an optionally substituted heteroaryl moiety selected from one of formulas a–y.

It will be appreciated that for compounds described directly above, preferred groups for ring A of formulas xi, xii or xvi (and substituents thereon), and Y (and substituents thereon), include those preferred groups as exemplified in subclasses and species above and herein.

Representative examples of compounds of formula IIIa(ii) or IIIb(ii) (described generally as III(ii) below but encompassing compounds of both formulas IIIa(ii) and IIIb(ii)), are depicted below in Table 7.

TABLE 7

Examples of Compounds of Formula III(ii):

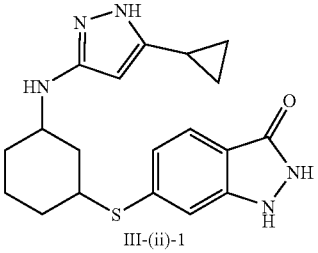

III-(ii)-1

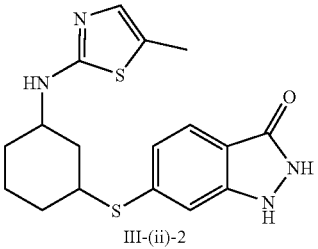

III-(ii)-2

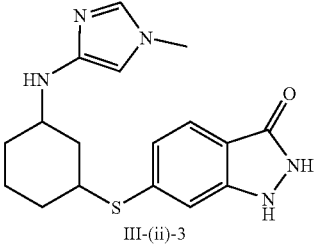

III-(ii)-3

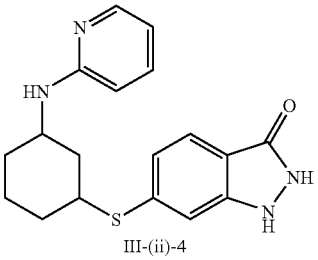

III-(ii)-4

TABLE 7-continued

Examples of Compounds of Formula III(ii):

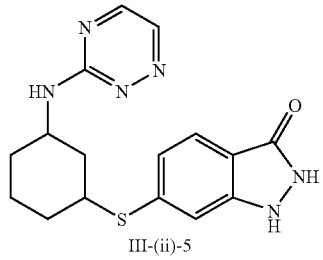

III-(ii)-5

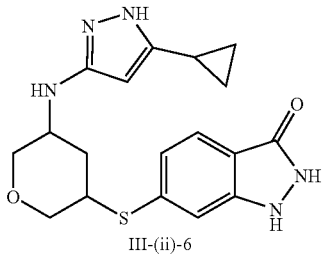

III-(ii)-6

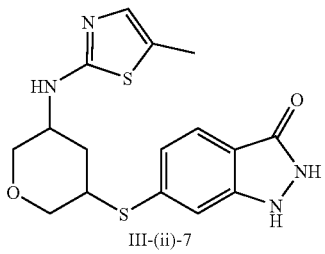

III-(ii)-7

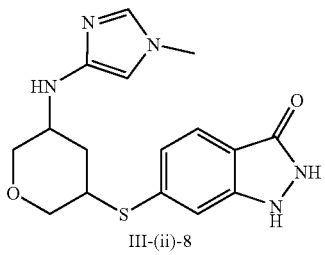

III-(ii)-8

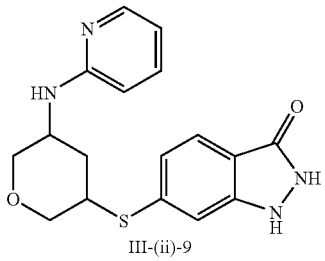

III-(ii)-9

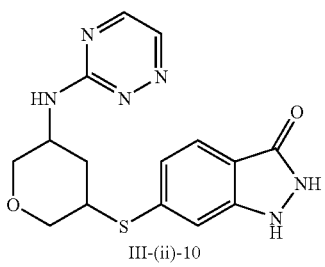

III-(ii)-10

TABLE 7-continued

Examples of Compounds of Formula III(ii):

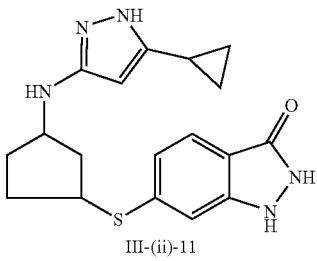
III-(ii)-11

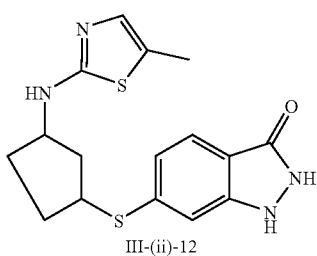
III-(ii)-12

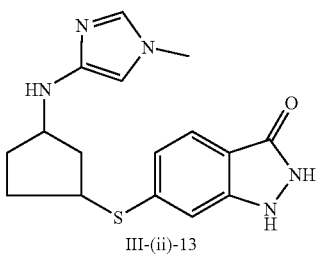
III-(ii)-13

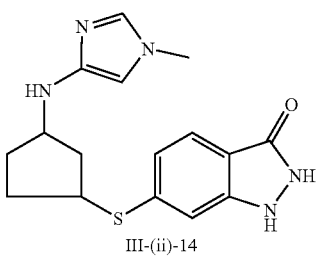
III-(ii)-14

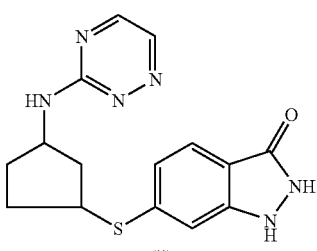
III-(ii)-15

In certain embodiments, a preferred subclass of compounds of general formula IIIa or IIIb include those compounds where $Q^1$ is O and $Q^2$ is NH. These compounds are defined by the general formula IIIa(iii) or IIIb(iii) and are depicted generally below:

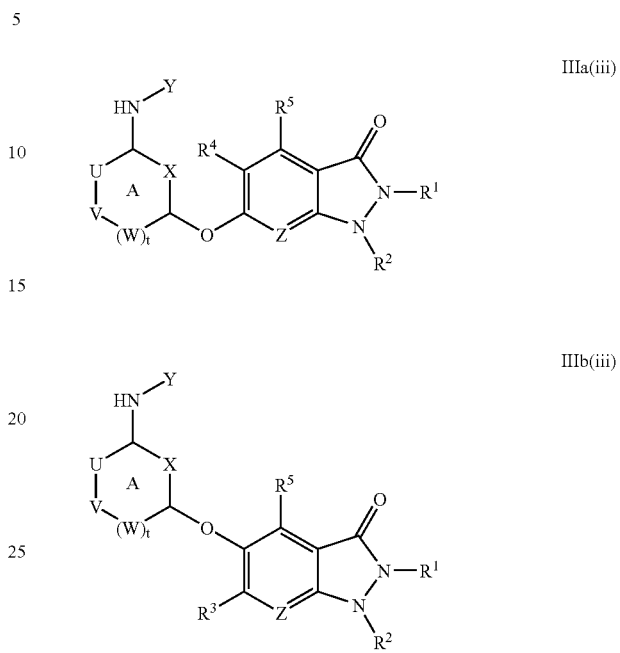

It will be appreciated that, for compounds of general formulas IIIa(iii) and IIIb(iii) certain additional subclasses are of special interest. Certain preferred embodiments of compounds of formula IIIa(iii) or IIIb(iii) include those compounds having any combination of the following features for each variable for formula IIIa(iii) or IIIb(iii):

i) Z is $CR^6$ or N;

ii) $R^1$, $R^2$, $R^4$ and $R^5$ are each hydrogen and wherein Z is $CHR^6$ and $R^6$ is hydrogen; or $R^1$, $R^2$, $R^3$ and $R^5$ are each hydrogen and wherein Z is $CHR^6$ and $R^6$ is hydrogen;

iii) ring A is defined according to one of the following groups:

a. ring A is selected from one of the groups:

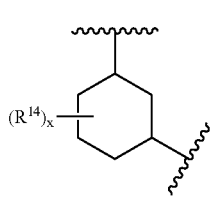
xi

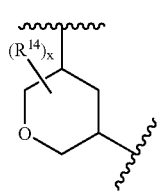
xii

-continued

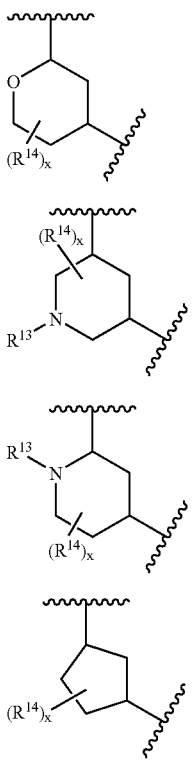

xiii xiv xv xvi wherein $R^{13}$ is hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring; $R^{14}$ is oxo or —R; and x is 0–4; or b. ring A is selected from one of xi, xii or xvi and x is 0 or 1; $R^{14}$ is -halo, —N(R$^7$)$_2$, —C$_{1-3}$ alkyl, —C$_{1-3}$ haloalkyl, —NO$_2$, —O(C$_{1-3}$ alkyl), —CO$_2$(C$_{1-3}$ alkyl), —CN, —SO$_2$(C$_{1-3}$ alkyl), —SO$_2$NH$_2$, —OC(O)NH$_2$, —NH$_2$SO$_2$(C$_{1-3}$ alkyl), —NHC(O)(C$_{1-3}$ alkyl), —C(O)NH$_2$, and —CO(C$_{1-3}$ alkyl), wherein the (C$_{1-3}$ alkyl) is most preferably methyl; and $R^{13}$ is hydrogen or C$_{1-4}$alkyl;

iv) Y is defined according to one of the following groups:
a. Y is an optionally substituted heteroaryl moiety;
b. Y is selected from one of the heteroaryl moieties a–y;
c. Y is selected from one of the following heteroaryl moieties:

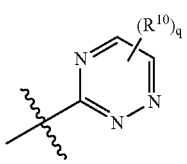

a

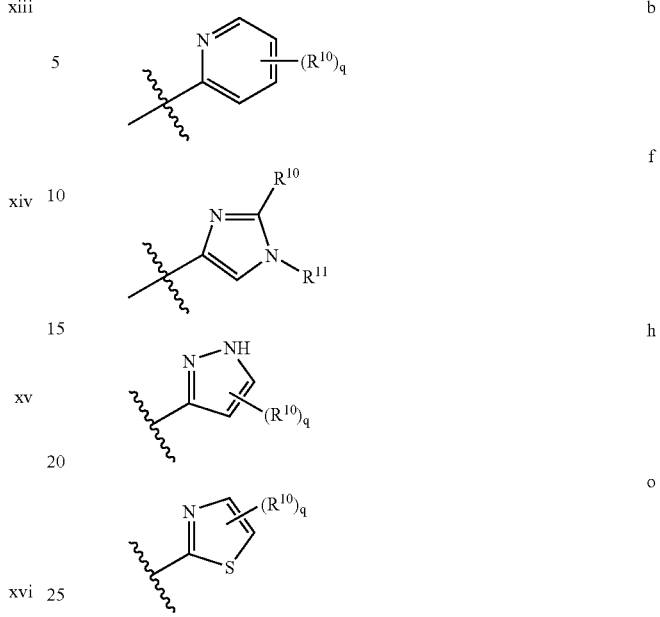

b f h o wherein q is 0–4, $R^{10}$ is —R, wherein —R is defined generally above and in classes and subclasses herein, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

d. Y is a pyrazole moiety, h;
e. Y is one of a, b, f, h or o, optionally substituted with one or more $R^{10}$ groups, wherein each occurrence of $R^{10}$ is independently hydrogen, C$_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle) carbonyl;
f. Y is one of a, b, f, h or o, optionally substituted with one or more $R^{10}$ groups, wherein each occurrence of $R^{10}$ is independently hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl).
g. Y is a pyrazole moiety, h', wherein the pyrazole is substituted with two occurrences of $R^{10}$ ($R^{10a}$ and $R^{10b}$ as depicted),

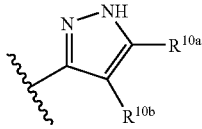

wherein each occurrence of $R^{10a}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl, and $R^{10b}$ is hydrogen;

h. Y is a pyrazole moiety, h', wherein the pyrazole is substituted with two occurrences of $R^{10}$ ($R^{10a}$ and $R^{10b}$ as depicted),

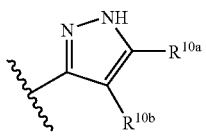

wherein each occurrence of $R^{10a}$ is hydrogen, methyl, cyclopropyl, ethyl, isopropyl, propyl, t-butyl, cyclopentyl, phenyl, $CO_2H$, $CO_2CH_3$, $CH_2OH$, $CH_2OCH_3$, $CH_2CH_2CH_2OH$, $CH_2CH_2CH_2OCH_3$, $CH_2CH_2CH_2OCH_2Ph$, $CH_2CH_2CH_2NH_2$, $CH_2CH_2CH_2NHCOOC(CH_3)_3$, $CONHCH(CH_3)_2$, $CONHCH_2CH=CH_2$, $CONHCH_2CH_2OCH_3$, $CONHCH_2Ph$, $CONH(cyclohexyl)$, $CON(Et)_2$, $CON(CH_3)CH_2Ph$, $CONH(n-C_3H_7)$, $CON(Et)CH_2CH_2CH_3$, $CONHCH_2CH(CH_3)_2$, $CON(n-C_3H_7)_2$, CO(3-methoxymethylpyrrolidin-1-yl), CONH(3-tolyl), CONH(4-tolyl), $CONHCH_3$, CO(morpholin-1-yl), CO(4-methylpiperazin-1-yl), $CONHCH_2CH_2OH$, $CONH_2$, and CO(piperidin-1-yl, and $R^{10b}$ is hydrogen;

i. Y is heteroaryl moiety substituted by at least two occurrences of $R^{10}$ and where two occurrences of $R^{10}$ taken together may represent an optionally substituted group selected from cycloaliphatic, cycloheteroaliphatic, aryl or heteroaryl;

j. Y represents one of the following heteroaryl moieties:

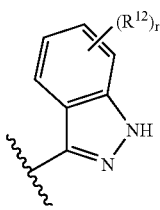

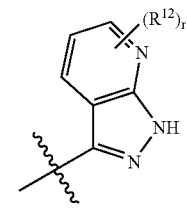

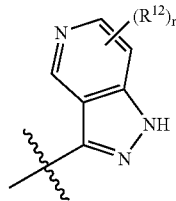

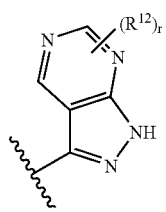

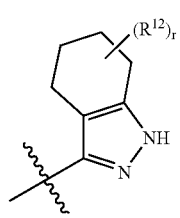

wherein r is 0–4 and $R^{12}$ is hydrogen, -halo, $—N(R^7)_2$, $—C_{1-3}$ alkyl, $—C_{1-3}$ haloalkyl, $—NO_2$, $—O(C_{1-3}$ alkyl), $—CO_2(C_{1-3}$ alkyl), $—CN$, $—SO_2(C_{1-3}$ alkyl), $—SO_2NH_2$, $—OC(O)NH_2$, $—NH_2SO_2(C_{1-3}$ alkyl), $—NHC(O)(C_{1-3}$ alkyl), $—C(O)NH_2$, and $—CO(C_{1-3}$ alkyl), wherein the ($C_{1-3}$ alkyl) is most preferably methyl;

v) for compounds of formula IIIa(iii), $R^4$ is defined according to one of the following groups:
a. $R^4$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
b. $R^4$ is hydrogen, methyl, ethyl, cyclopropyl, hydroxy, phenyl or $—CH_2NH_2$;

vi) for compounds of formula IIIb(iii), $R^3$ is defined according to one of the following groups:
a. $R^3$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
b. $R^3$ is hydrogen, methyl, ethyl, cyclopropyl, hydroxy, phenyl or $—CH_2NH_2$; and vii) $R^5$ is defined according to one of the following groups:
a. hydrogen, halogen, $—NO_2$, $—CN$, hydroxy, optionally substituted $C_{1-3}$alkyl, optionally substituted alkoxy, $—SO_2NH_2$, or $—C(O)$alkyl, or
b. $R^5$ is hydrogen, $C_1$, $CF_3$, $OCF_3$, $CH_3$, $—CN$, $—SO_2NH_2$ or $—C(O)Me$.

In certain preferred embodiments, compounds of the invention include those compounds having general formula IIIa(iii) and wherein the compounds have one or more of the following features:
a. Z is $NR^6$, wherein $R^1$ and $R^2$ are each independently hydrogen or a protecting group; $R^4$, $R^5$ and $R^6$ are each hydrogen,
b. ring A comprises one of the general formulas xi, xii or xvi, and c. Y is an optionally substituted heteroaryl moiety selected from one of formulas a–y.

It will be appreciated that for compounds described directly above, preferred groups for ring A of formulas xi, xii or xvi (and substituents thereon), and Y (and substituents thereon), include those preferred groups as exemplified in subclasses and species above and herein.

Representative examples of compounds of formula IIIa(iii) or IIIb(iii) (described generally as III(iii) below but encompassing compounds of both formulas IIIa(iii) and IIIb(i)), are depicted below in Table 8.

TABLE 8

Examples of Compounds of Formula III(iii):

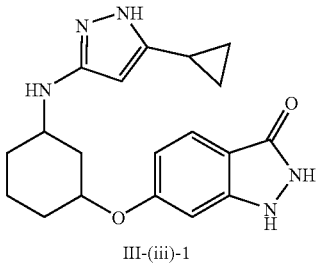

III-(iii)-1

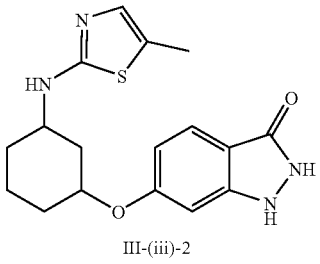

III-(iii)-2

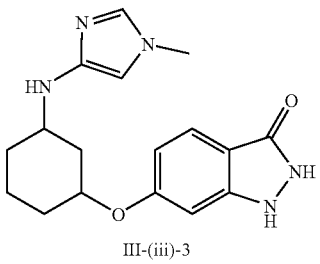

III-(iii)-3

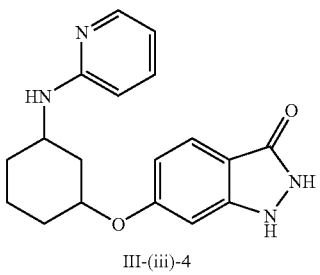

III-(iii)-4

TABLE 8-continued

Examples of Compounds of Formula III(iii):

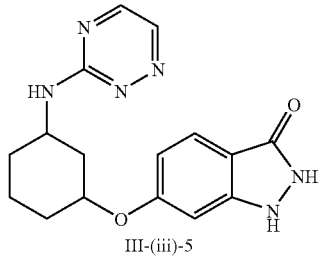

III-(iii)-5

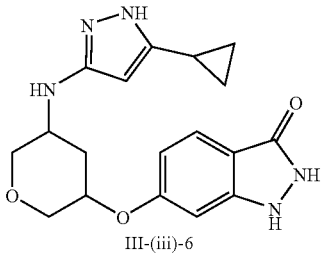

III-(iii)-6

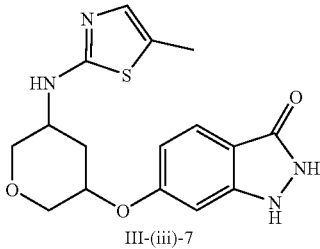

III-(iii)-7

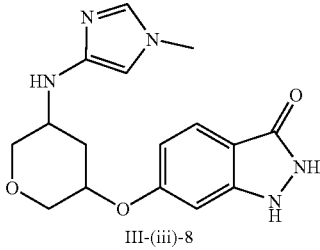

III-(iii)-8

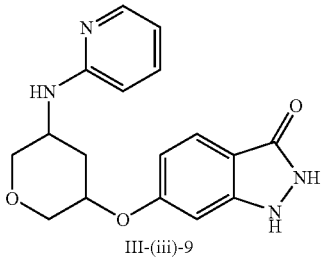

III-(iii)-9

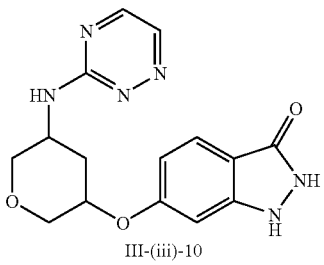

III-(iii)-10

TABLE 8-continued

Examples of Compounds of Formula III(iii):

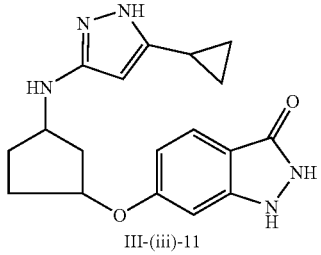

III-(iii)-11

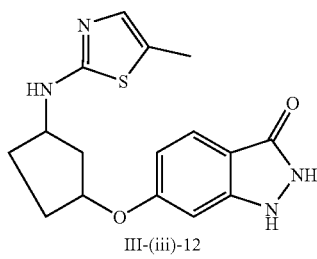

III-(iii)-12

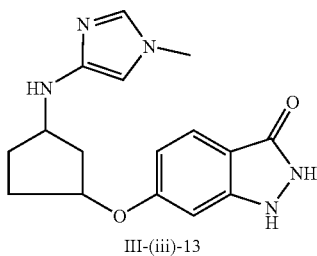

III-(iii)-13

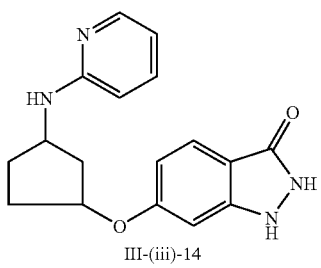

III-(iii)-14

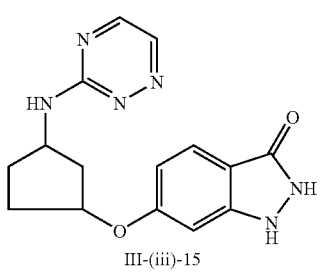

III-(iii)-15

In certain embodiments, a preferred subclass of compounds of general formula IIIa or IIIb include those compounds where $Q^2$ is NH, and $Q^1$ is defined below. These compounds are defined by the general formula IIIa(iv) or IIIb(iv) and are depicted generally below:

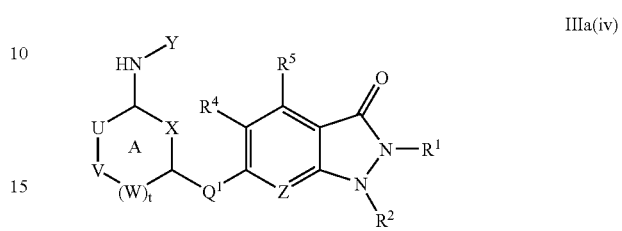

IIIa(iv)

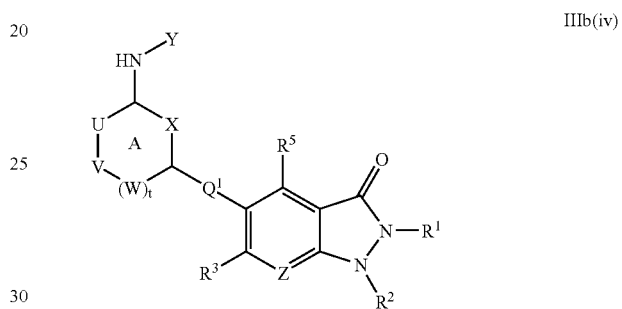

IIIb(iv)

wherein $Q^1$ is —$C(R^4)_2$—, 1,2-cyclopropyl, 1,2-cyclobutanediyl, or 1,3-cyclobutanediyl, an optionally substituted $C_{2-4}$alkylidene group, wherein one methylene unit of the optionally substituted $C_{2-4}$alkylidene chain is optionally replaced by —O—, —S—, or —$NR^4$—, wherein each occurrence of $R^4$ is independently hydrogen or optionally substituted $C_{1-4}$aliphatic.

It will be appreciated that, for compounds of general formulas IIIa(iv) and IIIb(iii) certain additional subclasses are of special interest. Certain preferred embodiments of compounds of formula IIIa(iv) or IIIb(iv) include those compounds having any combination of the following features for each variable for formula IIIa(iv) or IIIb(iv):

i) Z is $CR^6$ or N;

ii) $R^1$, $R^2$, $R^4$ and $R^5$ are each hydrogen and wherein Z is $CHR^6$ and $R^6$ is hydrogen; or $R^1$, $R^2$, $R^3$ and $R^5$ are each hydrogen and wherein Z is $CHR^6$ and $R^6$ is hydrogen;

iii) ring A is defined according to one of the following groups:

a. ring A is selected from one of the groups:

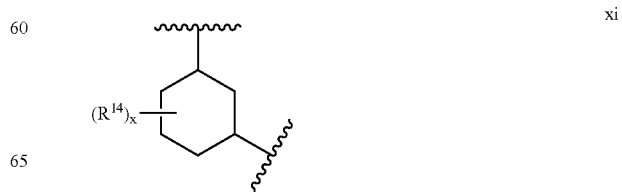

xi

-continued

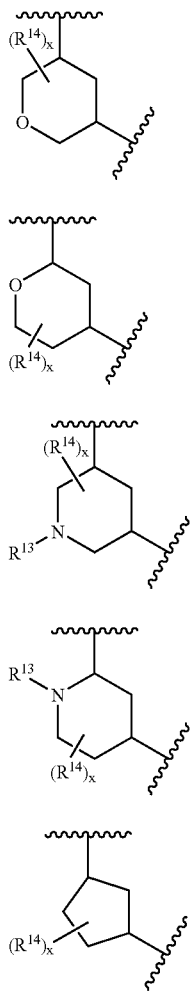

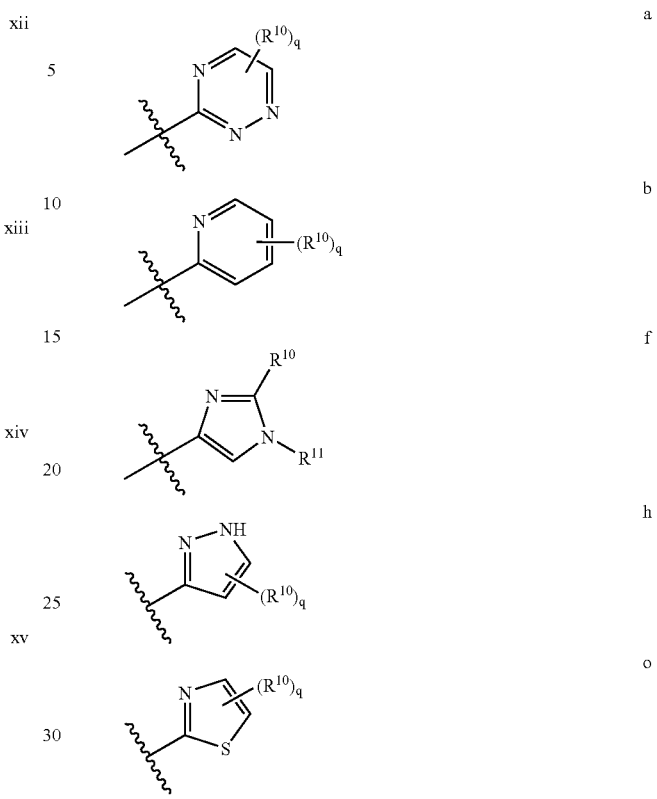

wherein R¹³ is hydrogen, —R', —COR', —CO₂(R'), —CON(R')₂, or —SO₂R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring; R¹⁴ is oxo or —R; and x is 0–4; or b. ring A is selected from one of xi, xii or xvi and x is 0 or 1; R¹⁴ is -halo, —N(R⁷)₂, —C₁₋₃ alkyl, —C₁₋₃ haloalkyl, —NO₂, —O(C₁₋₃ alkyl), —CO₂(C₁₋₃ alkyl), —CN, —SO₂(C₁₋₃ alkyl), —SO₂NH₂, —OC(O)NH₂, —NH₂SO₂(C₁₋₃ alkyl), —NHC(O)(C₁₋₃ alkyl), —C(O)NH₂, and —CO(C₁₋₃ alkyl), wherein the (C₁₋₃ alkyl) is most preferably methyl; and R¹³ is hydrogen or C₁₋₄alkyl;

iv) Y is defined according to one of the following groups:
a. Y is an optionally substituted heteroaryl moiety;
b. Y is selected from one of the heteroaryl moieties a–y;
c. Y is selected from one of the following heteroaryl moieties:

wherein q is 0–4, R¹⁰ is —R, wherein —R is defined generally above and in classes and subclasses herein, and wherein each occurrence of R¹¹ is independently hydrogen, —R', —COR', —CO₂(R'), —CON(R)₂, or —SO₂R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

d. Y is a pyrazole moiety, h;
e. Y is one of a, b, f, h or o, optionally substituted with one or more R¹⁰ groups, wherein each occurrence of R¹⁰ is independently hydrogen, C₁₋₄aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle) carbonyl;
f. Y is one of a, b, f, h or o, optionally substituted with one or more R¹⁰ groups, wherein each occurrence of R¹⁰ is independently hydrogen, methyl, cyclopropyl, ethyl, isopropyl, propyl, t-butyl, cyclopentyl, phenyl, CO₂H, CO₂CH₃, CH₂OH, CH₂OCH₃, CH₂CH₂CH₂OH, CH₂CH₂CH₂OCH₃, CH₂CH₂CH₂OCH₂Ph, CH₂CH₂CH₂NH₂, CH₂CH₂CH₂NHCOOC(CH₃)₃, CONHCH(CH₃)₂, CONHCH₂CH=CH₂, CONHCH₂CH₂OCH₃, CONHCH₂Ph, CONH(cyclohexyl), CON(Et)₂, CON(CH₃)CH₂Ph, CONH(n-C₃H₇), CON(Et)CH₂CH₂CH₃, CONHCH₂CH(CH₃)₂, CON(n-C₃H₇)₂, CO(3-methoxymethylpyrrolidin-1-yl), CONH(3-tolyl), CONH(4-tolyl), CONHCH₃, CO(morpholin-1-yl), CO(4-methylpiperazin-1-yl), CONHCH₂CH₂OH, CONH₂, and CO(piperidin-1-yl).

g. Y is a pyrazole moiety, h', wherein the pyrazole is substituted with two occurrences of $R^{10}$ ($R^{10a}$ and $R^{10b}$ as depicted),

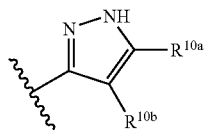

h' wherein each occurrence of $R^{10a}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl, and $R^{10b}$ is hydrogen;

h. Y is a pyrazole moiety, h', wherein the pyrazole is substituted with two occurrences of $R^{10}$ ($R^{10a}$ and $R^{10b}$ as depicted),

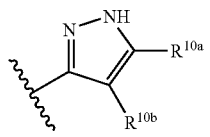

h' wherein each occurrence of $R^{10a}$ is hydrogen, methyl, cyclopropyl, ethyl, isopropyl, propyl, t-butyl, cyclopentyl, phenyl, CO₂H, CO₂CH₃, CH₂OH, CH₂OCH₃, CH₂CH₂CH₂OH, CH₂CH₂CH₂OCH₃, CH₂CH₂CH₂OCH₂Ph, CH₂CH₂CH₂NH₂, CH₂CH₂CH₂NHCOOC(CH₃)₃, CONHCH(CH₃)₂, CONHCH₂CH=CH₂, CONHCH₂CH₂OCH₃, CONHCH₂Ph, CONH(cyclohexyl), CON(Et)₂, CON(CH₃)CH₂Ph, CONH(n-C₃H₇), CON(Et)CH₂CH₂CH₃, CONHCH₂CH(CH₃)₂, CON(n-C₃H₇)₂, CO(3-methoxymethylpyrrolidin-1-yl), CONH(3-tolyl), CONH(4-tolyl), CONHCH₃, CO(morpholin-1-yl), CO(4-methylpiperazin-1-yl), CONHCH₂CH₂OH, CONH₂, and CO(piperidin-1-yl, and $R^{10b}$ is hydrogen;

i. Y is heteroaryl moiety substituted by at least two occurrences of $R^{10}$ and where two occurrences of $R^{10}$ taken together may represent an optionally substituted group selected from cycloaliphatic, cycloheteroaliphatic, aryl or heteroaryl;

j. Y represents one of the following heteroaryl moieties:

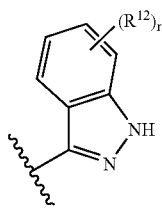

h-i

-continued

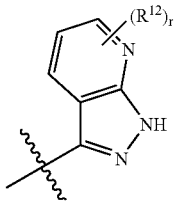

h-ii

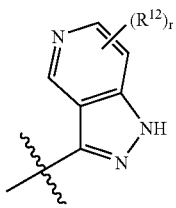

h-iii

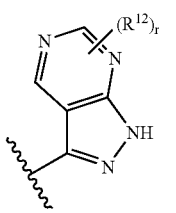

h-iv

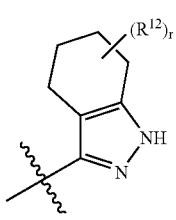

h-v wherein r is 0–4 and $R^{12}$ is hydrogen, -halo, —N(R⁷)₂, —$C_{1-3}$ alkyl, —$C_{1-3}$ haloalkyl, —NO₂, —O($C_{1-3}$ alkyl), —CO₂($C_{1-3}$ alkyl), —CN, —SO₂($C_{1-3}$ alkyl), —SO₂NH₂, —OC(O)NH₂, —NH₂SO₂($C_{1-3}$ alkyl), —NHC(O)($C_{1-3}$ alkyl), —C(O)NH₂, and —CO($C_{1-3}$ alkyl), wherein the ($C_{1-3}$ alkyl) is most preferably methyl;

v) for compounds of formula IIIa(iv), $R^4$ is defined according to one of the following groups:
  a. $R^4$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
  b. $R^4$ is hydrogen, methyl, ethyl, cyclopropyl, hydroxy, phenyl or —CH₂NH₂;

vi) for compounds of formula IIIb(iv), $R^3$ is defined according to one of the following groups:
  a. $R^3$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
  b. $R^3$ is hydrogen, methyl, ethyl, cyclopropyl, hydroxy, phenyl or —CH₂NH₂; and vii) $R^5$ is defined according to one of the following groups:
  a. hydrogen, halogen, —NO₂, —CN, hydroxy, optionally substituted $C_{1-3}$alkyl, optionally substituted alkoxy, —SO₂NH₂, or —C(O)alkyl, or
  b. $R^5$ is hydrogen, $C_1$, CF₃, OCF₃, CH₃, —CN, —SO₂NH₂ or —C(O)Me.

In certain preferred embodiments, compounds of the invention include those compounds having general formula IIIa(iv) and wherein the compounds have one or more of the following features:

a. Z is $NR^6$, wherein $R^1$ and $R^2$ are each independently hydrogen or a protecting group; $R^4$, $R^5$ and $R^6$ are each hydrogen,
b. ring A comprises one of the general formulas xi, xii or xvi, and
c. Y is an optionally substituted heteroaryl moiety selected from one of formulas a–y.

It will be appreciated that for compounds described directly above, preferred groups for ring A of formulas xi, xii or xvi (and substituents thereon), and Y (and substituents thereon), include those preferred groups as exemplified in subclasses and species above and herein.

Representative examples of compounds of formula IIIa (iv) or IIIb(iv) (described generally as III(iii) below but encompassing compounds of both formulas IIIa(iv) and IIIb(iv)), are depicted below in Table 9.

TABLE 9

Examples of Compounds of Formula III(iv):

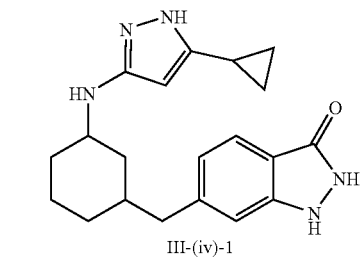

III-(iv)-1

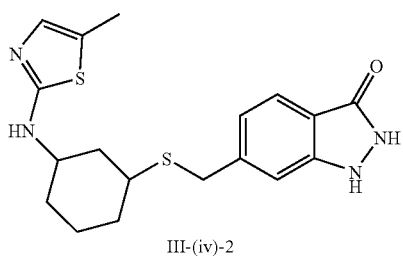

III-(iv)-2

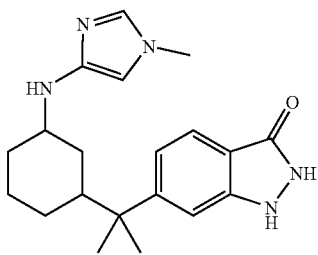

III-(iv)-3

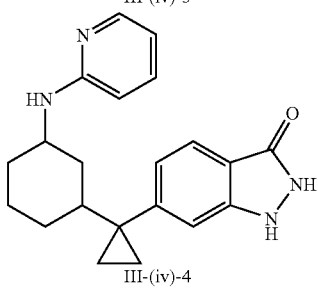

III-(iv)-4

TABLE 9-continued

Examples of Compounds of Formula III(iv):

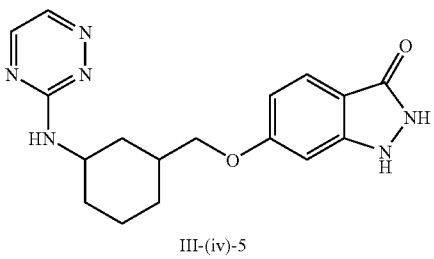

III-(iv)-5

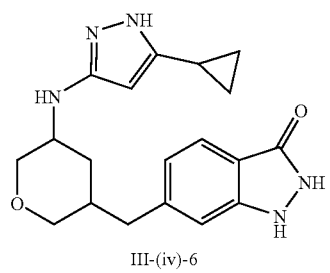

III-(iv)-6

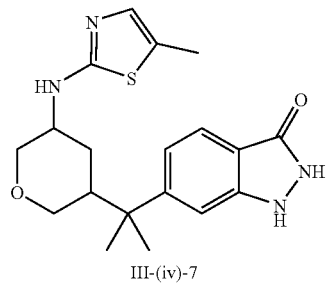

III-(iv)-7

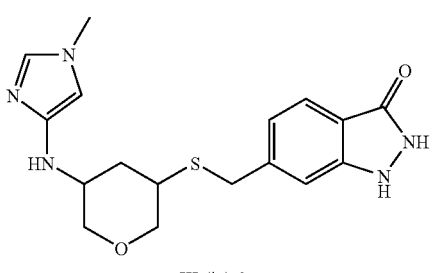

III-(iv)-8

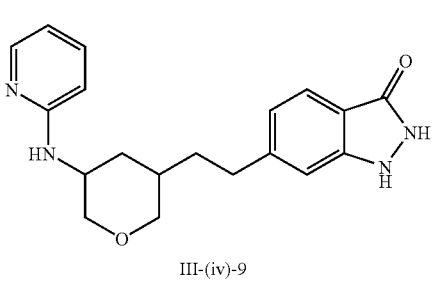

III-(iv)-9

TABLE 9-continued

Examples of Compounds of Formula III(iv):

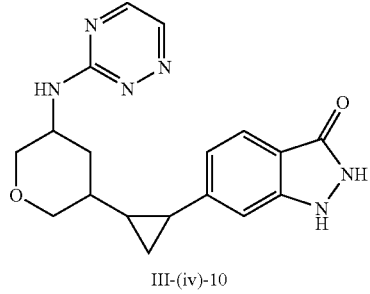

III-(iv)-10

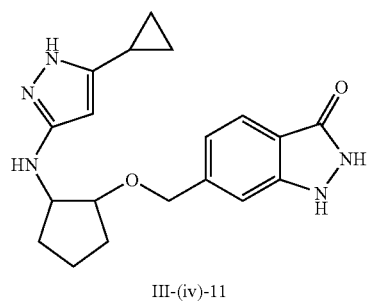

III-(iv)-11

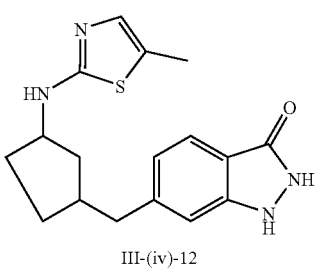

III-(iv)-12

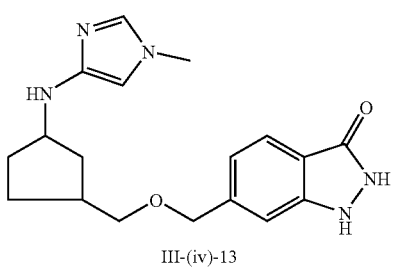

III-(iv)-13

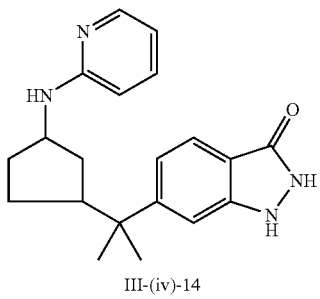

III-(iv)-14

TABLE 9-continued

Examples of Compounds of Formula III(iv):

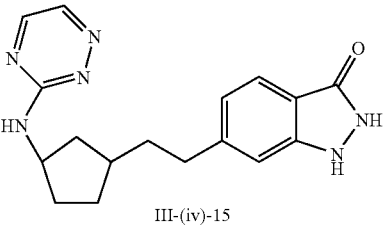

III-(iv)-15

In certain embodiments, a preferred subclass of compounds of general formula IIIa or IIIb include those compounds where $Q^2$ is NH, and $Q^1$ is a direct bond. These compounds are defined by the general formula IIIa(v) or IIIb(v) and are depicted generally below:

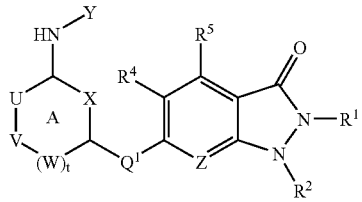

IIIa(v)

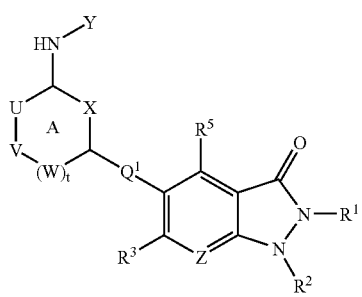

IIIb(v)

wherein $Q^1$ is a direct bond.

It will be appreciated that, for compounds of general formulas IIIa(v) and IIIb(v) certain additional subclasses are of special interest. Certain preferred embodiments of compounds of formula IIIa(v) or IIIb(v) include those compounds having any combination of the following features for each variable for formula IIIa(v) or IIIb(v):

i) Z is $CR^6$ or N;

ii) $R^1$, $R^1$, $R^4$ and $R^5$ are each hydrogen and wherein Z is $CHR^6$ and $R^6$ is hydrogen; or $R^1$, $R^2$, $R^3$ and $R^5$ are each hydrogen and wherein Z is $CHR^6$ and $R^6$ is hydrogen;

iii) ring A is defined according to one of the following groups:

a. ring A is selected from one of the groups:

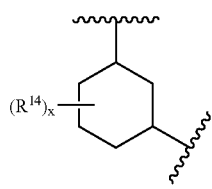

xi

-continued

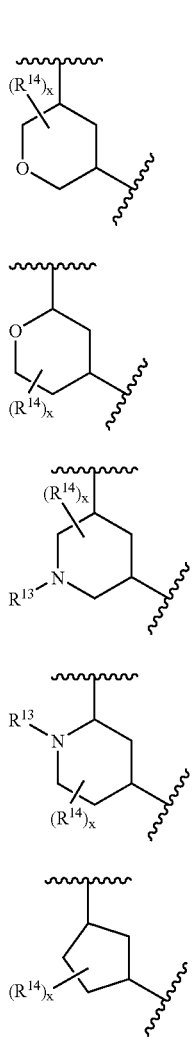

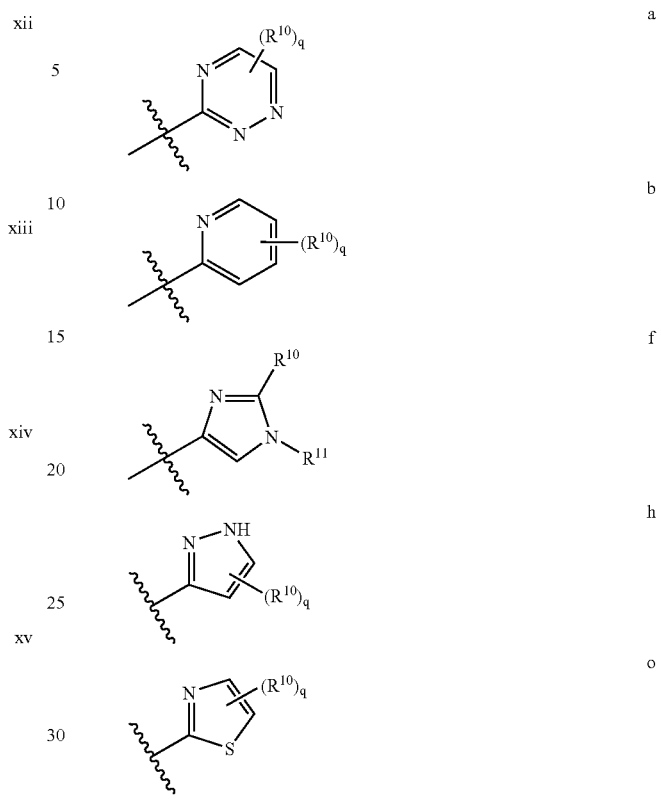

wherein $R^{13}$ is hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring; $R^{14}$ is oxo or —R; and x is 0–4; or b. ring A is selected from one of xi, xii or xvi and x is 0 or 1; $R^{14}$ is -halo, —N($R^7$)$_2$, —C$_{1-3}$ alkyl, —C$_{1-3}$ haloalkyl, —NO$_2$, —O(C$_{1-3}$ alkyl), —CO$_2$(C$_{1-3}$ alkyl), —CN, —SO$_2$(C$_{1-3}$ alkyl), —SO$_2$NH$_2$, —OC(O)NH$_2$, —NH$_2$SO$_2$(C$_{1-3}$ alkyl), —NHC(O)(C$_{1-3}$ alkyl), —C(O)NH$_2$, and —CO(C$_{1-3}$ alkyl), wherein the (C$_{1-3}$ alkyl) is most preferably methyl; and $R^{13}$ is hydrogen or C$_{1-4}$alkyl;

iv) Y is defined according to one of the following groups:
a. Y is an optionally substituted heteroaryl moiety;
b. Y is selected from one of the heteroaryl moieties a–y;
c. Y is selected from one of the following heteroaryl moieties:

wherein q is 0–4, $R^{10}$ is —R, wherein —R is defined generally above and in classes and subclasses herein, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

d. Y is a pyrazole moiety, h;
e. Y is one of a, b, f, h or o, optionally substituted with one or more $R^{10}$ groups, wherein each occurrence of $R^{10}$ is independently hydrogen, C$_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle) carbonyl;
f. Y is one of a, b, f, h or o, optionally substituted with one or more $R^{10}$ groups, wherein each occurrence of $R^{10}$ is independently hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH₂CH₂OH, CONH₂, and CO(piperidin-1-yl).

g. Y is a pyrazole moiety, h', wherein the pyrazole is substituted with two occurrences of $R^{10}$ ($R^{10a}$ and $R^{10b}$ as depicted),

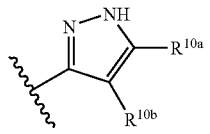

h' wherein each occurrence of $R^{10a}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl, and $R^{10b}$ is hydrogen;

h. Y is a pyrazole moiety, h', wherein the pyrazole is substituted with two occurrences of $R^{10}$ ($R^{10a}$ and $R^{10b}$ as depicted),

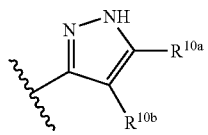

h' wherein each occurrence of $R^{10a}$ is hydrogen, methyl, cyclopropyl, ethyl, isopropyl, propyl, t-butyl, cyclopentyl, phenyl, CO₂H, CO₂CH₃, CH₂OH, CH₂OCH₃, CH₂CH₂CH₂OH, CH₂CH₂CH₂OCH₃, CH₂CH₂CH₂OCH₂Ph, CH₂CH₂CH₂NH₂, CH₂CH₂CH₂NHCOOC(CH₃)₃, CONHCH(CH₃)₂, CONHCH₂CH═CH₂, CONHCH₂CH₂OCH₃, CONHCH₂Ph, CONH(cyclohexyl), CON(Et)₂, CON(CH₃)CH₂Ph, CONH(n-C₃H₇), CON(Et)CH₂CH₂CH₃, CONHCH₂CH(CH₃)₂, CON(n-C₃H₇)₂, CO(3-methoxymethylpyrrolidin-1-yl), CONH(3-tolyl), CONH(4-tolyl), CONHCH₃, CO(morpholin-1-yl), CO(4-methylpiperazin-1-yl), CONHCH₂CH₂OH, CONH₂, and CO(piperidin-1-yl, and $R^{10b}$ is hydrogen;

i. Y is heteroaryl moiety substituted by at least two occurrences of $R^{10}$ and where two occurrences of $R^{10}$ taken together may represent an optionally substituted group selected from cycloaliphatic, cycloheteroaliphatic, aryl or heteroaryl;

j. Y represents one of the following heteroaryl moieties:

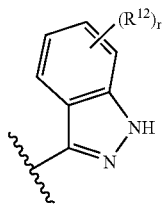

h-i

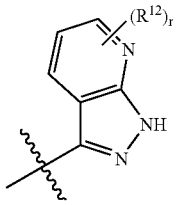

h-ii

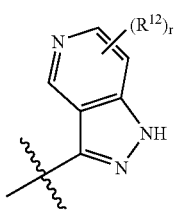

h-iii

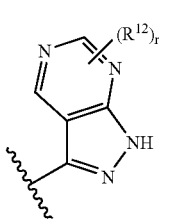

h-iv

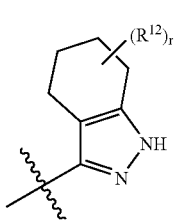

h-v wherein r is 0–4 and $R^{12}$ is hydrogen, -halo, —N($R^7$)₂, —C₁₋₃ alkyl, —C₁₋₃ haloalkyl, —NO₂, —O(C₁₋₃ alkyl), —CO₂(C₁₋₃ alkyl), —CN, —SO₂(C₁₋₃ alkyl), —SO₂NH₂, —OC(O)NH₂, —NH₂SO₂(C₁₋₃ alkyl), —NHC(O)(C₁₋₃ alkyl), —C(O)NH₂, and —CO(C₁₋₃ alkyl), wherein the (C₁₋₃ alkyl) is most preferably methyl;

and $R^{13}$ is hydrogen or $C_{1-4}$alkyl;

v) for compounds of formula IIIa(v), $R^4$ is defined according to one of the following groups:
 a. $R^4$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
 b. $R^4$ is hydrogen, methyl, ethyl, cyclopropyl, hydroxy, phenyl or —CH₂NH₂;

vi) for compounds of formula IIIb(v), $R^3$ is defined according to one of the following groups:
 a. $R^3$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
 b. $R^3$ is hydrogen, methyl, ethyl, cyclopropyl, hydroxy, phenyl or —CH₂NH₂; and vii) $R^5$ is defined according to one of the following groups:
 a. hydrogen, halogen, —NO₂, —CN, hydroxy, optionally substituted $C_{1-3}$alkyl, optionally substituted alkoxy, —SO₂NH₂, or —C(O)alkyl, or b. $R^5$ is hydrogen, $C_1$, $CF_3$, $OCF_3$, $CH_3$, —CN, —$SO_2NH_2$ or —C(O)Me.

In certain preferred embodiments, compounds of the invention include those compounds having general formula IIIa(v) and wherein the compounds have one or more of the following features:

a. Z is $NR^6$, wherein $R^1$ and $R^2$ are each independently hydrogen or a protecting group; $R^4$, $R^5$ and $R^6$ are each hydrogen,
b. ring A comprises one of the general formulas xi, xii or xvi, and
c. Y is an optionally substituted heteroaryl moiety selected from one of formulas a–y.

It will be appreciated that for compounds described directly above, preferred groups for ring A of formulas xi, xii or xvi (and substituents thereon), and Y (and substituents thereon), include those preferred groups as exemplified in subclasses and species above and herein.

Representative examples of compounds of formula IIIa(v) or IIIb(v) (described generally as III(v) below but encompassing compounds of both formulas IIIa(v) and IIIb(i)), are depicted below in Table 10.

TABLE 10

Examples of Compounds of Formula III(v):

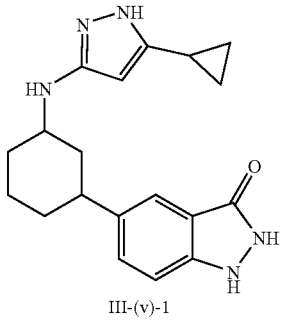

III-(v)-1

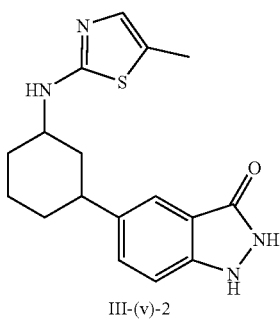

III-(v)-2

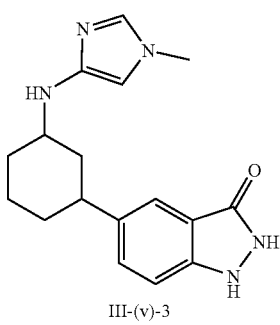

III-(v)-3

TABLE 10-continued

Examples of Compounds of Formula III(v):

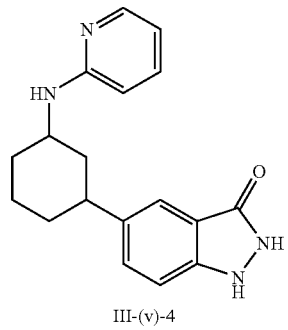

III-(v)-4

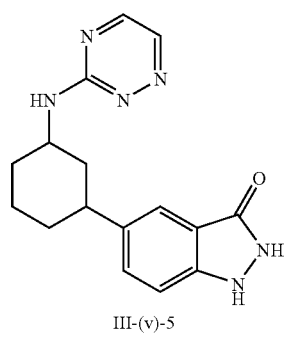

III-(v)-5

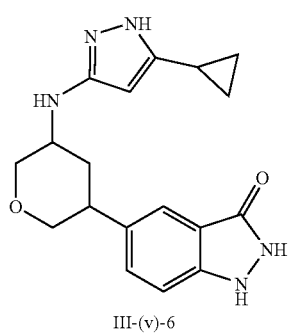

III-(v)-6

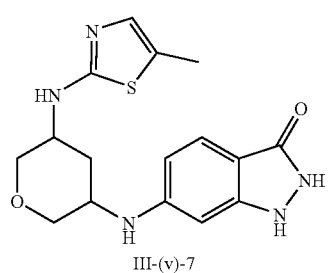

III-(v)-7

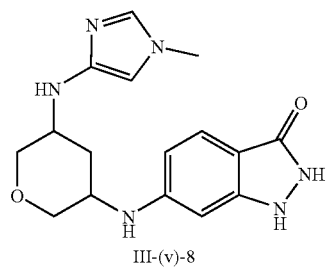

III-(v)-8

TABLE 10-continued

Examples of Compounds of Formula III(v):

III-(v)-9

III-(v)-10

III-(v)-11

III-(v)-12

III-(v)-13

TABLE 10-continued

Examples of Compounds of Formula III(v):

III-(v)-14

III-(v)-15

In certain other exemplary subsets, for compounds of formulas I, Ia and Ib, either of $R^3$ or $R^4$ is —$Q^1$—A—$Q^2$—Y, wherein A is an optionally substituted $C_{2-4}$alkylidene unit (represented by $A^1$—$A^2$—$A^3$—$A^4$) and compounds have the general formula IVa or IVb:

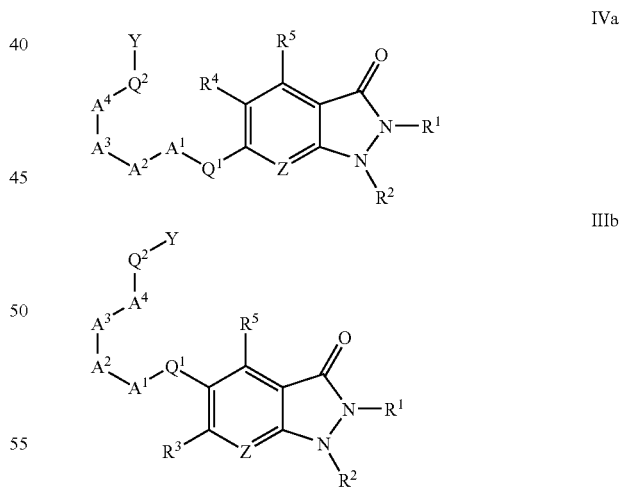

IVa

IIIb wherein $R^1$, $R^2$, $R^3$, $R^5$, $R^5$, Z, $Q^1$, $Q^2$, and Y are as defined generally above, each of $A^1$, $A^2$, $A^3$ or $A^4$ is independently absent or is an optionally substituted methylene unit, wherein each methylene unit is optionally replaced by —O—, —S—, —$NR^B$—, —$NR^B$CO—, —$NR^B$CONR$^B$—, —$NR^B$CO$_2$—, —CO—, —C(O)O—, —OC(O)—, —CONR$^B$—, —OC(O)NR$^B$—, —SO$_2$—, —SO$_2$NR$^B$—, —$NR^B$SO$_2$—, —$NR^B$SO$_2$NR$^B$—, —C(O)C(O)—, or —C(O)C(R$^B$)$_2$C(O)—, and each occurrence of $R^B$ is independently hydrogen or optionally substituted group selected from $C_{1-6}$ aliphatic, $C_{1-6}$heteroaliphatic, aryl or heteroaryl, with the limitation that no more than two of $A^1$, $A^2$, $A^3$ or $A^4$ is absent.

In certain embodiments, one of $A^1$, $A^2$, $A^3$ or $A^4$ is absent.

In certain other embodiments, one of $A^1$, $A^2$, $A^3$ or $A^4$ is absent, and the remaining three are each independently selected from an optionally substituted methylene unit, wherein each methylene unit is optionally replaced by —O— or —CO—.

In certain preferred embodiments, one or more of the methylene units is unsubstituted.

In certain other preferred embodiments, one or more of the methylene units is substituted with an aryl, aralkyl or $C_{1-6}$aliphatic group.

In certain other preferred embodiments, one or more of the methylene units is substituted with phenyl or benzyl.

In still other preferred embodiments, two or more substituents on the same or adjacent methylene units are taken together to form an optionally substituted 3–6-membered carbocyclic or heterocyclic group.

As described generally above, Y is an optionally substituted aryl, heteoaryl, aliphatic or heteoaliphatic moiety. In certain exemplary embodiments, for compounds of general formulas I, Ia, Ib, IVa or IVb (and subsets thereof as described in detail herein) Y is an optionally substituted heteroaryl moiety. In certain preferred embodiments, Y is selected from one of the following heteroaryl moieties a–y:

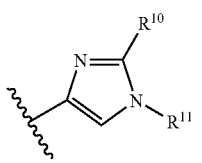
a

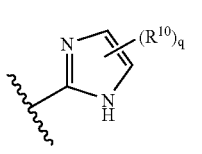
b

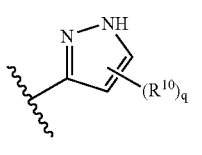
c

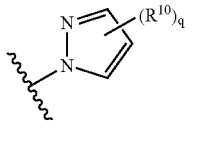
d

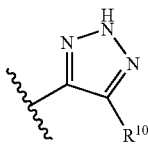
e

-continued

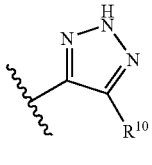
f

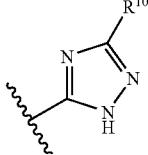
g

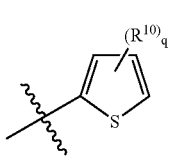
h

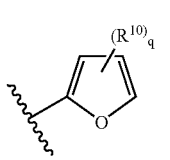
i

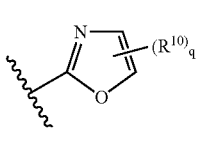
j

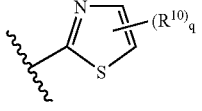
k

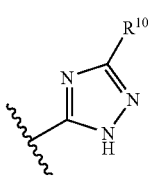
l

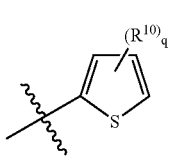
m

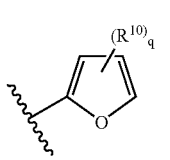
n

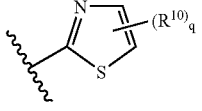
o

-continued

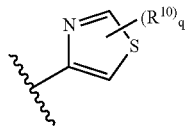
p

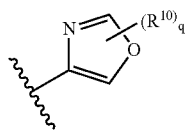
q

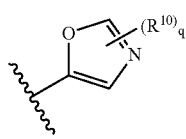
r

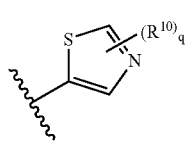
s

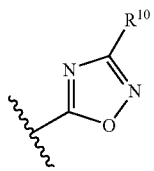
t

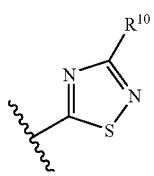
u

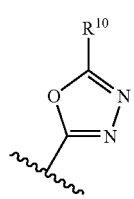
v

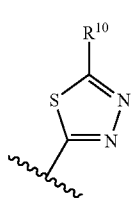
w

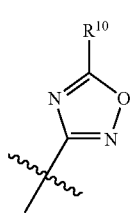
x

-continued

y wherein q is 0–4, $R^{10}$ is —R, wherein —R is defined generally above and in classes and subclasses herein, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

In certain other exemplary embodiments, Y is one of the following heteroaryl moieties:

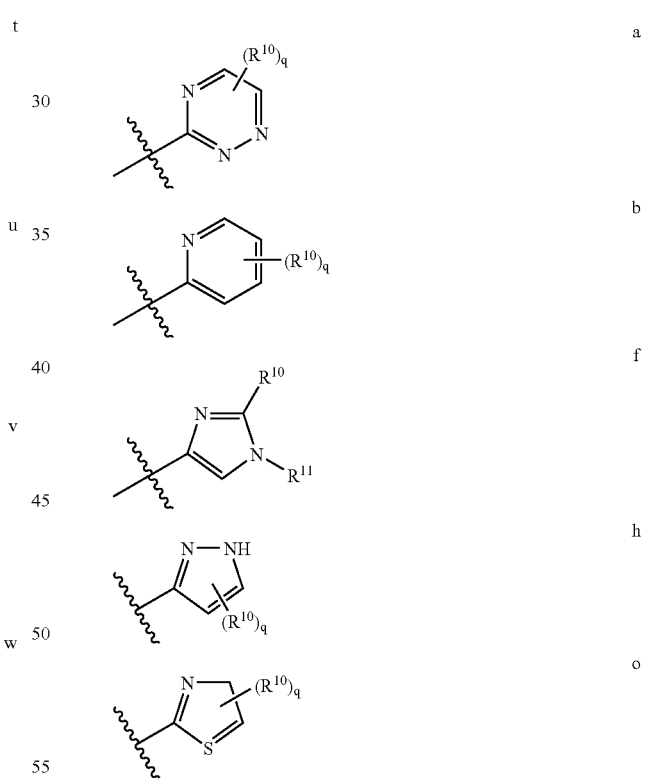

a b f h o wherein q is 0–4, $R^{10}$ is —R, wherein —R is defined generally above and in classes and subclasses herein, and wherein each occurrence of $R^1$ is independently hydrogen, —R', —COR', —CO$_2$(R'), —CON(R')$_2$, or —SO$_2$R', wherein each occurrence of R' is independently hydrogen, optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

In certain preferred embodiments, Y is a pyrazole moiety, h.

Preferred $R^{10}$ groups include hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl. Examples of such preferred $R^{10}$ substituents include methyl, cyclopropyl, ethyl, isopropyl, propyl, t-butyl, cyclopentyl, phenyl, $CO_2H$, $CO_2CH_3$, $CH_2OH$, $CH_2OCH_3$, $CH_2CH_2CH_2OH$, $CH_2CH_2CH_2OCH_3$, $CH_2CH_2CH_2OCH_2Ph$, $CH_2CH_2CH_2NH_2$, $CH_2CH_2CH_2NHCOOC(CH_3)_3$, $CONHCH(CH_3)_2$, $CONHCH_2CH=CH_2$, $CONHCH_2CH_2OCH_3$, $CONHCH_2Ph$, $CONH(cyclohexyl)$, $CON(Et)_2$, $CON(CH_3)CH_2Ph$, $CONH(n-C_3H_7)$, $CON(Et)CH_2CH_2CH_3$, $CONHCH_2CH(CH_3)_2$, $CON(n-C_3H_7)_2$, $CO(3$-methoxymethylpyrrolidin-1-yl), $CONH(3$-tolyl), $CONH(4$-tolyl), $CONHCH_3$, $CO(morpholin-1-yl)$, $CO(4$-methylpiperazin-1-yl), $CONHCH_2CH_2OH$, $CONH_2$, and $CO(piperidin-1-yl)$.

In certain preferred embodiments, Y is a pyrazole moiety, h', wherein the pyrazole is substituted with two occurrences of $R^{10}$ ($R^{10a}$ and $R^{10b}$ as depicted), wherein $R^{10a}$ and $R^{10b}$ are each independently —R.

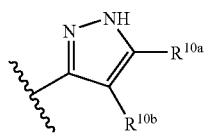

h'

Preferred groups for $R^{10a}$ and $R^{10b}$ include those preferred groups exemplified for $R^{10}$ above. In certain embodiments, preferred groups for $R^{10a}$ include hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl. Examples of such preferred $R^{10a}$ substituents include methyl, cyclopropyl, ethyl, isopropyl, propyl, t-butyl, cyclopentyl, phenyl, $CO_2H$, $CO_2CH_3$, $CH_2OH$, $CH_2OCH_3$, $CH_2CH_2CH_2OH$, $CH_2CH_2CH_2OCH_3$, $CH_2CH_2CH_2OCH_2Ph$, $CH_2CH_2CH_2NH_2$, $CH_2CH_2CH_2NHCOOC(CH_3)_3$, $CONHCH(CH_3)_2$, $CONHCH_2CH=CH_2$, $CONHCH_2CH_2OCH_3$, $CONHCH_2Ph$, $CONH(cyclohexyl)$, $CON(Et)_2$, $CON(CH_3)CH_2Ph$, $CONH(n-C_3H_7)$, $CON(Et)CH_2CH_2CH_3$, $CONHCH_2CH(CH_3)_2$, $CON(n-C_3H_7)_2$, $CO(3$-methoxymethylpyrrolidin-1-yl), $CONH(3$-tolyl), $CONH(4$-tolyl), $CONHCH_3$, $CO(morpholin-1-yl)$, $CO(4$-methylpiperazin-1-yl), $CONHCH_2CH_2OH$, $CONH_2$, and $CO(piperidin-1-yl)$. A preferred group for $R^{10b}$ is hydrogen.

As described generally above, two occurrences of $R^{10}$ (e.g., $R^{10a}$ and $R^{10b}$ as depicted above in formula h') taken together may represent an optionally substituted group selected from a cycloaliphatic, cycloheteroaliphatic, aryl or heteroaryl moiety. In certain preferred embodiments, Y is one of the following groups:

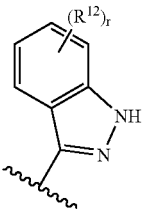

h-i

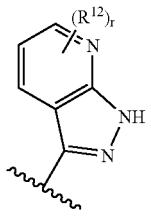

h-ii

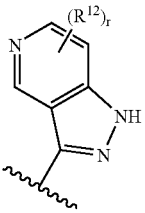

h-iii

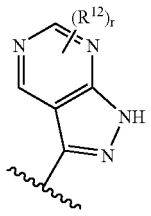

h-iv

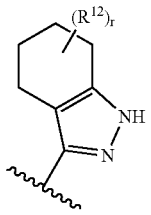

h-v wherein r is 0–4 and $R^{12}$ is —R, wherein —R is defined generally above and in classes and subclasses herein. Preferred substituents $R^{12}$ on the fused ring include one or more of the following: -halo, —$N(R^7)_2$, —$C_{1-3}$ alkyl, —$C_{1-3}$ haloalkyl, —$NO_2$, —$O(C_{1-3}$ alkyl), —$CO_2(C_{1-3}$ alkyl), —CN, —$SO_2(C_{1-3}$ alkyl), —$SO_2NH_2$, —$OC(O)NH_2$, —$NH_2SO_2(C_{1-3}$ alkyl), —$NHC(O)(C_{1-3}$ alkyl), —$C(O)NH_2$, and —$CO(C_{1-3}$ alkyl), wherein the ($C_{1-3}$ alkyl) is most preferably methyl, wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring.

In still other embodiments, for compounds of formulas I, Ia, Ib, IVa or IVb (or subsets thereof as detailed herein) when $R^3$ is —$Q^1$—A—$Q^2$—Y, $R^4$ is preferably hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl. In most preferred embodiments $R^4$ is hydrogen, methyl, ethyl, cyclopropyl, hydroxy, phenyl or —$CH_2NH_2$.

In yet other embodiments, for compounds of formulas I, Ia, Ib, IVa or IVb (or subsets thereof as detailed herein), when $R^4$ is —$Q^1$—A—$Q^2$—Y, $R^3$ is preferably hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl. In most preferred embodiments $R^3$ is hydrogen, methyl, ethyl, cyclopropyl, hydroxy, phenyl or —$CH_2NH_2$.

In certain other preferred embodiments, for compounds of formulas I, Ia, Ib, IVa or IVb (or subsets thereof as detailed herein), $R^5$ is hydrogen, halogen, —$NO_2$, —CN, hydroxy, optionally substituted $C_{1-3}$alkyl, optionally substituted alkoxy, —$SO_2NH_2$, or —C(O)alkyl. In more preferred embodiments, $R^5$ is $C_1$, $CF_3$, $OCF_3$, $CH_3$, —CN, —$SO_2NH_2$ or —C(O)Me.

In certain embodiments, a preferred subclass of compounds of general formula IVa or IVb includes those compounds where $Q^1$ is NH and $Q^2$ is NH and have the general formula IVa(i) or IVb(i).

In certain other embodiments, a preferred subclass of compounds of general formula IVa or IVb includes those compounds where $Q^1$ is O and $Q^2$ is NH, and have the general formula IVa(ii) or IVb(ii).

In still other embodiments, a preferred subclass of compounds of general formula IVa or IVb includes those compounds where $Q^1$ is S and $Q^2$ is NH, and have the general formula IVa(iii) or IVb(iii).

In yet other embodiments, a preferred subclass of compounds of general formula IVa or IVb includes those compounds where $Q^1$ is an optionally substituted methylene unit —$(C(R^4)_2)$— and $Q^2$ is NH, and have the general formula IVa(iv) or IVb(iv).

It will be appreciated that, for compounds of general formulas IVa and IVb (and subclasses represented by IVa(i), IVb(i), IVa(ii), IVb(ii), IVa(iii), IVb(iii), IVa(iv) and IVb(iv)) certain additional subclasses are of special interest. Certain preferred embodiments of compounds of formula IVa or IVb IVb (and subclasses represented by IVa(i), IVb(i), IVa(ii), IVb(ii), IVa(iii), IVb(iii), IVa(iv) and IVb(iv)) include those compounds having any combination of one or more of the following features:

i) Z is $CR^6$ or N;
ii) $R^1$, $R^2$, $R^4$ and $R^5$ are each hydrogen and wherein Z is $CHR^6$ and $R^6$ is hydrogen; or $R^1$, $R^2$, $R^3$ and $R^5$ are each hydrogen and wherein Z is $CHR^6$ and $R^6$ is hydrogen;
iii) ring A is defined according to one of the following groups:
  a. only one of $A^1$, $A^2$, $A^3$ or $A^4$ is absent;
  b. only one of $A^1$, $A^2$, $A^3$ or $A^4$ is absent, and the remaining three are each independently selected from an optionally substituted methylene unit, wherein each methylene unit is optionally replaced by —O— or —CO—;
  c. only one of $A^1$, $A^2$, $A^3$ or $A^4$ is absent, and the remaining three are each independently selected from an optionally substituted methylene unit, wherein each methylene unit is optionally replaced by —O— or —CO—; wherein one or more of the methylene units represented by $A^1$, $A^2$, $A^3$ or $A^4$ is unsubstituted or is substituted with an aryl, aralkyl or $C_{1-6}$aliphatic group;
  d. only one of $A^1$, $A^2$, $A^3$ or $A^4$ is absent, and the remaining three are each independently selected from an optionally substituted methylene unit, wherein each methylene unit is optionally replaced by —O— or —CO—; wherein one or more of the methylene units represented by $A^1$, $A^2$, $A^3$ or $A^4$ is unsubstituted or is substituted with an aryl, aralkyl or $C_{1-6}$aliphatic group, or wherein two subsitutents on the same methylene unit, or two substituents on adjacent methylene units are taken together to form a 3–6-membered carbocyclic or heterocyclic ring;

iv) Y is defined according to one of the following groups:
a. Y is an optionally substituted heteroaryl moiety;
b. Y is selected from one of the heteroaryl moieties a–y;
c. Y is selected from one of the following heteroaryl moieties:

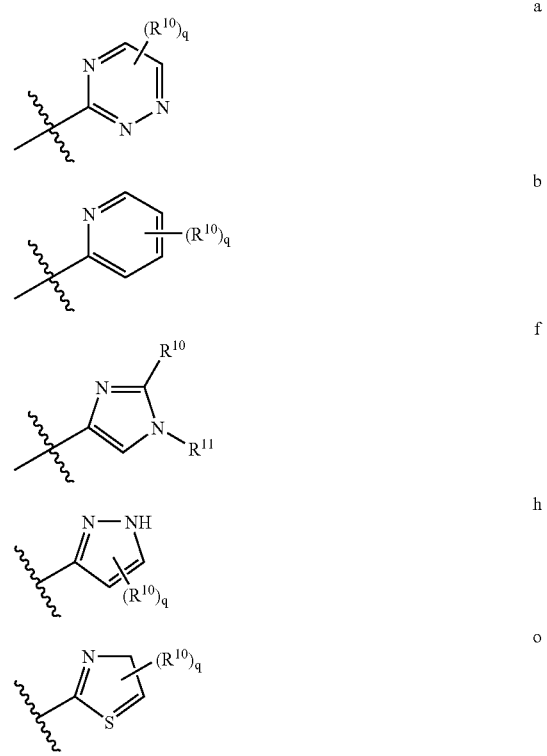

wherein q is 0–4, $R^{10}$ is —R, wherein —R is defined generally above and in classes and subclasses herein, and wherein each occurrence of $R^{11}$ is independently hydrogen, —R', —COR', —$CO_2(R')$, —$CON(R')_2$, or —$SO_2R'$, wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

d. Y is a pyrazole moiety, h;
e. Y is one of a, b, f, h or o, optionally substituted with one or more $R^{10}$ groups, wherein each occurrence of $R^{10}$ is independently hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl;

f. Y is one of a, b, f, h or o, optionally substituted with one or more $R^{10}$ groups, wherein each occurrence of $R^{10}$ is independently hydrogen, methyl, cyclopropyl, ethyl, isopropyl, propyl, t-butyl, cyclopentyl, phenyl, $CO_2H$, $CO_2CH_3$, $CH_2OH$, $CH_2OCH_3$, $CH_2CH_2CH_2OH$, $CH_2CH_2CH_2OCH_3$, $CH_2CH_2CH_2OCH_2Ph$, $CH_2CH_2CH_2NH_2$, $CH_2CH_2CH_2NHCOOC(CH_3)_3$, $CONHCH(CH_3)_2$, $CONHCH_2CH=CH_2$, $CONHCH_2CH_2OCH_3$, $CONHCH_2Ph$, $CONH(cyclohexyl)$, $CON(Et)_2$, $CON(CH_3)CH_2Ph$, $CONH(n-C_3H_7)$, $CON(Et)CH_2CH_2CH_3$, $CONHCH_2CH(CH_3)_2$, $CON(n-C_3H_7)_2$, $CO(3-methoxymethylpyrrolidin-1-yl)$, $CONH(3-tolyl)$, $CONH(4-tolyl)$, $CONHCH_3$, $CO(morpholin-1-yl)$, $CO(4-methylpiperazin-1-yl)$, $CONHCH_2CH_2OH$, $CONH_2$, and $CO(piperidin-1-yl)$.

g. Y is a pyrazole moiety, h', wherein the pyrazole is substituted with two occurrences of $R^{10}$ ($R^{10a}$ and $R^{10b}$ as depicted),

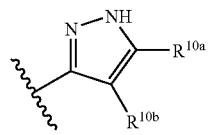
h' wherein each occurrence of $R^{10a}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl, and $R^{10b}$ is hydrogen;

h. Y is a pyrazole moiety, h', wherein the pyrazole is substituted with two occurrences of $R^{10}$ ($R^{10a}$ and $R^{10b}$ as depicted),

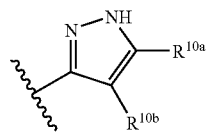
h' wherein each occurrence of $R^{10a}$ is hydrogen, methyl, cyclopropyl, ethyl, isopropyl, propyl, t-butyl, cyclopentyl, phenyl, $CO_2H$, $CO_2CH_3$, $CH_2OH$, $CH_2OCH_3$, $CH_2CH_2CH_2OH$, $CH_2CH_2CH_2OCH_3$, $CH_2CH_2CH_2OCH_2Ph$, $CH_2CH_2CH_2NH_2$, $CH_2CH_2CH_2NHCOOC(CH_3)_3$, $CONHCH(CH_3)_2$, $CONHCH_2CH=CH_2$, $CONHCH_2CH_2OCH_3$, $CONHCH_2Ph$, $CONH(cyclohexyl)$, $CON(Et)_2$, $CON(CH_3)CH_2Ph$, $CONH(n-C_3H_7)$, $CON(Et)CH_2CH_2CH_3$, $CONHCH_2CH(CH_3)_2$, $CON(n-C_3H_7)_2$, $CO(3-methoxymethylpyrrolidin-1-yl)$, $CONH(3-tolyl)$, $CONH(4-tolyl)$, $CONHCH_3$, $CO(morpholin-1-yl)$, $CO(4-methylpiperazin-1-yl)$, $CONHCH_2CH_2OH$, $CONH_2$, and $CO(piperidin-1-yl)$, and $R^{10b}$ is hydrogen;

i. Y is heteroaryl moiety substituted by at least two occurrences of $R^{10}$ and where two occurrences of $R^{10}$ taken together may represent an optionally substituted group selected from cycloaliphatic, cycloheteroaliphatic, aryl or heteroaryl;

j. Y represents one of the following heteroaryl moieties:

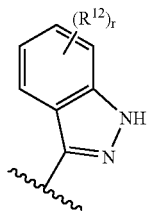
h-i

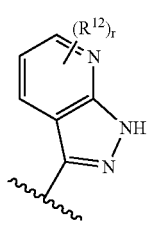
h-ii

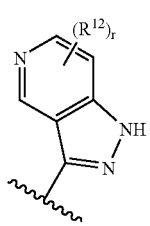
h-iii

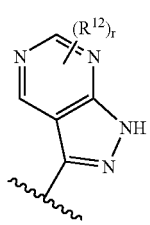
h-iv

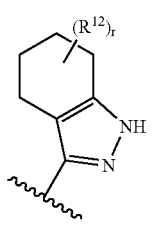
h-v wherein r is 0–4 and $R^{12}$ is hydrogen, -halo, $-N(R^7)_2$, $-C_{1-3}$ alkyl, $-C_{1-3}$ haloalkyl, $-NO_2$, $-O(C_{1-3}$ alkyl), $-CO_2(C_{1-3}$ alkyl), $-CN$, $-SO_2(C_{1-3}$ alkyl), $-SO_2NH_2$, $-OC(O)NH_2$, $-NH_2SO_2(C_{1-3}$ alkyl), $-NHC(O)(C_{1-3}$ alkyl), $-C(O)NH_2$, and $-CO(C_{1-3}$ alkyl), wherein the ($C_{1-3}$ alkyl) is most preferably methyl;

v) for compounds of formula IIIa(iv), $R^4$ is defined according to one of the following groups:
  a. $R^4$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
  b. $R^4$ is hydrogen, methyl, ethyl, cyclopropyl, hydroxy, phenyl or $-CH_2NH_2$;

vi) for compounds of formula IIIb(iv), $R^3$ is defined according to one of the following groups:
  a. $R^3$ is hydrogen, $C_{1-3}$aliphatic, hydroxy, hydroxyalkyl, alkoxy, amino, aminoalkyl, mono- or di- alkylamino, mono- or di-alkylaminoalkyl, or optionally substituted phenyl, or b. R³ is hydrogen, methyl, ethyl, cyclopropyl, hydroxy, phenyl or —CH₂NH₂; and vi) R⁵ is defined according to one of the following groups:
a. hydrogen, halogen, —NO₂, —CN, hydroxy, optionally substituted C₁₋₃alkyl, optionally substituted alkoxy, —SO₂NH₂, or —C(O)alkyl, or
b. R⁵ is hydrogen, C₁, CF₃, OCF₃, CH₃, —CN, —SO₂NH₂ or —C(O)Me.

In certain preferred embodiments, compounds of the invention include those compounds having one of the general formulas IVa(i), IVa(ii), IVa(iii), or IVa(iv) and wherein the compounds have one or more of the following features:

a. Z is NR⁶, wherein R¹ and R² are each independently hydrogen or a protecting group; R⁴, R⁵ and R⁶ are each hydrogen, b. only one of A¹, A², A³ or A⁴ is absent, and the remaining three are each independently selected from an optionally substituted methylene unit, wherein each methylene unit is optionally replaced by —O—, —S—, —NR^B—, —NR^BCO—, —NR^BCONR^B—, —NR^BCO₂—, —CO—, —C(O)O—, —OC(O)—, CONR^B—, —OC(O)NR^B—, —SO₂—, —SO₂NR^B—, —NR^BSO₂—, —NR^BSO₂NR^B—, —C(O)C(O)—, or —C(O)C(R^B)₂C(O)—, and each occurrence of R^B is independently hydrogen or optionally substituted group selected from C₁₋₆ aliphatic, C₁₋₆heteroaliphatic, aryl or heteroaryl, and c. Y is an optionally substituted heteroaryl moiety selected from one of formulas a–y.

It will be appreciated that for compounds described directly above, preferred groups for A¹, A², A³ or A⁴, and Y (and substituents thereon) also include those preferred groups as exemplified in subclasses and species above and herein.

Representative examples of compounds of formula IVa or IVb (and subclasses represented by IVa(i), IVb(i), IVa(ii), IVb(ii), IVa(iii), IVb(iii), IVa(iv) and IVb(iv)) are depicted generally as IV in Table II below but encompass compounds of both formulas IVa and IVb (and subclasses represented by IVa(i), IVb(i), IVa(ii), IVb(ii), IVa(iii), IVb(iii), IVa(iv) and IVb(iv).

TABLE 11

Examples of Compounds of Formula IV:

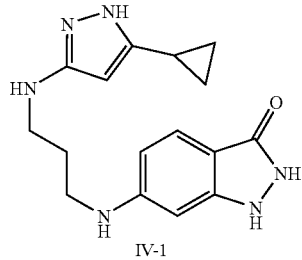

IV-1

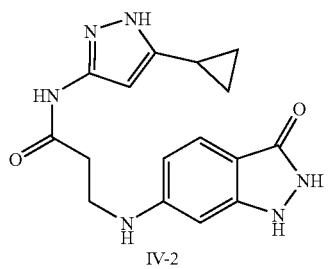

IV-2

TABLE 11-continued

Examples of Compounds of Formula IV:

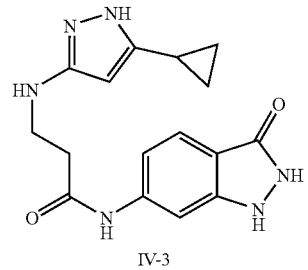

IV-3

IV-2

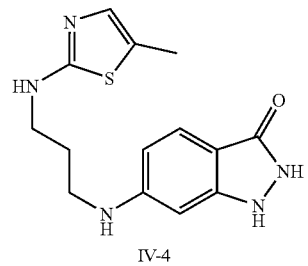

IV-4

IV-2

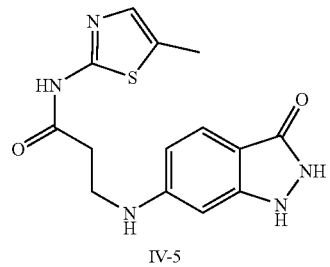

IV-5

IV-2

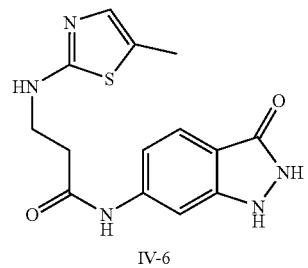

IV-6

TABLE 11-continued
Examples of Compounds of Formula IV:
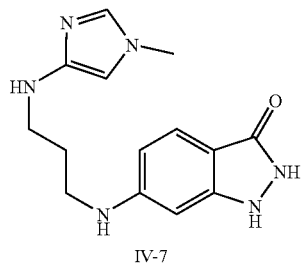
IV-7
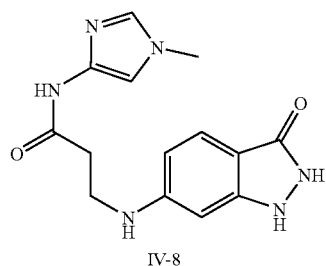
IV-8
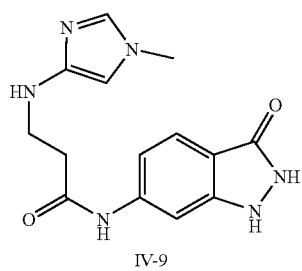
IV-9
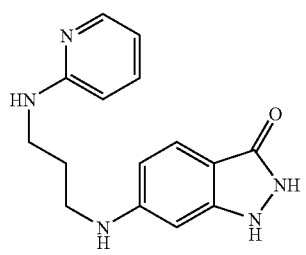
IV-10
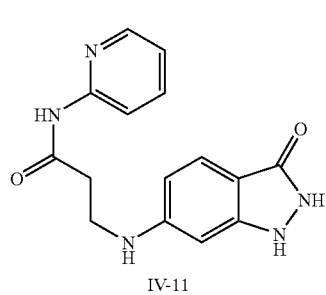
IV-11
TABLE 11-continued
Examples of Compounds of Formula IV:
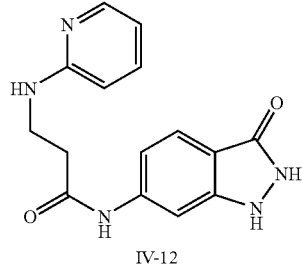
IV-12
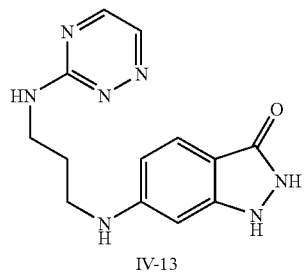
IV-13
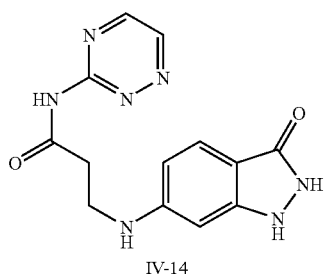
IV-14
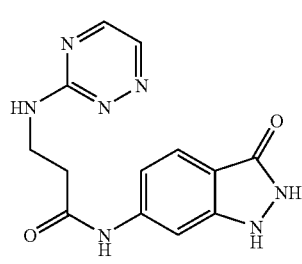
IV-15
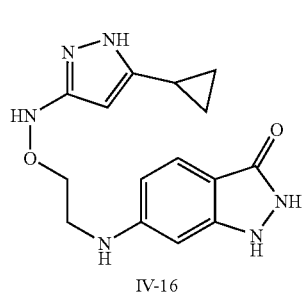
IV-16

TABLE 11-continued

Examples of Compounds of Formula IV:

IV-17

IV-18

IV-19

IV-20

IV-21

IV-22

TABLE 11-continued

Examples of Compounds of Formula IV:

IV-23

IV-24

IV-25

IV-26

IV-27

TABLE 11-continued
Examples of Compounds of Formula IV:
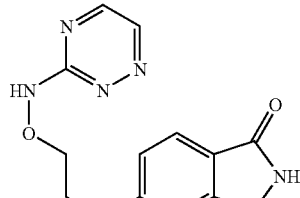
IV-28
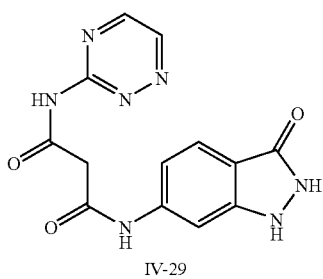
IV-29
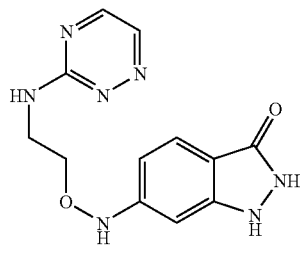
IV-30
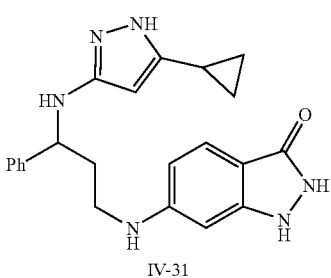
IV-31
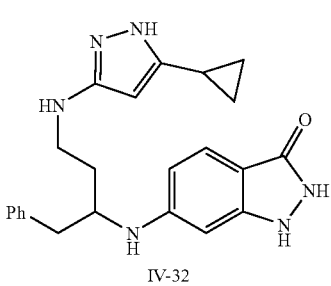
IV-32
TABLE 11-continued
Examples of Compounds of Formula IV:
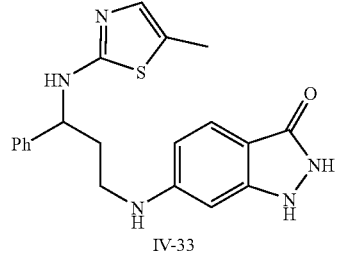
IV-33
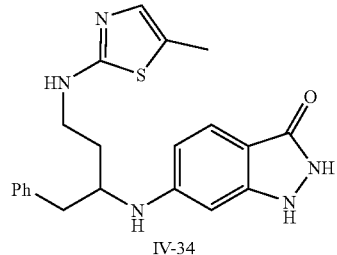
IV-34
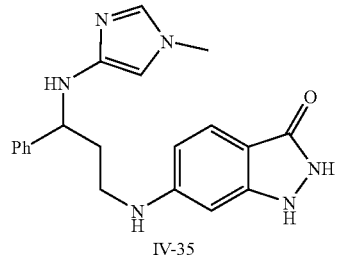
IV-35
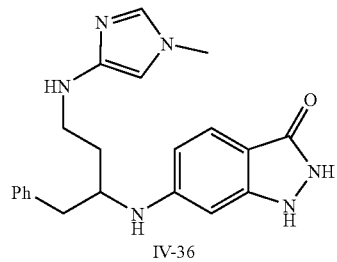
IV-36
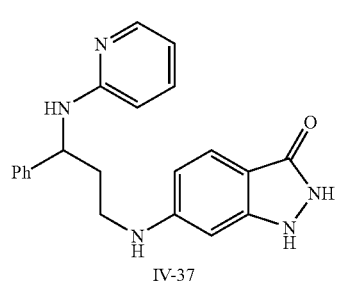
IV-37

TABLE 11-continued
Examples of Compounds of Formula IV:
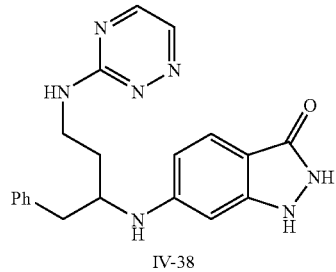
IV-38
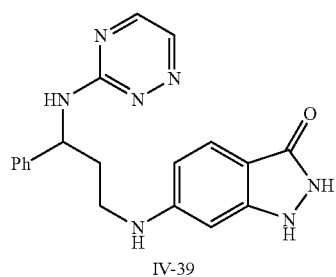
IV-39
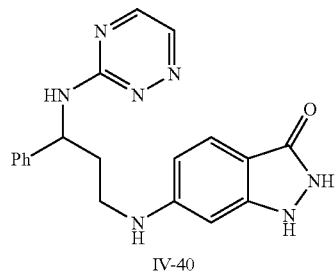
IV-40
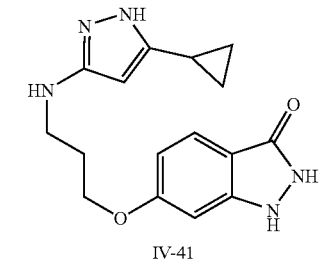
IV-41
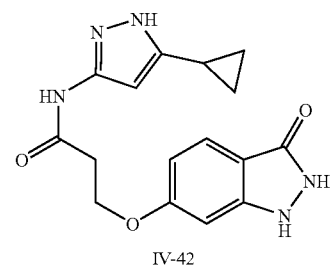
IV-42
TABLE 11-continued
Examples of Compounds of Formula IV:
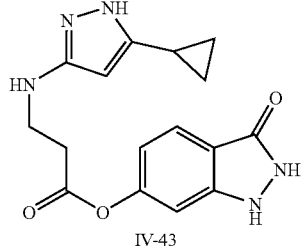
IV-43
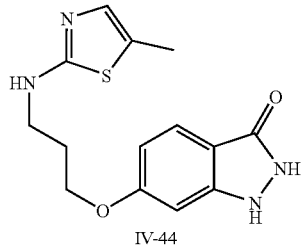
IV-44
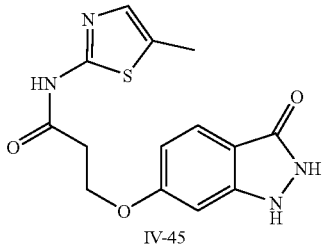
IV-45
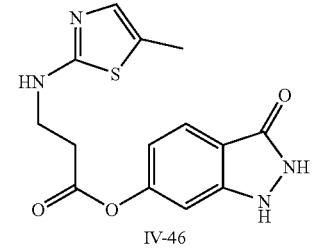
IV-46
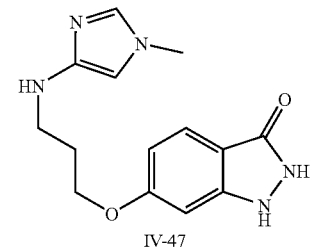
IV-47
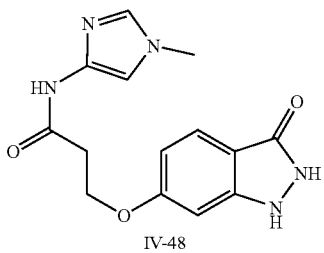
IV-48

TABLE 11-continued
Examples of Compounds of Formula IV:
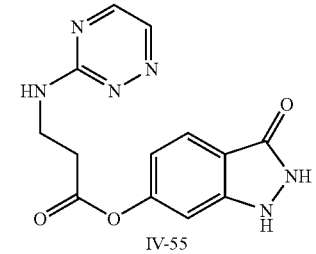
IV-49
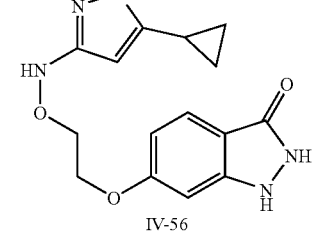
IV-50
IV-51
IV-52
IV-53
IV-54
TABLE 11-continued
Examples of Compounds of Formula IV:
IV-55
IV-56
IV-57
IV-58
IV-59
IV-60

TABLE 11-continued
Examples of Compounds of Formula IV:
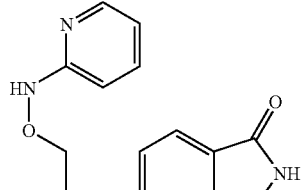
IV-61
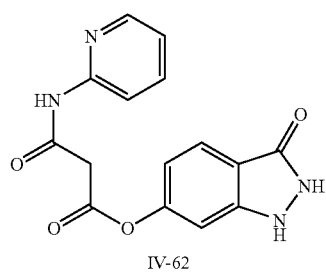
IV-62
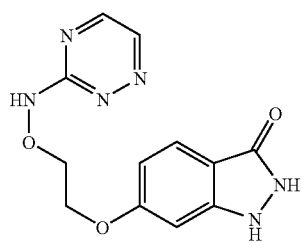
IV-63
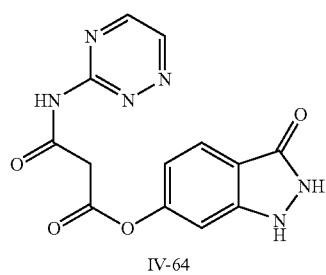
IV-64
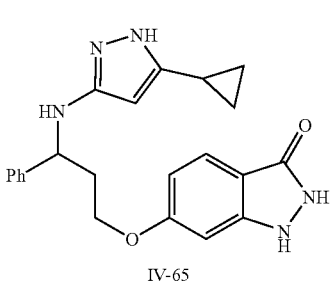
IV-65
TABLE 11-continued
Examples of Compounds of Formula IV:
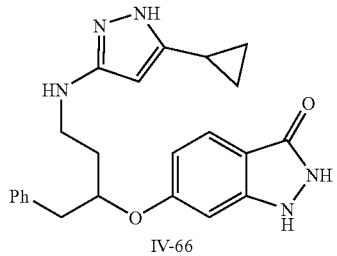
IV-66
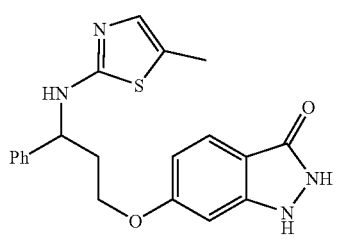
IV-67
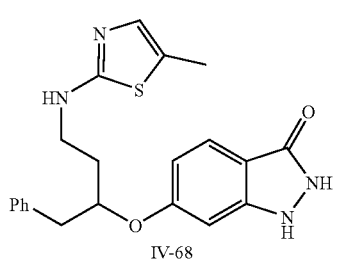
IV-68
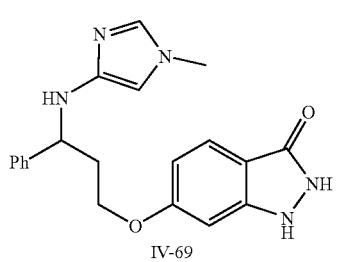
IV-69
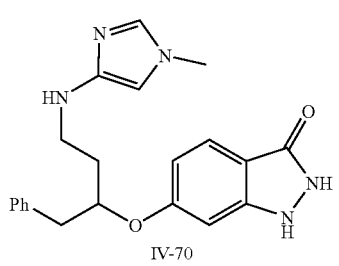
IV-70
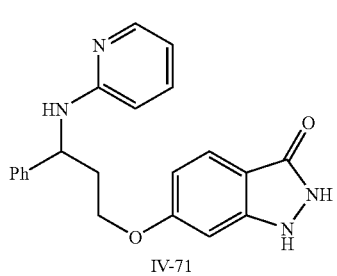
IV-71

TABLE 11-continued
Examples of Compounds of Formula IV:
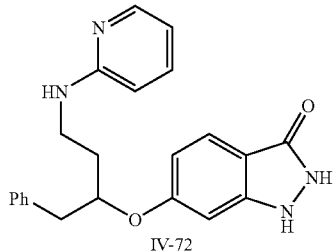
IV-72
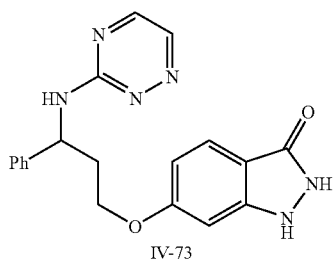
IV-73
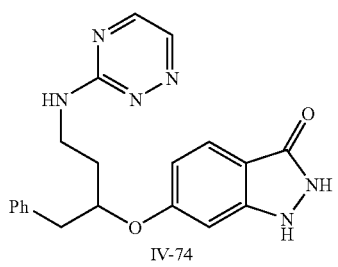
IV-74
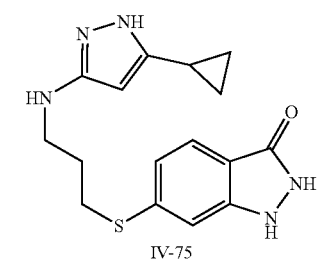
IV-75
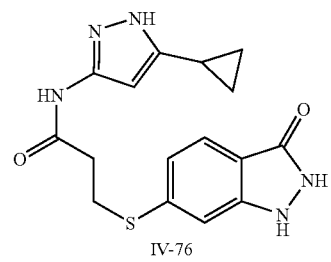
IV-76
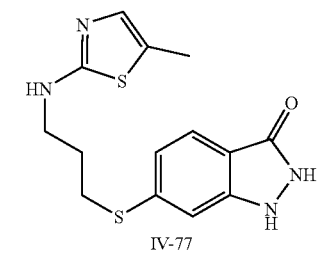
IV-77
TABLE 11-continued
Examples of Compounds of Formula IV:
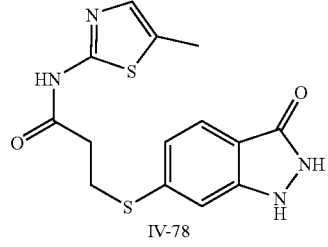
IV-78
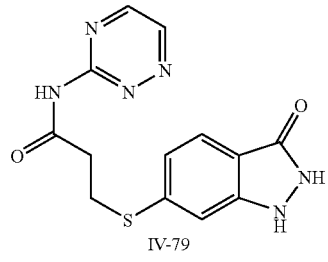
IV-79
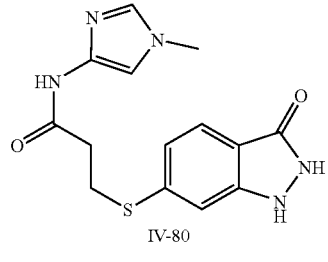
IV-80
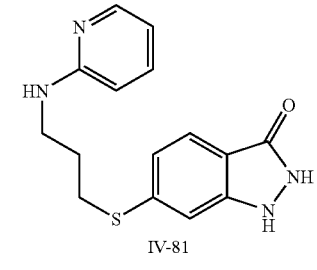
IV-81
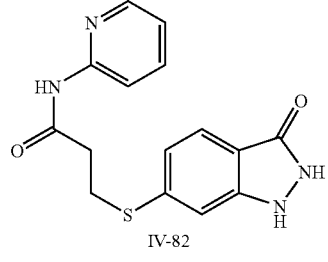
IV-82
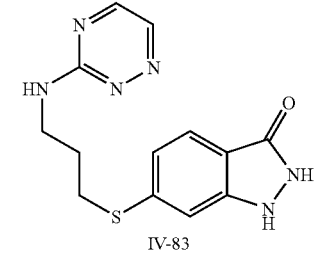
IV-83

TABLE 11-continued

Examples of Compounds of Formula IV:

IV-84

IV-85

IV-86

IV-87

IV-88

IV-89

TABLE 11-continued

Examples of Compounds of Formula IV:

IV-90

IV-91

IV-92

IV-93

IV-94

IV-95

TABLE 11-continued
Examples of Compounds of Formula IV:
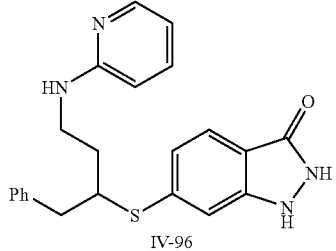
IV-96
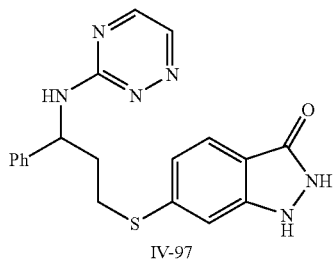
IV-97
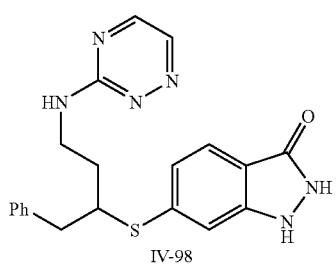
IV-98
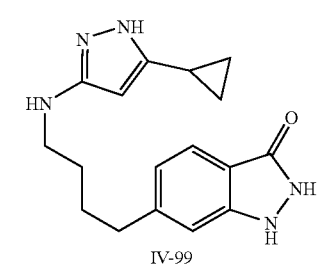
IV-99
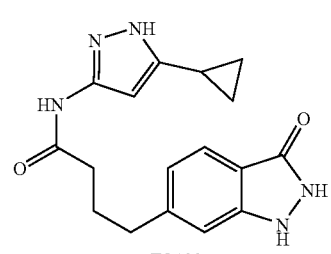
IV-100
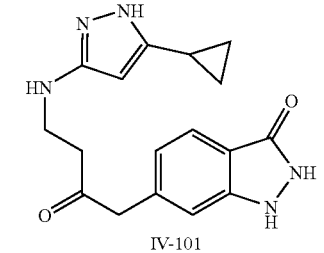
IV-101
TABLE 11-continued
Examples of Compounds of Formula IV:
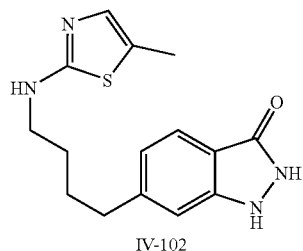
IV-102
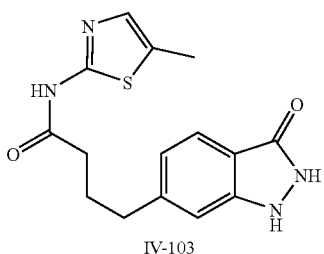
IV-103
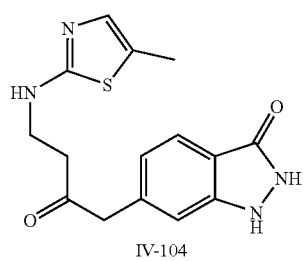
IV-104
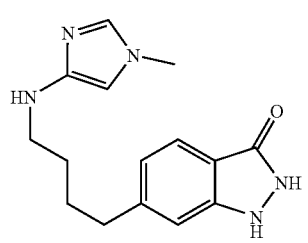
IV-105
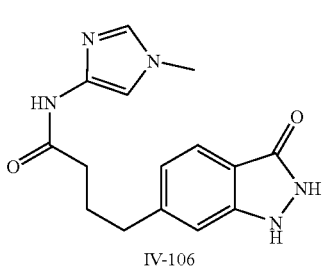
IV-106
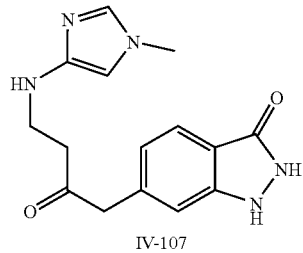
IV-107

TABLE 11-continued
Examples of Compounds of Formula IV:
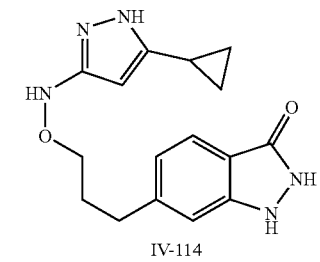
IV-108
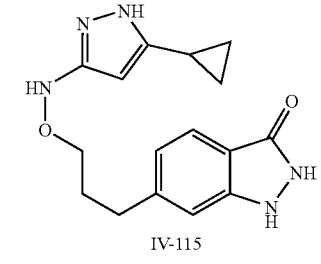
IV-109
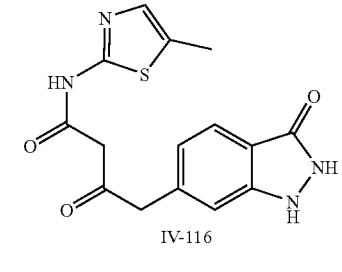
IV-110
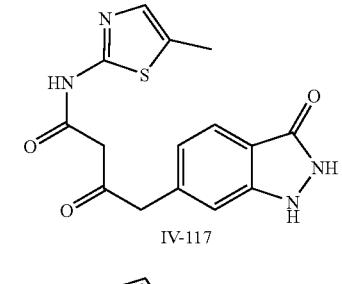
IV-111
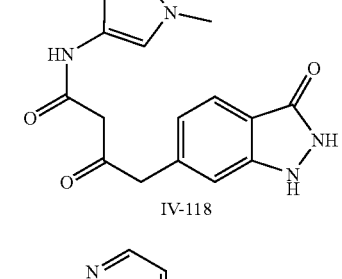
IV-112
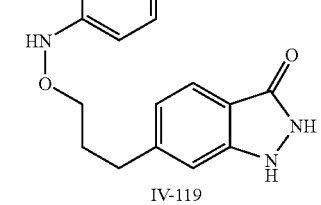
IV-113
TABLE 11-continued
Examples of Compounds of Formula IV:
IV-114
IV-115
IV-116
IV-117
IV-118
IV-119

TABLE 11-continued

Examples of Compounds of Formula IV:

IV-120

IV-121

IV-122

IV-123

IV-124

IV-125

IV-126

IV-127

IV-128

IV-129

IV-130

IV-131

TABLE 11-continued
Examples of Compounds of Formula IV:
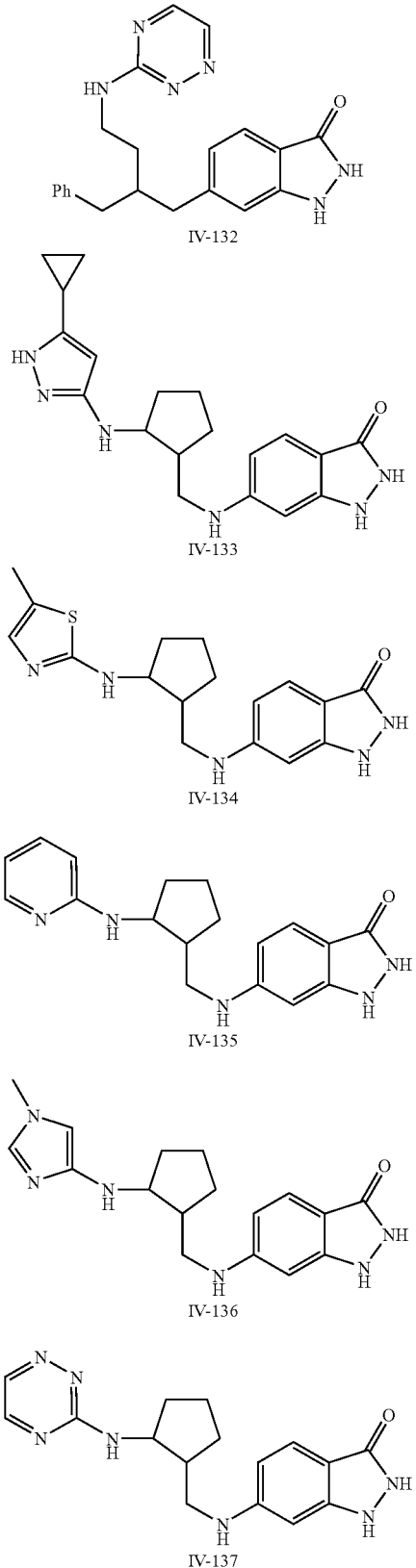
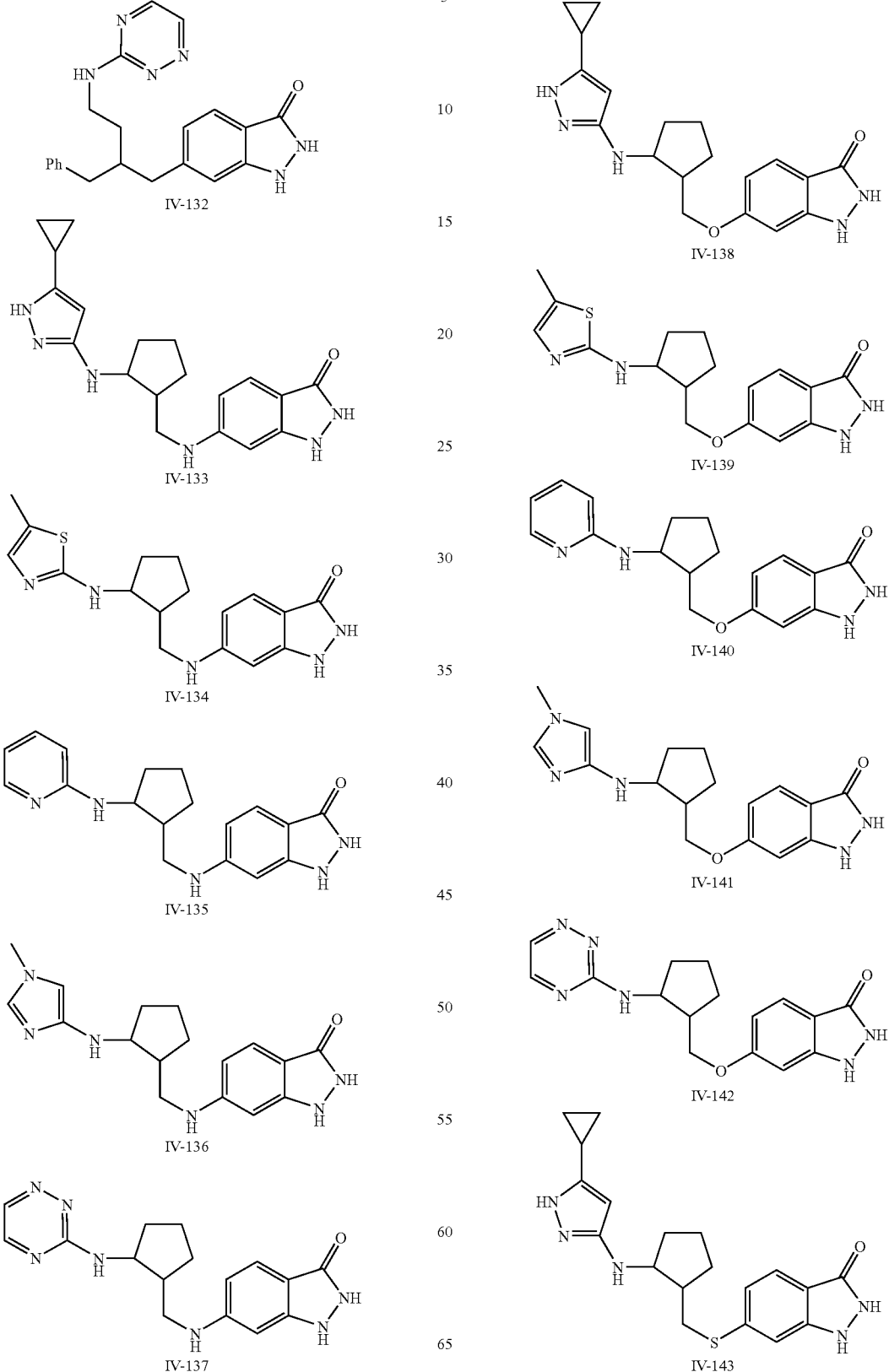

TABLE 11-continued

Examples of Compounds of Formula IV:

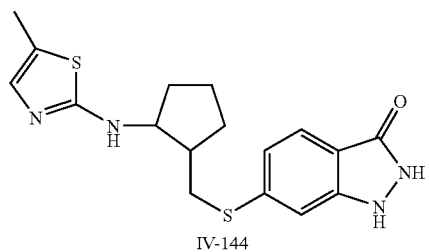
IV-144

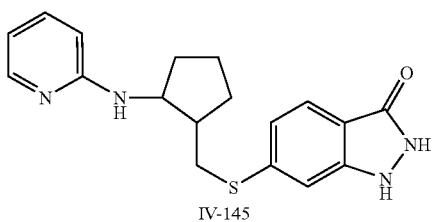
IV-145

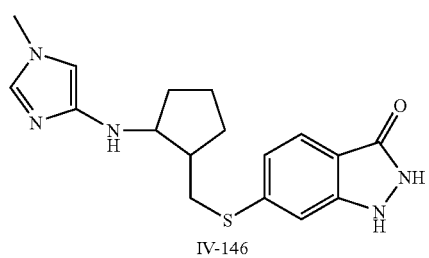
IV-146

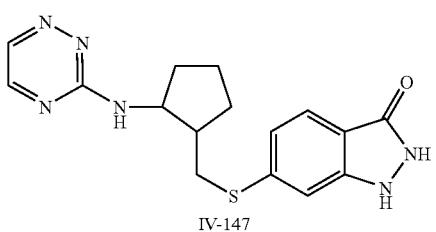
IV-147

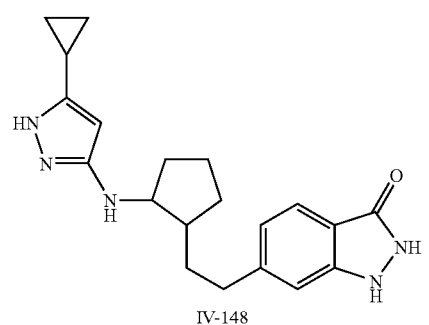
IV-148

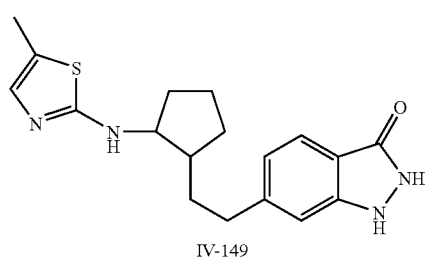
IV-149

TABLE 11-continued

Examples of Compounds of Formula IV:

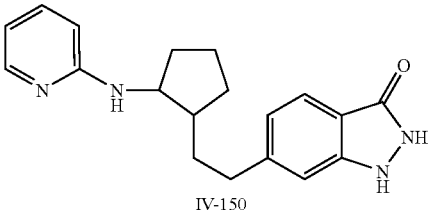
IV-150

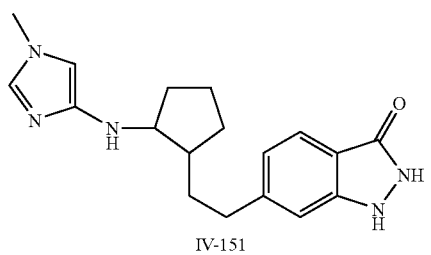
IV-151

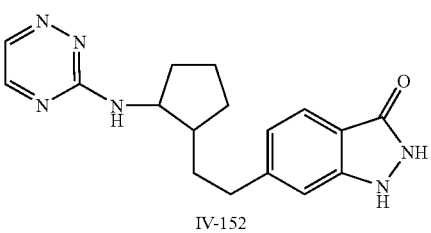
IV-152

III. General Synthetic Methodology:

The compounds of this invention may be prepared in general by methods known to those skilled in the art for analogous compounds, as illustrated by the general scheme below, and the preparative examples that follow.

Schemes I–IV below show general routes for the preparation of certain exemplary compounds of the invention having general the general formula Ia. It will be appreciated that although compounds of general formula Ia are depicted, compounds of general formula IIb can also be prepared according to the methods described generally below in Schemes I–IV.

Scheme I

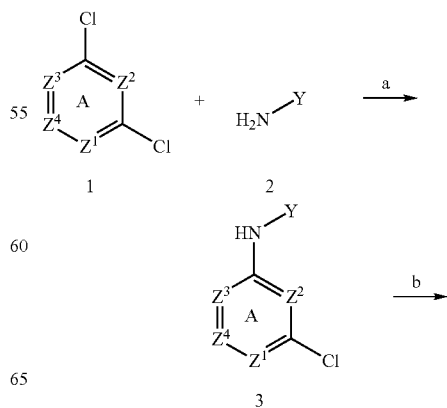

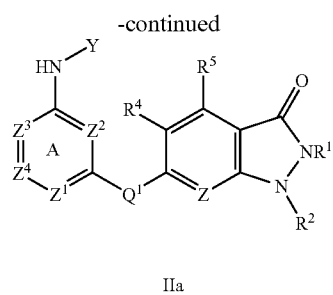

IIa

Reagents: (a) EtOH, Et₃N, room temperature; (b) (indazolinone)-Q¹H (Q = S, NH or O) or (indazolinone)-CH₂-M/catalyst (M is Al or Mg or Sn, catalyst = Pd° or Ni°)

The dichlorinated starting material 1 may be prepared using methods similar to those reported in *J. Indian. Chem. Soc.*, 61, 690–693 (1984) or in *J. Med. Chem.*, 37, 3828–3833 (1994). In certain embodiments, $Z^3$ and $Z^4$ are $CR^X$ and $CR^Y$, respectively, and $Z^1$ is $CR^V$ or N and $Z^2$ is $CR^W$ or N. The reaction of 1 with the substituted amine (preferably heteroaryl substituted amine) 2 in a manner similar to the method described in *Bioorg. Med. Chem. Lett*, 10, 11, 1175–1180, (2000) or in *J. Het. Chem*, 21, 1161–1167, (1984) provides the versatile monochloro intermediate 3. Conditions for displacing the chloro group of 3 by (indazolinone)-Q¹ will depend on the nature of the Q¹ linker moiety and are generally known in the field. See, for example, *J. Med. Chem*, 38, 14, 2763–2773, (1995) (where Q¹ is an N-Link), or *Chem. Pharm. Bull.*, 40, 1, 227–229, (1992) (S-Link), or *J. Het. Chem.*, 21, 1161–1167, (1984) (O-Link) or *Bioorg. Med. Chem. Lett*, 8, 20, 2891–2896, (1998) (C-Link).

Scheme II below shows an alternative route for the preparation of the present compounds.

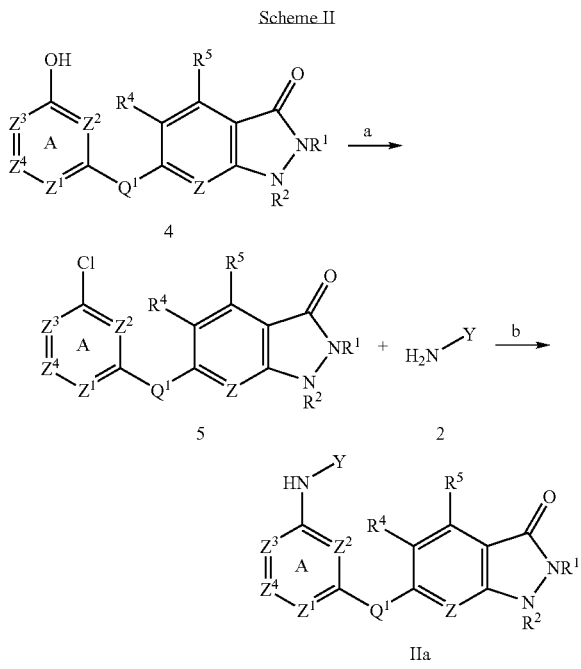

Reagents: (a) POCl₃, Pr₃N, 110° C.; (b) EtOH, Et₃N, room temperature.

As shown above, the starting material 4 may be prepared in a manner similar to that described for analogous compounds. See *Chem. Heterocycl. Compd.*, 35, 7, 818–820 (1999) (where Q¹ is an N-Link), *Indian J. Chem. Sect. B*, 22, 1, 37–42 (1983) (N-Link), *Pestic. Sci*, 47, 2, 103–114 (1996) (O-Link), *J. Med. Chem.*, 23, 8, 913–918 (1980) (S-Link), or *Pharmazie*, 43, 7, 475–476 (1988) (C-Link). The chlorination of 4 provides intermediate 5. See *J. Med. Chem.*, 43, 22, 4288–4312 (2000) (Q is an N-Link), *Pestic. Sci*, 47, 2, 103–114 (1996) (O-Link), *J. Med. Chem.*, 41, 20, 3793–3803 (1998) (S-Link), or *J. Med. Chem.*, 43, 22, 4288–4312 (2000) (C-Link). Displacement of the 4-Cl group in intermediate 5 with the substituted amine (preferably heteroaryl substituted amine) 2 to provide compounds of this invention may be performed according to known methods for analogous compounds. See *J. Med. Chem.*, 38, 14, 2763–2773 (1995) (where Q is an N-Link), *Bioorg. Med. Chem. Lett.*, 7, 4, 421424 (1997) (O-Link), *Bioorg. Med. Chem. Lett.*, 10, 8, 703–706 (2000) (S-Link), or *J. Med. Chem.*, 41, 21, 4021–4035 (1998) (C-Link).

Scheme III below shows another alternative route for preparing the present compounds.

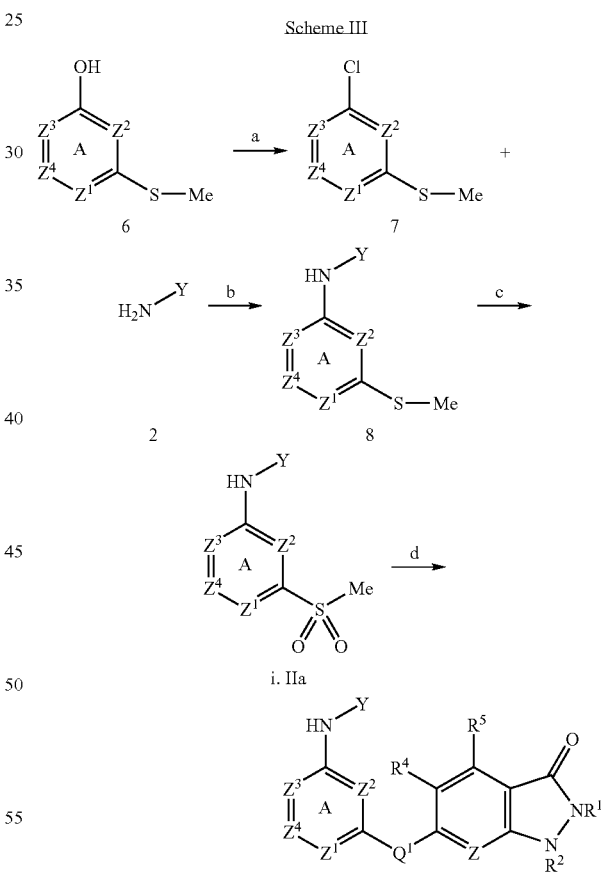

Reagents: (a) POCl₃; (b) EtOH, EtN, room temperature; (c) Oxone; (d) (indazolinone)-Q¹H (Q¹ = S, NH or O) or (indazolinone)-CH₂-M/catalyst (M is Al or Mg or Sn, catalyst = Pd° or Ni°)

The starting material 6 may be chlorinated to provide intermediate 7. Displacement of the 4-chloro group in 7 with substituted amino (preferably heteroaryl substituted amino) 2 gives intermediate 8 which, upon oxidation of the methylsulfanyl group, provides the methylsulfone 9. The methylsulfonyl group of 9 may be displaced readily with (indazolinone)-Q¹H to give the desired product I. See *J. Am. Chem. Soc.*, 81, 5997–6006 (1959) (where Q¹ is an N-Link) or in *Bioorg. Med. Chem. Lett.*, 10, 8, 821–826 (2000) (S—Link).

Scheme IV below shows a general route for the preparation of the present compounds wherein R$^y$ is a group attached to ring A via a nitrogen, oxygen or sulfur heteroatom. In certain embodiments, ring A is pyrimidine.

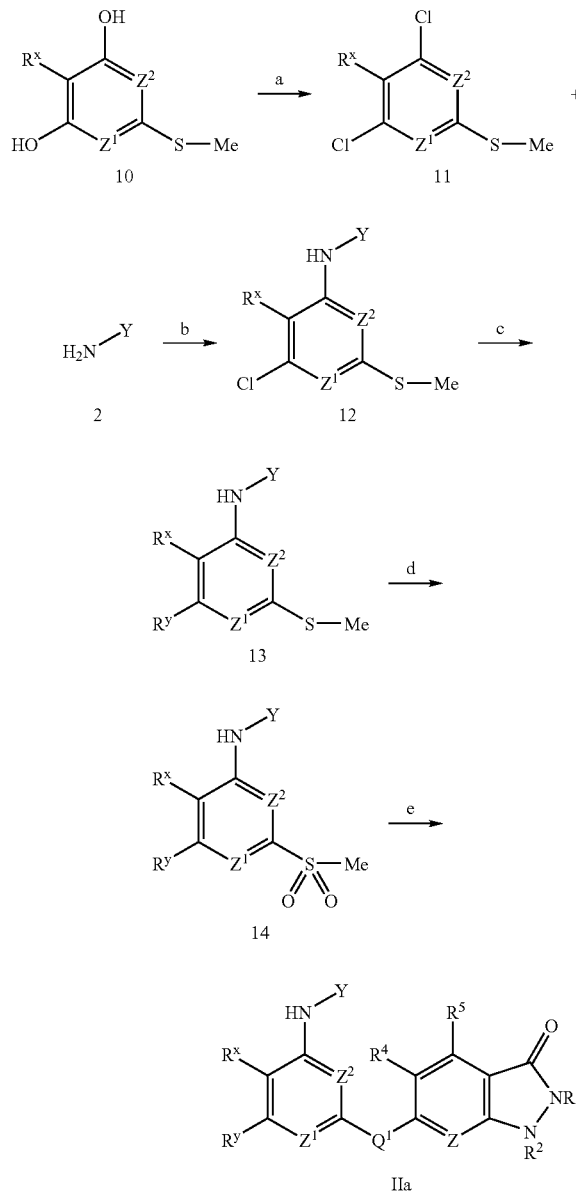

Reagents: (a) POCl₃; (b) EtOH, Et₃N, room temperature; (c) R$^y$—H (R = S, NH or O); (d) oxone; (e) (indazolinone)-Q¹H (Q¹ = S, NH or O) or (indazolinone-CH₂-M/catalyst (M is Al or Mg or Sn, catalyst = Pd° or Ni°)

The starting 4,6-dihydroxy-2-methylsulfanyl intermediate 10 may be prepared as described in *J. Med. Chem.*, 27, 12, 1621–1629 (1984). The chloro groups of intermediate 11 may be displaced sequentially with substituted amino (preferably heteroaryl substituted amino) 2 and then with another amine (or alcohol or thiol) following procedures similar to those reported in U.S. Pat. No. 2,585,906 (ICI, 1949). The methylsulfanyl group of 13 may then be oxidized to provide the methylsulfone 14. Displacement of the methylsulfonyl group of 14 gives the desired product IIa. Additional compounds where Q¹ is a direct bond may be prepared in a manner similar to that described in *Tetrahedron*, 48, 37, 1992, 8117–8126, where the indazolinone is introduced using a boronic ester under palladium catalysis.

Compounds of general formula IV are prepared according to the methods exemplified in Schemes V–IX below. It will be appreciated that although compounds of general formula IVa are depicted in these schemes, compounds of general formula IVb can also be prepared according to these methods.

Scheme V below depicts the preparation of compounds where Q¹ and Q² are each NH and A is a C$_{2-6}$ alkyl group.

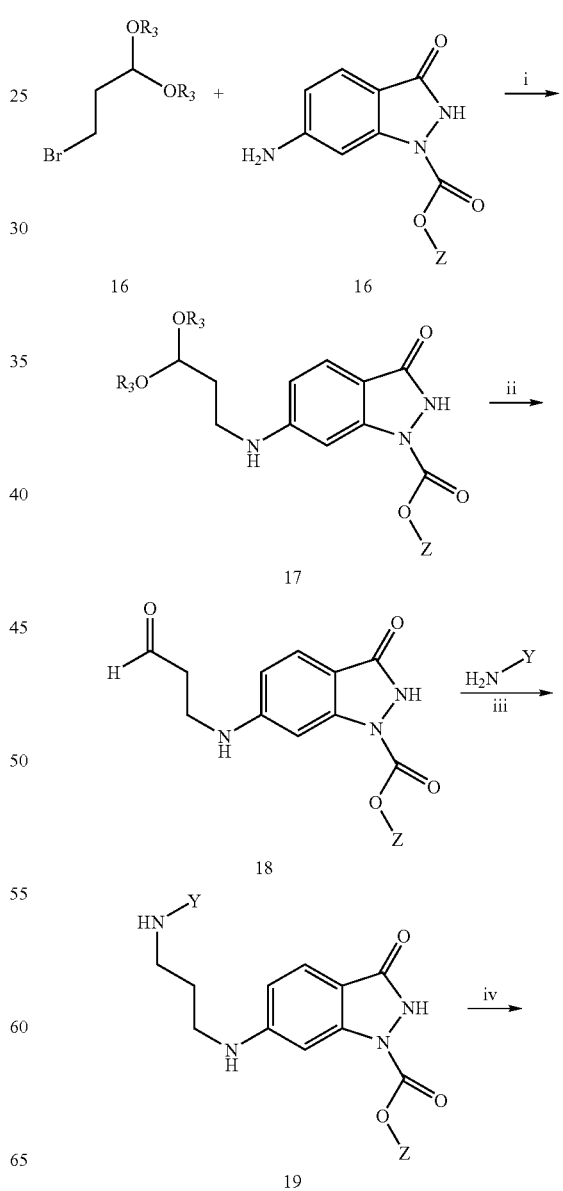

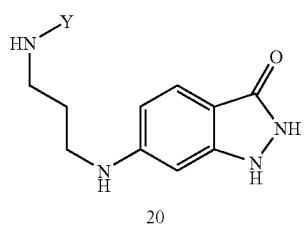

i. $K_2CO_3$, acetonitrile, RT; ii. $H_3O^+$; iii. amino-heteroaromatic, sodium borohydride, methanol; iv. deprotection: Method A (Z = t-Bu): TFA/dichloromethane or HCl(g)/ethyl acetate; or Method B (Z = $CH_2Ph$): Pd/C, $H_2$, ethanol.

Schemes VI–IX below depicts the preparation of compounds where $Q^1$ and $Q^2$ are each NH and A is an optionally substituted $C_{2-6}$ alkylidene chain, wherein one or more methylene units of the alkylidene chain are replaced with C=O. As shown below, the alkylidene chain may be substituted with R'', wherein R'' is $C_{1-6}$ aliphatic, aryl or alkaryl.

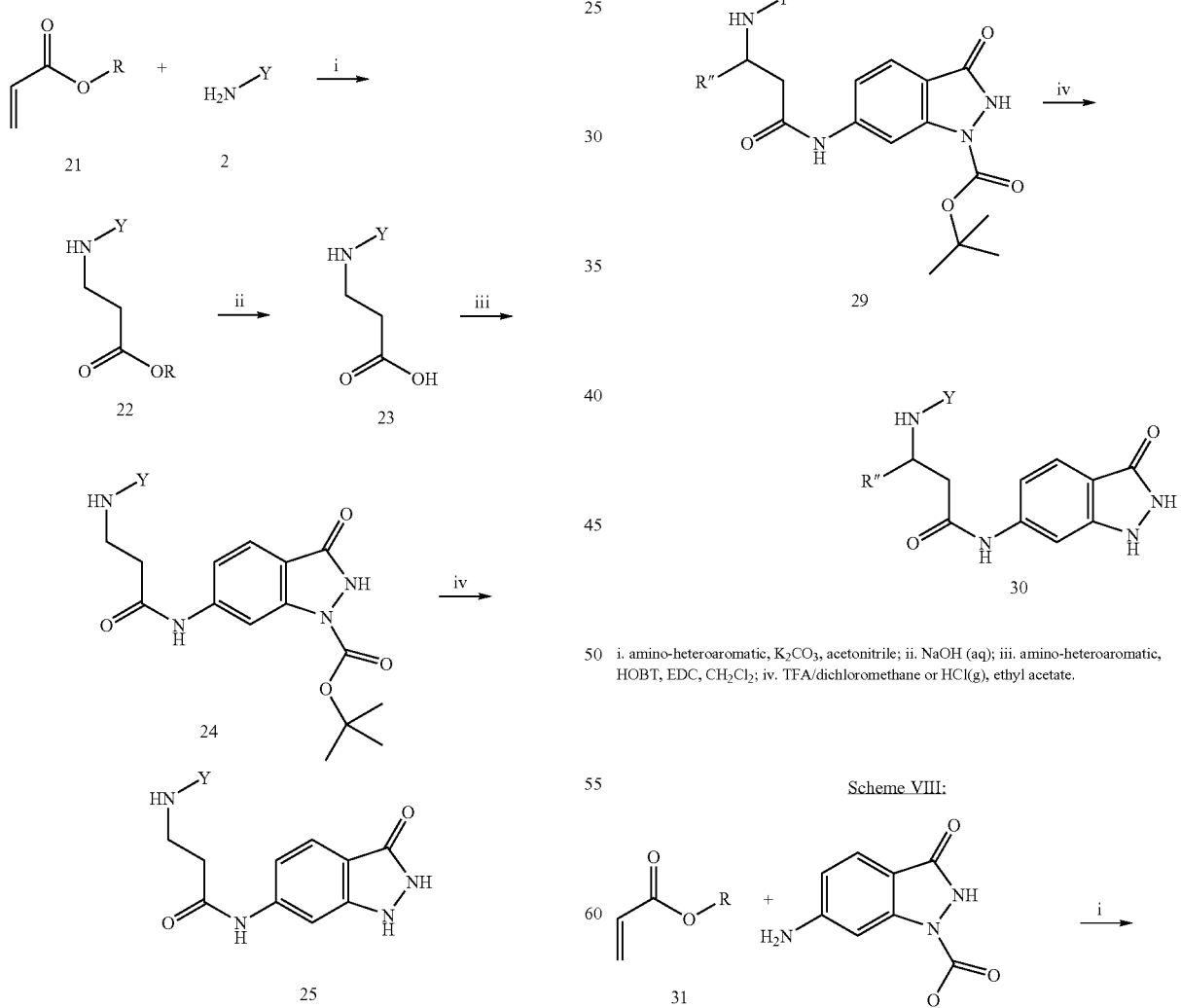

i. Methanol, reflux; ii. NaOH(aq); iii. 6-Amino-3-oxo-2,3-dihydro-indazole-1-carboxylic acid tert-butyl ester, HOBT, EDC, $CH_2Cl_2$

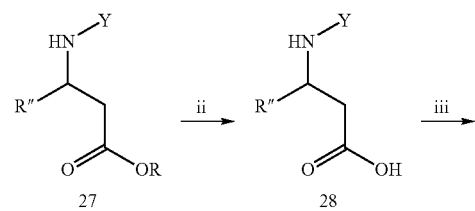

i. amino-heteroaromatic, $K_2CO_3$, acetonitrile; ii. NaOH (aq); iii. amino-heteroaromatic, HOBT, EDC, $CH_2Cl_2$; iv. TFA/dichloromethane or HCl(g), ethyl acetate.

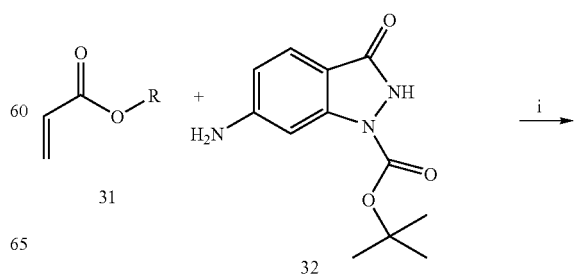

-continued

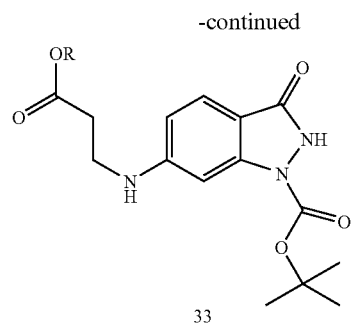
33

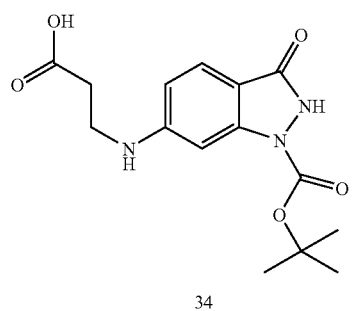
34

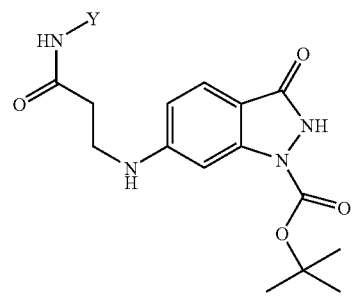
35

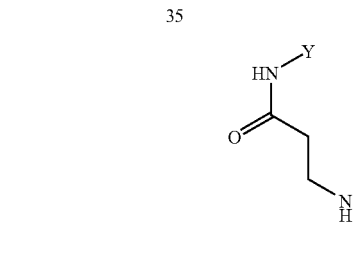
36 i. MeOH, reflux; ii. NaOH (aq); iii. aminoheteroaromatic, HOBT, EDC, CH₂Cl₂; iv. TFA/CH₂Cl₂ or HCl(g)/Ethyl acetate Scheme IX:

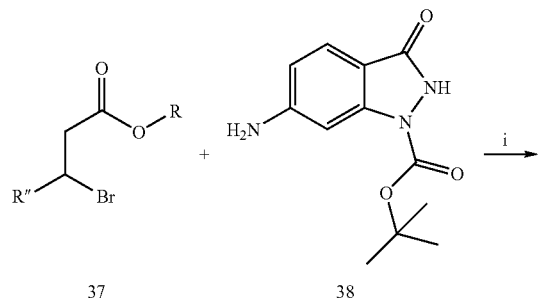

37        38

-continued

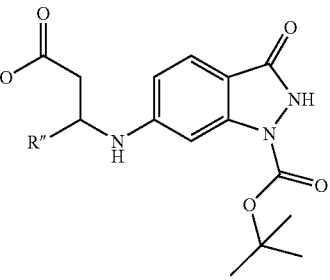
39

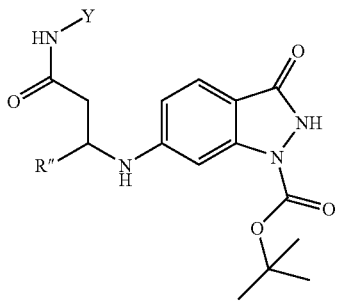
40

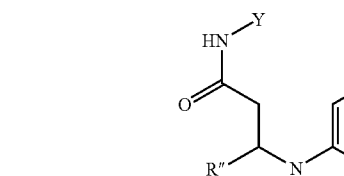
41 i. K₂CO₃, acetonitrile; ii. NaOH (aq); iii. amino-heteroaromatic, HOBT, EDC, CH₂Cl₂

IV. Uses of Compounds of the Invention:

The compounds and compositions described herein are generally useful for the inhibition of kinase activity of one or more enzymes. Kinases include, for example, protein kinases, lipid kinases (e.g., phosphatidylinositol kinases PI-3, PI-4) and carbohyhdrate kinases. Further information relating to kinase structure, function and their role in disease or disease symptoms is available at the Protein Kinase Resource website (http://Ikinases.sdsc.edu/html/index.shtml).

It will be appreciated that compounds described herein are preferably useful as inhibitors of tyrosine, serine/threonine or histidine protein kinases. Examples of kinases that are inhibited by the compounds and compositions described herein and against which the methods described herein are useful include, but are not limited to, LCK, IRK (=INSR=Insulin receptor), IGF-1 receptor, SYK, MK2, ZAP-70, Aurora-2, PRAK, ROCK, CAK, cMET, IRAK1, IRAK2, BLK, BMX, BTK, FRK, FGR, FYN, HCK, ITK, LYN, TEC, TXK, YES, ABL, SRC, EGF-R (=ErbB-1), ErbB-2 (=NEU=HER²), ErbB-3, ErbB-4, FAK, FGF1R (=FGR-1), FGF2R (=FGR-2), IKK-1 (=IKK-alpha=CHUK), IKK-2 (=IKK-beta), MET (=c-Met), NIK, PGDF receptor alpha, PDGF receptor beta, TIE1, TIE2 (=TEK), VEGFR¹ (=FLT-1), VEGFR² (=KDR), FLT-3, FLT-4, KIT, CSK, JAK1, JAK2, JAK3, TYK2, RIP, RIP-2, LOK, TAKI, RET, ALK, MLK3, COT, TRKA, PYK2, EPHB4, RON, GSK3, UL13, ORF47, ATM, CDK (including all subtypes), PKA, PKB (including all PKB subtypes) (=AKT- 1, AKT-2, AKT-3), PKC (including all PKC subtypes), REDK, SAPK, PIM, PDK, PIM, ERK and BARK, and all subtypes of these kinases. The compounds and compositions of the invention are therefore also particularly suited for the treatment of diseases and disease symptoms that involve one or more of the aforementioned kinases.

Pharmaceutically Acceptable Compositions

As discussed above, the present invention provides compounds that are inhibitors of protein kinases, and thus the present compounds are useful for the treatment of diseases, disorders, and conditions including, but not limited to a proliferative disorder, a cardiac disorder, a neurodegenerative disorder, psychotic disorders, an autoimmune disorder, a condition associated with organ transplant, an inflammatory disorder, an immunologically mediated disorder, a viral disease, or a bone disorder. In preferred embodiments, the compounds are useful for the treatment of allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia (e.g., stroke), baldness, cancer, hepatomegaly, cardiovascular disease including cardiomegaly, cystic fibrosis, viral disease, autoimmune diseases, atherosclerosis, restenosis, psoriasis, inflammation, hypertension, angina pectoris, cerebrovascular contraction, peripheral circulation disorder, premature birth, arteriosclerosis, vasospasm (cerebral vasospasm, coronary vasospasm), retinopathy, erectile dysfunction (ED), AIDS, osteoporosis, Crohn's Disease and colitis, neurite outgrowth, and Raynaud's Disease. In preferred embodiments, the disease, condition, or disorder is atherosclerosis, hypertension, erectile dysfunction (ED), reperfusion/ischemia (e.g., stroke), or vasospasm (cerebral vasospasm and coronary vasospasm).

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a PRAK, GSK3, ERK2, CDK2, MK2, SRC, SYK, or Aurora-2 kinase.

Pharmaceutically acceptable salts are well known in the art. For example, S. M. Berge et al., describe pharmaceutically acceptable salts in detail in *J. Pharmaceutical Sciences*, 1977, 66, 1–19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder. The compounds and compositions, according to the method of the present invention, may be administered using any amount and any route of administration effective for treating or lessening the severity of a proliferative disorder, a cardiac disorder, a neurodegenerative disorder, an autoimmune disorder, a condition associated with organ transplant, an inflammatory disorder, an immunologically mediated disorder, a viral disease, or a bone disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of PRAK, GSK3, ERK2, CDK2, MK2, SRC, SYK, or Aurora-2 kinase, and thus, without wishing to be bound by any particular theory, the compounds and compositions are particularly useful for treating or lessening the severity of a disease, condition, or disorder where activation of one or more of PRAK, GSK3, ERK2, CDK2, MK2, SRC, SYK, or Aurora-2 kinase is implicated in the disease, condition, or disorder. When activation of PRAK, GSK3, ERK2, CDK2, MK2, SRC, SYK, or Aurora-2 kinase is implicated in a particular disease, condition, or disorder, the disease, condition, or disorder may also be referred to as "PRAK, GSK3, ERK2, CDK2, MK2, SRC, SYK, or Aurora-2 kinase-mediated disease" or disease symptom. Accordingly, in another aspect, the present invention provides a method for treating or lessening the severity of a disease, condition, or disorder where activation or one or more of PRAK, GSK3, ERK2, CDK2, MK2, SRC, SYK, or Aurora-2 kinase is implicated in the disease state.

The activity of a compound utilized in this invention as an inhibitor of PRAK, GSK3, ERK2, CDK2, MK2, SRC, SYK, or Aurora-2 kinase, may be assayed in vitro, in vivo or in a cell line. In vitro assays include assays that determine inhibition of either the phosphorylation activity or ATPase activity of activated PRAK, GSK3, ERK2, CDK2, MK2, SRC, SYK, or Aurora-2 kinase. Alternate in vitro assays quantitate the ability of the inhibitor to bind to PRAK, GSK3, ERK2, CDK2, MK2, SRC, SYK, or Aurora-2 kinase. Inhibitor binding may be measured by radiolabelling the inhibitor prior to binding, isolating the inhibitor/PRAK, inhibitor/GSK3, inhibitor/ERK2, inhibitor/CDK2, inhibitor/MK2, inhibitor/SRC, inhibitor/SYK, or inhibitor/Aurora-2 kinase complex and determining the amount of radiolabel bound. Alternatively, inhibitor binding may be determined by running a competition experiment where new inhibitors are incubated with PRAK, GSK3, ERK2, CDK2, MK2, SRC, SYK, or Aurora-2 kinase bound to known radioligands.

The term "measurably inhibit", as used herein means a measurable change in PRAK, GSK3, ERK2, CDK2, MK2, SRC, SYK, or Aurora-2 kinase activity between a sample comprising said composition and a PRAK, GSK3, ERK2, CDK2, MK2, SRC, SYK, or Aurora-2 kinase kinase and an equivalent sample comprising PRAK, GSK3, ERK2, CDK2, MK2, SRC, SYK, or Aurora-2 kinase kinase in the absence of said composition.

The term "Aurora-2-mediated disease" or "Aurora-2-mediated condition", as used herein, means any disease or other deleterious condition in which Aurora is known to play a role. The terms "Aurora-2-mediated disease" or "Aurora-2-mediated condition" also mean those diseases or conditions that are alleviated by treatment with an Aurora-2 inhibitor. Such conditions include, without limitation, colon, breast, stomach, and ovarian cancer. The term "Aurora-2-mediated disease", as used herein, means any disease or other deleterious condition or disease in which Aurora-2 is known to play a role. Such diseases or conditions include, without limitation, cancers such as colon and breast cancer.

The terms "ERK-mediated disease" or "ERK-mediated condition", as used herein mean any disease or other deleterious condition in which ERK is known to play a role. The terms "ERK-2-mediated disease" or "ERK-2-mediated condition" also mean those diseases or conditions that are alleviated by treatment with an ERK-2 inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders, and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. ERK-2 protein kinase and its implication in various diseases has been described [Bokemeyer et al., Kidney Int. 1996, 49, 1187; Anderson et al., Nature 1990, 343, 651; Crews et al., Science 1992, 258, 478; Bjorbaek et al., J. Biol. Chem. 1995, 270, 18848; Rouse et al., Cell 1994, 78, 1027; Raingeaud et al., Mol. Cell Biol. 1996, 16, 1247; Chen et al., Proc. Natl. Acad. Sci. USA 1993, 90, 10952; Oliver et al., Proc. Soc. Exp. Biol. Med. 1995, 210, 162; Moodie et al., Science 1993, 260, 1658; Frey and Mulder, Cancer Res. 1997, 57, 628; Sivaraman et al., J. Clin. Invest. 1997, 99, 1478; Whelchel et al., Am. J. Respir. Cell Mol. Biol. 1997, 16, 589].

The term "GSK-3-mediated disease" as used herein, means any disease or other deleterious condition or disease in which GSK-3 is known to play a role. Such diseases or conditions include, without limitation, autoimmune diseases, inflammatory diseases, metabolic, neurological and neurodegenerative diseases (e.g., Alzheimer's disease, Huntington's disease, Parkinson's disease and basal ganglia movement disorders, chorea, dystonia, Wilson Disease, Pick Disease, frontal lobe degeneration, progessive supranuclear palsy (PSP), Creutzfeldt-Jakob Disease, taupathology and corticobasal degeneration (CBD)), psychotic disorders (e.g., schizophrenia, AIDS-associated dementia, depression, bipolar disorder, and anxiety disorders), cardiovascular diseases, allergy, asthma, diabetes, amyotrophic lateral sclerosis (AML, Lou Gehrig's disease), multiple sclerosis (MS), cardiomyocyte hypertrophy, reperfusion/ischemia, stroke, and baldness.

The term "Src-mediated disease" as used herein means any disease or other deleterious condition in which Src kinase plays a role. Such diseases or conditions include, without limitation, cancers such as colon, breast, hepatic and pancreatic cancer, autoimmune diseases such as transplant rejection, allergies, rheumatoid arthritis, leukemia, bone remodeling diseases such as osteoporosis and viral diseases such as hepatitus B infection.

The terms "CDK-2-mediated disease" or "CDK-2-mediated condition", as used herein, mean any disease or other deleterious condition in which CDK-2 is known to play a role. The terms "CDK-2-mediated disease" or "CDK-2-mediated condition" also mean those diseases or conditions that are alleviated by treatment with a CDK-2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis. See Fischer, P. M. and Lane, D. P., Current Medicinal Chemistry, 7, 1213–1245 (2000); Mani, S., Wang, C., Wu, K., Francis, R. and Pestell, R., Exp. Opin. Invest. Drugs, 9, 1849 (2000); Fry, D. W. and Garrett, M. D., Current Opinion in Oncologic, Endocrine & Metabolic Investigational Drugs, 2, 40–59 (2000).

The terms "PRAK-mediated disease" or "PRAK-mediated condition", as used herein mean any disease or other deleterious condition in which PRAK is known to play a role. The terms "PRAK-mediated disease" or "PRAK-mediated condition" also mean those diseases or conditions that are alleviated by treatment with a PRAK inhibitor. Such conditions include, without limitation, rheumatoid arthritis, multiple sclerosis (see Darlington, C. L, Current Opinion in Anti-inflammatory & Immunomodulatory Investigational Drugs, 1999, 1 (3),190–198), Crohns Disease cancer, autoimmune diseases, atherosclerosis, restenosis, psoriasis, allergic disorders including asthma, and inflammation.

The term "Syk-mediated disease" or "Syk-mediated condition", as used herein, means any disease or other deleterious condition in which Syk protein kinase is known to play a role. Such conditions include, without limitation, allergic disorders, especially asthma.

The term "MK2-mediated disease" or "MK2-mediated condition", as used herein, means any disease or other deleterious condition in which MK2 protein kinase is known to play a role. Such conditions include, without limitation, inflammatory disorders, arthritis, ischemia/reperfusion (see, J. Biol. Chem. 2002, 277 (46), 43968–72), and asthma (See., Am J Respir Crit Care Med. 2001 Dec. 1;164(11):2051–6).

In other embodiments, the invention relates to a method of enhancing glycogen synthesis and/or lowering blood levels of glucose in a patient in need thereof, comprising administering to said patient a therapeutically effective amount of a composition comprising a compound of formula I. This method is especially useful for diabetic patients.

In yet another embodiment, the invention relates to a method of inhibiting the production of hyperphosphorylated Tau protein in a patient in need thereof, comprising administering to said patient a therapeutically effective amount of a composition comprising a compound of formula I. This method is especially useful in halting or slowing the progression of Alzheimer's disease.

In still another embodiments, the invention relates to a method of inhibiting the phosphorylation of β-catenin in a patient in need thereof, comprising administering to said patient a therapeutically effective amount of a composition comprising a compound of formula I. This method is especially useful for treating schizophrenia.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http:/Hwww.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting PRAK, GSK3, ERK2, CDK2, MK2, SRC, SYK, or Aurora-2 kinase activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of PRAK, GSK3, ERK2, CDK2, MK2, SRC, SYK, or Aurora-2 kinase kinase activity in a biological sample is useful for a variety of purposes that are known to one of skill in the art. Examples of such purposes include, but are not limited to, blood transfusion, organ-transplantation, biological specimen storage, and biological assays.

In order that the invention described herein may be more fully understood, the following examples are set forth. It should be understood that these examples are for illustrative purposes only and are not to be construed as limiting this invention in any manner.

EXAMPLES

I. Preparation of Exemplary Compounds:

Example 1

Preparation of 6-[4-(5-Cyclopropyl-2H-pyrazol-3-ylamino)-quinazolin-2-ylamino]-1,2-dihydro-indazol-3-one

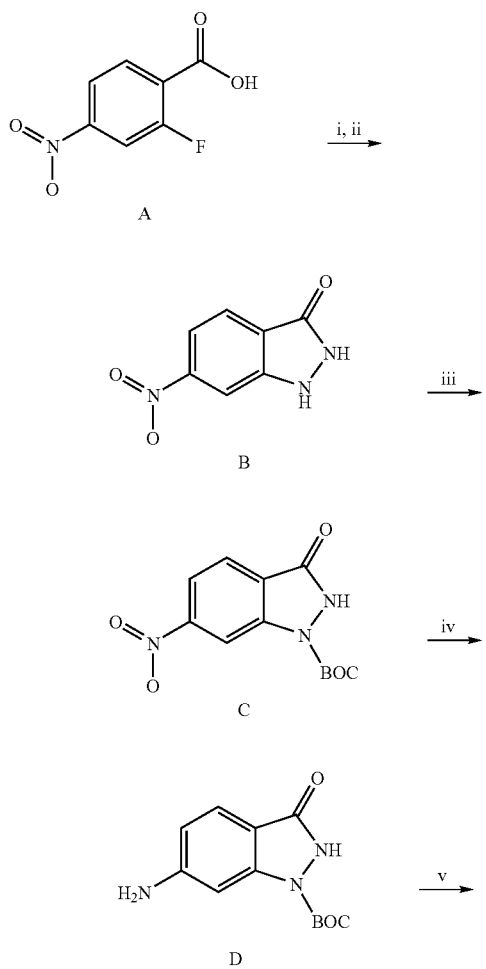

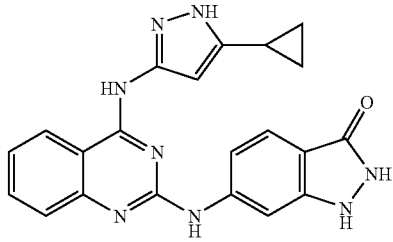

Reagents: (i) HCl(g), CH$_3$OH, room temperature; (ii) H$_2$NNH$_2$, ethanol, reflux; (iii) (t-BuO-CO)$_2$O, DMAP, Et$_3$N, CH$_2$Cl$_2$; (iv)

A) Preparation of 6-Amino-3-oxo-2,3-dihydro-indazole-1-carboxylic acid tert-butyl ester (D)

Step 1 & 2: 6-Nitro-1,2-dihydro-indazol-3-one (B)

To a solution of 2-fluoro-4-nitro-benzoic acid A(4.9 g, 26 mmol) in methanol (60 mL) was added hydrogen chloride gas at room temperature (exothermic reaction!). After 30 min of the addition of HCl gas, the reaction mixture was covered with a cap and stirred at room temperature for 16 hrs. The solvent was then carefully removed by evaporation, the resulted residue was treated with saturated NaHCO$_3$ solution, and the precipitate was collected by filtration. After drying on the vacuum pump for overnight, the crude material, 2-fluoro-4-nitro-benzoic acid methyl ester was directly used for the next step without further purification. LC/Method A/2.64 min.

The crude material, 2-fluoro-4-nitro-benzoic acid methyl ester, from above was treated with hydrazine (1.6 mL, 51 mmol) in ethanol under reflux for 14 hrs. After removal of solvent by evaporation, the residue was washed with water. The precipitate product was filtered and dried on the vacuum pump to give the title compound which was used without further purification(4.0 g, 85% for two steps). MS (ES+): m/e=180.1 (M+H), 178.0 (M−H); LC/Method A/1.83 min.

Step 3: 6-Nitro-3-oxo-2,3-dihydro-indazole-1-carboxylic acid tert-butyl ester (C)

To a solution of the crude material 2 (2.0 g, 11.2 mmol) in CH$_2$Cl$_2$ was added DMAP (1.4 g, 11.4 mmol). The resulted orange suspension was cooled to 0° C. and then was added triethylamine (1.7 g, 16.8 mmol). The mixture was stirred at 0° C. for 5 min and then was added a solution of di-tert-butyl dicarbonate (3.7 g, 16.9 mmol) in CH$_2$Cl$_2$ (4 mL). After stirring at 0° C. for another 20 min, the reaction was allowed to warm up to room temperature and stirred for 4 hrs. The solvent was then removed by evaporation, the residue was treated with 2N HCl solution, and the precipitate was filtered and washed with 2N HCl and water. The crude material was dried on the vacuum pump and used for the next step without further purification. MS (ES+): m/e=278.1 (M−H); LC/Method A/3.21 min.

6-Amino-3-oxo-2,3-dihydro-indazole-1-carboxylic acid tert-butyl ester (D)

The crude material from step 3 was treated with hydrogen in ethanol at 50 psi in the presence of Pd/C (10%) for 3 hrs. After filtration through celite, the solvent was removed by evaporation. The final product 6-Amino-3-oxo-2,3-dihydro-indazole-1-carboxylic acid tert-butyl ester was then obtained as white solid (93% of purity) and was used as it was. (2.0 g, 72% of yield for two steps). MS (ES+): m/e=250.2 (M+H); 248.1 (M−H); LC/Method A/2.48 min.

B) Preparation of 6-[4-(5-Cyclopropyl-2H-pyrazol-3-ylamino)-quinazolin-2-ylamino]-1,2-dihydro-indazol-3-one.

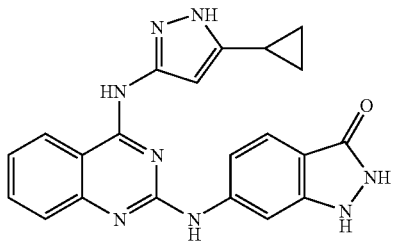

A solution of (2-chloro-quinazolin-4-yl)-(5-cyclopropyl-2H-pyrazol-3-yl)-amine (50.0 mg, 0.175 mmol) and 6-amino-3-oxo-2,3-dihydro-indazole-1-carboxylic acid tert-butyl ester (69.8 mg, 0.280 mmol) in NMP (1.0 mL) was heated up to 100° C. for 6 hrs. The reaction mixture was cooled to room temperature and poured into water, basified with saturated aqueous NaHCO$_3$ to pH=8–9. The crude material was collected by filtration and treated with TFA (0.5 mL, 6.5 mmol) in CH$_2$Cl$_2$ (5 mL) for 3 hrs. After evaporation of the solvent, the crude product was purified by HPLC to provide an off-white solid as TFA salt (15.0 mg, 20.6% yield).

$^1$H NMR (500 mHz, DMSO-d$_6$) δ12.53 (br s, 1H), 11.47 (br s, 1H), 10.61 (br s, 1H), 8.65 (d, 1H), 7.85 (t, 1H), 7.70 (d, 1H), 7.63 (d, 1H), 7.48 (t, 2H), 7.09 (d, 1H), 6.18 (br s, 1H), 1.73 (br s, 1H), 0.83 (s, 2H), 0.42 (br s, 2H) ppm. MS (ES+): m/e=399.3 (M+H), 397.3 (M−H); LC/Method A/3.76 min, 94.4% purity by area %.

Method A: solvent B: 0.1% TFA/1% MeCN/water, solvent D: 0.1% TFA/MeCN. Gradient 10% D to 90% D over 8 min. at a flow rate of 1 mL/min. Method length 12 min. Column1 (YMC 3×150).

Example 2

Preparation of 6-[6-Chloro-4-(5-cyclopropyl-2H-pyrazol-3-ylamino)-quinazolin-2-ylamino]-1,2-dihydro-indazol-3-one

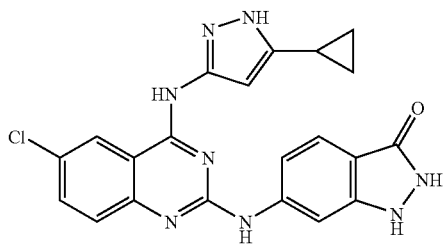

6-[6-Chloro-4-(5-cyclopropyl-2H-pyrazol-3-ylamino)-quinazolin-2-ylamino]-1,2-dihydro-indazol-3-one was prepared by a method similar to Example 1 to yield a light yellow solid (23.5% yield).

$^1$H NMR (500 mHz, DMSO-d$_6$) δ11.34 (br s, 1H), 10.54 (br s, 1H), 8.75 (s, 1H), 7.80 (d, 1H), 7.61 (d, 1H), 7.54 (d, 1H), 7.04 (d, 1H), 6.14 (br s, 1H), 1.68 (br s, 1H), 0.77 (s, 2H), 0.37 (br s, 2H) ppm. MS (ES+): m/e=433.3 (M+H), 431.2 (M−H); LC/Method A/4.17 min, 97.13% purity by area %.

Example 3

Preparation of 6-[7-Chloro-4-(5-cyclopropyl-2H-pyrazol-3-ylamino)-quinazolin-2-ylamino]-1,2-dihydro-indazol-3-one

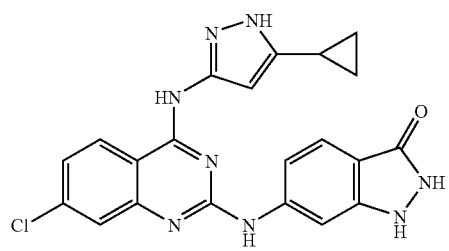

6-[7-Chloro-4-(5-cyclopropyl-2H-pyrazol-3-ylamino)-quinazolin-2-ylamino]-1,2-dihydro-indazol-3-one was prepared by a method similar to Example 1 to yield a yellow solid (29.6% yield).

$^1$H NMR (500 mHz, DMSO-d$_6$) δ12.51 (br s, 1H), 11.34 (br s, 1H), 10.54 (br s, 1H), 8.61 (s, 1H), 7.63 (m, 3H), 7.48 (d, 1H), 7.13 (d, 1H), 6.23 (br s, 1H), 1.79 (br s, 1H), 0.86 (s, 2H), 0.52 (br s, 2H). MS (ES+): m/e=433.3 (M+H), 431.2 (M−H); LC/Method A/4.13 min, 100.0% purity by area %.

Example 4

Prepartion of 6-[4-(1H-Indazol-3-ylamino)-quinazolin-2-ylamino]-1,2-dihydro-indazol-3-one

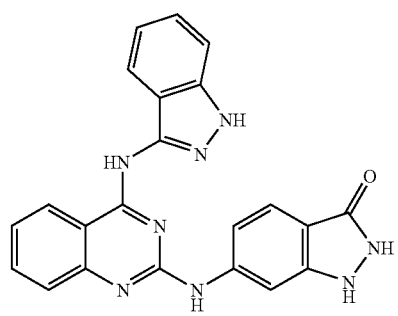

6-[4-(1H-Indazol-3-ylamino)-quinazolin-2-ylamino]-1,2-dihydro-indazol-3-one was prepared by a method similar to Example 1 to yield a light yellow solid (52.3% yield). $^1$H NMR (500 mHz, DMSO-d$_6$) δ 12.95 (br s, 1H), 11.35 (br s, 1H), 10.81 (br s, 1H), 10.44 (br s, 1H), 8.37(d, 1H), 7.59 (t, 1H), 7.48 (d, 1H), 7.43 (d, 1H), 7.37 (m, 1H), 7.19 (t, 1H), 6.97 (br s, 1H), 6.87 (t, 1H), 6.64 (d, 1H) ppm. MS (ES+): m/e=409.3 (M+H), 407.3 (M−H); LC/Method A/3.96 min, 100% purity by area %.

Example 5

Preparation of 6-[4-(5-Isopropyl-2H-pyrazol-3-ylamino)-quinazolin-2-ylamino]-1,2-dihydro-indazol-3-one

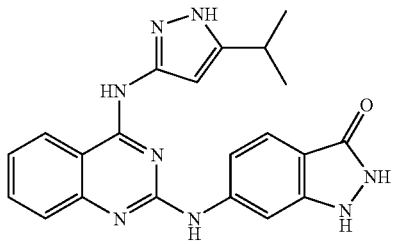

To a solution of (2-chloro-quinazolin-4-yl)-(5-isopropyl-2H-pyrazol-3-yl)-amine (50 mg, 0.17 mmol) in NMP (1 mL) was added 6-amino-3-oxo-2,3-dihydro-indazole-1-carboxylic acid tert-butyl ester (65 mg, 0.26 mmol). The mixture was heated at 130° C. for 3 hrs, cooled to room temperature, and then poured into water. The crude material was collected by filtration and treated with TFA in CH$_2$Cl$_2$ for 30 min.

After evaporation of the solvent, the crude product was purified by HPLC to provide a white solid as TFA salt. (34 mg, yield 49%) NMR (500 MHz, DMSO-d$_6$) δ12.5 (br s, 1H), 11.5 (br s, 2H), 10.6 (br s, 1H), 8.67 (d, 1H), 7.86 (t, 1H), 7.68 (d, 1H), 7.63 (d, 1H), 7.48 (t, 1H), 7.45 (br, 1H), 7.09 (d, 1H), 6.25 (br, s, 1H), 2.70 (br, 1H), 1.00 (brs, 6H) ppm. Ms (ES+): m/e=401.3 (M+H); LC/Method A/2.70 min.

Example 6

Preparation of 6-[4-(5-Cyclopentyl-2H-pyrazol-3-ylamino)-quinazolin-2-ylamino]-1,2-dihydro-indazol-3-one

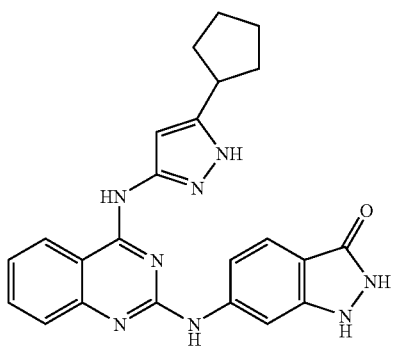

6-[4-(5-Cyclopentyl-2H-pyrazol-3-ylamino)-quinazolin-2-ylamino]-1,2-dihydro-indazol-3-one was prepared by a method similar to Example 5 to yield an off-white solid (47% yiled) NMR (500 MHz, DMSO-d$_6$) δ12.5 (br s, 1H), 11.5 (br s, 2H), 10.6 (br s, 1H), 8.68 (d, 1H), 7.86 (t, 1H), 7.68 (d, 1H), 7.63 (d, 1H), 7.48 (t, 1H), 7.45 (br, 1H), 7.08 (d, 1H), 6.25 (br, s, 1H), 2.77 (br, 1H), 1.50 (m, 8H) ppm. MS (ES+): m/e=427.3 (M+H); LC/Method A/2.81 min.

Example 7

Preparation of 6-[4-(5-Methyl-2H-pyrazol-3-ylamino)-quinazolin-2-ylamino]-1,2-dihydro-indazol-3-one

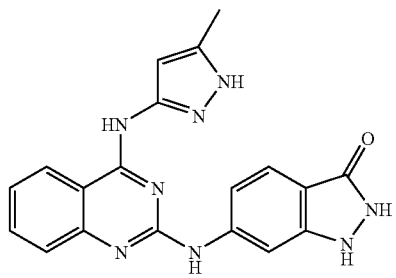

6-[4-(5-Methyl-2H-pyrazol-3-ylamino)-quinazolin-2-ylamino]-1,2-dihydro-indazol-3-one was prepared by a method similar to Example 5 to yield a white solid (57% yiled) NMR (500 MHz, DMSO-d$_6$) δ12.5 (br s, 1H), 11.5 (br s, 2H), 10.7 (br s, 1H), 8.63 (d, 1H), 7.85 (t, 1H), 7.68 (d, 1H), 7.62 (d, 1H), 7.49 (m, 2H), 7.09 (d, 1H), 6.33 (br, s, 1H), 2.08 (s, 3H) ppm. MS (ES+): m/e=373.3 (M+H); LC/Method A/2.88 min.

Example 8

Preparation of 6-[4-(5-Methoxymethyl-2H-pyrazol-3-ylamino)-quinazolin-2-ylamino]-1,2-dihydro-indazol-3-one

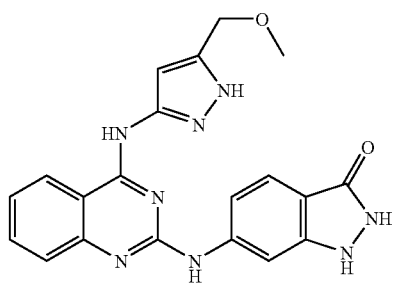

6-[4-(5-Methoxymethyl-2H-pyrazol-3-ylamino)-quinazolin-2-ylamino]-1,2-dihydro-indazol-3-one was prepared by a method similar to Example 5 to yield a white solid (12% yield) NMR (500 MHz, DMSO-d$_6$) δ12.8 (br s, 1H), 11.5 (br s, 2H), 10.6 (br s, 1H), 8.63 (d, 1H), 7.85 (t, 1H), 7.68 (d, 1H), 7.62 (d, 1H), 7.49 (m, 2H), 7.08 (d, 1H), 6.60 (br, s, 1H), 4.22 (s, 2H), 3.19 (s, 3H) ppm. MS (ES+): m/e=403.3 (M+H); LC/Method A/2.89 min.

Example 9

Preparation of 6-[4-(5-Cyclopropyl-2H-pyrazol-3-ylamino)-6-phenyl-pyrimidin-2-ylamino]1,2-dihydro-indazol-3-one

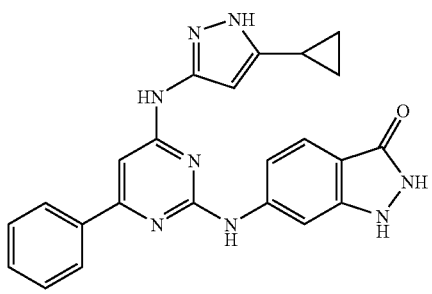

A solution of (2-chloro-6-phenyl-pyrimidin-4-yl)-(5-cyclopropyl-2H-pyrazol-3-yl)-amine (50.0 mg, 0.160 mmol) and 6-amino-3-oxo-2,3-dihydro-indazole-1-carboxylic acid tert-butyl ester (119.6 mg. 0.480 mmol) in tert-butanol (0.6 mL) was refluxed for 3 days. After 3 days reflux, the reaction mixture was concentrated and the residue was washed with water. The crude material was collected by filtration and treated with TFA (0.5 mL, 6.5 mmol) in $CH_2Cl_2$ (5 mL) for 3.5 hrs. After evaporation of the solvent, the crude product was purified by HPLC to provide a light yellow solid as TFA salt (32.5 mg, 37.7% yield).

$^1$H NMR (500 mHz, DMSO-$d_6$) δ 11.08 (br s, 1H), 9.64 (s, 1H), 7.95 (s, 3H), 7.59 (m, 4H), 7.20 (d, 1H), 6.89 (br s, 1H), 6.12 (s, 1H), 1.83 (br s, 1H), 0.88 (s, 2H), 0.60 (br s, 2H) ppm. MS (ES+): m/e=425.3 (M+H), 423.2 (M–H); LC/Method A/4.30 min, 100.0% purity by area %.

Example 10

Preparation of 6-[4-(5-Cyclopropyl-2H-pyrazol-3-ylamino)-6-methyl-pyrido[3,2-d]pyrimidin-2-ylamino]-1,2-dihydro-indazol-3-one

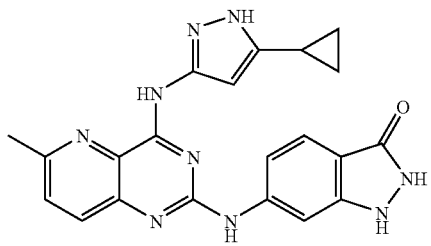

A solution of (2-chloro-6-methyl-pyrido[3,2-d]pyrimidin-4-yl)-(5-cyclopropyl-2H-pyrazol-3-yl)-amine (49.8 mg, 0.166 mmol) and 6-amino-3-oxo-2,3-dihydro-indazole-1-carboxylic acid tert-butyl ester (82.6 mg. 0.312 mmol) in NMP (1.0 mL) was heated up to 100° C. for 1.5 hours.

The reaction mixture was cooled to room temperature and poured into water, basified with saturated aqueous $NaHCO_3$ to pH=8–9. The crude material was collected by filtration and treated with TFA (0.5 mL, 6.5 mmol) in $CH_2Cl_2$ (5 mL) for 4 hrs. After evaporation of the solvent, the crude product was purified by HPLC to provide a light yellow solid as TFA salt.

Example 11

Preparation of 6-[4-(5-Cyclobutyl-2H-pyrazol-3-ylamino)-quinazolin-2-ylamino]-1,2-dihydro-indazol-3-one

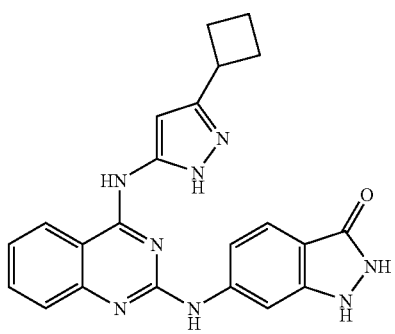

6-[4-(5-Cyclobutyl-2H-pyrazol-3-ylamino)-quinazolin-2-ylamino]-1,2-dihydro-indazol-3-one was prepared by a similar method as described above to yield a white solid (68% yield) NMR (500 MHz, DMSO-$d_6$) δ12.5 (br s, 1H), 11.5 (br s, 2H), 10.6 (br s, 1H), 8.6 (d, 1H), 7.87 (t, 1H), 7.86 (t, 1H), 7.70 (d, 1H), 7.63 (d, 1H), 7.49 (t, 1H), 7.45 (br, 1H), 7.11 (d, 1H), 6.25 (br, s, 1H), 3.30 (m, 1H), 2.15 (br, 2H), 1.89 (m, 4H) ppm. MS (ES+): m/e=413.3 (M+H); LC/Method A/2.69 min.

Example 12

6-[4-(5-Ethyl-2H-pyrazol-3-ylamino)-quinazolin-2-ylamino]-1,2-dihydro-indazol-3-one

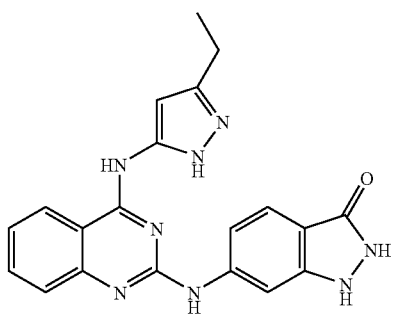

6-[4-(5-Ethyl-2H-pyrazol-3-ylamino)-quinazolin-2-ylamino]-1,2-dihydro-indazol-3-one was prepared by a similar method as described above to yield a pale-yellow solid. NMR (500 MHz, MeOD) δ 8.30 (br, 1H), 7.79 (br, 1H), 7.71 (br, 1H), 7.53 (br, 1H), 7.44 (br, 2H), 7.11 (br, 1H), 6.20 (br, 1H), 2.44 (br, 2H), 0.99 (m, 3H) ppm. MS (ES+): m/e=387.4 (M+H); LC/Method A/2.56 min.

Example 13

6-[4-(5-Furan-2-yl-2H-pyrazol-3-ylamino)-quinazolin-2-ylamino]-1,2-dihydro-indazol-3-one

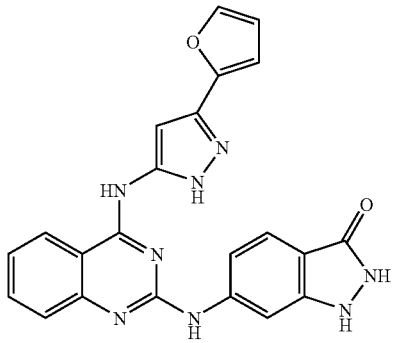

6-[4-(5-Furan-2-yl-2H-pyrazol-3-ylamino)-quinazolin-2-ylamino]-1,2-dihydro-indazol-3-one was prepared by a similar method as described above to yield a white solid. NMR (500 MHz, MeOD) δ 8.45 (d, 1H), 7.92 (t, 1H), 7.86 (d, 1H), 7.65 (d, 1H), 7.58 (m, 2H), 7.53 (br, 1H), 7.25 (dd, 1H), 6.75 (br, 1H), 6.53 (dd, 1H), 6.44 (br, 1H) ppm. MS (ES+): m/e=425.39 (M+H); LC/Method A/2.68 min.

Example 14

6-[6-Methyl-4-(5-methyl-2H-pyrazol-3-ylamino)-pyrido[3,2-d]pyrimidin-2-ylamino]-1,2-dihydro-indazol-3-one

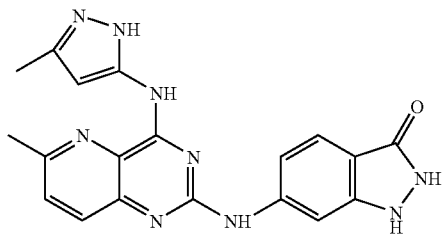

6-[6-Methyl-4-(5-methyl-2H-pyrazol-3-ylamino)-pyrido[3,2-d]pyrimidin-2-ylamino]-1,2-dihydro-indazol-3-one was prepared by a similar method as described above to yield a light yellow solid (34.0% yield). $^1$H NMR (500 mHz, DMSO-$d_6$) δ 11.26 (br s, 1H), 10.34 (br s, 1H), 7.84 (m, 2H), 7.66 (d, 1H), 7.58 (d, 1H), 7.09 (d, 1H), 6.47 (br s, 1H), 2.13 (s, 3H), 2.60 (d, 3H) ppm. MS (ES+): m/e=388.3 (M+H), 386.2 (M−H); LC/Method A/3.59 min, 100% purity by area %.

Example 15

6-[4-(5-Cyclopropyl-2H-pyrazol-3-ylamino)-6-methyl-pyrido[3,2-d]pyrimidin-2-ylamino]-1,2-dihydro-indazol-3-one

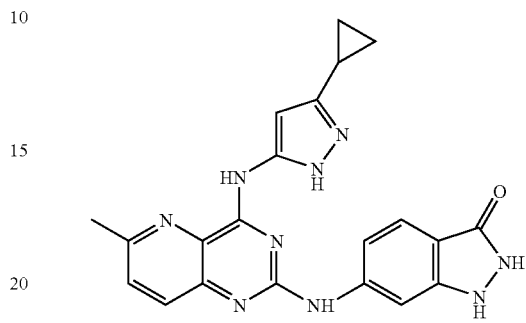

6-[4-(5-Cyclopropyl-2H-pyrazol-3-ylamino)-6-methyl-pyrido[3,2-d]pyrimidin-2-ylamino]-1,2-dihydro-indazol-3-one was prepared by a similar method as described above to yield a yellow solid (34.3% yield). $^1$H NMR (500 mHz, DMSO-$d_6$) δ 11.38 (br s, 1H), 10.40 (br s, 1H), 7.91 (d, 1H), 7.75 (d, 2H), 7.67 (d, 1H), 7.15 (d, 1H), 6.35 (br s, 1H), 1.82 (br s, 1H), 0.88 (s, 2H), 0.54 (d, 2H) ppm. MS (ES+): m/e=414.3 (M+H), 412.3 (M−H); LC/Method A/3.80 min, 100% purity by area %.

Example 16

6-[5-Methyl-4-(5-methyl-2H-pyrazol-3-ylamino)-quinazolin-2-ylamino]-1,2-dihydro-indazol-3-one

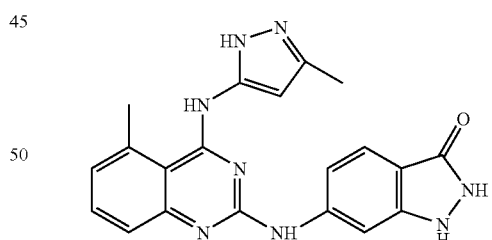

6-[5-Methyl-4-(5-methyl-2H-pyrazol-3-ylamino)-quinazolin-2-ylamino]-1,2-dihydro-indazol-3-one was prepared by a similar method as described above to yield an off-white solid (35.7% yield). $^1$H NMR (500 mHz, DMSO-$d_6$) δ 12.47 (br s, 1H), 11.43 (br s, 1H), 10.79 (br s, 1H), 9.80 (br s, 1H), 7.71 (t, 2H), 7.66 (d, 1H), 7.45 (d, 1H), 7.30 (d, 1H), 7.09 (d, 1H), 6.28 (br s, 1H), 2.92 (s, 3H), 2.08 (s, 3H) ppm. MS (ES+): m/e=387.3 (M+H), 385.3 (M−H); LC/Method A/3.68 min, 100% purity by area %.

Example 17

6-[4-(5-Cyclopropyl-2H-pyrazol-3-ylamino)-5-methyl-quinazolin-2-ylamino]-1,2-dihydro-indazol-3-one

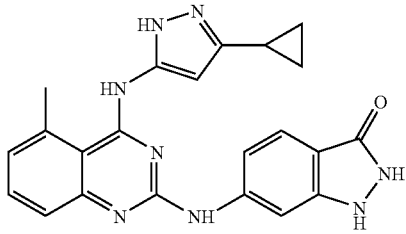

6-[4-(5-Cyclopropyl-2H-pyrazol-3-ylamino)-5-methyl-quinazolin-2-ylamino]-1,2-dihydro-indazol-3-one was prepared by a similar method as described above to yield an off-white solid (45.8% yield). $^1$H NMR (500 mHz, DMSO-$d_6$) δ 12.55 (br s, 1H), 11.43 (br s, 1H), 10.70 (br s, 1H), 9.82 (br s, 1H), 7.68 (m, 2H), 7.44 (d, 2H), 7.29 (d, 1H), 7.10 (d, 1H), 6.12 (br s, 1H), 1.71 (br s, 1H), 0.83 (s, 3H), 0.38 (br s, 3H) ppm. MS (ES+): m/e=413.3 (M+H), 411.3 (M−H); LC/Method A/4.01 min, 100% purity by area %.

Example 18

Preparation of 6-substituted 6-[4-(5-Cyclopropyl-2H-pyrazol-3-ylamino)-quinazolin-2-ylamino]-1,2-dihydro-indazol-3-one Scheme X:

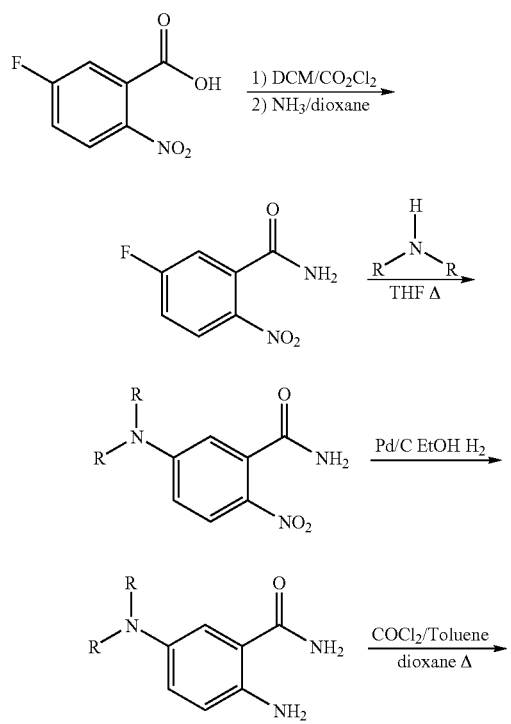

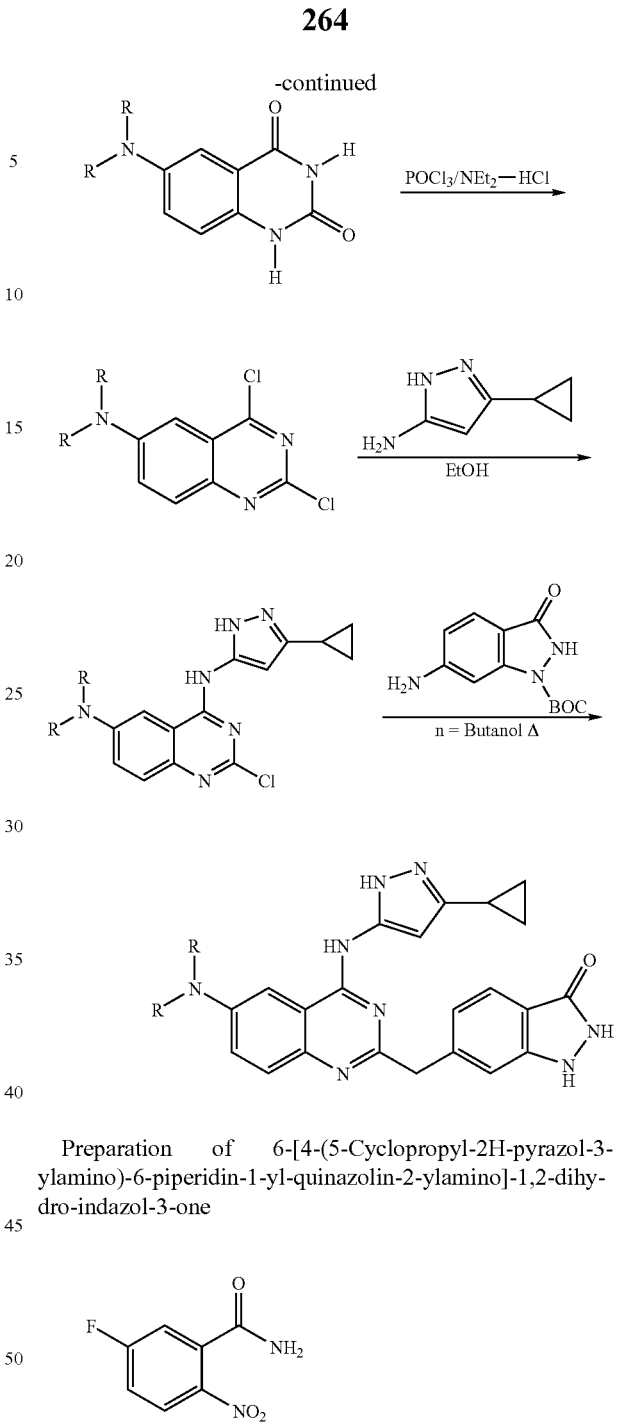

Preparation of 6-[4-(5-Cyclopropyl-2H-pyrazol-3-ylamino)-6-piperidin-1-yl-quinazolin-2-ylamino]-1,2-dihydro-indazol-3-one

Step A: 5-Fluoro-2-nitro-benzamide

To 5-Fluoro-2-nitro-benzoic acid (3 g, 16,2 mmol) in 200 mL of methylene chloride was added oxalyl chloride (2.26 g, 17.8 mmol) and a drop of DMF. After stirring for 2 h, the solution was poured into concentrated NH$_4$OH. The partial solution was poured into water, extracted with Ethyl acetate, dried (Na$_2$SO$_4$) and concentrated to give 5-Fluoro-2-nitro-benzamide (2.61 g, 88% yield) used without purification. LCMS m/e 185.1(M+H) 183.2 (M−H), HPLC tr=2,9 min (100%).

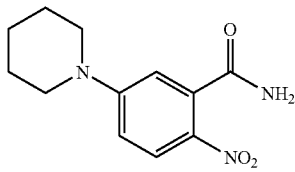

Step B: 2-Nitro-5-piperidin-1-yl-benzamide

To 5-Fluoro-2-nitro-benzamide (850 mg, 4.07 mmol) in THF (100 mL), was added piperdine (381 mg, 4.47 mmol) and diisopropyl ethyl amine (780 mL, 4.07 mmol) and the solution was heated to 70 C in a sealed tube for 12 h. The resulting yellow precipitate was collected to give 2-Nitro-5-piperidin-1-yl-benzamide 948 mg (100% yield) HPLC tr=3.58 min (100%), FIA m/e 250.2(M+H) 248.8 (M–H); $^1$HNMR (500 MHz, dmso): δ 7.95 (1H, d), 7.85 91H, bs), 7.50 (1H, bs), 6.97 (1H, d), 6.80 (1H, s), 3.50 (4H, m), 1.70–1.50 (6H, m).

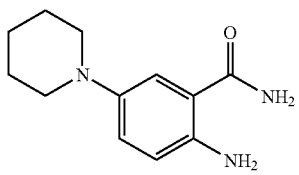

Step C: 2-Amino-5-piperidin-1-yl-benzamide

To 2-Nitro-5-piperidin-1-yl-benzamide (948 mg, 4.07 mmol) in Methanol (100 mL) was added Pd/C (10%) followed by $H_2$ (1 ATM). After 10 h, the solution was filtered and concentrated. Flash chromatography (0–5% methanol in methylene chloride) afforded the title compound as a white solid (510 mg, 51% yield). FIA m/z 220.1 (M+H) 218 (M–H)

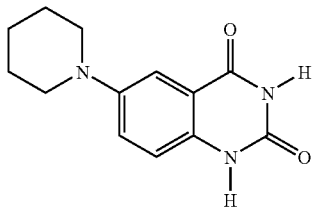

Step D: 6-Piperidin-1-yl-1H-quinazoline-2,4-dione

2-Amino-5-piperidin-1-yl-benzamide (210 mg, 2.33 mmol) in dry dioxane (50 mL) was treated with 2N phos- gene solution (1.28 mL in toluene). The resulting orange precipitate was heated to 80 C to give after 3 h, a pale yellow solid. The solution was cooled in an ice bath and the product was collect by filtration to give 6-Piperidin-1-yl-1H-quinazoline-2,4-dione 525 mg (91% yield) HPLC tr=3.6 min (85%), LCMS m/e 246.2 (M+H).

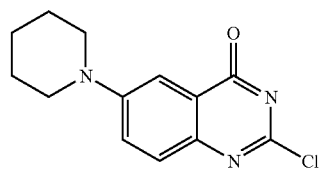

Step E: 2,4-Dichloro-6-piperidin-1-yl-quinazoline

To 6-Piperidin-1-yl-1H-quinazoline-2,4-dione (522 mg, 2.13 mmol) and triethyl amine hydrochloride (1.2 g, 8.5 mmol) was added $POCl_3$ (20 mL) and the solution was heated to 120 C for 72 h. $POCl_3$ was removed in vacuum and the resulting brown oil was quenched with ice water and treated with saturated NaHCO3, to afford a tan solid. Filtration and drying in vacuum gave title compound 550 mg (91% yield). HPLC tr=8.56 min (100%), FIA m/z 282.1 (M+H), HNMR (500 MHz, dmso): δ 8.05–8.00 (1H, d), 7.85–7.80 (1H, d), 7.20 (1H s), 5.50–4.40 (4H, m), 1.70–1.60 (6H, m).

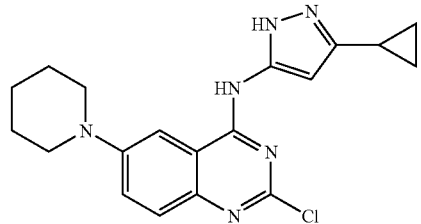

Step F: (2-Chloro-6-piperidin-1-yl-quinazolin-4-yl)-(5-cyclopropyl-2H-pyrazol-3-yl)-amine To 2,4-Dichloro-6-piperidin-1-yl-quinazoline (100 mg, 0.365 mmol), in ethanol (5 omL) was added 5-Cyclopropyl-2H-pyrazol-3-ylamine (88 mg 0.71 mmol). The additional resulted in the formation of a white precipitate. The partial solution was stirred for 10 hr and (2-Chloro-6-piperidin-1-yl-quinazolin-4-yl)-(5-cyclopropyl-2H-pyrazol-3-yl)-amine was colleted by filtration to give 80 mg (61% yield). HPLC tr=4.90 min (100%), LCMS m/e 369.31 (M+H), 367.28 (M–H) tr=3.41 min, HNMR (500 MHz, dmso): □12.30–12.25 (1H, bs), 10.67 (1H, s), 7.80–7.85 (1H, s), 7.65 91H, d), 7.50 (1H, d), 6.50 (1H, bs), 3.40 (4H, m0, 2.90 (1H, m), 1.70–1.55 (6H, m), 0.95 (2H, m), 0.70 (2H, m).

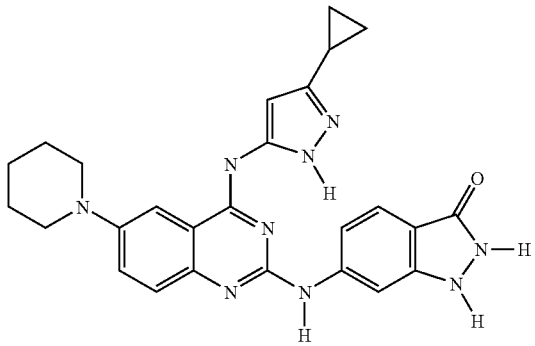

Step G: 6-[4-(5-Cyclopropyl-2H-pyrazol-3-ylamino)-6-piperidin-1-yl-quinazolin-2-ylamino]-1,2-dihydro-indazol-3-one To (2-Chloro-6-piperidin-1-yl-quinazolin-4-yl)-(5-cyclopropyl-2H-pyrazol-3-yl)-amine (80 mg, 0.217 mmol) in NMP (1 mL) was added 6-Amino-3-oxo-2,3-dihydro-indazole-1-carboxylic acid tert-butyl ester (65 mg, 0.26 mmol) and heated to 90° C. for 12 hr in a sealed tube. Solution was poured into sat. NaHCO₃, resulting in a brown solid. The dried solid was taken up in 5 ml of methylene chloride and treated with 5 mL of TFA for 6 hr. The reaction was evaporated and the title compound was isolated by preparative HPLC to give a yellow solid (47,5 mg). HNMR (500 MHz, dmso); δ11.45 (1H, bs), 10.45 (1H, bs), 8.0 (1H, s), 7.70 (1h, m), 7.6 (1H, m), 7.5 (1H, m), 7.4 (1H, s), 7.1 (1H, m), 6.25 (1H, bs), 3.3 (4H, bs), 2.80–2.55 (7H, m), 0.80 (2H, m), 0.40 (2H, m); HPLC t'=3.51 min (10% to 90% MeCN over 8 min, total time 12 min, 3×150 mm C18 column) FIA m/e 482.5 (M+H), 480.2 (M−H).

Example 19

6-[4-(5-Cyclopropyl-2H-pyrazol-3-ylamino)-5-phenyl-pyrimidin-2-ylamino]-1,2-dihydro-indazol-3-one Scheme XI:

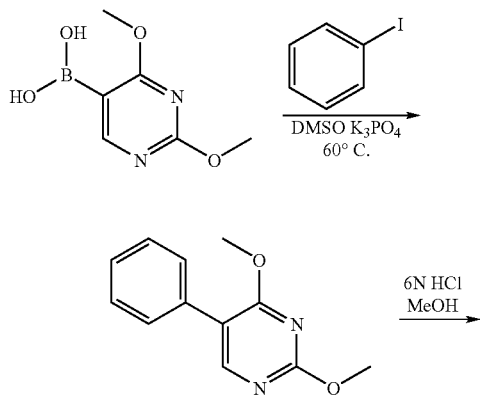

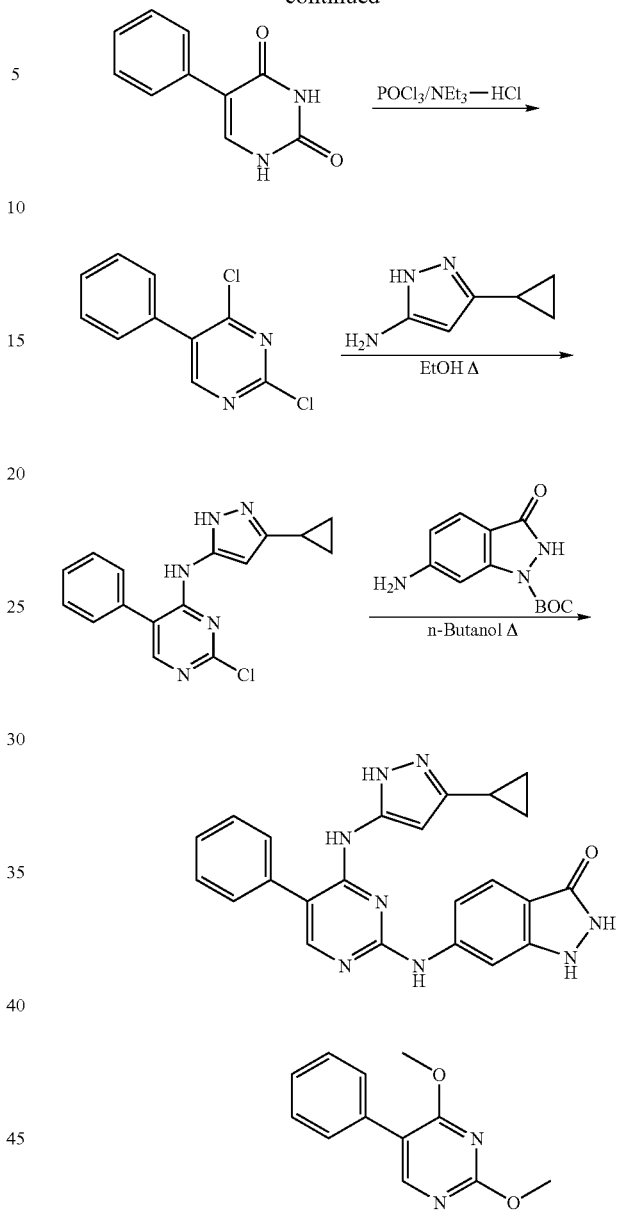

Step A: 2,4-Dimethoxy-5-phenyl-pyrimidine

To 2,4-Dimethoxypyrimidine-5-boronic acid (200 mg, 10.6 mmol), Iodobenzene (326 mg, 1.60 mmol) and K₃PO₄ (900 mg, 4.24 mmol) in DMSO (5 mL, purged with Ar) was added 1,1'bis(diphenylphosphino)ferrocene palladium chloride, complex with dichloromethane (12 mg) and the reaction solution was heated to 60 C in a sealed tube. The solution was heated for 2 h, stirred at room temperature for 10 hr and filtered through celite. The solution was poured into sat. NaHCO₃ to give a gray solid. This material was collected, dissolved in ethyl acetate, dried (Na₂SO₄). Flash chromatography 0 to 2% methanol in dichloromethane gave 2,4-Dimethoxy-5-phenyl-pyrimidine (171 mg, 75% yield). HPLC tr=5.62 min (83%), FIA m/e 217.2 (M+H), HNMR (500 MHz, CDCl₃); δ8.25 (1H, s), 7.45–7.29 (5H, m), 4.00 (3H, s), 3.98 (3H, s).

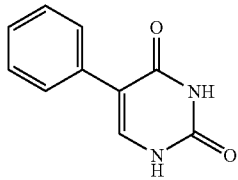

Step B: 5-Phenyl-1H-pyrimidine-2,4-dione 2,4-Dimethoxy-5-phenyl-pyrimidine was suspended in 6N HCl and heated to 100 C for 24 h. Solution was cooled in an ice bath to afford title compound as a white solid 119 mg (80% yield). HNMR (500 MHz, dmso); δ11.25 (1H, s), 11.15 (1H, d), 7.65 (1H, d), 7.55 (2H, d), 7.35 (2H, m), 7.25 (1H, t).

Step C: 2,4-Dichloro-5-phenyl-pyrimidine

To 5-Phenyl-1H-pyrimidine-2,4-dione (110 mg, 0.585 mmol) and triethyl amine hydrochloride (317 mg, 2.3 mmol) was added POCl₃ (15 mL) and the solution was heated to 120 C for 72 h. POCl₃ was removed in vacuum and the resulting brown oil was quenched with ice water and treated with saturated NaHCO₃, extracted with ethyl acetate, washed with brine, dried (Na₂SO₄) to give 2,4-Dichloro-5-phenyl-pyrimidine 131 mg (100% yield). HPLC tr=7.09 min (100%), FIA-MS 224.9 (M+H), HNMR (500 MHz, CDCl₃) δ8.49 (1H, s), 7.45 (3H, m), 7.35 (2H, m).

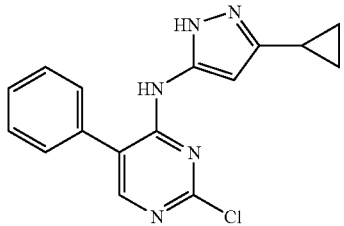

Step D: (2-Chloro-5-phenyl-pyrimidin-4-yl)-(5-cyclopropyl-2H-pyrazol-3-yl)-amine To 2,4-Dichloro-5-phenyl-pyrimidine (187 mg, 0.83 mmol) and trethylamine (255 µL, 1.83 mmol) in ethanol (25 mL) was added 5-Cyclopropyl-2H-pyrazol-3-ylamine (142 mg, 1.16 mmol) and the solution was heated to 80 C for 14 h. The solvent was removed in vacuum, and the title compound was obtained by flash chromatography (0–2% methanol in dichloromethane) to give: 150 mg (60% yield). HPLC tr=6.68 min (87%), LCMS m/e 312.1 (M+H), 310.0 (M−H).

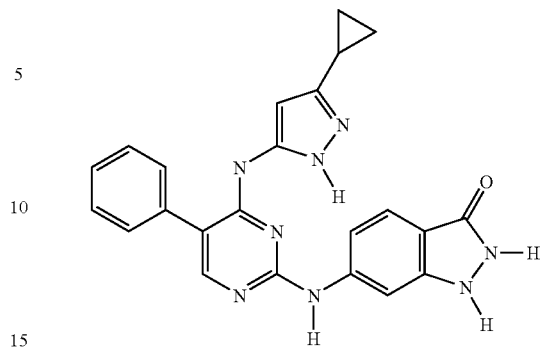

Step E: 6-[4-(5-Cyclopropyl-2H-pyrazol-3-ylamino)-5-phenyl-pyrimidin-2-ylamino]-1,2-dihydro-indazol-3-one To ((2-Chloro-5-phenyl-pyrimidin-4-yl)-(5-cyclopropyl-2H-pyrazol-3-yl)-amine (75 mg, 0.241 mmol), was added 6-Amino-3-oxo-2,3-dihydro-indazole-1-carboxylic acid tert-butyl ester (180 mg, 0.72 mmol) in n-butanol and the solution was heated to 95° C. in a sealed tube. After 12 hr, the solution was concentrated and the title compound was isolated by preparative HPLC as a white solid (5.2 mg, 5% yield) HNMR (500 MHz, MeOH d-6). □17.82–7.80 (2H, m), 7.59–7.50 (6H, m), 7.19–7.17 (1H, m), 6.08 (1H, s), 2.65 (1H, m), 0.91–0.89 (2H, m), 0.45 (2H, m); LCMS m/e: 1.9 min, 425.1 (M+H), 423.1 (M−H).

Example 20

Preparation of 6-[4-(5-Cyclopropyl-2H-pyrazol-3-ylamino)-5-thiophen-2-yl-pyrimidin-2-ylamino]-1,2-dihydro-indazol-3-one

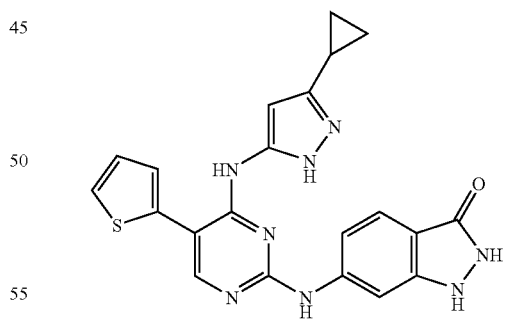

6-[4-(5-Cyclopropyl-2H-pyrazol-3-ylamino)-5-thiophen-2-yl-pyrimidin-2-ylamino]-1,2-dihydro-indazol-3-one was prepared in a similar manner as shown in Scheme XI to afford a white solid (12.6% yield). H-NMR(DMSO-d6, 500 mHz) δ 11.14(s, 1H), 10.08(s, 1H), 8.93(s, 1H), 8.07(s, 1H), 7.73(d, 2H), 7.58(d, 1H), 7.30(m, 1H), 7.23(m, 1H), 7.13(d, 1H), 6.15(s, 1H), 1.81(m, 1H), 0.86(m, 2H), 0.56(m, 2H). MS (ES+): m/e=431.1 (M+H), 429.0 (M−H); LC/Method A/3.739 min, 93.6% purity by area %.

Example 21
Preparation of 6-[4-(5-Cyclopropyl-2H-pyrazol-3-ylamino)-6-substituted-quinazolin-2-ylamino]-1,2-dihydro-indazol-3-one:
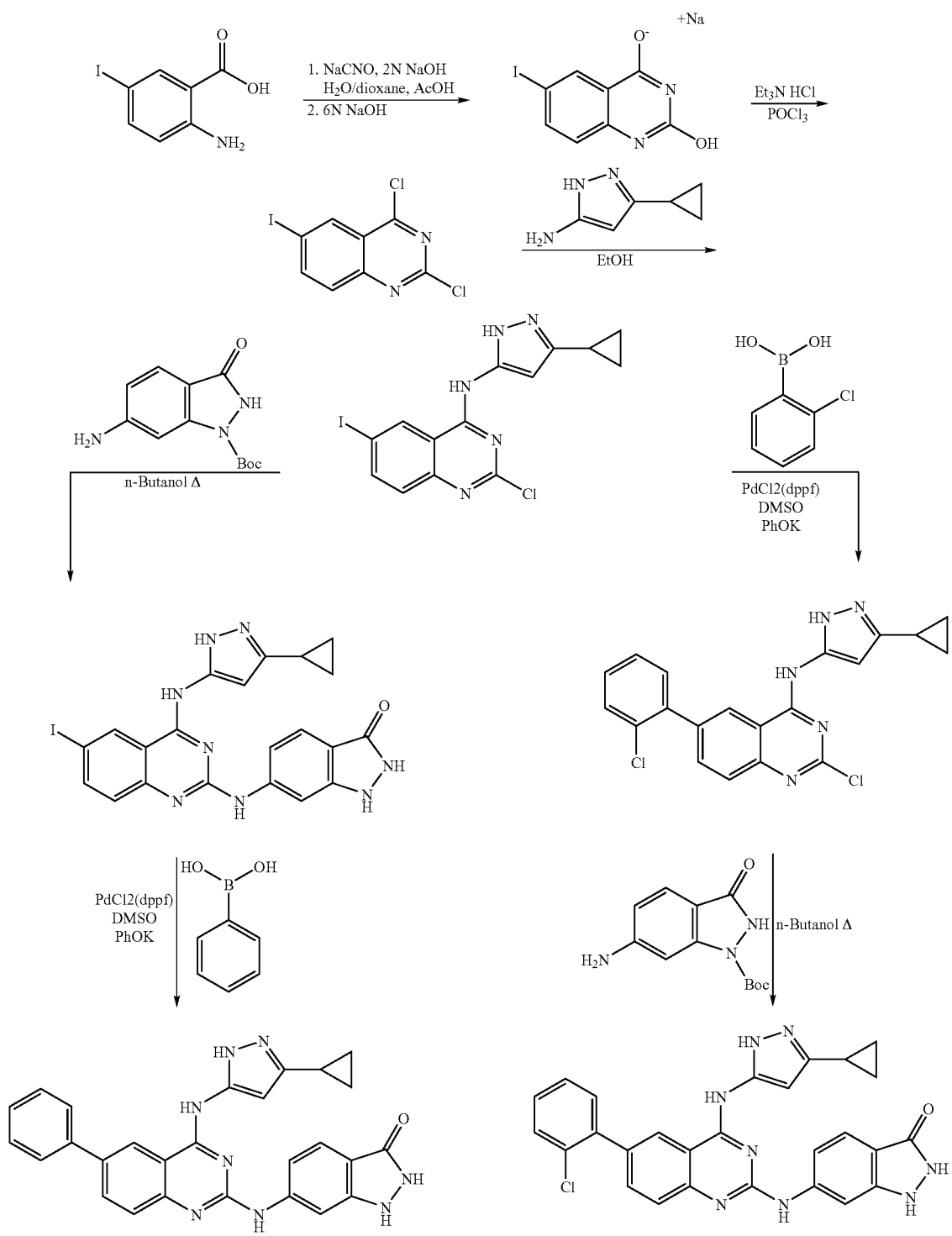
Scheme XII:

Preparation of 6-[4-(5-Cyclopropyl-2H-pyrazol-3-ylamino)-6-phenyl-quinazolin-2-ylamino]-1,2-dihydro-indazol-3-one

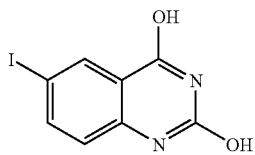

Step A: 6-Iodo-quinazoline-2,4-diol

To a solution of commercially available 2-amino-5-iodo-benzoic acid (1 g, 3.80 mmol) in water (5 mL) and 2N aqueous sodium hydroxide (1.9 mL, 3.80 mmol), was added sodium cyanate (272 mg, 4.18 mmol). The reaction mixture was then diluted with dioxane (3 mL). The reaction mixture was maintained at approximate pH 6–7 over the course of 3 hours, by the addition of acetic acid (228 μl). The mixture was stirred at room temperature for 18 hours then cooled to 0 C. The pH of the reaction was adjusted to 13–14 with the addition of 6N aqueous sodium hydroxide (1 mL), then the mixture was heated at 55 C for 3.5 hours. The reaction mixture was cooled to 0 C and the precipitate was collected, washed with water, then dried by lyophilization to give 6-iodo-quinazoline-2,4-diol as a lavender solid, (849 mg, 78%). HNMR (500 MHz, DMSO) δ6.72 (d, 1H), 7.53 (d, 1H), 7.95 (s, 1H), LCMS m/e 286.98 (M+H).

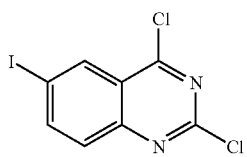

Step B: 2,4-Dichloro-6-iodo-quinazoline

To a suspension of 6-iodo-quinazoline-2,4-diol sodium salt (849 mg, 2.74 mmol) in phosphorus oxychloride (20 mL), was added triethylamine hydrochloride (1.70 g, 12.32 mmol). The reaction mixture was heated at 100 C for 16 hours, then concentrated in vacuum. Ice chips were added to the remaining residue, which was diluted with dichloromethane, washed with water and saturated aqueous sodium bicarbonate, then dried over magnesium sulfate to give 2,4-dichloro-6-iodo-quinazoline as an off-white solid (799 mg, 90%). HNMR (500 MHz, DMSO) δ7.82 (d, 1H), 8.45 (d, 1H), 8.63 (s, 1H). LCMS (ES+) m/e 324.8 (M+H).

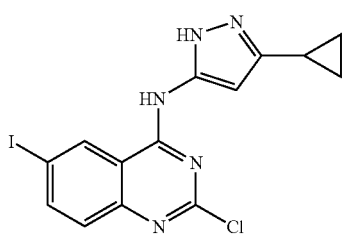

Step C: (2-Chloro-6-iodo-quinazolin-4-yl)-(5-cyclopropyl-2H-pyrazol-3-yl)-amine

To a suspension of 2,4-Dichloro-6-iodo-quinazoline (3.14 g, 9.66 mmol) in ethanol (200 mL) was added 5-Cyclopropyl-2H-pyrazol-3-ylamine (2,14 g, 19.3 mmol) in ethanol (50 mL) and the partial solution was stirred for 4 h. Filtration afforded (2-Chloro-6-iodo-quinazolin-4-yl)-(5-cyclopropyl-2H-pyrazol-3-yl)-amine (3.21 g, 81% yield). HNMR (500 MHz, dmso) δ 12.39 (1H, bs), 10.97 (1H, s), 9.15 (1H, s), 8.13 (1H, d), 7.45 (1H, d0, 1.99–1.90 91H, m), 0.99–0.90 (2H, m), 0.80–0.70 (2H, m).

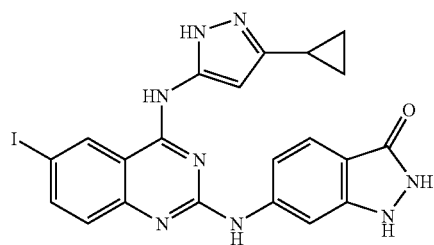

Step D: 6-[4-(5-Cyclopropyl-2H-pyrazol-3-ylamino)-6-iodo-quinazolin-2-ylamino]-1,2-dihydro-indazol-3-one To (2-Chloro-6-iodo-quinazolin-4-yl)-(5-cyclopropyl-2H-pyrazol-3-yl)-amine (208 mg, 0.606 mmol) in NMP (1 mL) was added 6-Amino-3-oxo-2,3-dihydro-indazole-1-carboxylic acid tert-butyl ester (252 mg, 1.01 mmol) and THF (3 mL) and the solution was heated to 100 C in a sealed tube. After 4 h, the solution was poured into sat. NaHCO3, and extracted with ethyl acetate, dried (Na2SO4) and concentrated in vacuum to give the title compound as a white solid (300 mg, 95% yield). LCMS m/e: 625.2 (M+H), 623.2 (M−H).

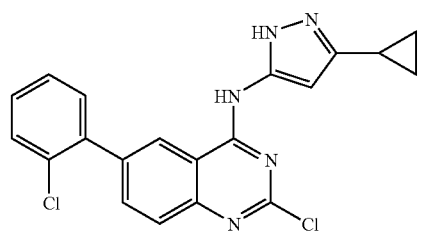

Step E: [2-Chloro-6-(2-chloro-phenyl)-quinazolin-4-yl]-(5-cyclopropyl-2H-pyrazol-3-yl)-amine To (2-Chloro-6-iodo-quinazolin-4-yl)-(5-cyclopropyl-2H-pyrazol-3-yl)-amine (100 mg, 0.243 mmol) and 2-chlorophenyl boronic acid (57 mg, 0.364 mmol) in DMSO (5 mL, purged with Ar) was added 1.5M potassium phenolate solution (648 μL, 0.97 mmol) and 1,1'bis(diphenylphosphino)ferrocene palladium chloride, complex with dichloromethane (27 mg) and the solution was heated to 60 C in a sealed tube. After 1 hr, solution was poured into sat. NaHCO$_3$ resulting in a yellow solid that was colleted by filtration. Flash chromatography (1–4% methanol in dichloromethane) to give: 73 mg (63% yield). LCMS m/e: 396.2 (M+H), 394.2 (M−H)

HNMR (500 MHz, dmso) δ 12.30 (1H, bs), 11.95 (1H, s), 8.80 (1H, s), 7.95 (1H, d), 7.75 (1H, d), 7.65 (1H, m), 7.59 (1H, m), 7.50–7.45 (2H, m), 6.50 (1 h, bs), 1.90 (1H, cm), 0.95 (2H, m), 0.75 (2H, m).

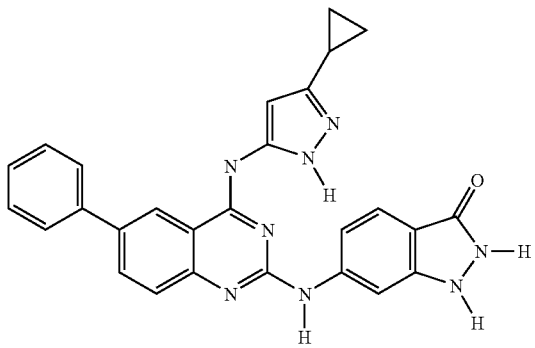

Step F: 6-[4-(5-Cyclopropyl-2H-pyrazol-3-ylamino)-6-phenyl-quinazolin-2-ylamino]-1,2-dihydro-indazol-3-one To 6-[4-(5-Cyclopropyl-2H-pyrazol-3-ylamino)-6-iodo-quinazolin-2-ylamino]-1,2-dihydro-indazol-3-one (300 mg, 0.48 mmol), and phenyl boronic acid (88 mg, 0.72 mmol) in DMSO and 1.5 M potassium phenolate (2.6 mL) was added PdCl$_2$(dppf)$_2$ (175 mg) and the solution was heated to 100° C. in a sealed tube. After 12 hr, the solution was diluted with water, extracted with ethyl acetate, dried (Na$_2$SO$_4$) and concentrated. The title compound was isolated by preparative HPLC as a white solid (0.82 mg). HPLC t$_r$=5.14 min (10% to 90% MeCN over 8 min, total time 12 min, 3×150 mm C18 column) FIA m/e 475.55 (M+H), 473.55 (M–H).

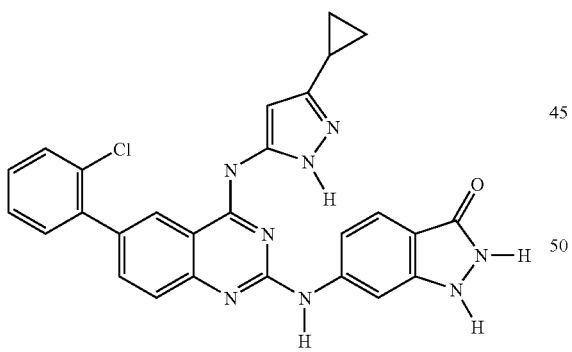

6-[6-(2-Chloro-phenyl)-4-(5-cyclopropyl-2H-pyrazol-3-ylamino)-quinazolin-2-ylamino]-1,2-dihydro-indazol-3-one To [2-Chloro-6-(2-chloro-phenyl)-quinazolin-4-yl]-(5-cyclopropyl-2H-pyrazol-3-yl)-amine (70 mg, 0.35 mmol) in NMP (3 mL) was added 6-Amino-3-oxo-2,3-dihydro-indazole-1-carboxylic acid tert-butyl ester (88 mg, 0.35 mmol) and the solution was heated to 120 C in a sealed tube. After 12 h, the solution was heated to 130 C for additional 2 h. The cooled solution was directly purified by preparative HPLC to give a pale yellow solid 2.4 mg, 2.7% yield). HPLC t$_r$=4.92 min (10% to 90% MeCN over 8 min, total time 12 min, 3×150 mm C18 column) LCMS m/e 509.28 (M+H), 507.17 (M–H), t$_r$=2.50 min (10% to 90% MeCN).

Example 22

6-[4-(5-Isopropyl-2H-pyrazol-3-ylamino)-6-phenyl-quinazolin-2-ylamino]-1,2-dihydro-indazol-3-one.

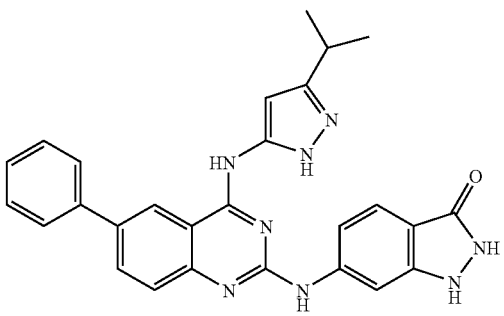

6-[4-(5-Isopropyl-2H-pyrazol-3-ylamino)-6-phenyl-quinazolin-2-ylamino]-1,2-dihydro-indazol-3-one was prepared by a similar method as described above to yield a white solid NMR (500 MHz, MeOD) δ 8.62 (s, 1H), 8.10 (d, 1H), 7.71 (m, 3H), 7.60 (d, 1H), 7.42–7.31 (m, 4H), 7.12 (d, 1H), 6.18 (br, 1H), 2.77 (m, br, 1H), 1.04 (d, 6H) ppm. MS (ES+): m/e=477.3 (M+H); LC/Method A/3.12 min.

Example 23

Preparation of 6-[4-(5-Ethyl-2H-pyrazol-3-ylamino)-6-phenyl-quinazolin-2-ylamino]-1,2-dihydro-indazol-3-one:

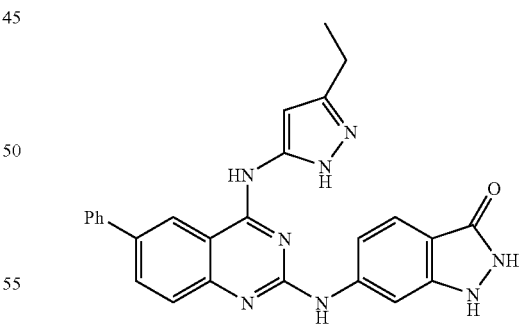

6-[4-(5-Ethyl-2H-pyrazol-3-ylamino)-6-phenyl-quinazolin-2-ylamino]-1,2-dihydro-indazol-3-one was prepared by a similar method as described above to yield a pale-yellow solid NMR (500 MHz, MeOD) δ 8.63 (s, 1H), 8.11 (d, 1H), 7.71 (m, 3H), 7.60 (d, 1H), 7.42 (m, 3H), 7.34 (t, 1H), 7.12 (d, 1H), 6.22 (br, 1H), 2.45 (q, 2H), 1.00 (t, 3H) ppm. MS (ES+): m/e=463.3 (M+H); LC/Method A/3.05 min.

Example 24

Preparation of 6-[4-(2-Chloro-phenyl)-6-(5-cyclopropyl-2H-pyrazol-3-ylamino)-pyrimidin-2-ylamino]-1,2-dihydro-indazol-3-one Scheme XIII:

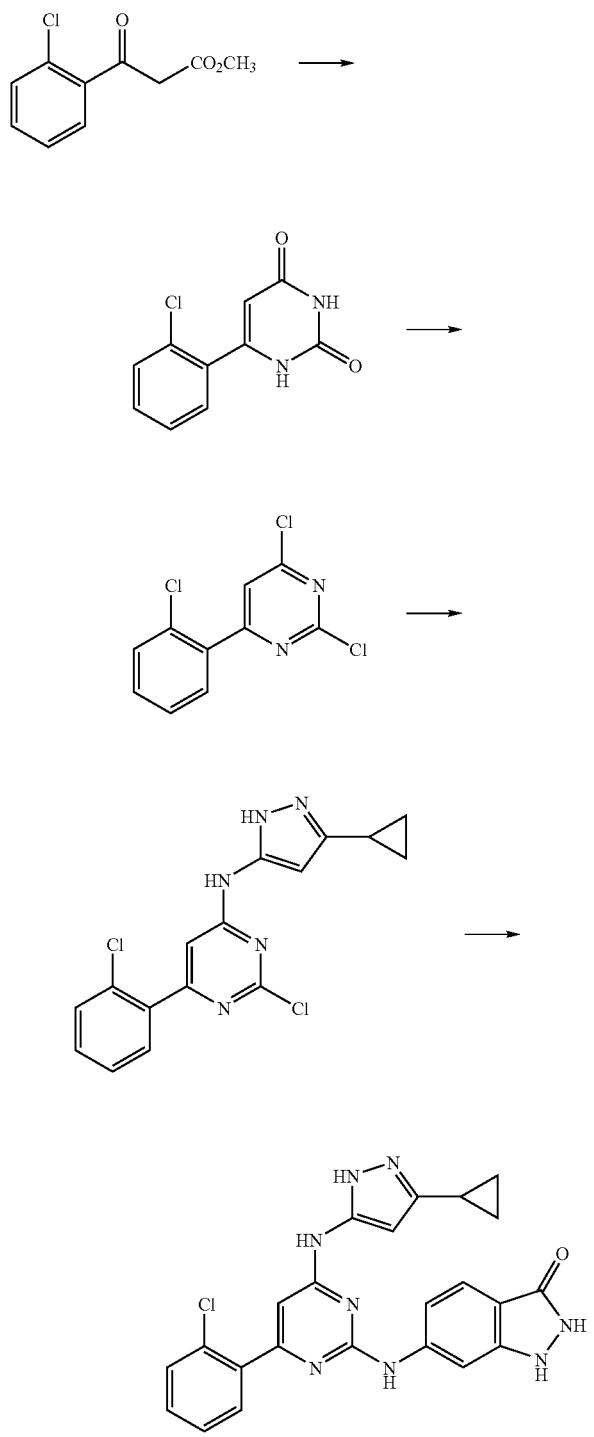

Step A:
6-(2-Chloro-phenyl)-1H-pyrimidine-2,4-dione

Methyl 2-chlorobenzoyl acetate (1 g, 4.7 mmol) and urea (0.282 g, 4.7 mmol) were taken into a sealed tube and heated at 125 C for 20 hours. The reaction was cooled to room temperature and ethanol was added to the reaction mixture. The solid was filtered to afford 0.14 g of the desired product. HPLC (Rt 3.336 mins., 95% purity). MS (ES+): m/e 221.1 (M−H); 223.1 (M+H)

Step B:
2,4-Dichloro-6-(2-chloro-phenyl)-pyrimidine 6-(2-Chloro-phenyl)-1H-pyrimidine-2,4-dione (200 mg, 0.9 mmol) was taken into 5 ml of POCl₃. Triethylamine hydrochloride (495 mg) was added to the mixture and heated at 100 C for 18 hours. The mixture was coiled and evaporated in vacuo to afford a white solid. The solid was suspended in ice water and was carefully basified with saturated sodium bicarbonate. A precipitate was collected by vacuum filtration and dried overnight to afford 183 mg (73% yield) of the desired product. HPLC Rt 8.006 mins (100% purity); MS (ES+) m/e 261.0 (M+H)

Step C: [2-Chloro-6-(2-chloro-phenyl)-pyrimidin-4-yl]-(5-cyclopropyl-1H-pyrazol-3-yl)-amine 2,4-Dichloro-6-(2-chloro-phenyl)-pyrimidine (180 mg, 0.694 mmol) and 5-cyclopropyl-1H-pyrazol-3-ylamine (128 mg, 1.04 mmol) was taken into 3 ml of ethanol. The reaction was stirred at room temperature for 4 days. The reaction was evaporated in vacuo and the crude product purified by flash chromatography (SiO2) eluting with ethyl acetate/hexane (1:1) to afford 93 mg of the desired product. HPLC (C18 column) Rt 6.23 mins.; MS m/z 346.1 (M+H) 344.1 (M−H)

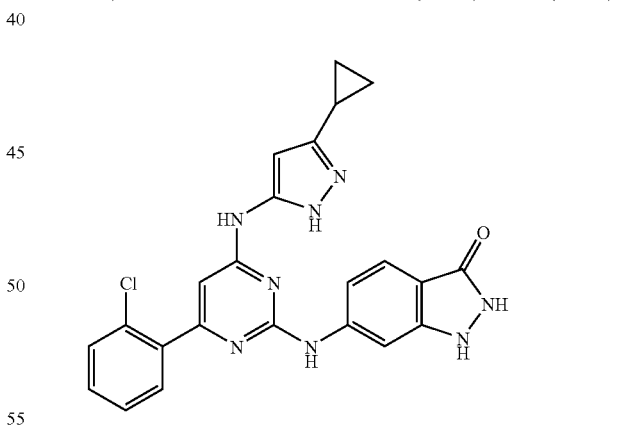

Step D: 6-[4-(2-Chloro-phenyl)-6-(5-cyclopropyl-2H-pyrazol-3-ylamino)-pyrimidin-2-ylamino]-1,2-dihydro-indazol-3-one was prepared in a similar manner as described above to afford a white solid (32.1% yield). H-NMR (DMSO-d6) δ 11.16(br s, 1H), 9.76(br, s, 1H), 7.68(br s, 1H), 7.57(m, 2H), 7.46(m, 4H), 7.12(d, 1H), 6.54(br s, 1H), 6.04(br s,1H), 1.74(s,1H), 0.80(d, 2H), 0.49(s, 2H). MS (ES+): m/e=459.2 (M+H), 457.2 (M−H); LC/Method A/3.574 min, 100% purity by area %.

Example 25

Preparation of 6-[6-(5-Cyclopropyl-2H-pyrazol-3-ylamino)-2-substituted-pyrimidin-4-ylamino]-1,2-dihydro-indazol-3-one

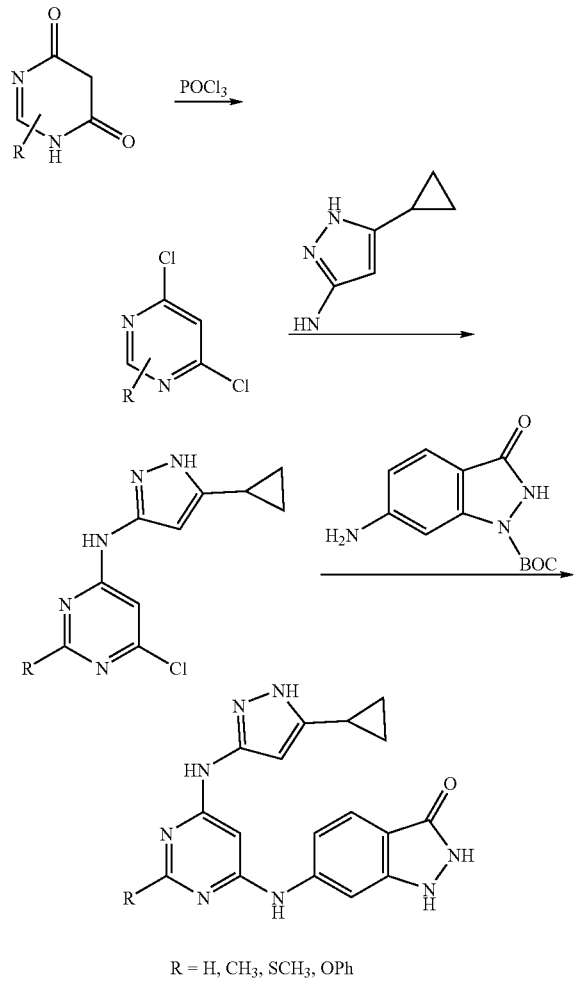

R = H, CH₃, SCH₃, OPh

6-[6-(5-Cyclopropyl-2H-pyrazol-3-ylamino)-2-methylsulfanyl-pyrimidin-4-ylamino]-1,2-dihydro-indazol-3-one was prepared as depicted generally above in Scheme XIV to yield a white solid. NMR (500 MHz, DMSO-d6) δ 10.88 (br, 1H), 9.43 (s, 1H), 9.39 (s, 1H), 7.86 (s, 1H), 7.46 (d, 1H), 7.00 (dd, 1H), 6.45 (br, 1H), 5.84 (br, 1H), 2.52 (s, 3H, covered by DMSO), 1.87 (m, 1H), 0.92 (m, 2H), 0.66 (m, 2H) ppm. MS (ES+): m/e=395.1 (M+H); LC/Method A/2.71 min.

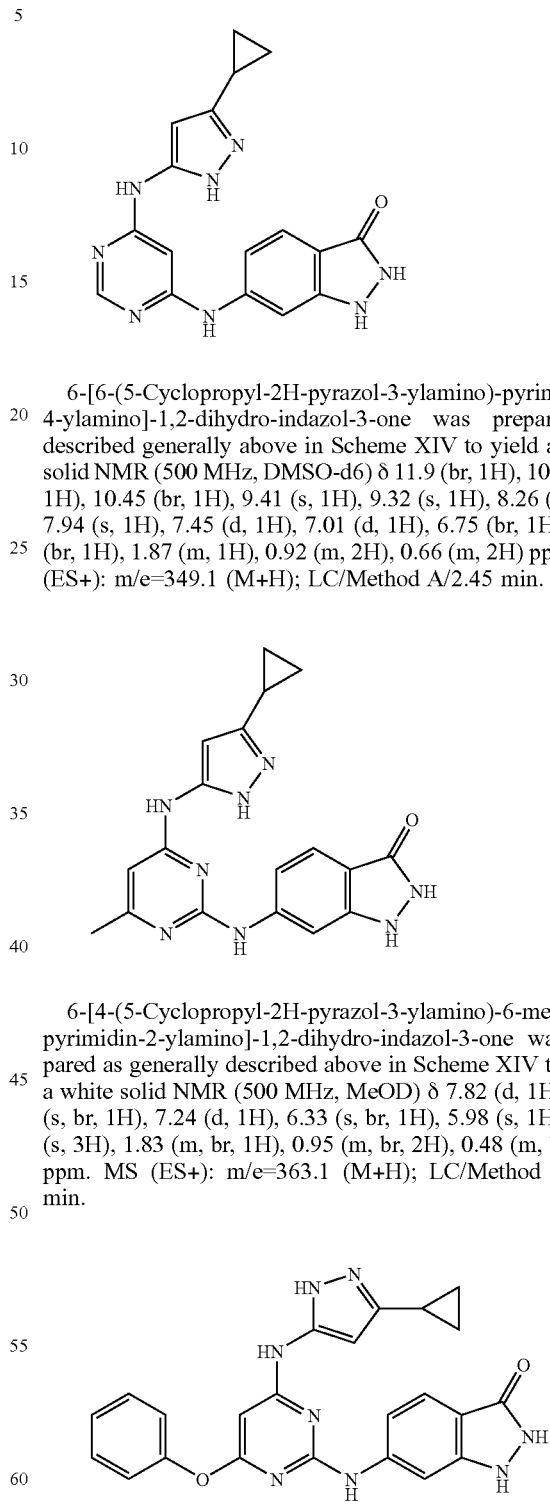

6-[6-(5-Cyclopropyl-2H-pyrazol-3-ylamino)-pyrimidin-4-ylamino]-1,2-dihydro-indazol-3-one was prepared as described generally above in Scheme XIV to yield a white solid NMR (500 MHz, DMSO-d6) δ 11.9 (br, 1H), 10.75 (br, 1H), 10.45 (br, 1H), 9.41 (s, 1H), 9.32 (s, 1H), 8.26 (s, 1H), 7.94 (s, 1H), 7.45 (d, 1H), 7.01 (d, 1H), 6.75 (br, 1H), 5.81 (br, 1H), 1.87 (m, 1H), 0.92 (m, 2H), 0.66 (m, 2H) ppm. MS (ES+): m/e=349.1 (M+H); LC/Method A/2.45 min.

6-[4-(5-Cyclopropyl-2H-pyrazol-3-ylamino)-6-methyl-pyrimidin-2-ylamino]-1,2-dihydro-indazol-3-one was prepared as generally described above in Scheme XIV to yield a white solid NMR (500 MHz, MeOD) δ 7.82 (d, 1H), 7.58 (s, br, 1H), 7.24 (d, 1H), 6.33 (s, br, 1H), 5.98 (s, 1H), 2.48 (s, 3H), 1.83 (m, br, 1H), 0.95 (m, br, 2H), 0.48 (m, br, 2H) ppm. MS (ES+): m/e=363.1 (M+H); LC/Method A/2.44 min.

6-[4-(5-Cyclopropyl-2H-pyrazol-3-ylamino)-6-phenoxy-pyrimidin-2-ylamino]-1,2-dihydro-indazol-3-one was prepared according to the general procedure described in Scheme XIV to yield an off-white solid (4.13% yield). H-NMR(DMSO-d6, 500 mHz) δ 10.5 (s br, 1H), 9.91(s, 1H), 7.87(s br, 1H), 7.50(m, 3H), 7.31(m, 3H), 7.06(d, 1H), 6.30(s, 1H), 5.96(s, 1H), 1.87(m, 1H), 0.86(m, 2H), 0.64(m, 2H). MS (ES+): m/e=441.1 (M+H), 439.1 (M−H); LC/Method A/4.647 min, 96.6% purity by area %.

Example 26

Preparation of 6-[4-(5-Cyclopropyl-2H-pyrazol-3-ylamino)-6-phenyl-[1,3,5]triazin-2-ylamino]-1,2-dihydro-indazol-3-one

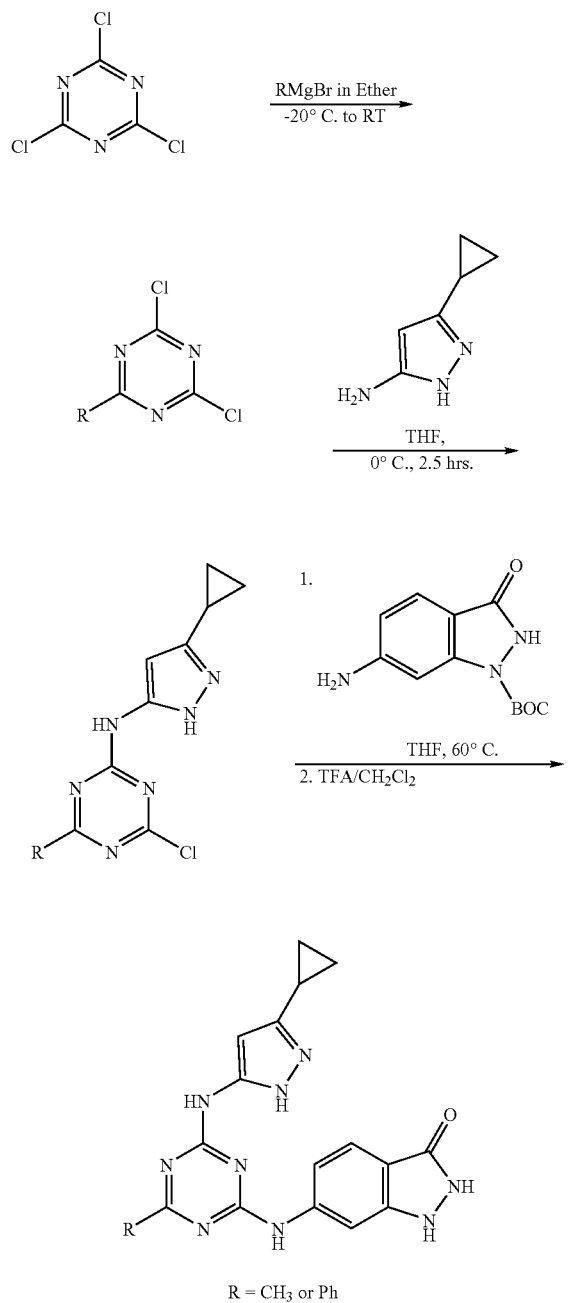

R = CH₃ or Ph

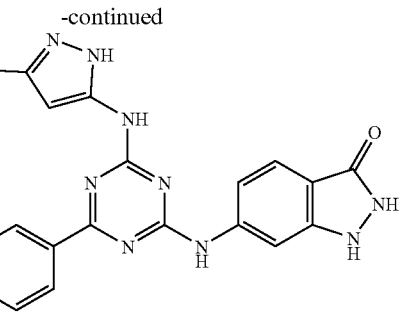

-continued

Step A: (4-Chloro-6-phenyl-[1,3,5]triazin-2-yl)-(5-cyclopropyl-2H-pyrazol-3-yl)-amine A solution of 5-cyclopropyl-2H-pyrazol-3-ylamine (172 mg, 1.4 mmol) in 5 ml of THF was added dropwise to a solution of 2,4-dichloro-6-phenyl-[1,3,5]triazine (452 mg, 2 mmol) (ref: WO 0125220, p.190) and diisopropylethylamine (0.35 ml, 2 mmol) in 15 ml of THF at room temperature then stirred for 18 hours. The reaction was filtered and the filtrate evaporated in vacuo and the residue purified by flash chromatography (SiO₂) eluting with 8:2 dichloromethane: ethyl acetate to afford 233 mg of the desired product. HPLC: Rt 6.803 mins. MS: m/z 313.0 (M+H)

Step B: 6-[4-(5-Cyclopropyl-2H-pyrazol-3-ylamino)-6-phenyl-[1,3,5]triazin-2-ylamino]-1,2-dihydro-indazol-3-one.

To a sealed tube was added (4-Chloro-6-phenyl-[1,3,5]triazin-2-yl)-(5-cyclopropyl-2H-pyrazol-3-yl)-amine (50 mg, 0.16 mmol) and 6-amino-3-oxo-2,3-dihydro-indazole-1-carboxylic acid tert-butyl ester (80 mg, 0.32 mmol) in 1 ml of n-butanol. The contents were heated to 85° C. for 3 hours. The reaction was concentrated in vacuo to give a white solid that was dissolved in 3 ml of dichloromethane and 1 ml of trifluoro acetic acid and stirred for 5 hours at room temperature. The reaction concentrated and the crude residue purified by prep HPLC to afford 34 mg of the desired product as a light yellow solid (39.4% yield). ¹H-NMR (DMSO-d⁶, 500 mHz) δ 10.95 (m, 1H), 10.30 (m, 1H), 9.91 (s, 1H), 8.32 (m, 2H), 8.04 (m,1H), 7.49 (m,4H), 7.25 (m, 1H), 6.14 (s br, 1H), 1.85 (s, 1H), 0.87 (s, 2H), 0.67 (s, 2H).

MS (ES+): m/e=426.1 (M+H), 424.1 (M−H); LC/Method A/4.723 min, 100% purity by area %.

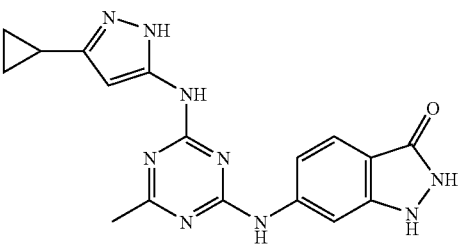

6-[4-(5-Cyclopropyl-2H-pyrazol-3-ylamino)-6-methyl-[1,3,5]triazin-2-ylamino]-1,2-dihydro-indazol-3-one was prepared as described generally in Scheme XV to yield a white solid (26.2% yield). H-NMR (DMSO-d6, 500 mHz) δ 11.25 (s, 1H), 10.60 (s br, 1H), 7.85 (m, 1H), 7.62 (d, 1H), 7.31 (m, 1H), 6.14 (s, 1H), 2.42 (s, 3H), 1.92 (m, 1H), 0.95 (s, 2H), 0.66 (m, 2H). MS (ES+): m/e=364.2 (M+H), 362.1 (M−H); LC/Method A/3.111 min, 98.0% purity by area %.

Example 27

Preparation of 6-[4-Chloro-6-(5-cyclopropyl-2H-pyrazol-3-ylamino)-[1,3,5]triazin-2-ylamino]-1,2-dihydro-indazol-3-one

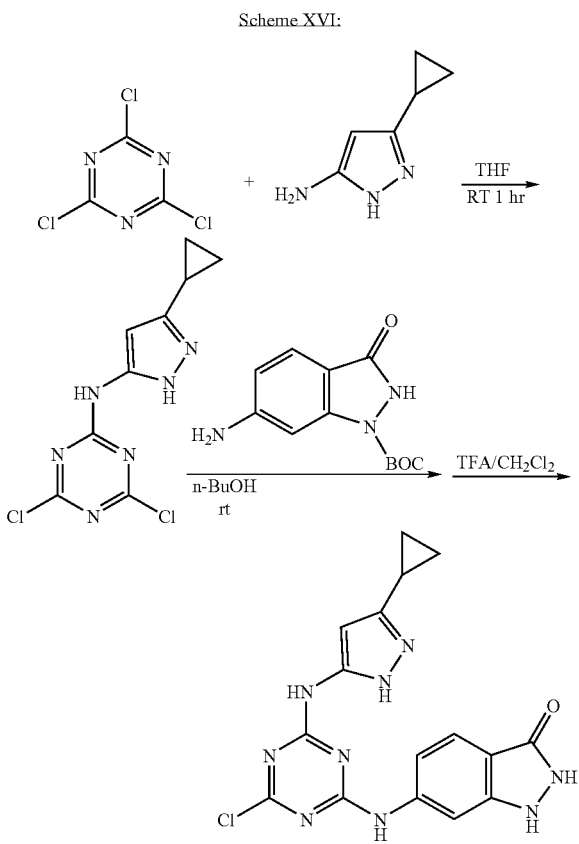

Step 1: (5-Cyclopropyl-2H-pyrazol-3-yl)-(4,6-dichloro-[1,3,5]triazin-2-yl)-amine A solution of 5-Cyclopropyl-2H-pyrazol-3-ylamine(334 mg, 2.71 mmol) in 2 ml of THF was added dropwise to a solution of 2,4,6-Trichloro-[1,3,5]triazine (500 mg, 2.71 mmol) in 5 ml of THF at room temperature. After 1 hour, the precipitate was collected to afford 370 mg (50.4% yield) of the desired product.

Step 2: 6-[4-Chloro-6-(5-cyclopropyl-2H-pyrazol-3-ylamino)-[1,3,5]triazin-2-ylamino]-1,2-dihydro-indazol-3-one 6-Amino-3-oxo-2,3-dihydro-indazole-1-carboxylic acid tert-butyl ester (69 mg, 0.277 mmol) and (5-Cyclopropyl-2H-pyrazol-3-yl)-(4,6-dichloro-[1,3,5]triazin-2-yl)-amine (50 mg, 0.184 mmol) were taken into 1 ml of n-butanol and stirred at room temperature for 2 hours. The solvent was evaporated in vacuo and the resulting white solid residue dissolved in dichloromethane-trifluoro acetic acid (1:1 mixture, 2 ml). After 3 hours, the solvent was evaporated in vacuo and the crude product purified by prep HPLC to afford 15 mg of the desired product as a white solid (16.4% yield). H-NMR(DMSO-d6, 500 mHz) δ 11.11(m, 1H), 10.41(s, 1H), 10.29(s, 1H), 7.11–7.82(m, 3H), 6.04(s, 1H), 1.84(m, 1H), 0.89(m, 2H), 0.60(m, 2H). MS (ES+): m/e=384.0 (M+H), 382.0 (M−H); LC/Method A/3.891 min, 98.0% purity by area %.

Example 28

Preparation of 6-[4-(5-Cyclopropyl-2H-pyrazol-3-ylamino)-6-methoxy-[1,3,5]triazin-2-ylamino]-1,2-dihydro-indazol-3-one

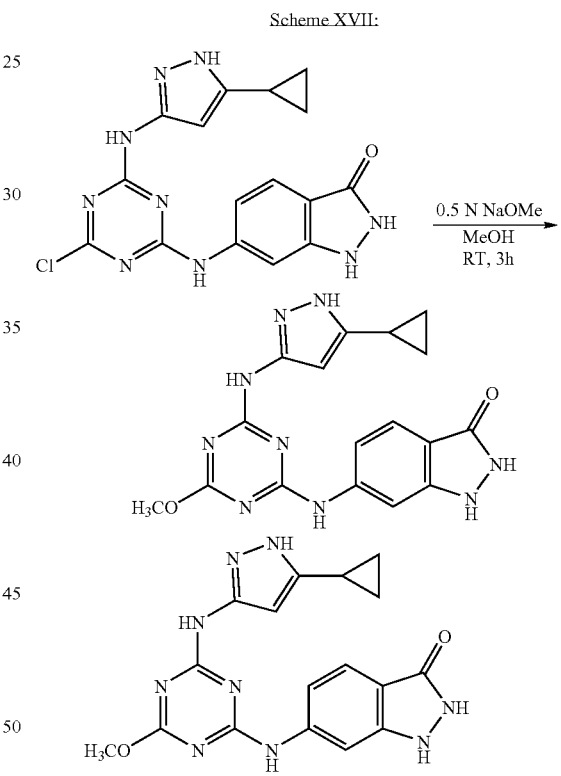

(6-[4-Chloro-6-(5-cyclopropyl-2H-pyrazol-3-ylamino)-[1,3,5]triazin-2-ylamino]-1,2-dihydro-indazol-3-one (70 mg, 0.14 mmol) was dissolved in 6 ml of 0.5 M solution of sodium methoxide in methanol and stirred at room temperature for 3 hours. The reaction was neutralized to pH 6–7 with 0.5 N hydrogen chloride. The cloudy solution was concentrated in vacuo. The resulting yellow solid was suspended in water, filtered, then purified by prep HPLC to afford 7.5 mg of the desired product as a white solid (10.8% yield). H-NMR(DMSO-d6, 500 mHz) δ 10.96(s br, 1H), 9.76(s br, 1H), 7.90(s br, 1H), 7.44(d, 1H), 7.18(m, 1H), 6.02(s br, 1H) 3.85(s, 3H), 1.80(s br, 1H), 0.84(m, 2H), 0.61(s br, 2H). MS (ES+): m/e=380.1 (M+H), 378.1 (M−H); LC/Method A/3.543 min, 90.0% purity by area %.

Example 29

Preparation of 6-[4-(5-Cyclopropyl-2H-pyrazol-3-ylamino)-6-dimethylamino-[1,3,5]triazin-2-ylamino]-1,2-dihydro-indazol-3-one

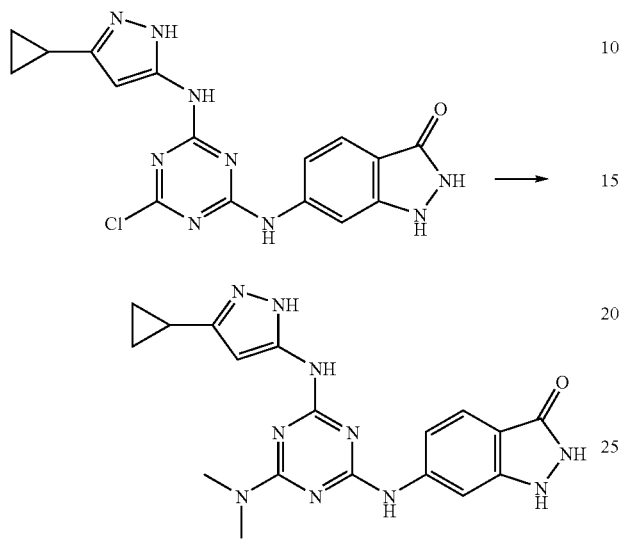

6-[4-Chloro-6-(5-cyclopropyl-2H-pyrazol-3-ylamino)-[1,3,5]triazin-2-ylamino]-1,2-dihydro-indazol-3-one (60 mg, 0.121 mmol) was dissolved in 5 ml of a 2 M solution of dimethylamine in THF and stirred at room temperature for 2 hours. The reaction was concentrated in vacuo and purified on prep HPLC to afford 38 mg (62% yield) of the desired product as a white solid (62.2% yield). H-NMR(DMSO-d6, 500 mHz) δ 11.20(s, 1H), 10.48(s br, 1H), 10.08(s, 1H), 7.92(s, 1H), 7.55(d, 1H), 7.13(s, 1H), 5.93(s, 1H), 3.20(d, 6H), 1.92(m, 1H), 0.96(m, 2H), 0.72(m, 2H). MS (ES+): m/e=393.2 (M+H), 391.2 (M−H); LC/Method A/3.835 min, 98.0% purity by area %.

Example 30

Preparation of 6-[4-(5-Cyclopropyl-2H-pyrazol-3-ylamino)-6-dimethylamino-[1,3,5]triazin-2-ylamino]1,2-dihydro-indazol-3-one

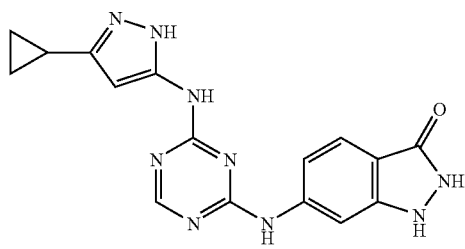

6-[4-(5-Cyclopropyl-2H-pyrazol-3-ylamino)-6-dimethylamino-[1,3,5]triazin-2-ylamino]1,2-dihydro-indazol-3-one was prepared according to the general procedures described above to yield an off-white solid (32.8% yield). H-NMR (DMSO-d6, 500 mHz) δ 11.02(s br, 1H), 10.15(s br, 1H), 9,97(s br, 1H), 8,38(s, 1H), 7.88(s br, 1H), 7.53(d, 1H), 7.25(s br, 1H), 6.13(s, 1H), 1.86(s br, 1H), 0.89(m, 2H), 0.66(s br, 2H). MS (ES+): m/e=350.1 (M+H), 348.0 (M−H); LC/Method A/3.041 min, 100% purity by area %.

Example 31

Preparation of 6-[5-Amino-6-(5-cyclopropyl-2H-pyrazol-3-ylamino)-pyrimidin-4-ylamino]-1,2-dihydro-indazol-3-one Scheme XVIII:

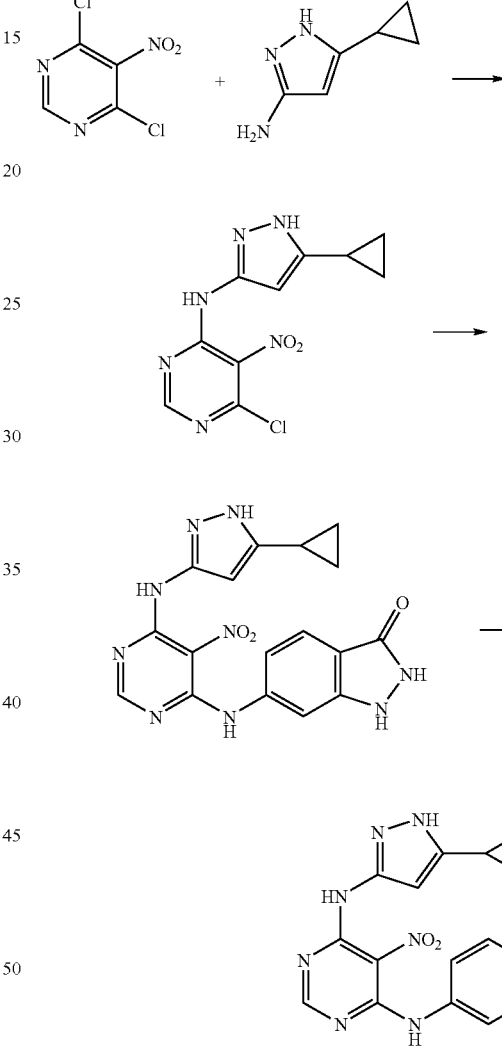

(6-Chloro-5-nitro-pyrimidin-4-yl)-(5-cyclopropyl-2H-pyrazol-3-yl)-amine

To a solution of 4,6-dichloro-5-nitro-pyrimidine (100 mg, 0.52 mmol) in anhydrous THF (2 mL) was added aminopyrazole (76 mg, 0.62 mmol). The solution was stirred at RT for 2 hrs and was filtered via short silica gel column. The filtrate that contained product and the unreacted starting pyrrimidine was concentrated under vacuum. The resulting residue was used directly without further purification.

NMR (500 MHz, DMSO-d6) δ 12.4 (br s, 1H), 10.45 (s, 1H), 8.55 (s, 1H), 6.23 (s, 1H), 1.90 (m, 1H), 0.95 (m, 2H), 0.70 (m, 2H) ppm. MS (ES+): m/e=281.1 (M+H); LC/Method A/3.05 min.

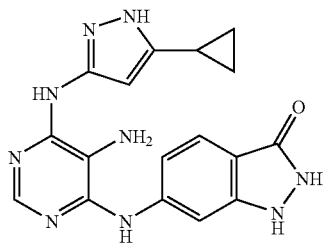

6-[5-Amino-6-(5-cyclopropyl-2H-pyrazol-3-ylamino)-pyrimidin-4-ylamino]-1,2-dihydro-indazol-3-one To a solution of (6-chloro-5-nitro-pyrimidin-4-yl)-(5-cyclopropyl-2H-pyrazol-3-yl)-amine (50 mg, 0.18 mmol) in anhydrous THF (2 mL) was added 6-amino-3-oxo-2,3-dihydro-indazole-1-carboxylic acid tert-butyl ester (67 mg, 0.27 mmol) and diisopropylethylamine (23 mg, 0.18 mmol). The mixture was stirred at RT for 14 hrs and the solvents were removed under vacuum. The residue was dissolved in CH$_2$Cl$_2$ (3 mL) and treated with TFA (2 mL) at RT for 2 hrs. After removal of the solvents via evaporation, the residue was reduced by hydrogen (50 psi) in MeOH (10 mL) in the presence of Pd/C (10%, 50 mg) for 3 hrs. The solution was filtered via celite, the filtrate was evaporated under vacuum, and the residue was purified by HPLC to give the desired product as white solid (22 mg). NMR (500 MHz, DMSO-d6) δ11.16 (br, 1H), 9.92 (br, 1H), 8.98 (s, 1H), 8.27 (s, 1H), 7.67 (s, 1H), 7.55 (d, 1H), 7.08 (d, 1H), 5.95 (s, 1H), 2.00 (m, 1H), 1.06 (m, 2H), 0.81 (m, 2H) ppm. MS (ES+): m/e=364.3 (M+H); LC/Method A/2.45 min.

Example 32

Preparation of 6-[4-(5-Cyclopropyl-2H-pyrazol-3-ylamino)-5-phenylamino-pyrimidin-2-ylamino]-1,2-dihydro-indazol-3-one

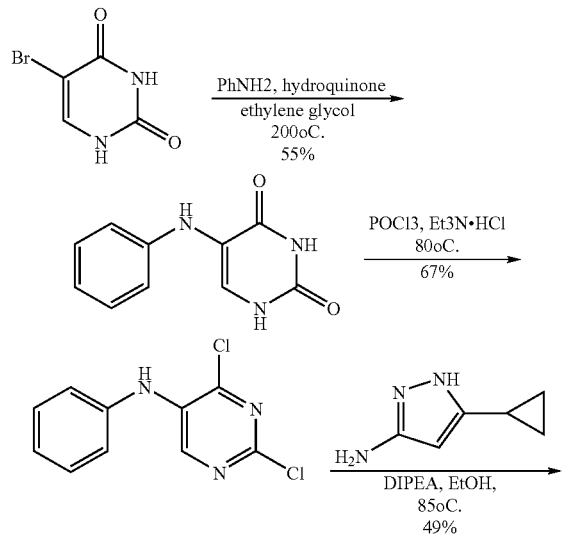

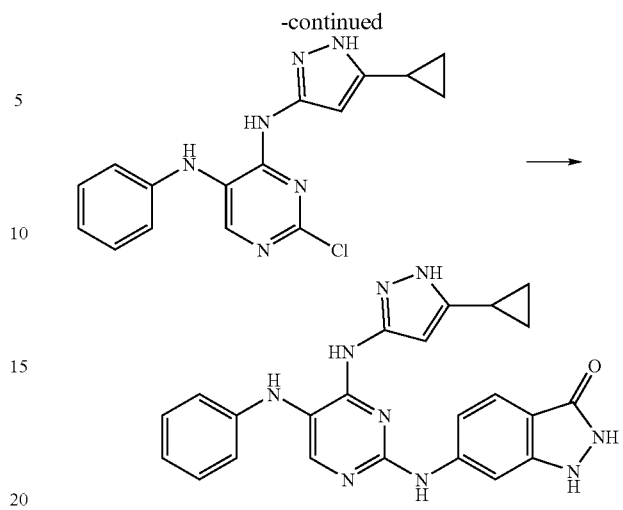

Preparation of 2-Chloro-N$^4$-(5-cyclopropyl-1H-pyrazol-3-yl)-N$^5$-phenyl-pyrimidine-4,5-diamine Preparation of 5-phenylamino-1H-pyrimidine-2,4-dione
A mixture of 5-bromo-uracil (2.82 g, 14.8 mmol), aniline (4.70 mL. 51.7 mmol) and hydroquinone (100 mg) in ethylene glycol was heated to 200° C. for 2 h, then cooled. The precipitate was filtered off and washed with water and acetone to provide 5-phenylamino-1H-pyrimidine-2,4-dione (1.65 g, 55% yield) as an off-white solid. $^1$H-NMR (500 MHz, dmso-d$_6$) δ 11.3 (s, 1H), 10.6 (s, 1H), 7.31 (d, 1H), 7.10 (t, 2H), 6.92 (s, 1H), 6.72 (d, 2H), 6.65 (t, 1H) ppm; MS (FIA) 202.1 (M–H); HPLC (method A) 2.246 min.

Preparation of (2,4-dichloro-pyrimidin-5-yl)-phenyl-amine
A mixture of 5-phenylamino-1H-pyrimidine-2,4-dione (0.25 g, 1.23 mmol) in phosphorous oxychloride (5 mL) was heated at 80° C. for 4 h, and room temperature for 20 h. Triethylamine hydrochloride (0.50 g, 3.69 mmol) was added and the reaction was stirred 6d at 80° C. and 6d at room temperature. Phosphorous oxychloride was evaporated (azeotroping with toluene), then the residue was cooled to 0° C. and diluted with ethyl acetate. Excess reagent was carefully quenched with ice-chips, then the mixture was washed with sodium bicarbonate and brine, was dried (sodium sulfate) and was evaporated. Purification by flash chromatography (SiO$_2$) eluted with 1:9 ethyl acetate:hexanes provided (2,4-dichloro-pyrimidin-5-yl)-phenyl-amine (0.20 g, 67% yield) as a yellow oil. $^1$H-NMR (500 MHz, CDCl$_3$) □ 8.33(s, 1H), 7.36 (t, 2H), 7.12 (m, 3H), 5.93 (s, 1H) ppm; MS (FIA) 335.9/337.9 (M+H); HPLC (method A) 3.554 min.

Preparation of 2-Chloro-N$^4$-(5-cyclopropyl-1H-pyrazol-3-yl)-N$^5$-phenyl-pyrimidine-4,5-diamine(2,4-Dichloro-pyrimidin-5-yl)-phenyl-amine (0.22 g, 0.93 mmol), 5-cyclopropyl-1H-pyrazol-3-ylamine (0.14 g, 1.02 mmol) and di-iso-propylethylamine(0.33 mL, 1.87 mmol) in ethanol (4 mL) were combined in a sealed tube and heated at 85° C. for 42 h. After cooling, solvent was evaporated and the residue was purified by flash chromatography (SiO2) eluted with 1:1 ethyl acetate:hexanes to provide (0.15 g, 49% yield, 77% yield based on recovered starting material) as a white solid. $^1$H-NMR (500 MHz, dmso-d$_6$)□ 10.2 (s, 1H), 9.26 (s, 1H), 8.07 (s, 1H), 7.53 (s, 1H), 7.23 (t, 2H), 6.90 (d, 2H), 6.84 (t, 1H), 6.39 (s, 1H), 1.92 (m, 1H), 0.94 (m, 2H), 0.70 (m, 2H) ppm; MS (FIA) 327.1 (M+H); HPLC (method A) 3.240 min.

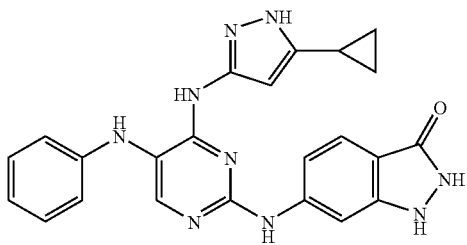

Preparation of 6-[4-(5-Cyclopropyl-2H-pyrazol-3-ylamino)-5-phenylamino-pyrimidin-2-ylamino]-1,2-dihydro-indazol-3-one.

Yellow solid (41.7% yield). H-NMR (DMSO-d6) δ 11.33 (br s, 1H), 10.28 (br s, 1H), 9.85 (br s, 1H), 7.90 (s, 1H), 7.64 (d, 1H), 7.57 (s, 1H), 7.32 (s, 1H), 7.20 (t, 2H), 7.09 (d, 1H), 6.79 (m, 4H), 6.16 (s, 1H), 1.73 (m, 1H), 0.82 (d, 2H), 0.46 (s, 2H). MS (ES+): m/e=440.3 (M+H), 438.3 (M–H); LC/Method A/3.426 min, 100% purity by area %.

Example 33

Preparation of 6-[4-(5-Cyclopropyl-2H-pyrazol-3-ylamino)-5-morpholin-4-yl-pyrimidin-2-ylamino]-1,2-dihydro-indazol-3-one Scheme XX:

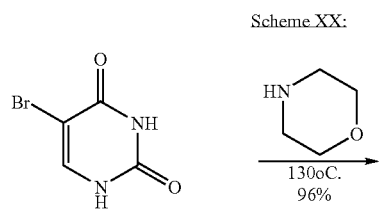

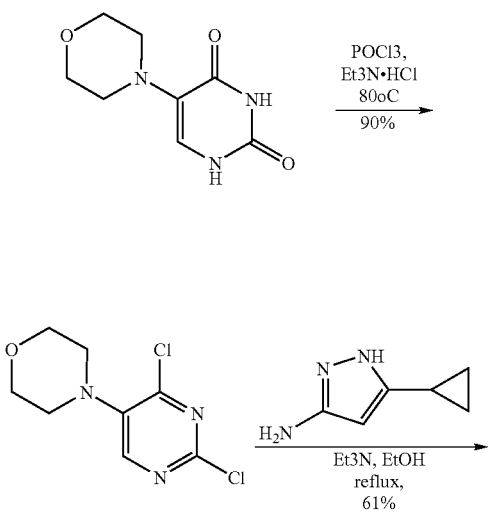

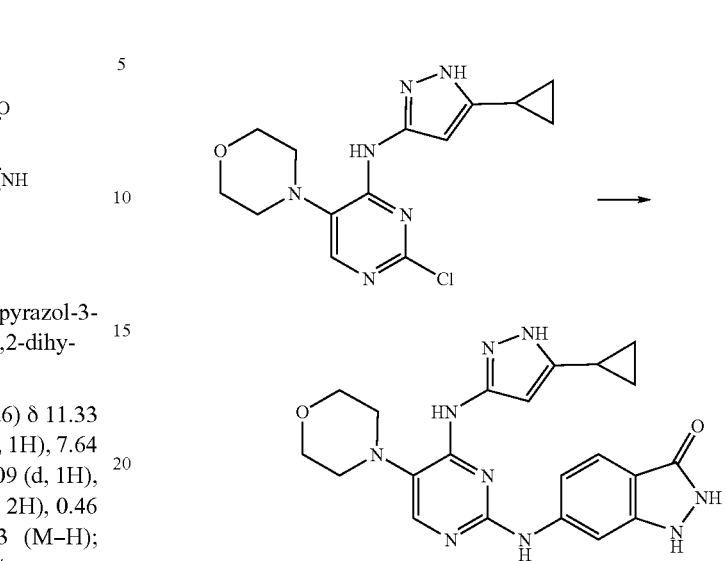

Preparation of (2-chloro-5-morpholino-4-yl-pyrimidin-4-yl)-(5-cyclopropyl-1H-pyrazol-3-yl)-amine Preparation of 5-morpholino-4-yl-1H-pyrimidine-2,4-dione To morpholine (4.80 mL, 55 mmol) stirring at 130° C. was added 5-bromo-uracil (3.02 g, 15.7 mmol). The mixture was stirred 15 min, then cooled. The solid was suspended in methanol and filtered, washing with methanol to provide 5-morpholino-4-yl-1H-pyrimidine-2,4-dione (2.98 g, 96% yield) as a white solid. $^1$H-NMR (500 MHz, dmso-d$_5$) δ 11.1 (s, 1H), 10.5 (s, 1H), 6.75 (s, 1H), 3.65 (m, 4H), 2.80 (m, 4H) ppm.

Preparation of 4-(2,4-dichloro-pyrimidin-5-yl)-morpholine

A mixture of 5-morpholino-4-yl-1H-pyrimidine-2,4-dione (2.98 g, 15.1 mmol) and triethylamine hydrochloride (6.24 g, 45.3 mmol) in phosphorous oxychloride (35 mL) was stirred at 80° C. for 4 d, then at reflux for 3 h. The solvent was evaporated, azeotroping with toluene. The residue was diluted with ethyl acetate, cooled to 0° C., carefully quenched with ice chips, washed with sodium bicarbonate and brine, dried (sodium sulfate) and evaporated. Purification by flash chromatography (SiO$_2$) eluted with 1:3 ethyl acetate:hexanes provided 4-(2,4-dichloro-pyrimidin-5-yl)-morpholine (3.18 g, 90% yield) as a white solid. $^1$H-NMR (500 MHz, CDCl$_3$) δ 8.25 (s, 1H), 3.90 (m, 4H), 3.20 (m, 4H) ppm; MS (FIA) 234.0/236.0 (M+H); HPLC (method A) 2.930 min.

Preparation of (2-chloro-5-morpholino-4-yl-pyrimidin-4-yl)-(5-cyclopropyl-1H-pyrazol-3-yl)-amine 4-(2,4-dichloro-pyrimidin-5-yl)-morpholine (0.75 g, 3.2 mmol), 5-cyclopropyl-1H-pyrazol-3-ylamine (0.47 g, 3.52 mmol) and triethylamine (0.90 mL, 6.41 mmol) in ethanol (10 mL) were refluxed for 4 d. After cooling, solvent was evaporated and the residue was purified by flash chromatography (SiO$_2$) eluted with 3:97 methanol:dichloromethane to provide 2-chloro-5-morpholino-4-yl-pyrimidin-4-yl)-(5-cyclopropyl-1H-pyrazol-3-yl)-amine(0.63 g, 61% yield).

$^1$H-NMR (500 MHz, dmso-d$_6$) δ 12.2 (s, 1H), 8.75 (s, 1H), 8.05 (s, 1H), 6.25 (s, 1H), 3.80 (m, 4H), 2.85 (m, 4H), 1.90 (m, 1H), 0.95 (m, 2H), 0.70 (m, 2H) ppm; MS (FIA) 321.1 (M+H), 319.2 (M–H); HPLC (method A) 2.888 min.

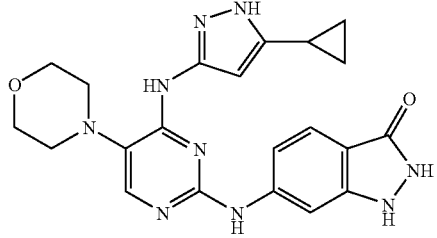

Preparation of 6-[4-(5-Cyclopropyl-2H-pyrazol-3-ylamino)-5-morpholin-4-yl-pyrimidin-2-ylamino]-1,2-dihydro-indazol-3-one Off-white solid (23.8% yield). H-NMR (DMSO-d6) δ 11.36 (s br, 1H), 10.48 (s, 1H), 9.64 (s, 1H), 7.93 (s, 1H), 7.62 (d, 1H), 7.46 (s, 1H), 7.08 (d, 1H), 6.09 (s, 1H), 3.80 (m, 4H), 2.83 (m, 4H), 1.78 (m, 1H), 0.85 (m, 2H), 0.45 (m, 2H). MS (ES+): m/e=434.3 (M+H), 432.3 (M−H); LC/Method A/3.135 min, 100% purity by area %.

Example 34

Preparation of 6-[6-(5-Cyclopropyl-2H-pyrazol-3-ylamino)-5-nitro-pyridin-2-ylamino]-1,2-dihydro-indazol-3-one Scheme XXI:

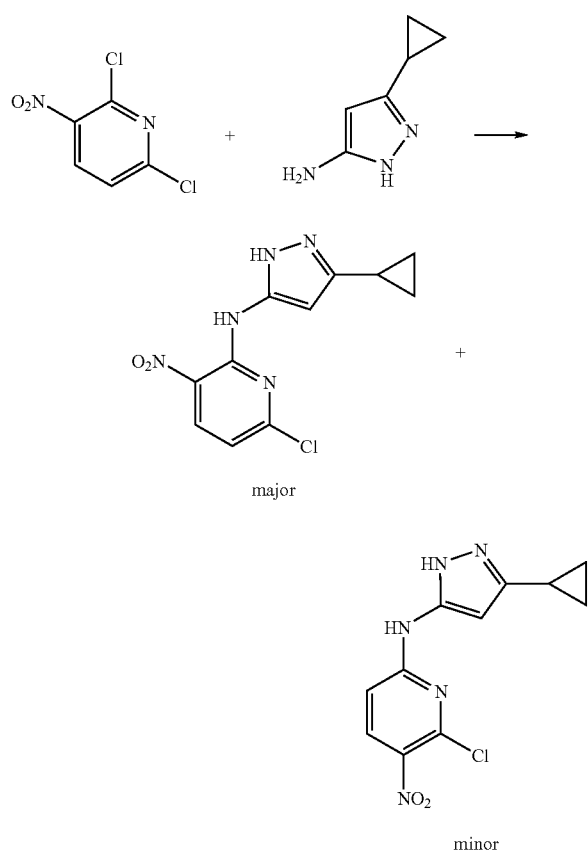

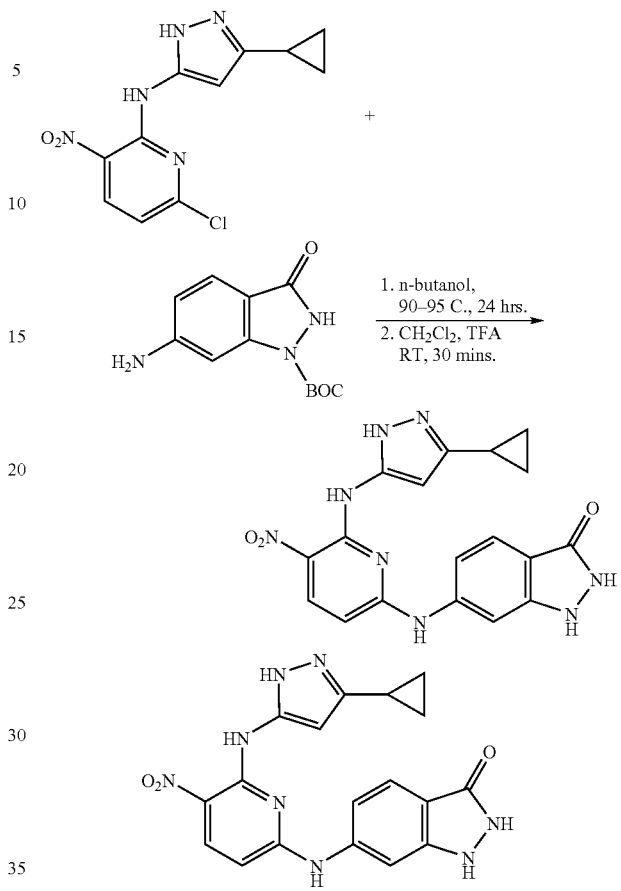

Step 1: (6-Chloro-3-nitro-pyridin-2-yl)-(5-cyclopropyl-2H-pyrazol-3-yl)-amine

A solution of 5-cyclopropyl-2H-pyrazol-3-ylamine (638 mg, 5.18 mmol) in 6 ml of acetonitrile was added dropwise over 10 minutes to a cooled (0 C) mixture of 2,6-dichloro-3-nitro-pyridine (1.0 g, 5.18 mmol) and potassium carbonate (860 mg, 6.22 mmol) in 20 ml of acetonitrile. After the addition, the reaction was warmed to room temperature and stirred for 18 hours. The reaction was filtered and the filtrate evaporated in vacuo to afford a brown residue which was purified by flash chromatography (SiO2) eluting with ethyl acetate-hexane (1:7) 257 mg (17.7% yield) of the desired product (major regioisomer). HPLC Rt 6.09, mins. MS: m/z 280.0 (M+1) 278.1 (M−1).

Step 2: 6-[6-(5-Cyclopropyl-2H-pyrazol-3-ylamino)-5-nitro-pyridin-2-ylamino]-1,2-dihydro-indazol-3-one was prepared by the reaction of (6-Chloro-3-nitro-pyridin-2-yl)-(5-cyclopropyl-2H-pyrazol-3-yl)-amine and 6-Amino-3-oxo-2,3-dihydro-indazole-1-carboxylic acid tert-butyl ester in a similar manner as described above to afford 17 mg of the desired product as a bright yellow solid (16.2% yield). H-NMR (CD$_3$OD) δ 8.32(d, 1H), 7.68(d, 1H), 7.65(s, 1H), 7.17(d, 1H), 6.38(d, 1H), 6.24(s, 1H), 1.79(m, 1H), 0.84(m, 2H), 0.48(m, 2H). MS (ES+): m/e=393.2 (M+H), 391.2 (M−H); LC/Method A/4.149 min, 100% purity by area %.

Example 34

Preparation of 6-[6-(5-Cyclopropyl-2H-pyrazol-3-ylamino)-3-nitro-pyridin-2-ylamino]-1,2-dihydro-indazol-3-one

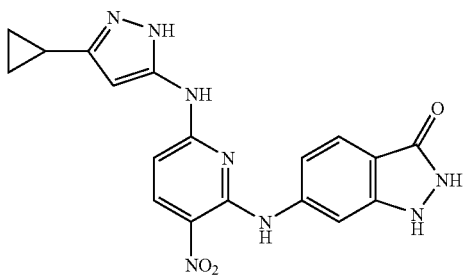

6-[6-(5-Cyclopropyl-2H-pyrazol-3-ylamino)-3-nitro-pyridin-2-ylamino]-1,2-dihydro-indazol-3-one was prepared in a similar manner to afford a bright yellow solid (5.3% yield). H-NMR (DMSO-d6) δ 12.36(s br, 1H), 10.46(s, 1H), 8.63(d, J=9.15 Hz, 1H), 7,19(d, 1H), 6.78(s br, 1H), 6.72(d, J=9.15 Hz, 1H), 6.58 (d, 1H), 5.07(s, 1H), 2.89(t, 1H), 1.56(m, 1H), 0.82(m, 2H), 0.32(m, 2H). MS (ES+): m/e=393.2 (M+H), 391.1 (M−H); LC/Method A/4.336 min, 100% purity by area %.

Example 35

Preparation of 6-[5-Amino-6-(5-cyclopropyl-2H-pyrazol-3-ylamino)-pyridin-2-ylamino]-1,2-dihydro-indazol-3-one

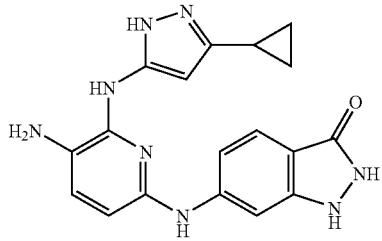

6-[5-Amino-6-(5-cyclopropyl-2H-pyrazol-3-ylamino)-pyridin-2-ylamino]-1,2-dihydro-indazol-3-one was prepared by the catalytic hydrogenolysis (Pd/C, Hydrogen, 1 atm) of 6-[6-(5-Cyclopropyl-2H-pyrazol-3-ylamino)-5-nitro-pyridin-2-ylamino]-1,2-dihydro-indazol-3-one to afford the desired product as a yellow solid. H-NMR(DMSO-d6) δ 9.16 (s, 1H) 9.03 (s br, 1H), 7.47 (d, J=8.2 Hz, 1H), 7.36 (m, 1H), 7.30 (s, 1H), 7.02 (d, J=8.2 Hz, 1H), 6.57(d, J=8.3 Hz, 1H), 6.41 (d, J=8.2 Hz, 1H), 6.03 (s, 1H), 1.85 (m, 1H), 0.88 (m, 2H), 0.62 (m, 2H). MS (ES+): m/e=363.2 (M+H), 361.5 (M−H); LC/Method A/3.014 min, 96.0% purity by area %.

Example 36

Preparation of 6-[4-(5-Cyclopropyl-2H-pyrazol-3-ylamino)-5-nitro-pyrimidin-2-ylamino]-1,2-dihydro-indazol-3-one

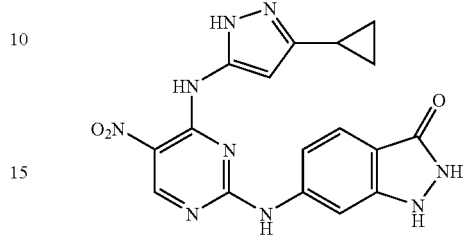

Bright yellow solid (13.3% yield). H-NMR (DMSO-d6, 500 MHz) δ 12.42(s, 1H), 11.23(s br, 1H), 10.61(s br, 1H), 10.45(s br, 1H), 9.11(s, 1H), 7.58(d, 2H), 7.23(d, 1H), 6.12(s, 1H), 1.75(m, 1H), 0.80(m, 2H), 0.40(m, 2H). MS (ES+): m/e=394.2 (M+H), 392.1 (M−H); LC/Method A/4.018 min, 100% purity by area %.

The following two compounds were prepared in a similar manner as the compounds described directly above.

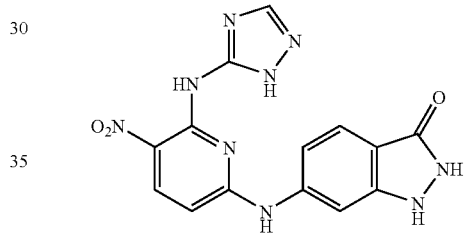

Preparation of 6-[5-Nitro-6-(2H-[1,2,4]triazol-3-ylamino)-pyridin-2-ylamino]-1,2-dihydro-indazol-3-one
Light yellow solid (28.8% yield). H-NMR(DMSO-d6, 500 mHz) δ 12.54(s, 1H), 8.52(d, 1H), 8.23(s, 1H), 7.42(d, 1H), 7.23(d, 1H), 6.98(s, 1H), 6.76(d, 1H). MS (ES+): m/e=354.1 (M+H), 352.1 (M−H); LC/Method A/3.118 min. 98% purity by area %.

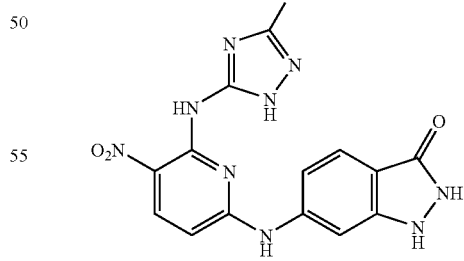

Preparation of 6-[6-(5-Methylsulfanyl-2H-[1,2,4]triazol-3-ylamino)-5-nitro-pyridin-2-ylamino]-1,2-dihydro-indazol-3-one Light yellow solid (28.0% yield). H-NMR (DMSO-d6, 500 mHz) δ 12.46(s, 1H), 8.56(d, 1H), 7.38(d, 1H), 7.28(d, 1H), 6.98(s, 2H), 6.84(s, 1H), 6.69(d, 1H), 2.35(s, 3H). MS (ES+): m/e=400.1 (M+H), 398.0 (M−H); LC/Method A/4.343 min, 100% purity by area %.

II. Biological Activity:

Example 1

$K_i$ Determination for the Inhibition of GSK-3

Compounds were screened for their ability to inhibit GSK-3β (AA 1-420) activity using a standard coupled enzyme system (Fox et al. (1998) *Protein Sci.* 7, 2249). Reactions were carried out in a solution containing 100 mM HEPES (pH 7.5), 10 mM MgCl$_2$, 25 mM NaCl, 300 μM NADH, 1 mM DTT and 1.5% DMSO. Final substrate concentrations in the assay were 20 μM ATP (Sigma Chemicals, St Louis, Mo.) and 300 μM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of interest. The assay stock buffer solution (175 μl) was incubated in a 96 well plate with 5 μl of the test compound of interest at final concentrations spanning 0.002 μM to 30 μM at 30° C. for 10 min. Typically, a 12 point titration was conducted by preparing serial dilutions (from 10 mM compound stocks) with DMSO of the test compounds in daughter plates. The reaction was initiated by the addition of 20 μl of ATP (final concentration 20 μM). Rates of reaction were obtained using a Molecular Devices Spectramax plate reader (Sunnyvale, Calif.) over 10 min at 30° C. The $K_i$ values were determined from the rate data as a function of inhibitor concentration.

Compounds of the invention were found to inhibit GSK-3. In certain embodiments, compounds were shown to have $K_i$ values less than 0.1 μM for GSK-3.

Example 2

$K_i$ Determination for the Inhibition of Aurora-2

Compounds were screened in the following manner for their ability to inhibit Aurora-2 using a standard coupled enzyme assay (Fox et al (1998) *Protein Sci* 7, 2249).

To an assay stock buffer solution containing 0.1M HEPES 7.5, 10 mM MgCl$_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 μM peptide (American Peptide, Sunnyvale, Calif.) was added a DMSO solution of a compound of the present invention to a final concentration of 30 μM. The resulting mixture was incubated at 30° C. for 10 min. The reaction was initiated by the addition of 10 μL of Aurora-2 stock solution to give a final concentration of 70 nM in the assay. The rates of reaction were obtained by monitoring absorbance at 340 nm over a 5 minute read time at 30° C. using a BioRad ultramark plate reader (Hercules, Calif.). The $K_i$ values were determined from the rate data as a function of inhibitor concentration.

Compounds of the invention were found to inhibit Aurora-2 In certain embodiments, compounds were shown to have $K_i$ values less than 0.1 μM for Aurora-2.

Example 3

CDK-2 Inhibition Assay

Compounds were screened in the following manner for their ability to inhibit CDK-2 using a standard coupled enzyme assay (Fox et al (1998) *Protein Sci* 7, 2249).

To an assay stock buffer solution containing 0.1M HEPES 7.5, 10 mM MgCl$_2$, 1 mM DTT, 25 mM NaCl, 2.5 mM phosphoenolpyruvate, 300 mM NADH, 30 mg/ml pyruvate kinase, 10 mg/ml lactate dehydrogenase, 100 mM ATP, and 100 μM peptide (American Peptide, Sunnyvale, Calif.) was added a DMSO solution of a compound of the present invention to a final concentration of 30 μM. The resulting mixture was incubated at 30° C. for 10 min.

The reaction was initiated by the addition of 10 μL of CDK-2/Cyclin A stock solution to give a final concentration of 25 nM in the assay. The rates of reaction were obtained by monitoring absorbance at 340 nm over a 5-minute read time at 30° C. using a BioRad Ultramark plate reader (Hercules, Calif.). The $K_i$ values were determined from the rate data as a function of inhibitor concentration.

Compounds of the invention were found to inhibit CDK-2. In certain embodiments, compounds were shown to have $K_i$ values less than 1.0 μM for CDK-2.

Example 4

ERK Inhibition Assay

Compounds were assayed for the inhibition of ERK2 by a spectrophotometric coupled-enzyme assay (Fox et al (1998) *Protein Sci* 7, 2249). In this assay, a fixed concentration of activated ERK2 (10 nM) was incubated with various concentrations of the compound in DMSO (2.5%) for 10 min. at 30° C. in 0.1 M HEPES buffer, pH 7.5, containing 10 mM MgCl$_2$, 2.5 mM phosphoenolpyruvate, 200 μM NADH, 150 μg/mL pyruvate kinase, 50 μg/mL lactate dehydrogenase, and 200 μM erktide peptide. The reaction was initiated by the addition of 65 μM ATP. The rate of decrease of absorbance at 340 nM was monitored.

Compounds of the invention were found to inhibit ERK2. In certain embodiments, compounds were shown to have $K_i$ values less than 1.0 μM for ERK2.

Example 5

PRAK Inhibition Assay

Compounds were screened for their ability to inhibit PRAK activity using a standard coupled enzyme system (Fox et al. (1998) *Protein Sci.* 7, 2249). Reactions were carried out in a solution containing 100 mM HEPES (pH 7.5), 10 mM MgCl$_2$, 25 mM NaCl, 300 μM NADH, 1 mM DTT and 1.5% DMSO. Final substrate concentrations in the assay were 12.5 μM ATP (Sigma Chemicals, St Louis, Mo.) and 300 μM peptide (American Peptide, Sunnyvale, Calif.). Reactions were carried out at 30° C. and 120 nM PRAK. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of interest. The assay stock buffer solution (175 μl) was incubated in a 96 well plate with 5 μl of the test compound of interest at final concentrations spanning 0.014 µM to 30 µM at 30° C. for 10 min. Typically, a 12 point titration was conducted by preparing serial dilutions (from 10 mM compound stocks) with DMSO of the test compounds in daughter plates. The reaction was initiated by the addition of 20 µl of ATP (final concentration 12.5 µM). Rates of reaction were obtained using a Molecular Devices Spectramax plate reader (Sunnyvale, Calif.) over 10 min at 30° C. The $K_i$ values were determined from the rate data as a function of inhibitor concentration.

Compounds of the invention were found to inhibit PRAK. In certain embodiments, compounds were shown to have $K_i$ values less than 1.0 µM for PRAK.

Example 6

SRC Inhibition Assay

The compounds are evaluated as inhibitors of human Src kinase using either a radioactivity-based assay or spectrophotometric assay.

Src Inhibition Assay A: Radioactivity-based Assay

The compounds are assayed as inhibitors of full length recombinant human Src kinase (from Upstate Biotechnology, cat. no. 14–117) expressed and purified from baculo viral cells. Src kinase activity is monitored by following the incorporation of $^{33}P$ from ATP into the tyrosine of a random poly Glu-Tyr polymer substrate of composition, Glu:Tyr=4:1 (Sigma, cat. no. P-0275). The following are the final concentrations of the assay components: 0.05 M HEPES, pH 7.6, 10 mM $MgCl_2$, 2 mM DTT, 0.25 mg/ml BSA, 10 µM ATP (1–2 µCi $^{33}P$-ATP per reaction), 5 mg/ml poly Glu-Tyr, and 1–2 units of recombinant human Src kinase. In a typical assay, all the reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with $^{33}P$-ATP. After 20 min of reaction, the reactions are quenched with 150 µl of 10% trichloroacetic acid (TCA) containing 20 mM $Na_3PO_4$. The quenched samples are then transferred to a 96-well filter plate (Whatman, UNI-Filter GF/F Glass Fiber Filter, cat no. 7700–3310) installed on a filter plate vacuum manifold. Filter plates are washed four times with 10% TCA containing 20 mM $Na_3PO_4$ and then 4 times with methanol. 200 µl of scintillation fluid is then added to each well. The plates were sealed and the amount of radioactivity associated with the filters is quantified on a TopCount scintillation counter. The radioactivity incorporated is plotted as a function of the inhibitor concentration. The data is fitted to a competitive inhibition kinetics model to get the $K_i$ for the compound.

Src Inhibition Assay B: Spectrophotometric Assay

The ADP produced from ATP by the human recombinant Src kinase-catalyzed phosphorylation of poly Glu-Tyr substrate is quantified using a coupled enzyme assay (Fox et al (1998) *Protein Sci* 7, 2249). In this assay one molecule of NADH is oxidised to NAD for every molecule of ADP produced in the kinase reaction. The disappearance of NADH is conveniently followed at 340 nm.

The following are the final concentrations of the assay components: 0.025 M HEPES, pH 7.6, 10 mM $MgCl_2$, 2 mM DTT, 0.25 mg/ml poly Glu-Tyr, and 25 nM of recombinant human Src kinase. Final concentrations of the components of the coupled enzyme system are 2.5 mM phosphoenolpyruvate, 200 µM NADH, 30 µg/ml pyruvate kinase and 10 µg/ml lactate dehydrogenase.

In a typical assay, all the reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with 100 µM ATP. The absorbance change at 340 nm with time, the rate of the reaction, is monitored on a molecular devices plate reader. The data of rate as a function of the inhibitor concentration is fitted to competitive inhibition kinetics model to get the $K_i$ for the compound.

Compounds of the invention were found to inhibit SRC. In certain embodiments, compounds were shown to have $K_i$ values less than 1.0 µM for SRC.

Example 7

SYK Inhibition Assay

Compounds were screened for their ability to inhibit Syk using a standard coupled enzyme assay (Fox et al (1998) *Protein Sci* 7, 2249). Reactions were carried out in 100 mM HEPES pH 7.5, 10 mM MgCl2, 25 mM NaCl, 1 mM DTT and 1.5% DMSO. Final substrate concentrations in the assay were 200 µM ATP (Sigma chemical Co.) and 4 µM poly Gly-Tyr peptide (Sigma Chemical Co.). Assays were carried out at 30° C. and 200 nM Syk. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of Syk, DTT and the test compound of interest. 56 µl of the test reaction was placed in a 96 well plate followed by the addition of 1 µl of 2 mM DMSO stock containing the test compound (final compound concentration 30 µM). The plate was pre-incubated for ~10 minutes at 30° C. and the reaction initiated by the addition of 10 µl of enzyme (final concentration 25 nM). Rates of reaction were obtained using a BioRad Ultramark plate reader (Hercules, Calif.) over a 5 minute read time at 30° C.

Compounds of the invention were found to inhibit SYK. In certain embodiments, compounds were shown to have $K_i$ values less than 1.0 µM for SYK.

Example 8

MK2 Inhibition Assay: $K_i$ Determination for the Inhibition of MK2

Compounds were screened for their ability to inhibit MK2 activity using a standard coupled enzyme system (Fox et al. (1998) *Protein Sci.* 7, 2249). Reactions were carried out in a solution containing 100 mM HEPES (pH 7.5), 10 mM $MgCl_2$, 25 mM NaCl, 300 µM NADH, 1 mM DTT and 1.5% DMSO. Final substrate concentrations in the assay were 30 µM ATP (Sigma Chemicals, St Louis, Mo.) and 300 µM peptide (American Peptide, Sunnyvale, Calif.). Reactions were carried out at 30° C. and 30 nM MK2. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and the test compound of interest. The assay stock buffer solution (175 µl) was incubated in a 96 well plate with 5 µl of the test compound of interest at final concentrations spanning 0.014 µM to 30 µM at 30° C. for 10 min. Typically, a 12 point titration was conducted by preparing serial dilutions (from 10 mM compound stocks) with DMSO of the test compounds in daughter plates. The reaction was initiated by the addition of 20 μl of ATP (final concentration 30 μM). Rates of reaction were obtained using a Molecular Devices Spectramax plate reader (Sunnyvale, Calif.) over 10 min at 30° C. The $K_i$ values were determined from the rate data as a function of inhibitor concentration.

Compounds of the invention were found to inhibit MK2. In certain embodiments, compounds were shown to have $K_i$ values less than 1.0 μM for MK2.

-continued
IV-63
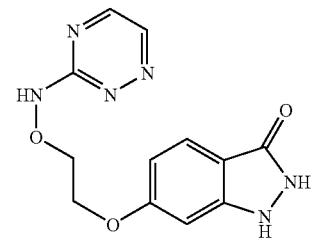
IV-64
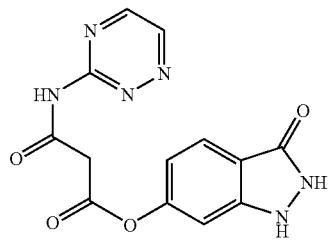
IV-65
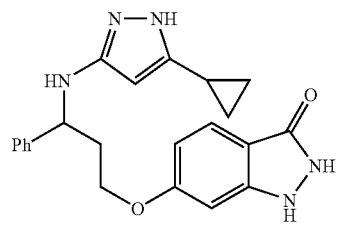
IV-66
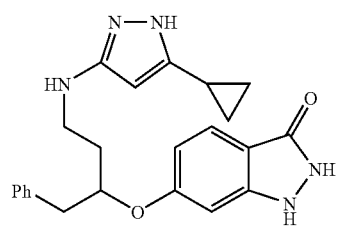
IV-67
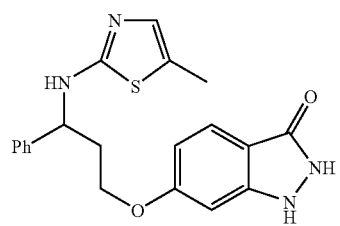
IV-68
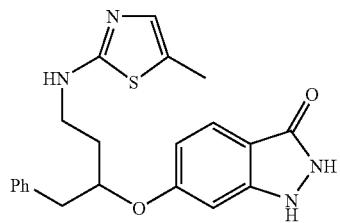
IV-69
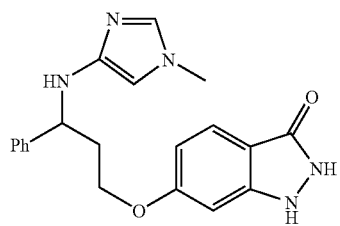
-continued
IV-70
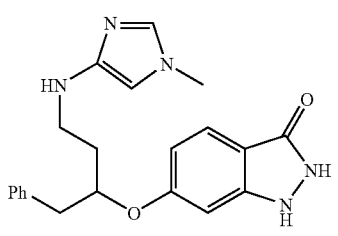
IV-71
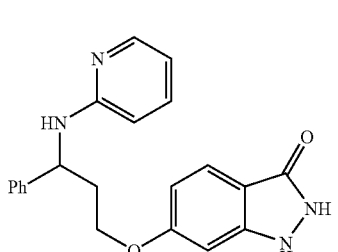
IV-72
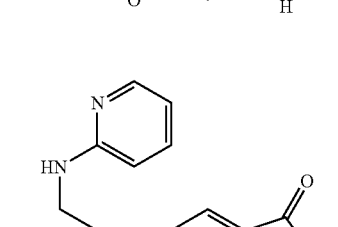
IV-73
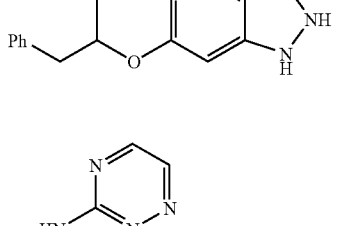
IV-74
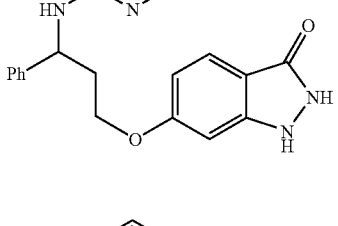
IV-75
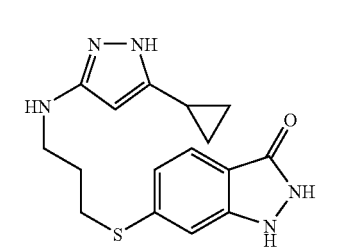

IV-76
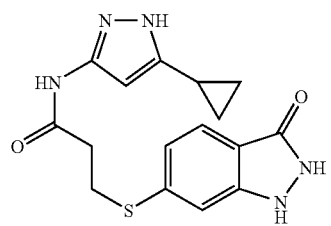
IV-77
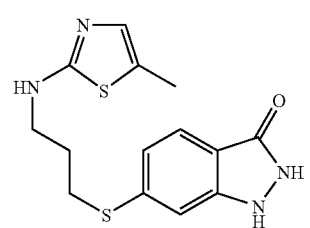
IV-78
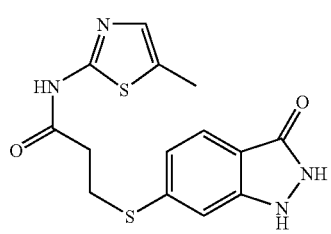
IV-79
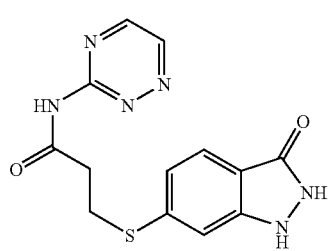
IV-80
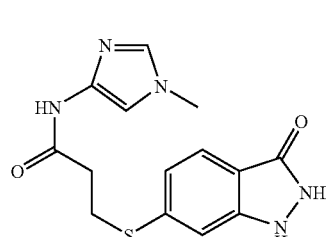
IV-81
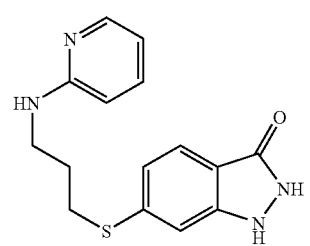
IV-82
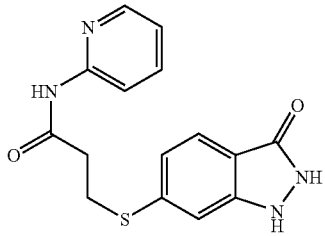
IV-83
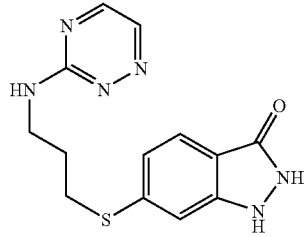
IV-84
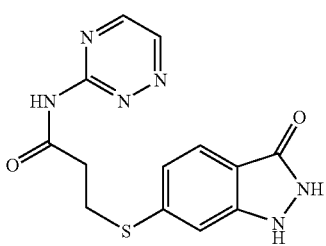
IV-85
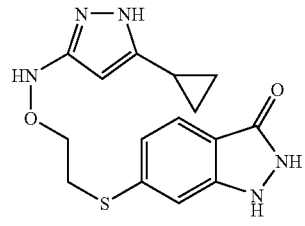
IV-86
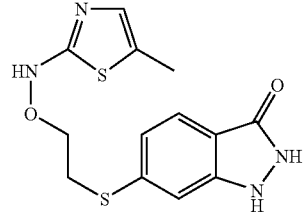
IV-87
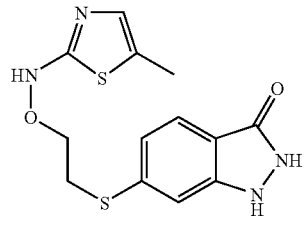

IV-88
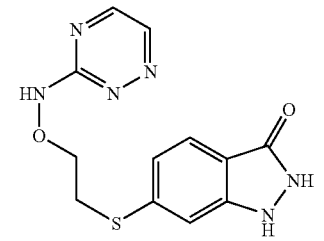
IV-89
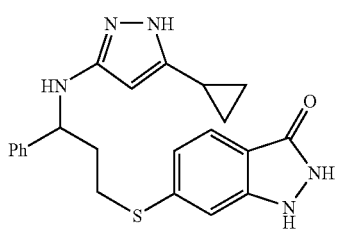
IV-90
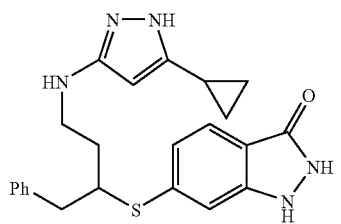
IV-91
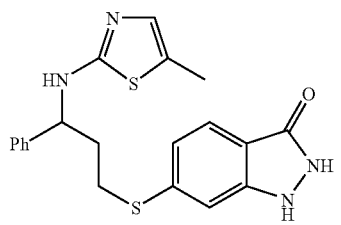
IV-92
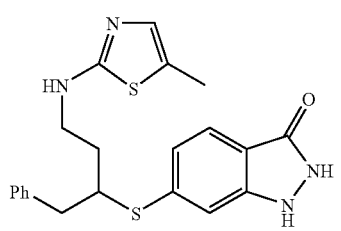
IV-93
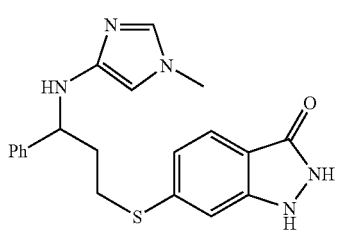
IV-94
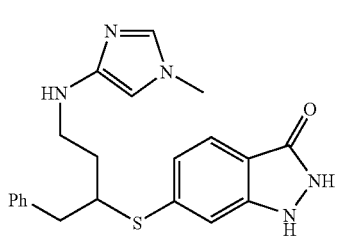
IV-95
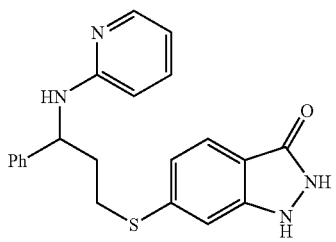
IV-96
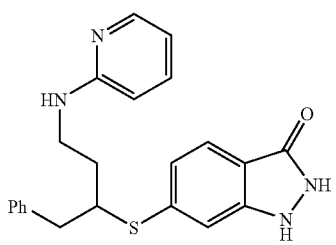
IV-97
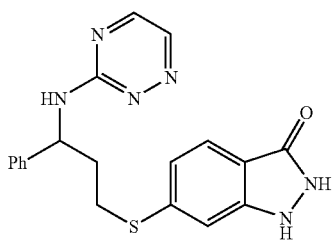
IV-98
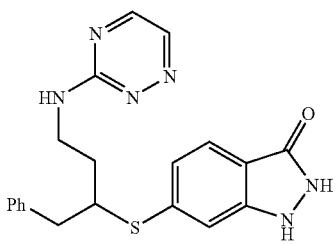
IV-99
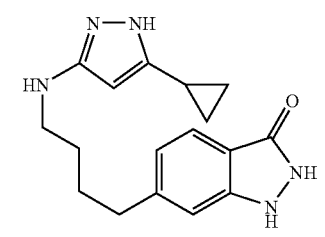
IV-100
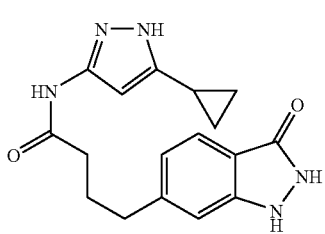

IV-101
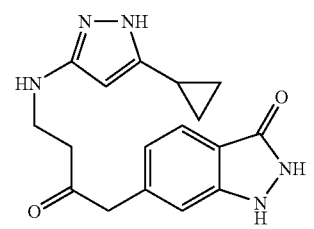
IV-102
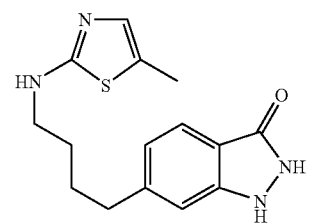
IV-103
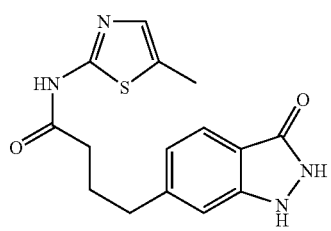
IV-104
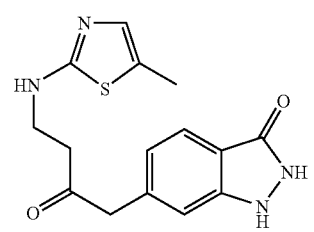
IV-105
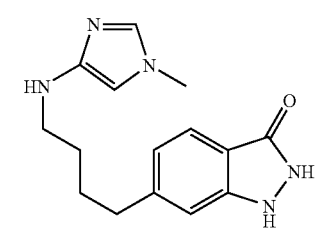
IV-106
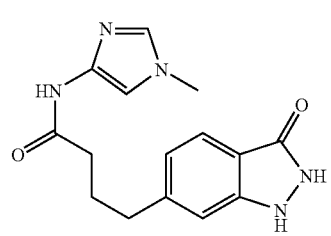
IV-107
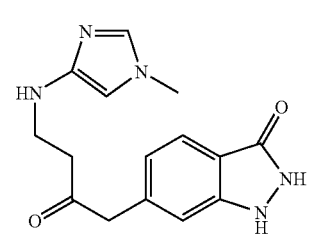
IV-108
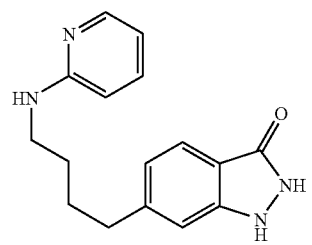
IV-109
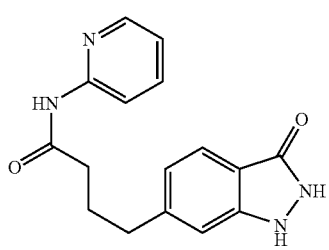
IV-110
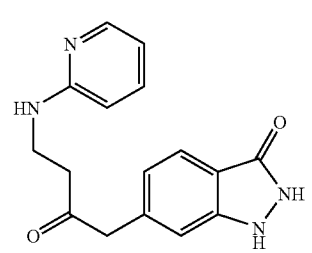
IV-111
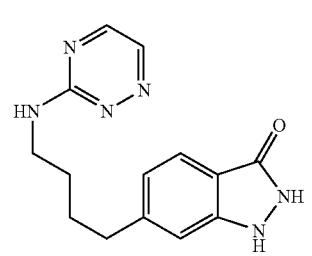
IV-112
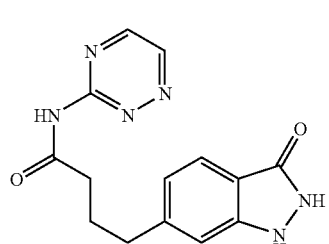
IV-113
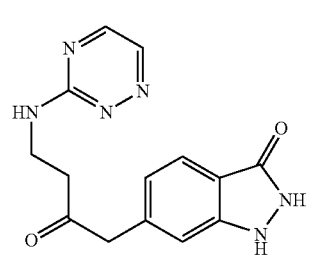

-continued
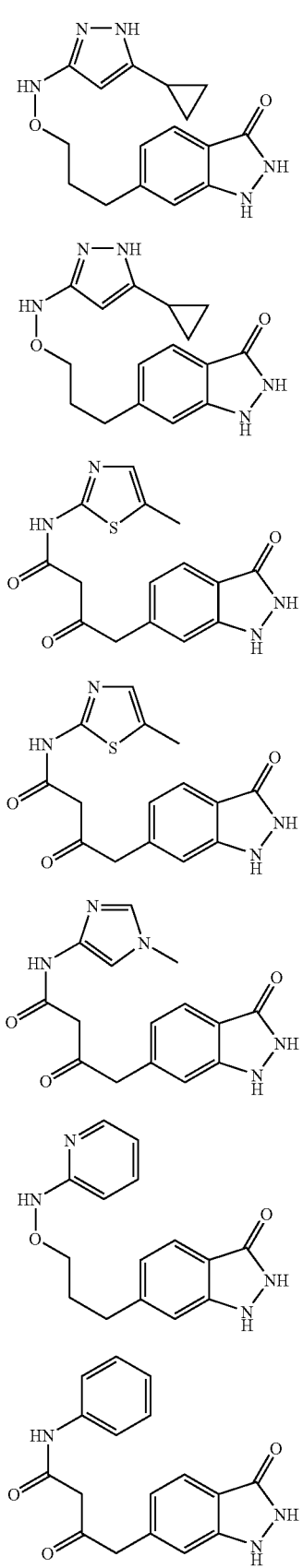
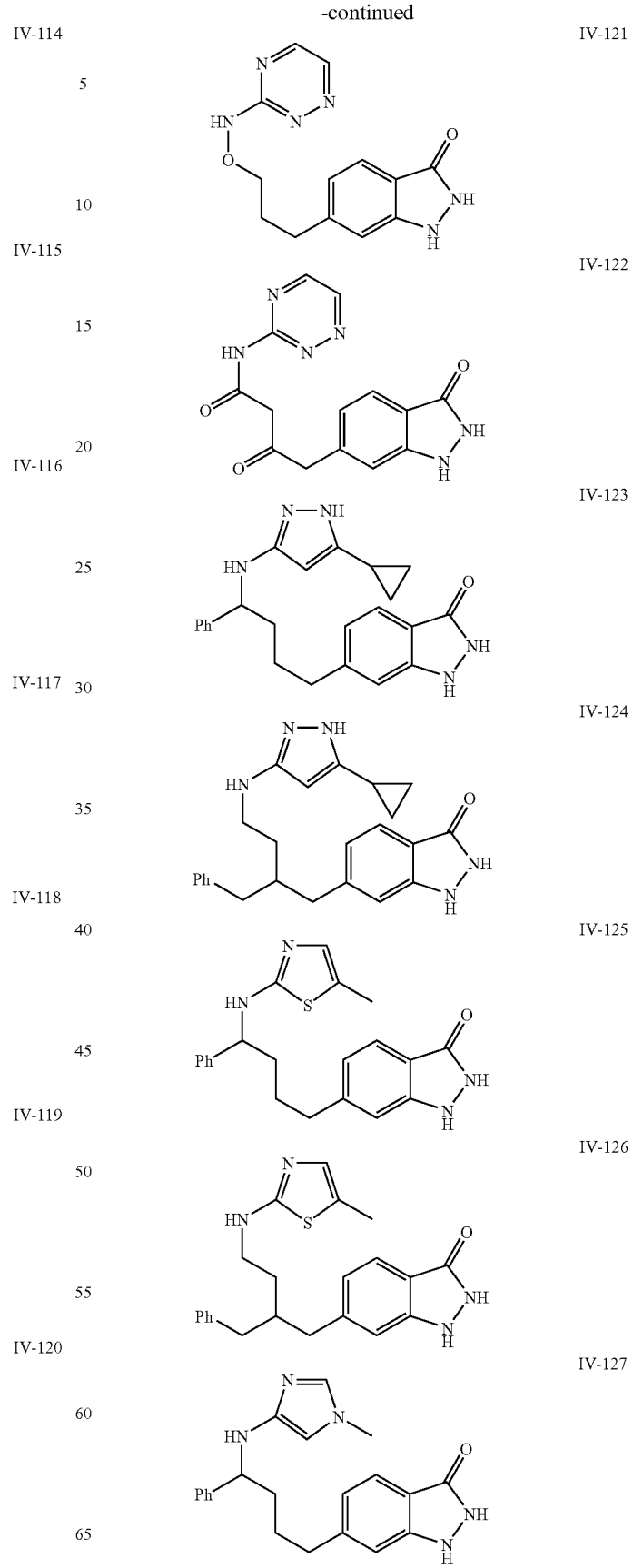

-continued
IV-128
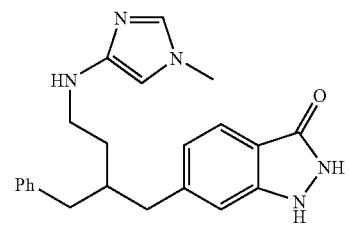
IV-129
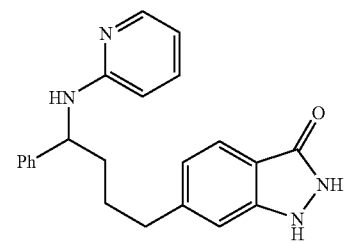
IV-130
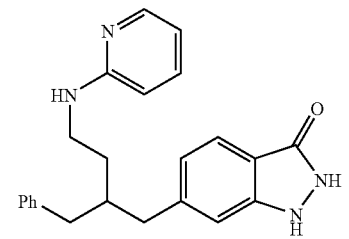
IV-131
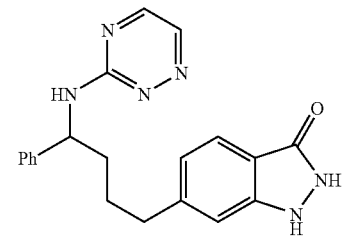
IV-132
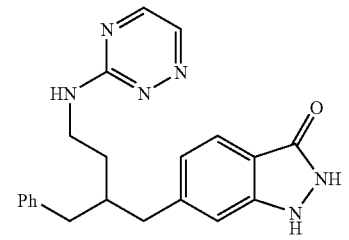
IV-133
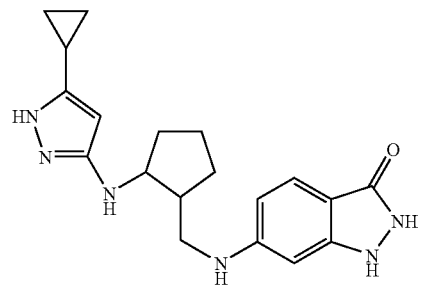
-continued
IV-134
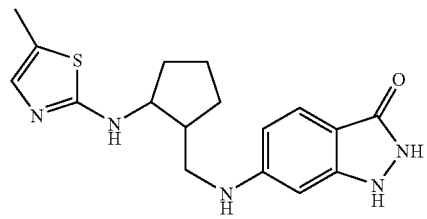
IV-135
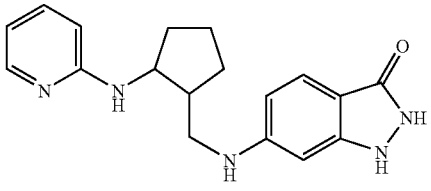
IV-136
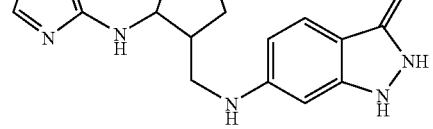
IV-137
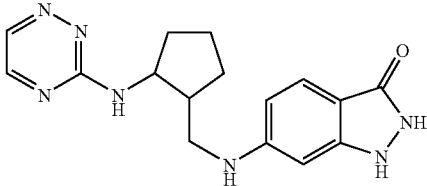
IV-138
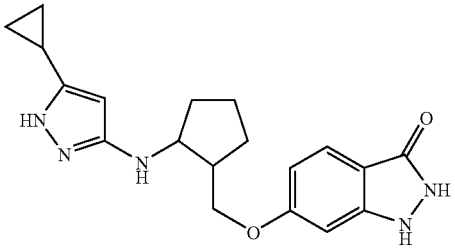
IV-139
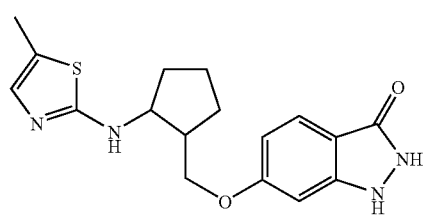
IV-140
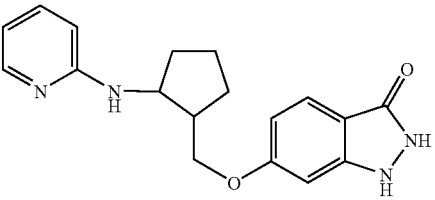

-continued
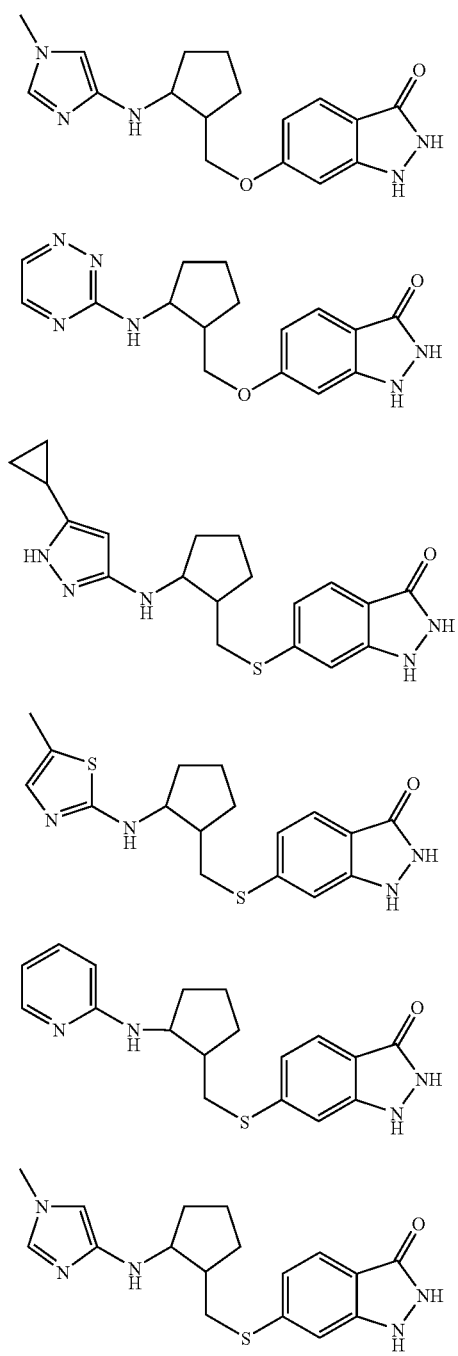
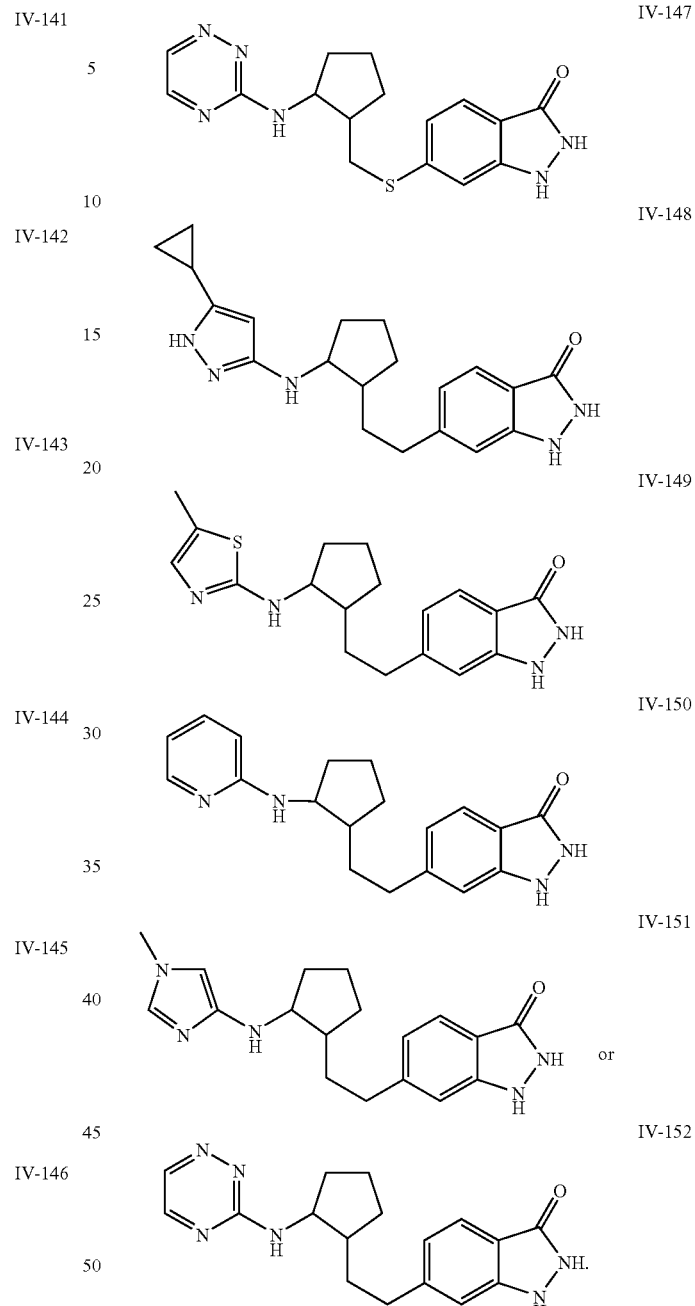

The invention claimed is:
1. A compound of formula I:

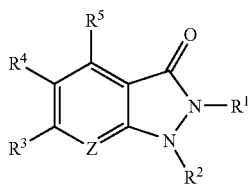

I or a pharmaceutically acceptable salt thereof, wherein:
$R^1$ and $R^2$ are each independently hydrogen or a nitrogen protecting group;
one of $R^3$ or $R^4$ is —R and the other one of $R^3$ or $R^4$ is —$Q^1$—A—$Q^2$—Y,
wherein $Q^1$ is a valence bond, —$NR^A$—, —$C(R^A)_2$—, —S—, —O—, —$SO_2$— or —CO—, wherein each occurrence of $R^A$ is independently hydrogen or optionally substituted $C_{1-4}$aliphatic, or two occurrences of $R^A$ on the same carbon atom are taken together to form an optionally substituted 3–6-membered carbocyclic ring;
A is an optionally substituted group selected from a 5–7-membered monocyclic or 8–10-membered bicyclic aryl, heteroaryl, heterocyclic or carbocyclic ring;
$Q^2$ is $NR^C$, S, O, or $C(R^C)_2$, wherein each occurrence of $R^C$ is independently hydrogen or optionally substituted $C_{1-4}$aliphatic;
Y is an optionally substituted group selected from a 5–7-membered monocyclic or 8–10 membered bicyclic aryl, heteroaryl, heterocyclic or carbocyclic ring;
$R^5$ is —R;
Z is $CR^6$, wherein $R^6$ is —R; and
each occurrence of —R is independently hydrogen, $Q_{(n)}$ halogen, $Q_{(n)}$CN, $Q_{(n)}NO_2$, or $Q_{(n)}R^7$, wherein n is zero or one, Q is an optionally substituted $C_{1-4}$alkylidene chain wherein one or more methylene units of Q is optionally replaced by —O—, —S—, —$NR^7$—, —$NR^7$CO—, —$NR^7$CONR$^7$—, —$NR^7CO_2$—, —CO—, —$CO_2$—, —$CONR^7$—, —OC(O)NR$^7$—, —$SO_2$—, —$SO_2NR^7$—, —$NR^7SO_2$—, —$NR^7SO_2NR^7$—, —C(O)C(O)—, or —C(O)C($R^7$)$_2$C(O)—, and each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8-membered heterocyclic or 5–8-membered heteroaryl ring;
wherein one or more optional substituents on the unsaturated carbon atom of an aryl or heteroaryl group are independently selected from halogen —$R^°$; —$OR^°$; —$SR^°$; 1,2-methylenedioxy; 1,2-ethylenedioxy, phenyl (Ph) optionally substituted with $R^°$; —O(Ph) optionally substituted with $R^°$; —$(CH_2)_{1-2}$(Ph), optionally substituted with $R^°$; —CH=CH(Ph), optionally substituted with $R^°$; —$NO_2$; —CN; —N($R^°$)$_2$; —NR°C(O)R°; —NR°C(S)R°; —NR°C(O)N($R^°$)$_2$; —NR°C(S)N($R^°$)$_2$; —NR°CO$_2$R°; —NR°NR°C(O)R°; —NR°NR°C(O)N($R^°$)$_2$; —NR°NR°CO$_2$R°; —C(O)C(O)R°; —C(O)CH$_2$C(O)R°; —CO$_2$R°; —C(O)R°; —C(S)R°; —C(O)N($R^°$)$_2$; —C(S)N($R^°$)$_2$; —OC(O)N($R^°$)$_2$; —OC(O)R°; —C(O)N(OR°) R°; —C(NOR°)R°; —S(O)$_2$R°; —S(O)$_3$R°; —SO$_2$N($R^°$)$_2$; —S(O)R°; —NR°SO$_2$N($R^°$)$_2$, —NR°SO$_2$R°; —N(OR°)R°; —C(=NH)—N($R^°$)$_2$; or —(CH$_2$)$_{0-2}$NHC(O)R°, wherein each independent occurrence of R° is selected from hydrogen optionally substituted $C_{1-6}$aliphatic, an unsubstituted 5–6 membered heteroaryl or heterocyclic ring, phenyl, —O(Ph), or —CH$_2$(Ph), or, two independent occurrences of R°, on the same substituent or different substituents, taken together with the atom(s) to which each R°group is bound, optionally form a 5–8-membered heterocyclyl, aryl, or heteroaryl ring or a 3–8-membered cycloalkyl ring having 0–3 heteroatoms independently selected from nitrogen, oxygen, or sulfur, wherein one or more optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$aliphatic), or haloC$_{1-4}$aliphatic, wherein each of the foregoing C$_{1-4}$aliphatic groups of R° is unsubstituted;
wherein one or more optional substituents on an aliphatic or heteroaliphatic group, or on a non-aromatic heterocyclic ring are independently selected from halogen; —R°; —OR°; —SR°; 1,2-methylenedioxy; 1,2-ethylenedioxy; phenyl (Ph) optionally substituted with R°; —O(Ph) optionally substituted with R°; —CH=CH (Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; or —(CH$_2$)$_{0-2}$NHC(O)R°, =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic, wherein one or more optional substituents on the aliphatic group of R* are selected from NH$_2$, NH(C$_{1-4}$aliphatic), N(C$_{1-4}$aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$aliphatic), or halo(C$_{1-4}$aliphatic), wherein each of the foregoing C$_{1-4}$aliphatic groups of R* is unsubstituted;
wherein one or more optional substituents on a nitrogen of a non-aromatic heterocyclic ring are independently selected from —R+, —N(R+)$_2$, —C(O)R+, —CO$_2$R+, —C(O)C(O)R+, —C(O)CH$_2$C(O)R+, —SO$_2$R+, —SO$_2$N(R+)$_2$, —C(=S)N(R+)$_2$, —C(=NH)—N(R+)$_2$, or —NR+SO$_2$R+; wherein R+ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH (Ph); or an unsubstituted 5–6 membered heteroaryl or heterocyclic ring having one to four heteroatoms independently selected from oxygen, nitrogen, or sulfur, or, two independent occurrences of $R^+$, on the same substituent or different substituents, taken together with the atom(s) to which each $R^+$ group is bound, optionally form a 5–8-membered heterocyclyl, aryl or heteroaryl ring or a 3–8-membered cycloalkyl ring having 0–3 heteroatoms independently selected from nitrogen, oxygen, or sulfur, wherein one or more optional substituents on the aliphatic group or the phenyl ring of $R^+$ are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$aliphatic groups of $R^{30}$ is unsubstituted.

2. The compound of claim 1, wherein either of $R^3$ or $R^4$ is $-Q^1-A-Q^2-Y$, wherein A is a substituted or unsubstituted aryl or heteroaryl moiety and compounds have the general formula IIa or IIb:

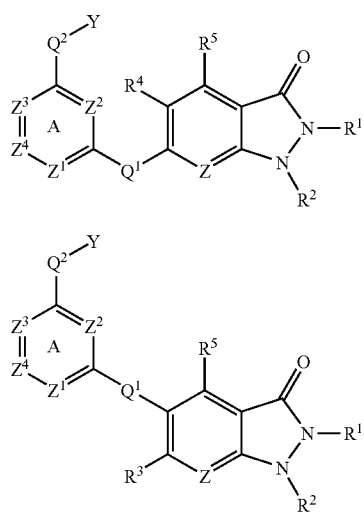

IIa

IIb wherein $Z^1$ is N or $CR^V$, $Z^2$ is N or $CR^W$, $Z^3$ is N or $CR^X$ and $Z^4$ is N or $CR^Y$, wherein $R^V$, $R^W$, $R^X$ and $R^Y$ are each independently $R^8$, or $R^X$ and $R^Y$, or $R^V$ and $R^Y$ are taken together with their intervening atoms to form a fused, unsaturated or partially unsaturated, 5–8 membered ring having 0–3 ring heteroatoms selected from oxygen, sulfur, or nitrogen, wherein any substitutable carbon on said fused ring formed by $R^X$ and $R^Y$ or by $R^V$ and $R^Y$ is substituted by oxo or $R^8$, and any substitutable nitrogen on said ring formed by $R^X$ and $R^Y$ or by $R^V$ and $R^Y$ is substituted by $R^9$;

wherein each occurrence of $R^8$ is independently —R; and each occurrence of $R^9$ is independently hydrogen, —R', —COR', —$CO_2$(R'), —CON(R')$_2$, or —$SO_2$R', wherein each occurrence of R' is independently hydrogen, optionally substituted aliphatic, heteroaliphatic, aryl or heteroaryl, or two occurrences of R' on the same nitrogen atom are taken together with the nitrogen to form an optionally substituted 5–8 membered heterocyclic or heteroaryl ring.

3. The compound of claim 2, wherein A represents one of the following moieties:

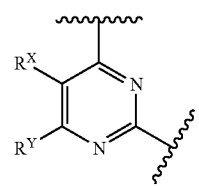

i

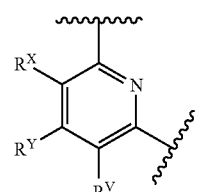

ii

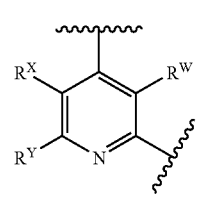

iii

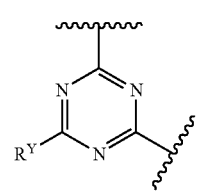

iv

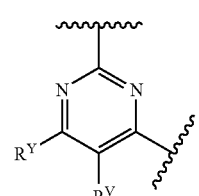

v

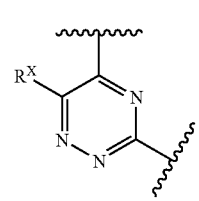

vi

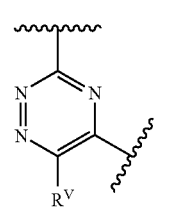

vii

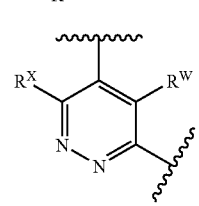

viii

-continued
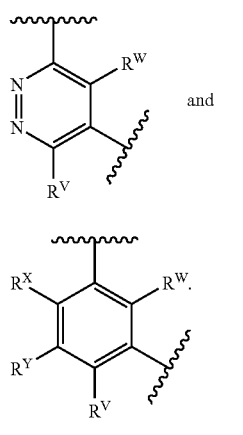
ix
and
x
4. The compound of claim 3, wherein ring A is one of formulas i, ii, iii or x.
5. The compound of claim 2, wherein Ring A is one of groups II-A through II-DD, wherein $Z^1$ is nitrogen or $CR^V$, $Z^2$ is nitrogen or $CR^W$, and p is 0–4:
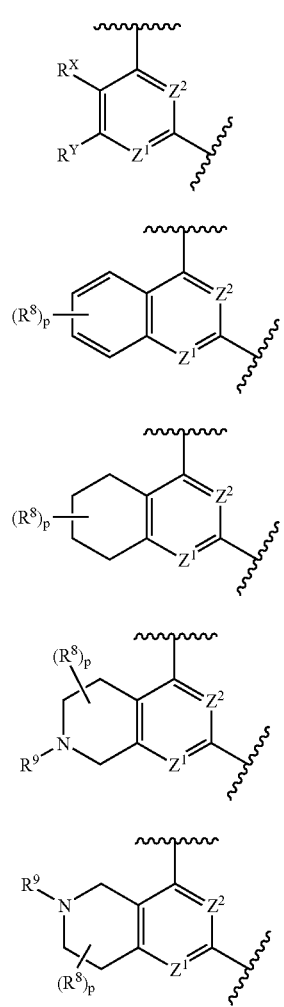
II-A
II-B
II-C
II-D
II-E
-continued
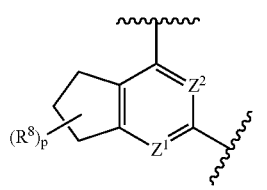
II-F
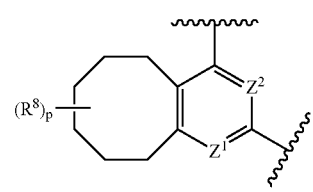
II-G
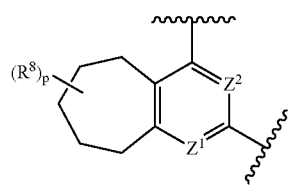
II-H
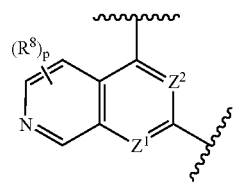
II-I
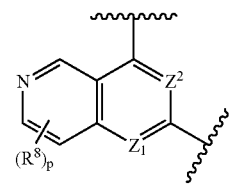
II-J
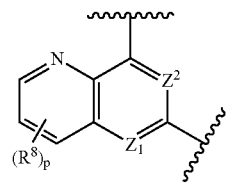
II-K
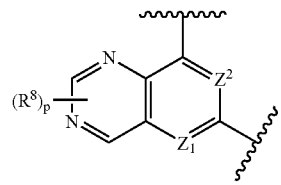
II-L
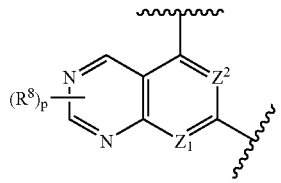
II-M -continued
II-N
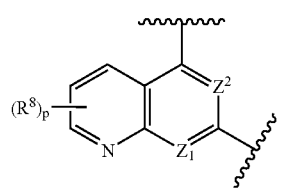
II-O
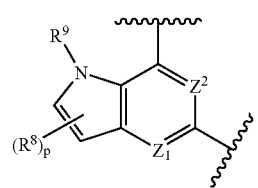
II-P
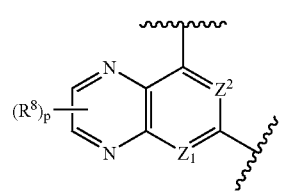
II-Q
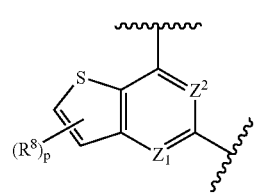
II-R
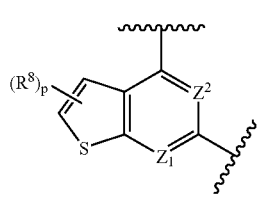
II-S
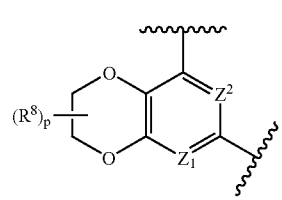
II-T
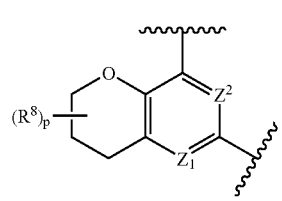
II-U
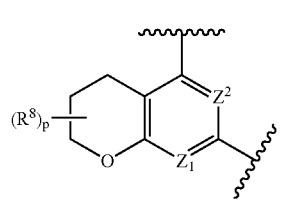
-continued
II-V
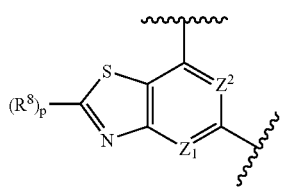
II-W
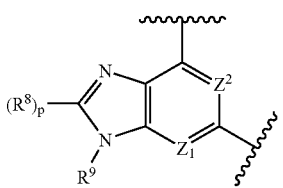
II-X
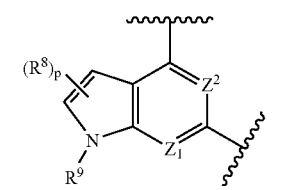
II-Y
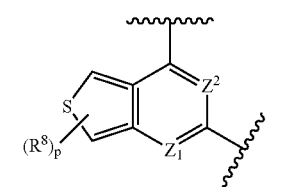
II-Z
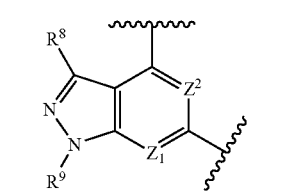
II-AA
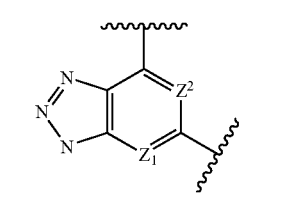
II-BB
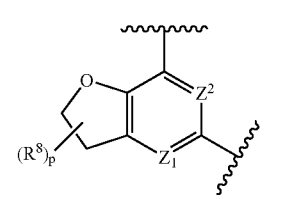
II-CC
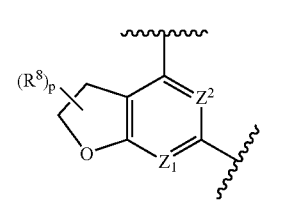

-continued

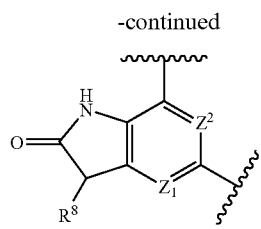

II-DD

6. The compound of claim 5, wherein ring A is one of II-A, II-B, II-C, II-D, II-E, II-F, II-H, II-I, II-J, II-K, II-L, II-N, II-O, or II-DD.

7. The compound of claim 5, wherein ring A is one of II-A, II-B, II-C, II-D, II-E, II-H, or II-K.

8. The compound of claim 5, wherein ring A is one of II-A or II-B.

9. The compound of claim 5, wherein $Z^1$ is $CR^V$ and $Z^2$ is $CR^W$.

10. The compound of claim 5, wherein $Z^1$ is N and $Z^2$ is N.

11. The compound of claim 5, wherein $Z^1$ is N and $Z^2$ is $CR^W$.

12. The compound of claim 5, wherein $Z^1$ is $CR^V$ and $Z^2$ is N.

13. The compound of claim 2, wherein A is a monocyclic ring system and $R^X$ groups, when present, are selected from hydrogen, alkyl- or dialkylamino, acetamido, or a $C_{1-4}$ aliphatic group; $R^Y$ groups, when present, are selected from hydrogen, an optionally substituted group selected from $C_{1-6}$ aliphatic, $C_{1-6}$ heteroaliphatic, aryl, or heteroaryl, —$Q_{(n)}$N$(R^7)_2$, —$Q_{(n)}$O$R^7$, —$Q_{(n)}$S$R^7$, —$Q_{(n)}$(C=O)O($R^7$), —$Q_{(n)}$C(O)N$(R^7)_2$, —$Q_{(n)}$NHC(O)$R^7$, —$Q_{(n)}$NHSO$_2R^7$, or —$Q_{(n)}$SO$_2$N$(R^7)_2$, wherein n is 0 or 1, and wherein Q is preferably —(C(R")$_2$)—, wherein R" is hydrogen or $C_{1-3}$alkyl, and wherein each occurrence of $R^7$ is independently hydrogen, optionally substituted aliphatic, heteroaliphatic, aryl or heteroaryl, or two occurrences of $R^7$ on the same nitrogen atom are taken together with the nitrogen atom to form an optionally group selected from a 5–8 membered heterocyclic or 5–8 membered heteroaryl ring.

14. The compound of claim 13, wherein $R^Y$ is one of the following groups: optionally substituted 5–6 membered heteroaryl or heterocyclyl rings, optionally substituted aryl or cycloalkyl rings; optionally substituted $C_{1-6}$ aliphatic; alkoxyalkylamino alkoxyalkyl; aminoalkyl; alkyl- or dialkylamino; alkyl- or dialkylaminoalkoxy; alkyl- or dialkylaminoalkoxyalkyl; or acetamido.

15. The compound of claim 2, wherein A is a bicyclic ring system and the bicyclic ring system A may be substituted by one or more occurrences of oxo, $R^8$ or $R^9$, wherein $R^8$ is —$R^7$, halo, —O(CH$_2$)$_{2-4}$—N$(R^7)_2$, —O(CH$_2$)$_{2-4}$—$R^7$, —O$R^7$, —N$(R^7)$—(CH$_2$)$_{2-4}$—N$(R^7)_2$, —N$(R^7)$—(CH$_2$)$_{2-4}$—$R^7$, —C(=O)$R^7$, —CO$_2R^7$, —COCO$R^7$, —NO$_2$, —CN, —S(O)$R^7$, —SO$_2R^7$, —S$R^7$, —N$(R^7)_2$, —CON$(R^7)_2$, —SO$_2$N$(R^7)_2$, —OC(=O)$R^7$, —N$(R^7)$COR$^7$, —N$(R^7)$CO$_2$(optionally substituted $C_{1-6}$ aliphatic), —N$(R^7)$N$(R^7)_2$, —C=NN$(R^7)_2$, —C=N—OR, —NHOR$^7$, —N$(R^7)$CON$(R^7)_2$, —N$(R^7)$SO$_2$N$(R^7)_2$, —N$(R^7)$SO$_2R^7$, or —OC(=O)N$(R^7)_2$, wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring.

16. The compound of claim 15 wherein each occurrence of $R^8$ is independently -halo, —$R^7$, —O$R^7$, —COR$^7$, —CO$_2R^7$, —CON$(R^7)_2$, —O(C=O)N$(R^7)_2$, —CN, —O(CH$_2$)$_{2-4}$—N$(R^7)_2$, —O(CH$_2$)$_{2-4}$—$R^7$, —NO$_2$, —N$(R^7)_2$, —N$R^7$COR$^7$, —N$R^7$SO$_2R^7$, —SO$_2$N$(R^7)_2$ wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring.

17. The compound of claim 2, wherein Y is an optionally substituted heteroaryl moiety.

18. The compound of claim 2, wherein Y is selected from one of the following heteroaryl moieties a–y:

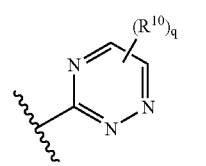

a

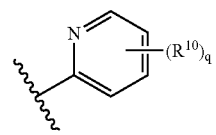

b

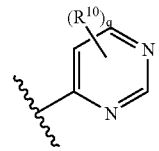

c

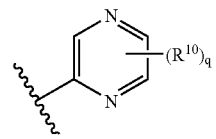

d

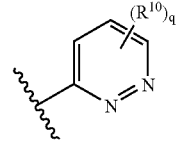

e

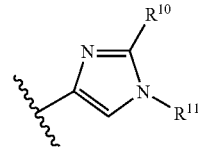

f

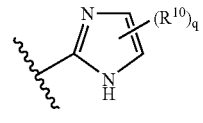

g

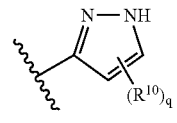

h

-continued

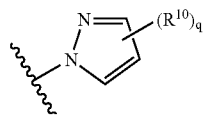
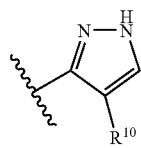
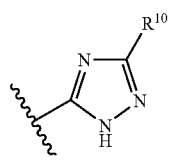
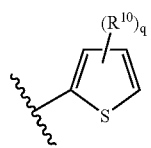
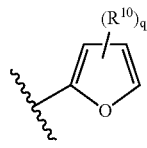
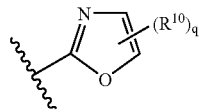
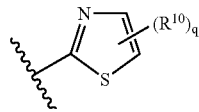
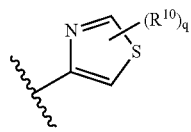
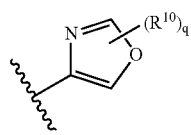
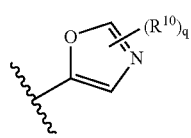
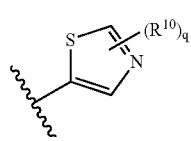

-continued i
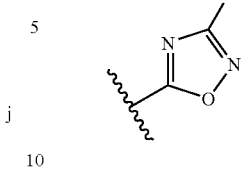

j
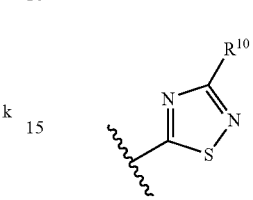

k l
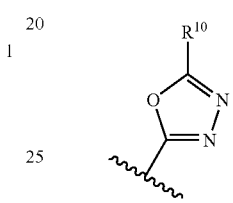

m n
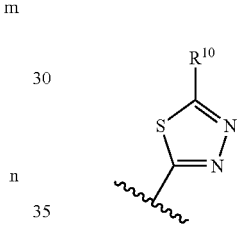

o

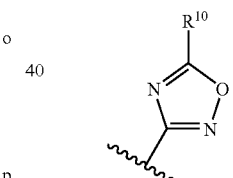

p

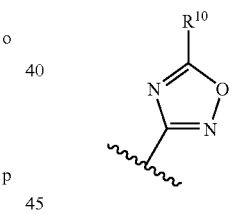

q
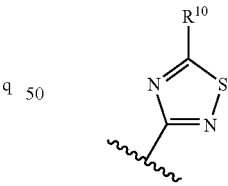

r s wherein q is 0–4, $R^{10}$ is —R, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

19. The compound of claim 18, wherein Y is one of the following heteroaryl moieties:

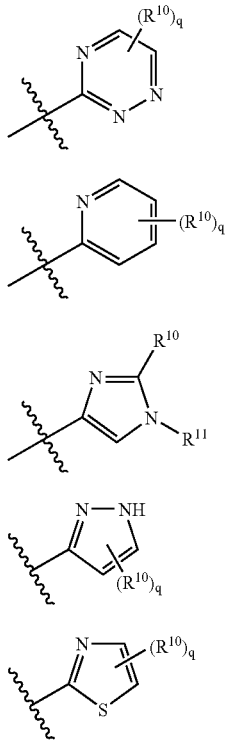

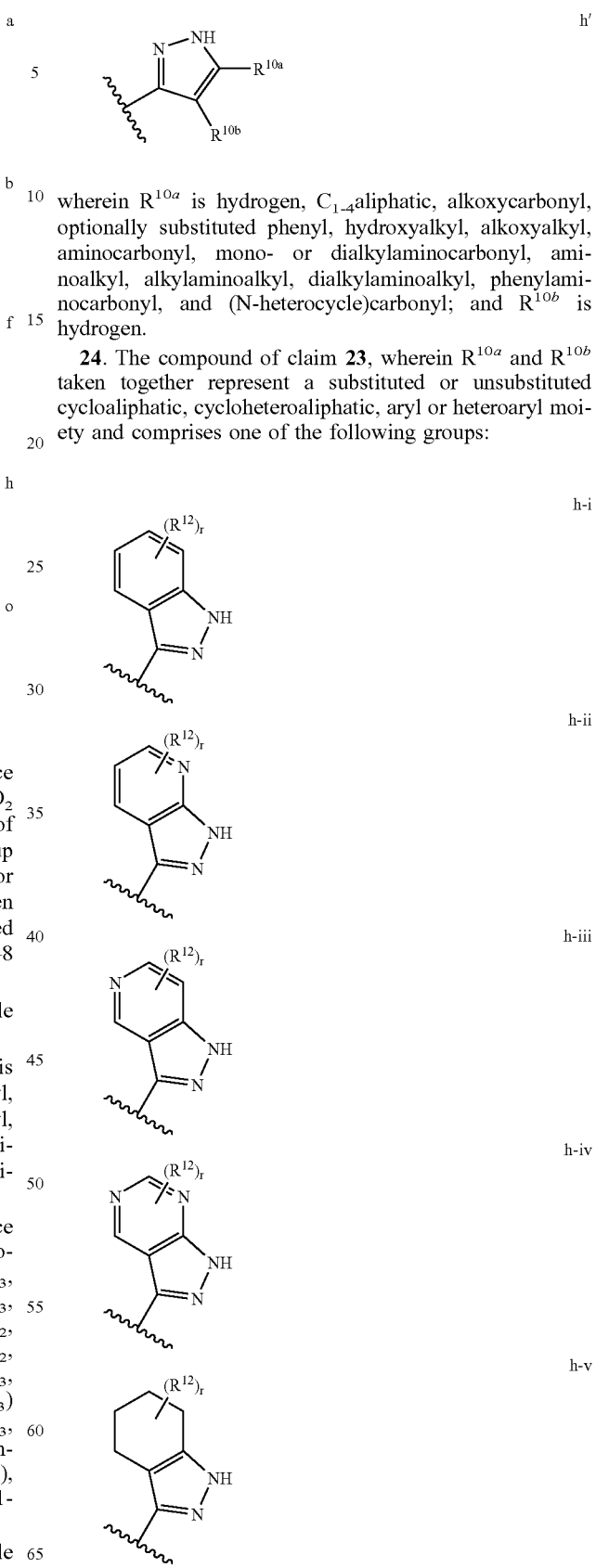

wherein q is 0–4, $R^{10}$ is —R, and wherein each occurrence of $R^{11}$ is independently hydrogen, —R', —COR', —CO$_2$(R'), —CON(R')$_2$, or —SO$_2$R', wherein each occurrence of R' is independently hydrogen, optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

20. The compound of claim 18, wherein Y is a pyrazole moiety, h.

21. The compound of claim 18, wherein each $R^{10}$ is independently hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, or (N-heterocycle)carbonyl.

22. The compound of claim 18, wherein each occurrence of $R^{10}$ is independently methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, or CO(piperidin-1-yl).

23. The compound of claim 18, wherein, Y is a pyrazole moiety, h', wherein the pyrazole is substituted with two occurrences of $R^{10}$ ($R^{10a}$ and $R^{10b}$)

wherein $R^{10a}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl; and $R^{10b}$ is hydrogen.

24. The compound of claim 23, wherein $R^{10a}$ and $R^{10b}$ taken together represent a substituted or unsubstituted cycloaliphatic, cycloheteroaliphatic, aryl or heteroaryl moiety and comprises one of the following groups:

wherein r is 0–4 and $R^{12}$ is hydrogen, -halo, —N($R^7$)$_2$, —C$_{1-3}$ alkyl, —C$_{1-3}$ haloalkyl, —NO$_2$, —O(C$_{1-3}$ alkyl), —CO$_2$(C$_{1-3}$ alkyl), —CN, —SO$_2$(C$_{1-3}$ alkyl), —SO$_2$NH$_2$, —OC(O)NH$_2$, —NH$_2$SO$_2$(C$_{1-3}$ alkyl), —NHC(O)(C$_{1-3}$ alkyl), —C(O)NH$_2$, and —CO(C$_{1-3}$ alkyl), wherein the (C$_{1-3}$ alkyl) is most preferably methyl, wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring.

25. The compound of claim 2, wherein when $R^3$ is —$Q^1$—A—$Q^2$—Y, $R^4$ is hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl.

26. The compound of claim 25, wherein $R^4$ is hydrogen, methyl, ethyl, cyclopropyl, hydroxy, phenyl or —CH$_2$NH$_2$.

27. The compound of claim 2, wherein when $R^4$ is —$Q^1$—A—$Q^2$—Y, $R^3$ is hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl.

28. The compound of claim 27, wherein $R^3$ is hydrogen, methyl, ethyl, cyclopropyl, hydroxy, phenyl or —CH$_2$NH$_2$.

29. The compound of claim 2, wherein $R^5$ is hydrogen, halogen, —NO$_2$, —CN, hydroxy, optionally substituted C$_{1-3}$alkyl, optionally substituted alkoxy, —SO$_2$NH$_2$, or —C(O)alkyl.

30. The compound of claim 29 wherein $R^5$ is Cl, CF$_3$, OCF$_3$, CH$_3$, —CN, —SO$_2$NH$_2$ or —C(O)Me.

31. The compound of claim 2, wherein $Q^1$ is NH and $Q^2$ is NH, and compounds are defined by the general formula IIa(i) or IIb(i):

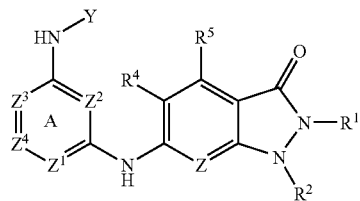

IIa(i)

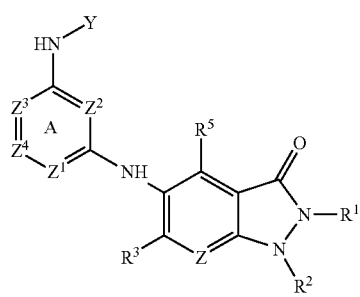

IIb(i)

32. The compound of claim 2, wherein $Q^1$ is S and $Q^2$ is NH, and compounds are defined by the general formula IIa(ii) or IIb(ii):

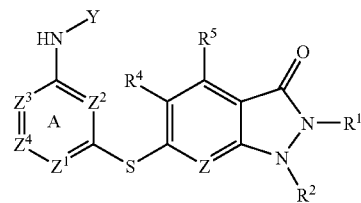

IIa(ii)

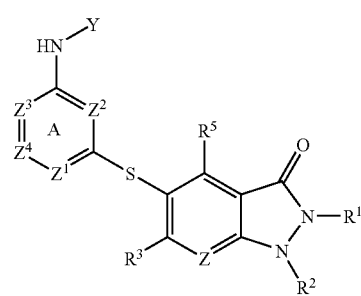

IIb(ii)

33. The compound of claim 2, wherein $Q^1$ is O and $Q^2$ is NH, and compounds are defined by the general formula IIa(iii) or IIb(iii):

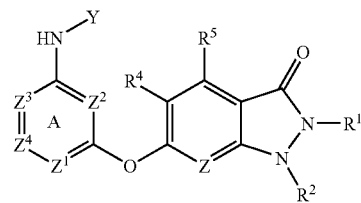

IIa(iii)

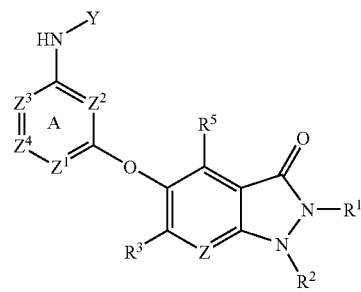

IIb(iii)

34. The compound of claim 2, wherein $Q^2$ is NH, and compounds are defined by the general formula IIa(iv) or IIb(iv):

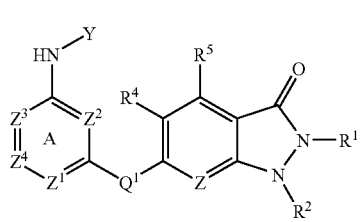

IIa(iv)

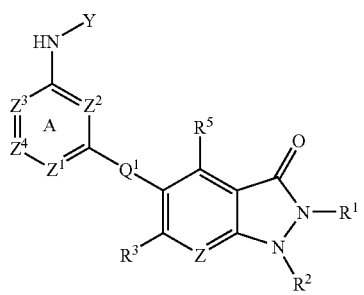

IIb(iv)

wherein $Q^1$ is —$C(R^4)_2$.

35. The compound of claim 2, wherein $Q^2$ is NH and Y is an optionally substituted heteroaryl moiety, and compounds are defined by the general formula IIa(v) or IIb(v):

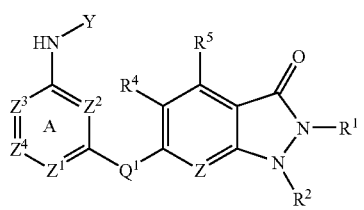

IIa(v)

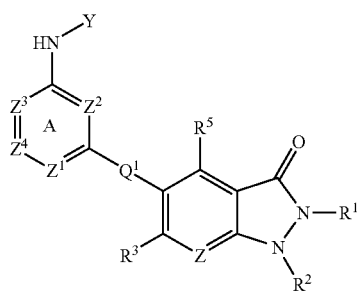

IIb(v)

wherein $Q^1$ is a direct bond.

36. The compound of any one of claims 31, 32, 33, 34 or 35, wherein:

(i) $R^1$, $R^2$, $R^4$ and $R^5$ are each hydrogen and wherein Z is $CR^6$ and $R^6$ is hydrogen; or $R^1$, $R^2$, $R^3$ and $R^5$ are each hydrogen and wherein Z is $CR^6$ and $R^6$ is hydrogen;

(ii) ring A is defined according to one of the following groups:

(a) a ring A is one of formulas

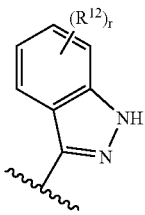

h-i

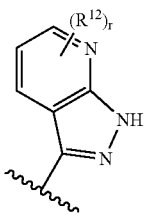

h-ii

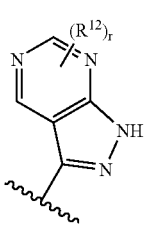

h-iii

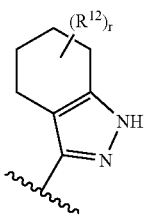

h-iv h-v (b) ring A is one of formulas

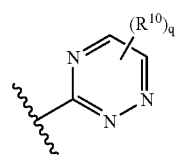

a

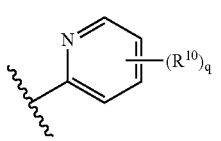

b

-continued
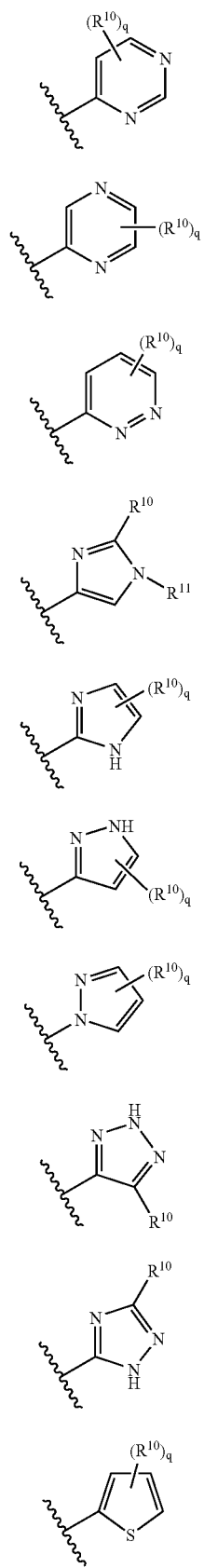
c
d
e
f
g
h
i
j
k
l
-continued
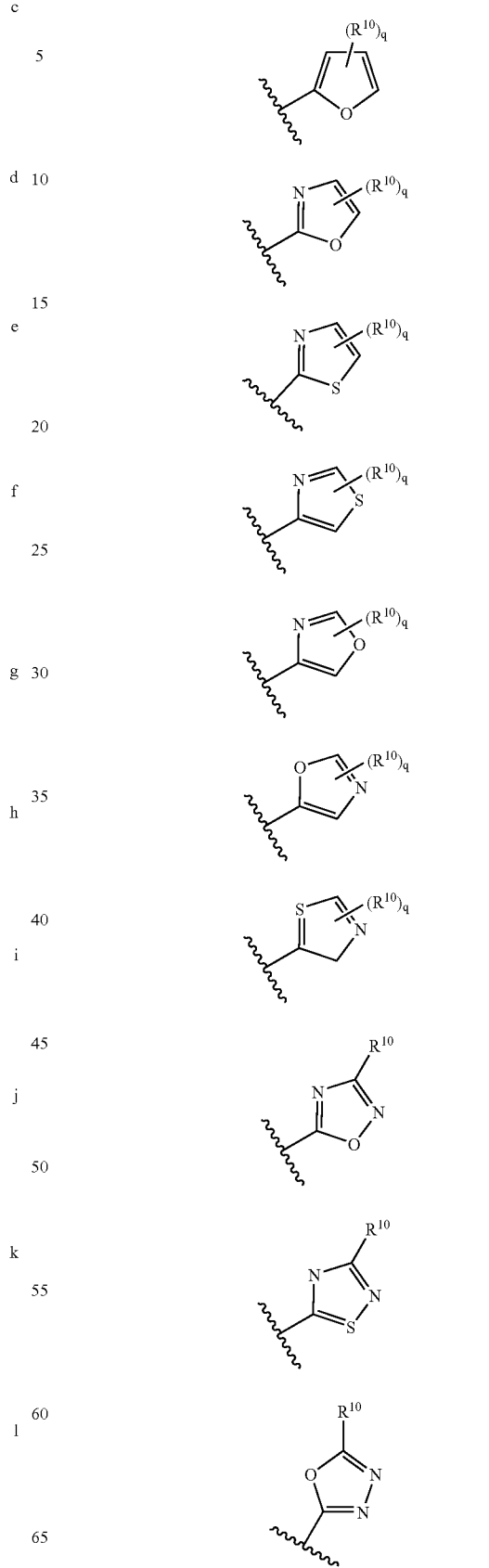
m
n
o
p
q
r
s
t
u
v -continued

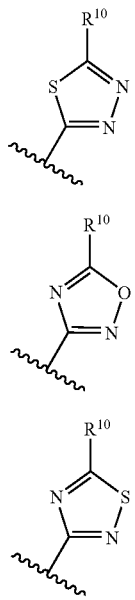

w x y (c) ring A is one of formulas II-A, II-B, II-C, II-D, II-E, II-F, II-H, II-I, II-J, II-K, II-L, II-N, II-O, or II-DD;
(d) ring A is one of the formulas II-A, II-B, II-C, II-D, II-E, II-H, or II-K;
(e) ring A is one of formulas II-A or II-B;
(f) ring A is II-A and $Z^1$ is $CR^V$ and $Z^2$ is $CR^W$;
(g) ring A is II-A and $Z^1$ is N and $Z^2$ is N;
(h) ring A is II-A and $Z^1$ is N and $Z^2$ is $CR^W$;
(i) ring A is II-A and $Z^1$ is $CR^V$ and $Z^2$ is N;
(j) ring A is an optionally substituted aryl or heteroaryl moiety of formula i, ii, i or x;
(k) ring A is a monocyclic ring system and $R^V$ and $R^W$, when present, are hydrogen or amino; $R^X$ groups, when present, is hydrogen, alkyl- or dialkylamino, acetamido, or a $C_{1-4}$ aliphatic group such as methyl, ethyl, cyclopropyl, or isopropyl; $R^Y$ groups, when present, is hydrogen, an optionally substituted group selected from hydrogen, $C_{1-6}$ aliphatic, $C_{1-6}$ heteroaliphatic, aryl, or heteroaryl, —$Q_{(n)}N(R^7)_2$, —$Q_{(n)}OR^7$, —$Q_{(n)}SR^7$, —$Q_{(n)}(C=O)O(R^7)$, —$Q_{(n)}C(O)N(R^7)_2$, —$Q_{(n)}NHC(O)R^7$, —$Q_{(n)}NHSO_2R^7$, or —$Q_{(n)}SO_2N(R^7)_2$, wherein n is 0 or 1, and wherein Q is preferably —$(C(R'')_2)$—, wherein R'' is hydrogen or $C_{1-3}$alkyl, and wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring;
(l) ring A is a monocyclic ring system and $R^V$, $R^W$ and $R^X$ groups, when present, are hydrogen or amino; $R^Y$ groups include groups selected from optionally substituted 5–6 membered heteroaryl or heterocyclyl rings, such as 2-pyridyl, 4-pyridyl, pyrrolidinyl, piperidinyl, morpholinyl, or piperazinyl; optionally substituted aryl or cycloalkyl rings such as phenyl, halogen substituted phenyl, alkoxy substituted phenyl, trifluoromethyl substituted phenyl, nitro substituted phenyl, methyl substituted phenyl; optionally substituted $C_{1-6}$ aliphatic, such as methyl, ethyl, cyclopropyl, cyclopentyl, cyclohexyl, amino substituted cycloalkyl, acetamido substituted cycloalkyl, isopropyl, or t-butyl; alkoxyalkylamino such as methoxyethylamino; alkoxyalkyl such as methoxymethyl or methoxyethyl; aminoalkyl such as aminoethyl, dimethylaminoethyl; alkyl- or dialkylamino such as ethylamino or dimethylamino; alkyl- or dialkylaminoalkoxy such as dimethylaminopropyloxy; alkyl- or dialkylaminoalkoxyalkyl such as dimethylaminoethoxymethyl; and acetamido;
(m) ring A system is a bicyclic ring system and the ring formed when $R^x$ and $R^y$ are taken together may be substituted or unsubstituted;
(n) ring A system is a bicyclic ring system formed by $R^X$ and $R^Y$ taken together and substituted by one or more occurrences of $R^8$ or $R^9$, wherein each occurrence of $R^8$ is independently —$R^7$, halo, —$O(CH_2)_{2-4}$—$N(R^7)_2$, —$O(CH_2)_{2-4}$—$R^7$, —$OR^7$, —$N(R^7)$—$(CH_2)_{2-4}$—$N(R^7)_2$, —$N(R^7)$—$(CH_2)_{2-4}$—$R^7$, —$C(=O)R^7$, —$CO_2R^7$, $COCOR^7$, —$NO_2$, —CN, —$S(O)R^7$, —$SO_2R^7$, —$SR^7$, —$N(R^7)_2$, —$CON(R^7)_2$, —$SO_2N(R^7)_2$, —$OC(=O)R^7$, —$N(R^7)COR^7$, —$N(R^7)CO_2$(optionally substituted $C_{1-6}$ aliphatic), —$N(R^7)N(R^7)_2$, —C=NN$(R^7)_2$, —C=N—OR, —NHOR$^7$, —$N(R^7)CON(R^7)_2$, —$N(R^7)SO_2N(R^7)_2$, —$N(R^7)SO_2R^7$, or —OC(=O)N$(R^7)_2$, wherein each occurrence of $R^7$ is independently hydrogen, an optionally substituted group selected from aliphatic, heteroaliphatic, aryl or heteroaryl, or two occurrences of $R^7$ on the same nitrogen atom are taken together with the nitrogen atom to form an optionally substituted group selected from a 5–8 membered heterocyclic or 5–8 membered heteroaryl ring; and each occurrence of $R^9$ is independently hydrogen, —R', —COR', —$CO_2$(R'), —CON(R')$_2$, or —$SO_2R'$, wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring,
(iii) Y is defined according to one of the following groups:
(a) Y is an optionally substituted heteroaryl moiety;
(b) Y is selected from one of the heteroaryl moieties a–y;
(c) Y is selected from one of the following heteroaryl moieties:

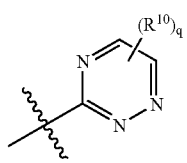

a

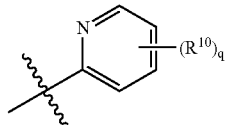

b

-continued

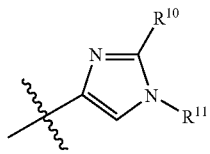
f

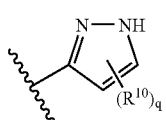
h

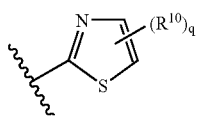
o wherein q is 0–4, $R^{10}$ is —R, wherein —R is defined generally above and in classes and subclasses herein, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring;

(d) Y is a pyrazole moiety, h;

(e) Y is one of a, b, f, h or o, optionally substituted with one or more $R^{10}$ groups, wherein each occurrence of $R^{10}$ is independently hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl;

(f) Y is one of a, b, f, h or o, optionally substituted with one or more $R^{10}$ groups, wherein each occurrence of $R^{10}$ is independently hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl).

(g) Y is a pyrazole moiety, h', wherein the pyrazole is substituted with $R^{10a}$ and $R^{10b}$,

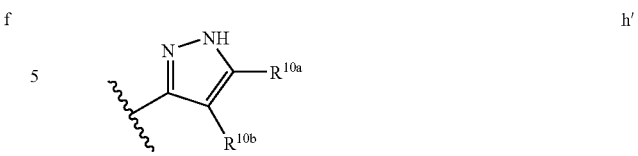

wherein each occurrence of $R^{10a}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl, and $R^{10b}$ is hydrogen;

(h) Y is a pyrazole moiety, h', wherein the pyrazole is substituted with $R^{10a}$ and $R^{10b}$,

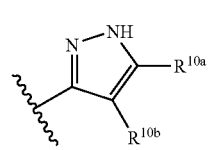
h' wherein each occurrence of $R^{10a}$ is hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl, and $R^{10b}$ is hydrogen;

(i) Y is heteroaryl moiety substituted by at least two occurrences of $R^{10}$ and where two occurrences of $R^{10}$ taken together may represent an optionally substituted group selected from cycloaliphatic, cycloheteroaliphatic, aryl or heteroaryl;

(j) Y represents one of the following heteroaryl moieties:

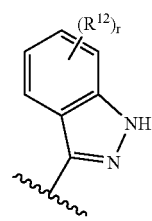
h-i

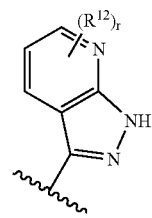
h-ii

-continued

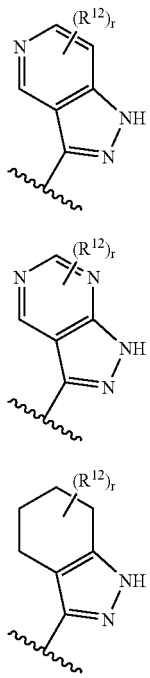

h-iii h-iv h-v

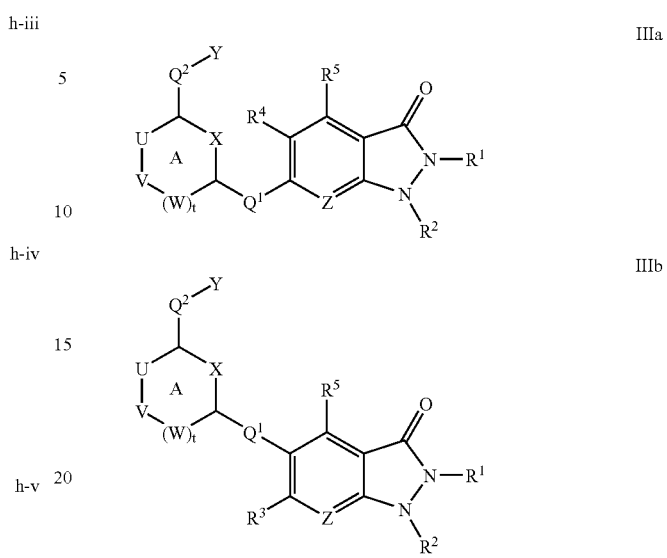

IIIa

IIIb wherein r is 0–4 and $R^{12}$ is hydrogen, -halo, $-N(R^7)_2$, $-C_{1-3}$ alkyl, $-C_{1-3}$ haloalkyl, $NO_2$, $-O(C_{1-3}$ alkyl), $-CO_2(C_{1-3}$ alkyl), $-CN$, $-SO_2(C_{1-3}$ alkyl), $-SO_2NH_2$, $-OC(O)NH_2$, $-NH_2SO_2(C_{1-3}$ alkyl), $-NHC(O)(C_{1-3}$ alkyl), $-C(O)NH_2$, and $-CO(C_{1-3}$ alkyl), wherein the $(C_{1-3}$ alkyl) is most preferably methyl;

(iv) for compounds of formula IIa(i), $R^4$ is defined according to one of the following groups:

(a) $R^4$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or (b) $R^4$ is hydrogen, methyl, ethyl, cyclopropyl, hydroxy, phenyl or $-CH_2NH_2$;

(v) for compounds of formula IIb(i), $R^3$ is defined according to one of the following groups:

(a) $R^3$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or (b) $R^3$ is hydrogen, methyl, ethyl, cyclopropyl, hydroxy, phenyl or $-CH_2NH_2$; and (vi) $R^5$ is defined according to one of the following groups:

(a) hydrogen, halogen, $-NO_2$, $-CN$, hydroxy, optionally substituted $C_{1-3}$alkyl, optionally substituted alkoxy, $-SO_2NH_2$, or $-C(O)$alkyl, or (b) $R^5$ is hydrogen, Cl, $CF_3$, $OCF_3$, $CH_3$, $-CN$, $-SO_2NH_2$ or $-C(O)Me$.

37. The compound of claim 1, wherein either of $R^3$ or $R^4$ is $-Q^1-A-Q^2-Y$, wherein A is an optionally substituted cycloaliphatic or heterocycloaliphatic moiety and compounds have the general formula IIIa or IIIb:

wherein U is $NR^{13}$, $C(R^{14})_2$, or O; V is $NR^{13}$, $C(R^{14})_2$, or O; W is $NR^{13}$, $C(R^{14})_2$, or O, and X is $NR^{13}$, $C(R^{14})_2$, or O, and t is 0, 1 or 2, wherein each occurrence of $R^{13}$ is independently hydrogen, $-R'$, $-COR'$, $-CO_2(R')$, $-CON(R')_2$, or $-SO_2R'$, wherein each occurrence of R' is independently hydrogen, optionally substituted group selected from $C_{1-6}$ aliphatic, $C_{1-6}$heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring; and wherein each occurrence of $R^{14}$ is independently $-R$, with the proviso that when any one of U, V, W, or X is O or $NR^{13}$, an adjacent group U, V, W or X is $C(R^{14})_2$.

38. The compound of claim 37, wherein ring A is selected from the following group:

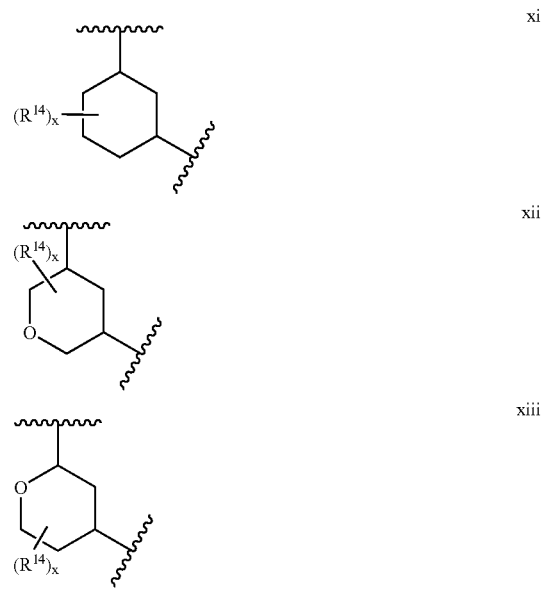

xi xii xiii

-continued

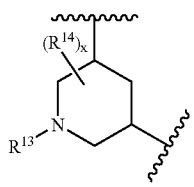
xiv

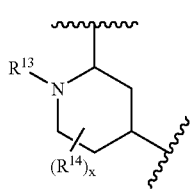
xv

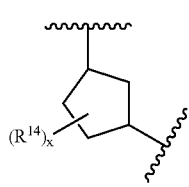
xvi wherein $R^{13}$ is hydrogen, —R', —COR', —CO$_2$(R'), —CON(R')$_2$, or —SO$_2$R', wherein each occurrence of R' is independently hydrogen, optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or heteroaryl ring; $R^{14}$ is oxo or —R; and x is 0–4.

39. The compound of claim 38, wherein x is 0 or 1 and $R^{14}$ is -halo, —N(R$^7$)$_2$, —C$_{1-3}$ alkyl, —haloalkyl, —NO$_2$, —O(C$_{1-3}$ alkyl), —CO$_2$(C$_{1-3}$ alkyl), —CN, —SO$_2$(C$_{1-3}$ alkyl), —SO$_2$NH$_2$, —OC(O)NH$_2$, —NH$_2$SO$_2$(C$_{1-3}$ alkyl), —NHC(O)(C$_{1-3}$ alkyl), —C(O)NH$_2$, and —CO(C$_{1-3}$ alkyl), wherein the (C$_{1-3}$ alkyl) is most preferably methyl.

40. The compound of claim 38, wherein $R^{13}$ is hydrogen or C$_{1-4}$alkyl.

41. The compound of claim 38, wherein ring A is selected from one of xi, xii or xvi and x is 0.

42. The compound of claim 37, wherein Y is an optionally substituted heteroaryl moiety.

43. The compound of claim 37, wherein Y is selected from one of the following heteroaryl moieties a–y:

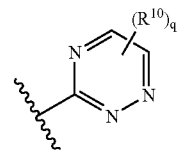
a

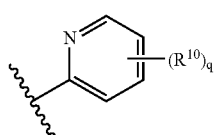
b

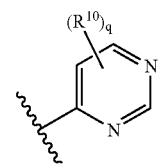
c

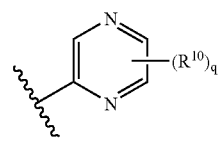
d

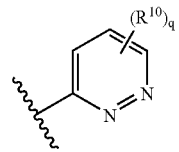
e

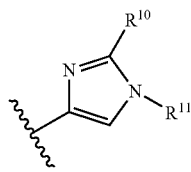
f

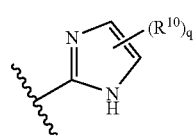
g

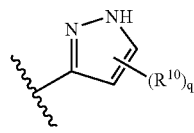
h

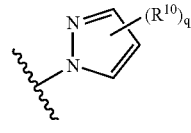
i

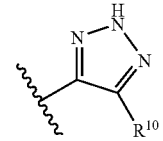
j

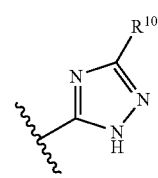
k

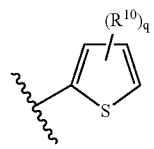
l

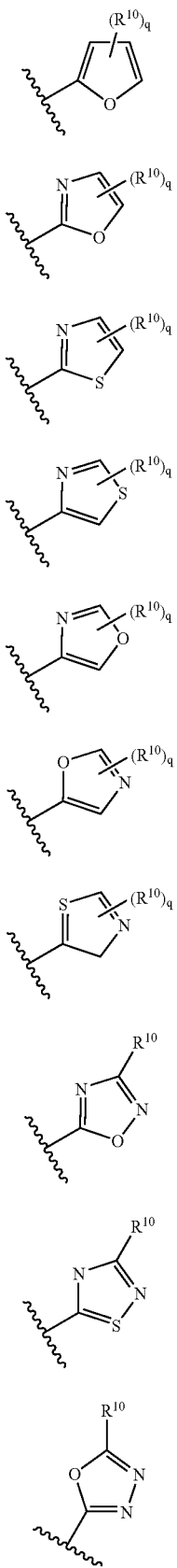

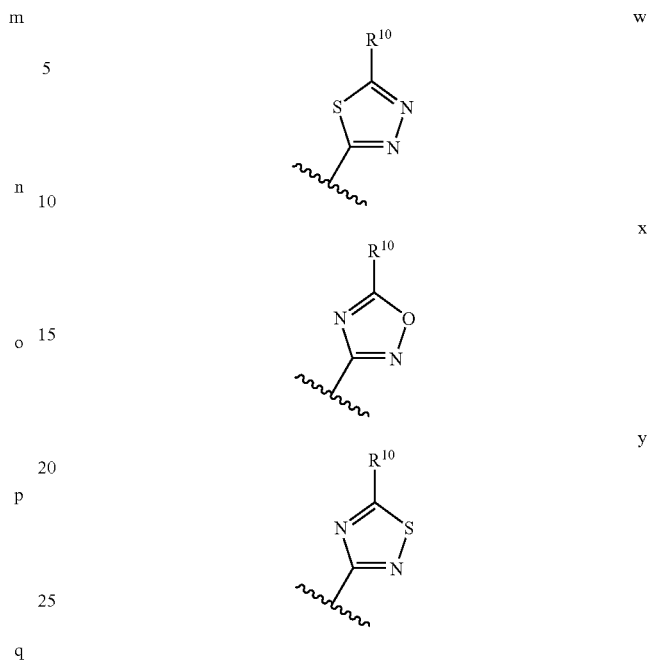

wherein q is 0–4, $R^{10}$ is —R, and wherein each occurrence of $R^{11}$ is independently hydrogen, —R', —COR', —CO$_2$(R'), —CON(R')$_2$, or —SO$_2$R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

44. The compound of claim 43, wherein Y is one of the following heteroaryl moieties:

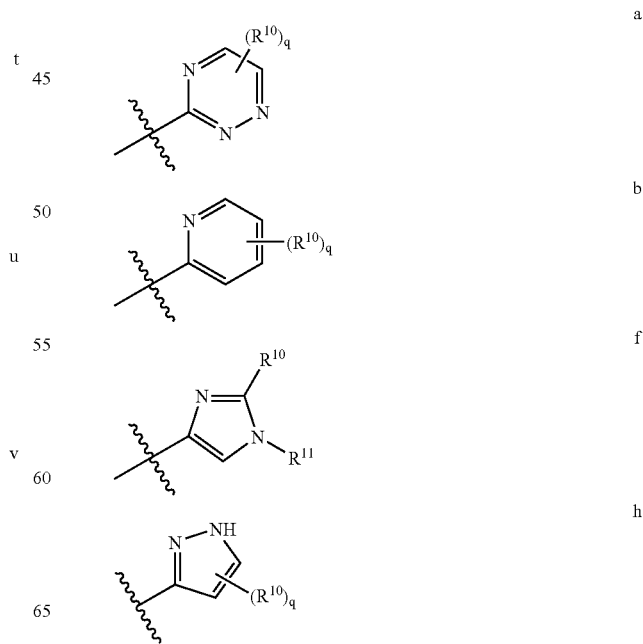

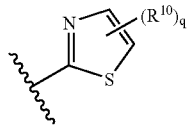

o wherein q is 0–4, $R^{10}$ is —R, and wherein each occurrence of $R^{11}$ is independently hydrogen, —R', —COR', —CO$_2$(R'), —CON(R')$_2$, or —SO$_2$R', wherein each occurrence of R' is independently hydrogen, optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring.

45. The compound of claim 43, wherein each $R^{10}$ is independently hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, or (N-heterocycle)carbonyl.

46. The compound of claim 43, wherein each occurrence of $R^{10}$ is independently methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$Ch$_2$Ch$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, or CO(piperidin-1-yl).

47. The compound of claim 43, wherein, Y is a pyrazole moiety, h', wherein the pyrazole is substituted with of $R^{10a}$ and $R^{10b}$,

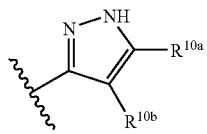

h' wherein $R^{10a}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl; and $R^{10b}$ is hydrogen.

48. The compound of claim 47, wherein $R^{10a}$ and $R^{10b}$ taken together represent a substituted or unsubstituted cycloaliphatic, cycloheteroaliphatic, aryl or heteroaryl moiety and comprises one of the following groups:

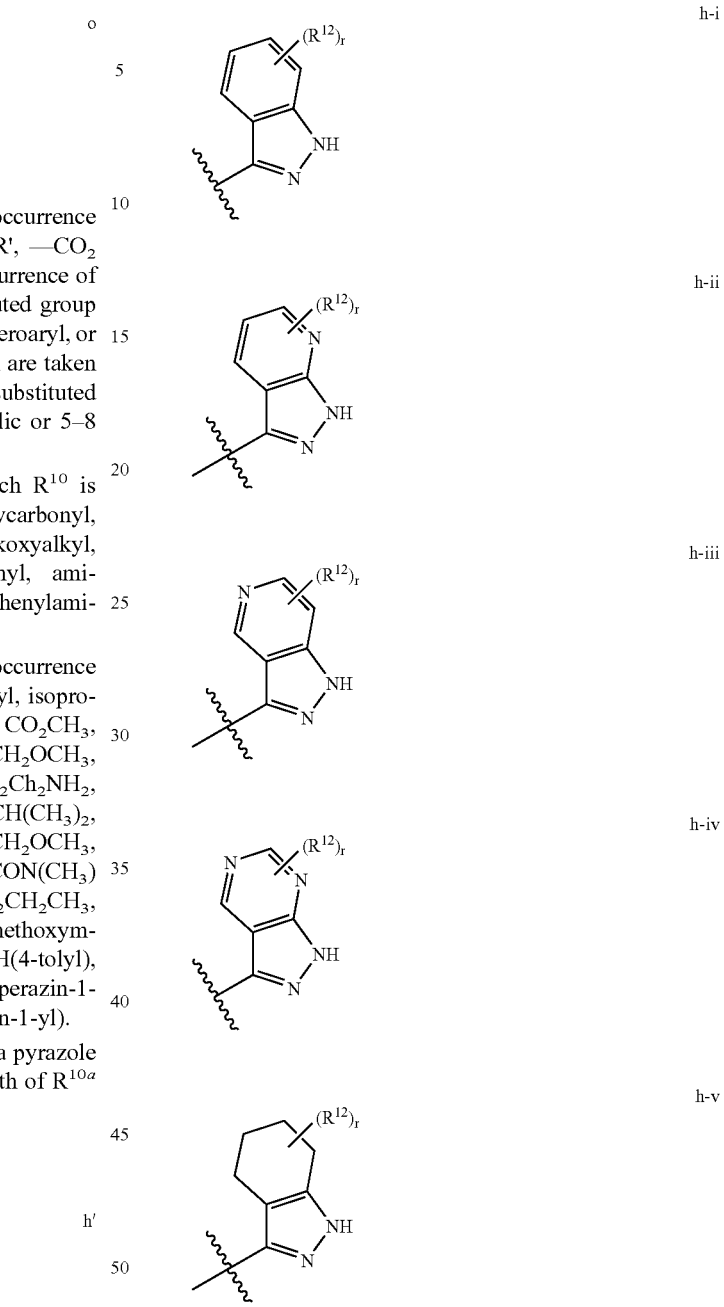

wherein r is 0–4 and $R^{12}$ is hydrogen, -halo, —N(R$^7$)$_2$, —C$_{1-3}$ alkyl, —C$_{1-3}$ haloalkyl, —NO$_2$, —O(C$_{1-3}$ alkyl), —CO$_2$(C$_{1-3}$ alkyl), —CN, —SO$_2$(C$_{1-3}$ alkyl), —SO$_2$NH$_2$, —OC(O)NH$_2$, —NH$_2$SO$_2$(C$_{1-3}$ alkyl), —NHC(O)(C$_{1-3}$ alkyl), —C(O)NH$_2$, and —CO(C$_{1-3}$ alkyl), wherein each occurrence of R$^7$ is independently hydrogen, an optionally substituted group selected from aliphatic, heteroaliphatic, aryl or heteroaryl, or two occurrences of R$^7$ on the same nitrogen atom are taken together with the nitrogen atom to form an optionally substituted group selected from a 5–8 membered heterocyclic or 5–8 membered heteroaryl ring.

49. The compound of claim 37, wherein when R$^3$ is —Q$^1$—A—Q$^2$—Y, R$^4$ is hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl.

50. The compound of claim 49, wherein $R^4$ is hydrogen, methyl, ethyl, cyclopropyl, hydroxy, phenyl or —CH$_2$NH$_2$.

51. The compound of claim 37, wherein when $R^4$ is —Q$^1$—A—Q$^2$—Y, $R^3$ is preferably hydrogen, C$_{1-3}$aliphatic, hydroxy, hydroxyalkyl, alkoxy, amino, aminoalkyl, mono- or di-alkylamino, mono- or di-alkylaminoalkyl, or optionally substituted phenyl.

52. The compound of claim 51, wherein $R^3$ is hydrogen, methyl, ethyl, cyclopropyl, hydroxy, phenyl or —CH$_2$NH$_2$.

53. The compound of claim 37, wherein $R^5$ is hydrogen, halogen, —NO$_2$, —CN, hydroxy, optionally substituted C$_{1-3}$alkyl, optionally substituted alkoxy, —SO$_2$NH$_2$, or —C(O)alkyl.

54. The compound of claim 53, wherein $R^5$ is Cl, CF$_3$, OCF$_3$, CH$_3$, —CN, —SO$_2$NH$_2$ or —C(O)Me.

55. The compound of claim 37, wherein Q$^1$ is NH and Q$^2$ is NH, and compounds are defined by the general formula IIIa(i) or IIIb(i):

57. The compound of claim 37 wherein Q$^1$ is O and Q$^2$ is NH, and compounds are defined by the general formula IIIa(iii) or IIIb(iii):

56. The compound of claim 37 wherein Q$^1$ is S, and Q$^2$ is NH, and compounds are defined by the general formula IIIa(ii) or IIIb(ii):

58. The compound of claim 37, wherein Q$^2$ is NH, and compounds are defined by the general formula IIIa(iv) or IIIb(iv):

-continued

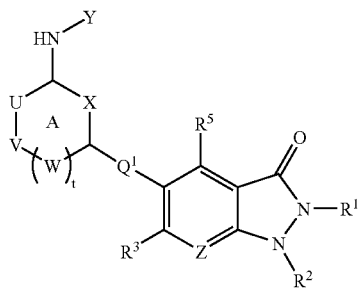

IIIb(iv)

wherein Q¹ is —C(R^A)₂—.

59. The compound of claim 37, wherein Q² is NH, and compounds are defined by the general formula IIIa(v) or IIIb(v):

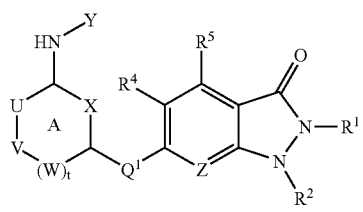

IIIa(v)

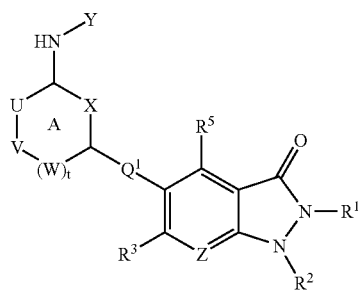

IIIb(v)

wherein Q¹ is a direct bond.

60. The compound of any one of claims 55, 56, 57, 58, or 59 wherein:

(i) $R^1$, $R^2$, $R^4$ and $R^5$ are each hydrogen and wherein Z is $CR^6$ and $R^6$ is hydrogen; or $R^1$, $R^2$, $R^3$ and $R^5$ are each hydrogen and wherein Z is $CR^6$ and $R^6$ is hydrogen;

(ii) ring A is defined according to one of the following groups:

(a) ring A is selected from one of the groups:

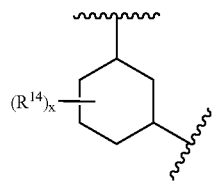

xi

-continued

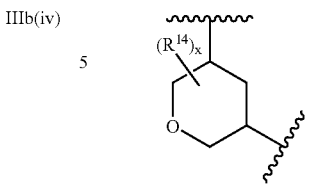

xii

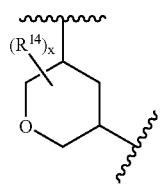

xiii

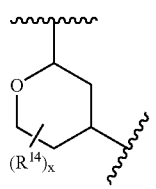

xiv

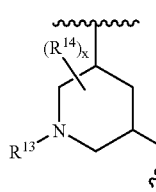

xv

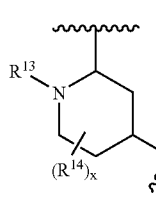

xvi

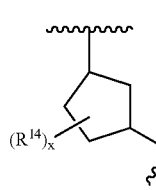

wherein $R^{13}$ is hydrogen, —R', —COR', —CO₂(R'), —CON(R')₂, or —SO₂R', wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring; $R^{14}$ is oxo or —R; and x is 0–4; or (b) ring A is selected from one of xi, xii or xvi and x is 0 or 1; $R^{14}$ is -halo, —N(R⁷)₂, —C₁₋₃ alkyl, —C₁₋₃ haloalkyl, —NO₂, —O(C₁₋₃ alkyl), —CO₂(C₁₋₃ alkyl), —CN, —SO₂(C₁₋₃ alkyl), —SO₂NH₂, —OC(O)NH₂, —NH₂SO₂(C₁₋₃ alkyl), —NHC(O)(C₁₋₃ alkyl), —C(O)NH₂, and —CO(C₁₋₃ alkyl), wherein the (C₁₋₃ alkyl) is most preferably methyl; and $R^{13}$ is hydrogen or C₁₋₄alkyl;

(iii) Y is defined according to one of the following groups:

(a) Y is an optionally substituted heteroaryl moiety;

(b) Y is selected from one of the heteroaryl moieties a–y;

(c) Y is selected from one of the following heteroaryl moieties:

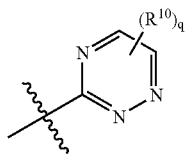 a

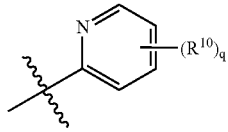 b

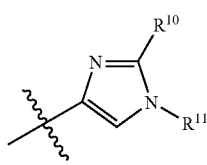 f

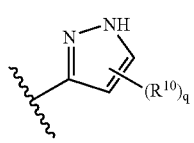 h

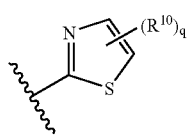 o wherein q is 0–4, $R^{10}$ is —R, wherein —R is defined generally above and in classes and subclasses herein, and wherein each occurrence of $R^{11}$ is independently hydrogen, —R', —COR', —CO$_2$(R'), —CON(R')$_2$, or —SO$_2$R, wherein each occurrence of R' is independently hydrogen, an optionally substituted group selected from aliphatic, heteroaliphatic, aryl or heteroaryl, or two occurrences of R' on the same nitrogen atom are taken together with the nitrogen to form an optionally substituted group selected from a 5–8 membered heterocyclic or 5–8 membered heteroaryl ring;

(d) Y is a pyrazole moiety, h;

(e) Y is one of a, b, f, h or o, optionally substituted with one or more $R^{10}$ groups, wherein each occurrence of $R^{10}$ is independently hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl;

(f) Y is one of a, b, f, h or o, optionally substituted with one or more $R^{10}$ groups, wherein each occurrence of $R^{10}$ is independently hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl);

(g) Y is a pyrazole moiety, h', wherein the pyrazole is substituted with $R^{10a}$ and $R^{10b}$,

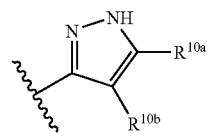 h' wherein each occurrence of $R^{10a}$ is hydrogen, $C_{1-4}$aliphatic, alkoxycarbonyl, optionally substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocycle)carbonyl, and $R^{10b}$ is hydrogen;

(h) Y is a pyrazole moiety, h', wherein the pyrazole is substituted with two occurrences of $R^{10}$ ($R^{10a}$ and $R^{10b}$ as depicted),

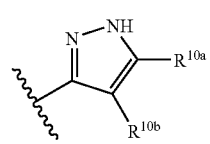 h' wherein each occurrence of $R^{10a}$ is hydrogen, methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(2-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl, and $R^{10b}$ is hydrogen;

(i) Y is heteroaryl moiety substituted by at least two occurrences of $R^{10}$ and where two occurrences of $R^{10}$ taken together may represent an optionally substituted group selected from cycloaliphatic, cycloheteroaliphatic, aryl or heteroaryl;

(j) Y represents one of the following heteroaryl moieties:

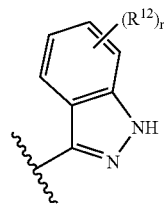 h-i

-continued

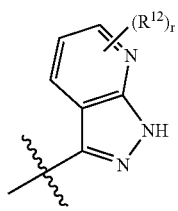 h-ii

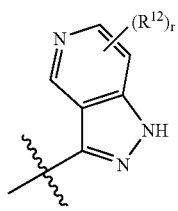 h-iii

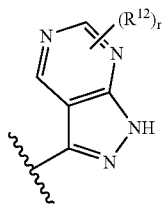 h-iv

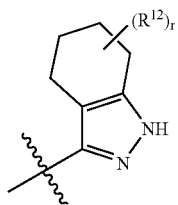 h-v wherein r is 0–4 and $R^{12}$ is hydrogen, -halo, —N($R^7$)$_2$, —$C_{1-3}$ alkyl, —$C_{1-3}$ haloalkyl, —NO$_2$, —O($C_{1-3}$ alkyl), —CO$_2$($C_{1-3}$ alkyl), —CN, —SO$_2$($C_{1-3}$ alkyl), —SO$_2$NH$_2$, —OC(O)NH$_2$, —NH$_2$SO$_2$($C_{1-3}$ alkyl), —NHC(O)($C_{1-3}$ alkyl), —C(O)NH$_2$, and —CO($C_{1-3}$ alkyl), wherein the ($C_{1-3}$ alkyl) is most preferably methyl;

(iv) $R^4$ is defined according to one of the following groups:
   (a) $R^4$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
   (b) $R^4$ is hydrogen, methyl, ethyl, cyclopropyl, hydroxy, phenyl or —CH$_2$NH$_2$;

(v) $R^3$ is defined according to one of the following groups:
   (a) $R^3$ is hydrogen, $C_{1-3}$aliphatic, hydroxy, hydroxyalkyl, alkoxy, amino, aminoalkyl, mono- or di-alkylamino, mono- or di-alkylaminoalkyl, or optionally substituted phenyl, or
   (b) $R^3$ is hydrogen, methyl, ethyl, cyclopropyl, hydroxy, phenyl or —CH$_2$NH$_2$; and (vi) $R^5$ is defined according to one of the following groups:
   (a) hydrogen, halogen, —NO$_2$, —CN, hydroxy, optionally substituted $C_{1-3}$alkyl, optionally substituted alkoxy, —SO$_2$NH$_2$, or —C(O)alkyl, or
   (b) $R^5$ is hydrogen, Cl, CF$_3$, OCF$_3$, CH$_3$, —CN, —SO$_2$NH$_2$ or —C(O)Me.

61. A pharmaceutical composition comprising a compound of claim 1, and a pharmaceutically acceptable carrier, adjuvant, or vehicle.

62. A method of inhibiting a PRAK, GSK3, ERK2, CDK2, MK2, SRC, SYK, or Aurora-2 kinase activity in a biological sample comprising the step of contacting said biological sample with:
   a) a composition according to claim 61; or
   b) a compound of claim 1.

63. The compound according to claim 1 selected from the following:

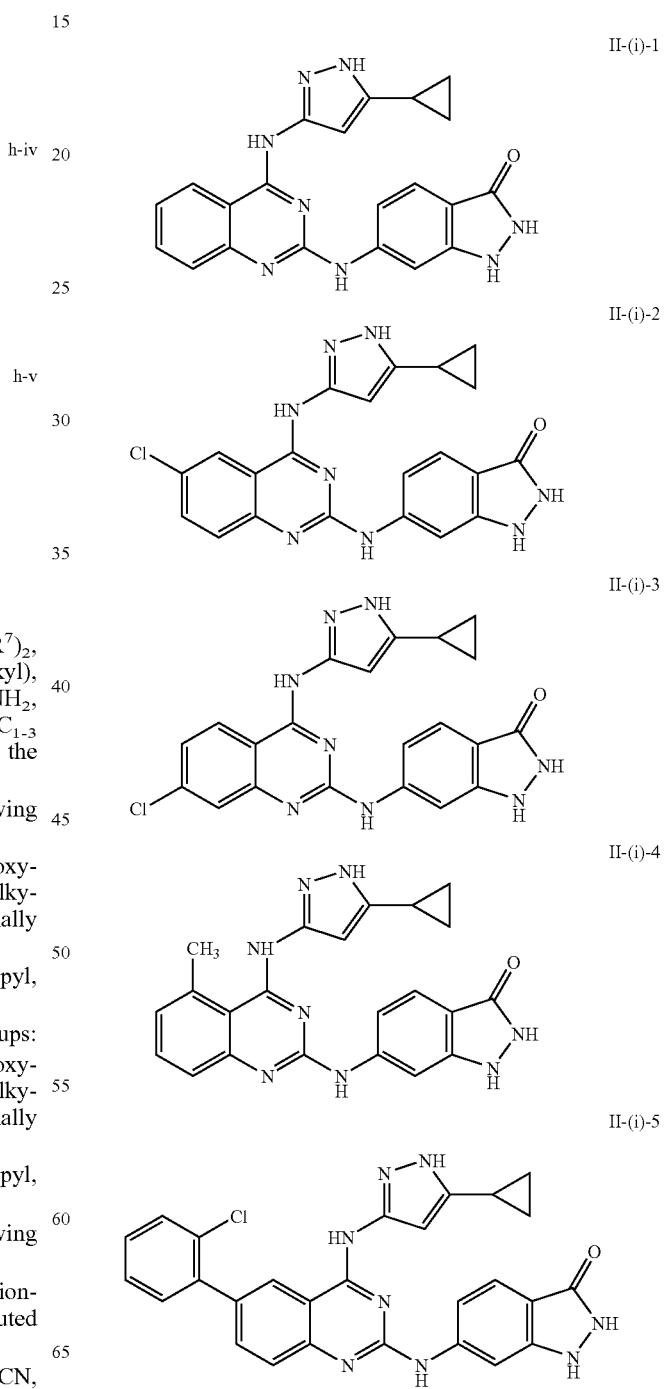

-continued

-continued
II-(i)-18
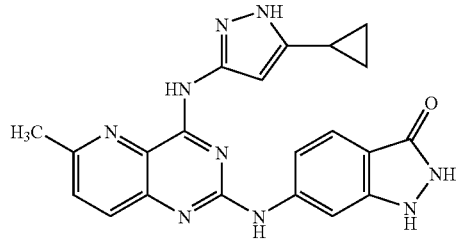
II-(i)-20
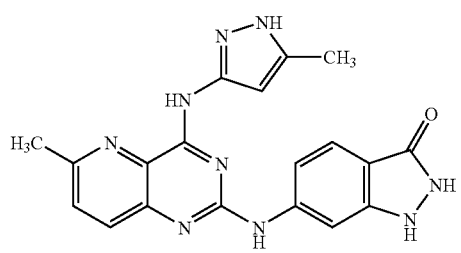
II-(i)-21
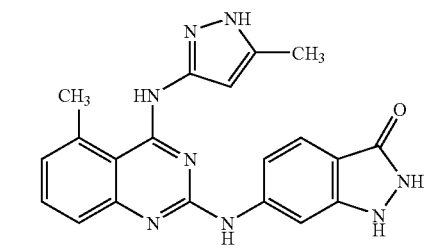
II-(i)-22
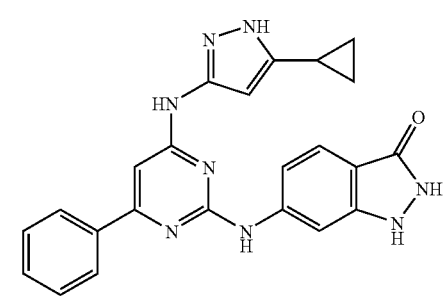
II-(i)-23
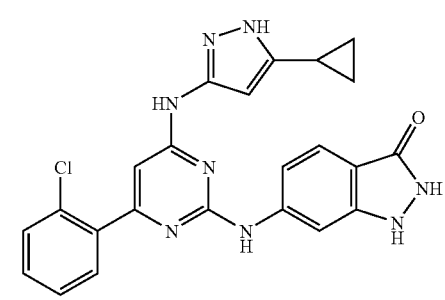
-continued
II-(i)-24
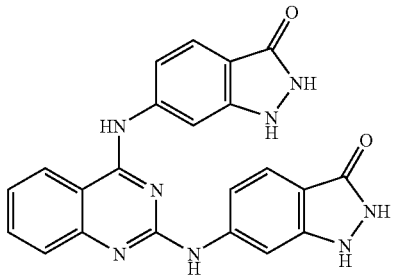
II-(i)-25
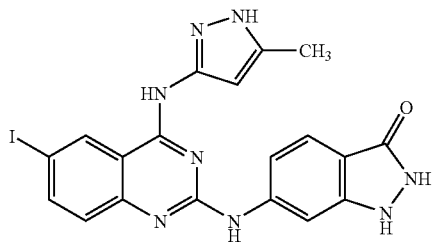
II-(i)-26
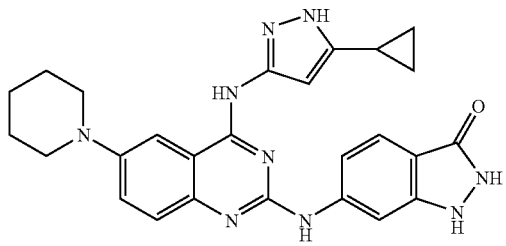
II-(i)-27
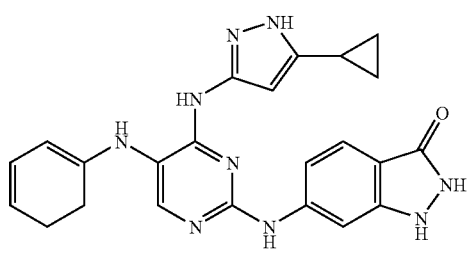
II-(i)-28
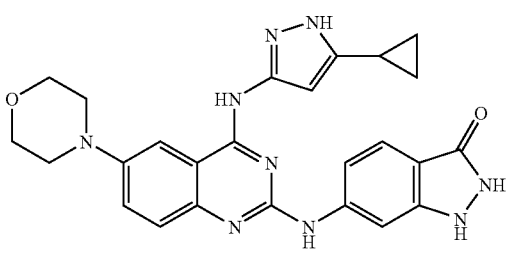
II-(i)-29
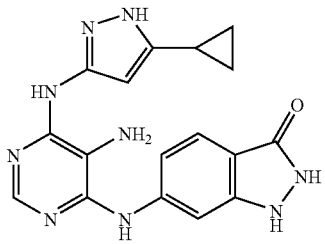

-continued
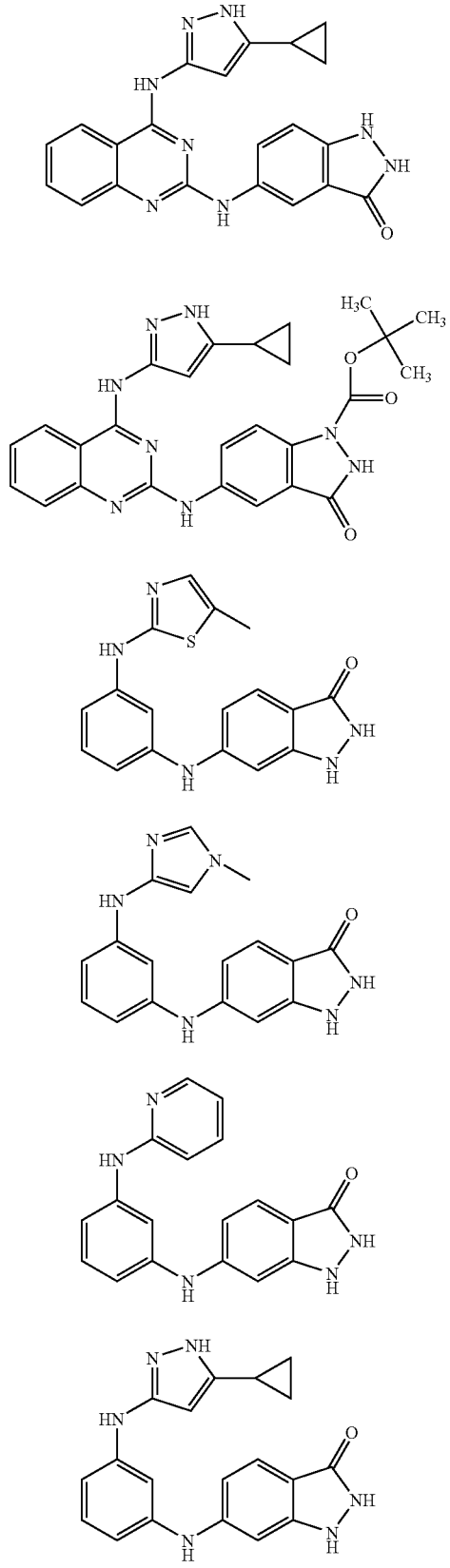
II-(i)-30
II-(i)-31
II-(i)-32
II-(i)-33
II-(i)-34
II-(i)-35
-continued
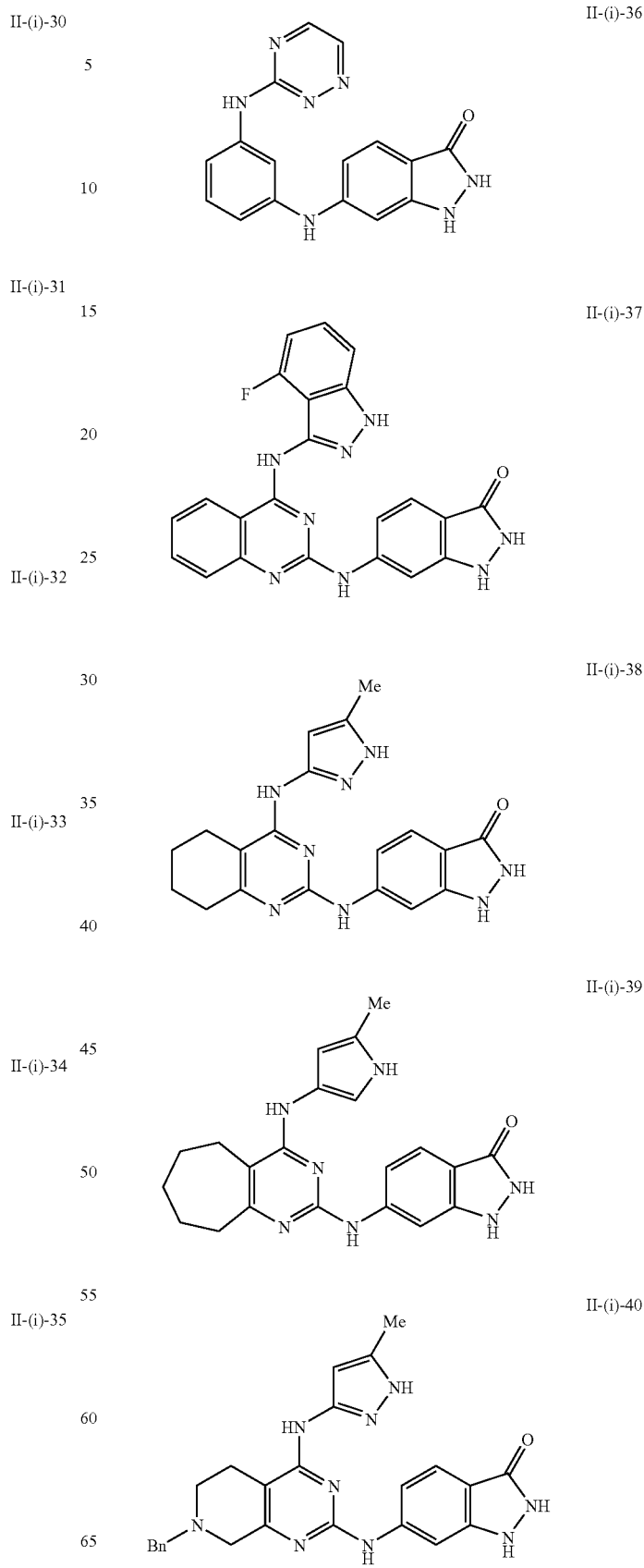
II-(i)-36
II-(i)-37
II-(i)-38
II-(i)-39
II-(i)-40

-continued
II-(i)-41
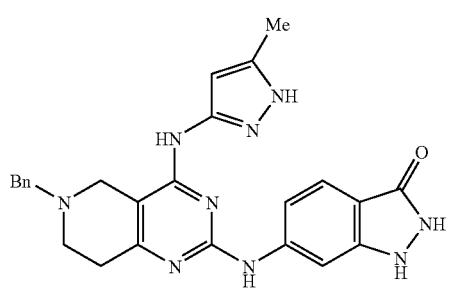
II-(i)-42
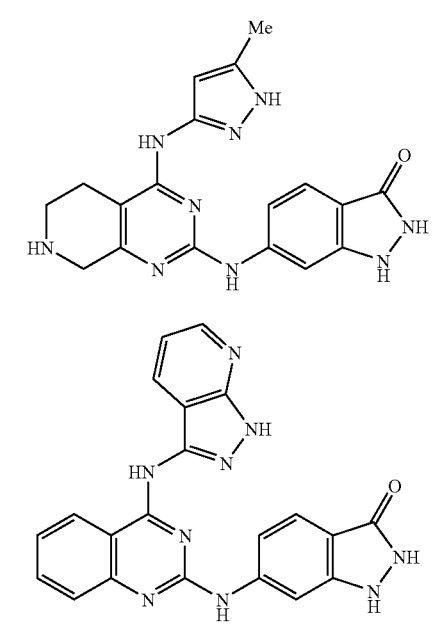
II-(i)-43
II-(i)-44
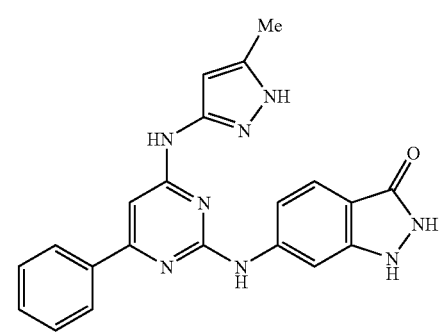
II-(i)-45
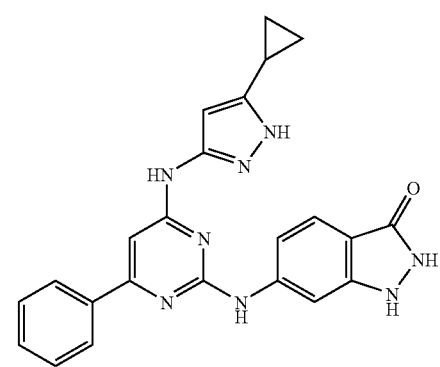
-continued
II-(i)-46
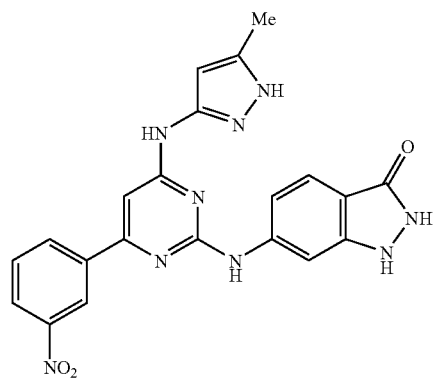
II-(i)-47
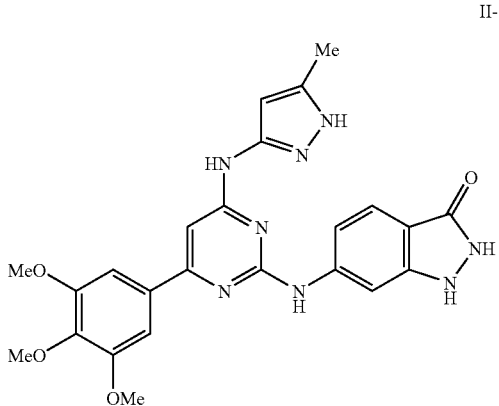
II-(i)-48
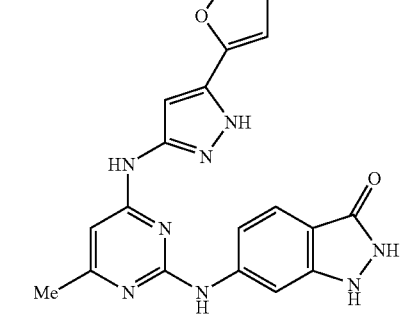
II-(i)-49
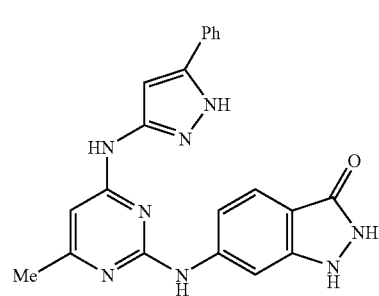

-continued
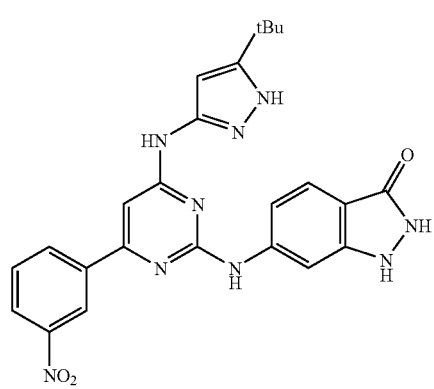
II-(i)-50
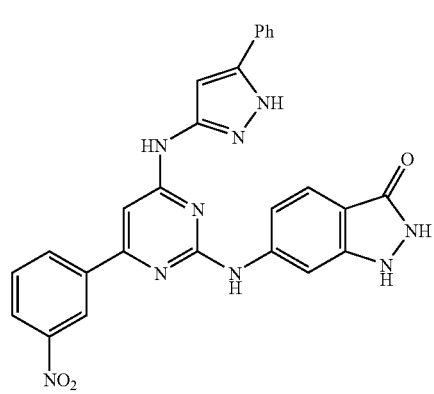
II-(i)-51
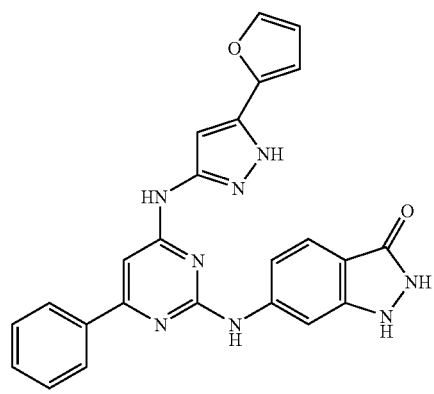
II-(i)-52
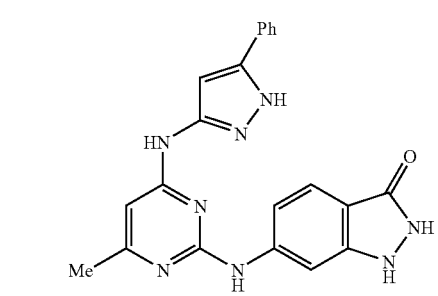
II-(i)-53
-continued
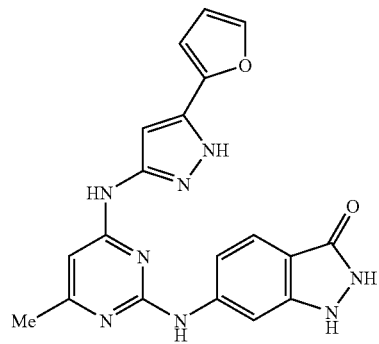
II-(i)-54
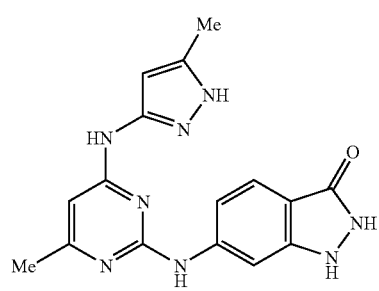
II-(i)-55
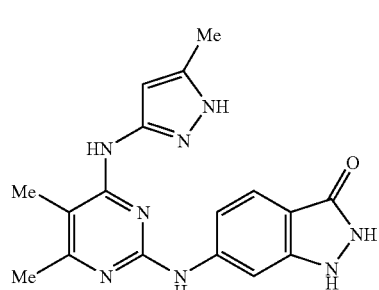
II-(i)-56
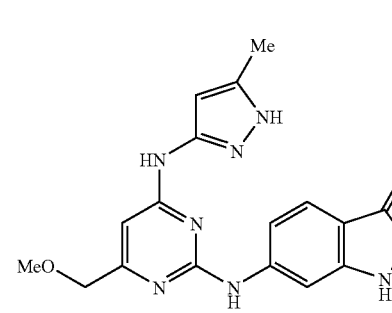
II-(i)-57
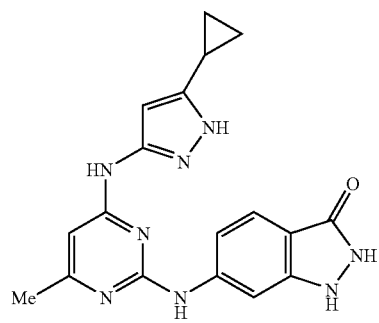
II-(i)-58

-continued
II-(i)-59
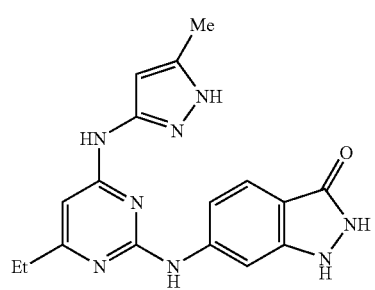
II-(i)-60
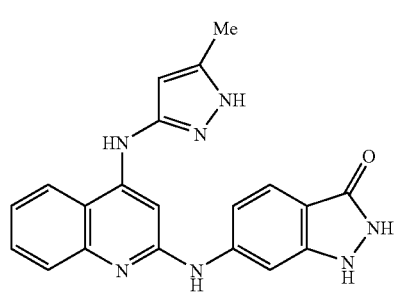
II-(i)-61
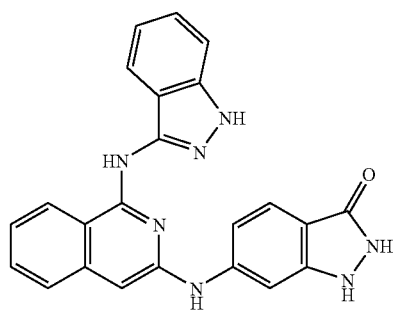
II-(i)-62
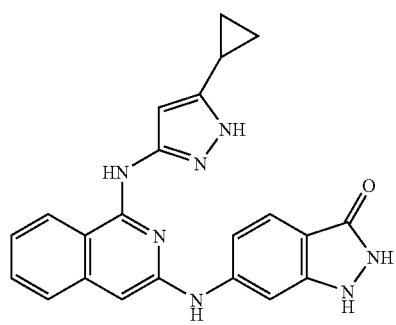
II-(i)-63
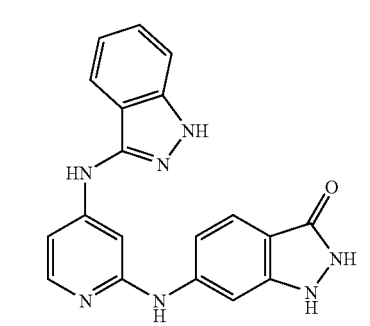
-continued
II-(i)-64
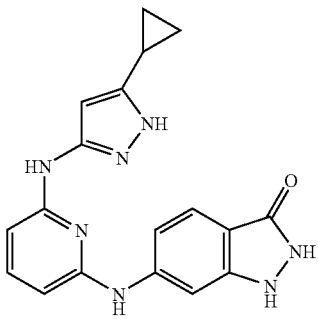
II-(i)-65
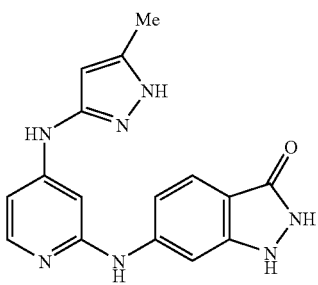
II-(i)-66
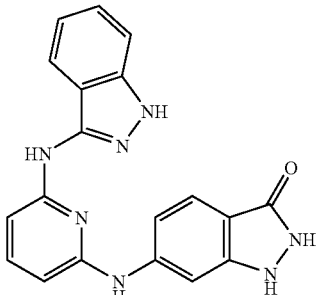
II-(i)-67
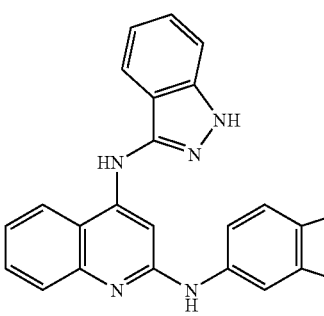
II-(i)-68
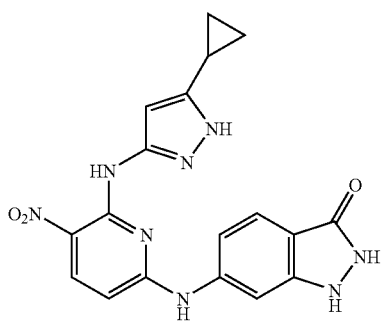

II-(i)-69
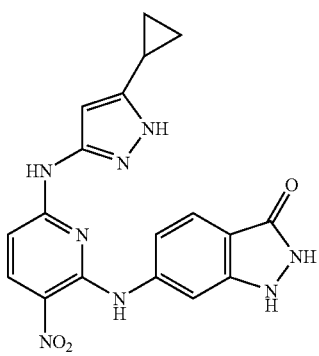
II-(ii)-1
II-(ii)-2
II-(ii)-3
II-(ii)-4
II-(ii)-5
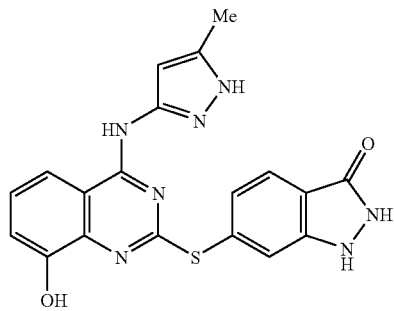
II-(ii)-6
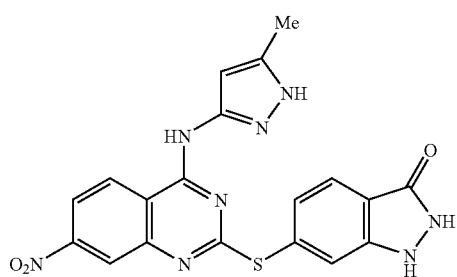
II-(ii)-7
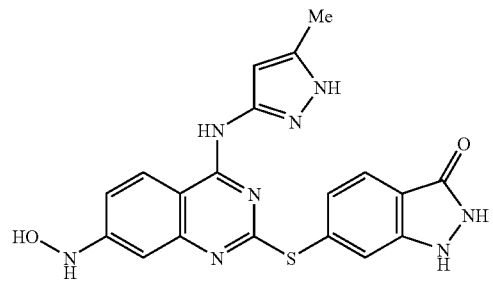
II-(ii)-8
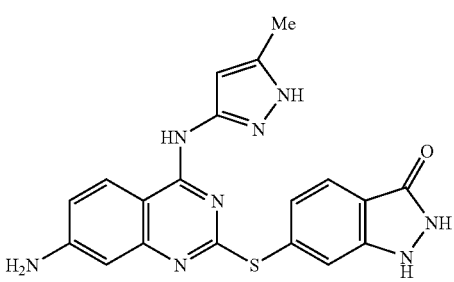
II-(ii)-9
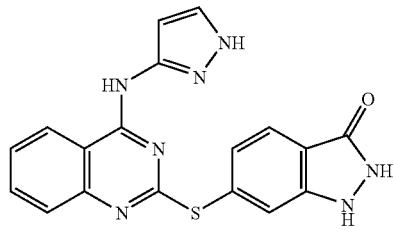

353
-continued
II-(ii)-10
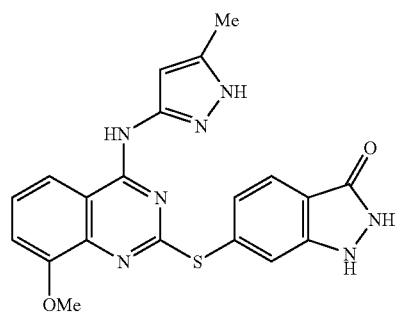
II-(ii)-11
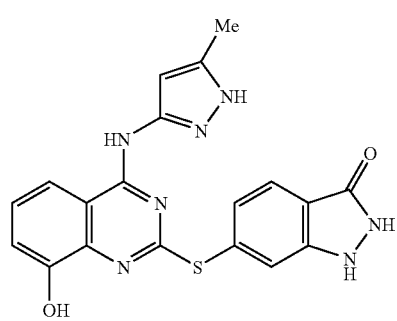
II-(ii)-12
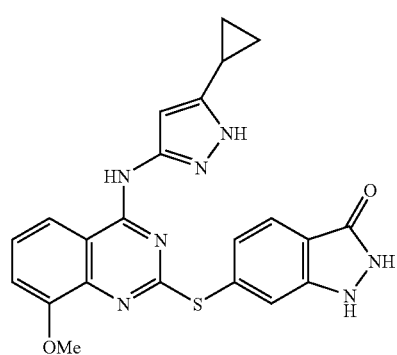
II-(ii)-13
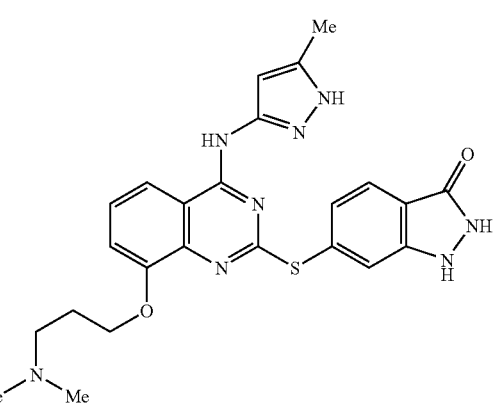
354
-continued
II-(ii)-14
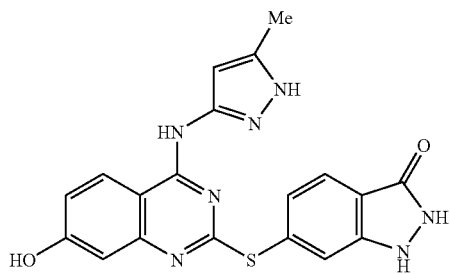
II-(ii)-15
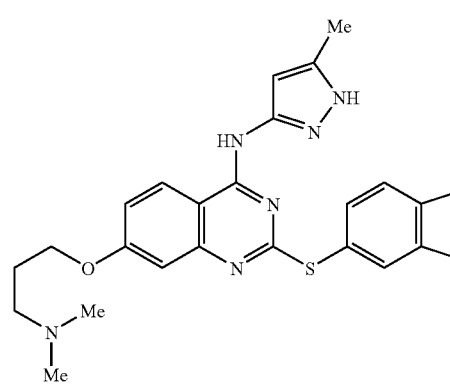
II-(ii)-16
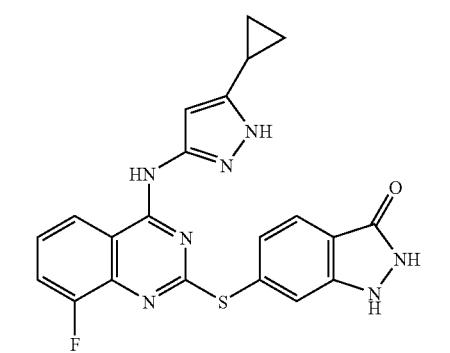
II-(ii)-17
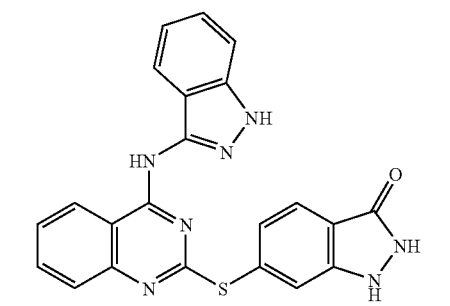

-continued
II-(ii)-18
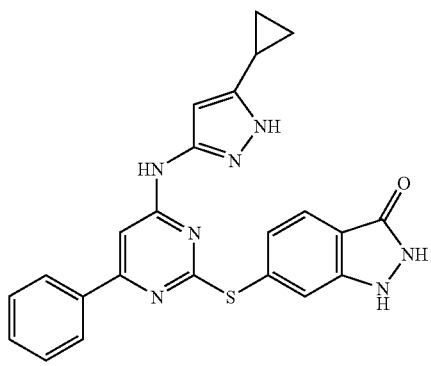
II-(ii)-19
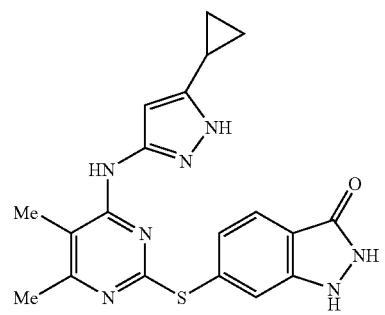
II-(ii)-20
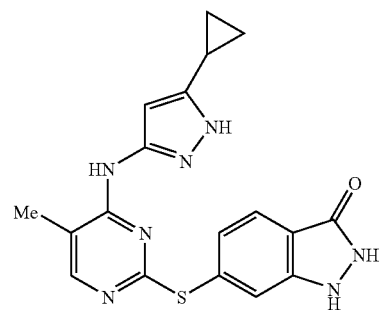
II-(ii)-21
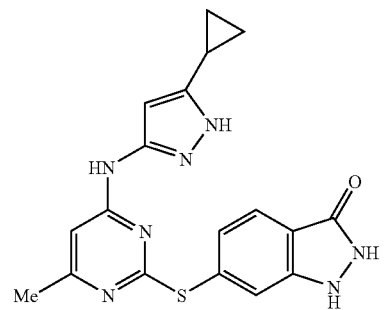
-continued
II-(ii)-22
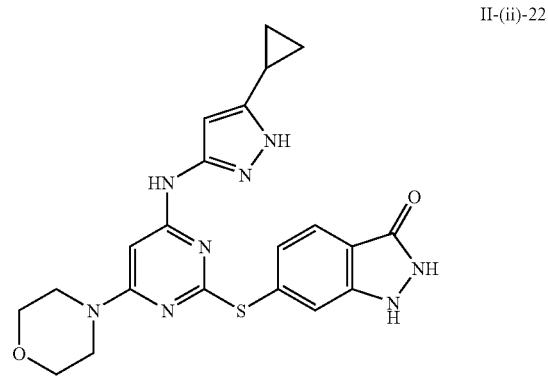
II-(ii)-23
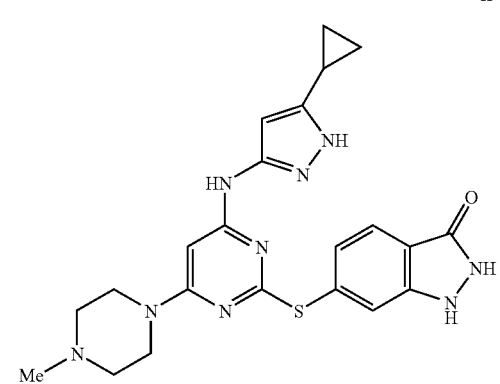
II-(ii)-24
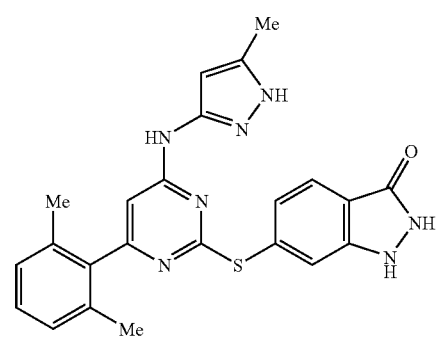
II-(ii)-25
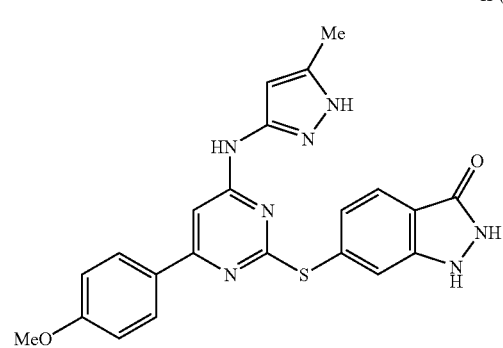

-continued
II-(ii)-26
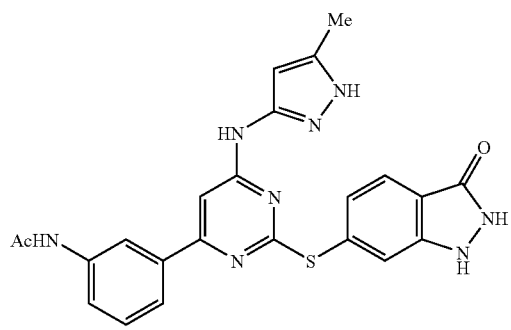
II-(ii)-27
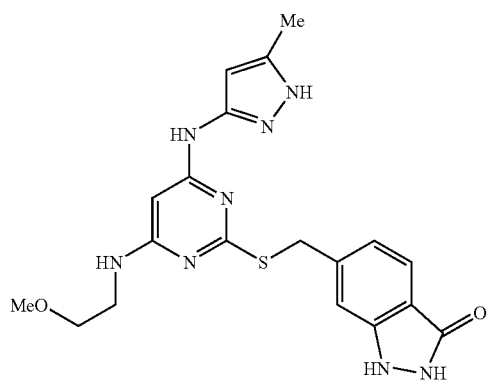
II-(ii)-28
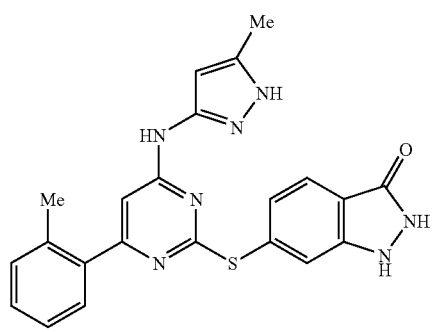
II-(ii)-29
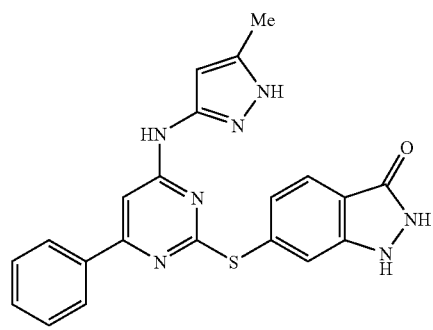
-continued
II-(ii)-30
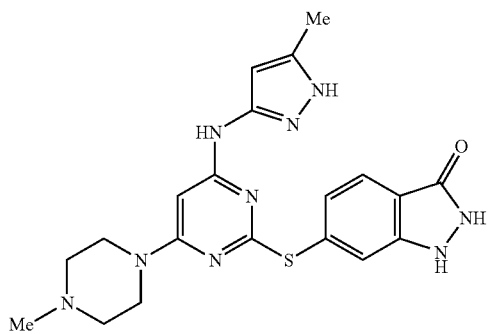
II-(ii)-31
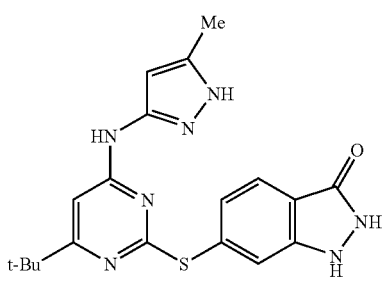
II-(ii)-32
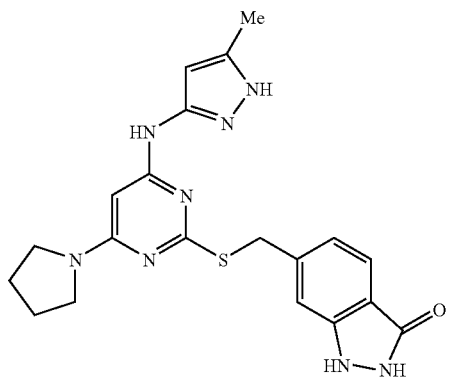
II-(ii)-33
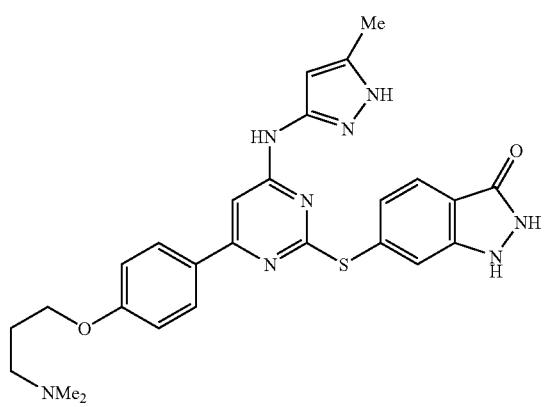

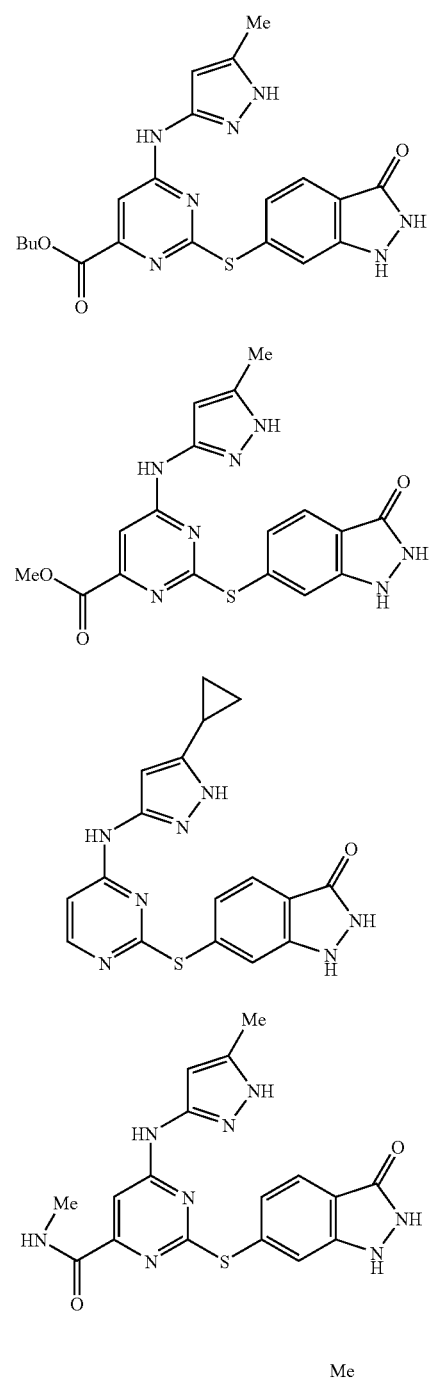
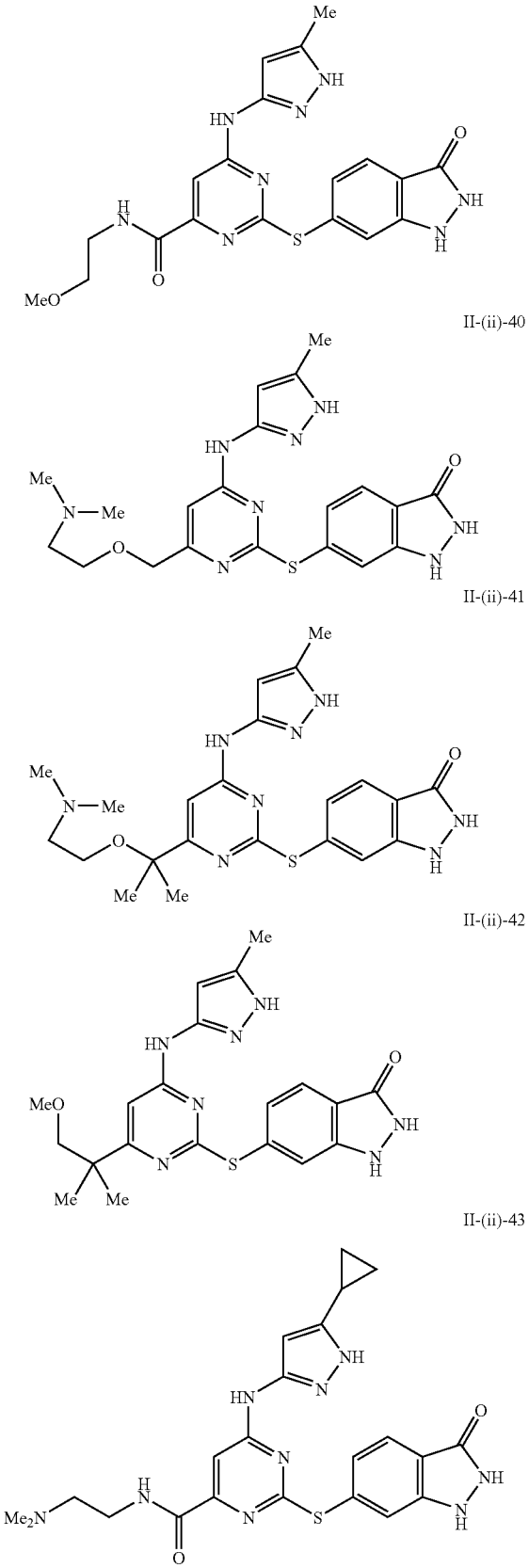

-continued
II-(ii)-44
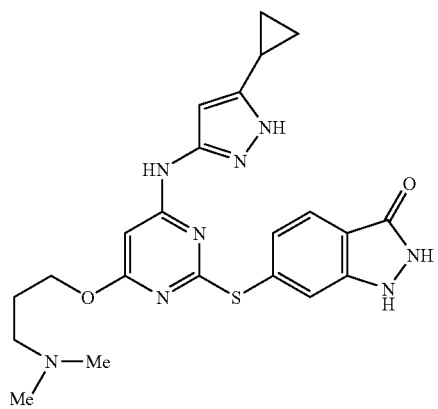
II-(ii)-45
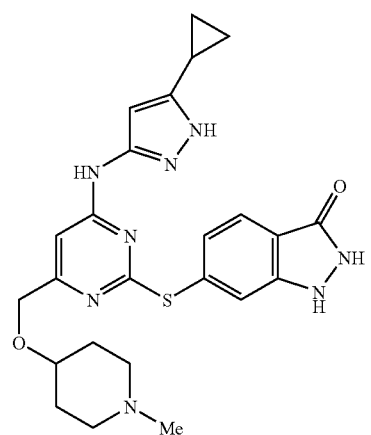
II-(ii)-46
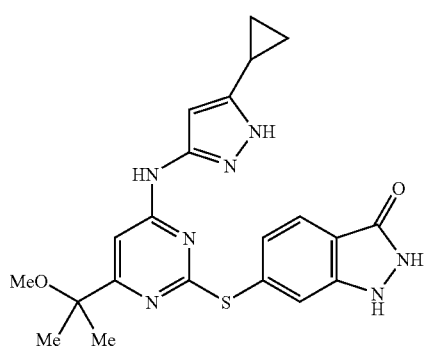
II-(ii)-47
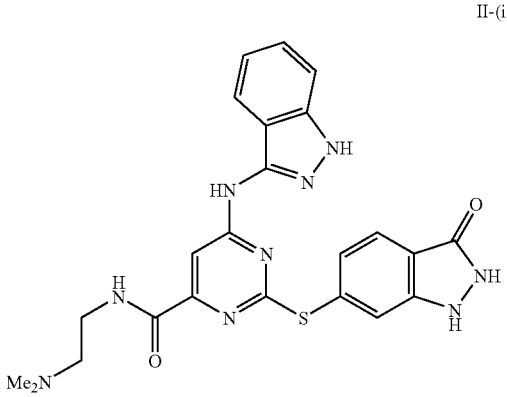
-continued
II-(ii)-48
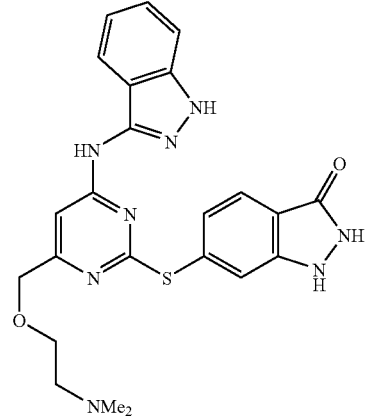
II-(ii)-49
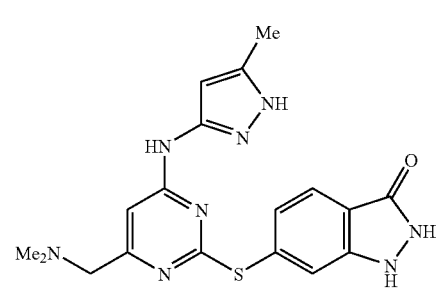
II-(ii)-50
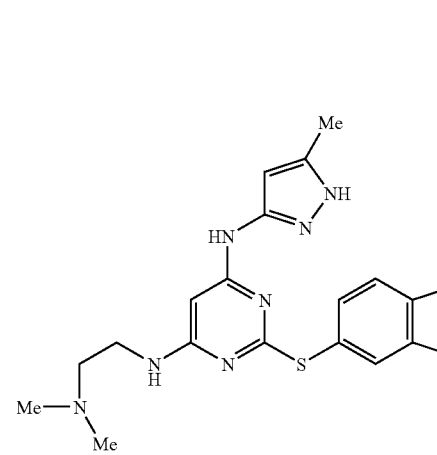
II-(ii)-51
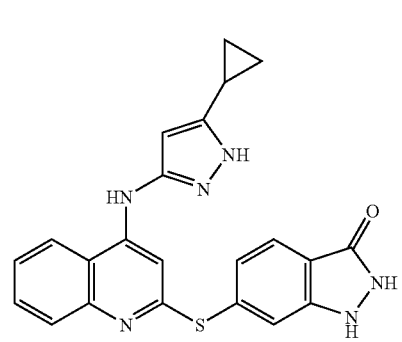

II-(ii)-52
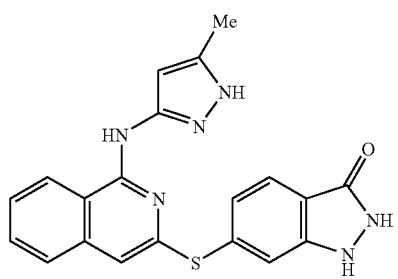
II-(ii)-53
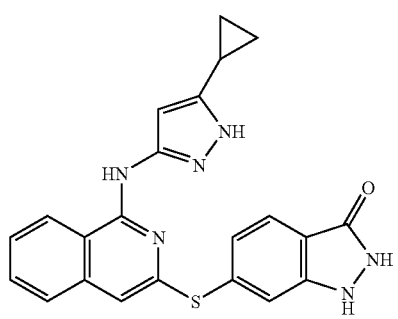
II-(ii)-54
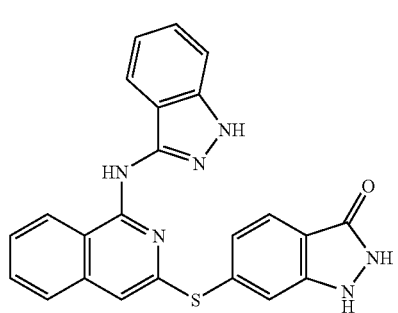
II-(ii)-55
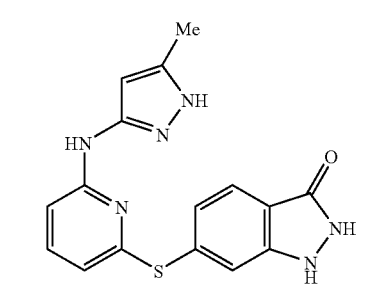
II-(ii)-56
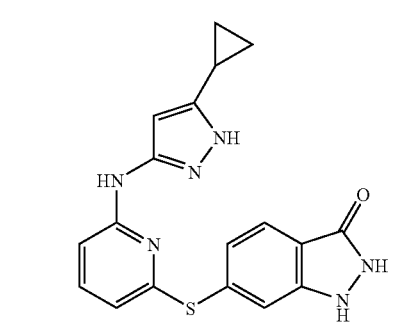
II-(ii)-57
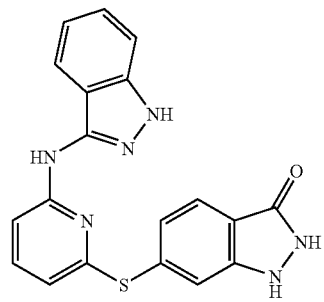
II-(ii)-58
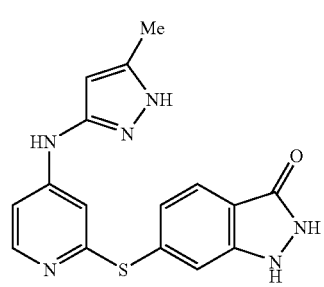
II-(ii)-59
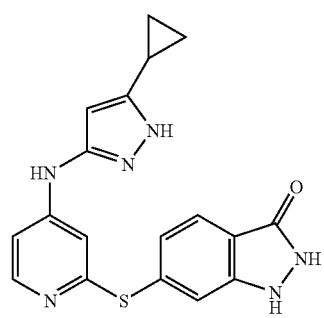
II-(ii)-60
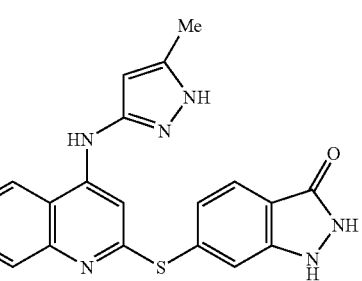
II-(iii)-1
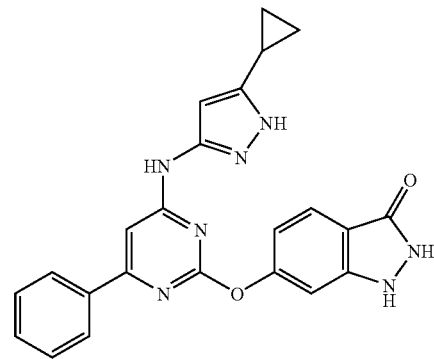

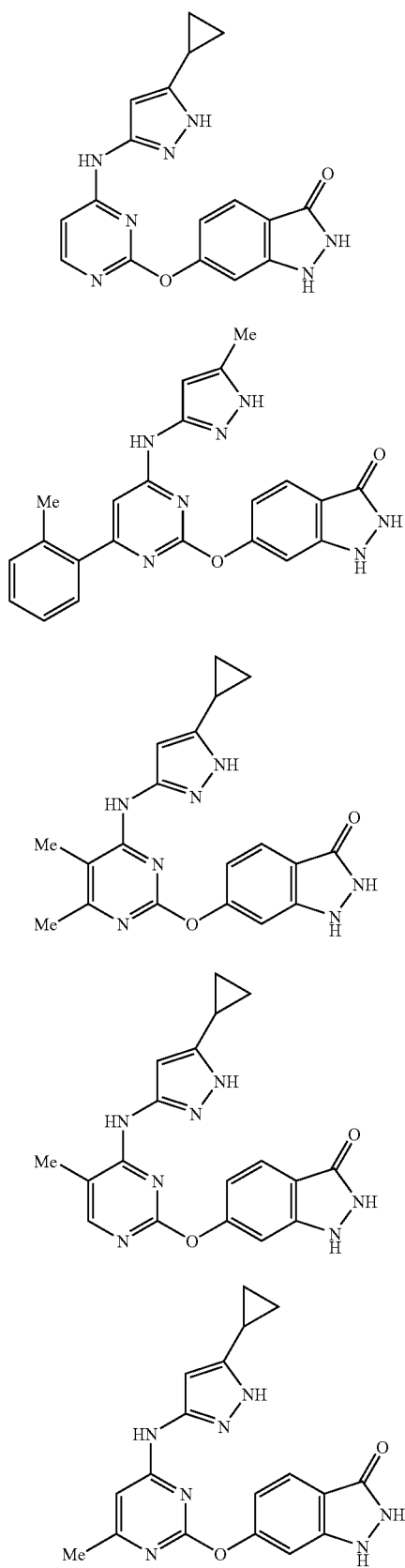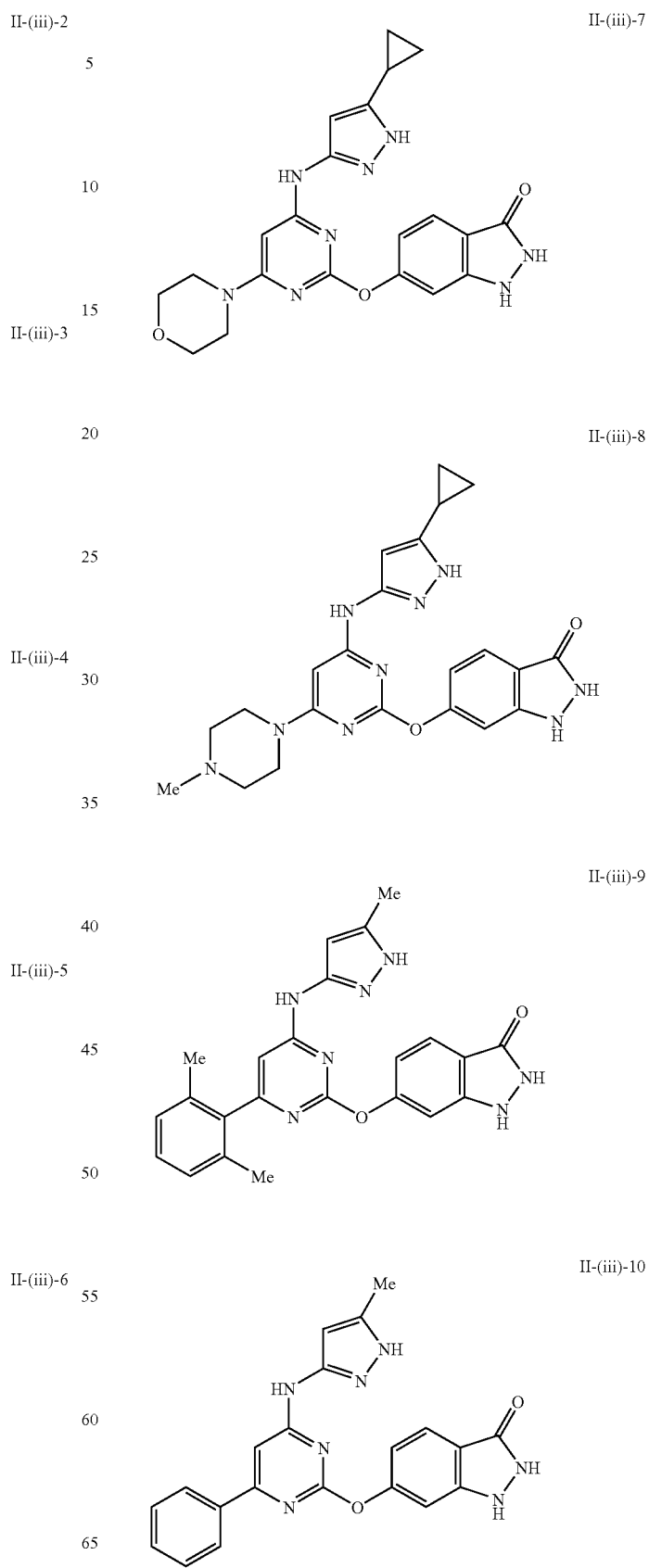

-continued
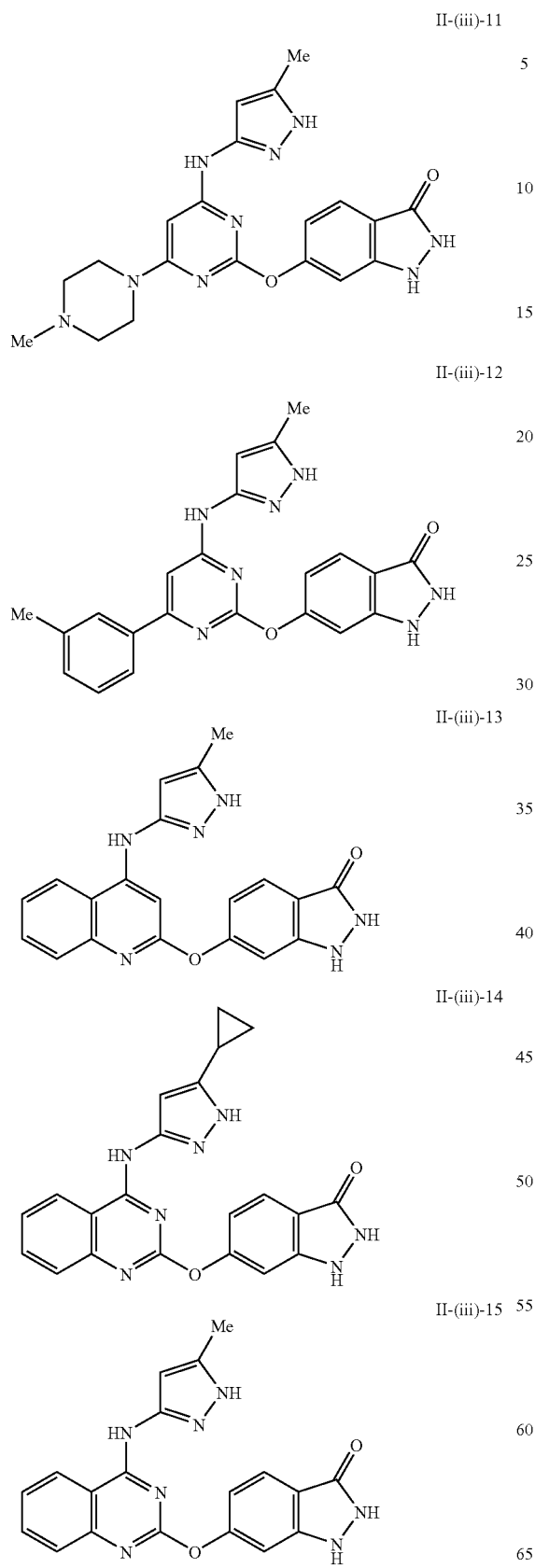
II-(iii)-11
II-(iii)-12
II-(iii)-13
II-(iii)-14
II-(iii)-15
-continued
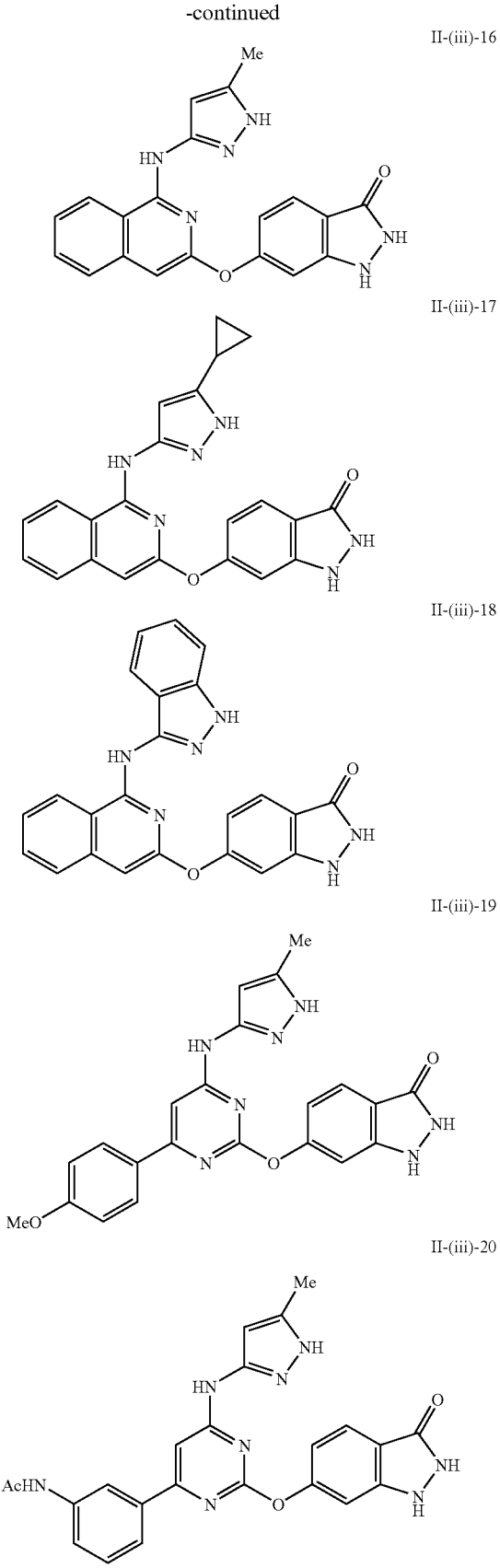
II-(iii)-16
II-(iii)-17
II-(iii)-18
II-(iii)-19
II-(iii)-20

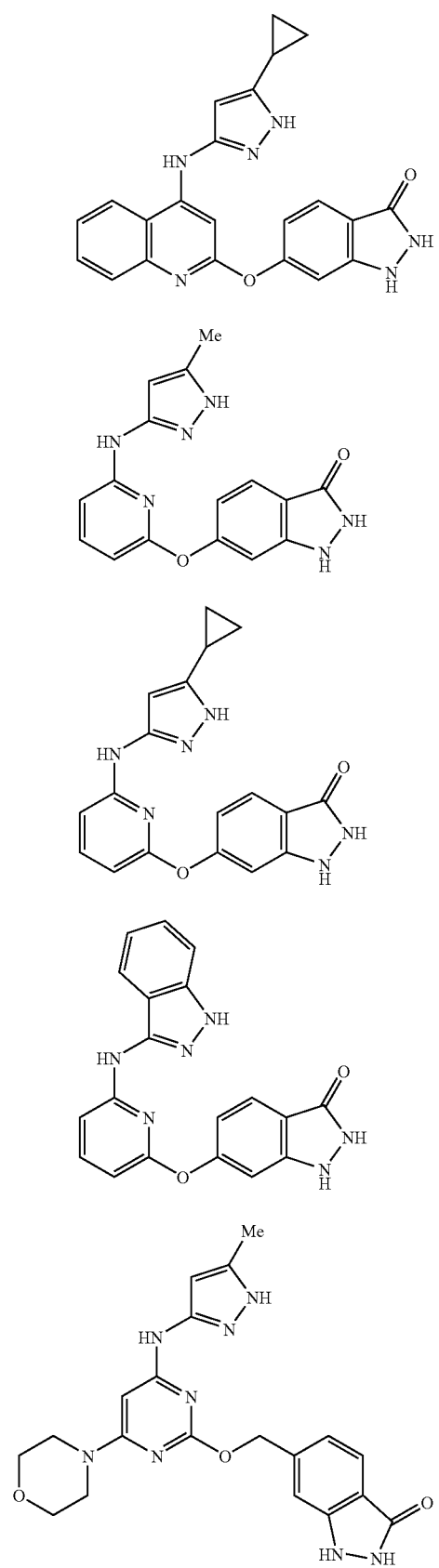
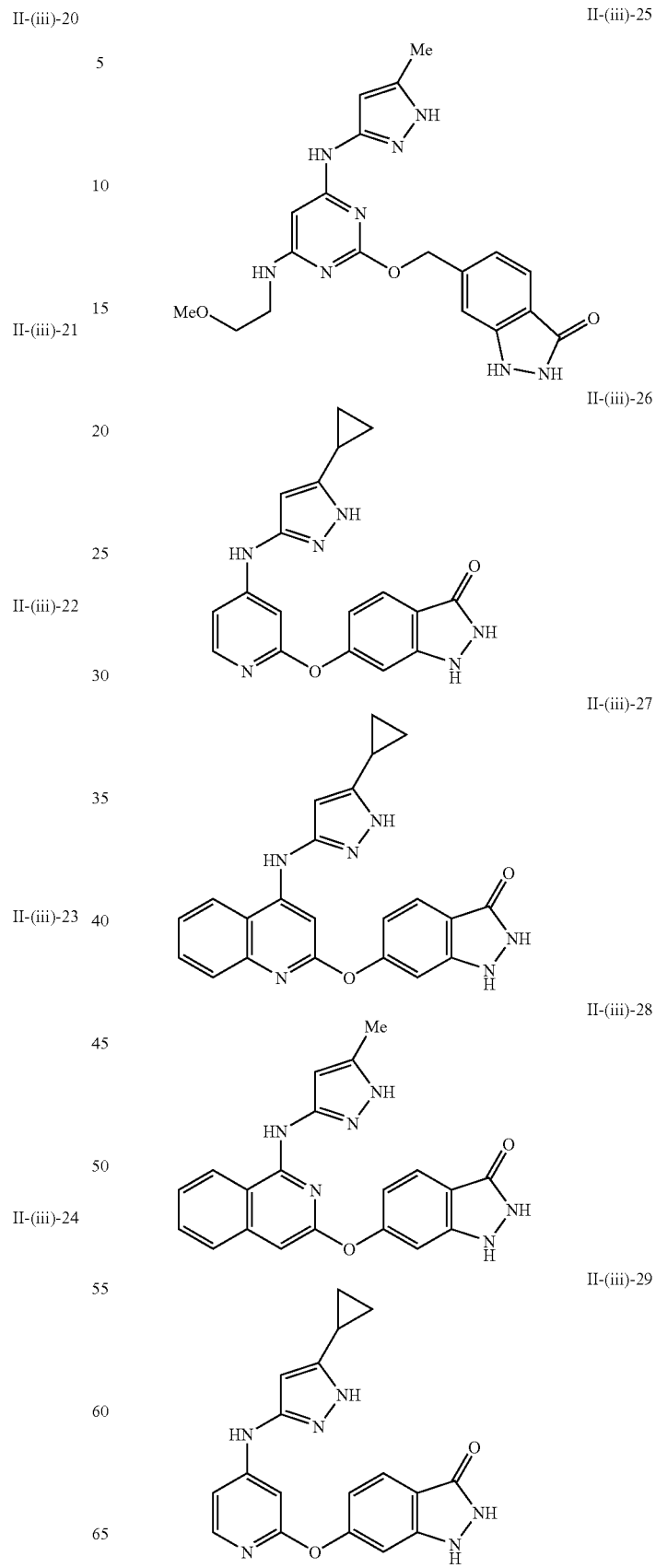

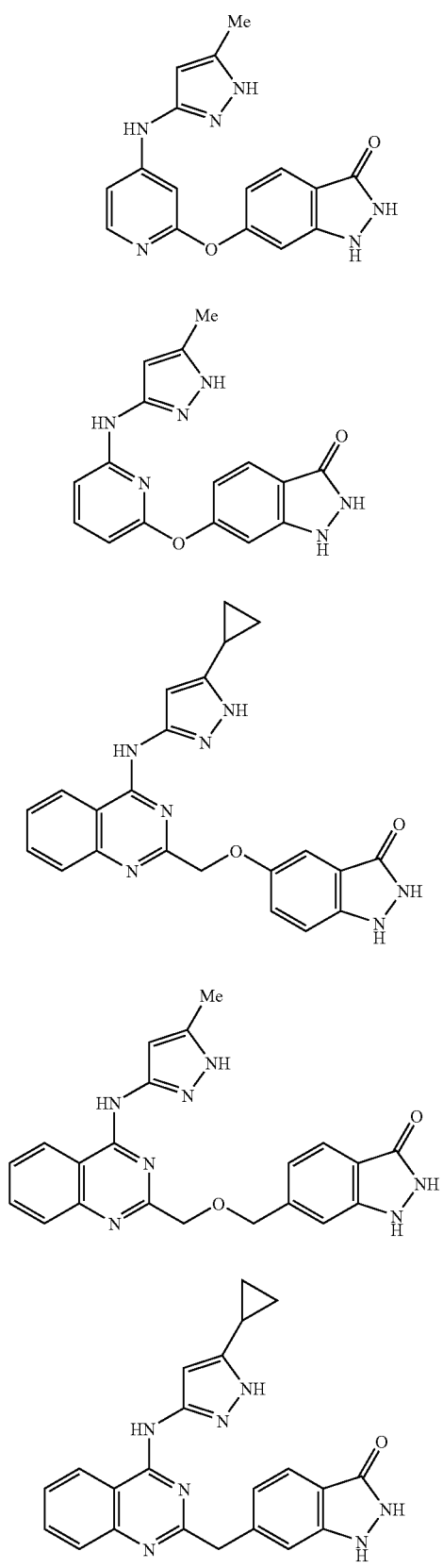
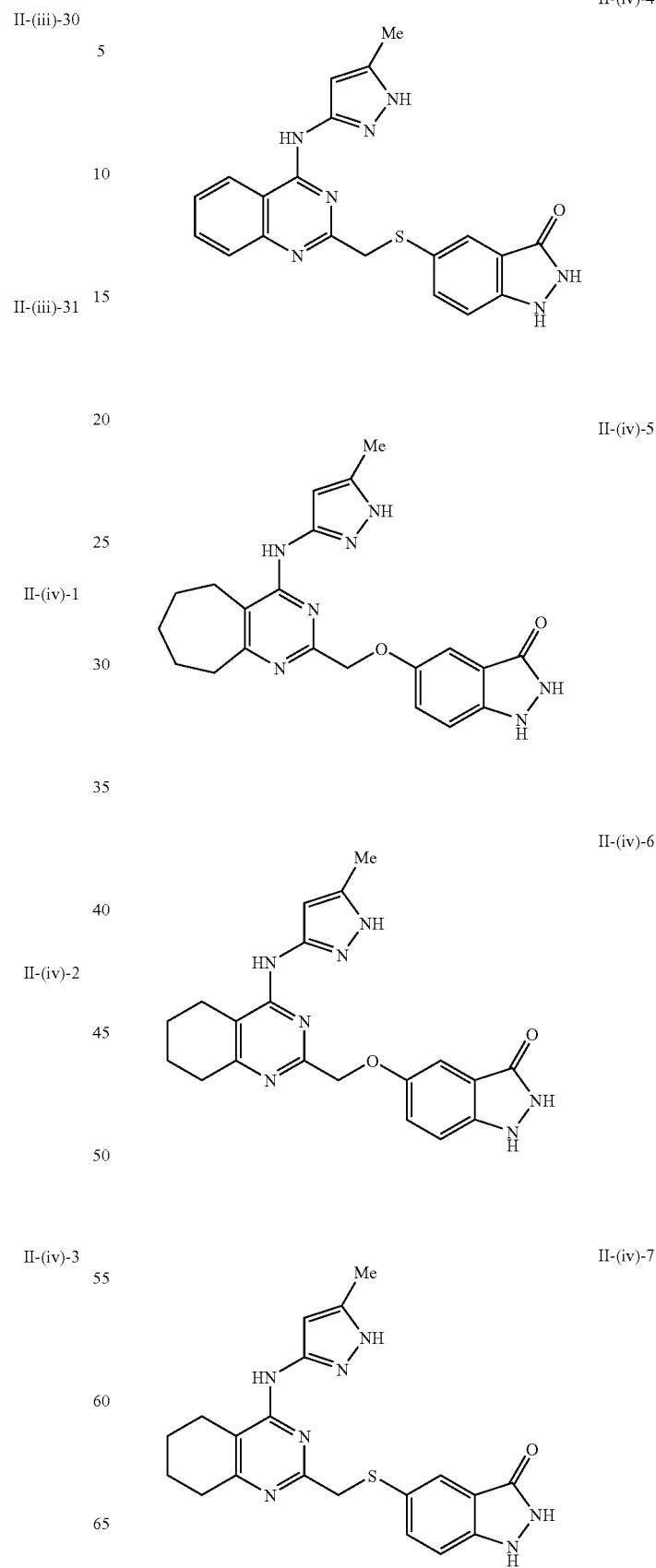

-continued
II-(iv)-8
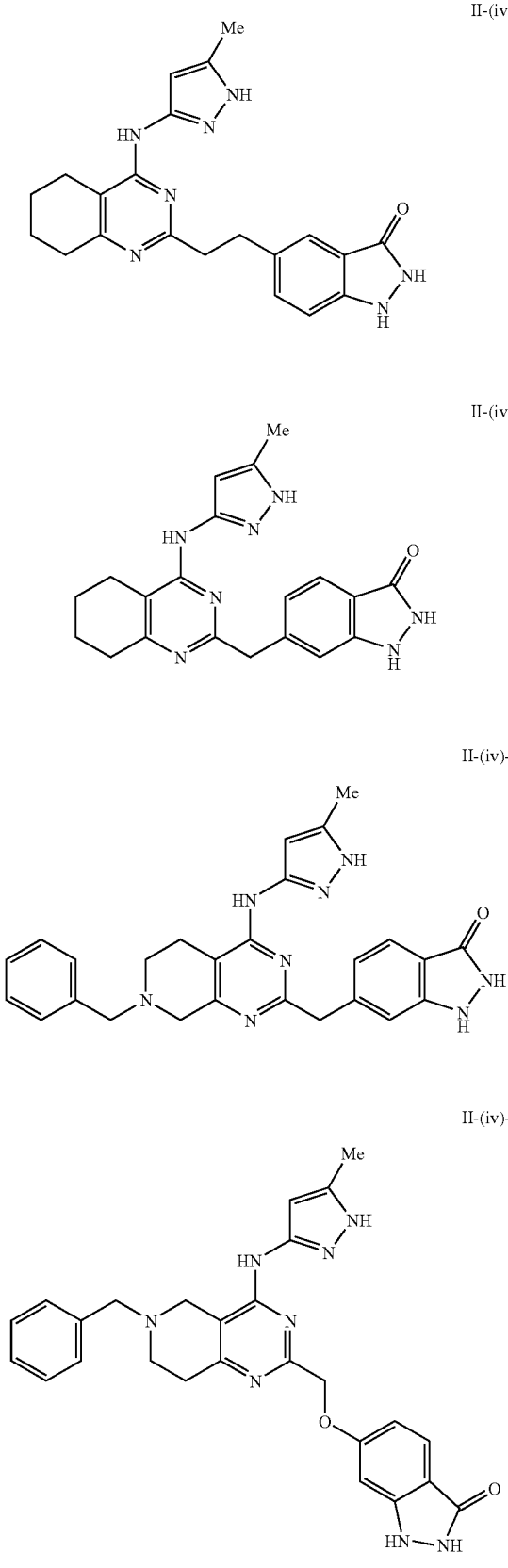
II-(iv)-9
II-(iv)-10
II-(iv)-11
-continued
II-(iv)-12
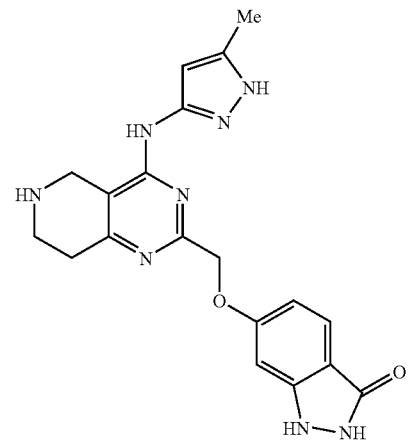
II-(iv)-13
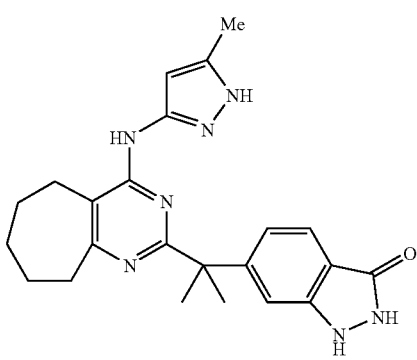
II-(iv)-14
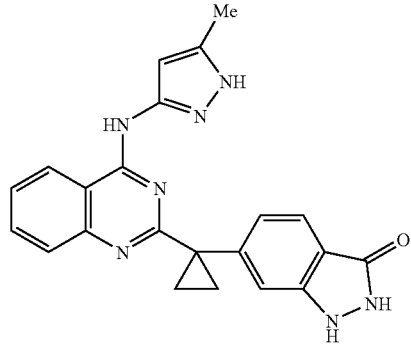
II-(iv)-15
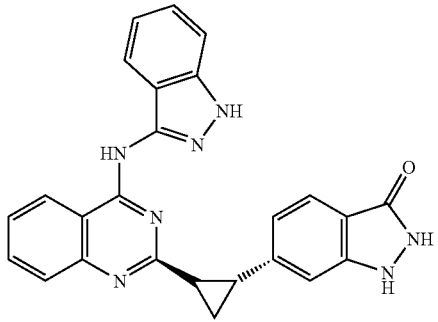

II-(iv)-16
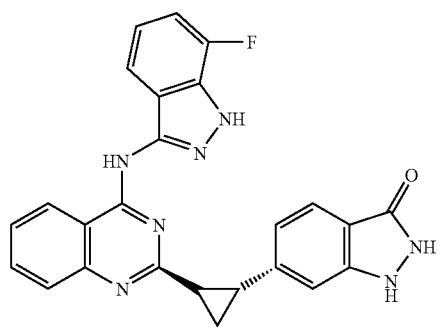
II-(iv)-17
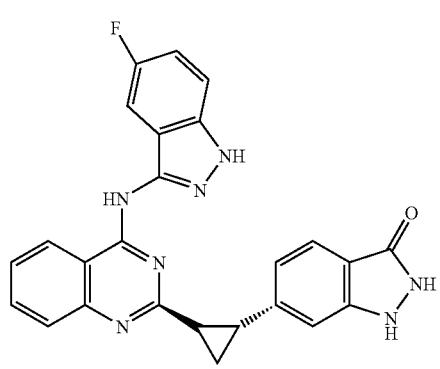
II-(iv)-18
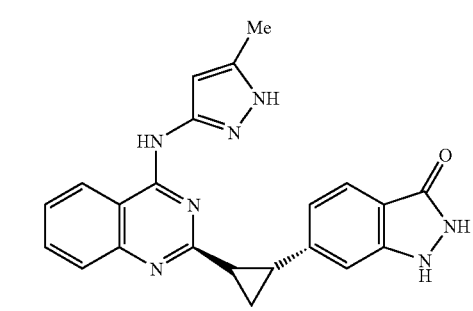
II-(iv)-19
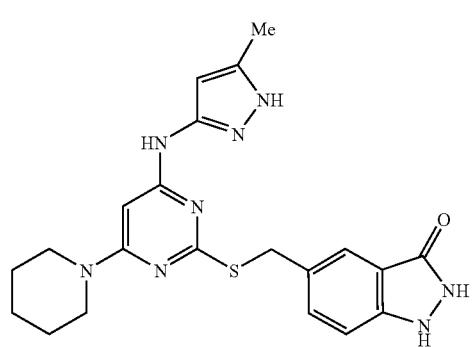
II-(iv)-20
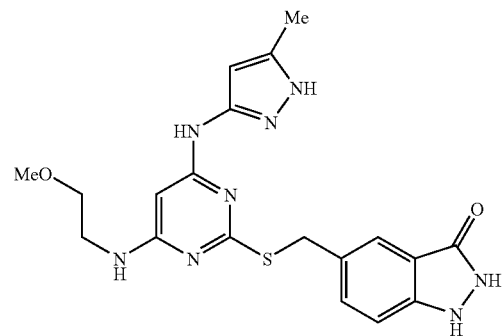
II-(iv)-21
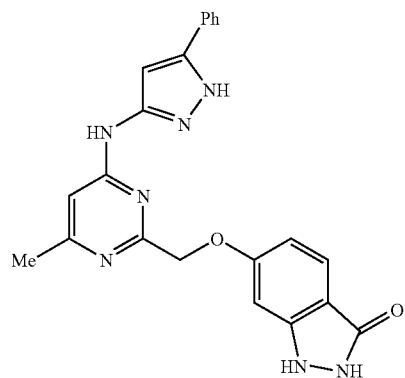
II-(iv)-22
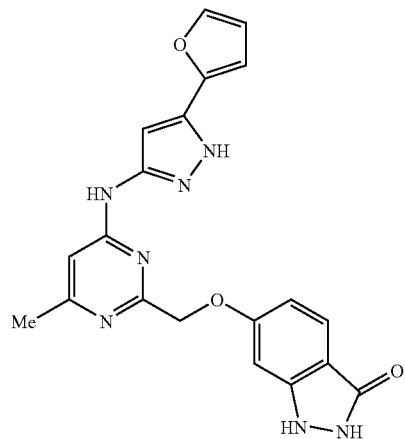
II-(iv)-23
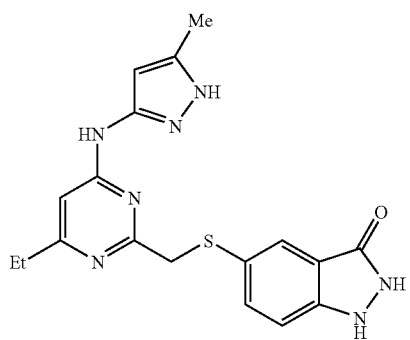

II-(iv)-24
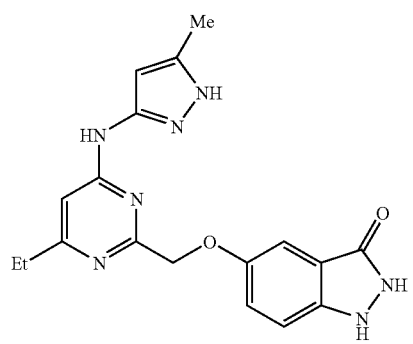
II-(iv)-25
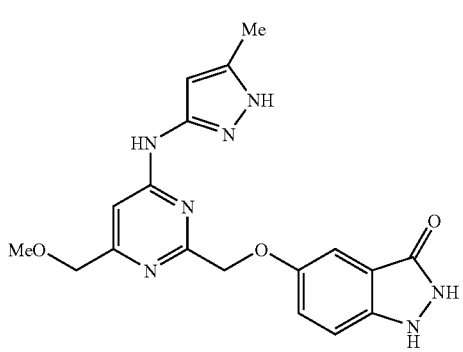
II-(iv)-26
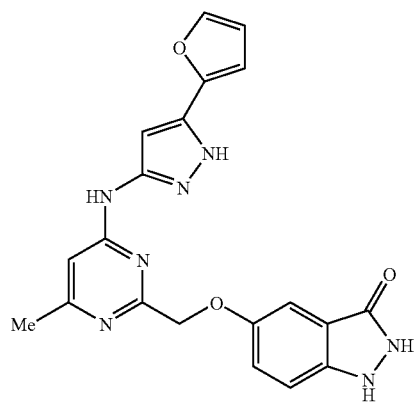
II-(iv)-27
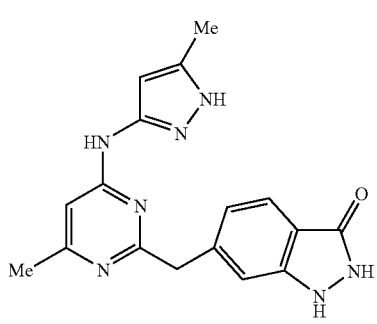
II-(iv)-28
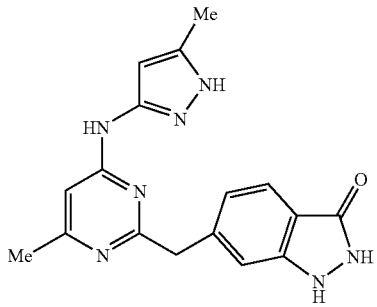
II-(iv)-29
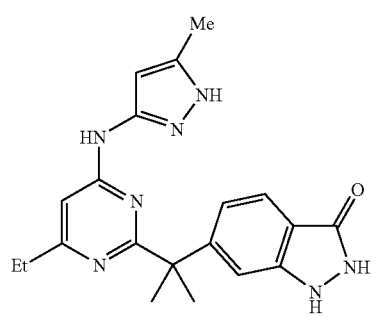
II-(iv)-30
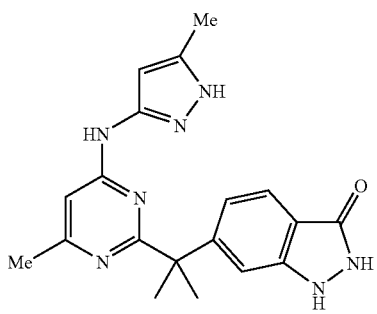
II-(iv)-31
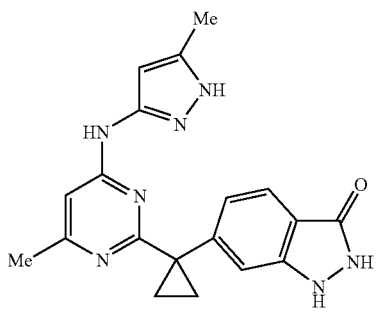
II-(iv)-32
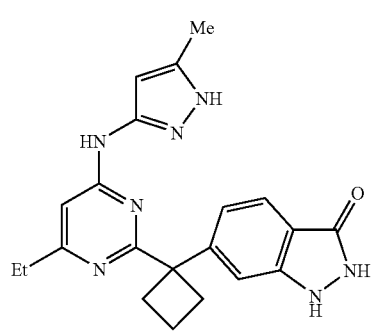

-continued
II-(iv)-33
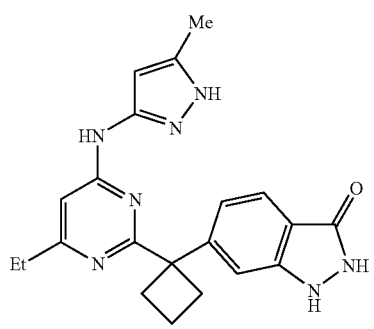
II-(iv)-34
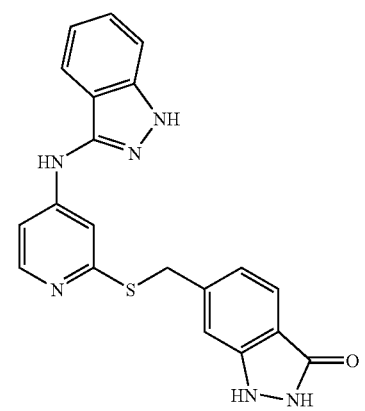
II-(iv)-35
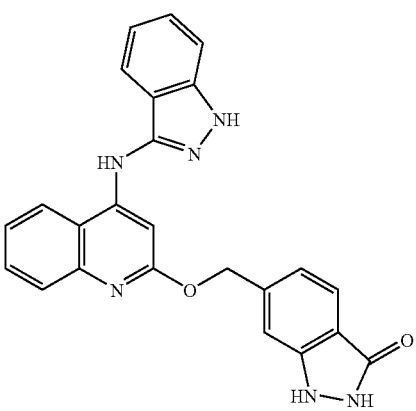
II-(iv)-36
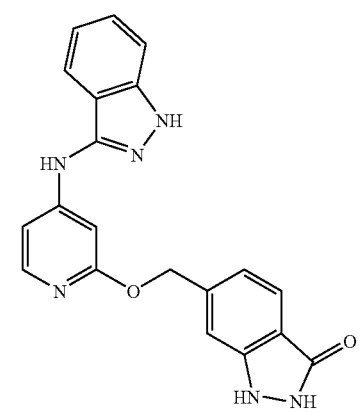
-continued
II-(iv)-37
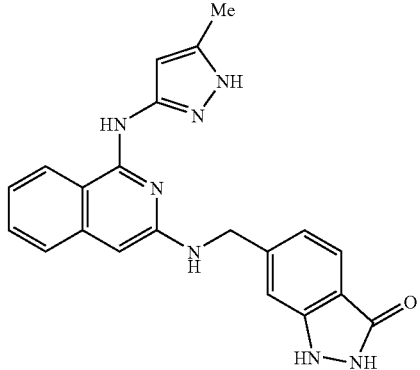
II-(iv)-38
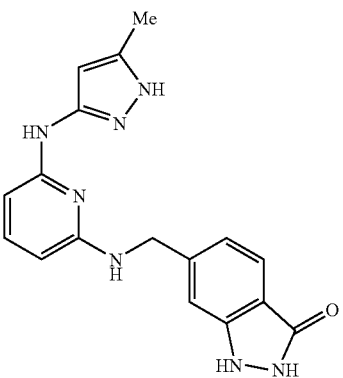
II-(iv)-39
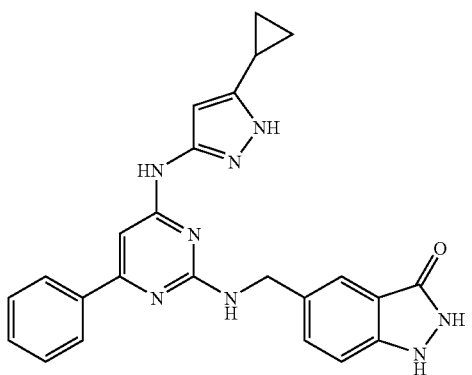
II-(iv)-40
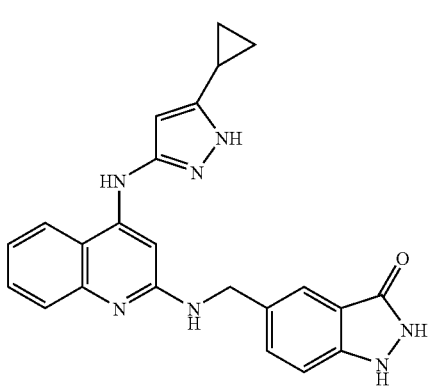

-continued
II-(iv)-41
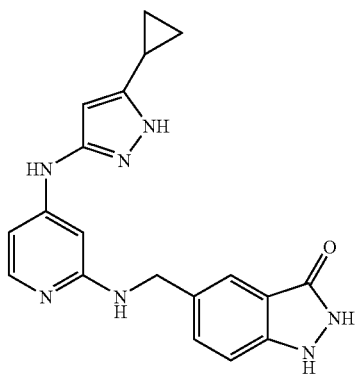
II-(iv)-42
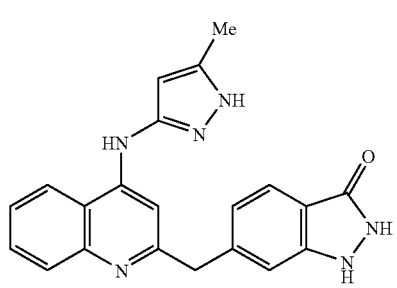
II-(iv)-43
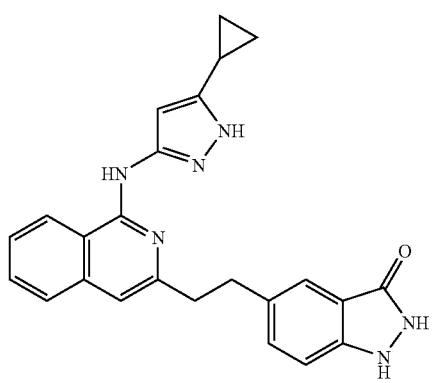
II-(iv)-44
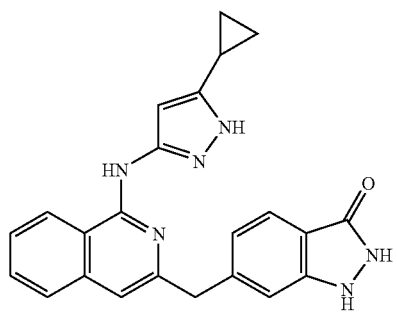
-continued
II-(iv)-45
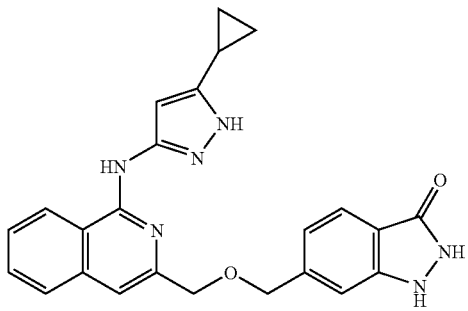
II-(iv)-46
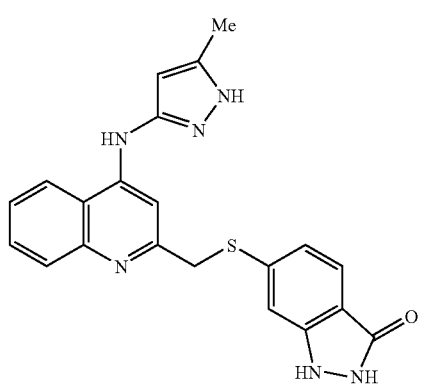
II-(iv)-47
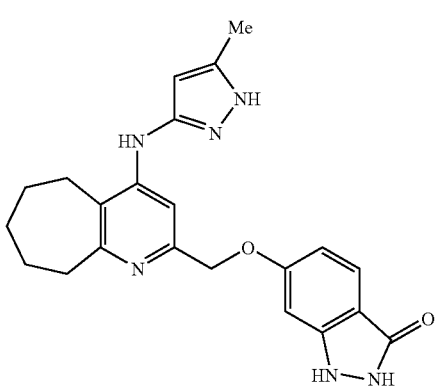
II-(iv)-48
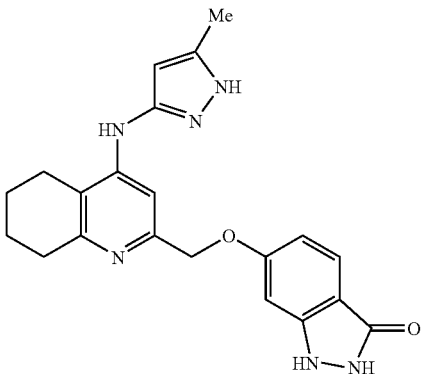

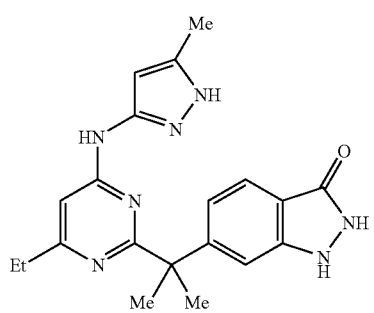
II-(iv)-49
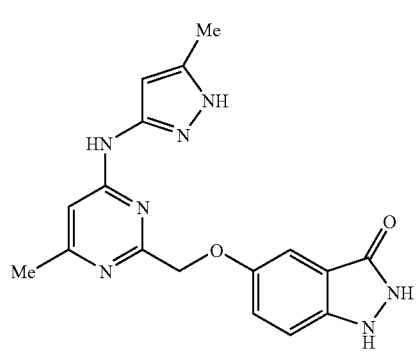
II-(iv)-50
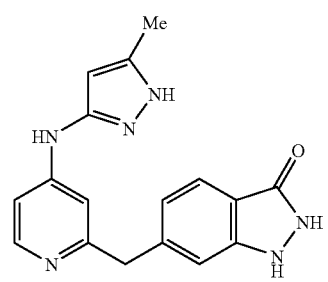
II-(iv)-51
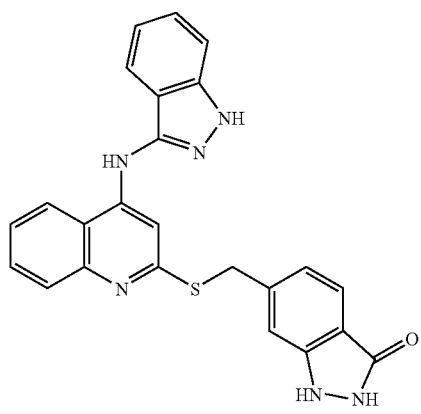
II-(iv)-52
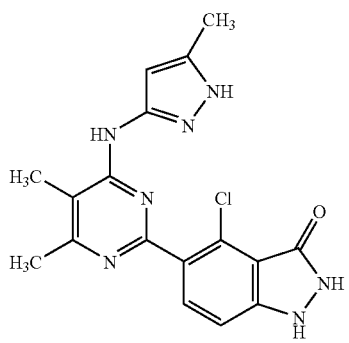
II-(v)-1
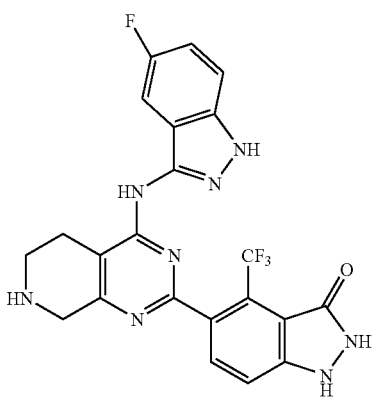
II-(v)-2
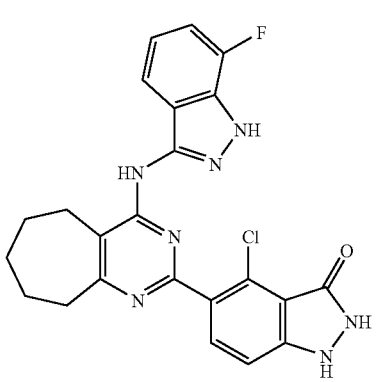
II-(v)-3
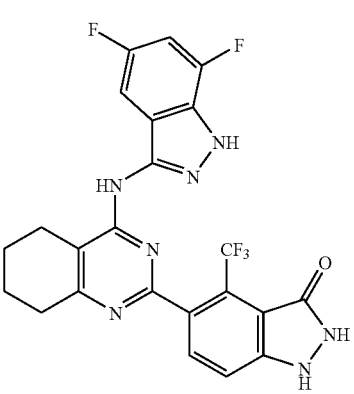
II-(v)-4

-continued
II-(v)-5
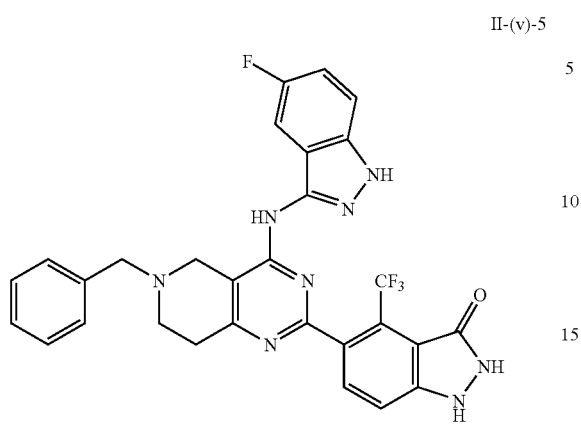
II-(v)-6
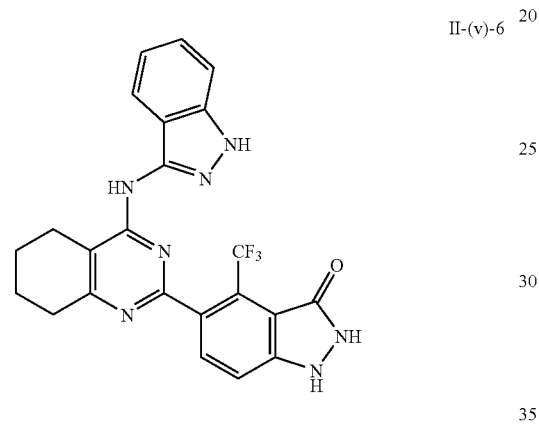
II-(v)-7
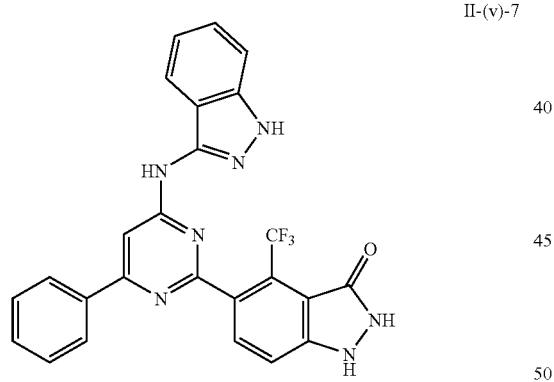
II-(v)-8
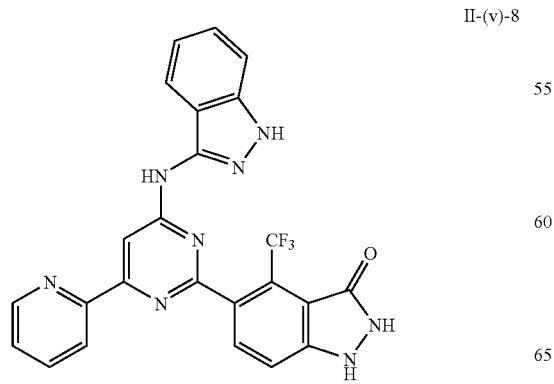
-continued
II-(v)-9
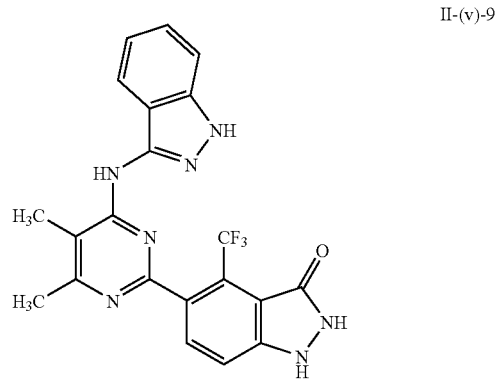
II-(v)-10
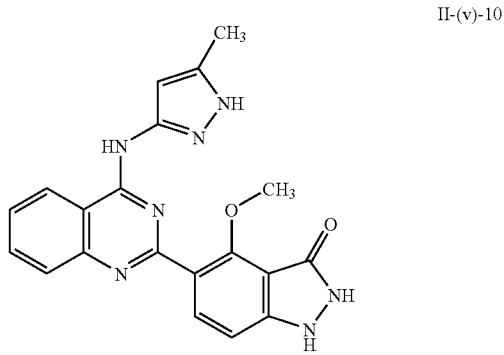
II-(v)-11
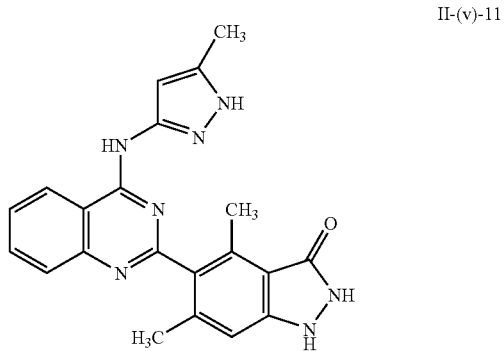
II-(v)-12
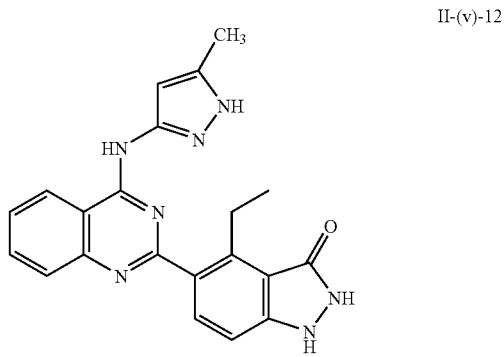

-continued

II-(v)-13

II-(v)-14

II-(v)-15

II-(v)-16

-continued

II-(v)-17

II-(v)-18

II-(v)-19

II-(v)-20

-continued

-continued
II-(v)-29
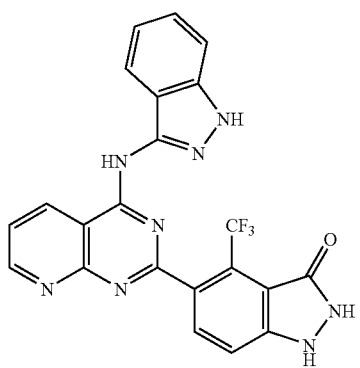
II-(v)-30
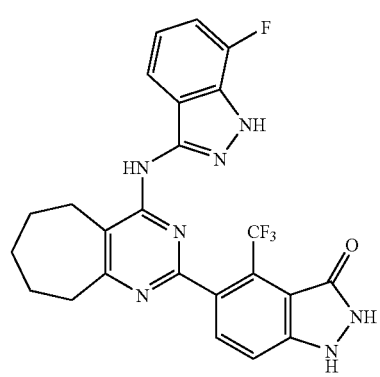
II-(v)-31
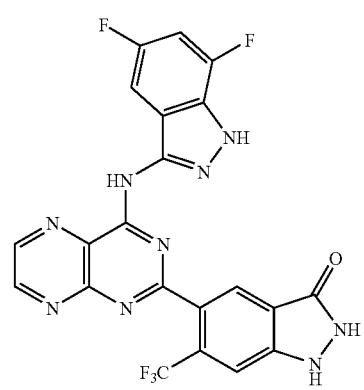
II-(v)-32
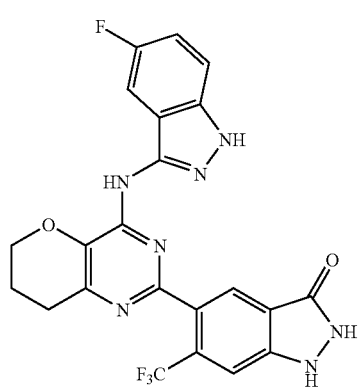
-continued
II-(v)-33
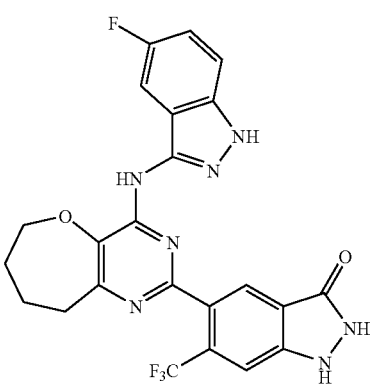
II-(v)-34
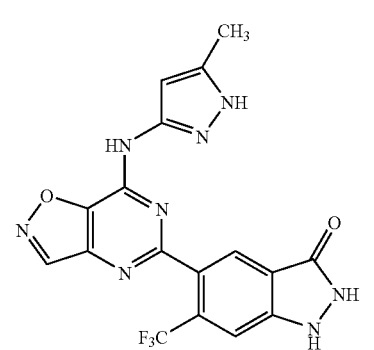
II-(v)-35
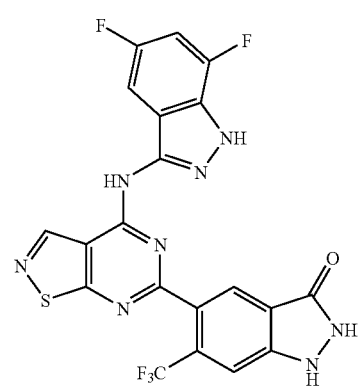
II-(v)-36
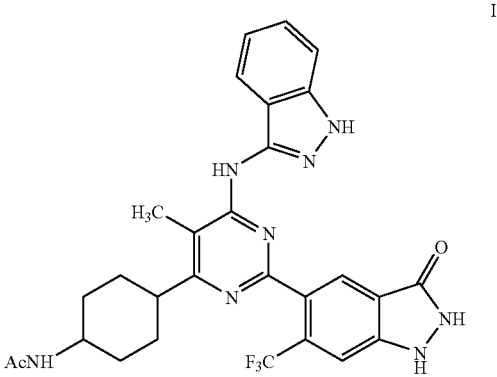

-continued
II-(v)-37
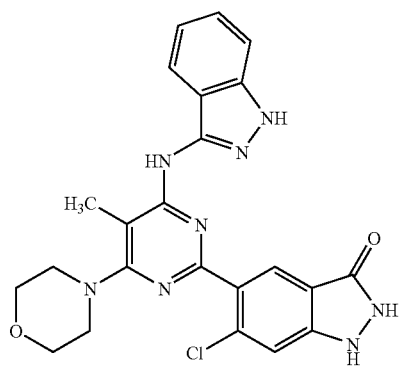
II-(v)-38
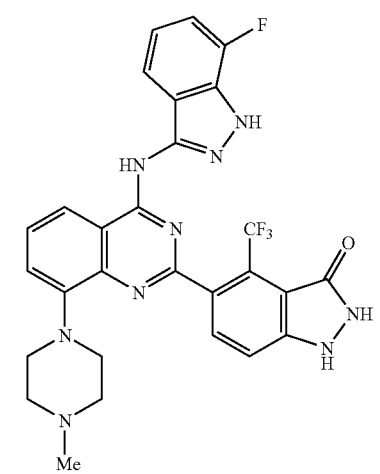
II-(v)-39
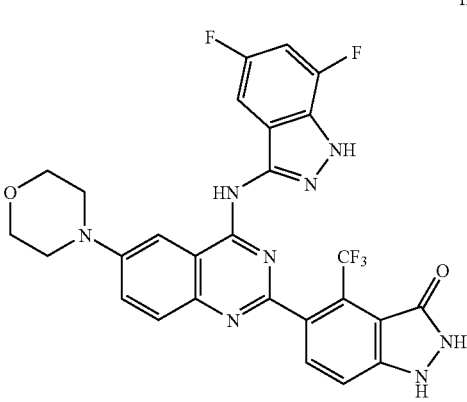
II-(v)-40
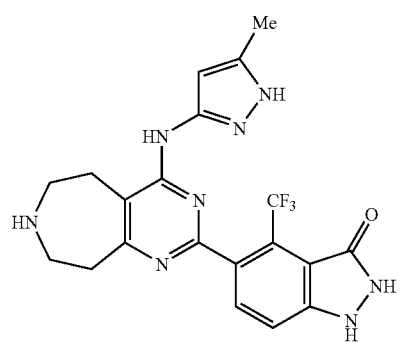
-continued
II-(v)-41
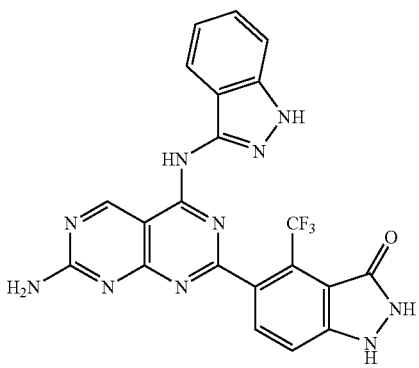
II-(v)-42
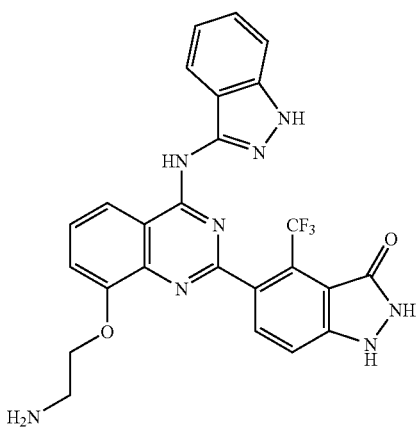
II-(v)-43
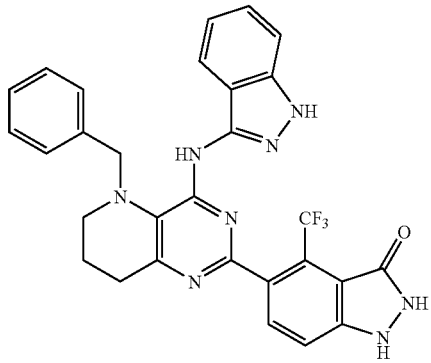
II-(v)-44
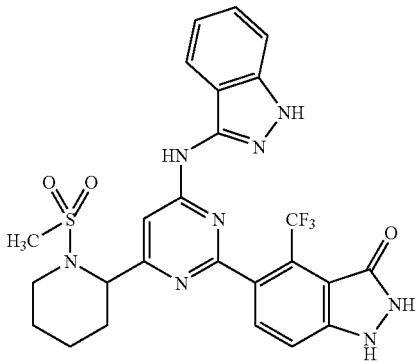

-continued
II-(v)-45
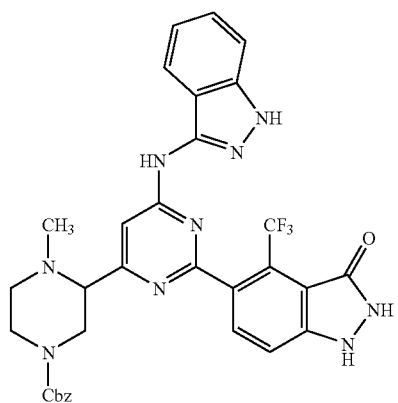
II-(v)-46
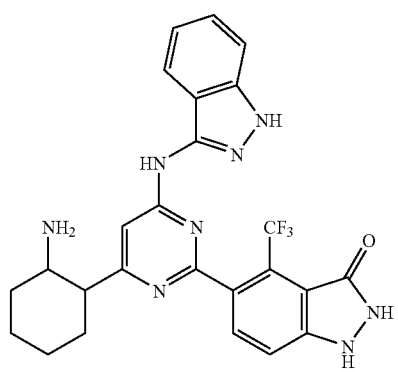
II-(v)-47
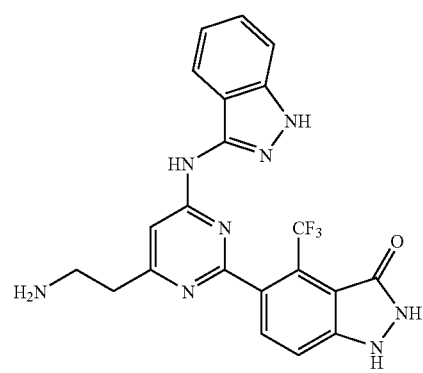
II-(v)-48
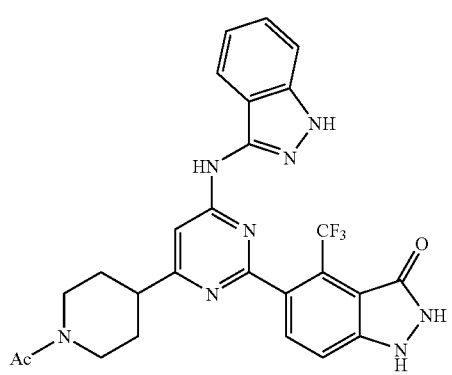
-continued
II-(v)-49
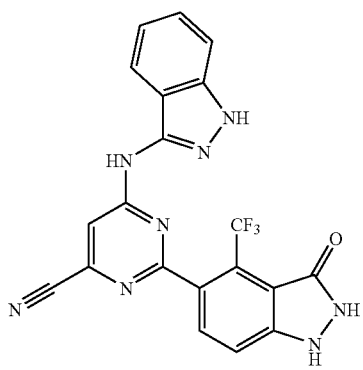
II-(v)-50
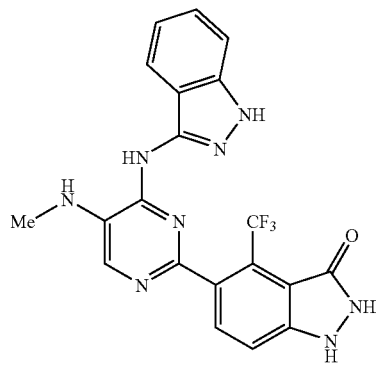
II-(v)-51
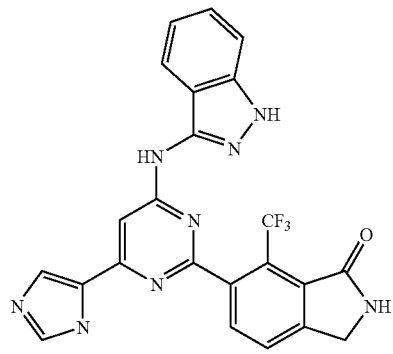
II-(v)-52
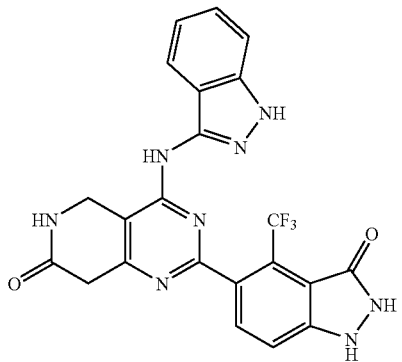

-continued
II-(v)-53
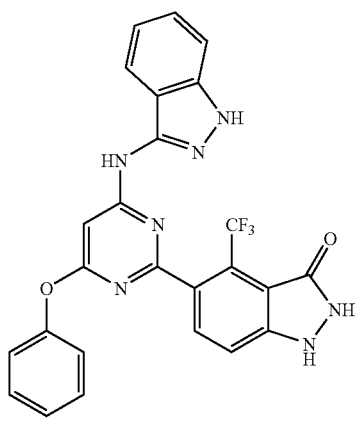
II-(v)-54
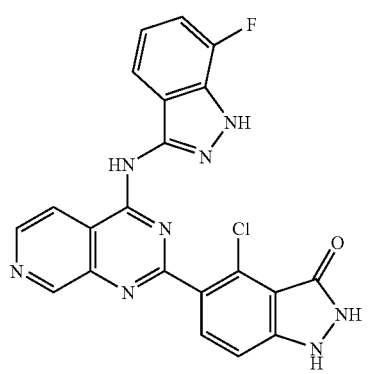
II-(v)-55
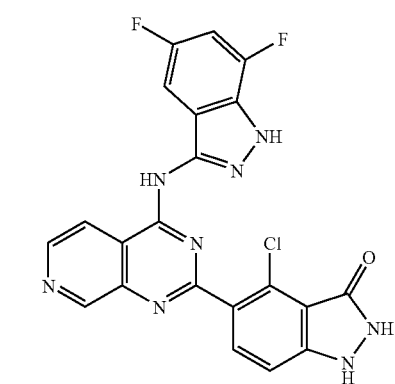
II-(v)-56
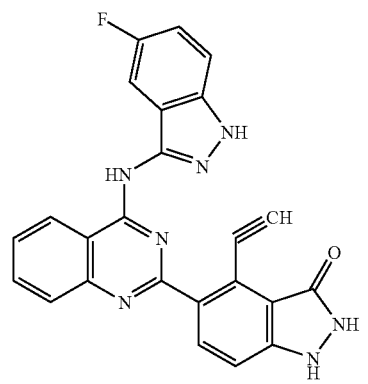
II-(v)-57
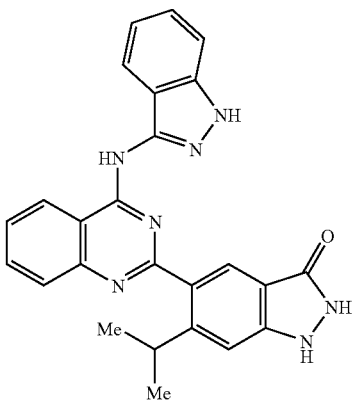
II-(v)-58
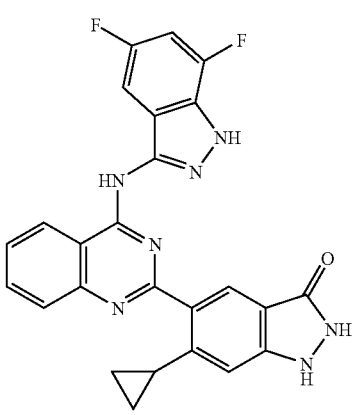
II-(v)-59
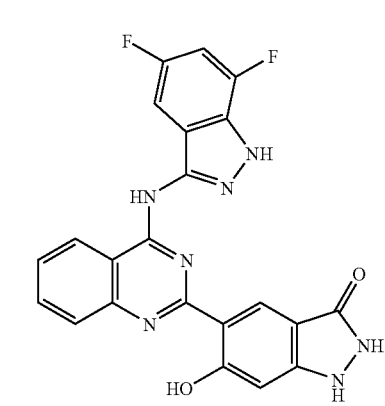
II-(v)-60
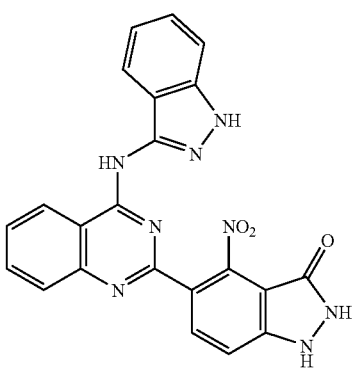

-continued
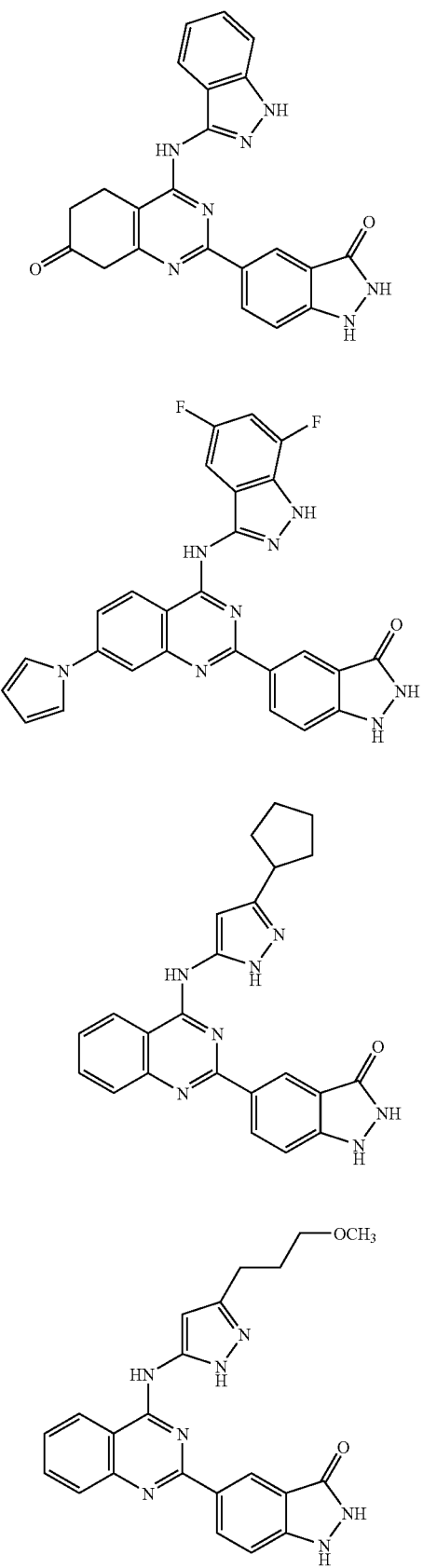
II-(v)-61
II-(v)-62
II-(v)-63
II-(v)-64
-continued
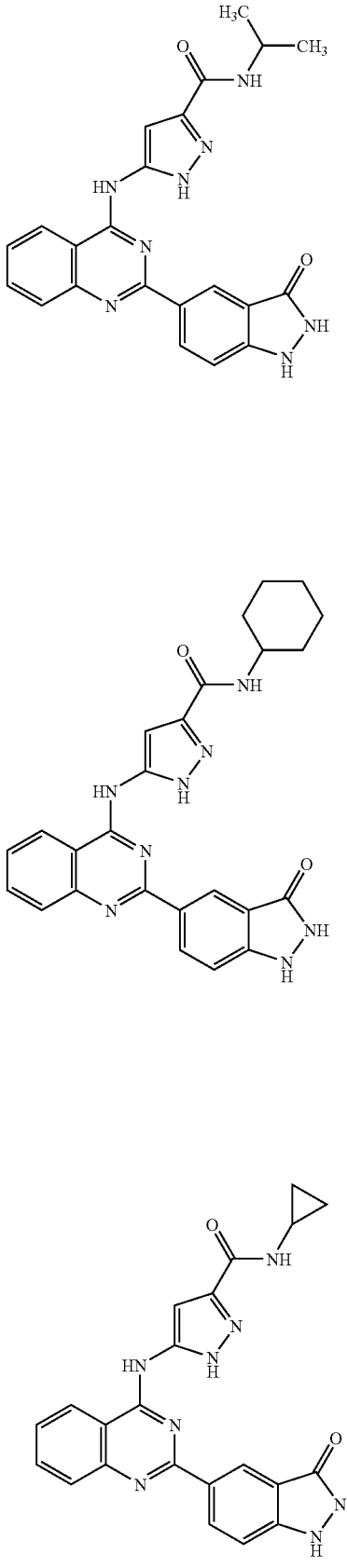
II-(v)-65
II-(v)-66
II-(v)-67

II-(v)-68
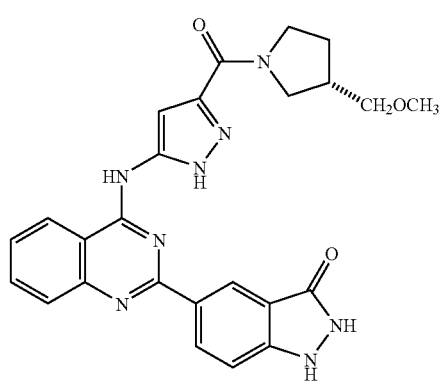
II-(v)-69
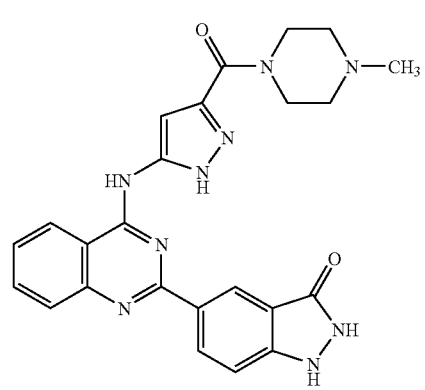
II-(v)-70
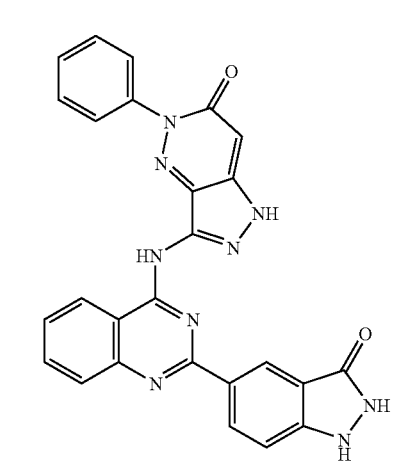
II-(v)-71
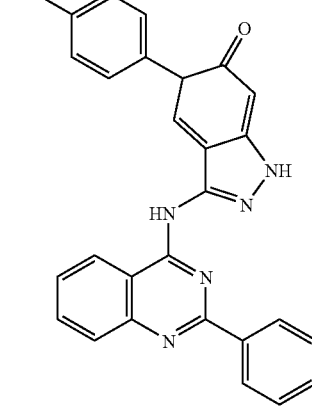
II-(v)-72
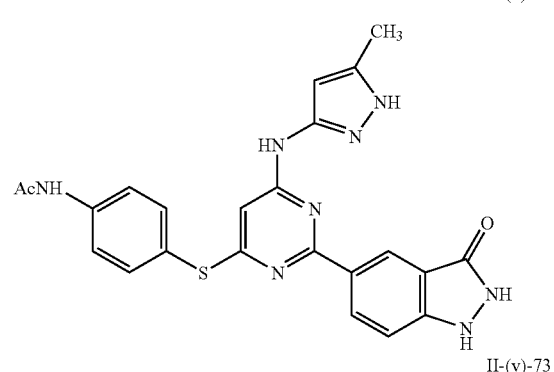
II-(v)-73
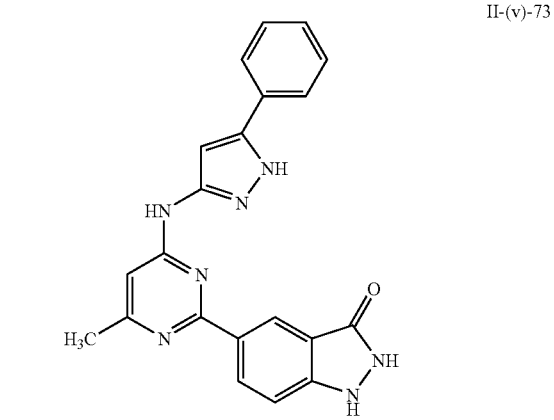
II-(v)-74
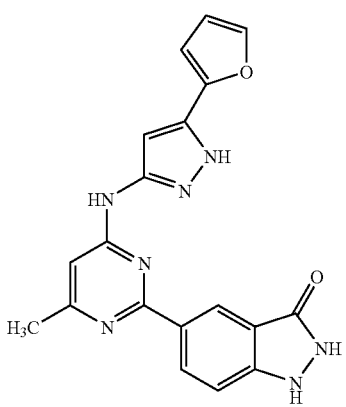

-continued
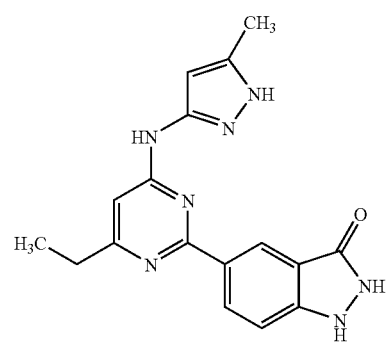
II-(v)-75
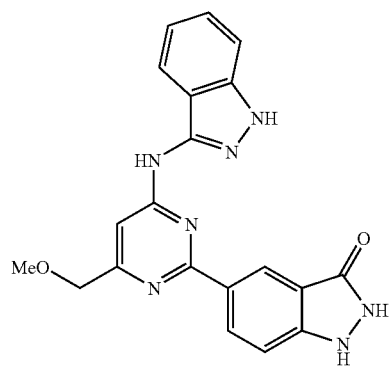
II-(v)-76
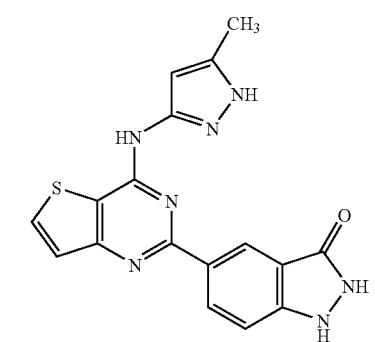
II-(v)-77
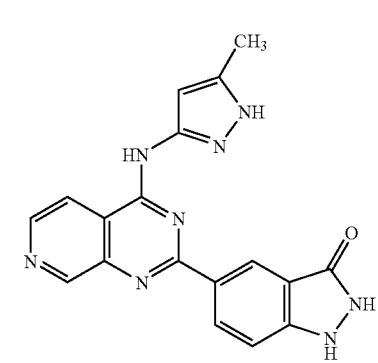
II-(v)-78
-continued
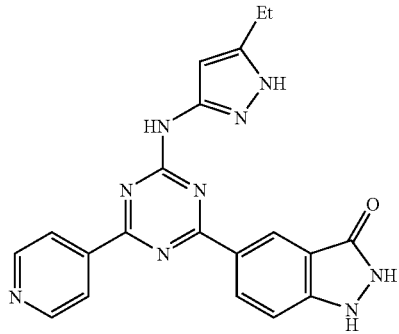
II-(v)-79
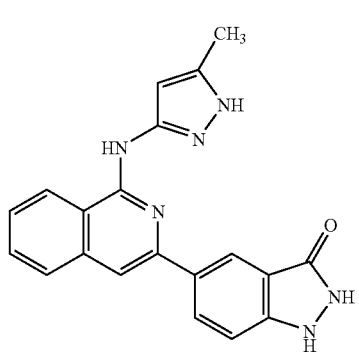
II-(v)-80
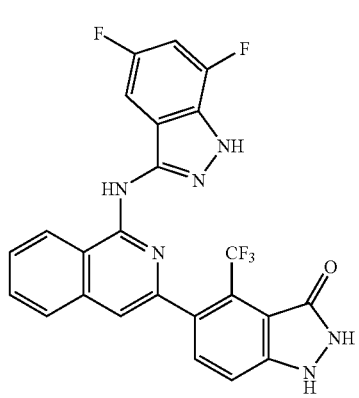
II-(v)-81
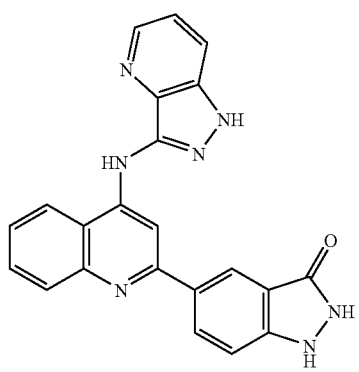
II-(v)-82

-continued
II-(v)-83
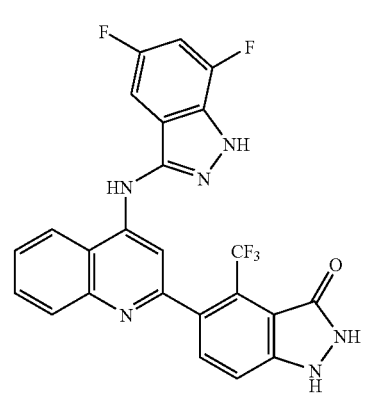
II-(v)-84
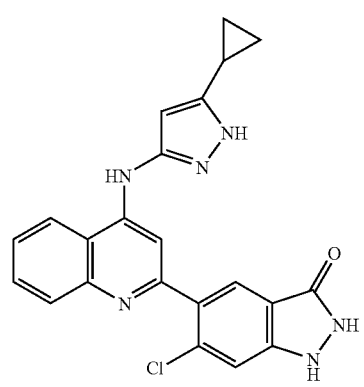
II-(v)-85
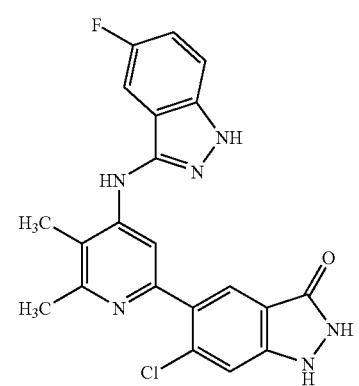
II-(v)-86
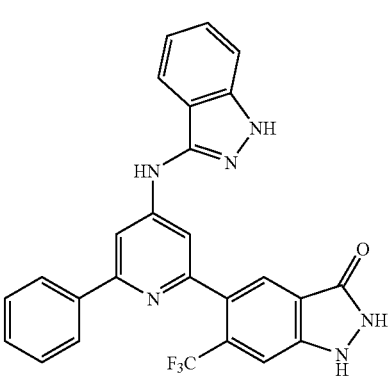
-continued
II-(v)-87
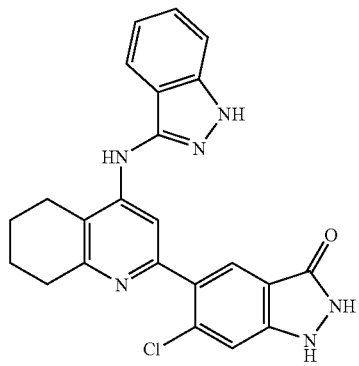
II-(v)-88
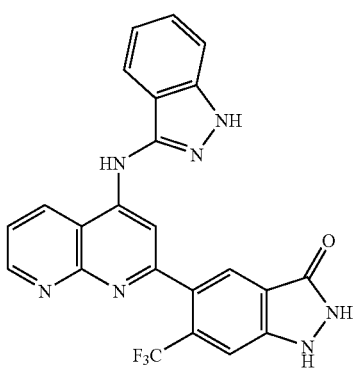
II-(v)-89
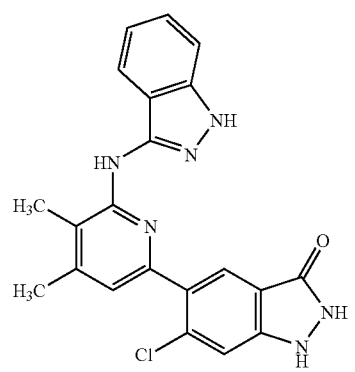
II-(v)-90
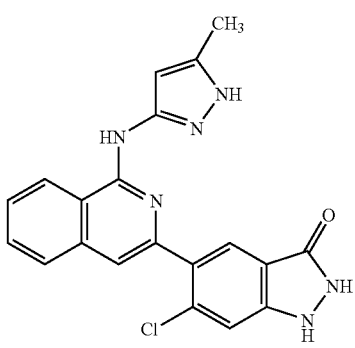

-continued
II-(v)-91
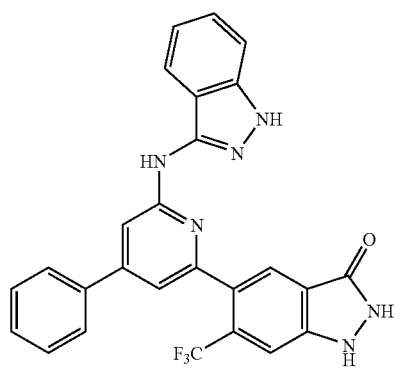
II-(v)-92
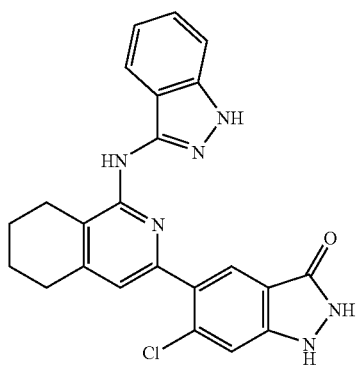
II-(v)-93
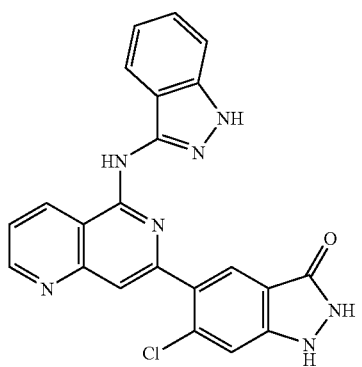
II-(v)-94
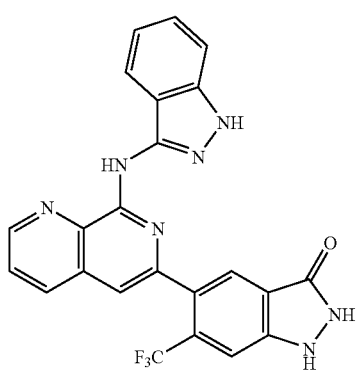
-continued
II-(v)-95
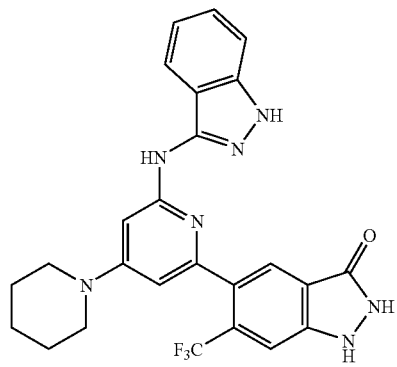
II-(v)-96
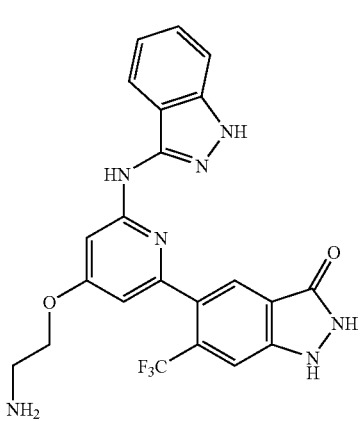
II-(v)-97
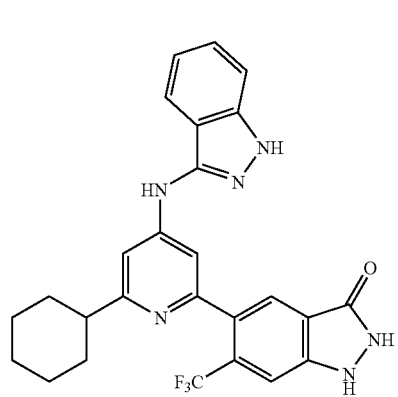
II-(v)-98
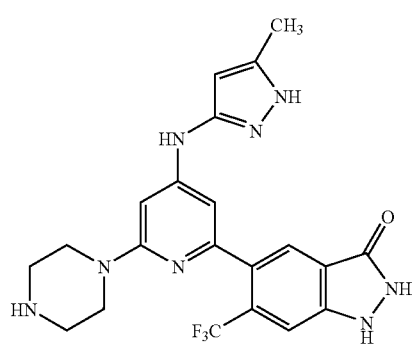

-continued
II-(v)-99
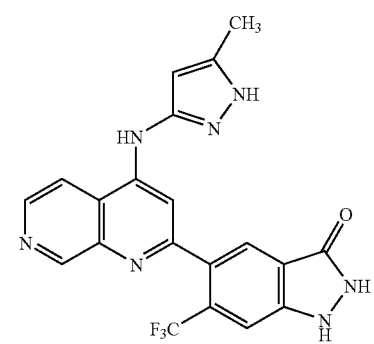
II-(v)-100
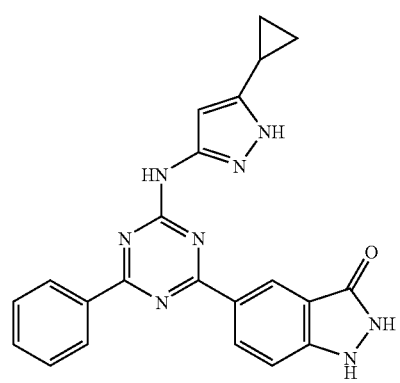
II-(v)-101
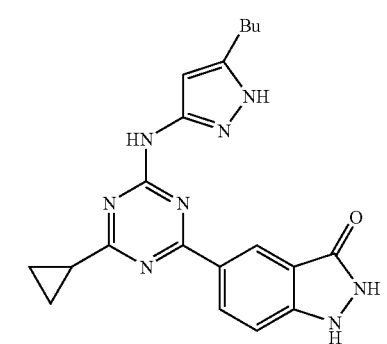
II-(v)-102
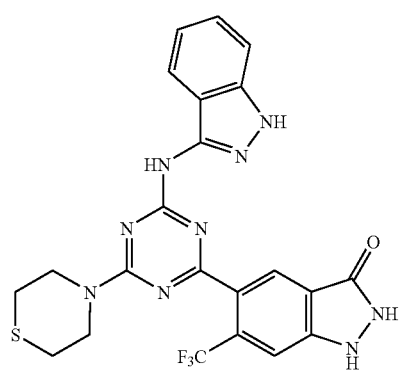
-continued
II-(v)-103
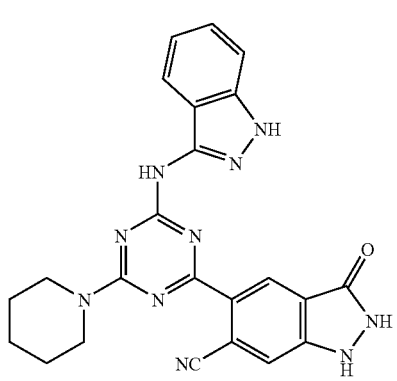
II-(v)-104
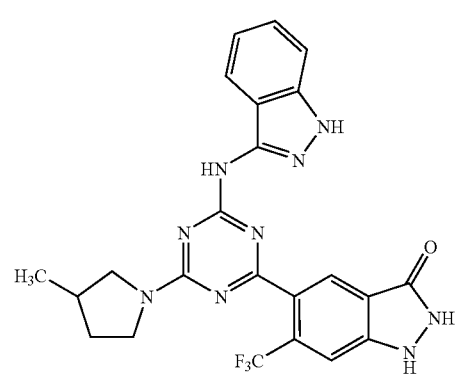
II-(v)-105
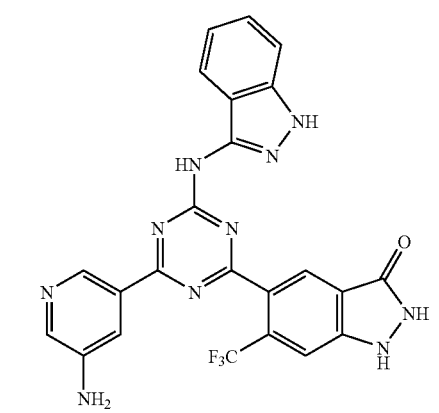
II-(v)-106
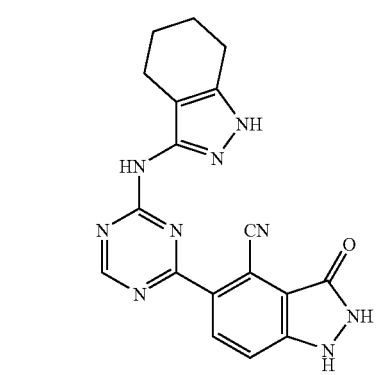

-continued
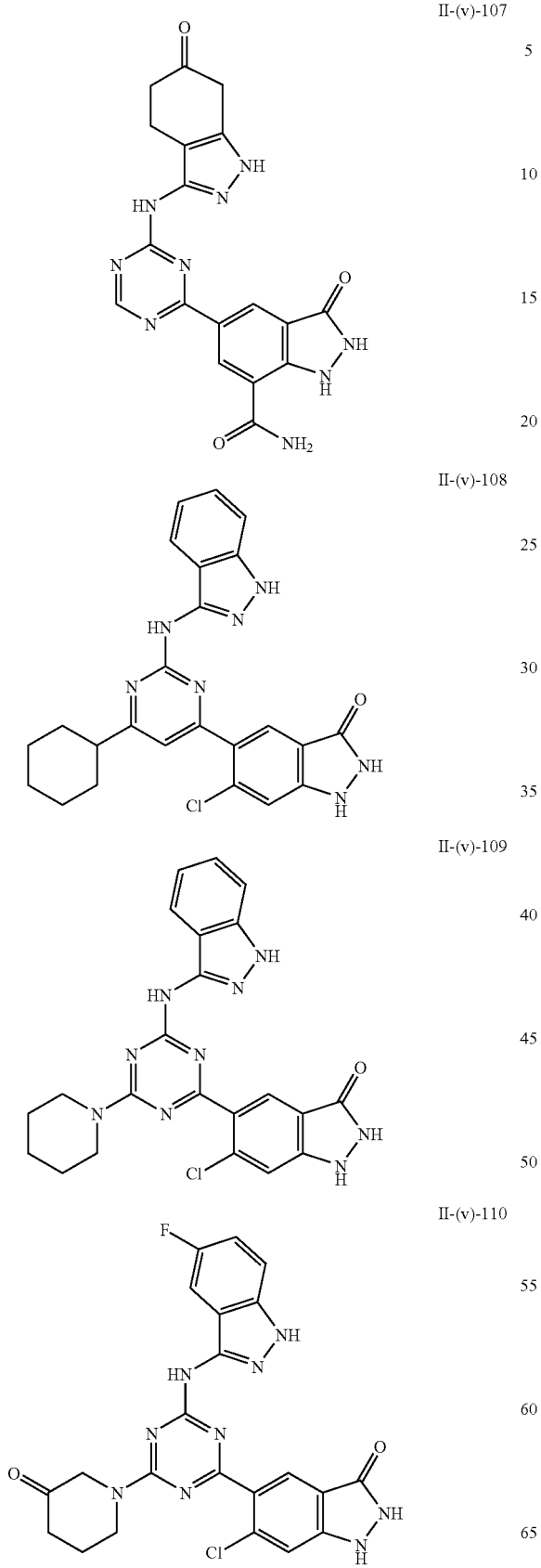
II-(v)-107
II-(v)-108
II-(v)-109
II-(v)-110
-continued
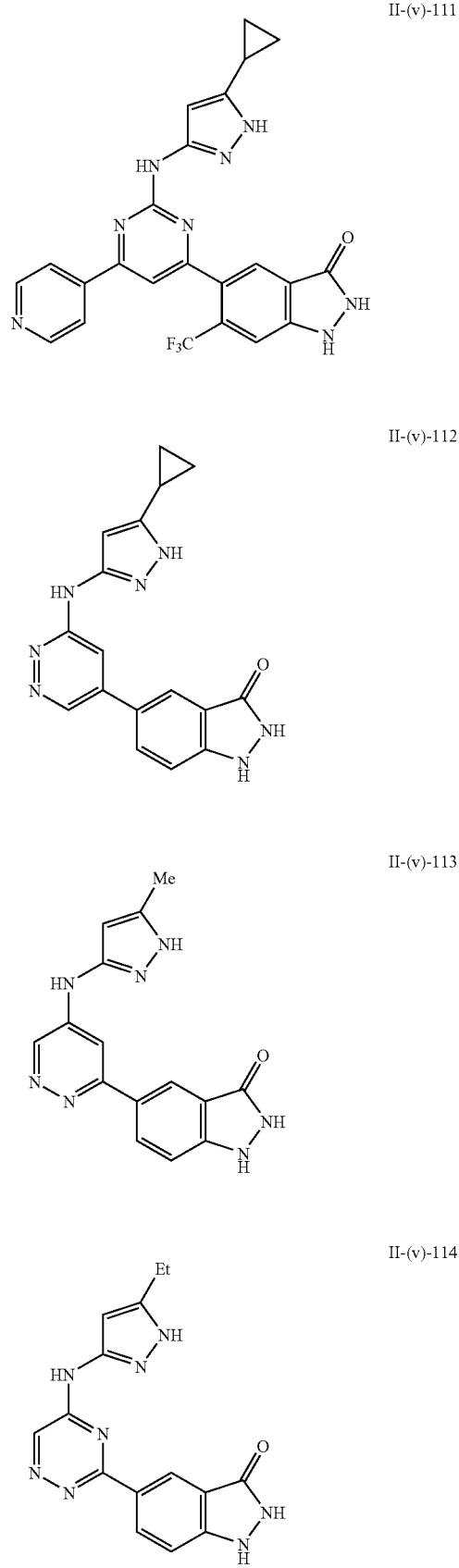
II-(v)-111
II-(v)-112
II-(v)-113
II-(v)-114

-continued
II-(v)-115
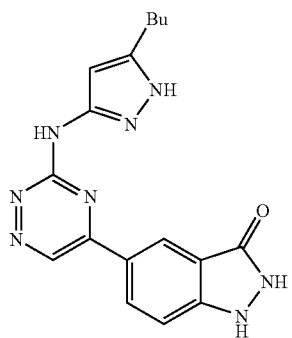
II-(v)-116
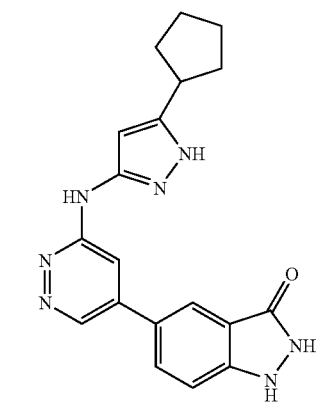
II-(v)-117
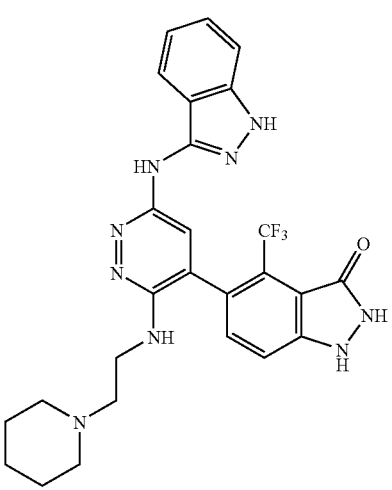
-continued
II-(v)-118
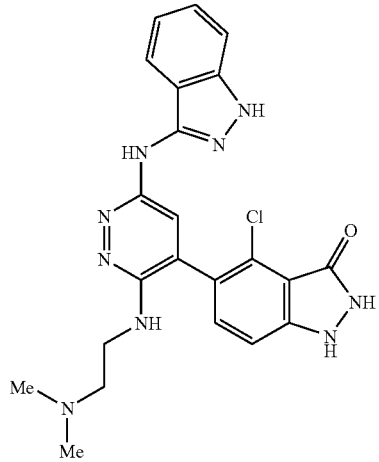
II-(v)-119
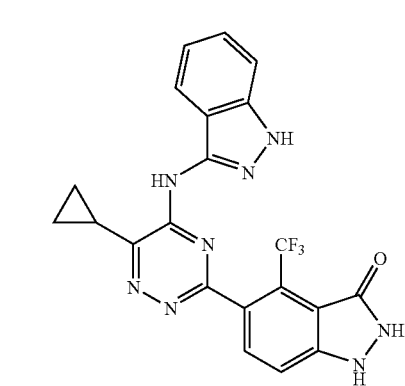
II-(v)-120
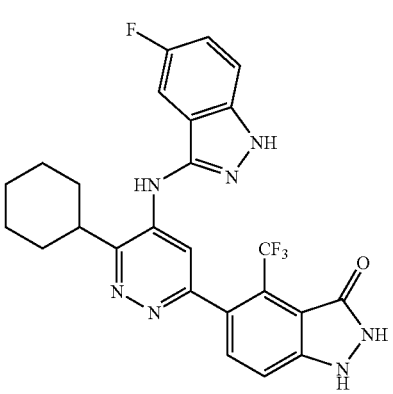
II-(v)-121
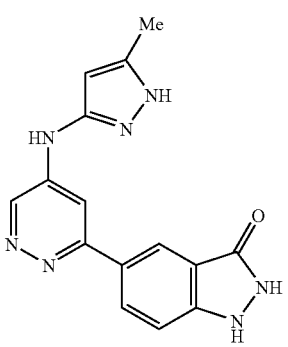

II-(v)-122

II-(v)-123

II-(v)-124

II-(v)-125

II-(v)-126

II-(v)-127

II-(v)-128

II-(v)-129

-continued
II-(v)-130
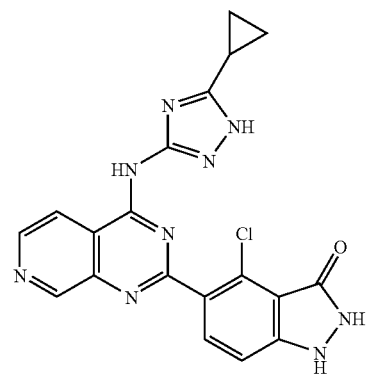
II-(v)-131
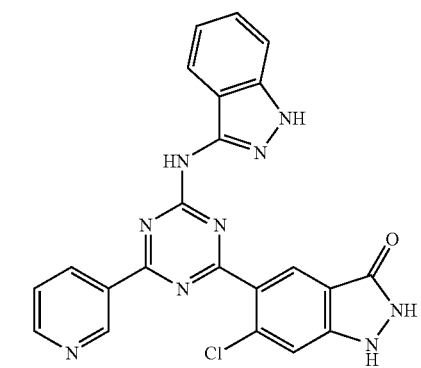
II-(v)-132
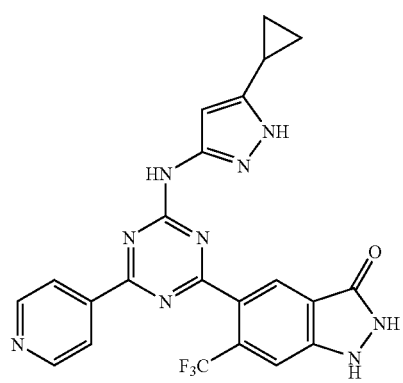
II-(v)-133
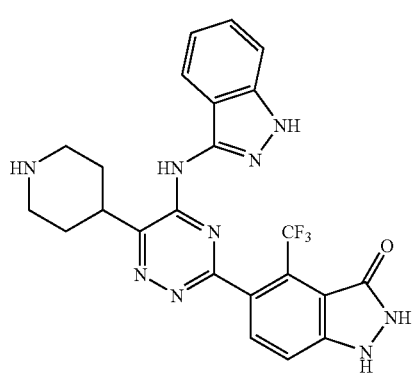
-continued
II-(v)-134
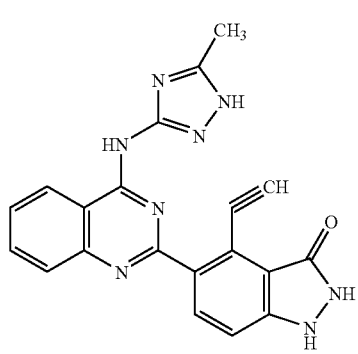
II-(v)-135
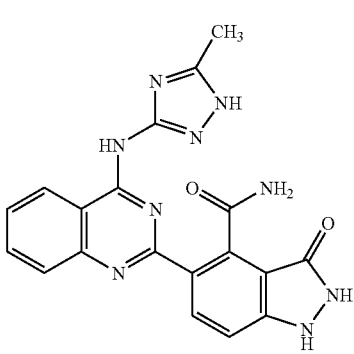
III-(i)-1
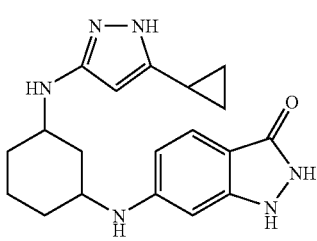
III-(i)-2
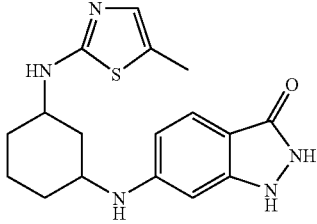
III-(i)-3
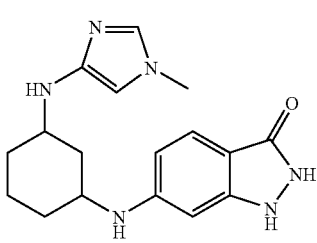

-continued
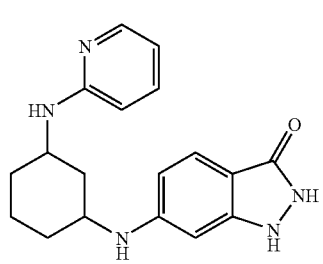
III-(i)-4
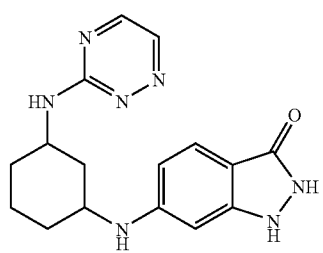
III-(i)-5
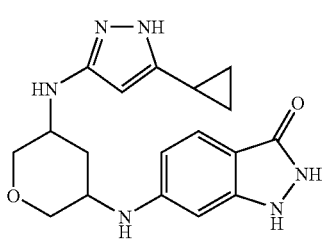
III-(i)-6
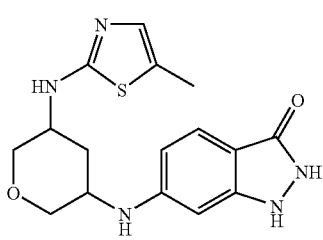
III-(i)-7
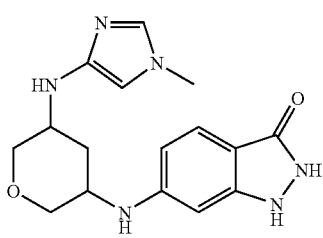
III-(i)-8
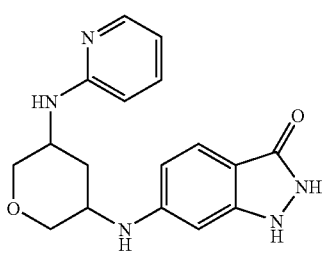
III-(i)-9
-continued
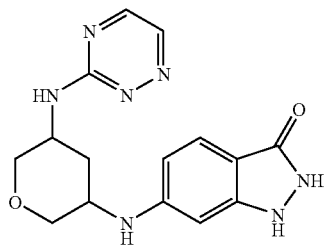
III-(i)-10
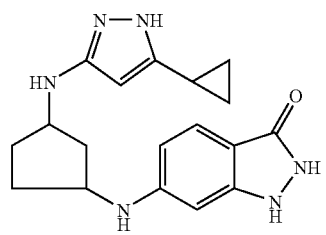
III-(i)-11
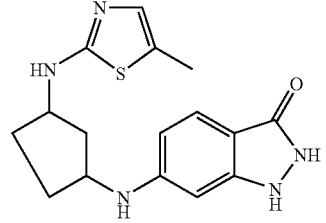
III-(i)-12
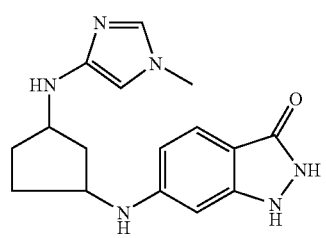
III-(i)-13
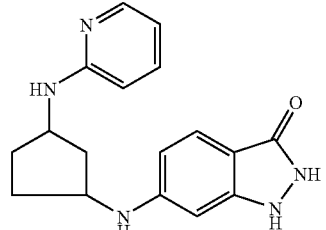
III-(i)-14
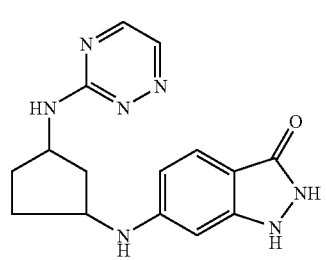
III-(i)-15

-continued
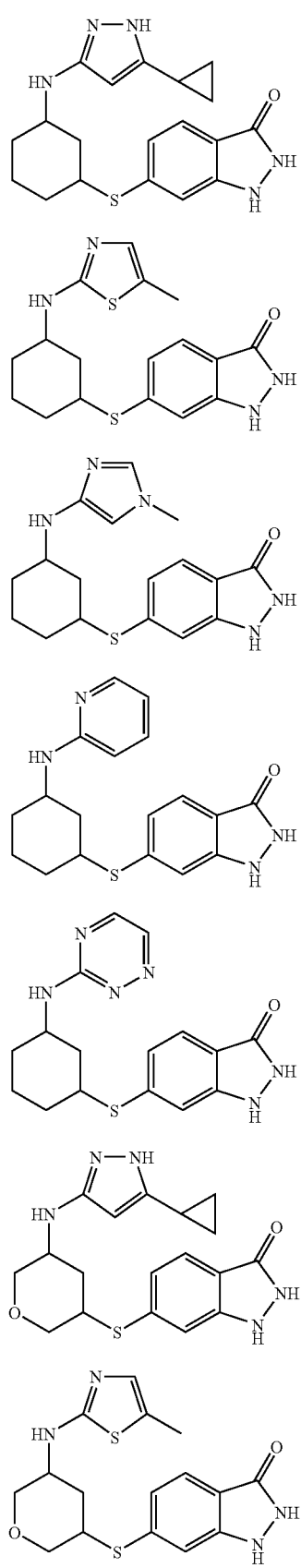
III-(ii)-1
III-(ii)-2
III-(ii)-3
III-(ii)-4
III-(ii)-5
III-(ii)-6
III-(ii)-7
-continued
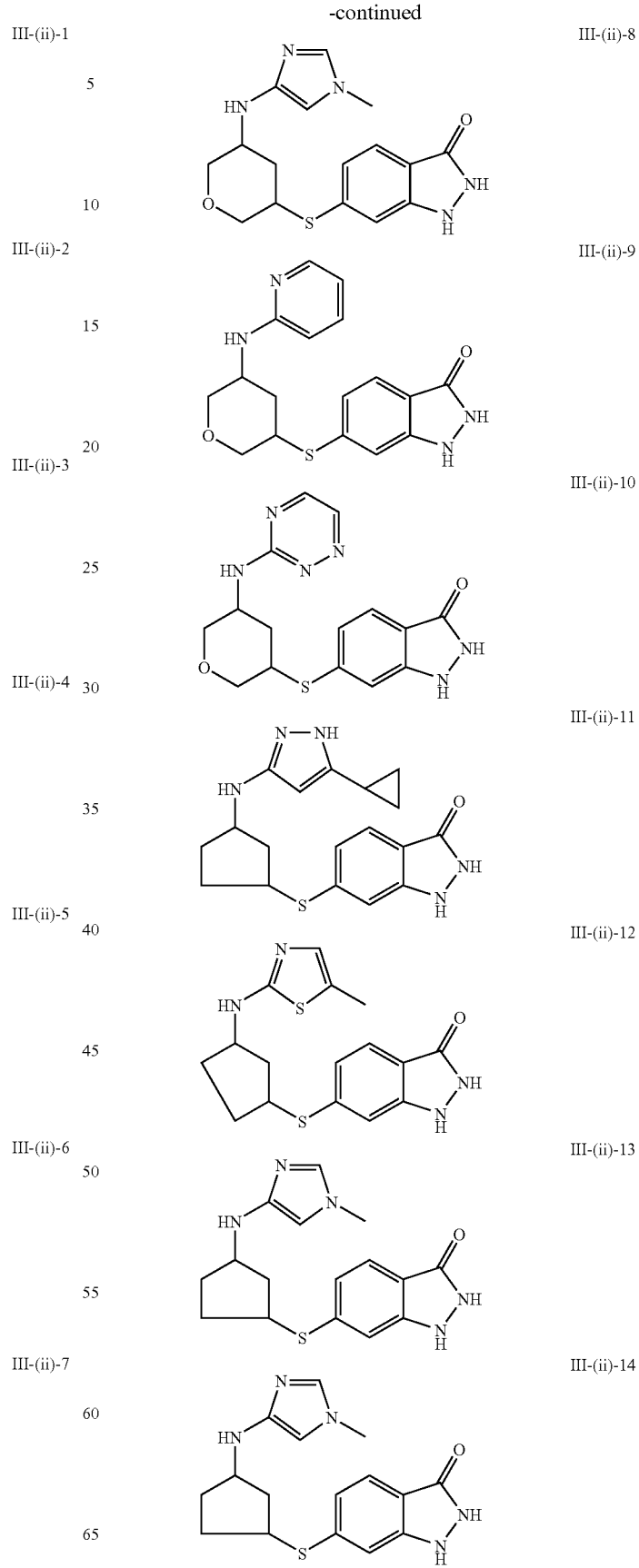
III-(ii)-8
III-(ii)-9
III-(ii)-10
III-(ii)-11
III-(ii)-12
III-(ii)-13
III-(ii)-14

-continued
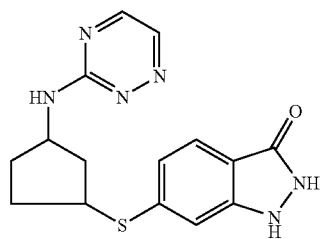
III-(ii)-15
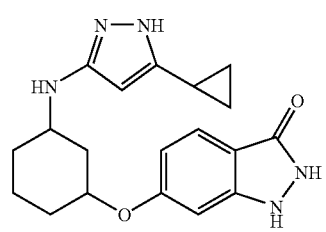
III-(iii)-1
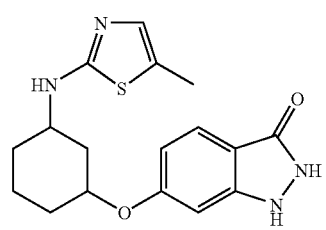
III-(iii)-2
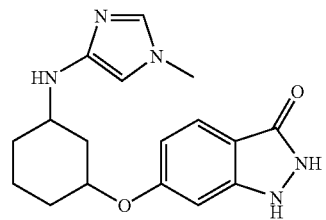
III-(iii)-3
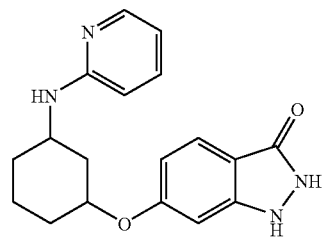
III-(iii)-4
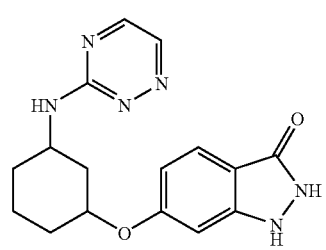
III-(iii)-5
-continued
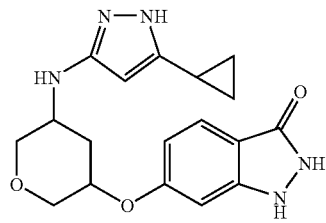
III-(iii)-6
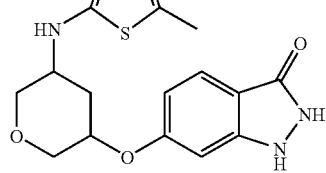
III-(iii)-7
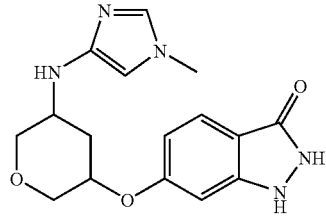
III-(iii)-8
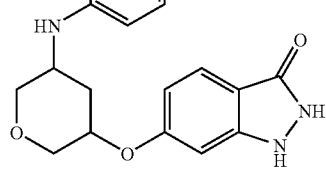
III-(iii)-9
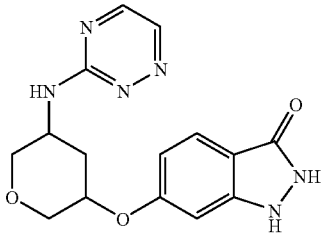
III-(iii)-10
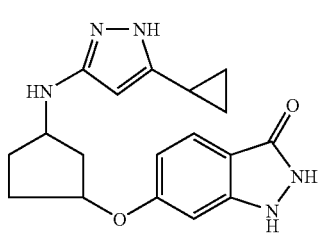
III-(iii)-11
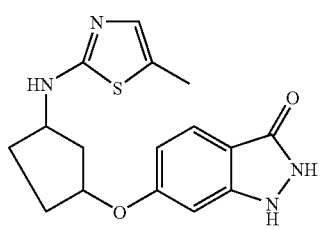
III-(iii)-12

-continued
III-(iii)-13
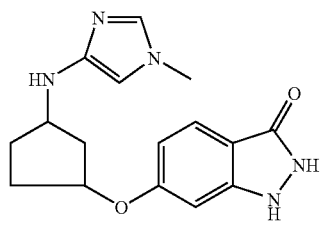
III-(iii)-14
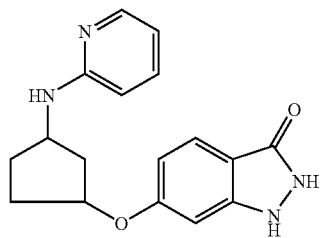
III-(iii)-15
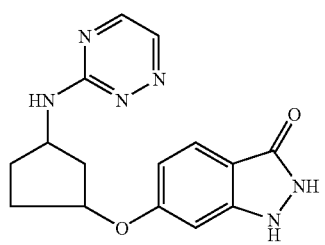
III-(iv)-1
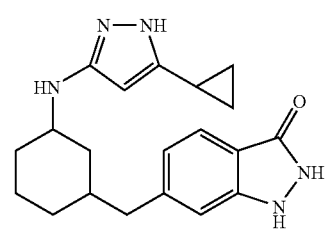
III-(iv)-2
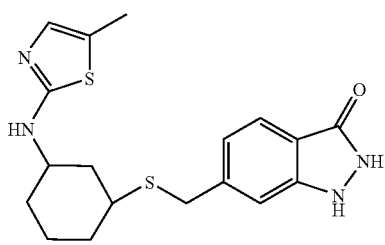
III-(iv)-3
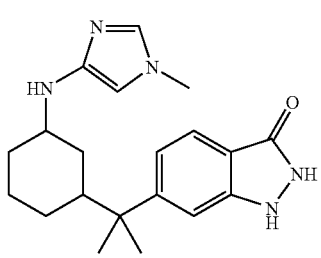
-continued
III-(iv)-4
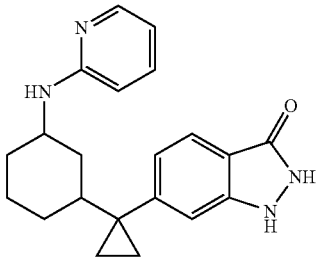
III-(iv)-5
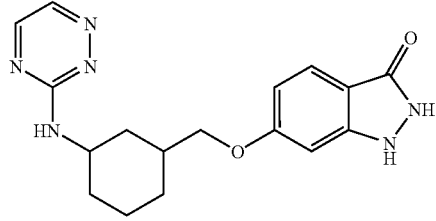
III-(iv)-6
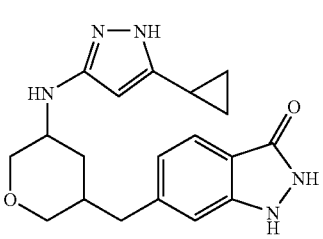
III-(iv)-7
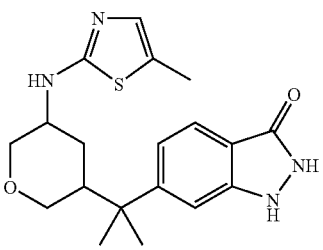
III-(iv)-8
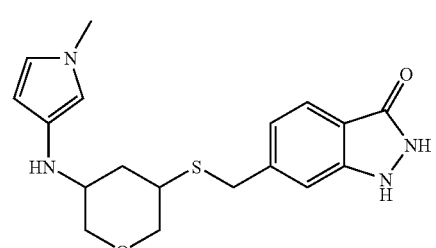
III-(iv)-9
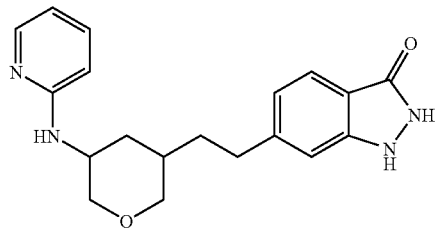

-continued
III-(iv)-10
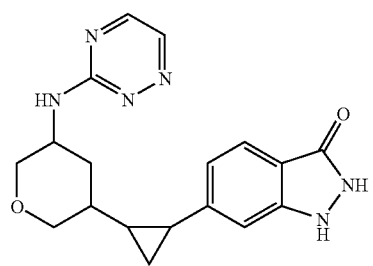
III-(iv)-11
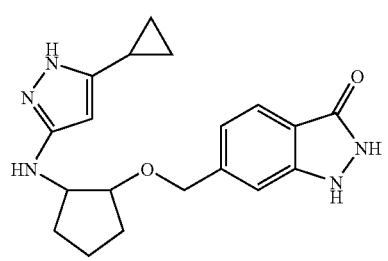
III-(iv)-12
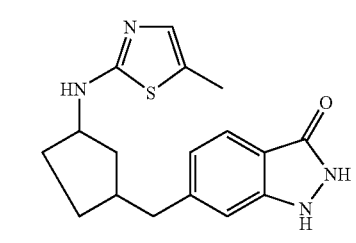
III-(iv)-13
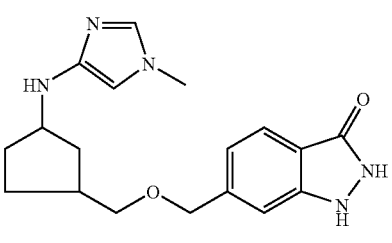
III-(iv)-14
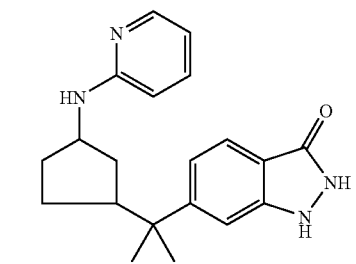
III-(iv)-15
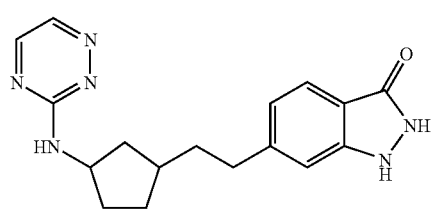
-continued
III-(v)-1
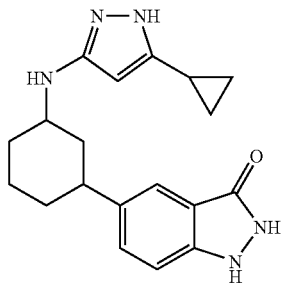
III-(v)-2
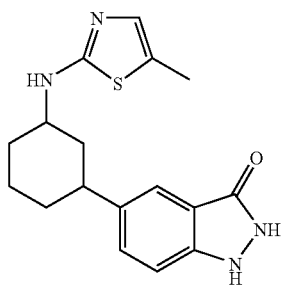
III-(v)-3
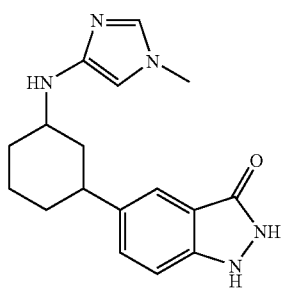
III-(v)-4
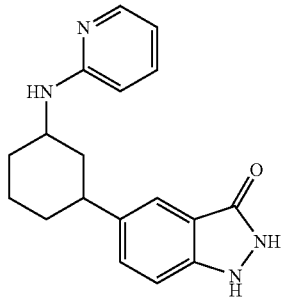
III-(v)-5
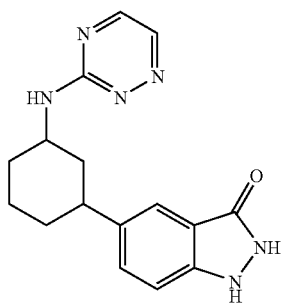

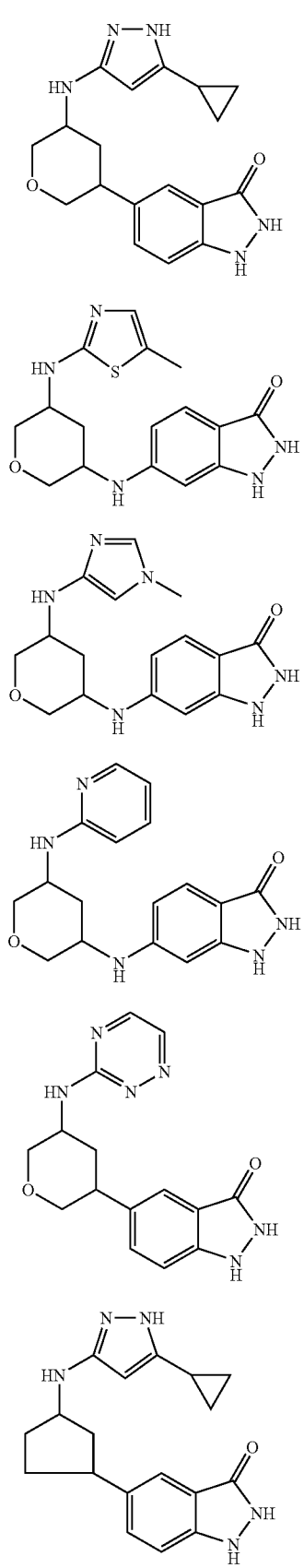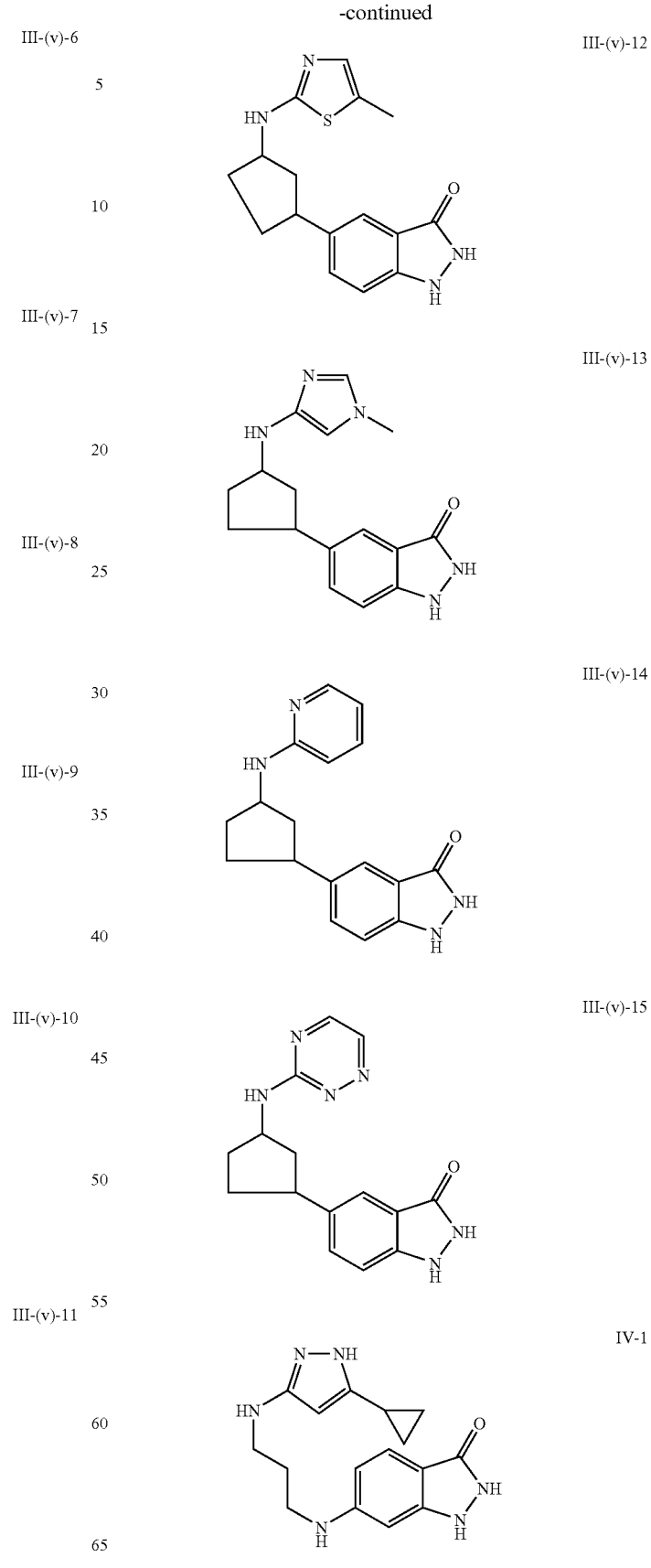

-continued
IV-2
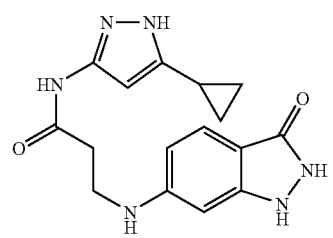
IV-3
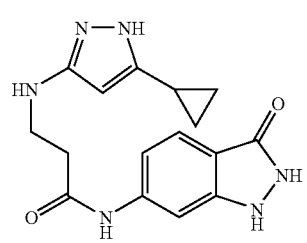
IV-4
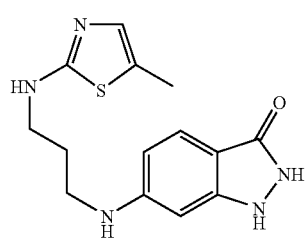
IV-5
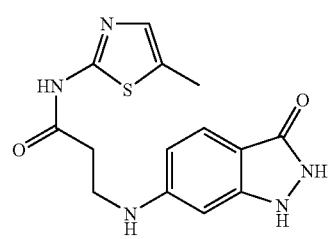
IV-6
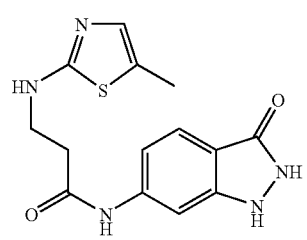
IV-7
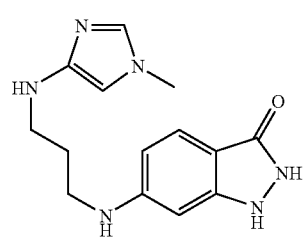
-continued
IV-8
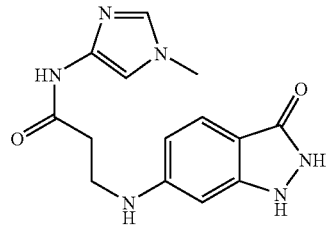
IV-9
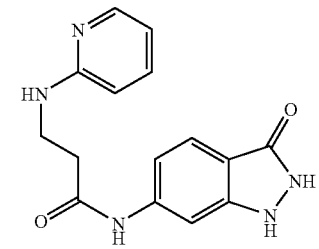
IV-10
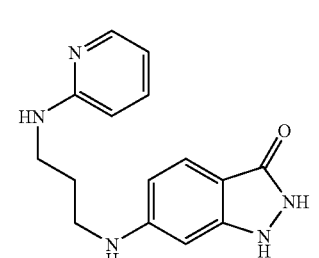
IV-11
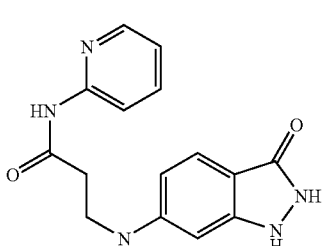
IV-12
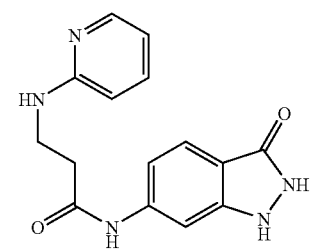
IV-13
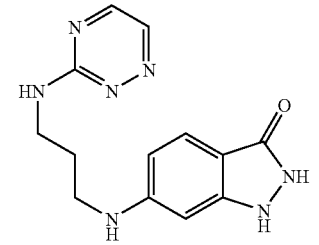

IV-14
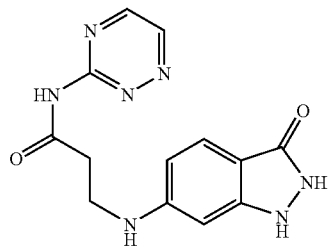
IV-15
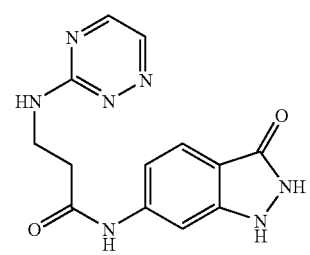
IV-16
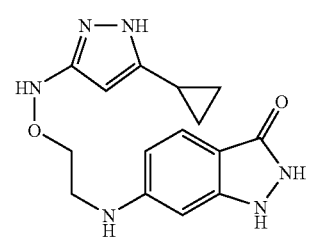
IV-17
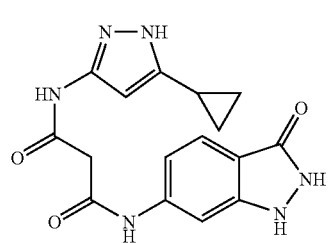
IV-18
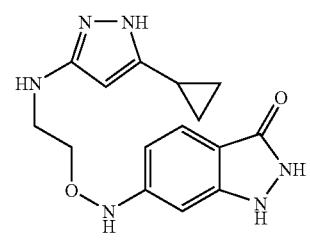
IV-19
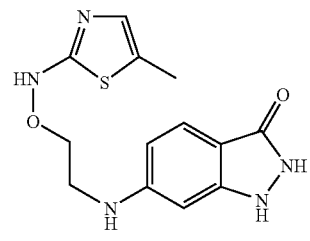
IV-20
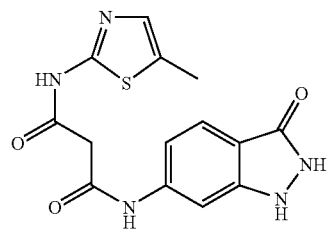
IV-21
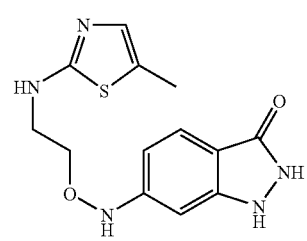
IV-22
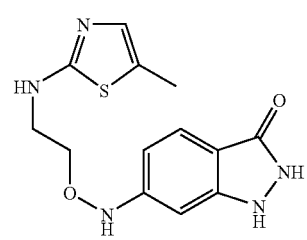
IV-23
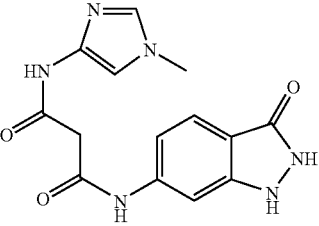
IV-24
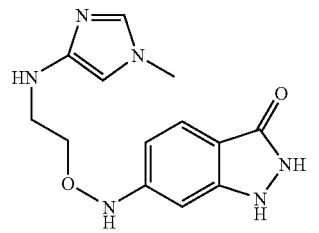
IV-25
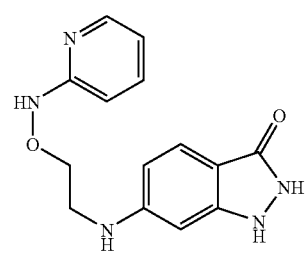

-continued

IV-26

IV-27

IV-28

IV-29

IV-30

IV-31

-continued

IV-32

IV-33

IV-34

IV-35

IV-36

IV-37

-continued
IV-38
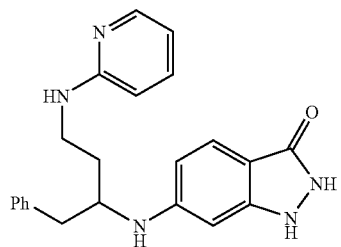
IV-39
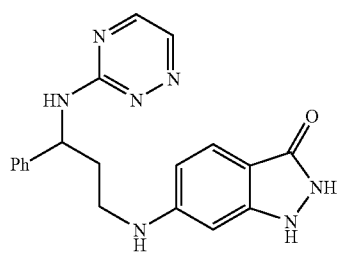
IV-40
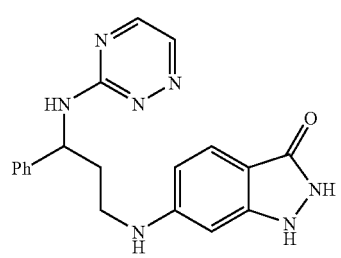
IV-41
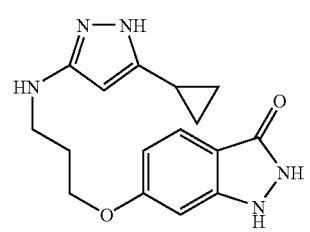
IV-42
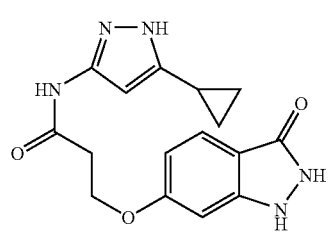
IV-43
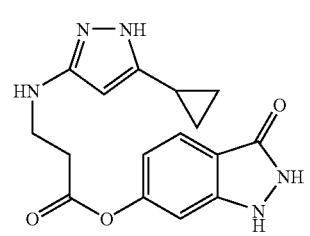
-continued
IV-44
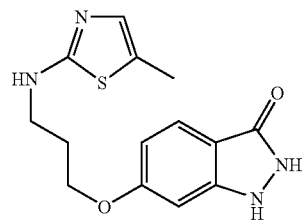
IV-45
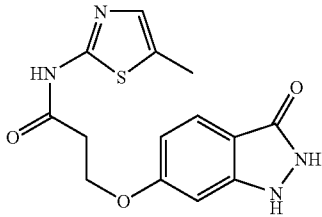
IV-46
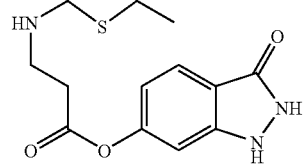
IV-47
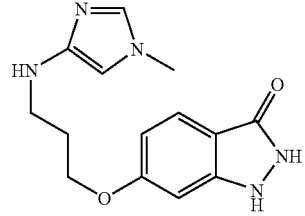
IV-48
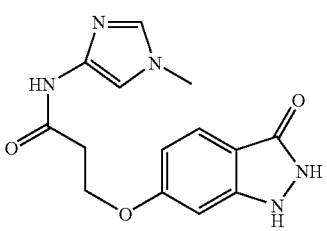
IV-49
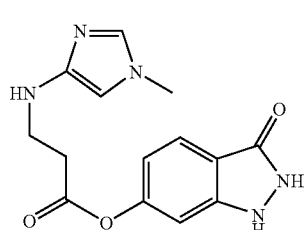
IV-50
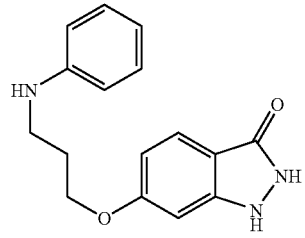

-continued

IV-51

IV-52

IV-53

IV-54

IV-55

IV-56

-continued

IV-57

IV-58

IV-59

IV-60

IV-61

IV-62